US008962298B2

(12) United States Patent
Donaldson et al.

(10) Patent No.: US 8,962,298 B2
(45) Date of Patent: *Feb. 24, 2015

(54) RECOMBINANT HOST CELL COMPRISING A DIOL DEHYDRATASE

(75) Inventors: Gail K. Donaldson, Newark, DE (US); Andrew C. Eliot, Wilmington, DE (US); Vasantha Nagarajan, Wilmington, DE (US); Charles E. Nakamura, Claymont, DE (US); Jean-Francois Tomb, Wilmington, DE (US)

(73) Assignee: Butamax Advanced Biofuels LLC DE (US)

( * ) Notice: Subject to any disclaimer, the term of this patent is extended or adjusted under 35 U.S.C. 154(b) by 27 days.

This patent is subject to a terminal disclaimer.

(21) Appl. No.: 11/741,916

(22) Filed: Apr. 30, 2007

(65) Prior Publication Data

US 2007/0292927 A1 Dec. 20, 2007

Related U.S. Application Data

(60) Provisional application No. 60/796,816, filed on May 2, 2006, provisional application No. 60/871,156, filed on Dec. 21, 2006.

(51) Int. Cl.
| | |
|---|---|
| *C12N 1/20* | (2006.01) |
| *C12P 7/16* | (2006.01) |
| *C12N 15/00* | (2006.01) |
| *C12N 9/00* | (2006.01) |
| *C07H 21/04* | (2006.01) |
| *C12N 9/88* | (2006.01) |
| *C12N 9/04* | (2006.01) |
| *C12N 9/12* | (2006.01) |
| *C12N 9/78* | (2006.01) |
| *C12P 7/26* | (2006.01) |

(52) U.S. Cl.
CPC ............... *C12N 9/88* (2013.01); *C12N 9/0006* (2013.01); *C12N 9/1205* (2013.01); *C12N 9/78* (2013.01); *C12P 7/16* (2013.01); *C12P 7/26* (2013.01); *Y02E 50/10* (2013.01)
USPC ........ 435/252.3; 435/160; 435/440; 435/190; 435/183; 435/320.1; 435/232; 536/23.2

(58) Field of Classification Search
CPC ...... C12N 9/88; C12N 15/63; C12N 2015/63; C12P 7/16; C12P 7/26
See application file for complete search history.

(56) References Cited

U.S. PATENT DOCUMENTS

| | | | |
|---|---|---|---|
| 2,198,104 | A | 4/1940 | Carnarius et al, |
| 4,424,275 | A | 1/1984 | Levy |
| 4,568,643 | A | 2/1986 | Levy |
| 5,063,156 | A | 11/1991 | Glassner et al. |
| 5,192,673 | A | 3/1993 | Jain et al. |
| 5,210,032 | A | 5/1993 | Kashket |
| 5,424,202 | A | 6/1995 | Ingram et al. |
| 5,523,223 | A | 6/1996 | Kula et al. |
| 5,686,276 | A | 11/1997 | Laffend et al. |
| 5,763,236 | A | 6/1998 | Kojima et al. |
| 6,358,717 | B1 | 3/2002 | Blaschek et al. |
| 6,432,688 | B1 | 8/2002 | Ito et al. |
| 6,514,733 | B1 | 2/2003 | Emptage et al. |
| 6,960,465 | B1 | 11/2005 | Papoutsakis et al. |
| 7,067,300 | B2 | 6/2006 | Emptage et al. |
| 7,504,250 | B2 | 3/2009 | Emptage et al. |
| 8,188,250 | B2 | 5/2012 | Bramucci et al. |
| 8,426,174 | B2 | 4/2013 | Bramucci et al. |
| 2002/0028492 | A1 | 3/2002 | Lenke et al. |
| 2004/0157305 | A1* | 8/2004 | Stampfer et al. ............... 435/189 |
| 2004/0234649 | A1 | 11/2004 | Lewis et al. |
| 2005/0003500 | A1 | 1/2005 | Kudoh et al. |
| 2007/0259410 | A1 | 11/2007 | Eliot et al. |
| 2007/0259411 | A1 | 11/2007 | Bramucci et al. |
| 2007/0265477 | A1 | 11/2007 | Gupta et al. |
| 2008/0124774 | A1 | 5/2008 | Bramucci et al. |
| 2009/0155870 | A1 | 6/2009 | Donaldson et al. |
| 2009/0239275 | A1 | 9/2009 | Donaldson et al. |
| 2012/0231515 | A1 | 9/2012 | Bramucci et al. |

FOREIGN PATENT DOCUMENTS

| | | |
|---|---|---|
| AU | 620802 | 10/1988 |
| CA | 2039245 | 4/1990 |
| EP | 0 112 459 A1 | 7/1984 |
| EP | 0 282 474 A1 | 9/1988 |
| EP | 0 315 949 A2 | 5/1989 |
| EP | 0 645 453 A2 | 3/1995 |
| EP | 1 149 918 B1 | 3/1995 |
| EP | 0 305 434 B1 | 6/1995 |
| JP | 61-209594 | 9/1986 |

(Continued)

OTHER PUBLICATIONS

Voloch et al. Reduction of acetoin to 2,3-butanediol in *Klebsiella pneumoniae*: a new model. Biotechnol Bioeng. Jan. 1983;25(1):173-83.*
Stewart et al Biotechnology and Genetic Engineering Reviews, 14:67-143, 1997.*
Nielsen et al. Metabolic Engineering. Appl Microbiol Biotechnol. Apr. 2001; 55(3):263-83.*
Blomqvist, Kristina et al., Characterization of the Genes of the 2,3-Butanediol Operons from *Klebsiella terrigena* and Enterobacter aerogenes, Journal of Bacteriology, Mar. 1993, pp. 1392-1404, vol. 175, No. 5, American Society for Microbiology.
Peng, Hwei-Ling et al., Cloning, sequencing and heterologous expression of a *Klebsiella pneumoniae* gene encoding an FAD-independent acetolactate synthase, Gene, 1992, pp. 125-130, vol. 117, Elsevier Science Publishers B.V.

(Continued)

*Primary Examiner* — Yong Pak

(57) ABSTRACT

Methods for the fermentive production of four carbon alcohols are provided. Specifically, butanol, preferably 2-butanol is produced by the fermentive growth of a recombinant bacteria expressing a 2-butanol biosynthetic pathway. The recombinant microorganisms and methods of the invention can also be adapted to produce 2-butanone, an intermediate in the 2-butanol biosynthetic pathways disclosed herein.

4 Claims, 4 Drawing Sheets

(56) References Cited

FOREIGN PATENT DOCUMENTS

| JP | 63-17695 | 4/1988 |
|---|---|---|
| JP | 63-102687 | 5/1988 |
| JP | 63-254986 | 10/1988 |
| WO | WO 90/02193 A1 | 3/1990 |
| WO | WO 98/51813 A1 | 11/1998 |
| WO | WO 03/078615 A1 | 9/2003 |
| WO | 2005108593 A1 | 11/2005 |
| WO | WO2007/130518 A2 | 11/2007 |
| WO | WO2008/006038 A2 | 1/2008 |

OTHER PUBLICATIONS

Tobimatsu, Takamasa et al., Molecular Cloning, Sequencing, and Expression of the Genes Encoding Adenosylcobalamin-dependent Diol Dehydrase of *Klebsiella oxytoca*, The Journal of Biological Chemistry, Mar. 31, 1995, pp. 7142-7148, vol. 270, No. 13, The American Society for Biochemistry and Molecular Biology, Inc.

International Search Report, International Application No. PCT/US2007/010744, International Filing Date Feb. 5, 2007.

Ullmann'S Encyclopedia of Industrial Chemistry, $6^{th}$ Edition, 2003, vol. 5:727-732.

Breen et al., Bimetallic Effects in the Liquid-Phase Hydrogenation of 2-Butanone, J. or Catalysis, 2005, vol. 236:270-281.

Ullmann's Encyclopedia of Industrial Chemistry, $6^{th}$ Edition, 2003, vol. 5:716-719.

Speranza et al., Conversion of Meso-2,3-Butanediol Into 2-Butanol by *Lactobacilli*, Stereochemical and Enzymatic Aspects, J. Agric. Food Chem., 1997, vol. 45:3476-3480.

Bermejo et al., Expression of *Clostridium acetobutylicum* ATCC 824 Genes in *Escherichia coli* for Acetone Production and Acetate Detoxification, Appied & Environmental Microbiology, 1998, vol. 64:1079-1085.

Cornillot et al., The Genes for Butanol and Acetone Formation in *Clostridium acetobutylicum* ATCC 824 Reside on a Large Plasmid Whose Loss Leads to Degeneration of the Strain, Journal of Bacteriology, 1997, vol. 179-5442-5447.

Fontaine et al., Molecular Characterization and Transcriptional Analysis of adhE2, The Encoding the NADH-Dependent Aldehyde/Alcohol Dehydrogenase Responsible for Butanol Production in Alcoholgenic cultures of *Clostridium acetobutylicum* ATCC 824, Journal of Bacteriology, 2002, vol. 184:821-830.

Girbal et al., Regulation of Solvent Production in *Clostridium acetobutylicum*, TIBTECH, 1998, vol. 16:11-16.

Woods, The Genetic Engineering of Microbial Solvent Production, TIBTECH, 1995, vol. 13:259-264.

Heipieper et al., "Mechanisms of resistance of whole cells to toxic organic solvents", Trends in Biotech, vol. 12, Oct. 1994, pp. 409-415.

Ly et al., "The influence of short-chain alcohols on interfacial tension, mechanical properties, area/molecule, and permeability of fluid lipid bilayers", Biophysical Journal, vol. 87, Aug. 2004, pp. 1013-1033.

Radler et al., "Characterization of the enzyme involved in formation of 2-butanol from meso-2,3-butanediol by lactic acid bacteria", American Journal of Enology and Viticulture, vol. 37, No. 3, pp. 206-210 (1986).

Kegg, S. bayanus 18810, downloaded on Dec. 9, 2011, 1 page.

Durre, P., "New Insights and Novel Developments in Clostridial acetone/butanol/isopropanol Fermentation Applied Microbiology and Biotechnology," 49: 639-648 (1998).

Duscehene, et al., "Control of radical chemistry in the AdoMet radical enzymes" Curent Opinion in Chemical Biology 13: 74-83 (2009).

Harris, et al., "Characterization of Recombinant Strains of the *Clostridium acetobutylicum* Butyrate Kinase Inactivation Mutant: Need for New Phenomenological Models for Solventogenesis and Butanol Inhibition?" Biotechnology and Bioengineering 67: 1-11 (2000).

Garcia-Alles, et al., "Phosphoenolpyruvate-and ATP-Dependent Dihydroxyacetone Kinases: Covalent Substrate-Binding and Kinetic Mechanism," Biochemistry 43: 13037-13045 (2004).

International Search Report International Application No. PCT/US2008/063852, mailed Jan. 21, 2009, European Patent Office, Netherlands.

Layer, et al., "Structural and functional comparison of HemN to other radical SAM enzymes," Biol. Chem. 386: 971-980 (2005).

Scott, K.., et al., "Whole-Genome Transcription Profiling Reveals Genes Up-Regulated by Growth on Fructose in the Human Gut Bacterium *Roseburia invulinivorans*," Journal of Bacteriology 188 (12): 4340-4349 (2006).

UNIPROT Database Accession No. QIA665 "Glycerol dehydratase activator," (2006) accessed Apr. 12, 2008.

UNIPROT Database Accession No. Q1A666, "Glycerol dehydratase," (2006) accessed Apr. 12, 2008.

Wang, at al., "*S*-adenosylmethionine as an oxidant: the radical SAM superfamily," Trends in Biochemical Sciences 32 (3): 101-110 (2007).

Seyfried et al., "Cloning, sequencing, and overexpression of the genes encoding coenzyme B12-dependent glycerol dehydratase of *Citrobacter freundii*," J. Bacteriol 178: 5793-5796 (1996).

BRENDA Database—EC 4.2.1.30—glycerol dehydratase. Retrieved from the internet via http://www.brenda-enzymes.org/php/flat_result.php4?ecno=4.2.1.30 on Sep. 23, 2009.

Jones, at al., "Acetone-Butanol Fermentation Revisited," Microbiol. Rev. 50: 484-524 (1986).

Branden et al., "Introduction to Protein Structure," Garland Publishing Inc. New York, p. 247 (1991).

O'Brien et al. "Insight Into the Mechanism of the $B_{12}$-Independent Glycerol Dehydratase from *Clostridium butyricum*: Preliminary Biochemical and Structural Characterization," Biochemistry 43: 4635-4645 (2004).

GenBank Accession ABC25539.1. "Glycerol dehydratase [*Roseburia inulinivorans*]," (2006) accessed Sep. 16, 2009.

Shin, et al., "Purification, characterization, and molecular cloning of a novel amine:pyruvate transaminase from *Vibrio fluvialis* JS17," Appl. Microbiol. Biotechnol. 61: 463-471 (2003).

Ui, at al., "Production of L-2,3-butanediol by a New Pathway Constructed in *Escherichia coli*," Lett. Appl. Microbiol. 39: 533-537 (2004).

Baer, et al., "Effect of Butanol Challenge and Temperature on Lipid Composition and Membrane Fluidity of Butanol-Tolerant *Clostridium acetobutylicum*," Appl. Environ. Microbiol. 53: 2854-2861 (1987).

Berovic, et al., "Influence of Temperature and Carbon Dioxide on Fermentation of Cabernet Sauvignon Must," Food Technol. Biotechnol. 41:353-359 (2003).

Poulsen, et al., "Purification and properties of *Saccharomyces cerevisiae* acetolactate synthase from recombinant *Escherichia coli*," J. Biochem. 185: 435-439 (1989).

Amartey, et al., "Effects of Temperature and Medium Composition on the Ethanol Tolerance of *Bacillus stearothermophilus*," Biotechnol. Lett., 13: 627-632 (1991).

Herrero, et al., "Development of Ethanol Tolerance in *Clostridium thermocellum*: Effect of Growth Temperature," Appl. Environ. Microbiol., 40: 571-577 (1980).

Brown, et al, "The Effect of Temperature on the Ethanol Tolerance of the Yeast *Saccharomyces uvarum*," Biotechnol. Lett. 4: 269-274 (1982).

Van Uden, et al., "Effects of Ethanol on the Temperature Relations of Viability and Growth in Yeast," Crc Crti. Rev. Biotechnol. 1: 263-273 (1984).

Harada, et al., "On the Butanol-Rich Production in Acetone-Butanol Fermentation of Molasses (Part 2) Temperature," Hakkp Kyokaishi 20: 155-156 (1962).

Keen et al., "The formation of 2-butanone and 2-butanol in cheddar cheese", Journal of Dairy Research, vol. 41, Issue 2, pp. 249-257, 1974 (Abstract only).

Herskovits et al., "On the structural stability and solvent denaturation of Proteins", The Journal of Biological Chemistry, vol. 245, No. 10, Issue of May 25, pp. 2588-2598, 1970.

\* cited by examiner

RECOMBINANT HOST CELL COMPRISING A DIOL DEHYDRATASE

CROSS-REFERENCE TO RELATED APPLICATION

This application claims priority under 35 U.S.C. §119 from U.S. Provisional Application Ser. No. 60/796,816, filed May 2, 2006 and U.S. Provisional Application Ser. No. 60/871,156, filed Dec. 21, 2006.

FIELD OF THE INVENTION

The invention relates to the field of industrial microbiology and the production of alcohols. More specifically, 2-butanol is produced via industrial fermentation of a recombinant microorganism. The recombinant microorganisms and methods of the invention can also be adapted to produce 2-butanone, an intermediate in the 2-butanol biosynthetic pathways disclosed herein.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase. 2-Butanone, also referred to as methyl ethyl ketone (MEK), is a widely used solvent and is the most important commercially produced ketone, after acetone. It is used as a solvent for paints, resins, and adhesives, as well as a selective extractant and activator of oxidative reactions.

Methods for the chemical synthesis of 2-butanone are known, such as by dehydrogenation of 2-butanol, or in a process where liquid butane is catalytically oxidized giving 2-butanone and acetic acid (*Ullmann's Encyclopedia of Industrial Chemistry*, 6th edition, 2003, Wiley-VCHVerlag GmbH and Co., Weinheim, Germany, Vol. 5, pp. 727-732). 2-Butanone may also be converted chemically to 2-butanol by hydrogenation (Breen et al., J. or Catalysis 236: 270-281 (2005)). Methods for the chemical synthesis of 2-butanol are known, such as n-butene hydration (*Ullmann's Encyclopedia of Industrial Chemistry*, 6th edition, 2003, Wiley-VCHVerlag GmbH and Co., Weinheim, Germany, Vol. 5, pp. 716-719). These processes use starting materials derived from petrochemicals and are generally expensive, and are not environmentally friendly. The production of 2-butanone and 2-butanol from plant-derived raw materials would minimize greenhouse gas emissions and would represent an advance in the art.

Methods for producing 2-butanol by biotransformation of other organic chemicals are also known. For example, Stampfer et al. (WO 03/078615) describe the production of secondary alcohols, such as 2-butanol, by the reduction of ketones which is catalyzed by an alcohol dehydrogenase enzyme obtained from *Rhodococcus ruber*. Similarly, Kojima et al. (EP 0645453) describe a method for preparing secondary alcohols, such as 2-butanol, by reduction of ketones which is catalyzed by a secondary alcohol dehydrogenase enzyme obtained from *Candida parapsilosis*. Additionally, Kuehnle et al. (EP 1149918) describe a process that produces both 1-butanol and 2-butanol by the oxidation of hydrocarbons by various strains of *Rhodococcus ruber*. The process favored 1-butanol production with a selectivity of 93.8%.

The production of 2-butanol by certain strains of *Lactobacilli* is also known (Speranza et. al. *J. Agric. Food Chem.* (1997) 45:3476-3480). The 2-butanol is produced by the transformation of meso-2,3-butanediol. The production of 2-butanol from acetolactate and acetoin by these *Lactobacilli* strains was also demonstrated. However, there have been no reports of a recombinant microorganism designed to produce 2-butanol.

There is a need, therefore, for environmentally responsible, cost-effective processes for the production of 2-butanol and 2-butanone. The present invention addresses this need through the discovery of recombinant microbial production hosts expressing 2-butanol and 2-butanone biosynthetic pathways.

SUMMARY OF THE INVENTION

The invention provides a recombinant microorganism having an engineered 2-butanol biosynthetic pathway. Also provided is a recombinant microorganism having an engineered 2-butanone biosynthetic pathway, which is the same as the 2-butanol biosynthetic pathway with omission of the last step. The engineered microorganisms may be used for the commercial production of 2-butanol or 2-butanone. Accordingly, the invention provides a recombinant microbial host cell comprising at least one DNA molecule encoding a polypeptide that catalyzes a substrate to product conversion selected from the group consisting of:
  i) pyruvate to alpha-acetolactate;
  ii) alpha-acetolactate to acetoin;
  iii) acetoin to 2,3-butanediol;
  iv) 2,3-butanediol to 2-butanone; and
  v) 2-butanone to 2-butanol;
wherein the at least one DNA molecule is heterologous to said microbial host cell and wherein said microbial host cell produces 2-butanol.

In another embodiment the invention provides a recombinant microbial host cell comprising at least one DNA molecule encoding a polypeptide that catalyzes a substrate to product conversion selected from the group consisting of:
  i) pyruvate to alpha-acetolactate;
  ii) alpha-acetolactate to acetoin;
  iii) acetoin to 2,3-butanediol; and
  iv) 2,3-butanediol to 2-butanone;
wherein the at least one DNA molecule is heterologous to said microbial host cell and wherein said microbial host cell produces 2-butanone.

In another embodiment the invention provides a method for the production of 2-butanol comprising:
  1) providing a recombinant microbial host cell comprising at least one DNA molecule encoding a polypeptide that catalyzes a substrate to product conversion selected from the group consisting of:
     i) pyruvate to alpha-acetolactate;
     ii) alpha-acetolactate to acetoin,
     iii) acetoin to 2,3-butanediol;
     iv) 2,3-butanediol to 2-butanone; and
     v) 2-butanone to 2-butanol;
     wherein the at least one DNA molecule is heterologous to said microbial host cell; and
  2) contacting the host cell of (1) with a fermentable carbon substrate in a fermentation medium under conditions whereby 2-butanol is produced.

Similarly the invention provides A method for the production of 2-butanone comprising:
  1) providing a recombinant microbial host cell comprising at least one DNA molecule encoding a polypeptide that catalyzes a substrate to product conversion selected from the group consisting of:
   i) pyruvate to alpha-acetolactate;
   ii) alpha-acetolactate to acetoin;
   iii) acetoin to 2,3-butanediol; and
   iv) 2,3-butanediol to 2-butanone;
wherein the at least one DNA molecule is heterologous to said microbial host cell; and 2) contacting the host cell of (1) with a fermentable carbon substrate in a fermentation medium under conditions whereby 2-butanone is produced.

In another embodiment the invention provides A 2-butanol or 2-butanone containing fermentation product medium produced by the method of the invention.

BRIEF DESCRIPTION OF THE FIGURES, TABLES AND SEQUENCE DESCRIPTIONS

The invention can be more fully understood from the following detailed description, figure, and the accompanying sequence descriptions, which form a part of this application.

FIG. 1 shows four different pathways for biosynthesis of 2-butanone and 2-butanol.

FIG. 2 shows a phylogenetic tree of full length large subunits of diol/glycerol dehydratases, with >95% identical sequences removed (except that all experimentally verified function sequences were retained), and a key listing the identity of each sequence in the tree. Sequences with experimentally determined function as diol or glycerol dehydratases are highlighted in dark or light grey, respectively.

Figure 1:
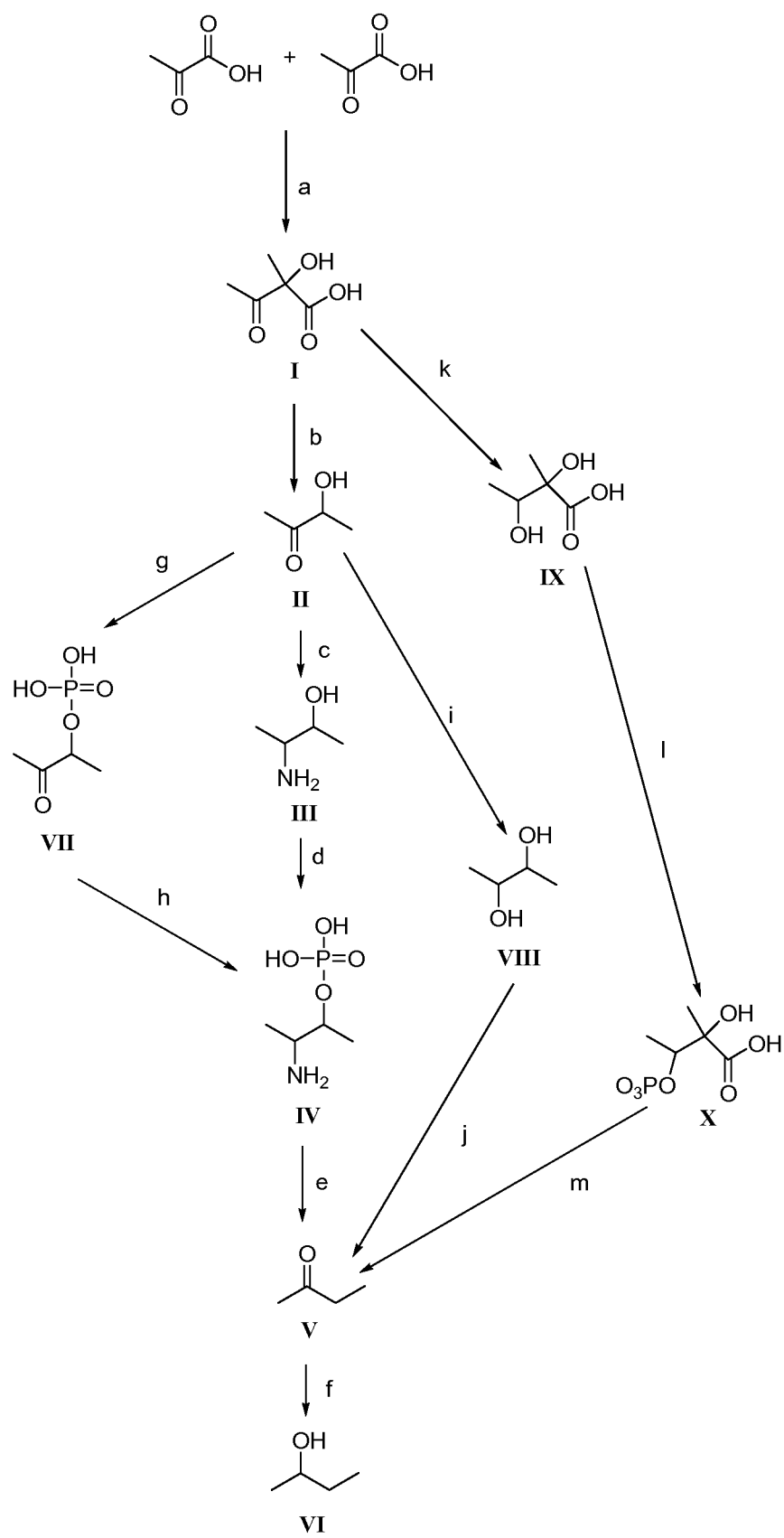

Table 12 is a table of the alpha large subunit Profile HMM for the diol/glycerol dehydratase enzyme. Table 12 is submitted herewith electronically and is incorporated herein by reference.

Table 13 is a table of the beta medium subunit Profile HMM for the diol/glycerol dehydratase enzyme. Table 13 is submitted herewith electronically and is incorporated herein by reference.

Table 14 is a table of the gamma small subunit Profile HMM for the diol/glycerol dehydratase enzyme. Table 14 is submitted herewith electronically and is incorporated herein by reference.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Nucleic Acid and Protein SEQ ID Numbers

| Description | SEQ ID Nucleic acid | SEQ ID Protein |
|---|---|---|
| budA, acetolactate decarboxylase from *Klebsiella pneumoniae* ATCC 25955 | 1 | 2 |
| alsD, acetolactate decarboxylase from *Bacillus subtilis* | 80 | 81 |
| budA, acetolactate decarboxylase from *Klebsiella terrigena* | 82 | 83 |
| budB, acetolactate synthase from *Klebsiella pneumoniae* ATCC 25955 | 3 | 4 |
| alsS, acetolactate synthase from *Bacillus subtilis* | 76 | 77 |
| budB, acetolactate synthase from *Klebsiella terrigena* | 78 | 79 |
| budC butanediol dehydrogenase from *Klebsiella pneumoniae* IAM1063 | 5 | 6 |
| butanediol dehydrogenase from *Bacillus cereus* | 84 | 85 |
| butanediol dehydrogenase from *Bacillus cereus* | 86 | 87 |
| butB, butanediol dehydrogenase from *Lactococcus lactis* | 88 | 89 |
| pddA, butanediol dehydratase alpha subunit from *Klebsiella oxytoca* ATCC 8724 | 7 | 8 |
| pddB, butanediol dehydratase beta subunit from *Klebsiella oxytoca* ATCC 8724 | 9 | 10 |
| pddC, butanediol dehydratase gamma subunit from *Klebsiella oxytoca* ATCC 8724 | 11 | 12 |
| pduC, B12 dependent diol dehydratase large subunit from *Salmonella typhimurium* | 92 | 93 |
| pduD, B12 dependent diol dehydratase medium subunit from *Salmonella typhimurium* | 94 | 95 |
| pduE, B12 dependent diol dehydratase small subunit from *Salmonella typhimurium* | 96 | 97 |
| pduC, B12 dependent diol dehydratase large subunit from *Lactobacillus collinoides* | 98 | 99 |
| pduD, B12 dependent diol dehydratase medium subunit from *Lactobacillus collinoides* | 100 | 101 |
| pduE, B12 dependent diol dehydratase small subunit from *Lactobacillus collinoides* | 102 | 103 |
| pddC, adenosylcobalamin-dependent diol dehydratase alpha subunit from *Klebsiella pneumoniae* | 104 | 105 |
| pddD, adenosylcobalamin-dependent diol dehydratase beta subunit from *Klebsiella pneumoniae* | 106 | 107 |
| pddD, adenosylcobalamin-dependent diol dehydratase gamma subunit from *Klebsiella pneumoniae* | 108 | 109 |
| ddrA, diol dehydratase reactivating factor large subunit from *Klebsiella oxytoca* | 110 | 111 |
| ddrB, diol dehydratase reactivating factor small subunit from *Klebsiella oxytoca* | 112 | 113 |
| pduG, diol dehydratase reactivating factor large subunit from *Salmonella typhimurium* | 114 | 115 |
| pduH, diol dehydratase reactivating factor small subunit from *Salmonella typhimurium* | 116 | 117 |
| pduG, diol dehydratase reactivating factor large subunit from *Lactobacillus collinoides* | 118 | 119 |
| pduH, diol dehydratase reactivating factor small subunit from *Lactobacillus collinoides* | 120 | 121 |
| sadH, butanol dehydrogenase from *Rhodococcus ruber* 219 | 13 | 14 |
| adhA, butanol dehydrogenase from *Pyrococcus furiosus* | 90 | 91 |
| chnA, cyclohexanol dehydrogenase from *Acinteobacter* sp. | 71 | 72 |
| yqhD, butanol dehydrogenase from *Escherichia coli* | 74 | 75 |
| amine:pyruvate transaminase from *Vibrio fluvialis* (an acetoin aminase) | 144 codon opt. | 122 |
| amino alcohol kinase from *Erwinia carotovora* subsp. *atroseptica* | 123 | 124 |
| amino alcohol O-phosphate lyase from *Erwinia carotovora* subsp. *atroseptica* | 125 | 126 |
| budC, acetoin reductase (butanediol dehydrogenase) from *Klebsiella terrigena* (now *Raoultella terrigena*) | 133 | 134 |

TABLE 1-continued

Summary of Nucleic Acid and Protein SEQ ID Numbers

| Description | SEQ ID Nucleic acid | SEQ ID Protein |
|---|---|---|
| glycerol dehydratase alpha subunit from *Klebsiella pneumoniae* | 145 | 146 |
| glycerol dehydratase beta subunit from *Klebsiella pneumoniae* | 147 | 148 |
| glycerol dehydratase gamma subunit from *Klebsiella pneumoniae* | 149 | 150 |
| glycerol dehydratase reactivase large subunit from *Klebsiella pneumoniae* | 151 | 152 |
| glycerol dehydratase reactivase small subunit from *Klebsiella pneumoniae* | 153 | 154 |

SEQ ID NOs:15-65 are the nucleotide sequences of oligonucleotide PCR, cloning, screening, and sequencing primers used in the Examples.

SEQ ID NO:66 is nucleotide sequence of the deleted region of the yqhD gene in *E. coli* strain MG1655 ΔyqhCD, described in Example 11.

SEQ ID NO:67 is the nucleotide sequence of a variant of the glucose isomerase promoter 1.6GI.

SEQ ID NO:68 is the nucleotide sequence of the 1.5GI promoter.

SEQ ID NO:69 is the nucleotide sequence of the diol dehydratase operon from *Klebsiella oxytoca*.

SEQ ID NO:70 is the nucleotide sequence of the diol dehydratase reactivating factor operon from *Klebsiella oxytoca*.

SEQ ID NO:73 is the nucleotide sequence of pDCQ2, which is described in Example 9.

SEQ ID NOs:127-132 are the nucleotide sequences of additional oligonucleotide PCR and cloning primers used in the Examples.

SEQ ID NO:155 is a codon optimized coding region for the amino alcohol kinase of *Erwinia carotovora* subsp. *atroseptica*.

SEQ ID NO:156 is a codon optimized coding region for the amino alcohol O-phosphate lyase of *Erwinia carotovora* subsp. *atroseptica*.

SEQ ID NOs:157-163 are the nucleotide sequences of additional oligonucleotide PCR and cloning primers used in the Examples.

SEQ ID NO:275 is the nucleotide sequence of an operon from *Erwinia carotovora* subsp. *atroseptica*.

TABLE 2

Additional glycerol and diol dehydratase large, medium and small subunits

| [a]Description | [b]subunit | protein SEQ ID |
|---|---|---|
| Corresponding subunits from same organism[c] | | |
| Glycerol dehydratase alpha subunit from *Clostridium pasteurianum* | L | 135 |
| Glycerol dehydratase beta subunit from *Clostridium pasteurianum* | M | 136 |
| Glycerol dehydratase gamma subunit from *Clostridium pasteurianum* | S | 137 |
| Glycerol dehydratase alpha subunit from *Escherichia blattae* | L | 138 |
| Glycerol dehydratase beta subunit from *Escherichia blattae* | M | 139 |
| Glycerol dehydratase gamma subunit from *Escherichia blattae* | S | 140 |
| Glycerol dehydratase alpha subunit from *Citrobacter freundii* | L | 141 |
| Glycerol dehydratase beta subunit from *Citrobacter freundii* | M | 142 |
| Glycerol dehydratase gamma subunit from *Citrobacter freundii* | S | 143 |
| Diol dehydratase alpha subunit from *Lactobacillus brevis* | L | 164 |
| Diol dehydratase beta subunit from *Lactobacillus brevis* | M | 165 |
| Diol dehydratase gamma subunit from *Lactobacillus brevis* | S | 166 |
| Diol dehydratase alpha subunit from *Salmonella enterica* subsp. *enterica* serovar *Choleraesuis* str. SC-B67 | L | 167 |
| Diol dehydratase beta subunit from *Salmonella enterica* subsp. *enterica* serovar *Choleraesuis* str. SC-B67 | M | 168 |
| Diol dehydratase gamma subunit from *Salmonella enterica* subsp. *enterica* serovar *Choleraesuis* str. SC-B67 | S | 169 |
| Propanediol dehydratase, large subunit from *Escherichia coli* E24377A | L | 170 |
| Diol/Glyderol Dehydratase medium subunit from *Escherichia coli* E24377A | M | 171 |
| Propanediol dehydratase, small subunit from *Escherichia coli* E24377A | S | 172 |
| diol dehydratase large subunit from *Shigella sonnei* Ss046 | L | 173 |
| diol dehydratase medium subunit from *Shigella sonnei* Ss046 | M | 174 |
| diol dehydratase small subunit from *Shigella sonnei* Ss046 | S | 175 |
| Propanediol dehydratase large subunit from *Yersinia bercovieri* ATCC 43970 | L | 176 |
| hypothetical protein YberA_01000484 from *Yersinia bercovieri* ATCC 43970 | M | 177 |
| Propanediol dehydratase small subunit from *Yersinia bercovieri* ATCC 43970 | S | 178 |
| Propanediol dehydratase large subunit from *Yersinia mollaretii* ATCC 43969 | L | 179 |

TABLE 2-continued

Additional glycerol and diol dehydratase large, medium and small subunits

| ªDescription | ᵇsubunit | protein SEQ ID |
|---|---|---|
| hypothetical protein YmolA_01001292 from *Yersinia mollaretii* ATCC 43969 | M | 180 |
| Propanediol dehydratase small subunit from *Yersinia mollaretii* ATCC 43969 | S | 181 |
| Diol dehydratase large subunit from *Yersinia enterocolitica* subsp. *enterocolitica* 8081 | L | 182 |
| Diol dehydratase medium subunit from *Yersinia enterocolitica* subsp. *enterocolitica* 8081 | M | 183 |
| diol dehydratase small subunit from *Yersinia enterocolitica* subsp. *enterocolitica* 8081 | S | 184 |
| Propanediol dehydratase large subunit from *Yersinia intermedia* ATCC 29909 | L | 185 |
| diol/glycerol dehydratase medium subunit from *Yersinia intermedia* ATCC 29909 | M | 186 |
| Propanediol dehydratase small subunit from *Yersinia intermedia* ATCC 29909 | S | 187 |
| glycerol dehydratase large subunit from *Listeria welshimeri* serovar 6b str. SLCC5334 | L | 188 |
| propanediol utilization dehydratase medium subunit from *Listeria welshimeri* serovar 6b str. SLCC5334 | M | 189 |
| propanediol utilization dehydratase small subunit from *Listeria welshimeri* serovar 6b str. SLCC5334 | S | 190 |
| hypothetical protein lin1117 from *Listeria innocua* Clip11262 | L | 191 |
| hypothetical protein lin1118 from *Listeria innocua* Clip11262 | M | 192 |
| hypothetical protein lin1119 from *Listeria innocua* Clip11262 | S | 193 |
| hypothetical protein lmo1153 from *Listeria monocytogenes* EGD-e | L | 194 |
| hypothetical protein lmo1154 from *Listeria monocytogenes* EGD-e | M | 195 |
| hypothetical protein lmo1155 from *Listeria monocytogenes* EGD-e | S | 196 |
| glycerol dehydratase large subunit from *Salmonella enterica* subsp. *enterica* serovar Typhi str. CT18 | L | 197 |
| diol dehydratase medium subunit from *Salmonella enterica* subsp. *enterica* serovar Typhi str. CT18 | M | 198 |
| diol dehydratase small subunit from *Salmonella enterica* subsp. *enterica* serovar Typhi str. CT18 | S | 199 |
| putative glycerol dehydratase large subunit [from *Escherichia coli* | L | 200 |
| putative diol dehydratase medium subunit from *Escherichia coli* | M | 201 |
| putative diol dehydratase small subunit from *Escherichia coli* | S | 202 |
| glycerol dehydratase large subunit from *Listeria monocytogenes* str. 4b F2365 | L | 203 |
| propanediol utilization: dehydratase, medium subunit from *Listeria monocytogenes* str. 4b F2365 | M | 204 |
| propanediol utilization: dehydratase, small subunit from *Listeria monocytogenes* str. 4b F2365 | S | 205 |
| Glycerol dehydratase large subunit pduC, putative from *Streptococcus sanguinis* SK36 | L | 206 |
| Propanediol utilization: dehydratase medium subunit, putative from *Streptococcus sanguinis* SK36 | M | 207 |
| B12-dependent diol dehydratase small subunit, putative from *Streptococcus sanguinis* SK36 | S | 208 |
| DhaB from *Escherichia blattae* | L | 209 |
| DhaC from *Escherichia blattae* | M | 210 |
| DhaE from *Escherichia blattae* | S | 211 |
| coenzyme B12-dependent glycerol dehydrogenase large subunit from *Clostridium perfringens* str. 13 | L | 212 |
| coenzyme B12-dependent glycerol dehydrogenase medium subunit from *Clostridium perfringens* str. 13 | M | 213 |
| coenzyme B12-dependent glycerol dehydrogenase small subunit from *Clostridium perfringens* str. 13 | S | 214 |
| Propanediol dehydratase large subunit from *Yersinia frederiksenii* ATCC 33641 | L | 215 |
| hypothetical protein YfreA_01000478 from *Yersinia frederiksenii* ATCC 33641] | M | 216 |
| Propanediol dehydratase, small subunit from *Yersinia frederiksenii* ATCC 33641 | S | 217 |
| Glycerol dehydratase from *Thermoanaerobacter ethanolicus* X514 | L | 218 |

TABLE 2-continued

Additional glycerol and diol dehydratase large, medium and small subunits

| <sup>a</sup>Description | <sup>b</sup>subunit | protein SEQ ID |
|---|---|---|
| dehydratase medium subunit from *Thermoanaerobacter ethanolicus* X514 | M | 219 |
| dehydratase small subunit from *Thermoanaerobacter ethanolicus* X514 | S | 220 |
| glycerol dehydratase large subunit GldC from *Lactobacillus hilgardii* | L | 221 |
| glycerol dehydratase medium subunit GldD from *Lactobacillus hilgardii* | M | 222 |
| glycerol dehydratase small subunit GldE from *Lactobacillus hilgardii* | S | 223 |
| Glycerol dehydratase from *Lactobacillus reuteri* JCM 1112 | L | 224 |
| similar to diol dehydratase gamma subunit from *Lactobacillus reuteri* JCM 1112 | M | 225 |
| Propanediol utilization: dehydratase small subunit from *Lactobacillus reuteri* JCM 1112 | S | 226 |
| glycerol dehydratase large subunit GldC from *Lactobacillus diolivorans* | L | 227 |
| glycerol dehydratase medium subunit GldD from *Lactobacillus diolivorans* | M | 228 |
| glycerol dehydratase small subunit GldE from *Lactobacillus diolivorans* | S | 229 |
| propanediol dehydratase large subunit from *Lactobacillus reuteri* | L | 230 |
| propanediol dehydratase medium subunit from *Lactobacillus reuteri* | M | 231 |
| propanediol dehydratase small subunit from *Lactobacillus reuteri* | S | 232 |
| glycerol dehydratase large subunit from *Mesorhizobium loti* MAFF303099 | L + M | 233 |
| glycerol dehydratase small subunit from *Mesorhizobium loti* MAFF303099 | S | 234 |
| Glycerol dehydratase from *Mycobacterium vanbaalenii* PYR-1 | L + M | 235 |
| propanediol utilization: dehydratase small subunit from *Mycobacterium vanbaalenii* PYR-1 | S | 236 |
| Glycerol dehydratase from *Mycobacterium* sp. MCS | L + M | 237 |
| dehydratase small subunit *Mycobacterium* sp. MCS | S | 238 |
| Dehydratase large subunit: Dehydratase medium subunit from *Mycobacterium flavescens* PYR-GCK | L + M | 239 |
| propanediol utilization: dehydratase, small subunit from *Mycobacterium flavescens* PYR-GCK | S | 240 |
| Glycerol dehydratase from *Mycobacterium* sp. JLS | L + M | 241 |
| dehydratase small subunit from *Mycobacterium* sp. JLS | S | 242 |
| glycerol dehydratase large subunit from *Mycobacterium smegmatis* str. MC2 155 | L | 243 |
| dehydratase medium subunit from *Mycobacterium smegmatis* str. MC2 155 | M | 244 |
| diol dehydrase gamma subunit from *Mycobacterium smegmatis* str. MC2 155 | S | 245 |
| Additional subunits | | |
| glycerol dehydratase large subunit from *Mycobacterium smegmatis* str. MC2 155 | L + M | 246 |
| glycerol dehydratase large subunit from *Mycobacterium smegmatis* str. MC2 155 | L + M | 247 |
| coenzyme B12-dependent glycerol dehydrogenase small subunit from *Mycobacterium smegmatis* str. MC2 155 | S | 248 |
| coenzyme B12-dependent glycerol dehydrogenase small subunit from *Mycobacterium smegmatis* str. MC2 155 | S | 249 |
| diol dehydratase medium subunit from *Salmonella enterica* subsp. *enterica serovar Paratyphi* A str. ATCC 9150 | M | 250 |
| diol dehydratase small subunit from *Salmonella enterica* subsp. *enterica serovar Paratyphi* A str. ATCC 9150 | S | 251 |
| glycerol dehydratase, beta subunit from *Clostridium perfringens* SM101 | M | 252 |
| glycerol dehydrase, gamma subunit from *Clostridium perfringens* SM101 | S | 253 |
| PduC from *Salmonella enterica* subsp. *enterica serovar Typhimurium* | L | 254 |
| glycerol dehydratase large subunit from *Listeria monocytogenes* str. 4b H7858 | L | 255 |
| DhaB from *Escherichia blattae* | L | 256 |
| DhaB from uncultured bacterium | L | 257 |
| DhaB from uncultured bacterium | L | 258 |

TABLE 2-continued

Additional glycerol and diol dehydratase large, medium and small subunits

| <sup>a</sup>Description | <sup>b</sup>subunit | protein SEQ ID |
|---|---|---|
| glycerol dehydratase large subunit GldC from *Lactobacillus collinoides* | L | 259 |
| PduD from uncultured bacterium | M | 260 |
| PduD from uncultured bacterium | M | 261 |
| DhaC from uncultured bacterium | M | 262 |
| DhaC from uncultured bacterium | M | 263 |
| DhaC from uncultured bacterium | M | 264 |
| coenzyme B12-dependent glycerol dehydratase, medium subunit from *Clostridium perfringens* ATCC 13124 | M | 265 |
| unknown | M | 266 |
| glycerol dehydratase beta subunit from *Escherichia blattae* | M | 267 |
| PduE from uncultured bacterium | S | 268 |
| PduE from uncultured bacterium | S | 269 |
| dehydratase, small subunit from *Listeria monocytogenes* str. 1/2a F6854 | S | 270 |
| DhaE from uncultured bacterium | S | 271 |
| DhaE from uncultured bacterium | S | 272 |
| DhaE from uncultured bacterium | S | 273 |
| dehydratase small subunit from *Listeria monocytogenes* FSL N1-017 | S | 274 |

<sup>a</sup>Description: from the Genbank annotation of the sequence and may not be correct including the glycerol or diol designation, or may not include subunit information.
<sup>b</sup>Subunit: identified by sequence homology to the large, medium, or small subunit.of the *Klebsiella oxytoca* enzyme.
<sup>c</sup>Subunits are listed together that are from the same organism and have annotations as the same enzyme, or have Genbank numbers close together indicating proximity in the genome.

DETAILED DESCRIPTION OF THE INVENTION

The present invention relates to methods for the production of 2-butanol using recombinant microorganisms. The present invention meets a number of commercial and industrial needs. Butanol is an important industrial commodity chemical with a variety of applications, where its potential as a fuel or fuel additive is particularly significant. Although only a four-carbon alcohol, butanol has an energy content similar to that of gasoline and can be blended with any fossil fuel. Butanol is favored as a fuel or fuel additive as it yields only $CO_2$ and little or no $SO_X$ or $NO_X$ when burned in the standard internal combustion engine. Additionally butanol is less corrosive than ethanol, the most preferred fuel additive to date.

In addition to its utility as a biofuel or fuel additive, butanol has the potential of impacting hydrogen distribution problems in the emerging fuel cell industry. Fuel cells today are plagued by safety concerns associated with hydrogen transport and distribution. Butanol can be easily reformed for its hydrogen content and can be distributed through existing gas stations in the purity required for either fuel cells or combustion engines in vehicles.

Finally the present invention produces 2-butanol from plant derived carbon sources, avoiding the negative environmental impact associated with standard petrochemical processes for butanol production.

The present invention also provides recombinant microorganisms and methods for producing 2-butanone, an intermediate in the 2-butanol biosynthetic pathways disclosed herein. 2-Butanone, also known as methyl ethyl ketone (MEK), is useful as a solvent in paints and other coatings. It is also used in the synthetic rubber industry and in the production of paraffin wax.

The following definitions and abbreviations are to be used for the interpretation of the claims and the specification.

The term "invention" or "present invention" as used herein is a non-limiting term and is not intended to refer to any single embodiment of the particular invention but encompasses all possible embodiments as described in the specification and the claims.

The term "2-butanol biosynthetic pathway" refers to the enzyme pathways to produce 2-butanol from pyruvate.

The term "2-butanone biosynthetic pathway" refers to the enzyme pathways to produce 2-butanone from pyruvate.

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* [GenBank Nos: AAA22222 NCBI (National Center for Biotechnology Information) amino acid sequence (SEQ ID NO:77), L04470 NCBI nucleotide sequence (SEQ ID NO:76)], *Klebsiella terrigena* [GenBank Nos: AAA25055 (SEQ ID NO:79), L04507 (SEQ ID NO:78)], and *Klebsiella pneumoniae* [GenBank Nos: AAA25079 (SEQ ID NO:4), M73842 (SEQ ID NO:3)].

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* [GenBank Nos: AAA22223 (SEQ ID NO:81), L04470 (SEQ ID NO:80)], *Klebsiella terrigena* [GenBank Nos: AAA25054 (SEQ ID NO:83), L04507 (SEQ ID NO:82)] and *Klebsiella pneumoniae* [GenBank Nos: AAU43774 (SEQ ID NO:2), AY722056 (SEQ ID NO:1)].

The term "acetoin aminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH-dependent acetoin aminase, also known as amino alcohol dehydrogenase, is described by Ito et al. (U.S. Pat. No. 6,432,688). An example of a pyridoxal-dependent acetoin aminase is the amine:pyruvate aminotransferase (also called amine:pyruvate transaminase) described by Shin and Kim (*J. Org. Chem.* 67:2848-2853 (2002)).

The term "butanol dehydrogenase" refers to a polypeptide (or polypeptides) having an enzyme activity that catalyzes the interconversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* [GenBank Nos: CAD36475 (SEQ ID NO:14), AJ491307 (SEQ ID NO:13)]. The NADP-dependent enzymes are known as EC 1.1.1.2 and are available, for example, from *Pyrococcus furiosus* [GenBank Nos: AAC25556 (SEQ ID NO:91), AF013169 (SEQ ID NO:90)]. Additionally, a butanol dehydrogenase is available from *Escherichia coli* [GenBank Nos:NP_417484 (SEQ ID NO:75), NC_000913 (SEQ ID NO:74)] and a cyclohexanol dehydrogenase is available from *Acinetobacter* sp. [GenBank Nos: AAG10026 (SEQ ID NO:72), AF282240 (SEQ ID NO:71)].

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Although there are no reports of enzymes catalyzing this reaction on acetoin, there are enzymes that catalyze the analogous reaction on the similar substrate dihydroxyacetone, for example, enzymes known as EC 2.7.1.29 (Garcia-Alles et al. (2004) *Biochemistry* 43:13037-13046).

The term "acetoin phosphate aminase" refers to a polypeptide (or polypeptides) having an enzyme activity that catalyzes the conversion of phosphoacetoin to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH- and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta et al. (2001) *Appl. Environ. Microbiol.* 67:4999-5009).

The term "aminobutanol phosphate phospho-lyase", also called "amino alcohol O-phosphate lyase", refers to a polypeptide (or polypeptides) having an enzyme activity that catalyzes the conversion of 3-amino-2-butanol O-phosphate to 2-butanone. Aminobutanol phosphate phospho-lyase may utilize the cofactor pyridoxal 5'-phosphate. There are no previous reports of enzymes catalyzing this reaction on aminobutanol phosphate, though there are reports of enzymes that catalyze the analogous reaction on the similar substrate 1-amino-2-propanol phosphate (Jones et al. (1973) *Biochem J.* 134:167-182). The present invention describes a newly identified aminobutanol phosphate phospho-lyase (SEQ ID NO: 126) from the organism *Erwinia carotovora*, with the activity demonstrated in Example 15 herein.

The term "aminobutanol kinase" refers to a polypeptide (or polypeptides) having an enzyme activity that catalyzes the conversion of 3-amino-2-butanol to 3-amino-2-butanol O-phosphate. Aminobutanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones et al., supra). The present invention describes, in Example 14, an amino alcohol kinase of *Erwinia carotovora* subsp. *atroseptica* (SEQ ID NO:124). The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085 (SEQ ID NO:6), D86412 (SEQ ID NO:5)). (R)-specific butanediol dehydrogenases are known as EC 1.1.1.4 and are available, for example, from *Bacillus cereus* [GenBank Nos. NP_830481 (SEQ ID NO:85), NC_004722 (SEQ ID NO:84); AAP07682 (SEQ ID NO:87), AE017000 (SEQ ID NO:86)], and *Lactococcus lactis* [GenBank Nos. AAK04995 (SEQ ID NO:89), AE006323 (SEQ ID NO:88)].

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (vitamin B12). Adenosyl cobalamin-dependent enzymes are known as EC 4.2.1.28 and are available, for example, from *Klebsiella oxytoca* [GenBank Nos: BAA08099 (alpha subunit) (SEQ ID NO:8), D45071 (SEQ ID NO:7); BAA08100 (beta subunit) (SEQ ID NO:10), D45071 (SEQ ID NO:9); and BBA08101 (gamma subunit) (SEQ ID NO:12), D45071 (SEQ ID NO:11) (Note all three subunits are required for activity)], and *Klebsiella pneumoniae* [GenBank Nos: AAC98384 (alpha subunit) (SEQ ID NO:105), AF102064 (SEQ ID NO:104); GenBank Nos: AAC98385 (beta subunit) (SEQ ID NO:107), AF102064 (SEQ ID NO:106), GenBank Nos: AAC98386 (gamma subunit) SEQ ID NO:109), AF102064 (SEQ ID NO:108)]. Other suitable diol dehydratases include, but are not limited to, B12-dependent diol dehydratases available from *Salmonella typhimurium* [GenBank Nos: AAB84102 (large subunit) (SEQ ID NO:93), AF026270 (SEQ ID NO:92); GenBank Nos: AAB84103 (medium subunit) (SEQ ID NO:95), AF026270 (SEQ ID NO:94); GenBank Nos: AAB84104 (small subunit) (SEQ ID NO:97), AF026270 (SEQ ID NO:96)]; and *Lactobacillus collinoides* [GenBank Nos: CAC82541 (large subunit) (SEQ ID NO:99), AJ297723 (SEQ ID NO:98); GenBank Nos: CAC82542 (medium subunit) (SEQ ID NO:101); AJ297723 (SEQ ID NO:100); GenBank Nos: CAD01091 (small subunit) (SEQ ID NO:103), AJ297723 (SEQ ID NO:102)]; and enzymes from *Lactobacillus brevis* (particularly strains CNRZ 734 and CNRZ 735, Speranza et al., supra), and nucleotide sequences that encode the corresponding enzymes. Methods of diol dehydratase gene isolation are well known in the art (e.g., U.S. Pat. No. 5,686,276). Additional diol dehydratases are listed in Table 2.

The term "glycerol dehydratase" refers to a polypeptide (or polypeptides) having an enzyme activity that catalyzes the conversion of glycerol to 3-hydroxypropionaldehyde. Adenosyl cobalamin-dependent glycerol dehydratases are known as EC 4.2.1.30. The glycerol dehydratases of EC 4.2.1.30 are similar to the diol dehydratases in sequence and in having three subunits. The glycerol dehydratases can also be used to convert 2,3-butanediol to 2-butanone. Some examples of glycerol dehydratases of EC 4.2.1.30 include those from *Klebsiella pneumoniae* (alpha subunit, SEQ ID NO:145, coding region and SEQ ID NO:146, protein; beta subunit, SEQ ID NO:147, coding region and SEQ ID NO:148, protein; and gamma subunit SEQ ID NO:149, coding region and SEQ ID NO:150, protein); from *Clostridium pasteurianum* [GenBank Nos: 3360389 (alpha subunit, SEQ ID NO:135), 3360390 (beta subunit, SEQ ID NO:136), and 3360391 (gamma subunit, SEQ ID NO:137)]; from *Escherichia blattae* [GenBank Nos: 60099613 (alpha subunit, SEQ ID NO:138), 57340191 (beta subunit, SEQ ID NO:139), and 57340192 (gamma subunit, SEQ ID NO:140)]; and from *Citrobacter freundii* [GenBank Nos: 1169287 (alpha subunit, SEQ ID NO:141), 1229154 (beta subunit, SEQ ID NO:142), and 1229155 (gamma subunit, SEQ ID NO:143)]. Note that all three subunits are required for activity. Additional glycerol dehydratases are listed in Table 2.

Diol and glycerol dehydratases may undergo suicide inactivation during catalysis. A reactivating factor protein, also referred to herein as "reactivase", can be used to reactivate the inactive enzymes (Mori et al., *J. Biol. Chem.* 272:32034 (1997)). Preferably, the reactivating factor is obtained from the same source as the diol or glycerol dehydratase used. For example, suitable diol dehydratase reactivating factors are available from *Klebsiella oxytoca* [GenBank Nos: AAC15871 (large subunit) (SEQ ID NO:111), AF017781 (SEQ ID NO:110); GenBank Nos: AAC15872 (small subunit) (SEQ ID NO:113), AF017781 (SEQ ID NO:112)]; *Salmonella typhimurium* [GenBank Nos: AAB84105 (large subunit) (SEQ ID NO:115), AF026270 (SEQ ID NO:114), GenBank Nos: AAD39008 (small subunit) (SEQ ID NO:117), AF026270 (SEQ ID NO:116)]; and *Lactobacillus collinoides* [GenBank Nos: CAD01092 (large subunit) (SEQ ID NO:119), AJ297723 (SEQ ID NO:118); GenBank Nos: CAD01093 (small subunit) (SEQ ID NO:121), AJ297723 (SEQ ID NO:120)]. Both the large and small subunits are required for activity. For example, suitable glycerol dehydratase reactivating factors are available from *Klebsiella pneumoniae* (large subunit, SEQ ID NO:151, coding region and SEQ ID NO:152, protein;, and small subunit, SEQ ID NO:153, coding region and SEQ ID NO:154, protein).

The term "a facultative anaerobe" refers to a microorganism that can grow in both aerobic and anaerobic environments.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, an "isolated nucleic acid fragment" or "isolated nucleic acid molecule" or "genetic construct" will be used interchangeably and will mean a polymer of RNA or DNA that is single-or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C. ) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

As used herein the term "coding sequence" or "CDS" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single-or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "fermentation product medium" refers to a medium in which fermentation has occurred such that product is present in the medium.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

The 2-Butanol and 2-Butanone Biosynthetic Pathways

Carbohydrate utilizing microorganisms employ the Embden-Meyerhof-Parnas (EMP) pathway, the Entner-Doudoroff pathway and the pentose phosphate cycle as the central, metabolic routes to provide energy and cellular precursors for growth and maintenance. These pathways have in common the intermediate glyceraldehyde-3-phosphate, and, ultimately, pyruvate is formed directly or in combination with the EMP pathway. The combined reactions of sugar conversion to pyruvate produce energy (e.g. adenosine-5'-triphosphate, ATP) and reducing equivalents (e.g. reduced nicotinamide adenine dinucleotide, NADH, and reduced nicotinamide adenine dinucleotide phosphate, NADPH). NADH and NADPH must be recycled to their oxidized forms (NAD$^+$ and NADP$^+$, respectively). In the presence of inorganic electron acceptors (e.g. $O_2$, $NO_3^-$ and $SO_4^{2-}$), the reducing equivalents may be used to augment the energy pool; alternatively, a reduced carbon by-product may be formed.

The invention enables the production of 2-butanone or 2-butanol from carbohydrate sources with recombinant microorganisms by providing a complete biosynthetic pathway from pyruvate to 2-butanone or 2-butanol. Three additional pathways are described. Although 2-butanol is not known to be the major product of any bacterial fermentation, there are a number of possible pathways for the production of 2-butanol via known biochemical reaction types. These pathways are shown in FIG. 1. The letters and roman numerals cited below correspond to the letters and roman numerals in FIG. 1, which are used to depict the conversion steps and products, respectively. As described below, 2-butanone is an intermediate in all of these 2-butanol biosynthetic pathways.

All of the pathways begin with the initial reaction of two pyruvate molecules to yield alpha-acetolactate(I), shown as the substrate to product conversion (a) in FIG. 1. From alpha-acetolactate, there are 4 possible pathways to 2-butanone(V), referred to herein as 2-butanone biosynthetic pathways:

Pathway 1) I--->II--->III--->IV--->V (substrate to product conversions b, c, d, e);
2) I--->II--->VII--->IV--->V (substrate to product conversions b, g, h, e)
3) I--->II--->VIII--->V (substrate to product conversions b, i, j): This is the pathway of the present invention.
4) I--->IX--->X--->V (substrate to product conversions k, l, m)

The 2-butanol biosynthetic pathways conclude with the conversion of 2-butanone (V) to 2-butanol(VI). A detailed discussion of the substrate to product conversions in each pathway is given below.

Pathway 1:

(a) pyruvate to alpha-acetolactate:

The initial step in pathway 1 is the conversion of two molecules of pyruvate to one molecule of alpha-acetolactate (compound I in FIG. 1) and one molecule of carbon dioxide catalyzed by a thiamin pyrophosphate-dependent enzyme. Enzymes catalyzing this substrate to product conversion (generally called either acetolactate synthase or acetohydroxy acid synthase; EC 2.2.1.6 [switched from 4.1.3.18 in 2002]) are well-known, and they participate in the biosynthetic pathway for the proteinogenic amino acids leucine and valine, as well as in the pathway for fermentative production of 2,3-butanediol and acetoin of a number of organisms.

The skilled person will appreciate that polypeptides having acetolactate synthase activity isolated from a variety of sources will be useful in the present invention independent of sequence homology. Some example of suitable acetolactate synthase enzymes are available from a number of sources, for example, *Bacillus subtilis* [GenBank Nos: AAA22222 NCBI (National Center for Biotechnology Information) amino acid sequence (SEQ ID NO:77), L04470 NCBI nucleotide sequence (SEQ ID NO:76)], *Klebsiella terrigena* [GenBank Nos: AAA25055 (SEQ ID NO:79), L04507 (SEQ ID NO:78)], and *Klebsiella pneumoniae* [GenBank Nos: AAA25079 (SEQ ID NO:4), M73842 (SEQ ID NO:3)]. Preferred acetolactate synthase enzymes are those that have at least 80%-85% identity to SEQ ID NO's 4, 77, and 79, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(b) alpha-acetolactate to acetoin:

Alpha-acetolactate (I) is converted to acetoin (II) by the action of an enzyme such as acetolactate decarboxylase (EC 4.1.1.5). Like acetolactate synthase, this enzyme is thiamin pyrophosphate-dependent and is also involved in the production of 2,3-butanediol and acetoin by a number of organisms. The enzymes from different sources vary quite widely in size (25-50 kilodaltons), oligomerization (dimer-hexamer), localization (intracellular of extracellular), and allosteric regulation (for example, activation by branched-chain amino acids). For the purpose of the present invention, an intracellular location is preferable to extracellular, but other variations are generally acceptable.

The skilled person will appreciate that polypeptides having acetolactate decarboxylase activity isolated from a variety of sources will be useful in the present invention independent of sequence homology. Some example of suitable acetolactate decarboxylase enzymes are available from a number of sources, for example, *Bacillus subtilis* [GenBank Nos: AAA22223 (SEQ ID NO:81), L04470 (SEQ ID NO:80)], *Klebsiella terrigena* [GenBank Nos: AAA25054 (SEQ ID NO:83), L04507 (SEQ ID NO:82)] and *Klebsiella pneumoniae* [GenBank Nos: AAU43774 (SEQ ID NO:2), AY722056 (SEQ ID NO:1)].

Preferred acetolactate decarboxylase enzymes are those that have at least 80%-85% identity to SEQ ID NO's 2, 81 and 83, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(c) acetoin to 3-amino-2-butanol:

There are two known types of biochemical reactions that could effect the substrate to product conversion of acetoin (II) to 3-amino-2-butanol (III), specifically, pyridoxal phosphate-dependent transamination utilizing an accessory amino donor and direct reductive amination with ammonia. In the latter case, the reducing equivalents are supplied in the form of a reduced nicotinamide cofactor (either NADH or NADPH). An example of an NADH-dependent enzyme catalyzing this reaction with acetoin as a substrate is reported by Ito et al. (U.S. Pat. No. 6,432,688). Any stereospecificity of this enzyme has not been assessed. An example of a pyridoxal phosphate-dependent transaminase that catalyzes the conversion of acetoin to 3-amino-2-butanol has been reported by Shin and Kim (supra). This enzyme was shown in Example 13 herein to convert both the (R) isomer of acetoin to the (2R,3S) isomer of 3-amino-2-butanol and the (S) isomer of acetoin to the (2S,3S) isomer of 3-amino-2-butanol. Either type of enzyme (i.e., transaminase or reductive aminase) is considered to be an acetoin aminase and may be utilized in the production of 2-butanol. Other enzymes in this group may have different stereospecificities.

The skilled person will appreciate that polypeptides having acetoin aminase activity isolated from a variety of sources will be useful in the present invention independent of sequence homology. One example of this activity has is described herein and is identified as SEQ ID NO:122. Accordingly preferred acetoin aminase enzymes are those that have at least 80%-85% identity to SEQ ID NO:122, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(d) 3-amino-2-butanol to 3-amino-2-butanol O-phosphate:

There are no enzymes known in the art that catalyze the substrate to product conversion of 3-amino-2-butanol (III) to 3-amino-2-butanol phosphate (IV). However, a few Pseudomonas and Erwinia species have been shown to express an ATP-dependent ethanolamine kinase (EC 2.7.1.82) which allows them to utilize ethanolamine or 1-amino-2-propanol as a nitrogen source (Jones et al. (1973) Biochem. J. 134:167-182). It is likely that this enzyme also has activity towards 3-amino-2-butanol or could be engineered to do so, thereby providing an aminobutanol kinase. The present invention describes in Example 14 a gene of Erwinia carotovora subsp. atroseptica (SEQ ID NO:123) that encodes a protein (SEQ ID NO:24) that is identified as an animo alcohol kinase. This enzyme may be used to convert 3-amino-2-butanol to 3-amino-2-butanol O-phosphate.

The skilled person will appreciate that polypeptides having aminobutanol kinase activity isolated from a variety of sources will be useful in the present invention independent of sequence homology. One example of this activity has is described herein and is identified as SEQ ID NO:124. Accordingly preferred aminobutanol kinase enzymes are those that have at least 80%-85% identity to SEQ ID NO:124, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(e) 3-amino-2-butanol phosphate to 2-butanone:

Although there are no enzymes reported to catalyze the substrate to product conversion of 3-amino-2-butanol phosphate (IV) to 2-butanone (V), the substrate is very similar to those utilized by the pyridoxal phosphate-dependent phosphoethanolamine phospho-lyase enzyme, which has been found in a small number of Pseudomonas and Erwinia species. These enzymes have activity towards phosphoethanolamine and both enantiomers of 2-phospho-1-aminopropane (Jones et al. (1973) Biochem. J. 134:167-182), and may also have activity towards 3-amino-2-butanol O-phosphate. The present invention describes a gene of Erwinia carotovora subsp. atroseptica (SEQ ID NO:125) that encodes a protein (SEQ ID NO:126) with homology to class III aminotransferases. Example 15 demonstrates that this enzyme is active on both aminopropanol phosphate and aminobutanol phosphate substrates. The newly identified and characterized enzyme was able to catalyze the conversion of a mixture of (R)-3-amino-(S)-2-butanol and (S)-3-amino-(R)-2-butanol O-phosphate, and a mixture of (R)-3-amino-(R)-2-butanol and (S)-3-amino-(S)-2-butanol O-phosphate to 2-butanone. The newly identified and characterized enzyme was also able to catalyze the conversion of both (R) and (S)-2-amino-1-propanol phosphate to propanone, with a preference for (S)-2-amino-1-propanol phosphate. The highest activity was observed with the proposed natural substrate DL-1-amino-2-propanol phosphate, which was converted to propionaldehyde.

The skilled person will appreciate that polypeptides having aminobutanol phosphate phospho-lyase activity isolated from a variety of sources will be useful in the present invention independent of sequence homology. One example of a suitable aminobutanol phosphate phospho-lyase enzyme is described herein as SEQ ID NO: 126. Accordingly preferred aminobutanol phosphate phospho-lyase enzymes are those that have at least 80%-85% identity to SEQ ID NO's 126, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(f) 2-butanone to 2-butanol:

The final step in all pathways to produce 2-butanol from pyruvic acid is the reduction of 2-butanone (V) to 2-butanol (VI). This substrate to product conversion is catalyzed by some members of the broad class of alcohol dehydrogenases (types utilizing either NADH or NADPH as a source of hydride, depending on the enzyme) that may be called butanol dehydrogenases. Enzymes of each type that catalyze the reduction of 2-butanone are well known, as described above in the definition for butanol dehydrogenase.

The skilled person will appreciate that polypeptides having butanol dehydrogenase activity isolated from a variety of sources will be useful in the present invention independent of sequence homology. Some example of suitable butanol dehydrogenase enzymes are available from a number of sources, for example, Rhodococcus ruber [GenBank Nos: CAD36475 (SEQ ID NO:14), AJ491307 (SEQ ID NO:13)]. The NADP-dependent enzymes are known as EC 1.1.1.2 and are available, for example, from Pyrococcus furiosus [GenBank Nos: AAC25556 (SEQ ID NO:91), AF013169 (SEQ ID NO:90)]. Additionally, a butanol dehydrogenase is available from Escherichia coli [GenBank Nos:NP_417484 (SEQ ID NO:75), NC_000913 (SEQ ID NO:74)] and a cyclohexanol dehydrogenase is available from Acinetobacter sp. [GenBank Nos: AAG10026 (SEQ ID NO:72), AF282240 (SEQ ID NO:71)]. Preferred butanol dehydrogenase enzymes are those that have at least 80%-85% identity to SEQ ID NO's 14, 91, 75, and 72, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

Pathway 2:

(a) pyruvate to alpha-acetolactate:

This substrate to product conversion is the same as described above for Pathway 1.

(b) alpha-acetolactate to acetoin:

This substrate to product conversion is the same as described above for Pathway 1.

(g) acetoin to phosphoacetoin:

Although enzymes that catalyze the substrate to product conversion of acetoin (II) to phosphoacetoin (VII) have not been described, the structure of the substrate acetoin is very similar to that of dihydroxyacetone, and therefore acetoin may be an acceptable substrate for dihydroxyacetone kinase (EC 2.7.1.29), an enzyme which catalyzes phosphorylation of dihydroxyacetone. Protein engineering techniques for the alteration of substrate specificity of enzymes are well known (Antikainen and Martin (2005) Bioorg. Med. Chem. 13:2701-2716) and may be used to generate an enzyme with the required specificity. In this conversion, the phosphate moiety may be supplied by any high energy biological phosphate donor, with the common substrates being phosphoenolpyruvate (as in the E. coli dihydroxyacetone kinase) and ATP (as in the Citrobacter freundii dihydroxyacetone kinase) (Garcia-Alles et al. (2004) Biochemistry 43:13037-13045).

(h) phosphoacetoin to 3-amino-2-butanol O-phosphate:

Although enzymes that catalyze the substrate to product conversion of phosphoacetoin (VII) to 3-amino-2-butanol O-phosphate (IV) have not been described, the structure of the substrate is very similar to that of dihydroxyacetone phosphate, a substrate for the proposed serinol phosphate aminotransferase encoded by the 5' portion of the rtxA gene in some species of *Bradyrhizobium* (Yasuta et al., supra). Thus a serinol phosphate aminotransferase may be functional in this step.

(e) 3-amino-2-butanol O-phosphate to 2-butanone:
This substrate to product conversion is the same as described above for Pathway 1.

(f) 2-butanone to 2-butanol:
This substrate to product conversion is the same as described above for Pathway 1.

Pathway 3:
(a) pyruvate to alpha-acetolactate:
This substrate to product conversion is the same as described above for Pathway 1.

(b) alpha-acetolactate to acetoin:
This substrate to product conversion is the same as described above for Pathway 1.

(i) acetoin to 2,3-butanediol:
The substrate to product conversion of acetoin (II) to 2,3-butanediol (VIII) may be catalyzed by a butanediol dehydrogenase that may either utilize NADH or NADPH as the source of reducing equivalents when carrying out reductions. Enzymes with activity towards acetoin participate in the pathway for production of 2,3-butanediol in organisms that produce that compound. The reported enzymes (e.g., BudC from *Klebsiella pneumoniae* (Ui et al. (2004) *Letters in Applied Microbiology* 39:533-537) generally utilize NADH. Either cofactor is acceptable for use in the production of 2-butanol by this pathway.

The skilled person will appreciate that polypeptides having butanediol dehydrogenase activity isolated from a variety of sources will be useful in the present invention independent of sequence homology. Some example of suitable butanediol dehydrogenase enzymes are available from a number of sources, for example, *Klebsiella pneumoniae* (GenBank Nos: BBA13085 (SEQ ID NO:6), D86412 (SEQ ID NO:5)). (R)-specific butanediol dehydrogenases are known as EC 1.1.1.4 and are available, for example, from *Bacillus cereus* [GenBank Nos. NP_830481 (SEQ ID NO:85), NC_004722 (SEQ ID NO:84); AAP07682 (SEQ ID NO:87), AE017000 (SEQ ID NO:86)], and *Lactococcus lactis* [GenBank Nos. AAK04995 (SEQ ID NO:89), AE006323 (SEQ ID NO:88)]. Preferred butanediol dehydrogenases enzymes are those that have at least 80%-85% identity to SEQ ID NO's 6, 85, 87, and 89, where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

(j) 2,3-butanediol to 2-butanone:
The substrate to product conversion of 2,3-butanediol (VIII) to 2-butanone (V) may be catalyzed by diol dehydratase enzymes (EC 4.2.1.28) and glycerol dehydratase enzymes (EC 4.2.1.30). The best characterized diol dehydratase is the coenzyme B12-dependent *Klebsiella oxytoca* enzyme, but similar enzymes are found in a number of enteric bacteria. The *K. oxytoca* enzyme has been shown to accept meso-2,3-butanediol as a substrate (Bachovchin et al. (1977) *Biochemistry* 16:1082-1092), producing the desired product 2-butanone. Example 17 demonstrates that the *Klebsiella pneumoniae* glycerol dehydratase was able to convert meso-2,3-butanediol to 2-butanone. The three subunit of the *Klebsiella pneumoniae* glycerol dehydratase (alpha: SEQ ID NO:145 (coding region) and 146 (protein); beta: SEQ ID NO: 147 (coding region) and 148 (protein); and gamma: SEQ ID NO: 149 (coding region) and 150 (protein)) were expressed in conjunction with the two subunits of the *Klebsiella pneumoniae* glycerol dehydratase reactivase (large subunit, SEQ ID NO: 151 (coding region) and 152 (protein); and small subunit, SEQ ID NO: 153 (coding region) and 154 (protein)) to provide activity.

There are also reports in the literature of a B12-independent diol dehydratase from *Clostridium glycolicum* (Hartmanis et al. (1986) *Arch. Biochem. Biophys.* 245:144-152). This enzyme has activity towards 2,3-butanediol, although this activity is less than 1% of the activity towards ethanediol, but the enzyme may be engineered to improve that activity. A better-characterized B12-independent dehydratase is the glycerol dehydratase from *Clostridium butyricum* (O'Brien et al. (2004) *Biochemistry* 43:4635-4645), which has high activity towards 1,2-propanediol as well as glycerol. This enzyme uses S-adenosylmethionine as a source of adenosyl radical. There are no reports of activity towards 2,3-butanediol, but such activity, if not already present, may possibly be engineered.

The skilled person will appreciate that polypeptides having butanediol dehydrogenase activity isolated from a variety of sources will be useful in the present invention independent of sequence homology. As noted above a variety of diol and glycerol dehydratases have been described in the literature and will be suitable for use in the present invention. Accordingly, in one aspect of the invention preferred diol and glycerol dehydratase enzymes are those that have at least 80%-85% identity to enzymes having the large, medium and small subunits, respectively of the sequences listed below:

a) SEQ ID NO:8, SEQ ID NO:10, and SEQ ID NO:12;
b) SEQ ID NO:93, SEQ ID NO:95, and SEQ ID NO:97;
c) SEQ ID NO:99, SEQ ID NO:101, and SEQ ID NO:103;
d) SEQ ID NO:105, SEQ ID NO:107, and SEQ ID NO:109;
e) SEQ ID NO:135, SEQ ID NO:136, and SEQ ID NO:137;
f) SEQ ID NO:138, SEQ ID NO:139, and SEQ ID NO:140;
g) SEQ ID NO:146, SEQ ID NO:148, and SEQ ID NO:150;
h) SEQ ID NO:141, SEQ ID NO:142, and SEQ ID NO:143; and
i) SEQ ID NO:164, SEQ ID NO:165, and SEQ ID NO:166.

where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

Similarly preferred diol and glycerol dehydratase enzymes are those that have at least 80%-85% identity to enzymes having the large, medium and small subunits, respectively of the sequences listed below:

Large subunit: SEQ ID NOs: 8, 99, 105, 135, 138, 141, 146, and 164;
Medium subunit: SEQ ID NOs: 10, 101, 107, 136, 139, 142, 148, and 165;
Small subunit: SEQ ID NOs:12, 103, 109, 137, 140, 143, 150, and 166;

where at least 85%-90% identity is more preferred and where at least 95% identity based on the Clustal W method of alignment using the default parameters of GAP PENALTY=10, GAP LENGTH PENALTY=0.1, and Gonnet 250 series of protein weight matrix, is most preferred.

Additional diol and glycerol dehydratase enzymes that may be used in the biosynthetic pathway 3 of the present invention were identified through a bioinformatics structure/function analysis that is described below and in Example 18.

(f) 2-butanone to 2-butanol:

This substrate to product conversion is the same as described above for Pathway 1.

Diol and Glycerol Dehydratases for Biosynthetic Pathway 3

Any enzyme that is a diol or glycerol dehydratase may be used in the present invention for the conversion of 2,3-butanediol to 2-butanone. A structure/function relationship for diol and glycerol dehydratases in the enzyme classes EC 4.2.1.28 and EC 4.2.1.30, respectively, was established herein in Example 18. The function is provided by experimental data and the structure is provided by bioinformatics analysis. Eight diol and glycerol dehydratase enzymes with activities that have been experimentally demonstrated were analyzed. In this group (listed in Table 10), the *Klebsiella oxytoca* diol dehydratase and the *Klebsiella pneumoniae* glycerol dehydratase enzymes were both shown to convert 2,3-butanediol to 2-butanone (Bachovchin et al. (1977) *Biochemistry* 16:1082-1092 and Example 17 herein, respectively), while the activities of the additional six enzymes were demonstrated using their natural substrates (references given in Table 10). This set of eight diol and glycerol dehydratases was analyzed using the hmmsearch algorithm of the HMMER software package (Janelia Farm Research Campus, Ashburn, Va.). The Z parameter of the hmmsearch algorithm was set to 1 billion. The output of the HMMER analysis using a set of protein sequences is a Profile Hidden Markov Model (Profile HMM). The theory behind Profile HMMs is described in Durbin et al., Biological sequence analysis: probabilistic models of proteins and nucleic acids, Cambridge University Press, 1998; Krogh et al., 1994; *J. Mol. Biol.* 235:1501-1531, incorporated herein by reference) that characterizes the set of proteins based on the probability of each amino acid occurring at each position in the alignment of the proteins of the set.

Since the eight diol and glycerol dehydratases (diol/glycerol dehydratases) with experimentally verified function that were used for the analysis each have three subunits (large or alpha, medium or beta, and small or gamma), a separate Profile HMM was prepared for each subunit. The large subunit Profile HMM (Table 12) was built using proteins with SEQ ID NOs: 8, 99, 105, 135, 138, 141, 146, and 164 that are described in Tables 1 and 2. The medium subunit Profile HMM (Table 13) was built using proteins with SEQ ID NOs: 10, 101, 107, 136, 139, 142, 148, and 165 that are described in Tables 1 and 2. The small subunit Profile HMM (Table 14) was built using proteins with SEQ ID NOs:12, 103, 109, 137, 140, 143, 150, and 166 that are described in Tables 1 and 2. References that provide the functional assay data are given in Table 10. The Profile HMM prepared for the large subunit gives a structural characterization for the functional large subunit of diol/glycerol dehydratases. Similarly the Profile HMMs for the medium and small subunits give structural characterizations for the functional medium and small subunits, respectively, of diol/glycerol dehydratases. Therefore any protein that has a significant match to either the large, medium, or small subunit Profile HMM is directly linked to the function of the subunit to which the profile was prepared. To be significant, the matching has an E-value of 0.01 or less, and further use of "match" is understood to be with this E-value criterion. Thus diol/glycerol dehydratase subunits that may be used in the present invention are proteins that match the Profile HMMs, that were prepared using the proteins with SEQ ID NOs listed above, with an E-value of 0.01 or less.

Proteins that are full length and have functional linkage to the large subunit of diol/glycerol dehydratases, through matching the large subunit Profile HMM, include but are not limited to, proteins with SEQ ID NOs; 93, 167, 170, 173, 176, 179, 182, 185, 188, 191, 194, 197, 200, 203, 206, 209, 212, 215, 218, 221, 224, 227, 130, 243, 254, 255, 256, 257, 258, and 259. Proteins that are full length and have functional linkage to the medium subunit of diol/glycerol dehydratases, through matching the medium subunit Profile HMM, include but are not limited to, proteins with SEQ ID NOs; 95, 168, 171, 174, 177, 180, 183, 186, 189, 192, 195, 198, 201, 204, 207, 210, 213, 216, 219, 222, 225, 228, 231, 244, 250, 252, 260, 261, 262, 263, 364, 265, 266, and 167. Proteins that are full length and have functional linkage to the small subunit of diol/glycerol dehydratases, through matching the small subunit Profile HMM, include but are not limited to, proteins with SEQ ID NOs;97, 169, 172, 175, 178, 181, 184, 187, 190, 193, 196, 199, 202, 205, 208, 211, 214, 217, 220, 223, 226, 229, 232, 234, 236, 238, 240, 242, 245, 248, 249, 251, 253, 268, 270, 271, 272, 273, and 274. In addition, proteins that are fused full length large and medium subunits that have functional linkage to the large and medium subunits of diol/glycerol dehydratases, through matching the large and medium subunit Profiles HMM, include but are not limited to, proteins with SEQ ID NOs; 233, 235, 237, 239, 241, 246, and 247.

Since the Profile HMMs described above provide a structure/function relationship for diol/glycerol dehydratases, newly identified proteins that match these profiles may also be used in the present invention. In addition, diol/glycerol dehydratase subunit protein sequences that may be used in the present invention include proteins with amino acid changes that have minimal effects on subunit function, which are substantially similar to the sequences of the SEQ ID NOs listed above. It is well known in the art that substitution of a chemically equivalent amino acid at a given site which does not effect the functional properties of the encoded protein is common. For the purposes of the present invention substitutions providing substantially similar proteins are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, substitutions of one amino acid for another in these groups can be expected to produce a functionally equivalent protein. In many cases, changes which result in alteration of the N-terminal and C-terminal portions of the protein would also not be expected to alter the activity of the protein.

Substantially similar proteins to those of SEQ IDs that match the Profile HMMs may be 90% or 95% identical in amino acid sequence to one of the matching proteins, and these may be used in the present invention.

One skilled in the art can readily identify a set of three subunits that may be used together to provide a functional diol/glycerol dehydratase. Particularly suitable is a combination of a large, medium and small subunit from the same strain of organism, whose coding regions are located near one another in the genome. These subunits would be most likely to form a natural diol or glycerol dehydratase. Many large, medium, and small subunits are grouped in this manner in Table 2. A combination of subunits from closely related strains or species is suitable for composing a diol dehydratase or a glycerol dehydratase. Any combination of subunits that catalyzes the conversion of 2,3-butanediol to 2-butanone may be used. Effective subunit combinations may readily be determined by one skilled in the art through amino acid sequence comparisons and/or functional assays.

Accordingly the invention provides diol and glycerol dehydratase enzymes having amino acid sequences comprising full length large, medium and small subunits that each give an E-value parameter of 0.01 or less when queried using a Profile Hidden Markov Model prepared using the large subunits of SEQ ID NOs: 8, 99, 105, 135, 138, 141, 146, and 164; the medium subunits of SEQ ID NOs: 10, 101, 107, 136, 139, 142, 148, and 165; and the small subunits of SEQ ID NOs:12, 103, 109, 137, 140, 143, 150, and 166; each query being carried out using the hmmsearch algorithm wherein the Z parameter is set to 1 billion.

Alternatively the invention provides diol and glycerol dehydratase enzymes having amino acid sequences identified by a process comprising a) generating a Profile Hidden Markov Model from the alignment of the amino acid sequences corresponding to the large, medium and small subunits of diol and glycerol dehydratase enzymes wherein;
  i) the large subunit comprises an amino acid sequence selected from the group consisting of SEQ ID NOs: 8, 99, 105, 135, 138, 141, 146, and 164;
  ii) the medium subunit comprises an amino acid sequence selected from the group consisting of SEQ ID NOs: 10, 101, 107, 136, 139, 142, 148, and 165; and
  iii) the small subunit comprises an amino acid sequence selected from the group consisting of SEQ ID NOs:12, 103, 109, 137, 140, 143, 150, and 166;
b) querying at least one public database of protein sequences containing sequences of diol and glycerol dehydratases with the Profile Hidden Markov Model of (a) using the hmmsearch algorithm wherein the Z parameter is set to 1 billion and the E-value parameter is set to 0.01, to identify a first data set of diol and glycerol dehydratase amino acid sequences; and
c) removing any partial sequences from the first data set of (b) to generate a second data set of diol and glycerol dehydratase amino acid sequences, wherein diol dehydratase and the glycerol dehydratase enzymes are identified.

With respect to large subunits of the diol and glycerol dehydratases of the invention the enzymes may comprise a large subunit comprising an amino acid sequence having at least 95% identity to an amino acid sequence selected from the group consisting of SEQ ID NOs: 8, 93, 99, 105, 135, 138, 141, 146, 164, 167, 170, 173, 176, 179, 182, 185, 188, 191, 194, 197, 200, 203, 206, 209, 212, 215, 218, 221, 224, 227, 130, 243, 254, 255, 256, 257, 258 and 259, based on the Clustal W method of alignment using the default parameters of GAP PENALTY=10, GAP LENGTH PENALTY=0.1, and Gonnet 250 series of protein weight matrix.

With respect to the medium subunits of the diol and glycerol dehydratases of the invention the enzymes may comprise a medium subunit comprising an amino acid sequence having at least 95% identity to an amino acid sequence selected from the group consisting of SEQ ID NOs: 10, 95, 101, 107, 136, 139, 142, 148, 165, 168, 171, 174, 177, 180, 183, 186, 189, 192, 195, 198, 201, 204, 207, 210, 213, 216, 219, 222, 225, 228, 231, 244, 250, 252, 260, 261, 262, 263, 364, 265, 266, and 167 based on the Clustal W method of alignment using the default parameters of GAP PENALTY=10, GAP LENGTH PENALTY=0.1, and Gonnet 250 series of protein weight matrix.

With respect to the small subunits of the diol and glycerol dehydratases of the invention the enzymes may comprise a medium subunit comprising a small subunit comprising an amino acid sequence having at least 95% identity to an amino acid sequence selected from the group consisting of SEQ ID NOs: 12, 97, 103, 109, 137, 140, 143, 150, 166, 169, 172, 175, 178, 181, 184, 187, 190, 193, 196, 199, 202, 205, 208, 211, 214, 217, 220, 223, 226, 229, 232, 234, 236, 238, 240, 242, 245, 248, 249, 251, 253, 268, 270, 271, 272, 273, and 274, based on the Clustal W method of alignment using the default parameters of GAP PENALTY=10, GAP LENGTH PENALTY=0.1, and Gonnet 250 series of protein weight matrix.

Alternatively the diol dehydratase or glycerol dehydratase may comprise fused large, medium and small subunits comprising an amino acid sequence having at least 95% identity to an amino acid sequence selected from the group consisting of SEQ ID NOs: 233, 235, 237, 239, 241, 246, and 247, based on the Clustal W method of alignment using the default parameters of GAP PENALTY=10, GAP LENGTH PENALTY=0.1, and Gonnet 250 series of protein weight matrix.

Alternatively the diol dehydratase or glycerol dehydratase enzymes may comprise a fused large, medium and small subunits and has at least 95% identity to an amino acid sequence comprising all three of the amino acid sequences encoding large, medium and small subunits, selected from the group consisting of:
  a) SEQ ID NO:8, SEQ ID NO:10, and SEQ ID NO:12;
  b) SEQ ID NO:93, SEQ ID NO:95, and SEQ ID NO:97;
  c) SEQ ID NO:99, SEQ ID NO:101, and SEQ ID NO:103;
  d) SEQ ID NO:105, SEQ ID NO:107, and SEQ ID NO:109;
  e) SEQ ID NO:135, SEQ ID NO:136, and SEQ ID NO:137;
  f) SEQ ID NO:138, SEQ ID NO:139, and SEQ ID NO:140;
  g) SEQ ID NO:146, SEQ ID NO:148, and SEQ ID NO:150;
  h) SEQ ID NO:141, SEQ ID NO:142, and SEQ ID NO:143; and
  i) SEQ ID NO:164, SEQ ID NO:165, and SEQ ID NO:166;
based on the Clustal W method of alignment using the default parameters of GAP PENALTY=10, GAP LENGTH PENALTY=0.1, and Gonnet 250 series of protein weight matrix.

Pathway 4:
  (a) pyruvate to alpha-acetolactate:
  This substrate to product conversion is the same as described above for Pathway 1.
  (k) alpha-acetolactate to 2,3-dihydroxy-2-methylbutanoic acid:
  The substrate to product conversion of acetolactate (I) to 2,3-dihydroxy-2-methylbutanoic acid (IX) is not known in the art. However, the product of this conversion has been reported as a component of fermentation broths (Ziadi et al. (1973) *Comptes Rendus des Seances de l'Academie des Sciences, Serie D: Sciences Naturelles* 276:965-8), but the mechanism of formation is unknown. The likely mechanism of formation is reduction of acetolactate with NADH or NADPH as the electron donor. To utilize this pathway for production of 2-butanol, an enzyme catalyzing this reaction needs to be identified or engineered. However, the precedent for enzymatic reduction of ketones to alcohols is well established.
  (l) 2,3-dihydroxy-2-methylbutanoic acid to 2-hydroxy-2-methyl-3-phosphobutanoic acid:
  There are no enzymes known that catalyze the substrate to product conversion of 2,3-dihydroxy-2-methylbutanoic acid (IX) to 2-hydroxy-2-methyl-3-phosphobutanoic acid (X). However, there are a large number of kinases in Nature that possess varying specificity. It is therefore likely that an enzyme could be isolated or engineered with this activity.
  (m) 2-hydroxy-2-methyl-3-phosphobutanoic acid to 2-butanone:
  There are no known enzymes that catalyze the substrate to product conversion of 2-hydroxy-2-methyl-3-phosphobutanoic acid (X) to 2-butanone (V). The combination of this reaction with the previous one is very similar to the multi-step reaction catalyzed by mevalonate-5-pyrophosphate (M5PP) decarboxylase, which consists of initial phosphorylation of M5PP to 3-phosphomevalonate-5-PP, followed by decarboxylation-dependent elimination of phosphate (Alvear et al. (1982) *Biochemistry* 21:4646-4650).

(f) 2-butanone to 2-butanol:

This substrate to product conversion is the same as described above for Pathway 1.

Thus, in providing multiple recombinant pathways from pyruvate to 2-butanol, there exists a number of choices to fulfill the individual conversion steps, and the person of skill in the art will be able to utilize publicly available sequences and sequences disclosed herein to construct the relevant pathways. A listing of a representative number of genes known in the art and useful in the construction of 2-butanol biosynthetic pathways is given above in Tables 1 and 2.

Microbial Hosts for 2-Butanol and 2-Butanone Production

Microbial hosts for 2-butanol or 2-butanone production may be selected from bacteria, cyanobacteria, filamentous fungi and yeasts. The microbial host used for 2-butanol or 2-butanone production should be tolerant to the product produced, so that the yield is not limited by toxicity of the product to the host. The selection of a microbial host for 2-butanol production is described in detail below. The same criteria apply to the selection of a host for 2-butanone production.

Microbes that are metabolically active at high titer levels of 2-butanol are not well known in the art. Although butanol-tolerant mutants have been isolated from solventogenic *Clostridia*, little information is available concerning the butanol tolerance of other potentially useful bacterial strains. Most of the studies on the comparison of alcohol tolerance in bacteria suggest that butanol is more toxic than ethanol (de Cavalho et al., *Microsc. Res. Tech.* 64:215-22 (2004) and Kabelitz et al., *FEMS Microbiol. Lett.* 220:223-227 (2003)). Tomas et al. (*J. Bacteriol.* 186:2006-2018 (2004)) report that the yield of 1-butanol during fermentation in *Clostridium acetobutylicum* may be limited by butanol toxicity. The primary effect of 1-butanol on *Clostridium acetobutylicum* is disruption of membrane functions (Hermann et al., *Appl. Environ. Microbiol.* 50:1238-1243 (1985)).

The microbial hosts selected for the production of 2-butanol should be tolerant to 2-butanol and should be able to convert carbohydrates to 2-butanol using the introduced biosynthetic pathway. The criteria for selection of suitable microbial hosts include the following: intrinsic tolerance to 2-butanol, high rate of carbohydrate utilization, availability of genetic tools for gene manipulation, and the ability to generate stable chromosomal alterations.

Suitable host strains with a tolerance for 2-butanol may be identified by screening based on the intrinsic tolerance of the strain. The intrinsic tolerance of microbes to 2-butanol may be measured by determining the concentration of 2-butanol that is responsible for 50% inhibition of the growth rate (IC50) when grown in a minimal medium. The IC50 values may be determined using methods known in the art. For example, the microbes of interest may be grown in the presence of various amounts of 2-butanol and the growth rate monitored by measuring the optical density at 600 nanometers. The doubling time may be calculated from the logarithmic part of the growth curve and used as a measure of the growth rate. The concentration of 2-butanol that produces 50% inhibition of growth may be determined from a graph of the percent inhibition of growth versus the 2-butanol concentration. Preferably, the host strain should have an IC50 for 2-butanol of greater than about 0.5%. More suitable is a host strain with an IC50 for 2-butanol that is greater than about 1.5%. Particularly suitable is a host strain with an IC50 for 2-butanol that is greater than about 2.5%.

The microbial host for 2-butanol production should also utilize glucose and/or other carbohydrates at a high rate. Most microbes are capable of utilizing carbohydrates. However, certain environmental microbes cannot efficiently use carbohydrates, and therefore would not be suitable hosts.

The ability to genetically modify the host is essential for the production of any recombinant microorganism. Modes of gene transfer technology that may be used include by electroporation, conjugation, transduction or natural transformation. A broad range of host conjugative plasmids and drug resistance markers are available. The cloning vectors used with an organism are tailored to the host organism based on the nature of antibiotic resistance markers that can function in that host.

The microbial host also may be manipulated in order to inactivate competing pathways for carbon flow by inactivating various genes. This requires the availability of either transposons or chromosomal integration vectors to direct inactivation. Additionally, production hosts that are amenable to chemical mutagenesis may undergo improvements in intrinsic 2-butanol tolerance through chemical mutagenesis and mutant screening.

Based on the criteria described above, suitable microbial hosts for the production of 2-butanol and 2-butanone include, but are not limited to, members of the genera *Clostridium, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Pediococcus pentosaceus, Pediococcus acidilactici, Bacillus subtilis* and *Saccharomyces cerevisiae*.

Construction of Production Host

Recombinant organisms containing the necessary genes that encode the enzymatic pathway for the conversion of a fermentable carbon substrate to 2-butanol or 2-butanone may be constructed using techniques well known in the art. In the present invention, genes encoding the enzymes of the 2-butanol biosynthetic Pathway 3: acetolactate synthase, acetolactate decarboxylase, butanediol dehydrogenase, butanediol dehydratase, and butanol dehydrogenase; or 2-butanone biosynthetic Pathway 3 omitting the butanol dehydrogenase, may be isolated from various sources, as described above.

Methods of obtaining desired genes from a bacterial genome are common and well known in the art of molecular biology. For example, if the sequence of the gene is known, primers may be designed and the desired sequence amplified using standard primer-directed amplification methods such as polymerase chain reaction (U.S. Pat. No. 4,683,202) to obtain amounts of DNA suitable for cloning into expression vectors. If a gene that is heterologous to a known sequence is to be isolated, suitable genomic libraries may be created by restriction endonuclease digestion and may be screened with probes having complementary sequence to the desired gene sequence. Once the sequence is isolated, the DNA may be amplified using standard primer-directed amplification methods such as polymerase chain reaction (U.S. Pat. No. 4,683,202) to obtain amounts of DNA suitable for cloning into expression vectors, which are then transformed into appropriate host cells.

In addition, given the amino acid sequence of a protein with desired enzymatic activity, the coding sequence may be ascertained by reverse translating the protein sequence. A DNA fragment containing the coding sequence may be prepared synthetically and cloned into an expression vector, then transformed into the desired host cell.

In preparing a synthetic DNA fragment containing a coding sequence, this sequence may be optimized for expression in the target host cell. Tools for codon optimization for expression in a heterologous host are readily available. Some tools for codon optimization are available based on the GC content of the host organism. The GC contents of some exemplary microbial hosts are given Table 3.

TABLE 3

GC Contents of Microbial Hosts

| Strain | % GC |
|---|---|
| B. licheniformis | 46 |
| B. subtilis | 42 |
| C. acetobutylicum | 37 |
| E. coli | 50 |
| P. putida | 61 |
| A. eutrophus | 61 |
| Paenibacillus macerans | 51 |
| Rhodococcus erythropolis | 62 |
| Brevibacillus | 50 |
| Paenibacillus polymyxa | 50 |

Once the relevant pathway genes are identified and isolated they may be transformed into suitable expression hosts by means well known in the art. Vectors useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector contains a selectable marker and sequences allowing autonomous replication or chromosomal integration in the desired host. In addition, suitable vectors comprise a promoter region which harbors transcriptional initiation controls and a transcriptional termination control region, between which a coding region DNA fragment may be inserted, to provide expression of the inserted coding region. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, promoters derived from the following genes: CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); as well as the lac, ara, tet, trp, $IP_L$, $IP_R$, T7, tac, and trc promoters (useful for expression in *Escherichia coli, Alcaligenes*, and *Pseudomonas*); the amy, apr, and npr promoters, and various phage promoters useful for expression in *Bacillus subtilis, Bacillus licheniformis*, and *Paenibacillus macerans*; nisA (useful for expression Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)).

Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors: pRK437, pRK442, and pRK442(H), are available. These derivatives have proven to be valuable tools for genetic manipulation in Gram-negative bacteria (Scott et al., *Plasmid* 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., *J. Bacteriol.* 174(17):5633-5638 (1992)). Additionally, in vitro transposomes are available from commercial sources such as EPICENTRE® to create random mutations in a variety of genomes.

The expression of a 2-butanol biosynthetic pathway in various preferred microbial hosts is described in more detail below. For the expression of a 2-butanone biosynthetic pathway, the same description applies, but the final substrate to product conversion of 2-butanone to 2-butanol is omitted.

Expression of a 2-Butanol or 2-Butanone Biosynthetic Pathway in *E. coli*

Vectors useful for the transformation of *E. coli* are common and commercially available from the companies listed above. For example, the genes of a 2-butanol biosynthetic pathway may be isolated from various sources, as described above, cloned onto a modified pUC19 vector and transformed into E. coli NM522, as described in Examples 6 and 7. Alternatively, the genes encoding a 2-butanol biosynthetic pathway may be divided into multiple operons, cloned onto expression vectors, and transformed into various *E. coli* strains, as described in Examples 9, 10, and 11. The 2-butanone biosynthesis pathway may be similarly expressed, omitting the butanol dehydrogenase.

Expression of a 2-Butanol or 2-Butanone Biosynthetic Pathway in *Rhodococcus erythropolis*

A series of *E. coli-Rhodococcus* shuttle vectors are available for expression in *R. erythropolis*, including, but not limited to pRhBR17 and pDA71 (Kostichka et al., *Appl. Microbiol. Biotechnol.* 62:61-68 (2003)). Additionally, a series of promoters are available for heterologous gene expression in *R. erythropolis* (see for example Nakashima et al., *Appl. Environ. Microbiol.* 70:5557-5568 (2004), and Tao et al., *Appl. Microbiol. Biotechnol.* 2005, DOI 10.1007/s00253-005-0064). Targeted gene disruptions in chromosomal genes of *R. erythropolis* may be created using the methods described by Tao et al., supra, and Brans et al. (*Appl. Envion. Microbiol.* 66: 2029-2036 (2000)).

The heterologous genes required for the production of 2-butanol, as described above, may be cloned initially in pDA71 or pRhBR71 and transformed into *E. coli*. The vectors may then be transformed into *R. erythropolis* by electroporation, as described by Kostichka et al., supra. The recombinants may be grown in synthetic medium containing glucose and the production of 2-butanol can be followed using fermentation methods known in the art. The 2-butanone biosynthesis pathway may be similarly expressed, omitting the butanol dehydrogenase.

Expression of a 2-Butanol or 2-Butanone Biosynthetic Pathway in *B. Subtilis*

Methods for gene expression and creation of mutations in *B. subtilis* are also well known in the art. For example, the genes of a 2-butanol biosynthetic pathway may be isolated from various sources, as described above, cloned into a modified *E. coli-Bacillus* shuttle vector and transformed into *Bacillus subtilis* BE1010, as described in Example 8, The desired genes may be cloned into a *Bacillus* expression vector and transformed into a strain to make a production host. Alternatively, the genes may be integrated into the *Bacillus* chromosome using conditional replicons or suicide vectors that are known to one skilled in the art. For example, the *Bacillus* Genetic Stock Center carries numerous integration vectors. The 2-butanone biosynthesis pathway may be similarly expressed, omitting the butanol dehydrogenase.

Expression of a 2-Butanol or 2-Butanone Biosynthetic Pathway in *B. licheniformis*

Most of the plasmids and shuttle vectors that replicate in *B. subtilis* may be used to transform *B. licheniformis* by either protoplast transformation or electroporation. The genes required for the production of 2-butanol may be cloned in plasmids pBE20 or pBE60 derivatives (Nagarajan et al., *Gene* 114:121-126 (1992)). Methods to transform *B. licheniformis* are known in the art (for example see Fleming et al. *Appl. Environ. Microbiol.*, 61(11):3775-3780 (1995)). The plasmids constructed for expression in *B. subtilis* may be transformed into *B. licheniformis* to produce a recombinant microbial host that produces 2-butanol. The 2-butanone biosynthesis pathway may be similarly expressed, omitting the butanol dehydrogenase.

Expression of a 2-Butanol or 2-Butanone Biosynthetic Pathway in *Paenibacillus macerans*

Plasmids may be constructed as described above for expression in *B. subtilis* and used to transform *Paenibacillus macerans* by protoplast transformation to produce a recombinant microbial host that produces 2-butanol. The 2-butanone biosynthesis pathway may be similarly expressed, omitting the butanol dehydrogenase.

Expression of a 2-Butanol or 2-Butanone biosynthetic Pathway in *Alcaligenes* (*Ralstonia*) *eutrophus*

Methods for gene expression and creation of mutations in *Alcaligenes eutrophus* are known in the art (see for example Taghavi et al., *Appl. Environ. Microbiol.*, 60(10):3585-3591 (1994)). The genes for a 2-butanol biosynthetic pathway may be cloned in any of the broad host range vectors described above, and electroporated into *Alcaligenes eutrophus* to generate recombinants that produce 2-butanol. The poly(hydroxybutyrate) pathway in *Alcaligenes* has been described in detail, a variety of genetic techniques to modify the *Alcaligenes eutrophus* genome are known, and those tools can be applied for engineering a 2-butanol biosynthetic pathway. The 2-butanone biosynthesis pathway may be similarly expressed, omitting the butanol dehydrogenase.

Expression of a 2-Butanol or 2-Butanone Biosynthetic Pathway in *Pseudomonas putida*

Methods for gene expression in *Pseudomonas putida* are known in the art (see for example Ben-Bassat et al., U.S. Pat. No. 6,586,229, which is incorporated herein by reference). The genes of a 2-butanol biosynthetic pathway may be inserted into pPCU18, and this ligated DNA may be electroporated into electrocompetent *Pseudomonas putida* DOT-T1 C5aAR1 cells to generate recombinants that produce 2-butanol. The 2-butanone biosynthesis pathway may be similarly expressed, omitting the butanol dehydrogenase.

Expression of a 2-Butanol or 2-Butanone Biosynthetic Pathway in *Lactobacillus plantarum*

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg et al., *Appl. Environ. Microbiol.* 71(3):1223-1230 (2005)).

The various genes for a 2-butanol biosynthetic pathway may be assembled into any suitable vector, such as those described above. The codons can be optimized for expression based on the codon index deduced from the genome sequences of *Lactobacillus plantarum* or *Lactobacillus arizonensis*. The plasmids may be introduced into the host cell using methods known in the art, such as electroporation (Cruz-Rodz et al. *Molecular Genetics and Genomics* 224:1252-154 (1990), Bringel, et al. *Appl. Microbiol. Biotechnol.* 33: 664-670 (1990), Alegre et al., *FEMS Microbiology letters* 241:73-77 (2004)), and conjugation (Shrago et al., *Appl. Environ. Microbiol.* 52:574-576 (1986)). The 2-butanol biosynthetic pathway genes can also be integrated into the chromosome of *Lactobacillus* using integration vectors (Hols et al., *Appl. Environ. Microbiol.* 60:1401-1403 (1990), Jang et al., *Micro. Lett.* 24:191-195 (2003)). The 2-butanone biosynthesis pathway may be similarly expressed, omitting the butanol dehydrogenase.

Expression of a 2-Butanol or 2-Butanone Biosynthetic Pathway in *Enterococcus faecium, Enterococcus gallinarium*, and *Enterococcus faecalis*

The *Enterococcus* genus belongs to the Lactobacillales family and many plasmids and vectors used in the transformation of *Lactobacillus, Bacillus subtilis*, and *Streptococcus*, described above, may be used for *Enterococcus*. Expression vectors for *E. faecalis* using the nisA gene from *Lactococcus* may also be used (Eichenbaum et al., *Appl. Environ. Microbiol.* 64:2763-2769 (1998). Additionally, vectors for gene replacement in the *E. faecium* chromosome may be used (Nallaapareddy et al., *Appl. Environ. Microbiol.* 72:334-345 (2006)).

The various genes for a 2-butanol biosynthetic pathway may be assembled into any suitable vector, such as those described above. The codons can be optimized for expression based on the codon index deduced from the genome sequences of *Enterococcus faecalis* or *Enterococcus faecium*. The plasmids may be introduced into the host cell using methods known in the art, such as electroporation, as described by Cruz-Rodz et al. (*Molecular Genetics and Genomics* 224:1252-154 (1990)) or conjugation, as described by Tanimoto et al. (*J. Bacteriol.* 184:5800-5804 (2002)) and Grohamann et al. (*Microbiol. Mol. Biol. Rev.* 67:277-301 (2003)). The 2-butanone biosynthesis pathway may be similarly expressed, omitting the butanol dehydrogenase.

Expression of a 2-Butanol or 2-Butanone Biosynthetic Pathway in *Pediococcus pentosaceus* and *Pediococcus acidilactici*.

The *Pediococcus* genus belongs to the Lactobacillales family and many plasmids and vectors used in the transformation of *Bacillus subtilis* and *Streptococcus*, described above, may be used for *Pediococcus*. A non-limiting example of a suitable vector is pHPS9 (Bukhtiyarova et al. *Appl. Environ. Microbiol.* 60:3405-3408 (1994)). Several plasmids from *Pediococcus* have also been reported (Alegre et al., *FEMS Microbiol. Lett.* 250:151-156 (2005); Shareck et al. *Crit. Rev Biotechnol.* 24:155-208 (2004)).

The genes for a 2-butanol biosynthetic pathway may be assembled into any suitable vector, such as those described above. The codons can be optimized for expression based on the codon index deduced from the genome sequence of *Pediococcus pentosaceus*. The plasmids may be introduced into the host cell using methods known in the art, such as electroporation (see for example, Osmanagaoglu et al., *J. Basic Microbiol.* 40:233-241 (2000); Alegre et al., *FEMS Microbiol. Lett.* 250:151-156 (2005)) and conjugation (Gonzalez and Kunka, *Appl. Environ. Microbiol.* 46:81-89 (1983)). The 2-butanol biosynthetic pathway genes can also be integrated into the chromosome of *Pediococcus* using integration vectors (Davidson et al. *Antonie van Leeuwenhoek* 70:161-183 (1996)). The 2-butanone biosynthesis pathway may be similarly expressed, omitting the butanol dehydrogenase.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose, as well as mixtures of any of these sugars. Sucrose may be obtained from feedstocks such as sugar cane, sugar beets, cassava, and sweet sorghum. Glucose and dextrose may be obtained through saccharification of starch based feedstocks including grains such as corn, wheat, rye, barley, and oats.

In addition, fermentable sugars may be obtained from cellulosic and lignocellulosic biomass through processes of pretreatment and saccharification, as described, for example, in co-owned and co-pending US patent application US20070031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

In addition to an appropriate carbon source, fermentation media must contain suitable minerals, salts, cofactors, buffers and other components, known to those skilled in the art, suitable for the growth of the cultures and promotion of an enzymatic pathway necessary for 2-butanol or 2-butanone production.

Culture Conditions

Typically cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 5.0 to pH 9.0, where pH 6.0 to pH 8.0 is preferred as the initial condition.

Fermentations may be performed under aerobic or anaerobic conditions, where anaerobic or microaerobic conditions are preferred.

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the turbidity of the culture medium, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 2-butanol or 2-butanone production.

Methods for 2-Butanol and 2-Butanone Isolation from the Fermentation Medium

The bioproduced 2-butanol may be isolated from the fermentation medium using methods known in the art for ABE fermentations (see for example, Durre, *Appl. Microbiol. Biotechnol.* 49:639-648 (1998), Groot et al., *Process Biochem.* 27:61-75 (1992), and references therein). For example, solids may be removed from the fermentation medium by centrifugation, filtration, decantation, or the like. Then, the 2-butanol may be isolated from the fermentation medium using methods such as distillation, azeotropic distillation, liquid-liquid extraction, adsorption, gas stripping, membrane evaporation, or pervaporation. These same methods may be adapted to isolate bioproduced 2-butanone from the fermentation medium.

EXAMPLES

The present invention is further defined in the following Examples. It should be understood that these Examples, while indicating a preferred embodiment of the invention, are given by way of illustration only. From the above discussion and these Examples, one skilled in the art can ascertain the essential characteristics of this invention, and, without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y., (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials described for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified. Bacterial strains are obtained from the American Type Culture Collection (ATCC, Manassas, Va.) unless otherwise noted.

TABLE 4

Oligonucleotide primers described in the following Examples are given in Table 4. All oligonucleotide primers were synthesized by Sigma-Genosys (Woodlands, TX).
Cloning and Screening Primers

| Gene | Primer Name | Sequence | SEQ ID NO: | Description |
|------|-------------|----------|------------|-------------|
| budB | B1 | CACCATGGACAAACAGTA TCCGGTACGCC | 15 | budB forward |
| budB | B2 | CGAAGGGCGATAGCTTTA CCAATCC | 16 | budB reverse |

TABLE 4-continued

Oligonucleotide primers described in the
following Examples are given in Table 4.
All oligonucleotide primers were synthesized
by Sigma-Genosys (Woodlands, TX).
Cloning and Screening Primers

| Gene | Primer Name | Sequence | SEQ ID NO: | Description |
|---|---|---|---|---|
| budA | B3 | CACCATGAATCATTCTGCTGAATGCACCTGCG | 17 | budA forward |
| budA | B4 | GATACTGTTTGTCCATGTGACC | 18 | budA reverse |
| budC | B5 | CACCATGAAAAAAGTCGCACTTGTTACC | 19 | budC forward |
| budC | B6 | TTAGTTAAATACCAT | 20 | budC reverse |
| pddA | B7 | CACCATGAGATCGAAAAGATTTG | 21 | pddABC forward |
| pddC | B8 | CTTAGAGAAGTTAATCGTCGCC | 22 | pddABC reverse |
| sadh | B9 | CACCATGAAAGCCCTCCAGTACACC | 23 | sadh forward |
| sadh | B10 | CGTCGTGTCATGCCCGGG | 24 | sadh reverse |
| budA | B11 | GATCGAATTCGTTTAAACTTAGTTTTCTACCGCACG | 25 | budABC forward |
| budC | B12 | GATCGCATGCAAGCTTTCATATAGTCGGAATTCC | 26 | budABC reverse |
| pddA | B13 | GATCGAATTCGTTTAAACAAAGGAGGTCTGATTCATGAGATCG | 27 | pddABC forward |
| pddC | B14 | GATCGGATTCTTAATCGTCGCC | 28 | pddABC reverse |
| sadh | B15 | GATCGGATCCAAAGGAGGTCGGGCGCATGAAAGCCC | 29 | sadh forward |
| sadh | B16 | GATCTCTAGAAAGCTTTCAGCCCGGGACGACC | 30 | sadh reverse |
| — | BenF | ACTTTCTTTCGCCTGTTTCAC | 31 | — |
| — | BenBPR | CATGAAGCTTGTTTAAACTCGGTGACCTTGAAAATAATGAAAACTTATATTGTTTTGAAAATAATGAAAACTTATATTG | 32 | — |
| budAB | BABC F | GAGCTCGAATTCAAAGGAGGAAGTGTATATGAATCATTC | 33 | budAB forward |
| budAB | BAB R | GGATCCTCTAGAATTAGTTAAATACCATCCCGCCG | 34 | budAB reverse |
| budC | BC Spe F | ACTAGTAAAGGAGGAAAGAGTATGAAGAAGGTCGCACT | 40 | budC forward |
| budC | BC Xba R | TCTAGAAAGCAGGGGCAAGCCATGTC | 41 | budC reverse |
| pddAB C-ddrAB | DDo For | AAGCTTAAAGGAGGCTGATTCATGAGATCGAAAAGATT | 44 | pddABC-ddrAB forward |

TABLE 4-continued

Oligonucleotide primers described in the
following Examples are given in Table 4.
All oligonucleotide primers were synthesized
by Sigma-Genosys (Woodlands, TX).
Cloning and Screening Primers

| Gene | Primer Name | Sequence | SEQ ID NO: | Description |
|---|---|---|---|---|
| pddABC-ddrAB | DDo Rev | TCTAGATTATTCATCCTGCTGTTCTCC | 45 | pddABC-ddrAB reverse |
| chnA | ChnA F | CATCAATTGACTACGTAGTCGTACGTGTAAGGAGGTTTGAAATGGAAAAAATTATG | 54 | chnA forward |
| chnA | ChnA R | CATGCTAGCCCCGGGTATCTTCTACTCATTTTTTATTTCG | 55 | chnA reverse |
| — | Top ter F1 | CTAGAAGTCAAAAGCCTCCGACCGGAGGCTTTTGA | 58 | forward |
| — | Top ter F2 | CTGCTCGAGTTGCTAGCAAGTTTAAACAAAAAAAAGCCCGCTCATTAGGCGGGCTGAGCT | 59 | forward |
| — | Bot ter R1 | CAGCCCGCCTAATGAGCGGGCTTTTTTTTGTTTAAAC | 60 | reverse |
| — | Bot ter R2 | TTGCTAGCAACTCGAGCAGTCAAAAGCCTCCGGTCGGAGGCTTTTGACTT | 61 | reverse |
| KA-AT | OT872 | CTCCGGAATTCATGTCTGACGGACGACTCACCGCA | 127 | Aminoalcohol kinase/lyase operon forward |
| KA-AT | OT873 | TTCCAATGCATTGGCTGCAGTTATCTCTGTGCACGAGTGCCGATGA | 128 | Aminoalcohol kinase/lyase operon reverse |
| KA | OT879 | AACAGCCAAGCTTGGCTGCAGTCATCGCGCATTCTCCGGG | 129 | Aminoalcohol kinase reverse |
| AT | OT880 | TCTCCGGAATTCATGACGTCTGAAATGACAGCGACAGAAG | 130 | Aminoalcohol lyase forward |
| pBAD.HisB | OT909 | GCTAACAGGAGGAAGAATTCATGGGGGGTTCTC | 131 | Adds EcoRI site to replace NcoI site |
| pBAD.HisB | OT910 | GAGAACCCCCCATGAATTCTTCCTCCTGTTAGC | 132 | Adds EcoRI site to replace NcoI site |
| BudAB | N84seqR3 | GGACCTGCTTCGCTTTATCG | 159 | reverse |
| APT | APTfor | GCGCGCCCGGGAAGAAGGAGCTCTTCACCATGAACAAACCACAGTCTTGG | 162 | APT forward |
| APT | APTrev | GCGCGCCCGGGTTCATGCCACCTCTGCG | 163 | APT reverse |

TABLE 5

Sequencing Primers

| Name | Sequence | Gene-specific | SEQ ID NO: |
|---|---|---|---|
| M13 Forward | GTAAAACGACGGCCAGT | — | 35 |
| M13 Reverse | AACAGCTATGACCATG | — | 36 |
| N83 SeqF2 | GCTGGATTACCAGCTCGACC | — | 37 |
| N83 SeqF3 | CGGACGCATTACCGGCAAAG | — | 38 |
| N84 Seq R2 | GCATCGAGATTATCGGGATG | — | 65 |
| N84 SeqR4 | CGAAGCGAGAGAAGTTATCC | — | 39 |
| Trc F | TTGACAATTAATCATCCGGC | all | 42 |
| Trc R | CTTCTCTCATCCGCCAAAAC | all | 43 |
| DDko seq F2 | GCATGGCGCGGATTTGACGAAC | pddABC-ddrAB | 46 |
| DDko seq F5 | CATTAAAGAGACCAAGTACGTG | pddABC-ddrAB | 47 |
| DDko seq F7 | ATATCCTGGTGGTGTCGTCGGCGT | pddABC-ddrAB | 48 |
| DDko seq F9 | TCTTTGTCACCAACGCCCTGCG | pddABC-ddrAB | 49 |
| DDko seq R1 | GCCCACCGCGCTCGCCGCCGCG | pddABC-ddrAB | 50 |
| DDko seq R3 | CCCCCAGGATGGCGGCTTCGGC | pddABC-ddrAB | 51 |
| DDko seq R7 | GGGCCGACGGCGATAATCACTT | pddABC-ddrAB | 52 |
| DDko seq R10 | TTCTTCGATCCACTCCTTAACG | pddABC-ddrAB | 53 |
| chnSeq F1 | CTCAACAGGGTGTAAGTGTAGT | chnA | 56 |
| chnSeq R1 | CGTTTTGATATAGCCAGGATGT | chnA | 57 |
| pCL1925 vec F | CGGTATCATCAACAGGCTTACC | all | 62 |
| pCL1925 vec R1 | AGGGTTTTCCCAGTCACGACGT | all | 63 |
| pCL1925 vec R2 | CGCAATAGTTGGCGAAGTAATC | all | 64 |
| APTseqRev | GCTAGAGATGATAGC | APT | 160 |
| APTseqFor | GGAAGAGACTATCCAGCG | APT | 161 |

Methods for Determining 2-Butanol and 2-Butanone Concentration in Culture Media

The concentration of 2-butanol and 2-butanone in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Under the conditions used, 2-butanone and 2-butanol had retention times of 39.5 and 44.3 min, respectively. Alternatively, gas chromatography (GC) methods are available. For example, a specific GC method utilized an HP-INNOWax column (30 m×0.53 mm id, 1 μm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention times of 2-butanone and 2-butanol were 3.61 and 5.03 min, respectively.

2-Butanone can also be detected by derivatization with 3-methyl-2-benzothiazolinone hydrazone (MBTH). An aqueous solution containing 2-butanone is mixed with an equal volume of an aqueous solution of 6 mg/mL MBTH in 375 mM glycine-HCl (pH 2.7) and incubated at 100° C. for 3 min. The resulting MBTH-derivatized samples are analyzed on a 25 cm×4.6 mm (id) Supelosil LC-18-D5 5 μm column (Supelco) using a mobile phase of 55% acetonitrile in water at a flow rate of 1 mL/min. The 2-butanone derivative appears as two peaks (cis and trans isomers) with retention times of approximately 12.3 and 13.3 min and absorbance maxima of 230 and 307 nm.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmol" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "wt %" means percent by weight, "HPLC" means high performance liquid chromatography, and "GC" means gas chromatography. The term "molar selectivity" is the number of moles of product produced per mole of sugar substrate consumed and is reported as a percent.

Example 1

Cloning and Expression of Acetolactate Synthase

The purpose of this Example was to clone and express in *E. coli* the budB gene that encodes the enzyme acetolactate synthase. The budB gene was amplified from *Klebsiella pneumoniae* strain ATCC 25955 genomic DNA using PCR.

The budB sequence which encodes acetolactate synthase was amplified from *Klebsiella pneumoniae* (ATCC 25955) genomic DNA by PCR using the primer pair B1 (SEQ ID NO:15) and B2 (SEQ ID NO:16). Other PCR amplification reagents (e.g. Kod HiFi DNA Polymerase (Novagen Inc., Madison, Wis.; catalog no. 71805-3)) were supplied in manufacturers' kits and used according to the manufacturer's protocol. *Klebsiella pneumoniae* genomic DNA was prepared using the Gentra Puregene Puregene kit (Gentra Systems, Inc., Minneapolis, Minn.; catalog number D-5000A). Amplification was carried out in a DNA Thermocycler GeneAmp 9700 (PE Applied Biosystems, Foster City, Calif.). The nucleotide sequence of the open reading frame (ORF) and the predicted amino acid sequence of the enzyme are given as SEQ ID NO:3 and SEQ ID NO:4, respectively.

For expression studies the Gateway cloning technology (Invitrogen Corp., Carlsbad, Calif.) was used. The entry vector pENTR/SD/D-TOPO allows directional cloning and provided a Shine-Dalgarno sequence for the gene of interest. The destination vector pDEST1 4 used a T7 promoter for expression of the gene with no tag. The forward primer incorporated four bases (CACC) immediately adjacent to the translational start codon to allow directional cloning of the budB acetolactate synthase coding region PCR product into pENTR/SD/D-TOPO (Invitrogen), generating the plasmid pENTRSDD-TOPObudB. The pENTR construct was transformed into *E. coli* Top10 (Invitrogen) cells and plated according to the manufacturer's recommendations. Transformants were grown overnight and plasmid DNA was prepared using the QIAprep Spin Miniprep kit (Qiagen, Valencia, Calif.; catalog no. 27106) according to the manufacturer's recommendations. To create an expression clone, the budB coding region from pENTRSDD-TOPObudB was transferred to the pDEST 14 vector by in vitro recombination using the LR Clonase mix (Invitrogen, Corp., Carlsbad, Calif.). The resulting vector, pDEST14budB, was transformed into BL-21-AI cells (Invitrogen Corp.). BL-21-AI cells carry a chromosomal copy of the T7 RNA polymerase under control of the arabinose-inducible araBAD promoter.

Transformants are inoculated into LB medium supplemented with 50 µg/mL of ampicillin and grown overnight. An aliquot of the overnight culture is used to inoculate 50 mL of LB medium supplemented with 50 µg/mL of ampicillin. The culture is incubated at 37° C. with shaking until the OD$_{600}$ reaches 0.6-0.8. The culture is split into two 25-mL portions and arabinose is added to one of the flasks to a final concentration of 0.2% w/v. The negative control flask is not induced with arabinose. The flasks are incubated for 4 h at 37° C. with shaking. Cells are harvested by centrifugation and the cell pellets are resuspended in 50 mM MOPS, pH 7.0 buffer. The cells are disrupted either by sonication or by passage through a French Pressure Cell. Each cell lysate is centrifuged yielding the supernatant and the pellet or the insoluble fraction. An aliquot of each fraction (whole cell lysate, from induced and control cells, is resuspended in SDS (MES) loading buffer (Invitrogen), heated to 85° C. for 10 min and subjected to SDS-PAGE analysis (NuPAGE 4-12% Bis-Tris Gel, catalog no. NP0322Box, Invitrogen). A protein of the expected molecular weight, as deduced from the nucleic acid sequence, is present in the induced culture but not in the uninduced control.

Acetolactate synthase activity in the cell free extracts is measured using the method described by Bauerle et al. (Bauerle et al. (1964) *Biochim. Biophys. Acta* 92:142-149). Protein concentration is measured by either the Bradford method or by the Bicinchoninic Kit (Sigma, catalog no. BCA-1; St. Louis, Mo.) using Bovine serum albumin (BSA) (Bio-Rad, Hercules, Calif.) as the standard.

Example 2

Cloning and Expression of Acetolactate Decarboxylase

The purpose of this Example was to clone and express in *E. coli* the budA gene that encodes the enzyme acetolactate decarboxylase. The budA gene was amplified from *Klebsiella pneumoniae* strain ATCC 25955 genomic DNA using PCR.

The budA sequence which encodes acetolactate decarboxylase, was cloned in the same manner as described for budB in Example 1, except that the primers used for PCR amplification were B3 (SEQ ID NO:17) and B4 (SEQ ID NO:18). The nucleotide sequence of the open reading frame (ORF) and the predicted amino acid sequence of the enzyme are given as SEQ ID NO:1 and SEQ ID NO:2, respectively. The resulting plasmid was named pENTRSDD-TOPObudA.

Acetolactate decarboxylase activity in the cell free extracts is measured using the method described by Bauerle et al., supra.

Example 3 (Prophetic)

Cloning and Expression of Butanediol Dehydrogenase

The purpose of this prophetic Example is to describe how to clone and express in *E. coli* the budC gene that encodes the enzyme butanediol dehydrogenase. The budC gene is amplified from *Klebsiella pneumoniae* strain IAM1063 genomic DNA using PCR.

The budC sequence encoding butanediol dehydrogenase is cloned and expressed in the same manner as described for budA in Example 1, except that the primers used for PCR amplification are B5 (SEQ ID NO:19) and B6 (SEQ ID NO:20) and the genomic template DNA is from *Klebsiella. pneumoniae* IAM1063 (which is obtained from the Institute of Applied Microbiology Culture Collection, Tokyo, Japan). *Klebsiella pneumoniae* IAM1063 genomic DNA is prepared using the Gentra Puregene Puregene kit (Gentra Systems, Inc., Minneapolis, Minn.; catalog number D-5000A). The nucleotide sequence of the open reading frame (ORF) and the predicted amino acid sequence of the enzyme are given as SEQ ID NO:5 and SEQ ID NO:6, respectively.

Butanediol dehydrogenase activity in the cell free extracts is measured spectrophotometrically by following NADH consumption at an absorbance of 340 nm.

Example 4 (Prophetic)

Cloning and Expression of Butanediol Dehydratase

The purpose of this prophetic Example is to describe how to clone and express in *E. Coli* the pddA, pddB and pddC genes that encode butanediol dehydratase. The pddA, pddB and pddC genes are amplified from *Klebsiella oxytoca* ATCC 8724 genomic DNA using PCR.

The pddA, pddB and pddC sequences which encode butanediol dehydratase are cloned and expressed in the same manner as described for budA in Example 1, except that the genomic template DNA is from *Klebsiella oxytoca* ATCC 8724, and the primers are B7 (SEQ ID NO:21) and B8 (SEQ ID NO:22). *Klebsiella oxytoca* genomic DNA is prepared using the Gentra Puregene Puregene kit (Gentra Systems, Inc., Minneapolis, Minn.; catalog number D-5000A). A single PCR product including all three open reading frames (ORFs) is cloned, so that all three coding regions are expressed as an operon from a single promoter on the expression plasmid. The nucleotide sequences of the open reading frames for the three subunits are given as SEQ ID NOs:7, 9, and 11, respectively, and the predicted amino acid sequences of the three enzyme subunits are given as SEQ ID NOs:8, 10, and 12, respectively.

Butanediol dehydratase activity in the cell free extracts is measured by derivatizing the ketone product with 2,4-dinitrophenylhydrazine (DNPH). Briefly, 100 µL of reaction mixture, cell extract containing approximately 0.0005 units of enzyme, 40 mM potassium phosphate buffer (pH 8.0), 2 µg of adenosylcobalamin, 5 µg of 2,3,-butanediol, and 1 µg of bovine serum albumin, is quenched by addition of an equal volume of 0.05 wt % DNPH in 1.0 N HCl. After 15 min at room temperature, the color is developed by addition of 100

μL of 4 N NaOH. The amount of product is determined from the absorbance of the final solution at 550 nm compared to a standard curve prepared with 2-butanone. All reactions are carried out at 37° C. under dim red light.

Example 5 (Prophetic)

Cloning and Expression of Butanol Dehydrogenase

The purpose of this prophetic Example is to describe how to clone and express in *E. coli* the sadh gene that encodes butanol dehydrogenase. The sadh gene is amplified from *Rhodococcus ruber* strain 219 genomic DNA using PCR.

The sadh sequence encoding butanol dehydrogenase is cloned and expressed in the same manner as described for budA in Example 1, except that the genomic template DNA is from *Rhodococcus ruber* strain 219 (Meens, Institut fuer Mikrobiologie, Universitaet Hannover, Hannover, Germany) and the primers are B9 (SEQ ID NO:23) and B10 (SEQ ID NO:24). *Rhodococcus ruber* genomic DNA is prepared using the Ultra Clean™ Microbial DNA Isolation Kit (MO BIO Laboratories Inc., Carlsbad, Calif.), according to the manufacturer's protocol. The nucleotide sequence of the open reading frame (ORF) and the predicted amino acid sequence of the enzyme are given as SEQ ID NO:13 and SEQ ID NO:14, respectively.

Butanol dehydrogenase activity in cell free extracts is measured by following the increase in absorbance at 340 nm resulting from the conversion of NAD to NADH when the enzyme is incubated with NAD and 2-butanol.

Example 6 (Prophetic)

Construction of a Transformation Vector for the Genes in a 2-Butanol Biosynthetic Pathway The purpose of this prophetic Example is to describe the preparation of a transformation vector for the genes in a 2-butanol biosynthetic pathway (i.e., Pathway 3 as described above). Like most organisms, *E. coli* converts glucose initially to pyruvic acid. The enzymes required to convert pyruvic acid to 2-butanol following Pathway 3, i.e., acetolactate synthase, acetolactate decarboxylase, butanediol dehydrogenase, butanediol dehydratase, and butanol dehydrogenase, are encoded by the budA, budB, budC, pddA, pddB, pddC and sadh genes. To simplify building the 2-butanol biosynthetic pathway in a recombinant organism, the genes encoding the 5 steps in the pathway are divided into two operons. The upper pathway comprises the first three steps catalyzed by acetolactate synthase, acetolactate decarboxylase, and butanediol dehydrogenase. The lower pathway comprises the last two steps catalyzed by butanediol dehydratase and butanol dehydrogenase.

The coding sequences are amplified by PCR with primers that incorporate restriction sites for later cloning, and the forward primers contain an optimized *E. coli* ribosome binding site (AAAGGAGG). PCR products are TOPO cloned into the pCR4Blunt-TOPO vector and transformed into Top10 cells (Invitrogen). Plasmid DNA is prepared from the TOPO clones, and the sequence of the cloned PCR fragment is verified. Restriction enzymes and T4 DNA ligase (New England Biolabs, Beverly, Mass.) are used according to manufacturer's recommendations. For cloning experiments, restriction fragments are gel-purified using QIAquick Gel Extraction kit (Qiagen).

After confirmation of the sequence, the coding regions are subcloned into a modified pUC19 vector as a cloning platform. The pUC19 vector is modified by a HindIII/SapI digest, followed by treatment with Klenow DNA polymerase to fill in the ends. The 2.4 kB vector fragment is gel-purified and religated creating pUC19dHS. Alternatively the pUC19 vector is modified by a SphI/SapI digest, followed by treatment with Klenow DNA polymerase to blunt the ends. The 2.4 kB vector fragment is gel-purified and religated creating pUC19dSS. The digests remove the lac promoter adjacent to the MCS (multiple cloning sites), preventing transcription of the operons from the vector.

Upper Pathway:

The budABC coding regions are amplified from *Klebsiella pneumoniae* genomic DNA by PCR using primer pair B11 and B12 (Table 4), given as SEQ ID NOs:25 and 26, respectively. The forward primer incorporates an EcoRI restriction site and a ribosome binding site (RBS). The reverse primer incorporates an SphI restriction site. The PCR product is cloned into pCR4 Blunt-TOPO creating pCR4 Blunt-TOPO-budABC.

To construct the upper pathway operon pCR4 Blunt-TOPO-budABC is digested with EcoRI and SphI releasing a 3.2 kbp budABC fragment. The pUC19dSS vector is also digested with EcoRI and SphI, releasing a 2.0 kbp vector fragment. The budABC fragment and the vector fragment are ligated together using T4 DNA ligase (New England Biolabs) to form pUC19dSS-budABC.

Lower Pathway:

The pddABC coding regions are amplified from *Klebsiella oxytoca* ATCC 8724 genomic DNA by PCR using primers B13 and B14 (Table 4), given as SEQ ID NOs:27 and 28, respectively, creating a 2.9 kbp product. The forward primer incorporates EcoRI and PmeI restriction sites and a RBS. The reverse primer incorporates the BamHI restriction site. The PCR product is cloned into pCRBlunt II-TOPO creating pCRBluntII-pdd.

The sadh gene is amplified from *Rhodococcus ruber* strain 219 genomic DNA by PCR using primers B15 and B16 (Table 4), given as SEQ ID NOs:29 and 30, respectively, creating a 1.0 kbp product. The forward primer incorporates a BamHI restriction site and a RBS. The reverse primer incorporates an XbaI restriction site. The PCR product is cloned into pCR-Blunt II-TOPO creating pCRBluntII-sadh.

To construct the lower pathway operon, a 2.9 kbp EcoRI and BamHI fragment from pCRBluntII-pdd, a 1.0 kbp BamHI and XbaI fragment from pCRBluntII-sadh, and the large fragment from an EcoRI and XbaI digest of pUC19dHS are ligated together. The three-way ligation creates pUC19dHS-pdd-sadh.

The pUC19dSS-budABC vector is digested with PmeI and HindIII, releasing a 3.2 kbp fragment that is cloned into pBenBP, an *E. coli-B. subtilis* shuttle vector. Plasmid pBenBP is created by modification of the pBE93 vector, which is described by Nagarajan (WO 93/2463, Example 4). To generate pBenBP, the *Bacillus amyloliquefaciens* neutral protease promoter (NPR) signal sequence and the phoA gene are removed from pBE93 with an NcoI/HindIII digest. The NPR promoter is PCR amplified from pBE93 by primers BenF and BenBPR, given by SEQ ID NOs:31 and 32, respectively. Primer BenBPR incorporates BstEII, PmeI and HindIII sites downstream of the promoter. The PCR product is digested with NcoI and HindIII, and the fragment is cloned into the corresponding sites in the vector pBE93 to create pBenBP. The upper operon fragment is subcloned into the PmeI and HindIII sites in pBenBP creating pBen-budABC.

The pUC19dHS-pdd-sadh vector is digested with PmeI and HindIII releasing a 3.9 kbp fragment that is cloned into the PmeI and HindIII sites of pBenBP, creating pBen-pdd-sadh.

Example 7 (Prophetic)

Expression of a 2-Butanol Biosynthetic Pathway in E. coli

The purpose of this prophetic Example is to describe how to express a 2-butanol biosynthetic pathway in E. coli.

The plasmids pBen-budABC and pBen-pdd-sadh, prepared as described in Example 6, are separately transformed into E. coli NM522 (ATCC No. 47000), and expression of the genes in each operon is monitored by SDS-PAGE analysis and enzyme assay. After confirmation of expression of all genes, pBen-budABC is digested with EcoRI and HindIII to release the NPR promoter-budABC fragment. The fragment is blunt ended using the Klenow fragment of DNA polymerase (New England Biolabs, catalog no. M0210S). The plasmid pBen-pdd-sadh is digested with EcoRI and similarly blunted to create a linearized, blunt-ended vector fragment. The vector and NPR-budABC fragments are ligated, creating p2BOH. This plasmid is transformed into E. coli NM522 to give E. coli NM522/p2BOH, and expression of the genes is monitored as previously described.

E. coli NM522/p2BOH is inoculated into a 250 mL shake flask containing 50 mL of medium and shaken at 250 rpm and 35° C. The medium is composed of: dextrose, 5 g/L; MOPS, 0.05 M; ammonium sulfate, 0.01 M; potassium phosphate, monobasic, 0.005 M; S10 metal mix, 1% (v/v); yeast extract, 0.1% (w/v); casamino acids, 0.1% (w/v); thiamine, 0.1 mg/L; proline, 0.05 mg/L; and biotin 0.002 mg/L, and is titrated to pH 7.0 with KOH. S10 metal mix contains: $MgCl_2$, 200 mM; $CaCl_2$, 70 mM; $MnCl_2$, 5 mM; $FeCl_3$, 0.1 mM; $ZnCl_2$, 0.1 mM; thiamine hydrochloride, 0.2 mM; $CuSO_4$, 172 µM; $COCl_2$, 253 µM; and $Na_2MoO_4$, 242 µM. After 18 h, 2-butanol is detected by HPLC or GC analysis using methods that are well known in the art, for example, as described in the General Methods section above.

Example 8 (Prophetic)

Expression of a 2-Butanol Biosynthetic Pathway in Bacillus subtilis

The purpose of this prophetic Example is to describe how to express a 2-butanol biosynthetic pathway in Bacillus subtilis.

The plasmids pBen-budABC and pBen-pdd-sadh, prepared as described in Example 6, are separately transformed into Bacillus subtilis BE1010 (J. Bacteriol. 173:2278-2282 (1991)) and expression of the genes in each operon is monitored as described in Example 7. The plasmid pBen-budABC is digested with EcoRI and HindIII to release the NPR promoter-budABC fragment. The fragment is blunt ended using the Klenow fragment of DNA polymerase (New England Biolabs, catalog no. M0210S). The plasmid pBen-pdd-sadh is digested with EcoRI and similarly blunted to create a linearized, blunt-ended vector fragment. The vector and NPR-budABC fragments are ligated, creating p2BOH. This plasmid is transformed into Bacillus subtilis BE1010 to give Bacillus subtilis BE1010/p2BOH, and expression of the genes is monitored as previously described.

Bacillus subtilis BE1010/p2BOH is inoculated into a 250 mL shake flask containing 50 mL of medium and shaken at 250 rpm and 35° C. for 18 h. The medium is composed of: dextrose, 5 g/L; MOPS, 0.05 M; glutamic acid, 0.02 M; ammonium sulfate, 0.01 M; potassium phosphate, monobasic buffer, 0.005 M; S10 metal mix (as described in Example 7), 1% (v/v); yeast extract, 0.1% (w/v); casamino acids, 0.1% (w/v); tryptophan, 50 mg/L; methionine, 50 mg/L; and lysine, 50 mg/L, and is titrated to pH 7.0 with KOH. After 18 h, 2-butanol is detected by HPLC or GC analysis using methods that are well known in the art, for example, as described in the General Methods section above.

Example 9

Construction of a Transformation Vector for the Genes in a 2-Butanol Biosynthetic Pathway The purpose of this Example was to prepare a recombinant E. coli host carrying the genes in a 2-butanol biosynthetic pathway (i.e., Pathway 3 as described above). Like most organisms, E. coli converts glucose initially to pyruvic acid. The enzymes required to convert pyruvic acid to 2-butanone in Pathway 3, i.e., acetolactate synthase, acetolactate decarboxylase, butanediol dehydrogenase, and butanediol dehydratase are encoded by the budA, budB, budC, pddA, pddB, and pddC genes. In the last step of the pathway, a butanol dehydrogenase converts 2-butanone to 2-butanol. Dehydrogenases that carry out this last step are promiscuous and may be found in many organisms. To simplify building the 2-butanol biosynthetic pathway in a recombinant organism, the genes encoding the 5 steps in the pathway were divided into multiple operons. The upper pathway operon comprised the first three steps catalyzed by acetolactate synthase, acetolactate decarboxylase, and butanediol dehydrogenase and were cloned onto an expression vector. The lower pathway comprised the last two steps catalyzed by butanediol dehydratase including the reactivating factor (Mori et al., J. Biol. Chem. 272:32034 (1997)) and a butanol dehydrogenase. The diol dehydratase can undergo suicide inactivation during catalysis. The reactivating factor protein encoded by ddrA and ddrB (GenBank AF017781, SEQ ID NO:70) reactivates the inactive enzyme. The ddrA and ddrB genes flank the diol dehydratase operon. The operons for the dehydratase/reactivating factor and the butanol dehydrogenase were either cloned onto another expression vector or the dehydratase/reactivating factor operon was cloned singly onto another expression vector and the last step was provided by an endogenous activity in the demonstration host.

Construction of Vector pTrc99a-budABC:

The budAB coding regions were amplified from K. pneumoniae ATCC 25955 genomic DNA by PCR using primer pair BABC F and BAB R, given as SEQ ID NOs:33 and 34, respectively (see Table 4), creating a 2.5 kbp product. The forward primer incorporated SacI and EcoRI restriction sites and a ribosome binding site (RBS). The reverse primer incorporated a SpeI restriction site. The PCR product was cloned into pCR4 Blunt-TOPO creating pCR4 Blunt-TOPO-budAB. Plasmid DNA was prepared from the TOPO clones and the sequence of the genes was verified with primers M13 Forward (SEQ ID NO:35), M13 Reverse (SEQ ID NO:36), N83 SeqF2 (SEQ ID NO:37), N83 SeqF3 (SEQ ID NO:38) and N84 SeqR4 (SEQ ID NO:39) (see Table 5).

The budC coding region was amplified from K. pneumoniae ATCC 25955 genomic DNA by PCR using primer pair BC Spe F and BC Xba R given as SEQ ID NOs:40 and 41, respectively, creating a 0.8 kbp product. The forward primer incorporated a SpeI restriction site, a RBS and modified the CDS by changing the second and third codons from AAA to AAG. The reverse primer incorporated an XbaI restriction site. The PCR product was cloned into pCR4 Blunt-TOPO creating pCR4 Blunt-TOPO-budC. Plasmid DNA was prepared from the TOPO clones and the sequence of the genes was verified with primers M13 Forward (SEQ ID NO:35) and M13 Reverse (SEQ ID NO:36).

To construct the budABC operon, pCR4 Blunt-TOPO-budC was digested with SnaBI and XbaI releasing a 1.0 kbp budC fragment. The vector pTrc99a (Amann et al., Gene 69(2):301-315 (1988)) was digested with SmaI and XbaI creating a 4.2 kbp linearized vector fragment. The vector and the budC fragment were ligated to create pTrc99a-budC and transformed into E. coli Top 10 cells (Invitrogen). Transformants were analyzed by PCR amplification with primers Trc F (SEQ ID NO:42) and Trc R (SEQ ID NO:43) for a 1.2 kbp product to confirm the presence of the budC insert. The budAB genes were subcloned from pCR4 Blunt-TOPO-budAB as a 2.5 kbp EcoRI/SpeI fragment. Vector pTrc99a-budC was digested with EcoRI and SpeI and the resulting 5.0 kbp vector fragment was gel-purified. The purified vector and budAB insert were ligated and transformed into E. coli Top 10 cells. Transformants were screened by PCR amplification with primers Trc F (SEQ ID NO:42) and N84 Seq R2 (SEQ ID NO:65) to confirm creation of pTrc99a-budABC. In this plasmid, the bud A, B, and C coding regions are adjacent to each other, in this order, and between the Trc promoter and the rrnB termination sequence.

Results:

Three independent isolates of E. coli Top 10/pTrc99a-budABC were examined for the production of butanediol, using E. coli Top 10/pCL1925-Kodd-ddr (described below) as a negative control. The strains were grown in LB medium containing 100 µg/mL carbenicillin. The resulting cells were used to inoculate shake flasks (approximately 175 mL total volume) containing 125 mL of TM3a/glucose medium with 100 µg/mL carbenicillin. In addition, the flasks inoculated with strains carrying pTrc99a-budABC contained 0.4 mM isopropyl β-D-1-thiogalactopyranoside (IPTG). TM3a/glucose medium contains (per liter): 10 g glucose, 13.6 g $KH_2PO_4$, 2.0 g citric acid monohydrate, 3.0 g $(NH_4)_2SO_4$, 2.0 g $MgSO_4.7H_2O$, 0.2 g $CaCl_2.2H_2O$, 0.33 g ferric ammonium citrate, 1.0 mg thiamine.HCl, 0.50 g yeast extract, and 10 mL trace elements solution, adjusted to pH 6.8 with $NH_4OH$. The solution of trace elements contained: citric acid.$H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L). The flasks, capped with vented caps, were inoculated at a starting $OD_{600}$ of approximately 0.03 units and incubated at 34° C. with shaking at 300 rpm.

Approximately 23 h after induction, an aliquot of the broth was analyzed by HPLC (Shodex Sugar SH1011 column) and GC (HP-INNOWax), using the same methods described in the General Methods section for 2-butanol and 2-butanone. The results of the analysis are given in Table 6. The three E. coli clones converted glucose to acetoin and meso-2,3-butanediol, the desired intermediates of the pathway, with a molar selectivity of 14%. This selectivity was approximately 35-fold higher than that observed with the E. coli control strain lacking budABC.

TABLE 6

Production of Acetoin and meso-2,3-butanediol by E. coli Top 10/pTrc99a-budABC

| Strain | $OD_{600}$ | Acetoin, mM | Meso-2,3-Butanediol, mM | Molar Selectivity[a], % |
|---|---|---|---|---|
| Negative control | 1.4 | 0.07 | 0.03 | 0.4 |
| Isolate #1 | 1.5 | 0.64 | 1.3 | 14 |

TABLE 6-continued

Production of Acetoin and meso-2,3-butanediol by E. coli Top 10/pTrc99a-budABC

| Strain | $OD_{600}$ | Acetoin, mM | Meso-2,3-Butanediol, mM | Molar Selectivity[a], % |
|---|---|---|---|---|
| Isolate #2 | 1.4 | 0.70 | 1.2 | 14 |
| Isolate #3 | 1.4 | 0.74 | 1.3 | 15 |

[a]Molar selectivity is (acetoin + meso-2,3-butanediol)/(glucose consumed).

Construction of vector PCL925-KoDD-ddr:

The diol dehydratase (GenBank D45071, SEQ ID NO:69) and reactivating factor (GenBank AF017781, SEQ ID NO:70) operons were PCR amplified from Klebsiella oxytoca ATCC 8724 as a single unit with primers DDo For (SEQ ID NO: 44) and DDo Rev (SEQ ID NO:45). The forward primer incorporated an optimized E. coli RBS and a HindIII restriction site. The reverse primer included an XbaI restriction site. The 5318 bp PCR product was cloned into pCR4Blunt-TOPO and clones of the resulting pCR4Blunt-TOPO-Kodd-ddr were sequenced with primers M13 Forward (SEQ ID NO:35), M13 Reverse (SEQ ID NO:36), DDko seq F2 (SEQ ID NO:46), DDko seq F5 (SEQ ID NO:47), DDko seq F7 (SEQ ID NO:48), DDko seq F9 (SEQ ID NO:49), DDko seq R1 (SEQ ID NO:50), DDko seq R3 (SEQ ID NO:51), DDko seq R7 (SEQ ID NO:52), and DDko seq R10 (SEQ ID NO:53). A clone having the insert with the expected sequence was identified.

For expression, the diol dehydratase/reactivating factor genes were subcloned into pCL1925 (U.S. Pat. No. 7, 074, 608), a low copy plasmid carrying the glucose isomerase promoter from Streptomyces. pCR4Blunt-TOPO-Kodd-ddr was digested with HindIII and XbaI and the resulting 5.3 kbp Kodd-ddr fragment was gel-purified. Vector pCL1925 was digested with HindIII and XbaI and the resulting 4539 bp vector fragment was gel purified. The vector and Kodd-ddr fragment were ligated and transformed into E. coli Top10. Transformants were screened by PCR with primers DDko Seq F7 (SEQ ID NO:48) and DDko Seq R7 (SEQ ID NO: 52). Amplification of the plasmid (pCL1925-Kodd-ddr) carrying the insert resulted in a product of approximately 797 bp.

Activity of diol dehydratase towards meso-2,3-butanediol was measured by incubating cell extract (total protein ~0.8 mg/mL) with 10 mM butanediol and 12 mM coenzyme $B_{12}$ in 80 mM HEPES (pH 8.2) for 17 h at room temperature. Formation of the expected product, 2-butanone, was determined by HPLC as described in the General Methods.

Construction of Vector pCL1925-KoDD-ddr::T5 chnA ter:

To provide a heterologous alcohol dehydrogenase activity, the chnA gene encoding cyclohexanol dehydrogenase from Acinetobacter sp. (Cheng et al., J. Bacteriol. 182:4744-4751 (2000)) was cloned into the pCL1925 vector with the diol dehydratase operon, pCL1925-Kodd-ddr. The chnA gene, given as SEQ ID NO:71 (Genbank No: AF282240, SEQ ID NO:73) was amplified from pDCQ2, a cosmid carrying the cyclohexanol gene cluster from Acinetobacter, with primers ChnA F (SEQ ID NO:54) and ChnA R (SEQ ID NO:55). The resulting 828 bp PCR product was cloned into pCR4Blunt-TOPO to create pCR4Blunt-TOPO-chnA and transformants were screened by colony PCR with primers M13 Forward (SEQ ID NO:35) and M13 Reverse (SEQ ID NO:36). Correct clones produced a PCR product of about 1 kbp and were sequenced with primers M13 Forward (SEQ ID NO:35) and M13 Reverse (SEQ ID NO:36).

After sequencing pCR4Blunt-TOPO-chnA to confirm the correct sequence, the chnA gene was subcloned from the plasmid as an 813 bp MfeI/SmaI fragment. The expression vector pQE30 (Qiagen) was digested with MfeI and SmaI and the resulting 3350 bp vector fragment was gel-purified. The chnA fragment and the purified vector were ligated and transformed into E. coli Top10 cells. Transformants were colony PCR screened with primers chnSeq F1 (SEQ ID NO:56) and chnseq R1 (SEQ ID NO:57) for a 494 bp PCR product. This cloning placed the chnA gene under the control of the T5 promoter in the plasmid, pQE30-chnA.

To prepare the pCL1925 vector to carry two operons, terminators were added to the vector. A tonB terminator-mcs-trpA terminator fragment was prepared by oligonucleotide annealing with primers Top ter F1 (SEQ ID NO:58), Top ter F2 (SEQ ID NO:59), Bot ter R1 (SEQ ID NO:60) and Bot ter R2 (SEQ ID NO:61). The annealed DNA was gel-purified on a 6% PAGE gel (Embi-tec, San Diego, Calif.). Vector pCL1925 was digested with SacI and XbaI and gel-purified. The annealed DNA and vector fragment were ligated to create pCL1925-ter. Transformants were screened by colony PCR amplification with primers pCL1925 vec F (SEQ ID NO:62) and pCL1925 vec R1(SEQ ID NO:63) for the presence of a PCR product of approximately 400 bp. Positive clones from the PCR screen were sequenced with the same primers.

Vector pCL1925-ter was digested with XhoI and PmeI and the resulting 4622 bp fragment was gel-purified. pQE30-chnA was digested with NcoI and the DNA was treated with Klenow DNA polymerase to blunt the ends. pQE30-chnA was then digested with XhoI and the resulting 1.2 kbp T5 promoter-chnA fragment was gel-purified. The pCL1925-ter vector and the chnA operon fragment were ligated together to give pCL1925-ter-T5chnA and transformed into E. coli Top10. Transformants were screened by colony PCR amplification with primers pCL1925 vec F (SEQ ID NO:64) and chnseq R1 (SEQ ID NO:59) for a product of approximately 1 kbp.

To finish building the pathway vector, the pCL1925-KoDD-ddr plasmid was digested with XbaI and SacI and the resulting 9504 bp vector fragment was gel-purified. The chnA operon flanked by terminators, with the trpA terminator (Koichi et al. (1997) Volume 272, Number 51, pp. 32034-32041) 3' to the chnA coding sequence, from pCL1925-ter-T5chnA was gel-purified as a 1271 bp XbaI/SacI fragment. After ligation of the fragments and transformation into E. coli Top10, transformants were screened by colony PCR. Primers chnSeq F1 (SEQ ID NO:58) and pCL1925 vec R2 (SEQ ID NO:64) amplified the expected 1107 bp PCR product in the resulting plasmid, pCL1925-KoDD-ddr::ter-T5chnA.

Example 10

Expression of a 2-Butanol Biosynthetic Pathway in E. coli with Overexpressed Endogenous Alcohol Dehydrogenase The purpose of this Example was to express a 2-butanol biosynthetic pathway in several E. coli strains.

Construction of E. coli Strains Constitutively Expressing yqhD:

E. coli contains a native gene (yqhD) that was identified as a 1,3-propanediol dehydrogenase (U.S. Pat. No. 6,514,733). The yqhD gene, given as SEQ ID NO:74, has 40% identity to the gene adhB in Clostridium, a probable NADH-dependent butanol dehydrogenase. The yqhD gene was placed under the constitutive expression of a variant of the glucose isomerase promoter 1.6GI (SEQ ID NO:67) in E. coli strain MG1655 1.6yqhD::Cm (WO 2004/033646) using λ Red technology (Datsenko and Wanner, Proc. Natl. Acad. Sci. U.S.A. 97:6640 (2000)). Similarly, the native promoter was replaced by the 1.5GI promoter (WO 2003/089621) (SEQ ID NO:68), creating strain MG1655 1.5yqhD::Cm, thus, replacing the 1.6GI promoter of MG1655 1.6yqhD::Cm with the 1.5GI promoter. The 1.5GI and 1.6GI promoters differ by 1 bp in the −35 region, thereby altering the strength of the promoters (WO 2004/033646). While replacing the native yqhD promoter with either the 1.5GI or 1.6GI promoter, the yqhC gene encoding the putative transcriptional regulator for the yqh operon was deleted. Butanol dehydrogenase activity was confirmed by enzyme assay using methods that are well known in the art.

Transformation of E. coli Strains:

Pathway plasmids pCL1925-Kodd-ddr and pTrc99a-budABC, described in Example 9, were co-transformed into E. coli strains MG1655, MG1655 1.6yqhD, and MG1655 1.5yqhD. The two latter strains overexpress the 1,3-propanediol dehydrogenase, YqhD, which also has butanol dehydrogenase activity. Strains were examined for the production of 2-butanone and 2-butanol essentially as described above. Cells were inoculated into shake flasks (approximately 175 mL total volume) containing either 50 or 150 mL of TM3a/ glucose medium (with 0.1 mg/L vitamin $B_{12}$, appropriate antibiotics and IPTG) to represent medium and low oxygen conditions, respectively. Spectinomycin (50 µg/mL) and carbenicillin (100 µg/mL) were used for plasmids pCL1925-Kodd-ddr and pTrc99a-budABC, respectively. The flasks were inoculated at a starting $OD_{600}$ of ≤0.04 units and incubated at 34° C. with shaking at 300 rpm. The flasks containing 50 mL of medium were capped with vented caps; the flasks containing 150 mL, were capped with non-vented caps to minimize air exchange. IPTG was present at time zero at a concentration of zero or 0.04 mM. Analytical results for 2-butanone and 2-butanol production are presented in Table 7. All the E. coli strains comprising a 2-butanol biosynthetic pathway produced 2-butanone under low and medium oxygen conditions and produced 2-butanol under low oxygen conditions.

TABLE 7

Production of 2-Butanone and 2-Butanol by E. coli MG1655 strains harboring pathway plasmids pCL1925-Kodd-ddr and pTrc99a-budABC

| Strain[a,b] | IPTG, mM | Volume of Medium, mL | 2-Butanone, mM | 2-Butanol, mM |
|---|---|---|---|---|
| MG1655 #1 | 0 | 50 | 0.08 | Not detected |
| MG1655 #2 | 0 | 50 | 0.11 | Not detected |
| MG1655 #1 | 0.04 | 50 | 0.12 | Not detected |
| MG1655 #2 | 0.04 | 50 | 0.11 | Not detected |
| MG1655 #1 | 0 | 150 | 0.15 | 0.047 |
| MG1655 #2 | 0 | 150 | 0.19 | 0.041 |
| MG1655 #1 | 0.04 | 150 | 0.10 | 0.015 |
| MG1655 #2 | 0.04 | 150 | 0.11 | 0.015 |
| MG1655 1.5yqhD #1 | 0 | 50 | 0.10 | Not detected |
| MG1655 1.5yqhD #2 | 0 | 50 | 0.07 | Not detected |
| MG1655 1.5yqhD #1 | 0.04 | 50 | 0.12 | Not detected |
| MG1655 1.5yqhD #2 | 0.04 | 50 | 0.18 | Not detected |
| MG1655 1.5yqhD #1 | 0 | 150 | 0.16 | 0.030 |
| MG1655 1.5yqhD #2 | 0 | 150 | 0.18 | 0.038 |
| MG1655 1.5yqhD #1 | 0.04 | 150 | 0.10 | 0.021 |

TABLE 7-continued

Production of 2-Butanone and 2-Butanol by *E. coli* MG1655 strains harboring pathway plasmids pCL1925-Kodd-ddr and pTrc99a-budABC

| Strain[a,b] | IPTG, mM | Volume of Medium, mL | 2-Butanone, mM | 2-Butanol, mM |
|---|---|---|---|---|
| MG1655 1.5yqhD #2 | 0.04 | 150 | 0.09 | 0.017 |
| MG1655 1.6yqhD #1 | 0 | 50 | 0.08 | Not detected |
| MG1655 1.6yqhD #2 | 0 | 50 | 0.07 | Not detected |
| MG1655 1.6yqhD #1 | 0.04 | 50 | 0.12 | Not detected |
| MG1655 1.6yqhD #2 | 0.04 | 50 | 0.15 | Not detected |
| MG1655 1.6yqhD #1 | 0 | 150 | 0.17 | 0.019 |
| MG1655 1.6yqhD #2 | 0 | 150 | 0.18 | 0.041 |
| MG1655 1.6yqhD #1 | 0.04 | 150 | 0.11 | 0.026 |
| MG1655 1.6yqhD #2 | 0.04 | 150 | 0.11 | 0.038 |
| Control (uninoculated medium) | | | Not detected | Not detected |

[a]#1 and #2 represent independent isolates.
[b]MG1655 is MG1655/pCL1925-Kodd-ddr/pTrc99a-budABC MG1655 1.6yqhD is MG1655 1.6yqhD/pCL1925-Kodd-ddr/pTrc99a-budABC MG1655 1.6yqhD is MG1655 1.5yqhD/pCL1925-Kodd-ddr/pTrc99a-budABC.

Example 11

Expression of a 2-Butanol Biosynthetic Pathway in *E. coli* with Heterologous Alcohol Dehydrogenase Plasmids pCL1925-KoDD-ddr::ter-T5chnA and pTrc99a-budABC, described in Example 9, were transformed into *E. coli* strains MG1655 and MG1655 ΔyqhCD for a demonstration of the production of 2-butanol.

MG1655 ΔyqhCD carries a yqhCD inactivation that was made using the method of Datsenko and Wanner (*Proc. Natl. Acad. Sci. U.S.A.* 97(12):6640-6645 (2000)). After replacement of the region with the FRT-CmR-FRT cassette of pKD3, the chloramphenicol resistance marker was removed using the FLP recombinase. The sequence of the deleted region is given as SEQ ID NO:66.

Strains MG1655/pTrc99a-budABC/pCL1925KoDD-ddr:: ter-T5 chnA and MG1655 ΔyqhCD/pTrc99a-budABC/ pCL1925KoDD-ddr::ter-T5 chnA were examined for the production of 2-butanone and 2-butanol essentially as described above. Strain MG1655 ΔyqhCD/pCL1925 was used as a negative control. Cells were inoculated into shake flasks (approximately 175 mL total volume) containing 50 or 150 mL of TM3a/glucose medium (with 0.1 mg/L vitamin $B_{12}$ and appropriate antibiotics) to represent medium and low oxygen conditions, respectively. Spectinomycin (50 µg/mL) and ampicillin (100 µg/mL) were used for selection of pCL1925 based plasmids and pTrc99a-budABC, respectively. Enzyme activity derived from pTrc99a-budABC was detected by enzyme assay in the absence of IPTG inducer, thus, IPTG was not added to the medium. The flasks were inoculated at a starting $OD_{600}$ of ≤0.01 units and incubated at 34° C. with shaking at 300 rpm for 24 h. The flasks containing 50 mL of medium were capped with vented caps; the flasks containing 150 mL, were capped with non-vented caps to minimize air exchange. Analytical results for 2-butanone and 2-butanol production are presented in Table 8. Both *E. coli* strains comprising a 2-butanol biosynthetic pathway produced 2-butanone under low and medium oxygen conditions and produced 2-butanol under low oxygen conditions, while the negative control strain did not produce detectable levels of either 2-butanone or 2-butanol.

TABLE 8

Production of 2-butanone and 2-butanol by *E. coli* strains

| Strain[a] | Volume, mL | 2-Butanone, mM | 2-Butanol, mM |
|---|---|---|---|
| Negative control, MG1655 ΔyqhCD/pCL1925 | 50 | Not detected | Not detected |
| MG1655/pTrc99a-budABC/pCL1925KoDD-ddr::T5 chnA ter | 50 | 0.33 | Not detected |
| MG1655 ΔyqhCD/pTrc99a-budABC/pCL1925KoDD-ddr::T5 chnA ter#1 | 50 | 0.23 | Not detected |
| MG1655 ΔyqhCD/pTrc99a-budABC/pCL1925KoDD-ddr::T5 chnA #2 | 50 | 0.19 | Not detected |
| Negative control, MG1655 ΔyqhCD/pCL1925 | 150 | Not detected | Not detected |
| MG1655/pTrc99a-budABC/pCL1925KoDD-ddr::T5 chnA ter | 150 | 0.41 | 0.12 |
| MG1655 ΔyqhCD/pTrc99a-budABC/pCL1925KoDD-ddr::T5 chnA #1 | 150 | 0.15 | 0.46 |
| MG1655 ΔyqhCD/pTrc99a-budABC/pCL1925KoDD-ddr::T5 chnA #2 | 150 | 0.44 | 0.14 |
| Medium | | Not detected | Not detected |

[a]#1 and #2 represent independent isolates.

Example 12

Cloning of Amino:Pyruvate Transaminase (APT)

An amino:pyruvate transaminase (APT) from *Vibrio Fluvialis* JS17 was identified by Shin et al. (Appl. Microbiol Biotechnol. (2003) 61:463-471). The amino acid sequence (SEQ ID NO:122) was found to have significant homology with ω-amino acid:pyruvate transaminases (Shin and Kim (*J. Org. Chem.* 67:2848-2853 (2002)). It was shown that the *Vibrio Fluvialis* APT has transaminase activity towards acetoin.

For expression of the APT enzyme in *E. coli*, a codon optimized APT coding region (SEQ ID NO:144) was designed using the preferred *E. coli* codons with additional considerations such as codon balance and mRNA stability, and synthesized (by DNA2.0; Redwood City, Calif.). The coding region DNA fragment was subcloned into the pBAD.HisB vector (Invitrogen) between the NcoI and HindIII sites and the resulting plasmid, hereafter referred to as pBAD.APT1, was transformed into TOP10 cells.

Example 13

Characterization of *Vibrio Fluvialis* APT Alanine:Acetoin Aminotransferase Activity A 5 mL volume of LB broth+100 µg/mL ampicillin was inoculated with a fresh colony of TOP10/pBAD:APT1 cells. The culture was incubated at 37° C. for approximately 16 h with shaking (225 rpm). A 300 µL aliquot of this culture was used to inoculate 300 mL of the same medium, which was incubated at 37° C. with shaking (225 rpm). When the culture reached an OD$_{600}$ of 0.8, L-arabinose was added to a final concentration of 0.2% (w/v). The culture was incubated for an additional 16 h, then harvested. The cells were washed once with 100 mM potassium phosphate buffer (pH 7.8) and then frozen and stored at −80° C.

To isolate the enzyme, the cell pellet was thawed and resuspended in 8 mL of 100 mM potassium phosphate buffer (pH 7) containing 0.2 mM ethylenediaminetetraacetate, 1 mM dithiothreitol and 1 tablet of protease inhibitor cocktail (Roche; Indianapolis, Ind.). The cells were lysed by two passes through a French pressure cell at 900 psi, and the resulting lysate was clarified by centrifugation for 30 min at 17000×g. Ammonium sulfate was added to 35% saturation, and the solution was stirred for 30 min at room temperature, at which point precipitated solids were removed by centrifugation (30 min, 17000×g). Additional ammonium sulfate was added to the supernatant to give 55% saturation, and the solution was again stirred for 30 min at room temperature. The precipitated solids were removed by centrifugation (30 min, 17000×g) and then resuspended in 5 mL of 100 mM potassium phosphate buffer (pH 7) containing 10 µM pyridoxal 5'-phosphate and 1 mM dithiothreitol. This solution was desalted by passage through a PD10 column equilibrated with Buffer A (50 mM bis-tris propane buffer (pH 6) containing 10 µM pyridoxal 5'-phosphate and 1 mM dithiothreitol). The desalted extract was then loaded onto a 20 mL Q-Fast Flow column pre-equilibrated with Buffer A. APT was eluted with a linear gradient of 0-0.1 M NaCl in Buffer A. The enzyme was detected in eluted fractions by the presence of a protein band of size ~50 kD when analyzed by SDS-polyacrylamide gel electrophoresis and by the characteristic absorbance at 418 nm. Fractions containing the enzyme eluted at ~0.3 M NaCl. These fractions were pooled to yield a total of 6 mL of a 5.45 mg/mL solution of enzyme, which was >90% pure, as judged by SDS-polyacrylamide gel electrophoresis.

The alanine:acetoin aminotransferase activity of APT was assayed using a lactic dehydrogenase coupled assay. Reaction mixtures contained 100 mM bis-tris propane (pH 9.0), 10 µM pyridoxal 5'-phosphate, 0-50 mM acetoin, 0-5 mM L-alanine, 0.14 or 0.28 mg/mL purified enzyme, 200 µM NADH and 20 U/mL lactic dehydrogenase (Sigma; St. Louis, Mo.). The reaction was followed by measuring the change in absorbance at 340 nm, indicative of the oxidation of NADH. Under these conditions, the $k_{cat}/K_m$ for acetoin was 10 M$^{-1}$ s$^{-1}$ and that for L-alanine was 400 M$^{-1}$ s$^{-1}$.

The identity of the expected product 3-amino-2-butanol was confirmed by comparison to a synthetic standard. A mixture of (R,R)- and (S,S)-3-amino-2-butanol was synthesized by the method of Dickey et al. [*J Amer Chem Soc* 74:944 (1952)]: 5 g of trans-2,3-epoxybutane were slowly stirred into 150 mL of cold (4° C.) NH$_4$OH. The reaction was slowly warmed to room temperature, sealed and stirred at room temperature for an additional 10 days. At this time, excess ammonia and water and residual epoxybutane were removed by rotary evaporation under vacuum at 40° C. The resulting clear oil (2.9 g) was resuspended in water to a concentration of 10% (w/v). Production of the desired product was confirmed by NMR analysis and comparison of the spectrum to that reported by Levy et al. [*Org. Magnetic Resonance* 14:214 (1980)]. A mixture of the corresponding (2R,3S)- and (2S,3R)-isomers was produced using the identical method with the exception that the starting material was the cis-isomer of 2,3-epoxybutane.

An analytical method for detection of 3-amino-2-butanol was developed based on the o-phthaldialdehyde derivatization method for amino acid determination reported by Roth [*Anal. Chem.* 43:880 (1971)]. A 200 µL aliquot of 1 mM 3-amino-2-butanol (mixture of isomers) was mixed with 200 µL of a 50 mM solution of borate (pH 9.5), to which was added 10 µL of 5 µL/mL 2-mercaptoethanol in ethanol and 10 µL of 10 mg/mL o-phthaldialdehyde in ethanol. The solution was incubated at room temperature for 10 min, at which time the derivative was extracted into 200 µL hexane. The hexane was separated from the aqueous solution by decanting, and 10 µL were injected onto a Chiracel OD HPLC column (Daicel Chemical Industries; Fort Lee, N.J.). The column was run isocratically with a mobile phase of 90:10 hexane:isopropanol at a rate of 1 mL/min. The derivatized isomers of 3-amino-2-butanol were detected by absorbance at 340 nm with retention times of approximately 15.7 and 16.8 min [(2S,3S) and (2R,3R)], and 18.4 and 21.9 min [(2R,3S) and (2S,3R)]. To differentiate the enantiomers in the first mixture, the pure (2R,3R) isomer (Bridge Organics; Vicksburg, Mich.) was also run under the identical conditions and found to be the 16.8 min peak. To differentiate the enantiomers in the second mixture, the mixture was first kinetically resolved using the alanine:acetoin aminotransferase: 0.28 mg of purified enzyme was incubated with 10 mM pyruvate and 10 mM 3-amino-2-butanol [1:1 mixture of (2R,3S) and (2S,3R) isomers] in 1 mL of 100 mM bis-tris propane (pH 9.0). After 24 h at room temperature, an aliquot was removed and analyzed as described above. Analysis revealed that the 18.4 min peak was 95% depleted, while the 21.9 min peak was >90% retained. A 100 µL aliquot of the remaining reaction mixture was mixed with 50 µL of 20 mM NADH and 10 µL of extract from the TOP10/pTrc99a-BudC strain described in Example 9. The BudC enzyme is known to reduce (R)-acetoin to meso-2,3-butanediol and (S)-acetoin to (S,S)-2,3-butanediol [Ui et al.(2004) *Letters in Applied Microbiology* 39:533-537]. After 3 h, samples were taken from the reaction and analyzed as described above for acetoin and butanediol. The analysis indicated that the primary product of the reduction was meso-2,3-butanediol, indicating that the product of the aminotransferase reaction was (R)-acetoin, and therefore the consumed 3-amino-2-butanol isomer was the (2R,3S) isomer. Thus the retention time of 18.4 min can be assigned to this isomer and 21.9 to the (2S,3R) isomer.

To confirm that the product of the APT-catalyzed alanine:acetoin aminotransferase reaction was 3-amino-2-butanol, 0.28 mg of purified enzyme was incubated with 10 mM acetoin, 10 mM L-alanine, 50 U lactic dehydrogenase and 200 µM NADH in 1 mL of 100 mM bis-tris propane (pH 9.0). The reaction mixture was incubated at room temperature for 20 h, after which a 200 µL aliquot was removed and derivatized as described above. The retention times of the derivatized products were 15.8 min (major product) and 18.5 min (minor product), matching that of the (2S,3S)-and (2R,3S)-3-amino-2-butanol standards.

Example 14

Identification and Cloning of *Erwinia carotovora* subsp. *atroseptica* Amino Alcohol Kinase and Amino Alcohol O-Phosphate Lyase The purpose of this example is to describe the identification and cloning of sequences encoding an amino alcohol kinase and amino alcohol O-phosphate lyase from the bacterium *Erwinia carotovora*. These two enzymes are part of Pathway 1 for the conversion of 3-amino-2-butanol to 2-butanone via the intermediate 3-amino-2-butanol phosphate as shown in FIG. 1.

Prediction of the *Erwinia* Amino Alcohol Kinase and the Amino Alcohol O-Phosphate Lyase ATP-dependent amino alcohol kinase and amino alcohol O-phosphate lyase activities have been detected in several *Pseudomonas* and *Erwinia* species, including *Pseudomonas* sp. P6 (NCIB10431), *Pseudomonas putida* NCIB 10558 (Jones et al. (1973) *Biochem. J.* 134:167-182), *Erwinia carotovora*, *Erwinia amanas*, *Erwinia milletiae*, and *Erwinia atroseptica* (Jones et al. (1973) *Biochem. J.* 134:959-968). In these studies, the extracts of the above species were shown to have activity for the enzymatic conversion of aminopropanol through aminopropanol O-phosphate to propionaldehyde, and the conversion of ethanolamine through ethanolamine O-phosphate to acetaldehyde.

The genomic sequence of the Erwinia atroseptica strain in which these activities were reported to exist (now designated as *Erwinia carotovora* subsp. *atroseptica* strain SCRI1043 (ATCC BAA-672)) has been determined at the Sanger Institute (Bell et al. *Proc. Natl. Acad. Sci. USA* 101(30): 11105-11110). Analysis of the putative kinases in the *Erwinia carotovora* subsp. *atroseptica* genome revealed an operon sequence (SEQ ID NO: 275) encoding a putative protein (ECA2059; SEQ ID NO:124) that is 39% identical to a *Rhizobium loti* homoserine kinase and a putative class-III pyridoxal phosphate (PLP)-dependent aminotransferase (ECA2060; SEQ ID NO:126) that is 58% identical to a putative aminotransferase from *Rhizobium meliloti*. It was expected that ECA2059 was an amino alcohol kinase and ECA2060 was an amino alcohol O-phosphate lyase which uses PLP as cofactor.

Cloning of the Putative Amino Alcohol Kinase and Putative Amino Alcohol O-Phosphase Lyase from *Erwinia carotovora* subsp. *atroseptica*

Genomic DNA of *Erwinia carotovora* subsp. *atroseptica* (ATCC #: BAA-672D) was obtained from American Type Culture Collection (ATCC). The operon encoding the putative amino alcohol kinase (KA) and amino alcohol O-phosphate lyase (AT) was named KA-AT (SEQ ID NO: 275). This operon was amplified from the *Erwinia genomic* DNA by Phusion DNA polymerase (Finnzymes; via New England Biolabs; Ipswich, Mass.) using primers OT872 (SEQ. ID. No.127) and OT873 (SEQ. ID. No128). A DNA fragment of 2.4 kb was obtained by the PCR reaction, which corresponds to the size of the KA-AT operon. The PCR product was digested with EcoRI and PstI restriction enzymes, and cloned into vector pKK223-3 (Amersham Biosciences; Piscataway, N.J.) which was digested with the same restriction enzymes. This produced plasmid pKK223.KA-AT, which contained the putative *Erwinia* amino alcohol kinase-lyase operon under control of the tac promoter. Similarly, plasmids pKK223.KA and pKK223.AT were made which placed the putative *Erwinia* kinase and the putative *Erwinia* lyase coding regions in separate vectors, each under the control of the tac promoter. For the PCR cloning of the KA coding region (SEQ ID NO:123), primers OT872 (SEQ. ID. No.127) and OT879 (SEQ. ID. No.129) were used; and for the PCR cloning of AT coding region (SEQ ID NO:125), primers OT873 (SEQ. ID. No.128) and OT880 (SEQ. ID. No.130) were used in the PCR amplifications, which generated PCR products of 1.1 kb and 1.3 kb respectively. The PCR products were each digested with EcoRI and PstI, and ligated into vector pKK223-3 to generate pKK223.KA and pKK223.AT.

In vivo Activity of the Putative Amino Alcohol Kinase and Putative Amino Alcohol O-Phosphase Lyase from *Erwinia carotovora* subsp. *atroseptica*

Plasmids pKK223.KA-AT, pKK223.KA, pKK223.AT and pKK223-3 were transformed into the *E. coli* MG1655 strain. The transformants were restreaked onto a MOPS minimal media plate containing 1% glucose, 0.5% aminopropanol as a sole nitrogen source, 1 mM IPTG and 100 µg/mL ampicillin. Expression of KA-AT, KA and AT genes were induced by the IPTG. A control plate had no IPTG included. The plates were incubated at 37° C. for 7 days. On the plate with IPTG, only the strain MG1655/pKK223.KA-AT grew, while all the other three strains did not grow. On the plate without added IPTG, the strain MG1655/pKK223.KA-AT grew, but the colonies were significantly smaller than those on the IPTG-containing plate, which corresponds to the lower expression levels of KA and AT in the uninduced cells. None of the other three strains grew on this plate. This indicates that the co-expression of the putative *Erwinia* KA and AT genes provided sufficient enzyme activities that allowed the *E. coli* strain MG1655/pKK223.KA-AT to utilize aminopropanol as a sole nitrogen source. Expression of each individual enzyme of either KA or AT was not sufficient to provide such enzyme activity in vivo.

Example 15

In vitro Activity of *Erwinia* putative Amino Alcohol Kinase and Amino Alcohol O-Phosphate Lyase Subcloning of the *Erwinia* KA-AT Operon into the pBAD.HisB Vector and Induction of Protein Expression The protein expression levels of *Erwinia* putative KA and AT enzymes expressed in MG1655 cells from the pKK223.KA-AT vector were analyzed by SDS-PAGE analysis. The expression level of the *Erwinia* AT enzyme was relatively low, with a new protein band detected at the correct molecular weight of 46 kD in the soluble fraction of a cell extract, while no new protein band was detected at the size predicted for the KA enzyme.

In an effort to improve the expression of the *Erwinia* putative KA and AT genes, the KA-AT operon was subcloned into the EcoRI and HindIII sites of vector pBAD.HisB-EcoRI. pBAD.HisB-EcoRI was derived from the pBAD.HisB vector (Invitrogen), by replacing the NcoI site in pBAD.HisB with an EcoRI site via QuickChange site-directed mutagenesis (Stratagene, La Jolla, Calif.) using primers OT909 (SEQ ID.#131) & OT910 (SEQ ID.#132). In the constructed plasmid pBAD.KA-AT, the KA-AT operon was placed directly under control of the araB promoter (without His-tag).

The pBAD.KA-AT plasmid was transformed into the *E. coli* TOP10 strain. A 50 mL culture of TOP10/pBAD.KA-AT strain was grown to mid log phase ($OD_{600}$=0.6) in LB, 100 µg/mL ampicillin media at 37° C. with shaking at 250 rpm. The culture was induced by addition of L-arabinose to a final concentration of 0.1% (w/v), and it was further incubated at 37° C. for 5 h before harvesting by centrifugation. The cell pellet was resuspended in ice cold 50 mM Tris-HCl, pH 8.0, and disrupted by sonication on ice with a Fischer Sonic Model 300 Dismembrator (Fischer, Pittsburgh, Pa.) at 50% power, repeating four cycles of 30 seconds sonication with 60 seconds rest in-between each cycle. Each sonicated sample was centrifuged (15,000×g, 4 min, 4° C.). Clarified cell free extracts were analyzed for protein expression level and amino alcohol O-phosphate lyase activity.

Chemical Synthesis of Aminobutanol O-Phosphate and Aminopropanol O-Phosphate

The substrate (R,R)-3-amino-2-butanol O-phosphate was synthesized by a method based on that reported by Ferrari and Ferrari (U.S. Pat. No. 2,730,542 [1956]) for phosphoethanolamine: 10 mmol of $H_3PO_4$ in a 50% (w/v) aqueous solution was mixed with a 50% (w/v) solution of (R,R)-3-amino-2-butanol (Bridge Organics; Vicksburg, Mich.) while stirring on ice. After mixing, the solution was slowly warmed to room temperature and then stirred under vacuum and heated to 70° C. After 1 h at 70° C., the temperature was slowly increased to 185° C. and maintained there for an additional 2 h. At that time, the reaction was cooled to room temperature and the vacuum released. The remaining material was dissolved in water, and analysis by NMR indicated that 80% of the starting material was converted to product with 20% remaining unreacted. No additional products were observed.

The additional substrates (2R,3S)-3-amino-2-butanol O-phosphate and (2S,3R)-3-amino-2-butanol O-phosphate were synthesized by the same procedure using a 1:1 mixture of (2R,3S)-3-amino-2-butanol and (2S,3R)-3-amino-2-butanol (synthesized as described in Example 13) as the starting material. DL-1-amino-2-propanol O-phosphate, (S)-2-amino-1-propanol O-phosphate, and (R)-2-amino-1-propanol O-phosphate were synthesized by the same procedure using DL-1-amino-2-propanol, (R)-2-amino-1-propanol, or (S)-2-amino-1-propanol as the starting material.

Analysis of the Aminopropanol O-Phosphate Lyase Activity Encoded by the Putative *Erwinia* KA-AT Operon The aminopropanol O-phosphate lyase assay was performed as described by Jones et al. (1973, *Biochem. J.* 134: 167-182) and G. Gori et al. (1995, Chromatographia 40:336) The formation of propionaldehyde from aminopropanol O-phosphate was assayed colorimetrically with MBTH, which allows the detection of aldehyde formation. The reaction was performed as follows. In a 1 mL reaction, 100 μg cell free extract of *E. coli* TOP10/pBAD.KA-AT was added to 10 mM DL-1-amino-2-propanol O-phosphate in 100 mM Tris-HCl, pH 7.8, with 0.1 mM PLP. The reaction was incubated at 37° C. for 10 min and 30 min, with an aliquot of 100 μL reaction mixture removed at each time point and mixed with 100 μL of 6 mg/mL MBTH in 375 mM glycine-HCl, pH 2.7. This mixture was incubated at 100° C. for 3 min, cooled on ice for 15-30 s, and 1 mL of 3.3 mg/mL $FeCl_3 \cdot 6H_2O$ (in 10 mM HCl) was added, followed by incubation for 30 min at room temperature. The absorbance of the reaction mixture which contains the aldehyde-MBTH adduct, was measured at 670 nm. The results of the assay are listed in Table 9. In the presence of the aminopropanol phosphate substrate, PLP and cell free extract, formation of aldehyde was detected, as indicated by an $Abs_{670}$ that was higher than the control background of up to 0.3. In the absence of either the substrate or the cell free extract, no aldehyde formation was detected. In the absence of added PLP, somewhat less amount aldehyde was detected, presumably due to the presence of PLP in the cell free extract. Cell free extract of the uninduced TOP10/pBAD.KA-AT-culture did not produce any detectable aldehyde in the reaction. These results indicated that the putative *Erwinia* amino alcohol O-phosphate lyase does catalyze the conversion of aminopropanol O-phosphate to propionaldehyde.

TABLE 9

Aminopropanol O-phosphate lyase assay. Sample 1 was the cell free extract of a non-induced control of *E. coli* TOP10/pBAD.KA-AT. Samples 2-5 contained the cell free extract of the induced culture *E. coli* TOP10/pBAD.KA-AT.

| Sample Number | Induction by 0.1% arabinose | Aminopropanol O-phosphate | PLP | Enzyme extract (100 μg/mL) | $OD_{670}$, 10 min | $OD_{670}$, 30 min |
|---|---|---|---|---|---|---|
| 1 | uninduced | (+) | (+) | (+) | 0.262 | 0.255 |
| 2 | induced | (+) | (+) | (+) | 1.229 | 2.264 |
| 3 | induced | (−) | (+) | (+) | 0.303 | 0.223 |
| 4 | induced | (+) | (−) | (+) | 0.855 | 1.454 |
| 5 | induced | (+) | (+) | (−) | 0.156 | 0.065 |

Analysis of the Activity of the *Erwinia* Amino Alcohol O-Phosphate Lyase towards Aminobutanol O-Phosphate Substrate The activity of the amino alcohol O-phosphate lyase towards the aminobutanol O-phosphate substrates was studied under the same conditions as described above. The reaction was carried out at 37° C. overnight in a 1 mL reaction that contained 100 μg of cell free extract of *E. coli* TOP10/pBAD.KA-AT, 10 mM aminobutanol O-phosphate (either the mixture of (R,R)+(S,S) or the mixture of (R,S)+(S,R) isomers described in Example 15) in 100 mM Tris-HCl, pH 7.8, with 0.1 mM PLP. An aliquot of 100 μL reaction mixture was removed and the 2-butanone product was detected using the MBTH derivatization method described in the General Methods. The two peaks representing the derivatized 2-butanone isomers were observed. Therefore the *Erwinia* amino alcohol O-phosphate lyase is an aminobutanol phosphate phospholyase in addition to an aminopropanol phosphate phospholyase.

Analysis of the Activity of the *Erwinia* Amino Alcohol O-Phosphate Lyase Towards Stereoisomers of Aminopropanol O-Phosphate and Aminobutanol O-Phosphate The activity of the *Erwinia* amino alcohol O-phosphate lyase towards various stereoisomers of aminopropanol O-phosphate and aminobutanol O-phosphate was studied under the same conditions as described above. In the presence of the *Erwinia* amino alcohol O-phosphate lyase, both (R) and (S)-2-amino-1-propanol O-phosphate were converted to propanone by the enzyme, but the product yield was much higher with the (S) isomer. The enzyme also produced butanone from both mixtures of 3-amino)-2-butanol O-phosphate isomers, with a higher product yield found in the reaction containing the (R,S) and (S,R) substrate isomers. Both propanone and butanone products were derivatized by MBTH, and detected by HPLC as described in General Methods.

Optimization of the Gene Expression Level for the *Erwinia* Amino Alcohol Kinase and Amino Alcohol O-Phosphate Lyase In order to improve the expression levels for the *Erwinia* amino alcohol kinase and the amino alcohol O-phosphate lyase in *E. coli*, codon optimized coding regions for both enzymes (named EKA: SEQ ID NO:155 and EAT: SEQ ID NO:156 respectively) were synthesized by DNA2.0 (Redwood City, Calif.). Each coding region was synthesized with 5' and 3' tails including restriction sites for cloning: EKA has 5' BbsI and 3' EcoRI, HindIII sites; EAT has 5' EcoRI and 3' HindIII sites. The EKA and EAT coding regions were provided from DNA2.0 as plasmids pEKA and pEAT, which were in the pJ51 vector of DNA2.0. The EKA optimized coding region was subcloned by ligating a BbsI and HindIII digested fragment of pEKA into the pBAD.HisB vector between the NcoII and HindIII sites, to generate plasmid pBAD.EKA. In the resulting plasmid the coding region is 5' to the His tag, so a coding region for an N-terminus $His_6$ tag fused to the *Erwinia* amino alcohol kinase was constructed by performing a QuickChange site-directed mutagenesis reaction using primers SEQ ID NO:157 and SEQ ID NO:158 to generate vector pBAD.His-EKA.

pBAD.His-EKA was transformed into *E. coli* strain BL21AI ($F^-$ ompT hsdSB ($rB^-$ $mB^-$) gal dcm araB:: T7RNAP-tetA; Invitrogen) to produce strain BL21AI/pBAD.HisA-EKA. A 50 mL culture of BL21AI/pBAD.HisA-EKA was grown to mid-log stage ($OD_{600}$=0.6), induced with 0.1% arabinose, and further incubated at 30° C. overnight. Cell free extracts were prepared by sonication. The $His_6$-tagged fusion protein of *Erwinia* amino alcohol kinase was purified using the ProBond™ Purification System (Invitrogen) under non-denaturing purification conditions following the manufacture's instructions.

Prophetic Result

The kinase activity of the His$_6$-tagged *Erwinia* amino alcohol kinase is analyzed by the ADP Quest Assay (DiscoveRx, Fremont, Calif.) following the manufacture's instructions. This is a biochemical assay that measures the accumulation of ADP, a product of the amino alcohol kinase reaction using either aminopropanol or aminobutanol as substrate. 10 mM substrate is mixed with His$_6$-tagged *Erwinia* amino alcohol kinase, in 100 mM Tris-HCl, pH 7.8, 10 mM MgCl$_2$, 2 mM KCl, 0.1 mM ATP, and incubated at 37° C. for 1 h in a 0.2 mL reaction. ADP reagent A (100 µL) and ADP reagent B (200 µL) are added and the mixture is incubated at room temperature for 30 min. The fluorescence signal indicating activity is measured with excitation wavelength of 530 nm and emission wavelength of 590 nm.

Example 16

Expression of Entire Pathway 3

Construction of Vector pCLBudAB-ter-T5chnA

The vector pTrc99a::BudABC (described in Example 9) is digested with EcoRI, and the DNA is treated with Klenow DNA polymerase to blunt the ends. The blunted vector is subsequently digested with SpeI to yield a 2.5 kb fragment containing the budA and budB genes. The vector pCL1925-ter-T5chnA (described in Example 9) is digested with HindIII, and the DNA was treated with Klenow DNA polymerase to blunt the ends. The blunted vector is subsequently digested with XbaI to yield a 4.6 kb fragment which is then ligated to the budAB fragment from pTrc99a::BudABC. The resulting plasmid, designated pCLBudAB-ter-T5chnA, is used to transform *E. coli* Top10 cells, and single colonies are screened for proper plasmid structure by PCR using primers pCL1925vecF (SEQ ID NO:62) and N84seqR3 (SEQ ID NO:159). Plasmid is prepared from a single colony which yields a PCR product of the expected size of 1.4 kb.

Construction of Vector pKK223.KA-AT-APT

The APT gene is amplified from the vector pBAD.APT (described in Example 12) by PCR using primers APT for (SEQ ID NO:162; 5' includes RBS and SmaI site) and APTrev (SEQ ID NO:163; 3' adds SmaI site). The product of expected size of 1.7 kbp is gel purified and digested with SmaI to yield blunt ends. The vector pKK223.KA-AT (described in Example 14) is digested with PstI, and the DNA is treated with Klenow DNA polymerase to blunt the ends. The resulting DNA fragment is ligated with the SmaI-digested PCR product, and the ligation product is used to transform *E. coli* Top10 cells. Individual ampicillin resistant colonies are screened by PCR using primers OT872 (SEQ ID NO:127) and APTrev (SEQ ID NO:163). The presence of a PCR product of the expected size of 4.1 kbp indicates that the gene encoding APT is present and oriented in the same direction as the genes encoding KA and AT. The sequence of the insert is verified using the primers APTseqRev (SEQ ID NO:160) and APTseqFor (SEQ ID NO:161). This plasmid is named pKK223.KA-AT-APT. Proper expression of all three genes is verified by growing a 5 mL culture of Top10/pKK223.KA-AT-APT in LB+100 µg/mL ampicillin at 37° C. with shaking. When the OD$_{600}$ reaches ~0.8, expression of the genes on the plasmid is induced by addition of IPTG to 0.4 mM. The expression is evaluated by SDS PAGE and activity assays as described above.

Construction of 2-Butanol Production Strain and Production of 2-Butanone and 2-Butanol

*E. coli* strain MG1655 is transformed with both pKK223.KA-AT-APT and pCLBudAB-ter-T5chnA, and transformants selected for ampicillin and spectinomycin resistance, indicative of the presence of the plasmids. The cells are inoculated into shake flasks (approximately 175 mL total volume) containing 50 or 150 mL of TM3a/glucose medium (with appropriate antibiotics) to represent medium and low oxygen conditions, respectively. IPTG is added to 0.4 mM to induce expression of genes from pKK223.KA-AT-APT. As a negative control, MG1655 cells are grown in the same medium lacking antibiotics. The flasks are inoculated at a starting OD$_{600}$ of ≤0.01 and incubated at 34° C. with shaking at 300 rpm for 24 h. The flasks containing 50 mL of medium are capped with vented caps; the flasks containing 150 mL are capped with non-vented caps to minimize air exchange. The MG1655/pKK223.KA-AT-APT/pCLBudAB-ter-T5chnA strain comprising a 2-butanol biosynthetic pathway produces both 2-butanone and 2-butanol under low and medium oxygen conditions while the negative control strain does not produce detectable levels of either 2-butanone or 2-butanol.

Example 17

Characterization of Glycerol Dehydratase Butanediol Dehydratase Activity

Glycerol dehydratase (E.C. 4.2.1.30) and diol dehydratase (E.C. 4.2.1.28), while structurally related, are often distinguished in the art based on various differences that include substrate specificity. This example demonstrates that glycerol dehydratase converts meso-2,3-butanediol to 2-butanone. The recombinant *E. coli* strain KLP23/pSYCO12, comprising *Klebsiella pneumoniae* genes encoding the multiple subunits of glycerol dehydratase (alpha: SEQ ID NO:145 (coding region) and 146 (protein); beta: SEQ ID NO: 147 (coding region) and 148 (protein); and gamma: SEQ ID NO: 149 (coding region) and 150 (protein)) and *Klebsiella pneumoniae* genes encoding the multiple subunits of glycerol dehydratase reactivase (large subunit, SEQ ID NO: 151 (coding region) and 152 (protein); and small subunit, SEQ ID NO: 153 (coding region) and 154 (protein)), is described in Emptage et al. U.S. Pat. No. 6,514,733 and in WO 2003089621, which are herein incorporated by reference. A crude, cell free extract of KLP23/pSYCO12 was prepared by methods known to one skilled in the art. Enzyme assay was performed in the absence of light in 80 mM HEPES buffer, pH 8.2 at 37° C. with 12 µM coenzyme B$_{12}$ and 10 mM meso-2, 3-butanediol. The formation of 2-butanone was monitored by HPLC (Shodex SH-1011 column and SH-G guard column with refractive index detection; 0.01 M H$_2$SO$_4$ as the mobile phase at a flow rate of 0.5 mL/min and a column temperature of 50° C.; 2-butanone retention time=40.2 min). The rate of 2-butanone formation by the glycerol dehydratase preparation was determined to be 0.4 nmol/min/mg of crude protein.

Example 18

Structural Analysis of Diol/Glycerol Dehydratases through Generation and Validation of a Profile HMM for Experimentally Proven Diol/Glycerol Dehydratases The diol dehydratase and glycerol dehydratase enzymes belong to the enzyme classes 4.2.1.28 and 4.2.1.30, respectively. The enzymes in both classes are each a complex of three subunits: large (also called alpha), medium (also called beta) and small (also called gamma). In some glycerol dehydratases the large and medium subunits were found to be fused.

Identifying Family Members by Sequence

The *Klebsiella oxytoca* butanediol dehydratase enzyme was used as a prototype enzyme for identifying a family of diol and glycerol dehydratase enzymes. The amino acid sequences of the alpha (GenBank No: BAA08099; SEQ ID NO: 8), beta (GenBank No: BAA08100; SEQ ID NO: 10) and gamma (GenBank No: BAA08101; SEQ ID NO: 12) subunits were each run as the query sequence in a BLASTP search against the GenBank non-redundant protein database using default parameters. Sequences with relevant matches were extracted. Relevance was judged by the E-value score, protein definition, details included in the GenBank report for the matched proteins, and literature review of the topic. For the large subunit, the BLAST output showed an abrupt decrease in the E-value from e-20 to an E-value of 1.5. All sequence matches with an E-value of 1.5 or larger had definitions inconsistent with them being dehydratases. Many of these sequences were labeled as DNA-directed RNA polymerase beta subunits. There were matches with E-values around e-20, which were partial sequences. Sequences with no annotation were included if the E-value was less than 1.5.

Using the *Klebsiella oxytoca* butanediol dehydratase alpha subunit as a query, 50 homologs were identified as members of this family of proteins. This group included some sequences that were not full length proteins. The full length sequences identified for the alpha subunit family of diol/glycerol dehydratases are the prototype SEQ ID No: 8 and SEQ ID NOs: 93, 99, 105, 135, 138, 141, 146, 164, 167, 170, 173, 176, 179, 182, 185, 188, 191, 194, 197, 200, 203, 206, 209, 212, 215, 218, 221, 224, 227, 130, 243, 254, 255, 256, 257, 258, and 259. SEQ ID NOs: 233, 235, 237, 239, 241, 246, 247 include both the alpha and beta subunits, which are fused in these cases.

Using the *Klebsiella oxytoca* butanediol dehydratase beta subunit as a query, 51 homologs were identified as members of this family of proteins. This group included some sequences that were not full length proteins. The full length sequences identified for the beta subunit family of diol/glycerol dehydratases are the prototype SEQ ID No: 10 and SEQ ID NOs: 95, 101, 107, 136, 139, 142, 148, 165, 168, 171, 174, 177, 180, 183, 186, 189, 192, 195, 198, 201, 204, 207, 210, 213, 216, 219, 222, 225, 228, 231, 244, 250, 252, 260, 261, 262, 263, 364, 265, 266, and 167.

Using the *Klebsiella oxytoca* butanediol dehydratase gamma subunit as a query, 48 homologs were identified as members of this family of proteins. This group included some sequences that were not full length proteins. The full length sequences identified for the gamma subunit family of diol/glycerol dehydratases are the prototype SEQ ID No: 12 and SEQ ID NOs: 97, 103, 109, 137, 140, 143, 150, 166, 169, 172, 175, 178, 181, 184, 187, 190, 193, 196, 199, 202, 205, 208, 211, 214, 217, 220, 223, 226, 229, 232, 234, 236, 238, 240, 242, 245, 248, 249, 251, 253, 268, 270, 271, 272, 273, and 274.

Identifying Family Members with Experimentally Assessed Function

For each sequence identified through the analysis described above, a search for experimental evidence of its biochemical function was conducted in the BRENDA, Uni-Prot and NCBI Entrez databases. BRENDA is a human-curated database that contains detailed information about enzyme kinetic, physical, and biochemical properties extracted from the experimental literature and with links to the relevant databases (Cologne University BioInformatics Center). The UniProt Knowledgebase is composed of a human-curated part the Swiss-Prot database and of a machine annotated supplement the TrEMBL database. The curated Swiss-Prot database (Swiss Institute of Bioinformatics) provides a high level of protein annotation that includes domain architecture, post-translational modifications and sequence variants. NCBI Entrez is the integrated, text-based search and retrieval system used at NCBI (National Center for Biotechnology Information, Bethesda, Md.) for the major databases, including PubMed, Nucleotide and Protein Sequences, Protein Structures, Complete Genomes, and Taxonomy.

Through the analysis of information and references identified from these databases, eight diol/glycerol dehydratases with experimentally verified function as a diol or glycerol dehydratase were identified. These are given in Table 10.

TABLE 10

Diol/glycerol dehydratases with experimentally verified function

| organism | subunit | Genbank # | SEQ ID No | type | reference |
|---|---|---|---|---|---|
| *Klebsiella oxytoca* | large | gi|6980836 | 8 | diol | Shibata et al., Structure 1999; 7: 997-1008 |
| *K. oxytoca* | medium | gi|6980837 | 10 | diol | |
| *K. oxytoca* | small | gi|6980838 | 12 | diol | |
| *Klebsialla pneumoniae* | large | gi|4063702 | 105 | diol | Tobimatsu et al., 1998; Biosci. Biotechnol. Biochem. 62: 1774-1777 |
| *K. pneumoniae* | medium | gi|94470233 | 107 | diol | |
| *K. pneumoniae* | small | gi|4063704 | 109 | diol | |
| *Clostridium pasteurianum* | large | gi|3360389 | 135 | glycerol | Macis et al., FEMS Microbiol Lett. 1998; 164(1): 21-8 |
| *C. pasteurianum* | medium | gi|3360390 | 136 | glycerol | |
| *C. pasteurianum* | small | gi|3360391 | 137 | glycerol | |
| *Escherichia blattae* | large | gi|60099613 | 138 | glycerol | Sonke et al. J. of Mol. Micro. and Biotech. 2004; 8: 150-168 |
| *E. blattae* | medium | gi|57340191 | 139 | glycerol | |
| *E. blattae* | small | gi|57340192 | 140 | glycerol | |
| *Klebsialla pneumoniae* | large | gi|24158719 | 146 | glycerol | Willard, Thesis (1994), U of Wisconsin-Madison |
| *K. pneumoniae* | medium | gi|24158720 | 148 | glycerol | |
| *K. pneumoniae* | small | gi|24158721 | 150 | glycerol | |
| *Citrobacter* | large | gi|1169287 | 141 | glycerol | Seyfried, Gottschalk; |

TABLE 10-continued

Diol/glycerol dehydratases with experimentally verified function

| organism | subunit | Genbank # | SEQ ID No | type | reference |
|---|---|---|---|---|---|
| *freundii* | | | | | J. Bacteriol. |
| *C. freundii* | medium | gi\|1229154 | 142 | glycerol | 178: 5793-5796 |
| *C. freundii* | small | gi\|1229155 | 143 | glycerol | (1996) |
| *Lactobacillus brevis* | large | gi\|116334196 | 164 | diol | Schuetz and Radler 1984; Arch. Microbiol. |
| *L. brevis* | medium | gi\|116334195 | 165 | diol | 139, 366-370 |
| *L. brevis* | small | gi\|116334194 | 166 | diol | |
| *Lactobacillus collinoides* | large | gi\|18857678 | 99 | diol | Sauvageot et al., 2002; Eur J Biochem. |
| *L. collinoides* | medium | gi\|18857679 | 101 | diol | 269(22): 5731-7. |
| *L. collinoides* | small | gi\|18857680 | 103 | diol | |

The set of 8 amino acid sequences of each subunit from diol/glycerol dehydratases with experimentally determined function, listed in Table 10, were compared by making a multiple sequence alignment using ClustalW with default parameters. The % identity for the large subunit sequences ranged from 97.6% to 58.4%. The % identity for the medium subunit sequences ranged from 89.5% to 41.7%. The % identity for the small subunit sequences ranged from 83.3% to 36.4%. Thus the amount of sequence identity between some subunit sequences was very low (such as 36.4%, 41.7%) even though these subunits were known to be components of enzymes known through experimental data to perform the same function. The low level of % sequence identity made it impractical to use this criterion for structure/function correlations Sequence Relationship of Experimentally Verified Diol/Glycerol Dehydratases to Other Diol/Glycerol Dehydratases To perform this analysis, highly redundant sequences that are >95% identical were removed from the sequence set for large, medium or small subunits, except that all experimentally verified function sequences were retained. Truncated or partial protein sequences were also removed. A multiple sequence alignment was performed on the remaining sequences using ClustalW with default parameters. The % identity for the large subunits ranged from 97.6% (highest % is from multiple experimentally verified sequences) to 42.8%. The % identity for the medium subunits ranged from 91.9% to 26.4%. The % identity for the small subunits ranged from 85.2% to 20.5%. These % identities are similar ranges to the % identities for the experimentally verified sequences.

Figure 2:
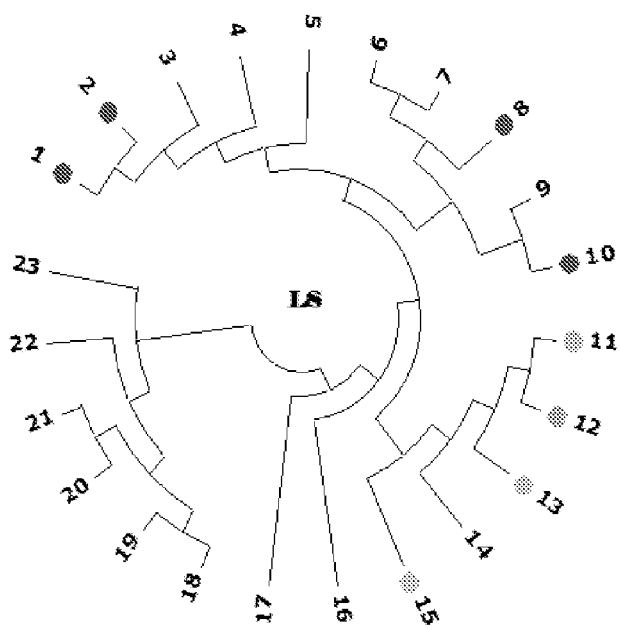

Based on the multiple sequence alignments, phylogenetic trees were built using the neighbor-joining algorithm (as implemented in the MEGA software version 3.1 package; Kumar et al., 2004 *Briefings in Bioinformatics* 5:150-163.) The phylogenetic trees are shown in FIGS. 2 (large subunit), 3 (medium subunit), and 4 (small subunit), with the identities of the mapped sequences listed in a key for each figure. As seen from the positions marked for the experimentally verified function sequences (in dark and light grey circles for diol dehydratase and glycerol dehydratase, respectively), these sequences are spread over most of the tree. However, each tree does include a branch with no experimentally verified members, but which appears to belong to the diol/glycerol dehydratase family.

Building a Profile Hidden Markov Model (HMM) of the Diol/Glycerol-Dehydratase Family Based on the Sets of Eight Subunit Sequences An alternative structure/function characterization of the sets of subunits of the diol/glycerol dehydratase family of enzymes was performed using the HMMER software package (The theory behind profile HMMs is described in R. Durbin, S. Eddy, A. Krogh, and G. Mitchison, *Biological sequence analysis: probabilistic models of proteins and nucleic acids*, Cambridge University Press, 1998; Krogh et al., 1994; J. Mol. Biol. 235:1501-1531), following the user guide which is available from HMMER (Janelia Farm Research Campus, Ashburn, Va.).

Each set of 8 amino acid sequences for the large, medium, and small subunits of functionally characterized diol/glycerol dehydratases (in Table 10) was separately analyzed using the HMMER software program. The output of the HMMER software program is a Profile Hidden Markov Model (HMM) that characterizes the input sequences. As stated in the user guide, Profile HMMs are statistical models of multiple sequence alignments. They capture position-specific information about how conserved each column of the alignment is, and which amino acid residues are most likely to occur at each position. Thus HMMs have a formal probabilistic basis. Profile HMMs for a large number of protein families are publicly available in the PFAM database (Janelia Farm Research Campus, Ashburn, Va.).

Each Profile HMM was built as follows:

Step 1. Build a Sequence Alignment

The eight sequences for the large subunit of the functionally verified diol/glycerol dehydratases (SEQ ID NOs:8, 99, 105, 135, 138, 141, 146, and 164) were aligned using Clustal W with default parameters. The same was done for the set of medium subunit sequences (SEQ ID NOs:10, 101, 107, 136, 139, 142, 148, and 165) and the set of small subunit sequences (SEQ ID NOs:12, 103, 109, 137, 140, 143, 150 and 166).

Step 2. Build a Profile HMM

The hmmbuild program was run on each set of the aligned sequences using default parameters. hmmbuild reads the multiple sequence alignment file, builds a new Profile HMM, and saves the Profile HMM to file. Using this program an uncalibrated profile was generated from the multiple alignment for each set of subunit sequences described above.

The following information based on the HMMER software user guide gives some description of the way that the hmmbuild program prepares a Profile HMM. A Profile HMM is capable of modeling gapped alignments, e.g. including insertions and deletions, which lets the software describe a complete conserved domain (rather than just a small ungapped motif). Insertions and deletions are modeled using insertion (I) states and deletion (D) states. All columns that contain more than a certain fraction x of gap characters will be assigned as an insert column. By default, x is set to 0.5. Each match state has an I and a D state associated with it. HMMER calls a group of three states (M/D/I) at the same consensus position in the alignment a "node". These states are interconnected with arrows called state transition probabilities. M and I states are emitters, while D states are silent. The transitions are arranged so that at each node, either the M state is used (and a residue is aligned and scored) or the D state is used (and no residue is aligned, resulting in a deletion-gap character, '-'). Insertions occur between nodes, and I states have a self-transition, allowing one or more inserted residues to occur between consensus columns.

The scores of residues in a match state (i.e. match state emission scores), or in an insert state (i.e. insert state emission scores) are proportional to Log_2 (p_x)/(null_x). Where p_x is the probability of an amino acid residue, at a particular position in the alignment, according to the Profile HMM and null_x is the probability according to the Null model. The Null model is a simple one state probabilistic model with pre-calculated set of emission probabilities for each of the 20 amino acids derived from the distribution of amino acids in the SWISSPROT release 24.

State transition scores are also calculated as log odds parameters and are propotional to Log_2 (t_x). Where t_x is the probability of transiting to an emitter or non-emitter state.

Step 3. Calibrate the Profile HMM

Each Profile HMM was read using hmmcalibrate which scores a large number of synthesized random sequences with the Profile (the default number of synthetic sequences used is 5,000), fits an extreme value distribution (EVD) to the histogram of those scores, and re-saves the HMM file now including the EVD parameters. These EVD parameters (μ and λ) are used to calculate the E-values of bit scores when the profile is searched against a protein sequence database. hmmcalibrate writes two parameters into the HMM file on a line labeled "EVD": these parameters are the μ (location) and λ(scale) parameters of an extreme value distribution (EVD) that best fits a histogram of scores calculated on randomly generated sequences of about the same length and residue composition as SWISS-PROT. This calibration was done once for each Profile HMM.

The calibrated Profiles HMM for the large subunit, medium subunit, and small subunit sets of sequences are provided in the appendix as alpha Profile HMM, beta Profile HMM, and gamma Profile HMM Excel charts. Each Profile HMM is provided in a chart that gives the probability of each amino acid occurring at each position in the amino acid sequence. The highest probability is highlighted for each position. Table 11 shows a few lines of the Profile HMM prepared for the large subunits of diol/glycerol dehydratases with function experimentally verified.

The amino acids are represented by the one letter code. The first line for each position reports the match emission scores: probability for each amino acid to be in that state (highest score is highlighted). The second line reports the insert emission scores, and the third line reports on state transition scores: M→M, M→I, M→D; I→M, I→I; D→M, D→D; B→M; M→E.

Table 11 shows that for the large subunits, methionine has a 4141 probability of being in the first position, the highest probability which is highlighted. In the second position lysine has the highest probability, which is 1954. In the third position arginine has the highest probability, which is 3077.

Step 4. Test the Specificity and Sensitivity of the Built Profile HMMs

Each Profile HMM was evaluated using hmmsearch, which reads a Profile HMM from hmmfile and searches a sequence file for significantly similar sequence matches. The sequence file searched was the GenBank non-redundant protein database. The size of the database (Z parameter) was set to 1 billion. This size setting ensures that significant E-values against the current database will remain significant in the foreseeable future. The E-value cutoff was set at 10.

The Profile HMMs for the large, medium and small subunits of diol/glycerol dehydratases with experimentally verified function were specific in that only diol/glycerol dehydratase subunits were recovered, as indicated by the annotation of the matched sequences, and sensitive in that even partial sequences of diol/glycerol dehydratase subunits were recovered. Each of the recovered sequences had an E-value of 0.01 or less.

Figure 3:
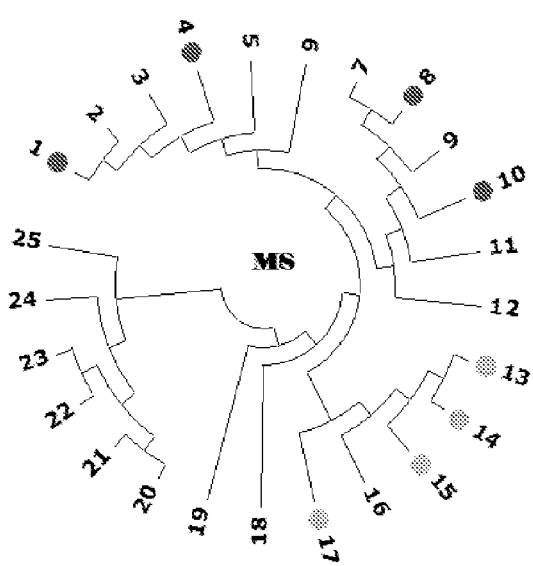
FIG. 3 shows a phylogenetic tree of full length medium subunits of diol/glycerol dehydratases, with >95% identical sequences removed, and a key listing the identity of each sequence in the tree. Sequences with experimentally determined function as diol or glycerol dehydratases are highlighted in dark or light grey, respectively.
Figure 4:
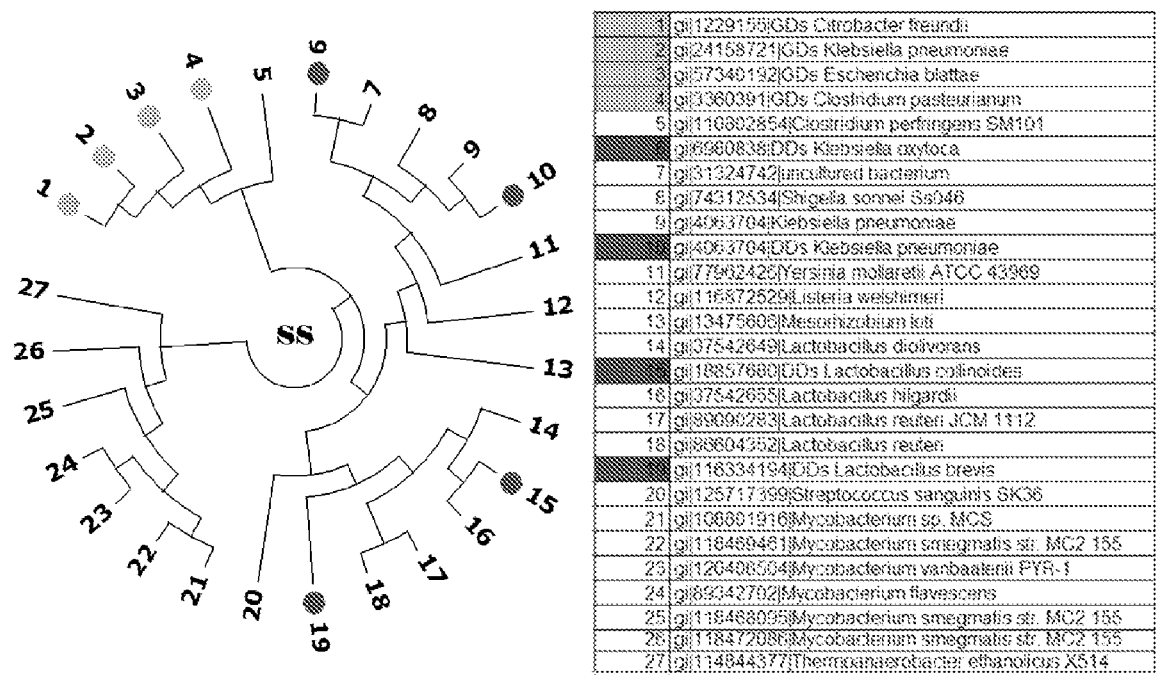
FIG. 4 shows a phylogenetic tree of full length small subunits of diol/glycerol dehydratases, with >95% identical sequences removed, and a key listing the identity of each sequence in the tree. Sequences with experimentally determined function as diol or glycerol dehydratases are highlighted in dark or light grey, respectively.

All of the sequences on the phylogenetic trees in FIGS. 2, 3, and 4 were recovered in the Profile HMM matching. All sequences in the branches of the trees which contain no sequence with experimentally verified function were matched. Thus all of the diol and glycerol dehydratases were linked to the 8 diol and glycerol dehydratases with experimentally verified function through matching with the Profile HMMs for the large, medium, or small subunits of the enzymes. The full length diol and glycerol dehydratase subunits that match the Profile HMMs have the following SEQ ID NOs:

Large (alpha) subunits: 8, 93, 99, 105, 135, 138, 141, 146, 164, 167, 170, 173, 176, 179, 182, 185, 188, 191, 194, 197, 200, 203, 206, 209, 212, 215, 218, 221, 224, 227, 130, 243, 254, 255, 256, 257, 258, and 259.

TABLE 11

A portion of the large subunit Profile HMM.

| HMM | A | C | D | E | F | G | H | I | K | L | M | N | P | Q | R | S | T | V | W | Y |
|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | |
| | -585 | * | -1585 | | | | | | | | | | | | | | | | | |
| 1(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | -585 | * | | | | | | | | | | | |
| 2(K) | -603 | -1732 | -469 | 811 | -2182 | -1397 | 205 | -1770 | 1954 | -1654 | -860 | -59 | -1465 | 629 | 1868 | -495 | -471 | -1439 | -1719 | -1294 |
| - | -149 | -500 | 233 | 43 | -381 | 399 | 106 | -626 | 210 | -466 | -720 | 275 | 394 | 45 | 96 | 359 | 117 | -369 | -294 | -294 |
| - | -350 | -6045 | -2321 | -894 | -1115 | -701 | -1378 | * | * | | | | | | | | | | | |
| 3(R) | -781 | -1268 | -994 | -512 | -1638 | -1313 | -151 | -1479 | 778 | -1459 | -913 | -539 | -1557 | 136 | 3077 | -831 | -760 | -1263 | -1437 | -1152 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -41 | -5736 | -6778 | -894 | -1115 | -535 | -1690 | * | * | | | | | | | | | | | |

Large+medium subunits fused (large subunit and medium subunit portion matches the large Profile and medium Profile, respectively): 233, 235, 237, 239, 241, 246, and 247.

Medium (beta) subunits: 10, 95, 101, 107, 136, 139, 142, 148, 165, 168, 171, 174, 177, 180, 183, 186, 189, 192, 195, 198, 201, 204, 207, 210, 213, 216, 219, 222, 225, 228, 231, 244, 250, 252, 260, 261, 262, 263, 364, 265, 266, and 167.

Small (gamma) subunits: 12, 97, 103, 109, 137, 140, 143, 150, 166, 169, 172, 175, 178, 181, 184, 187, 190, 193, 196, 199, 202, 205, 208, 211, 214, 217, 220, 223, 226, 229, 232, 234, 236, 238, 240, 242, 245, 248, 249, 251, 253, 268, 270, 271, 272, 273, and 274.

This analysis shows that the Profile HMM for each subunit, that was prepared using sequences with experimentally verified function, provides a structure that is linked to function of diol/glycerol dehydratase enzymes. Matching of all of the above sequences to the Profiles HMM in turn provides a structure/function link for these sequences.

TABLE 12

| | |
|---|---|
| HMMER2.0 [2.3.2] | Program name and version |
| NAME alpha_exp_seqs | Name of the input sequence alignment file |
| LENG 557 | Length of the alignment: include indels |
| ALPH Amino | Type of residues |
| MAP yes | Map of the match states to the columns of the alignment |
| COM hmmbuild alpha.hmm alpha_exp_seqs.aln | Commands used to generate the file: this one means that hmmbuild (default patrameters) was applied to the alignment file |
| COM hmmcalibrate alpha.hmm | Commands used to generate the file: this one means that hmmcalibrate (default parametrs) was applied to the hmm profile |
| NSEQ 8 | Number of sequences in the alignment file |
| DATE Fri Mar 30 19:02:15 2007 | When was the file generated |
| XT -8455 -4 -1000 -8455 -4 -8455 -4 | |
| NULT -4 -8455 | The transition probability distribution for the null model (single G state). |
| NULE   595  -1558   85   338  -294 | The symobol emission probability distribution for the null model (G state); consists of |
| 453  -1158   197   249   902  -1085 | K (e.g. 4 or 20) integers. The null probability used to convert these back to model |
| 142   -21  -313   45   531   201 | probabilities is 1/K. The extreme value distribution parameters μ and lambda |
| 384  -1998  -644 | respectively; both floating point values. Lambda is positive and nonzero. These values are set when the model is calibrated with hmmcalibrate |
| EVD -264.9891970.112643 | |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -585 | * | -1585 | | | | | | | | | | | | | | | | | | |
| 1(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 1 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 2(K) | -603 | -1732 | -469 | 811 | -2182 | -1397 | 205 | -1770 | 1954 | -1654 | -860 | -59 | -1465 | 629 | 1868 | -495 | -471 | -1439 | -1719 | -1294 | 2 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -350 | -6045 | -2321 | -894 | -1115 | -701 | -1378 | * | * | | | | | | | | | | | | |
| 3(R) | -781 | -1268 | -994 | -512 | -1638 | -1313 | -151 | -1479 | 778 | -1459 | -913 | -539 | -1557 | 136 | 3077 | -831 | -760 | -1263 | -1437 | -1152 | 3 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -41 | -5736 | -6778 | -894 | -1115 | -535 | -1690 | * | * | | | | | | | | | | | | |
| 4(Q) | -149 | -1077 | 25 | 226 | -1650 | -945 | -85 | -1408 | 309 | -1505 | -735 | 33 | -1280 | 1816 | -34 | 1644 | -225 | -1020 | -1731 | -1155 | 4 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 5(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 5 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 6(R) | -1181 | -1614 | -1431 | -903 | -2066 | -1632 | -446 | -1944 | 559 | -1867 | -1326 | -899 | -1873 | -156 | 3433 | -1225 | -1148 | -1717 | -1746 | -1529 | 6 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 7(F) | -1602 | -1340 | -2512 | -2455 | 3740 | -2315 | -379 | -478 | -2225 | -175 | -190 | -1874 | -2503 | -1781 | -2079 | -1892 | -1647 | -683 | 210 | 1257 | 7 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 8(E) | 37 | -1709 | 562 | 2097 | -2000 | -1013 | 65 | -1701 | 388 | -1724 | -924 | 314 | -1290 | 1204 | 3077 | -831 | -760 | -1263 | -1437 | -1152 | 8 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 9(V) | 428 | -898 | -212 | 744 | -1063 | -1160 | 90 | -556 | 881 | -841 | -94 | 22 | -1284 | 414 | 20 | -168 | -65 | 941 | -1268 | -753 | 9 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 10(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 10 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 11(E) | 995 | -1189 | 274 | 1599 | -1710 | -927 | -3 | -1362 | 257 | -1488 | -682 | 191 | -1227 | 366 | -212 | 521 | -177 | -986 | -1785 | -1178 | 11 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 12(K) | -509 | -1745 | 1 | 892 | -2124 | -1242 | 174 | -1769 | 2128 | -1689 | -880 | 106 | -1385 | 1310 | 676 | -383 | -416 | -1413 | -1802 | -1283 | 12 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 13(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 13 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 14(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 14 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 15(V) | -886 | -604 | -2944 | -2505 | -743 | -2731 | -2045 | 1944 | -2256 | 229 | 340 | -2308 | -2716 | -2086 | -2330 | -1950 | -884 | 2675 | -1910 | -1506 | 15 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 16(H) | -457 | -1514 | 304 | 388 | -1218 | -1098 | 2418 | -1597 | 328 | -1620 | -886 | 2258 | -1387 | 298 | -36 | -374 | -457 | -1264 | -1448 | -664 | 16 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 17(Q) | -346 | -1181 | -403 | 128 | -1300 | -1307 | 121 | -906 | 1166 | 365 | -294 | -69 | -1397 | 1890 | 525 | -356 | -260 | -706 | -1373 | -890 | 17 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 18(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 18 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 19(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 19 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 20(F) | -1300 | -1041 | -2794 | -2396 | 2872 | -2678 | -676 | 440 | -2076 | 1465 | 808 | -1982 | -2569 | -1598 | -1976 | -1862 | -1239 | 98 | -109 | 791 | 20 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 21(V) | -922 | -605 | -3064 | -2618 | -752 | -2841 | -2139 | 2359 | -2383 | 244 | 349 | -2414 | -2784 | -2191 | -2442 | -2058 | -911 | 2430 | -1948 | -1560 | 21 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 22(K) | -395 | -1326 | -130 | 117 | -1960 | 1239 | -86 | -1633 | 2073 | -1681 | -915 | -74 | -1403 | 278 | 289 | -375 | -423 | -1258 | -1820 | -1352 | 22 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 23(E) | -597 | -1990 | 829 | 2406 | -2276 | -963 | -75 | -2069 | 89 | -2078 | -1318 | 1286 | -1352 | 285 | -438 | -411 | -615 | -1663 | -2255 | -1512 | 23 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 24(W) | -1926 | -1577 | -2416 | -2370 | 192 | -2070 | -795 | -1602 | -1882 | -1347 | -1210 | -2018 | -2383 | -1854 | -1777 | -2150 | -1992 | -1643 | 5696 | 560 | 24 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| 25(P) | -136 | -963 | 748 | 291 | -1174 | -1080 | -2 | 367 | 217 | -956 | -244 | 51 | 1547 | 318 | -221 | -177 | -129 | -438 | -1415 | -860 | 25 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 26(E) | -704 | -2274 | 1609 | 2494 | -2517 | -929 | -118 | -2327 | -117 | -2302 | -1553 | 440 | -1360 | 238 | -777 | -462 | -729 | -1891 | -2491 | -1671 | 26 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 27(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 27 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 28(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 28 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 29(F) | -1300 | -1032 | -2939 | -2479 | 2085 | -2797 | -1060 | 610 | -2170 | 2072 | 1034 | -2173 | -2620 | -1672 | -2063 | -1972 | -1227 | 200 | -496 | 232 | 29 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 30(I) | -932 | -616 | -3069 | -2623 | -730 | -2845 | -2140 | 2586 | -2385 | 279 | 372 | -2420 | -2786 | -2188 | -2440 | -2065 | -921 | 2194 | -1936 | -1554 | 30 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 31(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 31 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 32(M) | -1097 | -948 | -2613 | -2098 | 66 | -2604 | -1439 | 782 | -1681 | 1487 | 3575 | -2007 | -2489 | -1444 | -1696 | -1772 | -1045 | 428 | -1173 | -886 | 32 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 33(E) | -103 | -1383 | 474 | 1130 | -1629 | -475 | 238 | -1330 | 588 | -1372 | 919 | 886 | -1165 | 659 | 86 | 417 | -51 | -967 | -1624 | -981 | 33 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 34(S) | 317 | -370 | -658 | -616 | -1967 | 1419 | -807 | -1713 | -760 | -1924 | -1109 | -411 | -1154 | -588 | -1027 | 2116 | -11 | -1006 | -2151 | -1737 | 34 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 35(P) | -405 | -1216 | -191 | 6 | -1782 | -1120 | -188 | -1451 | 1187 | -1561 | -850 | -164 | 2497 | 138 | 133 | -424 | -456 | -1124 | -1757 | -1301 | 35 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 36(N) | -556 | -847 | -1097 | -603 | 1232 | -1683 | 201 | -508 | -426 | -601 | -46 | 2198 | -1740 | -261 | -699 | -699 | -493 | -395 | 1687 | 1610 | 36 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 37(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 37 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 38(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 38 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 39(K) | 175 | -1085 | -247 | 253 | -1457 | -1107 | 109 | -1024 | 1939 | -1182 | -399 | 40 | -300 | 486 | 284 | -143 | -116 | -221 | -1500 | -977 | 39 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| 40(P) | 213 | -475 | -556 | -468 | -1769 | -628 | -656 | -1500 | -525 | -1718 | -950 | -359 | 2478 | -426 | -800 | 1259 | -70 | -926 | -1971 | -1515 | 40 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 41(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 41 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 42(I) | -935 | -625 | -3052 | -2609 | -708 | -2832 | -2125 | 2677 | -2364 | 307 | 391 | -2408 | -2777 | -2168 | -2419 | -2052 | -926 | 2060 | -1920 | -1540 | 42 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 43(K) | -489 | -1476 | -535 | 74 | -1899 | -1347 | 163 | -1474 | 2257 | -1467 | -693 | -94 | -1441 | 566 | 1161 | -436 | 566 | -1175 | -1619 | -1191 | 43 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 44(I) | -935 | -625 | -3052 | -2609 | -708 | -2832 | -2125 | 2677 | -2364 | 307 | 391 | -2408 | -2777 | -2168 | -2419 | -2052 | -926 | 2060 | -1920 | -1540 | 44 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 45(E) | -190 | -1482 | 610 | 1617 | -1728 | -1033 | 193 | -1411 | 949 | -1462 | -616 | 305 | -1203 | 607 | 49 | -87 | -141 | -15 | -1713 | -1064 | 45 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 46(N) | -508 | -1893 | 708 | 1172 | -2155 | -1000 | -2125 | -1908 | 309 | -1897 | -1104 | 2413 | -1320 | 976 | -163 | -338 | -492 | -1519 | -2096 | -1394 | 46 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 47(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 47 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 48(K) | 398 | -959 | -358 | 223 | -1120 | -1205 | 148 | -688 | 1297 | -524 | -121 | 6 | -1289 | 492 | 847 | -176 | -70 | 241 | -1260 | -760 | 48 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 49(V) | -905 | -603 | -3012 | -2567 | -752 | -2794 | -2098 | 2117 | -2327 | 233 | 342 | -2367 | -2755 | -2145 | -2394 | -2012 | -898 | 2593 | -1933 | -1537 | 49 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 50(V) | -367 | -384 | -1856 | -1345 | -565 | -1819 | -964 | 1486 | -1115 | 20 | 389 | -1247 | -1954 | -968 | -1285 | -941 | 1596 | 1684 | -1282 | -891 | 50 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 51(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 51 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 52(M) | -1262 | -1030 | -2945 | -2401 | 126 | -2872 | -1670 | 808 | -2031 | 2152 | 2757 | -2305 | -2645 | -1652 | -1984 | -2035 | -1186 | 370 | -1224 | -1041 | 52 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 53(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 53 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 54(G) | 291 | -380 | -629 | -669 | -2010 | 2409 | -887 | -1774 | -878 | -2000 | -1199 | -445 | -1175 | -694 | -1118 | 1047 | -53 | -1050 | -2199 | -1795 | 54 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 55(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 55 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 56(K) | 193 | -1311 | 14 | 503 | -1606 | -1067 | 229 | -1289 | 1052 | -1334 | -482 | 797 | 710 | 647 | 530 | 219 | -57 | -935 | -1580 | -977 | 56 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 57(R) | 381 | -1078 | -400 | 189 | -1317 | -1223 | 150 | -885 | 1141 | -1041 | -273 | -15 | -1318 | 514 | 1534 | -224 | -141 | 222 | -1367 | -879 | 57 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 58(A) | 1262 | -1516 | 1112 | 1074 | -1844 | -963 | 80 | -1548 | 308 | -1606 | -781 | 326 | -1230 | 469 | -228 | 238 | -247 | -1170 | -1872 | -1200 | 58 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 59(D) | -668 | -2298 | 2567 | 1387 | -2516 | -916 | -71 | -2332 | -49 | -2279 | -1509 | 475 | -1334 | 882 | -709 | -420 | -683 | -1885 | -2484 | -1642 | 59 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 60(F) | -1602 | -1340 | -2512 | -2455 | 3740 | -2315 | -379 | -478 | -2225 | -175 | -190 | -1874 | -2503 | -1781 | -2079 | -1892 | -1647 | -683 | 210 | 1257 | 60 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 61(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 61 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 62(M) | -1241 | -1016 | -2914 | -2371 | 122 | -2844 | -1644 | 806 | -1999 | 2066 | 2932 | -2273 | -2626 | -1630 | -1957 | -2005 | -1167 | 376 | -1215 | -1025 | 62 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 63(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 63 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 64(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 64 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 65(I) | -439 | -1400 | -571 | 103 | -1664 | -1368 | 1527 | -1291 | 1414 | -314 | -534 | -77 | -1418 | 594 | 1819 | -398 | -324 | -1021 | -1489 | -1036 | 65 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 66(F) | -1902 | -1421 | -2805 | -2692 | 3214 | -2763 | 351 | -984 | -2354 | -657 | -540 | -1668 | -2714 | -1627 | -2106 | -1950 | -1820 | -1082 | 1026 | 3156 | 66 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 67(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 67 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 68(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 68 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 69(D) | -196 | -1649 | 1118 | 1061 | -1949 | -1018 | 231 | -1691 | 1047 | -1647 | -758 | 919 | -1183 | 668 | 786 | -60 | -144 | -1263 | -1826 | -1142 | 69 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 70(Y) | -1667 | -1473 | -2001 | -1964 | 1181 | -2210 | -25 | -1224 | -1658 | 1018 | -871 | -1505 | -2415 | -1423 | -1618 | -1747 | -1692 | -1248 | 501 | 4149 | 70 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| 71(G) | 1432 | -310 | -885 | -866 | -1952 | 2267 | -962 | -1556 | -974 | -1871 | -1097 | -548 | -1176 | -789 | -1180 | 127 | -20 | -901 | -2164 | -1815 | 71 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 72(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 72 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 73(N) | -504 | -1608 | 307 | 389 | -1979 | -1097 | -14 | -1734 | 1180 | -1761 | -1004 | 2578 | -1393 | 350 | 215 | -409 | -498 | -1377 | -1890 | -1303 | 73 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 74(L) | -1081 | -806 | -3000 | -2464 | -132 | -2843 | -1790 | 1457 | -2184 | 2042 | 966 | -2321 | -2664 | -1813 | -2161 | -2002 | -1025 | 1443 | -1417 | -1198 | 74 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 75(E) | 88 | -1806 | 1193 | 1543 | -2082 | -964 | 125 | -1841 | 365 | -1812 | -954 | 1330 | -322 | 537 | -200 | -160 | -295 | -1412 | -2017 | -1284 | 75 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 76(R) | -369 | -1625 | 140 | 1001 | -1955 | -1144 | 172 | -1638 | 765 | -1611 | -784 | 1492 | -1309 | 587 | 1643 | -256 | -302 | -1274 | -1773 | -1195 | 76 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 77(A) | 2326 | -235 | -1178 | -992 | -1593 | -588 | -902 | -857 | -875 | -1381 | -703 | -620 | -1200 | -746 | -1059 | 114 | 1127 | -426 | -1928 | -1562 | 77 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 78(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 78 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 79(K) | -149 | -1571 | 689 | 1005 | -1882 | -1048 | 946 | -1613 | 1386 | -1568 | -672 | 314 | -1171 | 987 | 550 | -26 | -87 | -1190 | -1741 | -1082 | 79 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 80(V) | 995 | -264 | -1540 | -1124 | -837 | -1157 | -824 | 540 | -925 | -450 | 74 | -897 | -1545 | -777 | -1105 | -359 | 819 | 1919 | -1383 | -997 | 80 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 81(M) | -1089 | -847 | -2901 | -2332 | 41 | -2767 | -1601 | 1436 | -2029 | 1495 | 3271 | -2205 | -2566 | -1630 | -1990 | -1898 | -1014 | 653 | -1227 | -1042 | 81 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 82(K) | 758 | -1358 | 30 | 517 | -1633 | -495 | 241 | -1317 | 1032 | -1352 | -498 | 858 | -1194 | 944 | 553 | -51 | -69 | -963 | -1590 | -984 | 82 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 83(M) | -491 | -492 | -1884 | -1331 | -96 | -1923 | -814 | 701 | -1026 | 1207 | 2815 | -1254 | -1949 | -845 | -1137 | -1009 | 548 | 576 | -949 | -635 | 83 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 84(D) | -824 | -2383 | 2964 | 1142 | -2628 | -923 | -210 | -2461 | -314 | -2455 | -1761 | 430 | -1405 | 123 | -1021 | -562 | -876 | -2027 | -2629 | -1790 | 84 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 85(S) | 1394 | -260 | -956 | -822 | -1809 | -507 | -852 | -1408 | -809 | -1720 | -938 | -503 | -1137 | -658 | -1033 | 2235 | 57 | -788 | -2055 | -1662 | 85 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 86(V) | -466 | -415 | -2075 | -1571 | -506 | -1975 | -1108 | 1171 | -1302 | 688 | 460 | -1436 | -2079 | -1152 | -1427 | -1111 | 573 | 2199 | -1304 | -923 | 86 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 87(K) | -401 | -1577 | 34 | 922 | -1932 | -1184 | 156 | -1558 | 2117 | -1563 | -758 | 127 | -1342 | 565 | 523 | -304 | 237 | -1220 | -1742 | -1203 | 87 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 88(I) | -1120 | -818 | -3064 | -2567 | -204 | -2914 | -1888 | 2467 | -2246 | 1556 | 866 | -2411 | -2743 | -1931 | -2224 | -2108 | -1072 | 1115 | -1497 | -1212 | 88 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 89(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 89 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 90(N) | -477 | -1612 | -233 | 247 | -2000 | -1284 | 183 | -1637 | 1365 | -1583 | -780 | 1891 | -1397 | 598 | 1526 | -382 | -381 | -1301 | -1701 | -1216 | 90 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 91(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 91 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 92(L) | -1306 | -1067 | -2981 | -2443 | 125 | -2920 | -1717 | 814 | -2062 | 2337 | 2190 | -2353 | -2682 | -1686 | -2014 | -2092 | -1231 | 368 | -1248 | -1063 | 92 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 93(C) | -206 | 3367 | -2319 | -1919 | -689 | -1494 | -1270 | 951 | -1603 | -153 | 201 | -1455 | -1861 | -1411 | -1625 | -746 | -346 | 2000 | -1422 | -1027 | 93 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 94(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 94 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 95(I) | -274 | -522 | -1274 | -906 | -613 | -1430 | -689 | 1794 | -672 | -125 | 232 | -863 | 1767 | -614 | -872 | -631 | -339 | 493 | -1235 | -798 | 95 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 96(N) | -479 | -1529 | 346 | 390 | -1262 | -1084 | 1651 | -1642 | 280 | -1666 | -940 | 2606 | -1396 | 262 | -86 | -394 | -490 | -1304 | -1493 | -708 | 96 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 97(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 97 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 98(S) | -161 | -1453 | 838 | 607 | -1778 | -999 | 177 | -1491 | 1000 | -1517 | -659 | 304 | 145 | 593 | 16 | 1073 | -129 | -1102 | -1752 | -1097 | 98 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 99(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 99 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 100(K) | 639 | -1359 | 130 | 937 | -1666 | -1054 | 189 | -1344 | 1343 | -1395 | -554 | 234 | -1211 | 599 | 172 | 487 | -116 | -990 | -1644 | -1036 | 100 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 101(E) | -438 | -1909 | 1578 | 1930 | -2183 | -946 | 37 | -1928 | 199 | -1929 | -1110 | 415 | -1271 | 427 | -390 | -260 | 509 | -1512 | -2154 | -1401 | 101 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 102(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 102 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 103(I) | -933 | -617 | -3067 | -2622 | -727 | -2844 | -2139 | 2601 | -2382 | 283 | 375 | -2419 | -2785 | -2186 | -2438 | -2063 | -922 | 2174 | -1934 | -1553 | 103 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 104(E) | 375 | -1460 | 295 | 1605 | -1753 | -1028 | 168 | -1444 | 819 | -1486 | -644 | 282 | 190 | 577 | 63 | -106 | -163 | -1079 | -1731 | -1094 | 104 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 105(I) | -486 | -338 | -2295 | -1717 | 49 | -2053 | -856 | 1705 | -1424 | 1267 | 888 | -1489 | -2030 | -1121 | -1416 | -1138 | -425 | 1093 | -752 | 1040 | 105 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 106(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 106 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 107(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 107 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 108(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 108 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 109(M) | -967 | -770 | -2707 | -2179 | -75 | -2590 | -1515 | 1740 | -1841 | 1002 | 3350 | -2043 | -2485 | -1555 | -1846 | -1742 | -919 | 818 | -1266 | -1006 | 109 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 110(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 110 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 111(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 111 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 112(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 112 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 113(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 113 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 114(I) | 1297 | -396 | -1045 | -533 | -555 | -1309 | -316 | 1303 | -228 | -265 | 313 | -551 | -1491 | -201 | 106 | -396 | -102 | 374 | -1004 | -589 | 114 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 115(V) | 433 | -490 | -819 | 416 | -611 | -1396 | -259 | 391 | -179 | -21 | 288 | -448 | -1513 | -95 | -488 | -437 | -123 | 1568 | -1055 | -615 | 115 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 116(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 116 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 117(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 117 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 118(M) | -825 | -553 | -2869 | -2332 | -347 | -2619 | -1636 | 2067 | -2072 | 614 | 2211 | -2123 | -2524 | -1766 | -2066 | -1762 | -779 | 1949 | -1423 | -1130 | 118 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 119(S) | 1087 | -281 | -851 | -685 | -1876 | 620 | -774 | -1551 | -718 | -1778 | -951 | -428 | -1112 | -546 | -989 | 2116 | 79 | -874 | -2078 | -1684 | 119 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 120(H) | -303 | -1577 | 31 | 461 | -1878 | -1155 | 1852 | -1575 | 1230 | -1543 | -699 | 858 | -1278 | 1692 | 489 | -194 | -226 | -1208 | -1701 | -1118 | 120 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 121(M) | -1179 | -981 | -2799 | -2262 | 103 | -2750 | -1560 | 800 | -1878 | 1813 | 3295 | -2167 | -2570 | -1557 | -1859 | -1910 | -1112 | 400 | -1195 | -971 | 121 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 122(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 122 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 123(V) | -729 | -571 | -2495 | -2034 | 1817 | -2246 | -1008 | 992 | -1765 | 499 | 636 | -1745 | -2283 | -1457 | -1764 | -1410 | -714 | 2175 | -737 | -57 | 123 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 124(V) | 1219 | -338 | -1791 | -1461 | -919 | -1309 | -1142 | 796 | -1253 | -361 | 23 | -1160 | -1724 | -1114 | -1391 | -557 | -284 | 2221 | -1608 | -1213 | 124 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 125(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 125 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 126(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 126 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 127(M) | -964 | -751 | -2752 | -2222 | -95 | -2613 | -1544 | 1928 | -1891 | 980 | 3193 | -2075 | -2502 | -1594 | -1889 | -1765 | -914 | 876 | -1283 | -1026 | 127 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 128(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 128 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 129(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 129 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 130(M) | -415 | -454 | -1730 | -1175 | -135 | -1824 | -711 | 663 | -895 | 1350 | 1822 | -1122 | -1866 | -726 | -1035 | -898 | 1122 | 573 | -924 | -593 | 130 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 131(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 131 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 132(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 132 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 133(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 133 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 134(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 134 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 135(A) | 2048 | -367 | -849 | -680 | -1659 | -627 | -739 | -1190 | -650 | -1511 | -785 | -478 | 1606 | -534 | -899 | 74 | -21 | -698 | -1911 | -1515 | 135 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 136(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 136 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 137(R) | -957 | -1769 | -1130 | -344 | -2309 | -1642 | 117 | -1834 | 1694 | -1695 | -991 | -391 | -1689 | 518 | 2806 | -887 | -779 | -1577 | -1692 | -1419 | 137 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 138(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 138 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 139(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 139 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 140(S) | 752 | -403 | -804 | -361 | -945 | -914 | -314 | -429 | -202 | -754 | 1493 | -350 | -1267 | -115 | -505 | 1610 | 21 | -179 | -1285 | -846 | 140 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 141(N) | -187 | -1264 | 170 | 440 | -1640 | -1019 | 83 | -1319 | 462 | -1408 | -602 | 1650 | -1249 | 1233 | 52 | -142 | 1136 | -974 | -1676 | -1083 | 141 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 142(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 142 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 143(C) | 862 | 3823 | -1939 | -1540 | -778 | -1030 | -977 | 437 | -1267 | -438 | 89 | -1051 | -1495 | -1057 | -1327 | -271 | -71 | 1212 | -1336 | -978 | 143 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 144(H) | -1192 | -1547 | -812 | -781 | -520 | -1557 | 4586 | -1881 | -457 | -1789 | -1357 | -866 | -1913 | -669 | -600 | -1231 | -1258 | -1678 | -918 | -90 | 144 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 145(V) | 635 | -386 | -1965 | -1657 | -921 | -1492 | -1321 | 997 | -1438 | -274 | 47 | -1346 | -1881 | -1309 | -1555 | -752 | -394 | 3522 | -1700 | -1297 | 145 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 146(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 146 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 147(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 147 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

| | | | | | | | | | | | | | | | | | | | | |
|---|---|---|---|---|---|---|---|---|---|---|---|---|---|---|---|---|---|---|---|---|
| 148(I) | -581 | -428 | -2332 | -1778 | -276 | -2205 | -1155 | 1757 | -1518 | 1333 | 715 | -1623 | -2188 | -1273 | -1579 | -1307 | 519 | 1349 | -1155 | -831 | 148 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 149(K) | -594 | -1483 | -781 | -58 | -1796 | -1470 | 168 | -1358 | 2205 | -248 | -622 | -193 | -1513 | 562 | 1482 | -556 | -460 | -1115 | -1533 | -1139 | 149 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 150(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 150 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 151(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 151 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 152(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 152 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 153(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 153 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 154(Q) | -552 | -1780 | 447 | 1123 | -2047 | -1104 | 22 | -1774 | 497 | -1764 | -1012 | 208 | -1382 | 3726 | 153 | -415 | -517 | -1434 | -1946 | -1334 | 154 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 155(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 155 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 156(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 156 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 157(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 157 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 158(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 158 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 159(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 159 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 160(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 160 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 161(E) | -704 | -2274 | 1609 | 2494 | -2517 | -929 | -118 | -2327 | -117 | -2302 | -1553 | 440 | -1360 | 238 | -777 | -462 | -729 | -1891 | -2491 | -1671 | 161 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 162(A) | 2429 | -274 | -996 | -928 | -1860 | 817 | -956 | -1435 | -970 | -1770 | -1001 | -575 | -1171 | -793 | -1166 | 139 | 6 | -817 | -2094 | -1749 | 162 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 163(A) | 2297 | -276 | -974 | -901 | -1869 | 1169 | -940 | -1456 | -949 | -1779 | -1003 | -559 | -1165 | -770 | -1154 | 146 | 12 | -829 | -2099 | -1749 | 163 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 164(W) | -599 | -435 | -2434 | -1855 | 242 | -2141 | -835 | 1806 | -1510 | 1433 | 984 | -1586 | -2094 | -1181 | -1459 | -1234 | -532 | 589 | 2084 | -142 | 164 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | | |
|---|---|---|---|---|---|---|---|---|---|---|---|---|---|---|---|---|---|---|---|---|---|
| 165(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 165 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 166(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 166 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 167(F) | -889 | -760 | -2459 | -2062 | 2900 | -2246 | -675 | 598 | -1781 | 541 | 608 | -1693 | -2303 | -1420 | -1756 | -1432 | -885 | 1145 | -260 | 608 | 167 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 168(D) | -214 | -1405 | 1586 | 576 | -1945 | -895 | -13 | -1678 | 183 | -1732 | -907 | 283 | 1136 | 366 | -351 | 870 | -261 | -1244 | -1978 | -1306 | 168 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 169(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 169 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 170(Q) | -552 | -1780 | 447 | 1123 | -2047 | -1104 | 22 | -1774 | 497 | -1764 | -1012 | 208 | -1382 | 2726 | 153 | -415 | -517 | -1434 | -1946 | -1334 | 170 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 171(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 171 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 172(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 172 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 173(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 173 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 174(V) | -177 | -366 | -1747 | -1376 | -835 | -1408 | -1060 | 842 | -1132 | -278 | 103 | -1145 | -1767 | -1025 | -1282 | -633 | 1362 | 2195 | -1521 | -1119 | 174 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 175(A) | 2033 | -283 | -945 | -876 | -1891 | 1659 | -933 | -1488 | -939 | -1802 | -1022 | -547 | -1163 | -758 | -1150 | 148 | 11 | -850 | -2114 | -1762 | 175 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 176(I) | -932 | -615 | -3069 | -2624 | -731 | -2846 | -2141 | 2579 | 2386 | 277 | 371 | -2421 | -2787 | -2189 | -2441 | -2065 | -921 | 2203 | -1937 | -1555 | 176 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 177(A) | 2214 | -291 | -1447 | -1169 | -1154 | -884 | -959 | 74 | -982 | -736 | -262 | -833 | -1414 | -858 | -1151 | -156 | -103 | 1000 | -1694 | -1298 | 177 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 178(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 178 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 179(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 179 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 180(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 180 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 181(P) | -370 | -1016 | -600 | -377 | -1687 | -1102 | -432 | -1453 | 72 | -1566 | -902 | -444 | 2899 | -166 | 707 | -467 | -495 | -1110 | -1727 | -1330 | 181 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 182(F) | -1055 | -829 | -2811 | -2263 | 2475 | -2617 | -1120 | 681 | -1966 | 1473 | 2107 | -2020 | -2452 | -1505 | -1885 | -1736 | -975 | 308 | -672 | -125 | 182 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 183(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 183 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 184(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 184 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 185(I) | -1143 | -842 | -3082 | -2578 | -159 | -2929 | -1882 | 2333 | -2257 | 1719 | 917 | -2424 | -2743 | -1919 | -2225 | -2119 | -1091 | 1050 | -1466 | -1201 | 185 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 186(A) | 2106 | -237 | -1021 | -871 | -1767 | -506 | -866 | -1350 | -841 | -1674 | -895 | -527 | -1137 | -683 | -1055 | 1564 | 68 | -746 | -2025 | -1642 | 186 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 187(L) | -1259 | -980 | -3063 | -2554 | 2 | -2960 | -1832 | 1563 | -2204 | 2258 | 1077 | -2433 | -2742 | -1834 | -2157 | -2152 | -1198 | 733 | -1358 | -1124 | 187 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 188(M) | -1262 | -1030 | -2945 | -2401 | 126 | -2872 | -1670 | 808 | -2031 | 2152 | 2757 | -2305 | -2645 | -1652 | -1984 | -2035 | -1186 | 370 | -1224 | -1041 | 188 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 189(V) | -851 | -606 | -2839 | -2414 | -730 | -2622 | -1965 | 1760 | -2148 | 220 | 330 | -2216 | -2651 | -1999 | -2230 | -1847 | -862 | 2736 | -1875 | -1456 | 189 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 190(G) | -758 | -1103 | -1313 | -1487 | -2460 | 3333 | -1562 | -2502 | -1720 | -2644 | -2081 | -1324 | -1775 | -1590 | -1790 | -958 | -1093 | -1921 | -2198 | -2279 | 190 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 191(A) | 1930 | -244 | -1003 | -848 | -1775 | -507 | -852 | -1365 | -819 | -1681 | -899 | -516 | -1135 | -664 | -1041 | 1787 | 68 | -757 | -2027 | -1642 | 191 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 192(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 192 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 193(C) | 763 | 1755 | -1469 | -973 | -510 | -1023 | -517 | 135 | -756 | -355 | 310 | -727 | -1369 | -559 | -904 | 283 | 843 | 1335 | -953 | -582 | 193 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 194(G) | -758 | -1103 | -1313 | -1487 | -2460 | 3333 | -1562 | -2502 | -1720 | -2644 | -2081 | -1324 | -1775 | -1590 | -1790 | -958 | -1093 | -1921 | -2198 | -2279 | 194 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 195(R) | 94 | -1197 | -868 | -342 | -1810 | -1279 | -102 | -1370 | 814 | -1456 | -793 | -379 | -1529 | 246 | 2803 | -535 | -501 | -1085 | -1661 | -1286 | 195 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| 196(P) | -92 | -706 | -669 | -681 | -2057 | -743 | -909 | -1842 | -843 | -2030 | -1299 | -596 | 3040 | -724 | -1088 | -252 | -384 | -1257 | -2095 | -1813 | 196 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 197(G) | -758 | -1103 | -1313 | -1487 | -2460 | 3331 | -1562 | -2502 | -1720 | -2644 | -2081 | -1324 | -1775 | 1590 | -1790 | -958 | -1093 | -1921 | -2198 | -2279 | 197 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 198(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 198 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 199(L) | -1198 | -902 | -3098 | -2586 | -74 | -2954 | -1866 | 1998 | -2259 | 2016 | 1009 | -2444 | -2745 | -1887 | -2211 | -2142 | -1140 | 903 | -1411 | -1174 | 199 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 200(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 200 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 201(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 201 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 202(C) | -608 | 5196 | -2368 | -2362 | -1635 | -1253 | -1702 | -987 | -2034 | -1540 | -1191 | -1745 | -1831 | -1953 | -1922 | -934 | -927 | -770 | -1855 | -1692 | 202 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 203(S) | 1057 | -274 | -916 | -815 | -1832 | -508 | -865 | -1436 | -820 | -1752 | -977 | -502 | -1145 | -674 | -1039 | 2412 | 41 | -810 | -2079 | -1679 | 203 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 204(V) | -925 | -616 | -3000 | -2497 | -527 | -2814 | -1921 | 1840 | -2252 | 949 | 560 | -2316 | -2703 | -1995 | -2284 | -1988 | -889 | 2430 | -1695 | -1364 | 204 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 205(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 205 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 206(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 206 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 207(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 207 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 208(T) | -323 | -1596 | 1187 | 1153 | -1884 | -973 | 55 | -1567 | 265 | -1645 | -837 | 335 | -1257 | 437 | -273 | -205 | 1701 | -1205 | -1920 | -1239 | 208 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 209(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 209 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 210(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 210 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 211(E) | -293 | -1582 | 365 | 1545 | -1897 | -1040 | 140 | -1597 | 1076 | -1610 | -776 | 280 | -1253 | 546 | 110 | 939 | -255 | -1221 | -1825 | -1187 | 211 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 212(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 212 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 213(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 213 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 214(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 214 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 215(R) | -664 | -1241 | -1101 | -424 | -1173 | -1559 | -60 | -804 | 818 | 181 | -343 | -483 | -1657 | 246 | 2582 | -741 | -578 | -719 | -1332 | -877 | 215 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 216(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 216 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 217(F) | -707 | -668 | -1832 | -1360 | 2343 | -1971 | 1711 | -39 | -1065 | 993 | 361 | -1104 | -1992 | -805 | -1140 | -1047 | -642 | -73 | 294 | 1256 | 217 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 218(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 218 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 219(C) | 1104 | 2193 | -1323 | -968 | -1444 | 651 | -781 | -1064 | -812 | -1343 | -561 | -576 | -1127 | -634 | -1023 | 1662 | 138 | -550 | -1740 | -1381 | 219 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 220(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 220 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 221(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 221 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 222(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 222 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 223(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 223 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 224(I) | -929 | -611 | -3073 | -2627 | -742 | -2849 | -2145 | 2502 | -2391 | 262 | 361 | -2423 | -2789 | -2195 | -2447 | -2067 | -918 | 2293 | -1944 | -1560 | 224 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 225(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 225 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 226(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 226 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| 227(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 227 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 228(G) | -758 | -1103 | -1313 | -1487 | -2460 | 3333 | -1562 | -2502 | -1720 | -2644 | -2081 | -1324 | -1775 | -1590 | -1790 | -958 | -1093 | -1921 | -2198 | -2279 | 228 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 229(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 229 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 230(E) | -717 | -2337 | 2049 | 2259 | -2571 | -918 | -117 | -2393 | -138 | -2352 | -1602 | 461 | -1357 | 240 | -821 | -464 | -744 | -1944 | -2542 | -1698 | 230 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 231(K) | 397 | -1331 | 0 | 518 | -1619 | -1070 | 250 | -1306 | 1059 | -1341 | -481 | 786 | 38 | 674 | 793 | 224 | -41 | -946 | -1579 | -969 | 231 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 232(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 232 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 233(F) | -1602 | -1340 | -2512 | -2455 | 3740 | -2315 | -379 | -478 | -2225 | -175 | -190 | -1874 | -2503 | -1781 | -2079 | -1892 | -1647 | -683 | 210 | 1257 | 233 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 234(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 234 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 235(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 235 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 236(G) | -758 | -1103 | -1313 | -1487 | -2460 | 3333 | -1562 | -2502 | -1720 | -2644 | -2081 | -1324 | -1775 | -1590 | -1790 | -958 | -1093 | -1921 | -2198 | -2279 | 236 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 237(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 237 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 238(D) | -1130 | -2063 | 3441 | 243 | -2502 | -1157 | -662 | -2514 | -873 | -2578 | -2029 | -96 | -1658 | -421 | -1434 | -970 | -1239 | -2138 | -2388 | -1915 | 238 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 239(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 239 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 240(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 240 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 241(W) | -1926 | -1577 | -2416 | -2370 | 192 | -2070 | -795 | -1602 | -1882 | -1347 | -1210 | -2018 | -2383 | -1854 | -1777 | -2150 | -1992 | -1643 | 5696 | 560 | 241 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 242(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 242 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | |
|---|---|---|---|---|---|---|---|---|---|---|---|---|---|---|---|---|---|---|---|
| 243(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 243 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 244(G) | 1814 | -291 | -924 | -870 | -1911 | 1934 | -940 | -1512 | -947 | -1824 | -1045 | -544 | -1165 | -764 | -1158 | 144 | 3 | -867 | -2131 | -1779 | 244 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 245(F) | -1602 | -1340 | -2512 | -2455 | 3740 | -2315 | -379 | -478 | -2225 | -175 | -190 | -1874 | -2503 | -1781 | -2079 | -1892 | -1647 | -683 | 210 | 1257 | 245 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 246(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 246 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 247(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 247 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 248(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 248 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 249(C) | 1738 | 3050 | -1597 | -1286 | -1304 | -553 | -920 | -809 | -1074 | -1196 | -460 | -726 | -1161 | -870 | -1191 | 1014 | 128 | -366 | -1662 | -1327 | 249 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 250(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 250 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 251(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 251 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 252(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 252 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 253(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 253 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 254(G) | -758 | -1103 | -1313 | -1487 | -2460 | 3333 | -1562 | -2502 | -1720 | -2644 | -2081 | -1324 | -1775 | -1590 | -1790 | -958 | -1093 | -1921 | -2198 | -2279 | 254 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 255(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 255 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 256(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 256 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 257(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 257 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | | |
|---|---|---|---|---|---|---|---|---|---|---|---|---|---|---|---|---|---|---|---|---|---|
| 258(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 258 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 259(F) | -1868 | -1403 | -2783 | -2661 | 3327 | -2745 | 337 | -941 | -2325 | -619 | -501 | -1662 | -2699 | -1613 | -2087 | -1932 | -1788 | -1044 | 1008 | 2959 | 259 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 260(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 260 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 261(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 261 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 262(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 262 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 263(S) | 1057 | -279 | -958 | -668 | -1633 | -564 | -673 | -1214 | -584 | -1503 | -711 | -437 | -1133 | -450 | -856 | 1823 | 1396 | -673 | -1872 | -1473 | 263 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 264(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 264 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 265(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 265 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 266(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 266 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 267(A) | 1795 | -308 | -1596 | -1269 | -985 | -1098 | -1001 | 487 | -1073 | -504 | -67 | -970 | -1559 | -938 | -1234 | -348 | -181 | 1695 | -1593 | -1199 | 267 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 268(M) | -485 | -617 | -1471 | -910 | -110 | -1822 | -557 | 403 | -543 | 1390 | 2375 | -948 | -1827 | 805 | -720 | -871 | -418 | 228 | -912 | -567 | 268 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 269(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 269 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 270(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 270 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 271(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 271 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 272(A) | 1700 | -251 | -1028 | -731 | -1556 | -572 | -693 | -1113 | -631 | -1425 | -647 | -472 | -1141 | -490 | -887 | 934 | 1645 | -603 | -1818 | -1429 | 272 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 273(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 273 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| 274(G) | 307 | -371 | -641 | -650 | -1997 | 2231 | -857 | -1752 | -837 | -1971 | -1163 | -431 | -1164 | -654 | -1088 | 1356 | -32 | -1032 | -2185 | -1778 | 274 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 275(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 275 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 276(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 276 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 277(M) | -965 | -982 | -2125 | -1844 | -276 | -2022 | -1302 | 373 | -1390 | 610 | 4141 | -1701 | -2229 | -1356 | -1425 | -1444 | -1028 | 126 | -1279 | -880 | 277 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 278(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 278 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 279(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 279 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 280(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 280 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 281(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 281 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 282(A) | 1943 | -244 | -1004 | -849 | -1775 | -507 | -853 | -1364 | -820 | -1681 | -899 | -516 | -1135 | -665 | -1041 | 1773 | 68 | -756 | -2027 | -1641 | 282 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 283(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 283 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 284(C) | -608 | 3196 | -2368 | -2362 | -1635 | -1253 | -1702 | -987 | -2034 | -1540 | -1191 | -1745 | -1831 | -1953 | -1922 | -934 | -927 | -770 | -1855 | -1692 | 284 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 285(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 285 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 286(Y) | -1934 | -1442 | -2813 | -2708 | 2952 | -2777 | 363 | -1027 | -2370 | -696 | -580 | -1669 | -2726 | -1633 | -2118 | -1965 | -1850 | -1121 | 1040 | 3463 | 286 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 287(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 287 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 288(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 288 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 289(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 289 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 290(A) | 2297 | -276 | -974 | -901 | -1869 | 1169 | -940 | -1456 | -949 | -1779 | -1003 | -559 | -1165 | -770 | -1154 | 146 | 12 | -829 | -2099 | -1749 | 290 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 291(A) | 2106 | -237 | -1021 | -871 | -1767 | -506 | -866 | -1350 | -841 | -1674 | -895 | -527 | -1137 | -683 | -1055 | 1564 | 68 | -746 | -2025 | -1642 | 291 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 292(G) | -758 | -1103 | -1313 | -1487 | -2460 | 3333 | -1562 | -2502 | -1720 | -2644 | -2081 | -1324 | -1775 | -1590 | -1790 | -958 | -1093 | -1921 | -2198 | -2279 | 292 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 293(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 293 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 294(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 294 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 295(G) | -758 | -1103 | -1313 | -1487 | -2460 | 3333 | -1562 | -2502 | -1720 | -2644 | -2081 | -1324 | -1775 | -1590 | -1790 | -958 | -1093 | -1921 | -2198 | -2279 | 295 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 296(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 296 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 297(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 297 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 298(N) | -637 | -1349 | -5 | -148 | -1773 | -1078 | -624 | -1965 | -499 | -2112 | -1514 | 3486 | -1574 | -435 | -810 | -661 | -818 | -1560 | -1900 | -1327 | 298 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 299(G) | -758 | -1103 | -1313 | -1487 | -2460 | 3333 | -1562 | -2502 | -1720 | -2644 | -2081 | -1324 | -1775 | -1590 | -1790 | -958 | -1093 | -1921 | -2198 | -2279 | 299 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 300(S) | 1375 | -276 | -871 | -686 | -1859 | 1354 | -765 | -1534 | -710 | -1758 | -930 | -428 | -1109 | -536 | -985 | 1511 | 86 | -862 | -2062 | -1669 | 300 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 301(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 301 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 302(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 302 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 303(C) | -608 | 5196 | -2368 | -2362 | -1635 | -1253 | -1702 | -987 | -2034 | -1540 | -1191 | -1745 | -1831 | -1953 | -1922 | -934 | -927 | -770 | -1855 | -1692 | 303 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 304(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 304 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 305(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 305 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 306(M) | -837 | -618 | -2708 | -2158 | -178 | -2529 | -1480 | 1612 | -1882 | 830 | 3103 | -1991 | -2434 | -1567 | -1889 | -1657 | -786 | 1490 | -1279 | -1018 | 306 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 307(P) | 180 | -461 | -726 | -522 | -1558 | -715 | -605 | -1079 | -438 | -1388 | -684 | -414 | 2065 | -378 | -702 | 3 | 1812 | -655 | -1805 | -1384 | 307 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 308(G) | 293 | -379 | -630 | -667 | -2009 | 2397 | -884 | -1772 | -875 | -1997 | -1196 | -444 | -1174 | -691 | -1115 | 1071 | -51 | -1049 | -2198 | -1793 | 308 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 309(A) | 2330 | -226 | -1055 | -939 | -1760 | -504 | -915 | -1313 | -910 | -1669 | -905 | -561 | -1146 | -752 | -1102 | 1042 | 58 | -721 | -2034 | -1657 | 309 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 310(V) | -836 | -639 | -2662 | -2225 | -512 | 2495 | -1702 | -1367 | -1909 | 852 | 487 | -2046 | -2529 | -1758 | -1977 | -1708 | -841 | 2598 | -1613 | -1195 | 310 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 311(P) | 2 | -489 | -1031 | -785 | -1108 | -956 | -714 | -305 | -612 | -789 | -314 | -653 | 2544 | -567 | -828 | -238 | -203 | 890 | -1569 | -1119 | 311 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 312(S) | 311 | -370 | -673 | -637 | -1958 | 759 | -820 | -1708 | -773 | -1924 | -1114 | -425 | -1160 | -607 | -1031 | 2407 | -18 | -1005 | -2145 | -1732 | 312 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 313(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 313 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 314(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 314 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 315(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 315 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 316(A) | 1567 | -924 | 62 | 917 | -1556 | -884 | -105 | -1178 | 129 | -1361 | -576 | 63 | -1226 | 230 | -299 | 637 | -121 | -810 | -1700 | -1148 | 316 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 317(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 317 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 318(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 318 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 319(G) | 1867 | -289 | -929 | -871 | -1906 | 1873 | -938 | -1506 | -944 | -1818 | -1039 | -545 | -1165 | -761 | -1155 | 146 | 5 | -862 | -2126 | -1774 | 319 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 320(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 320 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 321(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 321 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 322(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 322 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 323(I) | -1123 | -822 | -3067 | -2569 | -197 | -2917 | -1887 | 2447 | -2248 | 1582 | 875 | -2413 | -2743 | -1929 | -2225 | -2110 | -1075 | 1105 | -1492 | -1210 | 323 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 324(C) | 1325 | 3551 | -1712 | -1385 | -1146 | -650 | -942 | -408 | -1136 | -968 | -296 | -812 | -1233 | -935 | -1223 | 78 | 996 | -79 | -1561 | -1227 | 324 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 325(M) | 79 | -386 | -845 | -374 | -744 | -1030 | -267 | -221 | -185 | -543 | 2173 | -382 | -1318 | -104 | -470 | 1220 | 702 | -27 | -1118 | -688 | 325 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 326(M) | 433 | -323 | -1005 | -574 | -677 | -1039 | -385 | -108 | -368 | -444 | 2884 | -511 | -1361 | -278 | -604 | 837 | -22 | 63 | -1103 | -689 | 326 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 327(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 327 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 328(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 328 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 329(L) | -1060 | -771 | -3035 | -2500 | -172 | -2852 | -1816 | 1635 | -2228 | 1939 | 929 | -2342 | -2674 | -1854 | -2200 | -2012 | -1004 | 1515 | -1444 | -1221 | 329 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 330(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 330 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 331(C) | -206 | 3367 | -2319 | -1919 | -689 | -1494 | -1270 | -951 | -1603 | -153 | 201 | -1455 | -1861 | -1411 | -1625 | -746 | -346 | 2000 | -1422 | -1027 | 331 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 332(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 332 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 333(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 333 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 334(A) | 2078 | -244 | -950 | -773 | -1815 | 720 | -810 | -1474 | -782 | -1719 | -902 | -471 | -1112 | -603 | -1033 | 1059 | 91 | -820 | -2040 | -1661 | 334 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 335(N) | 73 | 2062 | -715 | -459 | -1269 | -837 | -491 | -919 | -332 | -1269 | -568 | 2714 | -1301 | -294 | -604 | -98 | -125 | -565 | -1556 | -1049 | 335 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 336(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 336 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 337(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 337 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 338(T) | 1532 | -257 | -1123 | -898 | -1523 | -620 | -822 | -803 | -773 | -1312 | -629 | -583 | -1207 | -654 | -978 | 96 | 2243 | -396 | -1854 | -1476 | 338 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 339(F) | -1602 | -1340 | -2512 | -2455 | 3740 | -2315 | -379 | -478 | -2225 | -175 | -190 | -1874 | -2503 | -1781 | -2079 | -1892 | -1647 | -683 | 210 | 1257 | 339 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 340(S) | 337 | -317 | -860 | -701 | -1734 | -558 | -753 | -1328 | -649 | -1636 | -869 | -457 | -1159 | -543 | -888 | 2313 | 1114 | -760 | -1977 | -1560 | 340 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 341(H) | -1192 | -1547 | -812 | -781 | -520 | -1557 | 4586 | -1881 | -457 | -1789 | -1357 | -866 | -1913 | -669 | -600 | -1231 | -1258 | -1678 | -918 | -90 | 341 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 342(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 342 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 343(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 343 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 344(M) | -962 | -721 | -2832 | -2307 | -165 | -2664 | -1626 | 2366 | -1987 | 903 | 2608 | -2145 | -2549 | -1688 | -1979 | -1822 | -914 | 1020 | -1353 | -1088 | 344 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 345(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1745 | -1529 | 345 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 346(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | -346 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 347(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 347 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 348(A) | 1597 | -978 | 151 | 960 | -1634 | 273 | -124 | -1266 | 89 | -1438 | -652 | 85 | -1234 | 211 | -352 | -94 | -159 | -886 | -1767 | -1206 | 348 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 349(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 349 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 350(M) | -441 | -455 | -1810 | -1252 | -103 | -1867 | -749 | 679 | -965 | 1297 | 2343 | -1183 | -1898 | -782 | -1087 | -944 | 877 | 573 | -915 | -594 | 350 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 351(L) | -1259 | -980 | -3063 | -2554 | 2 | -2960 | -1832 | 1563 | -2204 | 2258 | 1077 | -2433 | -2742 | -1834 | -2157 | -2152 | -1198 | 733 | -1358 | -1124 | 351 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 352(M) | -73 | -469 | -1004 | -675 | -744 | 1014 | -512 | -220 | -464 | -456 | 3139 | -614 | -1458 | -414 | -675 | -331 | -188 | -84 | -1209 | -778 | 352 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 353(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 353 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 354(M) | -997 | -819 | -2602 | -2110 | 2400 | -2453 | -884 | 573 | -1803 | 986 | 2860 | -1838 | -2371 | -1404 | -1756 | -1593 | -939 | 253 | -467 | 230 | 354 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 355(L) | -1198 | -902 | -3098 | -2586 | -74 | -2954 | -1866 | 1998 | -2259 | 2016 | 1009 | -2444 | -2745 | -1887 | -2211 | -2142 | -1140 | 903 | -1411 | -1174 | 355 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 356(P) | 1545 | -393 | -808 | -668 | -1689 | -637 | -750 | -1218 | -653 | -1539 | -824 | -478 | 2324 | -545 | -899 | 53 | -48 | -726 | -1936 | -1539 | 356 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 357(G) | -758 | -1103 | -1313 | -1487 | -2460 | 3331 | -1562 | -2502 | -1720 | 2607 | 742 | -2168 | -2539 | -1724 | -1835 | -1992 | -1384 | 130 | -1284 | -897 | 318 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 358(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 358 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 359(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 359 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 360(F) | -1902 | -1421 | -2805 | -2692 | 3214 | -2763 | 351 | -984 | -2354 | -657 | -540 | -1668 | -2714 | -1627 | -2106 | -1950 | -1820 | -1082 | 1026 | 3156 | 360 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 361(I) | -1076 | -780 | -3002 | -2529 | -309 | -2874 | -1898 | 2697 | -2198 | 1168 | 740 | -2371 | -2742 | -1949 | -2205 | -2081 | -1040 | 1240 | -1569 | -1227 | 361 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 362(F) | -151 | -497 | -1152 | -820 | 2062 | -1206 | -264 | -329 | -685 | -526 | -9 | -681 | -1538 | -520 | -889 | 1555 | -260 | -181 | -431 | 409 | 362 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 363(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 363 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 264(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 364 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 365(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 365 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 366(S) | 1123 | -271 | -926 | -817 | -1828 | -508 | -863 | -1430 | -818 | -1746 | -969 | -502 | -1143 | -671 | -1038 | 2382 | 45 | -805 | -2074 | -1676 | 366 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 367(A) | 2139 | -236 | -1024 | -877 | -1766 | -505 | -870 | -1347 | -846 | -1673 | -895 | -530 | -1137 | -689 | -1059 | 1515 | 68 | -744 | -2025 | -1643 | 367 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 368(V) | -151 | -569 | -631 | 524 | -788 | -1293 | -269 | 234 | -134 | -481 | 122 | -371 | -1478 | -70 | -451 | -389 | 637 | 1708 | -1201 | -747 | 368 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 369(P) | -478 | -1420 | 327 | 1138 | -1929 | -1032 | -248 | -1622 | -3 | -1747 | -1039 | 36 | 2562 | 70 | -402 | -436 | -543 | -1278 | -1965 | -1426 | 369 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 370(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 370 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 371(Y) | -806 | -794 | -1826 | -1397 | 917 | -2006 | -90 | -29 | -1025 | 35 | 1798 | -1154 | -2057 | -849 | -1103 | -1127 | -760 | -95 | 211 | 3273 | 371 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 372(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 372 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 373(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 373 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 374(M) | -204 | -445 | -1398 | -949 | -453 | -1403 | -637 | 369 | -636 | 129 | 3007 | -865 | -1648 | -574 | -809 | -563 | 1278 | 377 | -1116 | -731 | 374 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 375(F) | -1602 | -1340 | -2512 | -2455 | 3740 | -2315 | -379 | -478 | -2225 | -175 | -190 | -1874 | -2503 | -1781 | -2079 | -1892 | -1647 | -683 | 210 | 1257 | 375 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 376(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 376 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 377(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 377 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 378(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 378 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 379(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 379 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 380(M) | -79 | -344 | -907 | 352 | 1390 | -1364 | -137 | 182 | -190 | -87 | 1450 | -439 | -1442 | -63 | -461 | -376 | 598 | 278 | -733 | -299 | 380 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 381(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 381 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 382(A) | 1918 | -240 | -1121 | -794 | -1248 | 520 | -675 | -589 | -672 | -1071 | -369 | -547 | -1218 | -526 | -907 | 65 | 56 | 766 | -1598 | -1207 | 382 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 383(E) | -411 | -1179 | -46 | 1823 | -1097 | -1265 | -120 | -540 | 187 | 648 | -221 | -83 | -1466 | 183 | -172 | -447 | -380 | -443 | -1459 | -905 | 383 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 384(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 384 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 385(F) | -1902 | -1421 | -2805 | -2692 | 3214 | -2763 | 351 | -984 | -2354 | -657 | -540 | -1668 | -2714 | -1627 | -2106 | -1950 | -1820 | -1082 | 1026 | 3156 | 385 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 386(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 386 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 387(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 387 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 388(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 388 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 389(N) | -199 | -701 | -549 | -93 | -228 | -1316 | 21 | 533 | 64 | -536 | 109 | 1814 | -1432 | 121 | -268 | -348 | -154 | -118 | -681 | 1083 | 389 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 390(V) | -596 | -427 | -2444 | -1942 | -648 | -2270 | -1439 | 1955 | -1702 | 78 | 364 | -1768 | -2320 | -1523 | -1801 | -1418 | 532 | 2258 | -1522 | -1137 | 390 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 391(M) | -1151 | -859 | -3123 | -2554 | 25 | -2901 | -1760 | 1894 | -2267 | 1875 | 2113 | -2393 | -2661 | -1798 | -2177 | -2046 | -1074 | 735 | -1288 | -1136 | 391 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 392(Q) | -513 | -1819 | 522 | 1560 | -2087 | -1069 | 43 | -1821 | 462 | -1801 | -1025 | 265 | -1348 | 2403 | 72 | -362 | -480 | -1458 | -1986 | -1342 | 392 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 393(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 393 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 394(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 394 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 395(L) | -1306 | -1067 | -2981 | -2443 | 125 | -2920 | -1717 | 814 | -2062 | 2337 | 2190 | -2353 | -2682 | -1686 | -2014 | -2092 | -1231 | 368 | -1248 | -1063 | 395 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 396(M) | 872 | -604 | -643 | -123 | -730 | -1240 | -67 | -190 | 798 | -479 | 2200 | -252 | -1378 | 160 | -90 | -281 | -76 | -42 | -1061 | -617 | 396 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 397(V) | -916 | -603 | -3047 | -2601 | -754 | -2826 | -2126 | 2255 | -2365 | 237 | 345 | -2398 | -2775 | -2177 | -2427 | -2043 | -906 | 2508 | -1944 | -1553 | 397 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 398(D) | -673 | -2181 | 2496 | 794 | -2461 | -904 | -143 | -2337 | -175 | -2319 | -1575 | 1933 | -1355 | 203 | -844 | -448 | -722 | -1882 | -2482 | -1647 | 398 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 399(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 399 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 400(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 400 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 401(L) | -1198 | -902 | -3098 | -2586 | -74 | -2954 | -1866 | 1998 | -2259 | 2016 | 1009 | -2444 | -2745 | -1887 | -2211 | -2142 | -1140 | 903 | -1411 | -1174 | 401 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 402(R) | -345 | -1126 | -591 | 42 | -1183 | -1345 | 1446 | -901 | 819 | -996 | 1243 | -126 | -1412 | 479 | 1981 | -372 | -253 | -690 | -1261 | -760 | 402 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 403(P) | -934 | -1220 | -1352 | -1451 | -2187 | -1314 | -1456 | -2160 | -1488 | -2268 | -1827 | -1359 | 1760 | -1471 | -1571 | -1129 | -1216 | -1780 | -2050 | -2023 | 403 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 404(V) | -886 | -604 | -2944 | -2505 | -743 | -2731 | -2045 | 1944 | -2256 | 229 | 340 | -2308 | -2716 | -2086 | -2330 | -1950 | -884 | 2675 | -1910 | -1506 | 404 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 405(T) | -79 | -1241 | 710 | 507 | -1575 | -1016 | 183 | -1259 | 542 | -1330 | -485 | 230 | -1179 | 590 | 737 | 676 | 1004 | -901 | -1599 | -987 | 405 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 406(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 406 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 407(E) | 39 | -1704 | 551 | 2063 | -1995 | -1015 | 71 | -1696 | 401 | -1718 | -915 | 313 | -1287 | 1274 | -58 | -256 | -368 | -1326 | -1952 | -1286 | 407 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 408(E) | -414 | -1855 | 1337 | 2003 | -2133 | -952 | 45 | -1867 | 223 | -1879 | -1060 | 402 | -1266 | 436 | -354 | -246 | 592 | -1459 | -2110 | -1370 | 408 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 409(V) | -82 | -237 | -1362 | -829 | -406 | -1408 | -463 | 1109 | -622 | -139 | 448 | -766 | -1572 | -466 | -821 | 288 | 937 | 1440 | -906 | -511 | 409 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 410(I) | -1016 | -805 | -2637 | -2367 | -591 | -2470 | -1853 | 3039 | -2040 | 329 | 346 | -2180 | -2589 | -1943 | -2070 | -1879 | -1051 | 1184 | -1698 | -1261 | 410 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 411(K) | 1191 | -905 | -299 | 140 | -1432 | -1011 | -7 | -980 | 1412 | -1186 | -412 | -29 | -1257 | 344 | 101 | -104 | 626 | -667 | -1531 | -1026 | 411 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 412(I) | 442 | -488 | -2154 | -1781 | -680 | -1947 | -1383 | 2623 | -1524 | 86 | 307 | -1582 | -2159 | -1402 | -1631 | -1169 | -575 | 1239 | -1576 | -1178 | 412 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 413(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 413 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 414(N) | -406 | -1604 | 364 | 514 | -1650 | -1088 | 1550 | -1590 | 512 | -1604 | -816 | 2266 | -1324 | 905 | 133 | -295 | -367 | -1249 | -1692 | -1010 | 414 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 415(K) | -1028 | -1686 | -800 | -442 | -2171 | -1521 | -263 | -1873 | 3103 | -1859 | -1251 | -547 | -1750 | 74 | 599 | -1004 | -972 | -1620 | -1812 | -1528 | 415 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 416(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 416 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 417(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 417 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 418(R) | -426 | -1022 | -965 | -360 | -1251 | -1374 | -109 | -634 | 663 | -894 | -340 | -418 | -1549 | 198 | 2485 | -538 | -408 | 540 | -1406 | -969 | 418 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 419(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 419 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 420(I) | -1039 | -725 | -3101 | -2580 | -296 | -2896 | -1918 | 2322 | -2317 | 1504 | 807 | -2405 | -2727 | -1971 | -2296 | -2068 | -990 | 1488 | -1558 | -1305 | 420 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 421(Q) | -862 | -1548 | -321 | -247 | -1672 | -1336 | -419 | -1721 | 130 | -1660 | -1161 | -427 | -1678 | 3540 | -59 | -855 | -904 | -1495 | -1728 | -1237 | 421 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 422(A) | 2439 | -274 | -998 | -931 | -1859 | 786 | -957 | -1433 | -972 | -1769 | -1001 | -577 | -1172 | -795 | -1167 | 139 | 6 | -816 | -2094 | -1749 | 422 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 423(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 423 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 424(F) | -1602 | -1340 | -2512 | -2455 | 3740 | -2315 | -379 | -478 | -2225 | -175 | -190 | -1874 | -2503 | -1781 | -2079 | -1892 | -1647 | -683 | 210 | 1257 | 424 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 425(E) | 394 | -1564 | 893 | 1329 | -1847 | -1017 | 212 | -1570 | 575 | -1566 | -695 | 332 | -1188 | 639 | 992 | -66 | -138 | -1170 | -1778 | -1108 | 425 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 426(E) | -547 | -2038 | 1492 | 1544 | -2334 | 1402 | -46 | -2115 | 24 | -2100 | -1309 | 431 | -1308 | 325 | -605 | -346 | -562 | -1682 | -2320 | -1536 | 426 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 427(L) | -1304 | -1065 | -2981 | -2443 | 126 | -2919 | -1716 | 814 | -2063 | 2331 | 2215 | -2353 | -2680 | -1685 | -2014 | -2091 | -1230 | 368 | -1247 | -1063 | 427 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 428(G) | -330 | -1125 | -91 | -18 | -1933 | 2258 | -329 | -1639 | 1029 | -1762 | -1028 | -173 | -1409 | -22 | -158 | -369 | -453 | -1229 | -1912 | -1465 | 428 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| Pos | A | R | N | D | C | Q | E | G | H | I | L | K | M | F | P | S | T | W | Y | V | Pos |
|---|---|---|---|---|---|---|---|---|---|---|---|---|---|---|---|---|---|---|---|---|---|
| 429(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 429 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 430(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 430 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 431(Q) | 337 | -1173 | -102 | 413 | -1398 | -1116 | 203 | -1043 | 1032 | -735 | -333 | 153 | 727 | 1159 | 238 | -88 | -61 | -748 | -1447 | -885 | 431 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 432(I) | -938 | -664 | -2954 | -2530 | -626 | -2743 | -2041 | 2838 | -2253 | 397 | 449 | -2334 | -2724 | -2070 | -2306 | -1976 | -939 | 1704 | -1845 | -1460 | 432 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 433(T) | 737 | -257 | -1006 | -798 | -1590 | -576 | -766 | -1064 | -703 | -1448 | -698 | -511 | -1166 | -583 | -923 | 595 | 2548 | -574 | -1871 | -1487 | 433 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 434(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 434 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 435(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 435 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 436(E) | -988 | -1921 | 379 | 3052 | -2309 | -1196 | -495 | -2108 | -350 | -2194 | -1612 | -103 | -1621 | -210 | -770 | -862 | -1042 | -1799 | -2207 | -1742 | 436 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 437(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 437 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 438(E) | -462 | -1877 | 1098 | 2281 | -2164 | -948 | 4 | -1884 | 157 | -1917 | -1119 | 395 | -1290 | 383 | -418 | -292 | 231 | -1485 | -2158 | -1417 | 438 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 439(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 439 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 440(A) | 2214 | -291 | -1447 | -1169 | -1154 | -884 | -959 | 74 | -982 | -736 | -262 | -833 | -1414 | -858 | -1151 | -156 | -103 | 1000 | -1694 | -1298 | 440 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 441(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 441 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 442(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 442 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 443(A) | 2125 | -240 | -956 | -787 | -1817 | 725 | -821 | -1474 | -799 | -1722 | -906 | -477 | -1113 | -618 | -1045 | 968 | 90 | -818 | -2044 | -1667 | 443 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 444(H) | -241 | -1271 | 205 | 405 | -1420 | -1027 | 2877 | -1354 | 381 | -1435 | -651 | 1012 | -1286 | 387 | -16 | 526 | -247 | -1015 | -1560 | -893 | 444 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 445(G) | 115 | -688 | -127 | -9 | -1770 | 1729 | -357 | -1446 | -174 | -1623 | -822 | 1088 | -1193 | -53 | -556 | 21 | 909 | -938 | -1917 | -1403 | 445 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 446(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 446 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 447(K) | -546 | -1647 | -8 | 263 | -2054 | -1224 | 81 | -1743 | 2289 | -1711 | -938 | 1349 | -1428 | 473 | 604 | -449 | -488 | -1398 | -1805 | -1294 | 447 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 448(D) | -824 | -2383 | 2964 | 1142 | -2628 | -923 | -210 | -2461 | -314 | -2455 | -1761 | 430 | -1405 | 123 | -1021 | -562 | -876 | -2027 | -2629 | -1790 | 448 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 449(M) | -764 | -700 | -2351 | -1867 | -159 | -2218 | -1306 | 906 | -1516 | 830 | 3513 | -1724 | -2266 | -1323 | -1574 | -1392 | -764 | 1232 | -1247 | -932 | 449 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 450(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 450 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 451(E) | 99 | -1520 | 298 | 1621 | -1816 | -1039 | 179 | -1514 | 1042 | -1533 | -686 | 287 | 196 | 594 | 120 | -117 | -179 | -1138 | -1759 | -1119 | 451 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 452(R) | -1181 | -1614 | -1431 | -903 | -2066 | -1632 | -446 | -1944 | 559 | -1867 | -1326 | -899 | -1873 | 156 | 3432 | -1225 | -1148 | -1717 | -1746 | -1529 | 452 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 453(N) | -607 | -1987 | 1547 | 723 | -2300 | -917 | -146 | -2176 | -128 | -2194 | -1447 | 2758 | -1353 | 195 | -745 | -420 | -660 | -1739 | -2343 | -1556 | 453 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 454(M) | -798 | -549 | -2776 | -2235 | -304 | -2552 | -1547 | 1726 | -1970 | 646 | 2483 | -2039 | -2467 | -1670 | -1974 | -1687 | -751 | 2029 | -1361 | -1070 | 454 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 455(V) | -700 | -665 | -2337 | -2135 | -873 | -1965 | -1727 | 1107 | -1863 | -105 | 22 | -1851 | -2286 | -1794 | -1920 | -1368 | -823 | 2927 | -1816 | -1362 | 455 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 456(E) | -565 | -1912 | 661 | 2316 | -2164 | -1033 | -4 | -1917 | 326 | -1900 | -1139 | 305 | -1356 | 1326 | -107 | -396 | -548 | -1547 | -2092 | -1413 | 456 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 457(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 457 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 458(M) | -1168 | -891 | -3079 | -2505 | 76 | -2283 | -1714 | 1503 | -2212 | 1892 | 2710 | -2358 | -2638 | -1740 | -2126 | -2022 | -1087 | 602 | -1243 | -1101 | 458 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 459(K) | 182 | -1171 | -183 | 203 | -1755 | -1060 | 40 | -1376 | 2110 | -1461 | -666 | 13 | -1300 | 422 | 353 | 563 | -217 | -1012 | -1691 | -1179 | 459 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 460(A) | 1995 | -401 | -1320 | -961 | 1082 | -1166 | -569 | 41 | -802 | -291 | 135 | -791 | -1531 | -642 | -991 | -375 | -205 | 143 | -927 | -304 | 460 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 461(A) | 1982 | -301 | -1528 | -1215 | -1040 | -1011 | -971 | 334 | -1023 | -585 | -132 | -907 | -1498 | -891 | -1190 | -268 | -147 | 1432 | -1620 | -1225 | 461 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 462(Q) | -508 | -1830 | 541 | 1702 | -2097 | -1060 | 45 | -1834 | 449 | -1813 | -1033 | 277 | -1342 | 2366 | 48 | -354 | -475 | -1466 | -1998 | -1347 | 462 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 463(E) | -565 | -2113 | 1507 | 2151 | -2387 | 321 | -37 | -2180 | 33 | -2146 | -1350 | 447 | -1307 | 338 | -604 | -350 | -576 | -1736 | -2355 | -1553 | 463 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 464(M) | -1145 | -875 | -3042 | -2468 | 69 | -2853 | -1685 | 1502 | -2175 | 1789 | 2881 | -2322 | -2619 | -1717 | -2097 | -1990 | -1065 | 616 | -1235 | -1085 | 464 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 465(M) | -964 | -754 | -2746 | -2216 | -92 | -2609 | -1540 | 1901 | -1884 | 984 | 3216 | -2071 | -2499 | -1589 | -1883 | -1761 | -915 | 868 | -1280 | -1023 | 465 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 466(N) | -212 | -1586 | 953 | 652 | -1877 | -1008 | 188 | -1602 | 1202 | -1601 | -736 | 1422 | -1199 | 610 | 33 | -89 | 555 | -1202 | -1814 | -1139 | 466 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 467(R) | -957 | -1779 | -1134 | -338 | -2324 | -1645 | 124 | -1844 | 1755 | -1699 | -992 | -386 | -1687 | 527 | 2771 | -884 | -776 | -1586 | -1694 | -1422 | 467 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 468(N) | -145 | -1016 | 214 | 150 | -2012 | 1688 | -401 | -1836 | -268 | -1957 | -1185 | 2176 | -1294 | -105 | -680 | -181 | -340 | -1299 | -2102 | -1535 | 468 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 469(I) | -462 | -597 | -1498 | -959 | -506 | -1717 | -547 | 2312 | -237 | -2 | 349 | -933 | -1823 | -455 | 761 | -864 | -432 | 572 | -1103 | -678 | 469 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 470(T) | 49 | -672 | -270 | -138 | -1544 | -795 | -385 | -1139 | -160 | -1431 | -698 | 1092 | -1260 | -119 | -475 | -71 | 2357 | -741 | -1759 | -1248 | 470 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 471(G) | 164 | -379 | -1029 | -881 | -1405 | 2294 | -838 | -705 | -813 | -1237 | -627 | -637 | -1312 | -705 | -1013 | -66 | -112 | 840 | -1767 | -1349 | 471 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 472(V) | -973 | -676 | -3010 | -2484 | -310 | -2805 | -1822 | 1723 | -2225 | 1595 | 781 | -2304 | -2660 | -1894 | -2215 | -1965 | -925 | 1960 | -1517 | -1250 | 472 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 473(D) | -792 | -2412 | 2801 | 1455 | -2641 | -913 | -169 | -2475 | -253 | -2443 | -1727 | 459 | -1383 | 174 | -964 | -525 | -834 | -2028 | -2631 | -1771 | 473 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 474(V) | -924 | -606 | -3067 | -2621 | -751 | -2843 | -2142 | 2385 | -2386 | 247 | 351 | -2416 | -2786 | -2193 | -2444 | -2061 | -913 | 2407 | -1948 | -1560 | 474 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 475(V) | -886 | -604 | -2944 | -2505 | -743 | -2731 | -2045 | 1944 | -2256 | 229 | 340 | -2308 | -2716 | -2086 | -2330 | -1950 | -884 | 2675 | -1910 | -1506 | 475 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 476(K) | -494 | -1536 | -395 | 133 | -1991 | -6 | 152 | -1602 | 2266 | -1562 | -774 | -53 | -1428 | 560 | 1152 | -424 | -406 | -1276 | -1682 | -1238 | 476 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 477(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 477 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 478(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 478 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 479(Y) | 499 | -364 | -899 | -371 | 787 | -1296 | -82 | 7 | -211 | -277 | 393 | -419 | -1419 | -73 | -488 | 927 | -30 | 144 | -587 | 1023 | 479 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 480(K) | -84 | -1454 | 654 | 613 | -1738 | -1039 | 285 | -1458 | 1165 | -1450 | -558 | 861 | -1146 | 994 | 487 | 248 | -23 | -503 | -1655 | -1002 | 480 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 481(H) | -138 | -1185 | 181 | 434 | -1561 | 117 | 2574 | -1298 | 368 | -1392 | -582 | 681 | -1230 | 426 | -73 | 519 | -152 | -942 | -1647 | -1037 | 481 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 482(G) | -478 | -1458 | 1461 | 350 | -2273 | 3341 | -418 | -2092 | -439 | -2185 | -1451 | 76 | -1399 | -120 | -981 | -425 | -627 | -1604 | -2284 | -1711 | 482 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 483(F) | -1075 | -853 | -2688 | -2263 | 2906 | -2522 | -760 | 1338 | -1963 | 741 | 748 | -1891 | -2464 | -1545 | -1898 | -1690 | -1030 | 450 | -271 | 583 | 483 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 484(K) | -186 | -1612 | 1105 | 1050 | -1898 | -1008 | 220 | -1635 | 1350 | -1612 | -730 | 353 | -372 | 652 | 63 | -56 | 254 | -1218 | -1811 | -1126 | 484 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 485(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 485 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 486(V) | -913 | -603 | -3038 | -2592 | -754 | -2818 | -2119 | 2212 | -2355 | 235 | 344 | -2390 | -2769 | -2168 | -2418 | -2035 | -904 | 2536 | -1941 | -1549 | 486 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 487(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 487 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 488(Q) | -287 | -1670 | 472 | 1418 | -1956 | -1010 | 152 | -1686 | 494 | -1676 | -825 | 781 | -1230 | 1735 | 6 | 468 | -249 | -1287 | -1883 | -1205 | 488 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 489(N) | 982 | -1511 | 1230 | 624 | -1958 | -918 | 1 | -1675 | 186 | -1740 | -924 | 1829 | -1246 | 379 | -358 | -177 | -306 | -1265 | -1993 | -1307 | 489 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 490(I) | -844 | -558 | -2919 | -2391 | -410 | -2672 | -1718 | 2212 | -2137 | 556 | 1861 | -2182 | -2573 | -1841 | -2137 | -1823 | -801 | 2017 | -1502 | -1199 | 490 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 491(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 491 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 492(N) | -436 | -1887 | 1302 | 728 | -2163 | -972 | 57 | -1926 | 969 | -1904 | -1081 | 2205 | -1277 | 450 | -237 | -263 | -420 | -1510 | -2102 | -1373 | 492 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 493(M) | -1145 | -875 | -3042 | -2468 | 69 | -2853 | -1685 | 1502 | -2175 | 1789 | 2881 | -2322 | -2619 | -1717 | -2097 | -1990 | -1065 | 616 | -1235 | -1085 | 493 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 494(Q) | 438 | -738 | -549 | -83 | -752 | -1276 | -87 | -244 | 206 | 754 | 150 | -239 | -1416 | 1553 | -92 | -333 | -154 | -140 | -1136 | -668 | 494 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 495(K) | -768 | -1791 | -831 | -81 | -2307 | -1536 | 199 | -1845 | 2218 | -1687 | -922 | -205 | -1567 | 1413 | 1839 | -665 | -601 | -1541 | -1705 | -1361 | 495 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 496(Q) | 607 | -1101 | -64 | 144 | -1616 | -1017 | -115 | -1247 | 345 | -1377 | -685 | -39 | -1340 | 2700 | 48 | -248 | -291 | -931 | -1715 | -1175 | 496 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 497(K) | -930 | -1812 | -1098 | -282 | -2373 | -1635 | 152 | -1883 | 2344 | -1718 | -994 | -346 | -1664 | 564 | 2242 | -842 | -743 | -1611 | -1705 | -1425 | 497 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 498(V) | -925 | -616 | -3000 | -2497 | -527 | -2814 | -1921 | 1840 | -2252 | 949 | 560 | -2316 | -2703 | -1995 | -2284 | -1988 | -889 | 2430 | -1695 | -1364 | 498 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 499(C) | 375 | 2958 | -1479 | -1118 | -1141 | -638 | -785 | -629 | -894 | -1021 | -301 | -681 | -1196 | -724 | -1042 | 842 | 1871 | -256 | -1509 | -1153 | 499 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 500(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 500 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 501(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 501 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 502(Y) | -1894 | -1443 | -2713 | -2588 | 2338 | -2734 | 353 | -1021 | -2261 | -702 | -584 | -1632 | -2696 | -1582 | -2053 | -1924 | -1818 | -1110 | 1018 | 3836 | 502 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 503(L) | -1369 | -1199 | -2542 | -2295 | -129 | -2453 | -1603 | 488 | -1867 | 2607 | 742 | -2168 | -2539 | -1724 | -1835 | -1992 | -1384 | 130 | -1284 | -897 | 503 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 504(Q) | -528 | -1553 | -18 | 249 | -1355 | -1246 | 1676 | -1537 | 686 | -1512 | -787 | 17 | -1438 | 2674 | 436 | -447 | -468 | -1245 | -1443 | -765 | 504 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 505(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 505 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 506(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 506 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 507(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 507 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 508(I) | -938 | -642 | -3015 | -2577 | -673 | -2799 | -2092 | 2768 | -2321 | 349 | 419 | -2380 | -2757 | -2128 | -2375 | -2024 | -932 | 1888 | -1889 | -1511 | 508 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 509(F) | -1021 | -751 | -2984 | -2430 | 1835 | -2690 | -1365 | 1831 | -2140 | 1558 | 1076 | -2171 | -2517 | -1668 | -2032 | -1822 | -947 | 667 | -916 | -487 | 509 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 510(D) | -228 | -933 | 1676 | 139 | -980 | -1247 | -106 | -126 | 97 | 59 | -65 | -98 | -1412 | 196 | -332 | -320 | -202 | 651 | -1373 | -816 | 510 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 511(K) | -125 | -1470 | 735 | 601 | -1768 | -117 | 251 | -1483 | 1009 | -1480 | -601 | 299 | -1169 | 685 | 990 | 468 | -71 | -1087 | -1689 | -1041 | 511 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 512(Q) | -215 | -1686 | 744 | 1127 | -1974 | -31 | 209 | -1725 | 1008 | -1685 | -799 | 954 | -1185 | 1224 | 24 | -72 | -169 | -1293 | -1872 | -1170 | 512 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 513(W) | -590 | -560 | -1824 | -1369 | 2316 | 64 | 40 | -143 | -1101 | -278 | 223 | -1055 | -1904 | -810 | -1154 | -929 | -548 | -80 | 3223 | 1325 | 513 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 514(H) | -169 | -1619 | 601 | 1061 | -1918 | -1017 | 1341 | -1660 | 1041 | -1619 | -725 | 901 | -1171 | 1254 | 132 | -37 | -116 | -1232 | -1801 | -1117 | 514 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 515(V) | -337 | 1937 | -2456 | -2043 | -721 | -1722 | -1414 | 1163 | -1743 | -109 | 212 | -1622 | -2030 | -1552 | -1771 | -966 | -446 | 2551 | -1519 | -1120 | 515 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 516(V) | -571 | -393 | -2384 | -1841 | -446 | -2249 | -1248 | 1704 | -1594 | 738 | 539 | -1678 | -2244 | -1375 | -1669 | -1360 | 519 | 2046 | -1284 | -924 | 516 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 517(S) | 116 | -498 | -840 | -867 | -1751 | -671 | -949 | -1625 | -916 | -1896 | -1218 | -622 | -1304 | -824 | -1097 | 2786 | -220 | -1038 | -1992 | -1530 | 517 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 518(A) | 2806 | -444 | -1270 | -1265 | -1732 | -744 | -1182 | -1034 | -1212 | -1545 | -1010 | -869 | -1380 | -1102 | -1325 | -156 | -259 | -640 | -2039 | -1721 | 518 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 519(V) | -886 | -604 | -2944 | -2505 | -743 | -2731 | -2045 | 1944 | -2256 | 229 | 340 | -2308 | -2716 | -2086 | -2330 | -1950 | -884 | 2675 | -1910 | -1506 | 519 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 520(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 520 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 521(D) | -710 | -2209 | 2783 | 792 | -2489 | -901 | -175 | -2383 | -242 | -2372 | -1646 | 1391 | -1370 | 162 | -925 | -480 | -769 | -1927 | -2525 | -1680 | 521 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 522(I) | 926 | 1569 | -2066 | -1523 | -360 | -1740 | -859 | 1653 | -1268 | 36 | 522 | -1286 | -1866 | -1039 | -1329 | -859 | -244 | 1499 | -985 | -613 | 522 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 523(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 523 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 524(D) | -1130 | -2063 | 3441 | 243 | -2502 | -1157 | -662 | -2514 | -843 | -2578 | -2029 | -96 | -1658 | -421 | -1434 | -970 | -1239 | -2138 | -2388 | -1915 | 524 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 525(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 525 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 526(Q) | 394 | -1108 | -203 | 338 | -1300 | -1159 | 184 | -918 | 1042 | -1043 | 968 | 94 | -1255 | 1737 | 277 | -133 | -76 | -656 | -1380 | -845 | 526 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 527(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 527 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 528(P) | -934 | -1220 | -1352 | -1451 | -2187 | -1314 | -1456 | -2160 | -1488 | -2268 | -1827 | -1359 | 3760 | -1471 | -1571 | -1129 | -1216 | -1780 | -2050 | -2023 | 528 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 529(G) | 1163 | -332 | -849 | -861 | -1983 | 2434 | -981 | -1591 | -996 | -1909 | -1142 | -553 | -1190 | -813 | -1198 | 105 | -47 | -932 | -2188 | -1842 | 529 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 530(T) | -52 | -555 | -1173 | -1112 | -1571 | -872 | -1041 | -862 | -950 | -1353 | -866 | -843 | -1455 | -937 | -1084 | -285 | 3069 | -557 | -1898 | -1539 | 530 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 531(G) | -758 | -1103 | -1313 | -1487 | -2460 | 3331 | -1562 | -2502 | -1720 | -2644 | -2081 | -1324 | -1775 | -1590 | -1790 | -958 | -1093 | -1921 | -2198 | -2279 | 531 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 532(Y) | -1667 | -1473 | -2001 | -1964 | 1181 | -2210 | -25 | -1224 | -1658 | -1018 | -871 | -1505 | -2415 | -1423 | -1618 | -1747 | -1692 | -1248 | 501 | 4149 | 532 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 533(R) | -1181 | -1614 | -1431 | -903 | -2066 | -1632 | -446 | -1944 | 559 | -1867 | -1326 | -899 | -1873 | -156 | 3432 | -1225 | -1148 | -1717 | -1746 | -1529 | 533 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 534(L) | -1227 | -936 | -3091 | -2579 | -37 | -2962 | -1855 | 1807 | -2244 | 2137 | 1045 | -2445 | -2745 | -1867 | -2194 | -2151 | -1166 | 827 | -1387 | -1156 | 534 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 535(W) | -110 | -1096 | -68 | 835 | -1238 | -1114 | 184 | -918 | 540 | -1049 | -251 | 146 | -1227 | 1144 | 118 | 925 | -52 | -647 | 4332 | -790 | 535 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -33 | -6045 | -7087 | -894 | -1115 | -701 | -1378 | * | * | | | | | | | | | | | |
| 536(E) | 374 | -1428 | 234 | 1314 | -1721 | -59 | 206 | -1425 | -962 | -1455 | -596 | 292 | -335 | 625 | 87 | -51 | -101 | -1049 | -1693 | -1050 | 536 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -660 | -6045 | -1506 | -894 | -1115 | -701 | -1378 | * | * | | | | | | | | | | | |
| 537(D) | -431 | -1310 | 2676 | 692 | -1656 | -655 | -71 | -1520 | -129 | -1690 | -1117 | 380 | -1112 | 179 | -645 | -333 | -523 | -1206 | -1668 | -1155 | 537 |
| - | -149 | -500 | 233 | 43 | -381 | 399 | 106 | -626 | 210 | -466 | -720 | 275 | 394 | 45 | 96 | 359 | 117 | -369 | -294 | -249 |
| - | -50 | -5435 | -6477 | -894 | -1115 | -1219 | -810 | * | * | | | | | | | | | | | |

TABLE 12-continued

| | | | | | | | | | | | | | | | | | | | | |
|---|---|---|---|---|---|---|---|---|---|---|---|---|---|---|---|---|---|---|---|---|
| 538(K) | -15 | -765 | -73 | 241 | -1227 | -873 | 152 | -678 | 1382 | -945 | -263 | 98 | -1144 | 476 | 501 | -77 | 963 | -426 | -1324 | -852 | 538 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -50 | -5435 | -6477 | -894 | -1115 | -451 | -1896 | * | * | | | | | | | | | | | | |
| 539(E) | -567 | -2146 | 1487 | 2236 | -2383 | -935 | -11 | -2178 | 98 | -2131 | -1330 | 451 | -1305 | 974 | -516 | -347 | -566 | -1739 | -2332 | -1532 | 539 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 540(R) | -635 | -1728 | -475 | 809 | -2174 | -1411 | 191 | -1754 | 1549 | -1647 | -864 | -79 | -1485 | 610 | 2276 | -530 | -501 | -1435 | -1716 | -1303 | 540 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 541(W) | -1926 | -1577 | -2416 | -2370 | 192 | -2070 | -795 | -1602 | -1882 | -1347 | -1210 | -2018 | -2383 | -1854 | -1777 | -2150 | -1992 | -1643 | 5696 | 560 | 541 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 542(E) | 376 | -1973 | 1778 | 1849 | -2250 | -935 | 10 | -2003 | 135 | -2000 | -1190 | 428 | -1283 | 394 | -473 | -289 | -479 | -1580 | -2225 | -1454 | 542 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 543(E) | -502 | -1664 | 66 | 1892 | -2010 | -1207 | 100 | -1682 | 762 | -1657 | -874 | 90 | -1392 | 499 | 1653 | -394 | -434 | -1344 | -1798 | -1268 | 543 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 544(I) | -1076 | -780 | -3002 | -2529 | -309 | -2874 | -1898 | 2697 | -2198 | 1168 | 740 | -2371 | -2742 | -1949 | -2205 | -2081 | -1040 | 1240 | -1569 | -1227 | 544 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 545(K) | -636 | -1780 | 35 | 978 | -2175 | -1268 | 89 | -1797 | 2425 | -1748 | -984 | 44 | -1457 | 488 | 647 | -514 | -552 | -1469 | -1853 | -1366 | 545 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 546(N) | -637 | -1349 | -5 | -148 | -1773 | -1078 | -624 | -1965 | -499 | -2112 | -1514 | 3456 | -1574 | -435 | -810 | -661 | -818 | -1560 | -1900 | -1327 | 546 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 547(I) | -985 | -659 | -3098 | -2595 | -475 | -2895 | -1995 | 2517 | -2348 | 1018 | 628 | -2411 | -2755 | -2059 | -2358 | -2076 | -945 | 1794 | -1699 | -1395 | 547 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 548(P) | 1061 | -433 | -770 | -684 | -1731 | -657 | -791 | -1256 | -689 | -1580 | -892 | -499 | 2706 | -594 | -921 | 8 | -100 | -769 | -1976 | -1581 | 548 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 549(W) | -38 | -416 | -726 | -186 | 608 | 365 | -32 | -47 | -33 | -324 | 375 | 490 | -1365 | 81 | -348 | -269 | 377 | 100 | 1582 | -231 | 549 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 550(A) | 982 | -301 | -1528 | -1215 | -1040 | -1011 | -971 | 334 | -1023 | -585 | -132 | -907 | -1498 | -891 | -1190 | -268 | -147 | 1432 | -1620 | -1225 | 550 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 551(M) | -956 | -675 | -3000 | -2437 | -98 | -2720 | -1640 | 1822 | -2169 | 1596 | 921 | -2230 | -2553 | -1752 | -2099 | -1856 | -891 | 1429 | -1284 | -1077 | 551 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |
| 552(D) | -409 | -1868 | 1976 | 711 | -2139 | -994 | 95 | -1893 | 949 | -1858 | -1023 | 375 | -1268 | 1572 | -112 | -239 | -379 | -1478 | -2048 | -1334 | 552 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

TABLE 12-continued

| 553(P) | -934 | -1220 | -1352 | -1451 | -2187 | -1314 | -1456 | -2160 | -1488 | -2268 | -1827 | -1359 | 1760 | -1471 | -1571 | -1129 | -1216 | -1780 | -2050 | -2023 | 553 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 554(Q) | -349 | -1867 | 1242 | 1165 | -2138 | -348 | 120 | -1907 | 361 | -1863 | -1004 | 1155 | -1230 | 1761 | -205 | -176 | -320 | -1469 | -2057 | -1314 | 554 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 555(E) | -176 | -1613 | 862 | 1081 | -1899 | -1001 | 224 | -1641 | 1004 | -1615 | -729 | 978 | -1172 | 658 | 47 | 503 | 231 | -1220 | -1813 | -1122 | 555 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 556(I) | -1082 | -793 | -3068 | -2508 | -48 | -2847 | -1738 | 2225 | -2221 | 1561 | 2060 | -2337 | -2638 | -1795 | -2152 | -1992 | -1013 | 884 | -1319 | -1134 | 556 |
|---|---|---|---|---|---|---|---|---|---|---|---|---|---|---|---|---|---|---|---|---|---|
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -33 | -6045 | -7087 | -894 | -1115 | -701 | -1378 | * | * | | | | | | | | | | | | |

| 557(E) | -271 | -1743 | 826 | 1604 | -2026 | -378 | 175 | -1775 | 955 | -1737 | -865 | 378 | -1208 | 1258 | -25 | -120 | -230 | -1349 | -1927 | -1220 | 557 |
|---|---|---|---|---|---|---|---|---|---|---|---|---|---|---|---|---|---|---|---|---|---|
| - | * | * | * | * | * | * | * | * | * | * | * | * | * | * | * | * | * | * | * | * | |
| - | * | * | * | * | * | * | * | * | 0 | | | | | | | | | | | | |

What is claimed is:

1. A recombinant microbial host cell comprising heterologous DNA molecules encoding polypeptides that catalyze the substrate to product conversions below:
   i) pyruvate to alpha acetolactate;
   ii) alpha acetolactate to acetoin;
   iii) acetoin to 2,3-butanediol; and
   iv) 2,3-butanediol to 2-butanone;
   wherein said microbial host cell produces 2-butanol; and
   wherein the polypeptide that catalyzes the substrate to product conversion of 2,3-butanediol to 2-butanone is diol dehydratase or glycerol dehydratase, comprising an amino acid sequence having at least 95% identity to an amino acid sequence comprising all three of the amino acid sequences encoding large, medium and small subunits, as set forth in SEQ ID NO:8, SEQ ID NO:10, and SEQ ID NO:12; based on the Clustal W method of alignment using the default parameters of GAP PENALTY=10, GAP LENGTH PENALTY=0.1, and Gonnet 250 series of protein weight matrix.

2. The recombinant microbial host cell according to claim 1 wherein conversion of the substrate 2-butanone to the product 2-butanol is catalyzed by a polypeptide having butanol dehydrogenase activity encoded by a heterologous DNA molecule.

3. The recombinant microbial host cell according to claim 1 wherein conversion of the substrate 2-butanone to the product 2-butanol is catalyzed by a polypeptide having butanol dehydrogenase activity encoded by an endogenous DNA molecule.

4. A method for the production of 2-butanol comprising:
  1) providing a recombinant microbial host cell according to claim 1; and
  2) contacting the host cell of (1) with a fermentable carbon substrate in a fermentation medium under conditions whereby 2-butanol is produced.

* * * * *

SEQUENCE LISTING

<160> NUMBER OF SEQ ID NOS: 275

<210> SEQ ID NO 1
<211> LENGTH: 780
<212> TYPE: DNA
<213> ORGANISM: Klebsiella pneumoniae

<400> SEQUENCE: 1

```
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc      180 ggcacctta tgagctgga cggggagctg atcgccttca gcagtcaggt ctatcagctg       240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420
ggccatttcc gccatgccca tacccgcacc gtgccgcgcc agacgccgcc gtaccgggcg     480
atgaccgacg tcctcgacga tcagccggtg ttccgcttta ccagcgcga aggggtgctg      540 gtcggcttcc ggaccccgca gcatatgcag gggatcaacg tcgccgggta tcacgagcac     600
tttattaccg atgaccgcaa aggcggcggt cacctgctgg attaccagct cgaccatggg     660
gtgctgacct tcggcgaaat tcacaagctg atgatcgacc tgcccgccga cagcgcgttc     720
ctgcaggcta atctgcatcc cgataatctc gatgccgcca tccgttccgt agaaagttaa    780
```

<210> SEQ ID NO 2
<211> LENGTH: 259
<212> TYPE: PRT
<213> ORGANISM: Klebsiella pneumoniae

<400> SEQUENCE: 2

Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 3
<211> LENGTH: 1680
<212> TYPE: DNA
<213> ORGANISM: Klebsiella pneumoniae

<400> SEQUENCE: 3
atggacaaac agtatccggt acgccagtgg gcgcacggcg ccgatctcgt cgtcagtcag      60
ctggaagctc agggagtacg ccaggtgttc ggcatccccg cgccaaaat tgacaaggtc     120 ttcgactcac tgctggattc ctcgattcgc attattccgg tacgccacga agccaacgcc     180
gcgtttatgg ccgccgccgt cggacgcatt accggcaaag cgggcgtggc gctggtcacc     240
tccggtccgg gctgttccaa cctgatcacc ggcatggcca ccgcgaacag cgaaggcgac     300
ccggtggtgg ccctgggcgg cgcggtaaaa cgcgccgata agcgaagca ggtccaccag     360 agtatggata cggtggcgat gttcagcccg gtcaccaaat acgccgtcga ggtgacggcg     420
ccggatgcgc tggcggaagt ggtctccaac gccttccgcg ccgccgagca gggccggccg     480
ggcagcgcgt tcgttagcct gccgcaggat gtggtcgatg cccggtcag cggcaaagtg     540 ctgccggcca gcggggcccc gcagatgggc gccgcgccgg atgatgccat cgaccaggtg     600
gcgaagctta tcgcccaggc gaagaacccg atcttcctgc tcggcctgat ggccagccag     660
ccggaaaaca gcaaggcgct gcgccgtttg ctggagacca gccatattcc agtcaccagc     720
acctatcagg ccgccggagc ggtgaatcag gataacttct ctcgcttcgc cggccgggtt     780

-continued

```
gggctgttta caaccaggc cggggaccgt ctgctgcagc tcgccgacct ggtgatctgc    840
atcggctaca gcccggtgga atacgaaccg gcgatgtgga acagcggcaa cgcgacgctg    900
gtgcacatcg acgtgctgcc cgcctatgaa gagcgcaact acaccccgga tgtcgagctg    960
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctgaa ccagtttgcc ctgcatccgc tgcgcatcgt tcgcgccatg   1140
caggacatcg tcaacagcga cgtcacgttg accgtggaca tgggcagctt ccatatctgg   1200
attgcccgct acctgtacag cttccgcgcc cgtcaggtga tgatctccaa cggccagcag   1260
accatgggcg tcgccctgcc ctgggctatc ggcgcctggc tggtcaatcc tgagcgaaaa   1320
gtggtctccg tctccggcga cggcggcttc ctgcagtcga gcatggagct ggagaccgcc   1380
gtccgcctga aagccaacgt actgcacctg atctgggtcg ataacggcta caacatggtg   1440
gccattcagg aagagaaaaa ataccagcgc ctgtccggcg tcgagttcgg gccgatggat   1500
tttaaagcct atgccgaatc cttcggcgcg aaagggtttg ccgtgaaaag cgccgaggcg   1560
ctggagccga ccctgcacgc ggcgatggac gtcgacggcc cggcggtggt ggccattccg   1620
gtggattatc gcgataaccc gctgctgatg ggccagctgc atctgagtca gattctgtaa   1680
```

<210> SEQ ID NO 4
<211> LENGTH: 559
<212> TYPE: PRT
<213> ORGANISM: Klebsiella pneumoniae

<400> SEQUENCE: 4

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220
```

| | | | | | | | | | | | | |
|---|---|---|---|---|---|---|---|---|---|---|---|---|
|Lys|Ala|Leu|Arg|Arg|Leu|Leu|Glu|Thr|Ser|His|Ile|Pro|Val|Thr|Ser|
|225| | | | |230| | | | |235| | | | |240|

Lys Ala Leu Arg Arg Leu Leu Glu Thr Ser His Ile Pro Val Thr Ser
225     230     235     240

Thr Tyr Gln Ala Ala Gly Ala Val Asn Gln Asp Asn Phe Ser Arg Phe
     245     250     255

Ala Gly Arg Val Gly Leu Phe Asn Asn Gln Ala Gly Asp Arg Leu Leu
    260     265     270

Gln Leu Ala Asp Leu Val Ile Cys Ile Gly Tyr Ser Pro Val Glu Tyr
    275     280     285

Glu Pro Ala Met Trp Asn Ser Gly Asn Ala Thr Leu Val His Ile Asp
   290     295     300

Val Leu Pro Ala Tyr Glu Arg Asn Tyr Thr Pro Val Glu Leu
305     310     315     320

Val Gly Asp Ile Ala Gly Thr Leu Asn Lys Leu Ala Gln Asn Ile Asp
    325     330     335

His Arg Leu Val Leu Ser Pro Gln Ala Ala Glu Ile Leu Arg Asp Arg
    340     345     350

Gln His Gln Arg Glu Leu Leu Asp Arg Arg Gly Ala Gln Leu Asn Gln
    355     360     365

Phe Ala Leu His Pro Leu Arg Ile Val Arg Ala Met Gln Asp Ile Val
370     375     380

Asn Ser Asp Val Thr Leu Thr Val Asp Met Gly Ser Phe His Ile Trp
385     390     395     400

Ile Ala Arg Tyr Leu Tyr Ser Phe Arg Ala Arg Gln Val Met Ile Ser
    405     410     415

Asn Gly Gln Gln Thr Met Gly Val Ala Leu Pro Trp Ala Ile Gly Ala
    420     425     430

Trp Leu Val Asn Pro Glu Arg Lys Val Val Ser Val Ser Gly Asp Gly
    435     440     445

Gly Phe Leu Gln Ser Ser Met Glu Leu Glu Thr Ala Val Arg Leu Lys
   450     455     460

Ala Asn Val Leu His Leu Ile Trp Val Asp Asn Gly Tyr Asn Met Val
465     470     475     480

Ala Ile Gln Glu Glu Lys Lys Tyr Gln Arg Leu Ser Gly Val Glu Phe
    485     490     495

Gly Pro Met Asp Phe Lys Ala Tyr Ala Glu Ser Phe Gly Ala Lys Gly
   500     505     510

Phe Ala Val Glu Ser Ala Glu Ala Leu Glu Pro Thr Leu His Ala Ala
   515     520     525

Met Asp Val Asp Gly Pro Ala Val Val Ala Ile Pro Val Asp Tyr Arg
   530     535     540

Asp Asn Pro Leu Leu Met Gly Gln Leu His Leu Ser Gln Ile Leu
545     550     555

<210> SEQ ID NO 5
<211> LENGTH: 771
<212> TYPE: DNA
<213> ORGANISM: Klebsiella pneumoniae

<400> SEQUENCE: 5

```
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt gaacaggcgc gcaaaacgct gggcggcttc     240
```

```
gacgtcatcg tcaataacgc cggtgtggca ccgtctacgc cgatcgagtc cattaccccg    300
gagattgtcg acaaagtcta caacatcaac gtcaaagggg tgatctgggg tattcaggcg    360
gcggtcgagg cctttaagaa agaggggcac ggcgggaaaa tcatcaacgc ctgttcccag    420
gccggccacg tcggcaaccc ggagctggcg gtgtatagct ccagtaaatt cgcggtacgc    480
ggcttaaccc agaccgccgc tcgcgacctc gcgccgctgg gcatcacggt caacggctac    540
tgcccgggga ttgtcaaaac gccaatgtgg gccgaaattg accgccaggt gtccgaagcc    600
gccggtaaac cgctgggcta cggtaccgcc gagttcgcca aacgcatcac tctcggtcgt    660
ctgtccgagc cggaagatgt cgccgcctgc gtctcctatc ttgccagccc ggattctgat    720
tacatgaccg tcagtcgtt gctgatcgac ggcgggatgg tatttaacta a             771
```

<210> SEQ ID NO 6
<211> LENGTH: 256
<212> TYPE: PRT
<213> ORGANISM: Klebsiella pneumoniae

<400> SEQUENCE: 6

```
Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
                20                  25                  30

Asp Tyr Asn Asp Ala Thr Ala Lys Ala Val Ala Ser Glu Ile Asn Gln
            35                  40                  45

Ala Gly Gly His Ala Val Ala Val Lys Val Asp Val Ser Asp Arg Asp
        50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255
```

<210> SEQ ID NO 7
<211> LENGTH: 1665
<212> TYPE: DNA

<213> ORGANISM: Klebsiella oxytoca

<400> SEQUENCE: 7

```
atgagatcga aaagatttga agcactggcg aaacgccctg tgaatcagga cggcttcgtt      60
aaggagtgga tcgaagaagg ctttatcgcg atggaaagcc cgaacgaccc aaaaccgtcg     120
attaaaatcg ttaacggcgc ggtgaccgag ctggacggga accggtaagc gattttgac      180
ctgatcgacc actttatcgc ccgctacggt atcaacctga accgcgccga agaagtgatg     240
gcgatggatt cggtcaagct ggccaacatg ctgtgcgatc gaacgttaa acgcagcgaa      300
atcgtcccgc tgaccaccgc gatgacgccg gcgaaaattg tcgaagtggt ttcgcatatg     360
aacgtcgtcg agatgatgat ggcgatgcag aaaatgcgcg cccgccgcac cccgtcccag     420
caggcgcacg tcaccaacgt caaagataac ccggtacaga ttgccgccga cgccgccgaa     480
ggggcatggc gcggatttga cgaacaggaa accaccgttg cggtagcgcg ctatgcgccg     540
ttcaacgcca tcgcgctgct ggtgggctcg caggtaggcc gtccgggcgt gctgacgcag     600
tgctcgctgg aagaagccac cgagctgaag ctcggcatgc tgggccacac ctgctacgcc     660
gaaaccatct ccgtctacgg caccgagccg gtctttaccg acggcgacga cacgccgtgg     720
tcgaagggct tcctcgcctc gtcctacgcc tctcgcgggc tgaaaatgcg ctttacctcc     780
ggctccggct cggaagtgca gatgggctac gccgaaggca atccatgct  ttatctggaa     840
gcgcgctgca tctacatcac caaagccgcg ggcgtacagg tctgcaaaa cggttccgta     900
agctgcatcg gcgtgccgtc tgcggtgcct tccggcattc gcgcggtgct ggcggaaaac     960
ctgatctgtt cgtcgctgga tctggagtgc gcctccagca acgaccagac cttcacccac    1020
tccgatatgc gtcgtaccgc gcgcctgctg atgcagttcc tgccgggcac cgactttatc    1080
tcctccggtt attccgcggt gccgaactac gacaacatgt cgccggctc caacgaagat     1140
gccgaagact ttgacgacta caacgtcatc cagcgcgacc tgaaggtgga cggcggtttg    1200
cgtccggttc gcgaagagga cgtcatcgcc atccgtaaca aagccgcccg cgcgctgcag    1260
gccgtgtttg ccggaatggg gctgccgccg attaccgatg aagaagttga agccgcgacc    1320
tacgcccacg gttcgaaaga tatgccggag cgcaacatcg tcgaagacat caagttcgcc    1380
caggaaatca tcaataaaaa ccgcaacggt ctggaagtgg tgaaagcgct ggcgcagggc    1440
ggattcaccg acgtggccca ggacatgctc aacatccaga agctaagct gaccggggac     1500
tacctgcata cctccgcgat tatcgtcggc gacgggcagg tgctgtcagc cgtcaacgac    1560
gtcaacgact atgccggtcc ggcaacgggc tatcgcctgc agggcgaacg ctgggaagag    1620
attaaaaaca tccctggcgc tcttgatccc aacgagattg attaa                   1665
```

<210> SEQ ID NO 8
<211> LENGTH: 554
<212> TYPE: PRT
<213> ORGANISM: Klebsiella oxytoca

<400> SEQUENCE: 8

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60
```

```
Phe Ile Ala Arg Tyr Gly Ile Asn Leu Asn Arg Ala Glu Glu Val Met
 65                  70                  75                  80

Ala Met Asp Ser Val Lys Leu Ala Asn Met Leu Cys Asp Pro Asn Val
                 85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480
```

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Ile Lys Asn Ile
    530                 535                 540

Pro Gly Ala Leu Asp Pro Asn Glu Ile Asp
545                 550

<210> SEQ ID NO 9
<211> LENGTH: 675
<212> TYPE: DNA
<213> ORGANISM: Klebsiella oxytoca

<400> SEQUENCE: 9
atggaaatta atgaaaaatt gctgcgccag ataattgaag acgtgctcag cgagatgaag      60
ggcagcgata aaccggtctc gtttaatgcg ccggcggcct ccgcggcgcc ccaggccacg     120
ccgcccgccg cgacggcttc cctgacggaa gtgggcgaag cgcgtcaggg aacccagcag     180
gacgaagtga ttatcgccgt cggcccggct ttcggcctgg cgcagaccgt caatatcgtc     240
ggcatcccgc ataagagcat tttgcgcgaa gtcattgccg gtattgaaga agaaggcatt     300
aaggcgcgcg tgattcgctg ctttaaatcc tccgacgtgg ccttcgtcgc cgttgaaggt     360
aatcgcctga cggctccgg catctctatc ggcatccagt cgaaaggcac cacggtgatc     420
caccagcagg ggctgccgcc gctctctaac ctggagctgt ccccgcaggc gccgctgctg     480
accctggaaa cctatcgcca gatcggcaaa aacgccgccc gctatgcgaa cgcgaatcg     540 ccgcagccgg tcccgacgct gaatgaccag atggcgcggc cgaagtacca ggcgaaatcg     600
gccattttgc acattaaaga gaccaagtac gtggtgacgg gcaaaaaccc gcaggaactg     660
cgcgtggcgc tttga                                                      675

<210> SEQ ID NO 10
<211> LENGTH: 224
<212> TYPE: PRT
<213> ORGANISM: Klebsiella oxytoca

<400> SEQUENCE: 10

Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

```
Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 11
<211> LENGTH: 522
<212> TYPE: DNA
<213> ORGANISM: Klebsiella oxytoca

<400> SEQUENCE: 11

```
atgaataccg acgcaattga atcgatggta cgcgacgtat tgagccgcat gaacagcctg      60
cagggcgagg cgcctgcggc ggctccggcg gctggcggcg cgtcccgtag cgccagggtc     120
agcgactacc cgctggcgaa caagcacccg gaatgggtga aaaccgccac caataaaacg     180
ctggacgact ttacgctgga aaacgtgctg agcaataaag tcaccgccca ggatatgcgt     240
attaccccgg aaaccctgcg cttacaggct tctattgcca agacgcgggg ccgcgaccgg     300
ctggcgatga acttcgagcg cgccgccgag ctgaccgcgg taccggacga tcgcattctt     360
gaaatctaca cgccctccg cccctatcgc tcgacgaaag aggagctgct ggcgatcgcc     420
gacgatctcg aaagccgcta tcaggcgaag atttgcgccg ctttcgttcg cgaagcggcc     480
acgctgtacg tcgagcgtaa aaaactcaaa ggcgacgatt aa                       522
```

<210> SEQ ID NO 12
<211> LENGTH: 173
<212> TYPE: PRT
<213> ORGANISM: Klebsiella oxytoca

<400> SEQUENCE: 12

```
Met Asn Thr Asp Ala Ile Glu Ser Met Val Arg Asp Val Leu Ser Arg
1               5                   10                  15

Met Asn Ser Leu Gln Gly Glu Ala Pro Ala Ala Ala Pro Ala Ala Gly
                20                  25                  30

Gly Ala Ser Arg Ser Ala Arg Val Ser Asp Tyr Pro Leu Ala Asn Lys
            35                  40                  45

His Pro Glu Trp Val Lys Thr Ala Thr Asn Lys Thr Leu Asp Asp Phe
        50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140
```

```
Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170
```

<210> SEQ ID NO 13
<211> LENGTH: 1041
<212> TYPE: DNA
<213> ORGANISM: Rhodococcus ruber

<400> SEQUENCE: 13

```
atgaaagccc tccagtacac cgagatcggc tccgagccgg tcgtcgtcga cgtccccacc      60
ccggcgcccg ggccgggtga gatcctgctg aaggtcaccg cggccggctt gtgccactcg     120
gacatcttcg tgatggacat gccggcagag cagtacatct acggtcttcc cctcaccctc     180
ggccacgagg gcgtcggcac cgtcgccgaa ctcggcgccg gcgtcaccgg attcgagacg     240
ggggacgccg tcgccgtgta cgggccgtgg gggtgcggtg cgtgccacgc gtgcgcgcgc     300
ggccgggaga actactgcac ccgcgccgcc gagctgggca tcaccccgcc cggtctcggc     360
tcgcccgggt cgatggccga gtacatgatc gtcgactcgg cgcgccacct cgtcccgatc     420
ggggacctcg accccgtcgc ggcggttccg ctcaccgacg cgggcctgac gccgtaccac     480
gcgatctcgc gggtcctgcc cctgctggga cccggctcga ccgcggtcgt catcggggtc     540
ggcggactcg gcacgtcgg catccagatc ctgcgcgccg tcagcgcggc ccgcgtgatc     600
gccgtcgatc tcgacgacga ccgactcgcg ctcgcccgcg aggtcggcgc cgacgcggcg     660
gtgaagtcgg cgccggggc ggcggacgcg atccgggagc tgaccggcgg tgagggcgcg     720
acggcggtgt cgacttcgt cggcgcccag tcgacgatcg acacggcgca gcaggtggtc     780
gcgatcgacg gcacatctc ggtggtcggc atccatgccg cgcccacgc caaggtcggc     840
ttcttcatga tcccgttcgg cgcgtccgtc gtgacgccgt actggggcac gcggtccgag     900
ctgatggacg tcgtggacct ggccgtgcc ggccggctcg acatccacac cgagacgttc     960
accctcgacg agggacccac ggcctaccgg cggctacgcg agggcagcat ccgcggccgc    1020
ggggtggtcg tcccgggctg a                                              1041
```

<210> SEQ ID NO 14
<211> LENGTH: 346
<212> TYPE: PRT
<213> ORGANISM: Klebsiella oxytoca

<400> SEQUENCE: 14

```
Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
                20                  25                  30

Thr Ala Ala Gly Leu Cys His Ser Asp Ile Phe Val Met Asp Met Pro
            35                  40                  45

Ala Glu Gln Tyr Ile Tyr Gly Leu Pro Leu Thr Leu Gly His Glu Gly
        50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110
```

Gly Ile Thr Pro Pro Gly Leu Gly Ser Pro Gly Ser Met Ala Glu Tyr
            115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
caccatggac aaacagtatc cggtacgcc                                    29

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
cgaagggcga tagctttacc aatcc                                        25

<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17

```
caccatgaat cattctgctg aatgcacctg cg                                   32

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
gatactgttt gtccatgtga cc                                              22

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
caccatgaaa aaagtcgcac ttgttacc                                        28

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
ttagttaaat accat                                                      15

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
caccatgaga tcgaaaagat ttg                                             23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
cttagagaag ttaatcgtcg cc                                              22

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
caccatgaaa gccctccagt acacc                                           25

<210> SEQ ID NO 24
<211> LENGTH: 18
<212> TYPE: DNA
<213> ORGANISM: Artificial Sequence
```

```
<220> FEATURE:
<223> OTHER INFORMATION: Primer

<400> SEQUENCE: 24
cgtcgtgtca tgcccggg                                                  18

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
gatcgaattc gtttaaactt agttttctac cgcacg                              36

<210> SEQ ID NO 26
<211> LENGTH: 34
<212> TYPE: DNA
<213> ORGANISM: Artificial Sequence
<220> FEATURE:
<223> OTHER INFORMATION: Primer

<400> SEQUENCE: 26
gatcgcatgc aagctttcat atagtcggaa ttcc                                34

<210> SEQ ID NO 27
<211> LENGTH: 43
<212> TYPE: DNA
<213> ORGANISM: Artificial Sequence
<220> FEATURE:
<223> OTHER INFORMATION: Primer

<400> SEQUENCE: 27
gatcgaattc gtttaaacaa aggaggtctg attcatgaga tcg                      43

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gatcggattc ttaatcgtcg cc                                             22

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
gatcggatcc aaaggaggtc gggcgcatga aagccc                              36

<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30
gatctctaga aagctttcag cccgggacga cc                                  32
```

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
actttctttc gcctgtttca c                                      21

<210> SEQ ID NO 32
<211> LENGTH: 79
<212> TYPE: DNA
<213> ORGANISM: Artificial Sequence
<220> FEATURE:
<223> OTHER INFORMATION: Primer

<400> SEQUENCE: 32
catgaagctt gtttaaactc ggtgaccttg aaaataatga aaacttatat tgttttgaaa     60
ataatgaaaa cttatattg                                         79

<210> SEQ ID NO 33
<211> LENGTH: 39
<212> TYPE: DNA
<213> ORGANISM: Artificial Sequence
<220> FEATURE:
<223> OTHER INFORMATION: Primer BABC F

<400> SEQUENCE: 33
gagctcgaat tcaaaggagg aagtgtatat gaatcattc                   39

<210> SEQ ID NO 34
<211> LENGTH: 35
<212> TYPE: DNA
<213> ORGANISM: Artificial Sequence
<220> FEATURE:
<223> OTHER INFORMATION: Primer BAB R

<400> SEQUENCE: 34
ggatcctcta gaattagtta aataccatcc cgccg                       35

<210> SEQ ID NO 35
<211> LENGTH: 17
<212> TYPE: DNA
<213> ORGANISM: Artificial Sequence
<220> FEATURE:
<223> OTHER INFORMATION: Primer M13 Forward

<400> SEQUENCE: 35
gtaaaacgac ggccagt                                           17

<210> SEQ ID NO 36
<211> LENGTH: 16
<212> TYPE: DNA
<213> ORGANISM: Artificial Sequence
<220> FEATURE:
<223> OTHER INFORMATION: Primer M13 Reverse

<400> SEQUENCE: 36
aacagctatg accatg                                            16

<210> SEQ ID NO 37
<211> LENGTH: 20
<212> TYPE: DNA
<213> ORGANISM: Artificial Sequence

```
<220> FEATURE:
<223> OTHER INFORMATION: Primer N83 SeqF2

<400> SEQUENCE: 37
gctggattac cagctcgacc                                                    20

<210> SEQ ID NO 38
<211> LENGTH: 20
<212> TYPE: DNA
<213> ORGANISM: Artificial Sequence
<220> FEATURE:
<223> OTHER INFORMATION: Primer N83SeqF3

<400> SEQUENCE: 38
cggacgcatt accggcaaag                                                    20

<210> SEQ ID NO 39
<211> LENGTH: 20
<212> TYPE: DNA
<213> ORGANISM: Artificial Sequence
<220> FEATURE:
<223> OTHER INFORMATION: Primer N84 SeqR4

<400> SEQUENCE: 39
cgaagcgaga gaagttatcc                                                    20

<210> SEQ ID NO 40
<211> LENGTH: 38
<212> TYPE: DNA
<213> ORGANISM: Artificial Sequence
<220> FEATURE:
<223> OTHER INFORMATION: Primer BC Spe F

<400> SEQUENCE: 40
actagtaaag gaggaaagag tatgaagaag gtcgcact                                 38

<210> SEQ ID NO 41
<211> LENGTH: 26
<212> TYPE: DNA
<213> ORGANISM: Artificial Sequence
<220> FEATURE:
<223> OTHER INFORMATION: Primer BC Xba R

<400> SEQUENCE: 41
tctagaaagc aggggcaagc catgtc                                             26

<210> SEQ ID NO 42
<211> LENGTH: 20
<212> TYPE: DNA
<213> ORGANISM: Artificial Sequence
<220> FEATURE:
<223> OTHER INFORMATION: Primer Trc F

<400> SEQUENCE: 42
ttgacaatta atcatccggc                                                    20

<210> SEQ ID NO 43
<211> LENGTH: 20
<212> TYPE: DNA
<213> ORGANISM: Artificial Sequence
<220> FEATURE:
<223> OTHER INFORMATION: Primer Trc R

<400> SEQUENCE: 43
cttctctcat ccgccaaaac                                                    20
```

```
<210> SEQ ID NO 44
<211> LENGTH: 38
<212> TYPE: DNA
<213> ORGANISM: Artificial Sequence
<220> FEATURE:
<223> OTHER INFORMATION: Primer DDo For

<400> SEQUENCE: 44
aagcttaaag gaggctgatt catgagatcg aaaagatt                            38

<210> SEQ ID NO 45
<211> LENGTH: 27
<212> TYPE: DNA
<213> ORGANISM: Artificial Sequence
<220> FEATURE:
<223> OTHER INFORMATION: Primer DDo Rev

<400> SEQUENCE: 45
tctagattat tcatcctgct gttctcc                                        27

<210> SEQ ID NO 46
<211> LENGTH: 22
<212> TYPE: DNA
<213> ORGANISM: Artificial Sequence
<220> FEATURE:
<223> OTHER INFORMATION: Primer DDko seq F2

<400> SEQUENCE: 46
gcatggcgcg gatttgacga ac                                             22

<210> SEQ ID NO 47
<211> LENGTH: 22
<212> TYPE: DNA
<213> ORGANISM: Artificial Sequence
<220> FEATURE:
<223> OTHER INFORMATION: Primer DDko seq F5

<400> SEQUENCE: 47
cattaaagag accaagtacg tg                                             22

<210> SEQ ID NO 48
<211> LENGTH: 24
<212> TYPE: DNA
<213> ORGANISM: Artificial Sequence
<220> FEATURE:
<223> OTHER INFORMATION: Primer DDko seq F7

<400> SEQUENCE: 48
atatcctggt ggtgtcgtcg gcgt                                           24

<210> SEQ ID NO 49
<211> LENGTH: 22
<212> TYPE: DNA
<213> ORGANISM: Artificial Sequence
<220> FEATURE:
<223> OTHER INFORMATION: Primer DDko seq F9

<400> SEQUENCE: 49
tctttgtcac caacgccctg cg                                             22

<210> SEQ ID NO 50
<211> LENGTH: 22
<212> TYPE: DNA
<213> ORGANISM: Artificial Sequence
<220> FEATURE:
<223> OTHER INFORMATION: Primer DDko seq R1
```

```
<400> SEQUENCE: 50
gcccaccgcg ctcgccgccg cg                                              22

<210> SEQ ID NO 51
<211> LENGTH: 22
<212> TYPE: DNA
<213> ORGANISM: Artificial Sequence
<220> FEATURE:
<223> OTHER INFORMATION: Primer DDko seq R3

<400> SEQUENCE: 51
cccccaggat ggcggcttcg gc                                              22

<210> SEQ ID NO 52
<211> LENGTH: 22
<212> TYPE: DNA
<213> ORGANISM: Artificial Sequence
<220> FEATURE:
<223> OTHER INFORMATION: Primer DDko seq R7

<400> SEQUENCE: 52
gggccgacgg cgataatcac tt                                              22

<210> SEQ ID NO 53
<211> LENGTH: 22
<212> TYPE: DNA
<213> ORGANISM: Artificial Sequence
<220> FEATURE:
<223> OTHER INFORMATION: Primer DDko seq R10

<400> SEQUENCE: 53
ttcttcgatc cactccttaa cg                                              22

<210> SEQ ID NO 54
<211> LENGTH: 56
<212> TYPE: DNA
<213> ORGANISM: Artificial Sequence
<220> FEATURE:
<223> OTHER INFORMATION: Primer ChnA F

<400> SEQUENCE: 54
catcaattga ctacgtagtc gtacgtgtaa ggaggtttga aatggaaaaa attatg         56

<210> SEQ ID NO 55
<211> LENGTH: 40
<212> TYPE: DNA
<213> ORGANISM: Artificial Sequence
<220> FEATURE:
<223> OTHER INFORMATION: Primer ChnA R

<400> SEQUENCE: 55
catgctagcc ccgggtatct tctactcatt ttttatttcg                           40

<210> SEQ ID NO 56
<211> LENGTH: 22
<212> TYPE: DNA
<213> ORGANISM: Artificial Squence
<220> FEATURE:
<223> OTHER INFORMATION: Primer chnSeq F1

<400> SEQUENCE: 56
ctcaacaggg tgtaagtgta gt                                              22

<210> SEQ ID NO 57
```

```
<211> LENGTH: 22
<212> TYPE: DNA
<213> ORGANISM: Artificial Sequence
<220> FEATURE:
<223> OTHER INFORMATION: Primer chnSeq R1

<400> SEQUENCE: 57
cgttttgata tagccaggat gt                                           22

<210> SEQ ID NO 58
<211> LENGTH: 35
<212> TYPE: DNA
<213> ORGANISM: Artificial Sequence
<220> FEATURE:
<223> OTHER INFORMATION: Primer Top ter F1

<400> SEQUENCE: 58
ctagaagtca aaagcctccg accggaggct tttga                             35

<210> SEQ ID NO 59
<211> LENGTH: 60
<212> TYPE: DNA
<213> ORGANISM: Artificial Sequence
<220> FEATURE:
<223> OTHER INFORMATION: Primer Top ter F2

<400> SEQUENCE: 59
ctgctcgagt tgctagcaag tttaaacaaa aaaaagcccg ctcattaggc gggctgagct   60

<210> SEQ ID NO 60
<211> LENGTH: 37
<212> TYPE: DNA
<213> ORGANISM: Artificial Sequence
<220> FEATURE:
<223> OTHER INFORMATION: Primer Bot ter R1

<400> SEQUENCE: 60
cagcccgcct aatgagcggg cttttttttg tttaaac                           37

<210> SEQ ID NO 61
<211> LENGTH: 50
<212> TYPE: DNA
<213> ORGANISM: Artificial Sequence
<220> FEATURE:
<223> OTHER INFORMATION: Primer Bot ter R2

<400> SEQUENCE: 61
ttgctagcaa ctcgagcagt caaaagcctc cggtcggagg cttttgactt             50

<210> SEQ ID NO 62
<211> LENGTH: 22
<212> TYPE: DNA
<213> ORGANISM: Artificial Sequence
<220> FEATURE:
<223> OTHER INFORMATION: Primer pCL1925 vec F

<400> SEQUENCE: 62
cggtatcatc aacaggctta cc                                           22

<210> SEQ ID NO 63
<211> LENGTH: 22
<212> TYPE: DNA
<213> ORGANISM: Artificial Sequence
<220> FEATURE:
<223> OTHER INFORMATION: Primer pCL1925 vec R1

<400> SEQUENCE: 63
```

```
agggtttttcc cagtcacgac gt                                              22
```

<210> SEQ ID NO 64
<211> LENGTH: 22
<212> TYPE: DNA
<213> ORGANISM: Artificial Sequence
<220> FEATURE:
<223> OTHER INFORMATION: Primer pCL1925 vec R2

<400> SEQUENCE: 64

```
cgcaatagtt ggcgaagtaa tc                                               22
```

<210> SEQ ID NO 65
<211> LENGTH: 20
<212> TYPE: DNA
<213> ORGANISM: Artificial Sequence
<220> FEATURE:
<223> OTHER INFORMATION: Primer N84 Seq R2

<400> SEQUENCE: 65

```
gcatcgagat tatcgggatg                                                  20
```

<210> SEQ ID NO 66
<211> LENGTH: 208
<212> TYPE: DNA
<213> ORGANISM: Escherichia coli

<400> SEQUENCE: 66

```
atcgcccgca ttcttgccgc atcttccccc ggcgtcacac cgaagtaacg tttaaactca      60
cggctgtgta ggctggagct gcttcgaagt tcctatactt tctagagaat aggaacttcg     120
gaataggaac taaggaggat attcatatga ttacgttgga tgtcagccgc cgtatatacg     180
aagccgcccg ctaagctttt tacgcctc                                       208
```

<210> SEQ ID NO 67
<211> LENGTH: 42
<212> TYPE: DNA
<213> ORGANISM: Artificial Squence
<220> FEATURE:
<223> OTHER INFORMATION: Promoter 1.6GI Variant

<400> SEQUENCE: 67

```
gcccttgaca atgccacatc ctgagcaaat aattcaacca ct                         42
```

<210> SEQ ID NO 68
<211> LENGTH: 42
<212> TYPE: DNA
<213> ORGANISM: Artificial Sequence
<220> FEATURE:
<223> OTHER INFORMATION: Promoter 1.5 GI

<400> SEQUENCE: 68

```
gcccttgact atgccacatc ctgagcaaat aattcaacca ct                         42
```

<210> SEQ ID NO 69
<211> LENGTH: 3240
<212> TYPE: DNA
<213> ORGANISM: Klebsiella oxytoca

<400> SEQUENCE: 69

```
ggcgcggtcc gccaggcggt cacctccgcg cgcgaaatcg gcaaaaccgt ccttgcgacc      60
ctcggtgctg aaccgaaaaa cgatcgcccg tcctacatct gatacccacg aggctgattc     120
```

| | |
|---|---|
| atgagatcga aaagatttga agcactggcg aaacgccctg tgaatcagga cggcttcgtt | 180 |
| aaggagtgga tcgaagaagg ctttatcgcg atggaaagcc cgaacgaccc aaaaccgtcg | 240 |
| attaaaatcg ttaacggcgc ggtgaccgag ctggacggga aaccggtaag cgattttgac | 300 |
| ctgatcgacc actttatcgc ccgctacggt atcaacctga accgcgccga agaagtgatg | 360 |
| gcgatggatt cggtcaagct ggccaacatg ctgtgcgatc cgaacgttaa acgcagcgaa | 420 |
| atcgtcccgc tgaccaccgc gatgacgccg gcgaaaattg tcgaagtggt ttcgcatatg | 480 |
| aacgtcgtcg agatgatgat ggcgatgcag aaaatgcgcg cccgccgcac cccgtcccag | 540 |
| caggcgcacg tcaccaacgt caaagataac ccggtacaga ttgccgccga cgccgccgaa | 600 |
| ggggcatggc gcggatttga cgaacaggaa accaccgttg cggtagcgcg ctatgcgccg | 660 |
| ttcaacgcca tcgcgctgct ggtgggctcg caggtaggcc gtccgggcgt gctgacgcag | 720 |
| tgctcgctgg aagaagccac cgagctgaag ctcggcatgc tgggccacac ctgctacgcc | 780 |
| gaaaccatct ccgtctacgg caccgagccg gtctttaccg acggcgacga cacgccgtgg | 840 |
| tcgaagggct tcctcgcctc gtcctacgcc tctcgcgggc tgaaaatgcg ctttacctcc | 900 |
| ggctccggct cggaagtgca gatgggctac gccgaaggca atccatgct ttatctggaa | 960 |
| gcgcgctgca tctacatcac caaagccgcg ggcgtacagg tctgcaaaa cggttccgta | 1020 |
| agctgcatcg gcgtgccgtc tgcggtgcct tccggcattc gcgcggtgct ggcggaaaac | 1080 |
| ctgatctgtt cgtcgctgga tctggagtgc gcctccagca cgaccagac cttcacccac | 1140 |
| tccgatatgc gtcgtaccgc gcgcctgctg atgcagttcc tgccgggcac cgactttatc | 1200 |
| tcctccggtt attccgcggt gccgaactac gacaacatgt tcgccggctc caacgaagat | 1260 |
| gccgaagact ttgacgacta caacgtcatc cagcgcgacc tgaaggtgga cggcggtttg | 1320 |
| cgtccggttc gcgaagagga cgtcatcgcc atccgtaaca agccgcccg cgcgctgcag | 1380 |
| gccgtgtttg ccggaatggg gctgccgccg attaccgatg aagaagttga agccgcgacc | 1440 |
| tacgcccacg gttcgaaaga tatgccggag cgcaacatcg tcgaagacat caagttcgcc | 1500 |
| caggaaatca tcaataaaaa ccgcaacggt ctggaagtgg tgaaagcgct ggcgcagggc | 1560 |
| ggattcaccg acgtggccca ggacatgctc aacatccaga aagctaagct gaccggggac | 1620 |
| tacctgcata cctccgcgat tatcgtcggc gacgggcagg tgctgtcagc cgtcaacgac | 1680 |
| gtcaacgact atgccggtcc ggcaacgggc tatcgcctgc agggcgaacg ctgggaagag | 1740 |
| attaaaaaca tccctggcgc tcttgatccc aacgagattg attaaggggt gagaaatgga | 1800 |
| aattaatgaa aaattgctgc gccagataat tgaagacgtg ctcagcgaga tgaagggcag | 1860 |
| cgataaaccg gtctcgtttta atgcgccggc ggcctccgcg gcgccccagg ccacgccgcc | 1920 |
| cgccggcgac ggcttcctga cggaagtggg cgaagcgcgt cagggaaccc agcaggacga | 1980 |
| agtgattatc gccgtcggcc cggctttcgg cctggcgcag accgtcaata tcgtcggcat | 2040 |
| cccgcataag agcatttttgc gcgaagtcat tgccggtatt gaagaagaag cattaaggc | 2100 |
| gcgcgtgatt cgctgcttta atcctccga cgtggccttc gtcgccgttg aaggtaatcg | 2160 |
| cctgagcggc tccggcatct ctatcggcat ccagtcgaaa ggcaccacgg tgatccacca | 2220 |
| gcaggggctg ccgccgctct ctaacctgga gctgttcccg caggcgccgc tgctgaccct | 2280 |
| ggaaacctat cgccagatcg gcaaaaacgc cgcccgctat gcgaacgcg aatcgccgca | 2340 |
| gccggtcccg acgctgaatg accagatggc gcggccgaag taccaggcga atcggccat | 2400 |
| tttgcacatt aaagagacca agtacgtggt gacgggcaaa aacccgcagg aactgcgcgt | 2460 |
| ggcgctttga taaaggataa ctccatgaat accgacgcaa ttgaatcgat ggtacgcgac | 2520 |

```
gtattgagcc gcatgaacag cctgcagggc gaggcgcctg cggcggctcc ggcggctggc    2580
ggcgcgtccc gtagcgccag ggtcagcgac tacccgctgg cgaacaagca cccggaatgg    2640
gtgaaaaccg ccaccaataa aacgctggac gactttacgc tggaaaacgt gctgagcaat    2700
aaagtcaccg cccaggatat gcgtattacc ccggaaaccc tgcgcttaca ggcttctatt    2760
gccaaagacg cgggccgcga ccggctggcg atgaacttcg agcgcgccgc cgagctgacc    2820
gcggtaccgg acgatcgcat tcttgaaatc tacaacgccc tccgcccta tcgctcgacg     2880 aaagaggagc tgctggcgat cgccgacgat ctcgaaagcc gctatcaggc gaagatttgc    2940
gccgctttcg ttcgcgaagc ggccacgctg tacgtcgagc gtaaaaaact caaaggcgac    3000
gattaacttc tctaagtaat tcgagatgca ttgaggcggc aagtgagtga caaattcgtc    3060
tggaacgaat tgaacagcc ataggctggc tttagtgagg gacagggatg tccctcataa      3120
ccccgatgag cttactgtag taagtgattc gggtgaaaga acgcagccaa caaaaaggca    3180
gtttgaagta cgacgagaaa aggggcatgt gatgcgatat atagctggca ttgatatcgg    3240

<210> SEQ ID NO 70
<211> LENGTH: 2640
<212> TYPE: DNA
<213> ORGANISM: Klebsiella oxytoca

<400> SEQUENCE: 70
acgtcgagcg taaaaaactc aaaggcgacg attaacttct ctaagtaatt cgagatgcat      60
tgaggcggca agtgagtgac aaattcgtct ggaacgaatt gaacagcca taggctggct     120 ttagtgaggg acagggatgt ccctcataac cccgatgagc ttactgtagt aagtgattcg     180
ggtgaaagaa cgcagccaac aaaaaggcag tttgaagtac gacgagaaaa ggggcatgtg    240
atgcgatata tagctggcat tgatatcggc aactcatcga cggaagtcgc cctggcgacc     300
ctggatgagg ctggcgcgct gacgatcacc cacagcgcgc tggcggaaaac caccggaatc     360 aaaggcacgt tgcgtaacgt gttcgggatt caggaggcgc tcgccctcgt cgccagaggc    420
gccgggatcg ccgtcagcga tatttcgctc atccgcatca acgaagcgac gccggtgatt    480
ggcgatgtgg cgatggaaac cattaccgaa accatcatca ccgaatcgac catgatcggc    540
cataacccga aaacgcccgg cggcgcgggg cttggcacag gcatcaccat tacgccgcag     600
gagctgctaa ccccgccggc ggacgcgccc tatatcctgg tggtgtcgtc ggcgttcgat     660
tttgccgata tcgccagcgt gattaacgct tccctgcgcg ccgggtatca gattaccggc    720
gtcattttac agcgcgacga tggcgtgctg gtcagcaacc ggctggaaaa accgctgccg    780
atcgttgacg aagtgctgta catcgaccgc attccgctgg ggatgctggc ggcgattgag    840
gtcgccgttc cggggaaggt catcgaaacc ctctctaacc cttacggcat cgccaccgtc    900
tttaacctca gccccgagga gacgaagaac atcgtcccga tggcccgggc gctgattggc    960
aaccgttccg ccgtggtggt caaaacgcca tccggcgacg tcaaagcgcg cgcgatacc    1020 gccggtaatc ttgagctgct ggcccagggc cgtagcgtgc gcgtggatgt ggccgccggc    1080
gccgaagcca tcatgaaagc ggtcgacggc tgcggcaggc tcgataacgt caccggcgaa    1140
tccggcacca atatcggcgg catgctggaa cacgtgcgcc agaccatggc cgagctgacc    1200
aacaagccga gcagcgaaat atttattcag gacctgctgg ccgttgatac ctcggtaccg     1260
gtgagcgtta ccgcggtct ggccggggag ttctcgctgg agcaggccgt gggcatcgcc     1320
tcgatggtga atcggatcg cctgcagatg gcaatgatcg cccgcgaaat cgagcagaag    1380
```

-continued

```
ctcaatatcg acgtgcagat cggcggcgca gaggccgaag ccgccatcct ggggggcgctg    1440 accacgccgg gcaccacccg accgctggcg atcctcgacc tcggcgcggg ctccaccgat    1500
gcctccatca tcaaccccaa aggcgacatc atcgccaccc atctcgccgg cgcaggcgac    1560
atggtgacga tgattattgc ccgcgagctg gggctggaag accgctatct ggcggaagag    1620
atcaagaagt acccgctggc taaggtggaa agcctgttcc atttacgcca cgaggacggc    1680
agcgtgcagt tcttctccac gccgctgccg cccgccgtgt tcgcccgcgt ctgcgtggtg    1740
aaagcggacg aactggtgcc gctgcccggc gatttagcgc tggaaaaagt gcgcgccatt    1800
cgccgcagcg ccaaagagcg ggtctttgtc accaacgccc tgcgcgcgct gcgtcaggtc    1860
agccccaccg gcaacattcg cgatattccg ttcgtggtgc tggtcggcgg ttcgtcgctg    1920
gatttcgaag tcccgcagct ggtcaccgat gcgctggcgc actaccgcct ggttgccgga    1980
cggggaaata ttcgcggcag cgagggcccc cgaaacgcgg tggccaccgg cctgattctc    2040
tcctggcata aggagtttgc gcatgaacgg taatcacagc gccccggcca tcgcgatcgc    2100
cgtcatcgac ggctgcgacg gcctgtgcgc gaagtgctg ctgggtatcg aagaggaagg    2160
tatccctttc cggctccagc atcacccggc cggagaggtc gtggacagcg cctggcaggc    2220
ggcgcgcagc tcgccgctgc tggtgggcat cgcctgcgac cgccatatgc tggtcgtgca    2280
ctacaagaat ttacccgcat cggcgccgct ttttacgctg atgcatcatc aggacagtca    2340
ggcccatcgc aacaccggta ataacgcggc acggctggtc aaggggatcc ctttccggga    2400
tctgaatagc gaagcaacag gagaacagca ggatgaataa cgcactggga ctggttgaaa    2460
caaaagggtt agtgggcgcc attgaggccg ccgatgcgat ggtgaaatcc gccaacgtgc    2520
agctggtcgg ctacgaaaaa attggctcgg gcctcgtcac cgtgatggtg cgcggcgacg    2580
tcggcgcggt caaagcggcg gtagacgcgg gcagcgcggc ggcgagcgcg gtgggcgaag    2640
```

<210> SEQ ID NO 71
<211> LENGTH: 756
<212> TYPE: DNA
<213> ORGANISM: Acinetobacter sp.

<400> SEQUENCE: 71

```
atggaaaaaa ttatgtcaaa taaattcaac aataaagtcg ctttaattac tggcgctggt     60
tcaggtattg gtaaaagcac cgcactgctt ttggctcaac agggtgtaag tgtagtggtt    120
tcagatatta acctggaagc agcacagaaa gttgtggacg aaattgtcgc tttaggcggg    180
aaagcggctg cgaataaggc caatactgct gagcctgaag acatgaaagc tgcagtcgag    240
tttgcggtca gcacttttgg tgcactgcat ttggccttca ataatgcggg aattctgggt    300
gaagttaact ccaccgaaga attgagcatt gaaggatggc gtcgtgtgat tgatgtgaac    360
ttgaatgcgg ttttctacag catgcattat gaagttcctg caatcttggc cgcagggggc    420
ggagcgattg tcaataccgc ttctattgca ggcttgatcg ggattcaaaa tatttcaggc    480
tatgtcgctg caaaacatgg cgtaacgggt ctaacgaaag cggcggcatt ggaatatgca    540
gataaaggga ttcgcattaa ttcagtacat cctggctata tcaaaacgcc tttgattgca    600
gaatttgaag aagcagaaat ggtaaaacta catccgattg gtcgtttggg acagccggaa    660
gaagttgctc aggttgttgc cttcctactt tctgatgatg cttcatttgt gaccggtagt    720
cagtatgtgg tcgatggtgc atataccctcg aaataa                              756
```

<210> SEQ ID NO 72
<211> LENGTH: 251

```
<212> TYPE: PRT
<213> ORGANISM: Acinetobacter sp.

<400> SEQUENCE: 72
```

| | | | | | | | | | | | | | | |
|---|---|---|---|---|---|---|---|---|---|---|---|---|---|---|
|Met|Glu|Lys|Ile|Met|Ser|Asn|Lys|Phe|Asn|Asn|Lys|Val|Ala|Leu|Ile
1| | | |5| | | | |10| | | | |15| |
|Thr|Gly|Ala|Gly|Ser|Gly|Ile|Gly|Lys|Ser|Thr|Ala|Leu|Leu|Leu|Ala
| | | |20| | | | |25| | | | |30| | |
|Gln|Gln|Gly|Val|Ser|Val|Val|Val|Ser|Asp|Ile|Asn|Leu|Glu|Ala|Ala
| | | |35| | | | |40| | | | |45| | |
|Gln|Lys|Val|Val|Asp|Glu|Ile|Val|Ala|Leu|Gly|Gly|Lys|Ala|Ala|Ala
| | | |50| | | | |55| | | | |60| | |
|Asn|Lys|Ala|Asn|Thr|Ala|Glu|Pro|Glu|Asp|Met|Lys|Ala|Ala|Val|Glu
65| | | | |70| | | | |75| | | | |80
|Phe|Ala|Val|Ser|Thr|Phe|Gly|Ala|Leu|His|Leu|Ala|Phe|Asn|Asn|Ala
| | | | |85| | | | |90| | | | |95| |
|Gly|Ile|Leu|Gly|Glu|Val|Asn|Ser|Thr|Glu|Glu|Leu|Ser|Ile|Glu|Gly
| | | | |100| | | | |105| | | | |110| |
|Trp|Arg|Arg|Val|Ile|Asp|Val|Asn|Leu|Asn|Ala|Val|Phe|Tyr|Ser|Met
| | | |115| | | | |120| | | | |125| | |
|His|Tyr|Glu|Val|Pro|Ala|Ile|Leu|Ala|Ala|Gly|Gly|Ala|Ile|Val|
| | | |130| | | | |135| | | | |140| | |
|Asn|Thr|Ala|Ser|Ile|Ala|Gly|Leu|Ile|Gly|Ile|Gln|Asn|Ile|Ser|Gly
145| | | | |150| | | | |155| | | | |160
|Tyr|Val|Ala|Ala|Lys|His|Gly|Val|Thr|Gly|Leu|Thr|Lys|Ala|Ala|
| | | | |165| | | | |170| | | | |175| |
|Leu|Glu|Tyr|Ala|Asp|Lys|Gly|Ile|Arg|Ile|Asn|Ser|Val|His|Pro|Gly
| | | |180| | | | |185| | | | |190| | |
|Tyr|Ile|Lys|Thr|Pro|Leu|Ile|Ala|Glu|Phe|Glu|Ala|Glu|Met|Val|
| | | |195| | | | |200| | | | |205| | |
|Lys|Leu|His|Pro|Ile|Gly|Arg|Leu|Gly|Gln|Pro|Glu|Glu|Val|Ala|Gln
| | | |210| | | | |215| | | | |220| | |
|Val|Val|Ala|Phe|Leu|Leu|Ser|Asp|Asp|Ala|Ser|Phe|Val|Thr|Gly|Ser
225| | | | |230| | | | |235| | | | |240
|Gln|Tyr|Val|Val|Asp|Gly|Ala|Tyr|Thr|Ser|Lys| | | | | |
| | | | |245| | | | |250| | | | | | |

```
<210> SEQ ID NO 73
<211> LENGTH: 17417
<212> TYPE: DNA
<213> ORGANISM: Acinetobacter sp.

<400> SEQUENCE: 73
ctagcattta cgcgtgaggt aggtgggtag gtctgtaatg tgaagatcta cgaggaaatc      60
ggcgtcatga cgtgaggtcc agcgaaccgt cttgcgtaat ccgtcattca tggtgagtaa     120
cattgcccgt atttcgcgtt cagtatatag cagaccagca tgattaacga gatcctgggt     180
attttagtcc ggacacccaa agtcccatgc ggtcgccaga tccagtaagt cgactacgac     240
ttgctcatct gtagccaacc ccgcaatcac ttccacaatt ttcatcagtg gaaccggatt     300
gaagaaatgg aaacctgcga tacggccctg atgctgacac gcagatgcaa ttgaggtcac     360
agatagtgag gatgtatttg aaaccagaat agtttcttca gccacaatcc tttcaagctg     420
tttaaacaaa gtttgcttga tttcagatt ttcataatt gcttctacga ccagatcaac      480
gccagcaacc tcttcaatgc tttccaagat aatcaatcgg gctaaggtat ccacaagctg     540
```

```
ctgttcggtt aactttcctt tagcagctag tttgtgcaag gttactttta atttttccaa    600
gccttgctca gcagcgccgg gtttagcatc aaataaacgg acctcaacac ccgcctgtgc    660
tgcaatttgc gcaataccca ttcccattac gcctgtgcca atcaaggcca tttttgaat     720
cgtcatgact tattttcctt gatattgagg gcttcgcttt tcgaaaaagg cattgacgcc    780
ttctttttga tcttgtgtat caaataaaat ttggaaggct ttacgctcta atgccaaagc    840
accatcgagt ggcatattgg cacctagtgt tgtgacttct ttgatctgtt caacggcaat    900
cggtgagagt tgggcaatct gtgtcgcaat ttcaaccgct ttagcaaggg tttgatcatc    960
ctcaaccact tcggaaacca accccatttt gtcagcttct tctgcagaaa agatctttcc   1020
tgttaacact atttgcatgg ctttaaactt ccctaccgca cgcagtaagc gttgggtacc   1080
accagcacct ggcatcagcc ccaatttgac ttcaggctga ccaaactggg ctgattttcc   1140
ggcaataatg atgtctgcat gcattgcaag ttcacaccca ccacccaatg catatccatt   1200
cacagcagcc acaatcggtt tagggcaatc aataatggcc cgccagtact gttccgtatg   1260
gcgtaaatac atgtctacgg tttttgcagt ggtgaagtcc cggatatccg cacctgctgc   1320
aaatactttt tcaccaccag taatgacaat tgcgcggact gtatcagatg cagcgagctg   1380
ctcaaacatt gctgcgagct gttggcgcag ttccagattc aatgcatttc tagtatctgg   1440
acgatgtagt tcaacaatgg ccacaccatt actttgaata tctaaattca atatttcatt   1500
ttccataaca acctacatgt ttcgcatagc ggtttattta aaccaaatat acctgttttt   1560
ttgcaacaat aaagcccaca ggaacatagt tttaaattaa aaattggcta aaaatattta   1620
aaaaacacaa ataaaatacc gcacagcggt atttgatatc aatattattg catttatttt   1680
tccattctgt catattattt tcattccaaa gcattagatc acccctgcat gaagcagaga   1740
tggctaaatt tacctatcta atacaagggc ttaaaaatga ttcgcgatca agacacatta   1800
aatcagctgg ttgacatgat ccgtcagttt gtcgatggcg ttcttattcc caatgaagaa   1860
attgttgcgg aaaccgatga aattccagct gaaatcgtgc agcaaatgaa agaactgggt   1920
ctttttggtc tcaccattcc tgaggaatat gagggtcttg gcctgaccat ggaggaagag   1980
gtttacattg catttgaact gggacgtacc tctcctgctt tccgttcact gatcggcact   2040
aacaatggga tcggttcatc aggcttaatt attgatggct ccgaagagca gaaacagtat   2100
tttttgccac gtctggcaag tggtgaaatt attggttcat tctgtttaac tgaacctgat   2160
tccggttcag atgctgcctc tttaaaaacc acagcggtga aagatggtga tcattacatt   2220
ttaaatggca ctaagcgtta catcaccaat gcaccgcatg cggtgtgtctt tactgtcatg   2280
gcacgtacca gtaccgaaat taaaggtaca ggtggaattt cagcctttat cgtggacagt   2340
aaaactcctg gtatttcctt gggtaaacgt gataagaaga tgggccaaaa aggtgcacat   2400
acctgtgatg tgatttttga aaactgtcgt attcctgcat ctgcactcat tggtggtgtt   2460
gaaggtgtag gttttaaaac tgcaatgaag gtacttgata aaggccgtat tcatattgct   2520
gcattaagtg taggtgctgc tacgcgtatg ctggaagatt ccctacaata tgccgttgag   2580
cgcaaacagt ttggtcaagc gattgcgaac ttccagttga ttcaaggtat gttagccgat   2640
tctaaagctg aaatttacgc agcaaaatgt atggtattag atgctgcccg acttcgtgat   2700
gctggacaga atgtcagcac ggaagcatct tgtgccaaga tgtttgccac tgaaatgtgt   2760
ggccgtgtcg cagatcgtgg cgtacagatc catggtggtg cgggttatat cagtgaatat   2820
gctattgagc gtttttaccg tgatgtacgt ttattccgtt tgtatgaagg tacaacgcaa   2880
atccaacagg tcattattgc ccgcaatatg atccgtgaag cgactcaata attgtataac   2940
```

| | |
|---|---|
| aggtattgag tgtatctaaa aggacgggat tagtgattta agctataact tgaatactaa | 3000 |
| tcctgacttt ttgatggcaa ggctataaaa cctcctagct cattttatct ctaagctaat | 3060 |
| cacagctgaa agatattttc agtcttcatc cttaccagac agttcacaat acaaaattgg | 3120 |
| attttatgaa tatgcaagaa caagaaatcg aacgcgaatc aatggagttt gacgtcgtga | 3180 |
| ttgtcggcgc aggaccggcc ggtctttctg cagcgatcaa gatccgtcaa cttgcaattg | 3240 |
| aaaacaacct gaacgatctg tcggtttgtg tggtggaaaa aggctctgaa gtcggtgcgc | 3300 |
| acatcttgtc cggtgcggta ctggaaccac gtgccatgaa tgagctgttc ccgaactgga | 3360 |
| aggaagaagg tgcaccttta aatgttccag tgaccgaaga caagacctat ttcctgctct | 3420 |
| cggatgaaaa atcacaagaa gcgccacact ggatggtgcc taaaaccatg cataacgatg | 3480 |
| gcaactatgt tatctcgctc ggcaacgtag tgcgctggtt gggtcaaaaa gcggaagagc | 3540 |
| tggaagtatc tattttcccg ggctttgccg ctgctgaaat tctgtaccat gcagatggtt | 3600 |
| cggtgaaagg cattcaaacc ggtgacatgg gcattggcaa ggatggcgaa ccgacccata | 3660 |
| actttactcc gggctatgaa ctgcatgcca aatacaccct gtttgctgaa ggctgccgtg | 3720 |
| gccacctcgg caagcgttta attgccaaat acaacctcga taaagattca gatccacaac | 3780 |
| attacggtat cggtatcaaa gagctgtggg aaatcgaccc ggcgaaacac aagccaggtc | 3840 |
| tggtgatgca cggtgccggc tggccattgt ctgaaaccgg ttcttcaggc ggctggtggt | 3900 |
| tgtatcatgc ggaaaacaat caggtgactt tgggcatgat cgtcgatctg tcttacacca | 3960 |
| acccgcatat gtatccgttt atggaaatgc agcgctggaa aacccatccg ctgatcaagc | 4020 |
| agtatctgga aggtggcaaa cgtatttctt atggcgcgcg tgcggtaacc aaaggcggct | 4080 |
| ttaactcgct accgaaattt accttcccgg gcggatcgct gattggtgac gatgccggct | 4140 |
| tcctgaactt tgccaaaatc aagggctcac ataccgcgat gaaatccggc atgctctgcg | 4200 |
| gtgaagcagt gtttgaagcc attgctgccg gtgtggaaaa aggtggtgac cttgcggttg | 4260 |
| cgcgtgtgac ggaaggcgaa gacttgtttg ccaaaaaact gacttcttac accgacaagt | 4320 |
| tcaataatag ctggctgaaa gaagagctgt acaactcgcg taactttggc ccggccatgc | 4380 |
| acaagtttgg tcagtggctc ggtggtgcgt ttaactttat cgaccagaac gtgtttaagg | 4440 |
| tgccgtttac cctgcatgac ctggtgacgg atttcggtgc gctgaaaacc gtcgatgcgg | 4500 |
| tgaacttcaa gccgaattat ccaaaaccgg atggcaaact gaccttttgac cgtctgtctt | 4560 |
| cggtgtttgt atccaacacg gtgcatgaag aaaaccagcc agcgcattta aaactgactg | 4620 |
| acacttcgat tccggtgaat gtcaacctgc caaaatggga tgaaccggcg cagcgctact | 4680 |
| gccccgcggg tgtatacgaa atcatggaaa atgatgacgg ttcgaaacgc ttccagatca | 4740 |
| atgcagccaa ctgtgtgcac tgcaagacct gtgcatcaa ggatccttca cagaacatca | 4800 |
| cctgggtaac accggaaggt ggtggtggtc caaactatcc gaatatgtaa gtctaatcac | 4860 |
| ttcaaggaag aggtttccca tttcccttct ttctagcaga tgaagaagct tgcaactaaa | 4920 |
| agagattgtt tggatcagtt acccaaaatc gttgaaaaga ttttaactct tcgatttta | 4980 |
| tttttaggt aatcctagcc ctctcggggg ctaggattaa aaattttaag ttattccaac | 5040 |
| acgaatgaca aattgttcaa tgcaaaataa aaacatacaa tatataaata tatttttaa | 5100 |
| ttaaaacata agattacaat aaaataagaa ttttatttg gagtttgttt ttttctaca | 5160 |
| atgatcatta tgtacaattt ttaggttcac cccatccaag ccttgtgatt gcattcctgc | 5220 |
| gattctttat tcaatgaata agcaatgcta ttaatcagca atgaataacc agcactgcag | 5280 |

```
attttgaata aattcacatg tcgtaatgga gattatcatg tcacaaaaaa tggatttga    5340
tgctatcgtg attggtggtg gttttggcgg actttatgca gtcaaaaaat taagagacga   5400
gctcgaactt aaggttcagg cttttgataa agccacggat gtcgcaggta cttggtactg   5460
gaaccgttac ccaggtgcat tgtcggatac agaaacccac ctctactgct attcttggga   5520
taaagaatta ctacaatcgc tagaaatcaa gaaaaaatat gtgcaaggcc ctgatgtacg   5580
caagtattta cagcaagtgg ctgaaaagca tgatttaaag aagagctatc aattcaatac   5640
cgcggttcaa tcggctcatt acaacgaagc agatgccttg tgggaagtca ccactgaata   5700
tggtgataag tacacggcgc gtttcctcat cactgcttta ggcttattgt ctgcgcctaa   5760
cttgccaaac atcaaaggca ttaatcagtt taaaggtgag ctgcatcata ccagccgctg   5820
gccagatgac gtaagttttg aaggtaaacg tgtcggcgtg attggtacgg gttccaccgg   5880
tgttcaggtt attacggctg tggcacctct ggctaaacac ctcactgtct tccagcgttc   5940
tgcacaatac agcgttccaa ttggcaatga tccactgtct gaagaagatg ttaaaaagat   6000
caaagacaat tatgacaaaa tttgggatgg tgtatggaat tcagcccttg cctttggcct   6060
gaatgaaagc acagtgccag caatgagcgt atcagctgaa gaacgcaagg cagttttttga  6120
aaaggcatgg caaacaggtg gcggtttccg tttcatgttt gaaactttcg gtgatattgc   6180
caccaatatg gaagccaata tcgaagcgca aaatttcatt aagggtaaaa ttgctgaaat   6240
cgtcaaagat ccagccattg cacagaagct tatgccacag gatttgtatg caaaacgtcc   6300
gttgtgtgac agtggttact acaacaccct taaccgtgac aatgtccgtt agaagatgt    6360
gaaagccaat ccgattgttg aaattaccga aaacggtgtg aaactcgaaa atggcgattt   6420
cgttgaatta gacatgctga tatgtgccac aggttttgat gccgtcgatg caactatgt    6480
gcgcatggac attcaaggta aaacggcctt ggccatgaaa gactactgga agaaggtcc    6540
gtcgagctat atgggtgtca ccgtaaataa ctatccaaac atgttcatgg tgcttggacc   6600
gaatggcccg tttaccaacc tgccgccatc aattgaatca caggtggaat ggatcagtga   6660
taccattcaa tacacggttg aaaacaatgt tgaatccatt gaagcgacaa agaagcgga    6720
agaacaatgg actcaaactt gcgccaatat tgcggaaatg accttattcc ctaaagcgca   6780
atcctggatt tttggtgcga atatcccggg caagaaaaac acggtttact tctatctcgg   6840
tggtttaaaa gaatatcgca gtgcgctagc caactgcaaa aaccatgcct atgaaggttt   6900
tgatattcaa ttcaacgtt cagatatcaa gcaacctgcc aatgcctaaa tatatggggg    6960
gcatccccca tattccattt tgtttaacat cagtcatatg ccagggatgt cttatcatga   7020
actatccaaa tatacctta tatatcaacg gtgagtttct agatcatacc aatagagacg    7080
tcaaagaagt ttttaatcca gtgaaccatg aatgtattgg actcatggcc tgtgcatcac   7140
aagcagacct ggactacgca cttgaaagtt cacaacaggc ttttctaagg tggaaaaaaa   7200
cttctcctat cacccgtagt gaaatcctca gaacctttgc gaaactagcg cgtgaaaaag   7260
cagcagaaat cgggcgcaat attacccttg atcaaggtaa gcccctgaaa gaagccattg   7320
cagaagtcac tgtctgtgca gaacatgcag aatggcatgc agaagaatgc cgacgcattt   7380
atggccgtgt tattccaccg cgtaacccaa atgtacagca actagtagtc agagaaccgc   7440
tgggcgtatg tctggcattt tcaccgtgga atttcccgtt taatcaggca attcgtaaaa   7500
tttctgctgc aattgctgcc ggctgcacca tcattgtgaa aggttctggc gacacaccaa   7560
gcgcggtata tgcgattgcc cagctatttc atgaggcggg tttgccgaat ggtgtgctga   7620
atgtgatttg gggtgactca aacttcattt ctgattacat gatcaaatcg ccgatcatcc   7680
```

```
aaaagatttc attcacaggc tcaaccccgg tgggtaaaaa attagcctcg caagcgagtc   7740
tgtatatgaa gccttgcacc atggaattgg gtggtcatgc accggtcatc gtctgtgatg   7800
atgctgatat tgatgccgct gttgaacatc tggtcggtta taaattccgt aatgcaggac   7860
aggtctgtgt atcaccaacc cgttttatg tgcaggaagg tatttataag gaattttctg    7920
agaaagtggt gttaagagcc aaacagatca agtgggttg tggcttagac gcatcctcag    7980
atatgggacc attggctcaa gctcgccgca tgcatgcaat gcaacaaatt gttgaagatg   8040
cggttcataa aggctcaaaa ttactgcttg gcggaaataa aatttctgac aaaggcaatt   8100
tttttgaacc aacggtactc ggtgacttgt gcaatgacac ccagtttatg aatgacgagc   8160
catttggtcc gatcattggt ttgatacctt ttgacacaat agaccatgtc ctggaagaag   8220
caaatcgatt accatttgga ttagcctctt acgcttttac cacatccagc aaaaatgcgc   8280
atcaaatctc atacggactg gaggctggca tggtttcgat taaccacatg ggattggcgc   8340
tcgctgaaac accttttggt ggtattaagg atagcggttt tggtagtgaa gggggtatcg   8400
aaacctttga cggttaccte agaaccaaat ttattacgca actcaattag aaatggatct   8460
tggtgtgcgt aggcacacca attctctttt gactttaagg atgaaagtta aatgagcaca   8520
gacaaagcaa atacgctgat caaacccgaa gatgtcgtgt tatggattcc gggtaatgtc   8580
acaattgaca gcatgaatgc cggttgggaa acattgcaa tcagagggta cgaatatacc    8640
aacctcgatg tgcatattcc tgccatgcgt gactacatga tcgtcaacta taaaaaaagt   8700
gcggcggaaa tgcgtagaaa aggcgatgcc tcttgggata cccaagtggt taagccgggt   8760
tatgtctcct tgttgacctg tggtgaagat tcccgctggg cgtggaatga ccatattgcc   8820
gtcacccatg tctacatttc gcatgactcc atcacctcaa tggcgaataa ggtgtttgat   8880
tatgatatcg cttcgatccg aatcagagac gaagtcggtg tggaagatca tgttttacct   8940
gctctgactt cacttttaga actagaatta aagcaaggtg gtttaggtgg aaacctgtat   9000
ttagagagca ttaaaaacca gatcgccctg catttactcc gtcagtatgc caaattagat   9060
tttaaggaag acagtgccg ttctggtttt actcccctac aacgcagact gttattagaa    9120
tttatcaatg aaaacatgag cattaaaatt accctcgaag atttagcggg attagtcaag   9180
atgagcgtgc ctcatttaat gagaaaattt aaagtcgatt ttggtaattc ccctgctgcc   9240
tacatcatga atctcagggt gcaatttgct aaacgtttgc tcacttcaaa aaagaaatt    9300 ccactgaaag tgattgccag tgaagccggt ttttgcgatc agagccatat gacccgagta   9360
tttcaaaaat ttttgggaa aacacccatc gaaatcagac aggaacacac caatctcgtg    9420
tctgaaaatt cagtctcctc tattgttttt tgagtactaa gagccacgca agaacctgat   9480
tttcaataaa gcatccactg aaaaccagtg tggacttaca tgcattattt atgcaaaata   9540
acaaatgtca tgtgagtatc aagatatact ttctatcgct atcaagaact tgccagtaca   9600
ggcaatatgg atgcactcat caaccagagt cgcagaactc caaatttaaa aaaccgagtg   9660
gatgagcaaa ctgaataagc tgttgttgat tttgcaatcc aatatccagc ttatggtcag   9720
catcggacca gtaatgagct acgtcagatt ggcatcttcg tatctggcag cggtgtgcgc   9780
tctatctggc ttagacacaa tcttgagaat ttcaaaaagc gattaaaggc acttgaaatt   9840
aaagttgctc aagaaggcat tcagttgaat gatcagcaga ttgccgcatt agaacgtaaa   9900
catgaagatg atgttgcttg tggtgaaatt gaaacacatc atccaggtta ccttggagca   9960
caagatactt tttatgtcgg aaatctaaaa ggtgttgggc atatttatca gcaaactttt  10020
```

```
attgatactt atagcaaagt ggttcactgc aagctgtaca caaccaagac accaatcaca    10080
gccgcagatt tattgaatga ccgcgtgtta ccattctatg agtcacaagg attgccaatg    10140
cttcgcattt tgaccgacag aggcaccgaa tattgcggta aagttgaaca tcacgattat    10200
gagctttatt tggctctgaa tgatattgat cacactaaaa ctaaagcagc atcaccacaa    10260
acaaatggga tctgtgagcg cttccataag acgatcttgc aggagtttta tcagattact    10320
tttcgaaaga aactctatag ctcattagaa gagttacagc ttgatctaga cggttggctg    10380
aaattctata atactgaacg aacccatcag ggtaaggtgt gtaatggcag atgagcagca    10440
ttgctgcgca agattgcaac attacttgat ggaaaacgta tttgggctga aaagaattta    10500
gttcaaattt aacctgacag tcttaagcaa atatcggtaa ctatcagatc aggtttgaga    10560
taccgtctga aacgtcaagt aaatgattga gaattcatgc tcaataatct gcttgataag    10620
gctgttggtg tttgagcaca ccataacaaa gatgaatcaa cttcctcatc gcggctccaa    10680
tcgctatcat cttggtttta ccattcgcca ataaacgttc attcattgcc ctgatgtgag    10740
ggttatgccg agttgcgaca atggctgcca tatataaacc agcacgtatt ttggaagagc    10800
ccgctttgga taaacggctt ctgccatgaa tggaactacc cgattgcttt tgaatgggga    10860
ccaaaccgac aaaggcagcc gcttgactag cccttttcaaa agtatggctg cgcaagaaac    10920
tgagcattaa taaactggtt cgatctgcaa tggctggaat actgctgagc agttctttat    10980
cattttttaa atcaggattc tgattaatgt gatcatcaat ttgctggtcg atacccctgaa    11040
tgtgtttgtt taactgttca atactcttgt ggatagactg aagtacaggt tccatcgtga    11100
aggtcgactc tgcttttttcc aaacgattct tttcacgttg taaatcttca caagaatag    11160
ctcttctatc cagcaaagca ttcagcaatt gaatatgttt aggtaaaggt tgccaaaaat    11220
gtagatcggc agtcatcgca aatcgagcta ggacctcact atccaccttg tctgttttat    11280
tcagcttaga catactctga gcaaaatatc gagctctggc aggattggtt acacagactt    11340
gatagcccgc atcaaataaa tatttaacca agagttcatg ataaatagat gttgcttcca    11400
ttaaaataat ggtctgcgta gaagttgcag catgctgctt tagccaggtt tgaagttgct    11460
caaaaccttt tggtgtattt gaaaaagttt tggttttctt tttatttgca gaattttcta    11520
aaattaaaca gcaatcaatt ttagctttag caacatcaat accaagataa aacataatct    11580
ttacctgctt tatttatcca attattgttt tagcataacc accgtctttt cttgtgaatg    11640
cagcatcaaa gtgcttgtta ccgtccagag ttgtgcaagt ggttagggca aattacaggt    11700
tttatctcaa actctaactt tatgtttttgc tagtacacga aactctgcaa tttgcaatat    11760
agtgatagct aatcactatg aatggtaaga tacaagctag tacacataag aagatattac    11820
ttcttctcag gcagattcgc agcaaagaaa aattttccct tacaacaata gataaaagaa    11880
aagagggtat caccctctt tcctctttat atggggtat cttctactca ttttttattt    11940
cgaggtatat gcaccatcga ccacatactg actaccggtc acaaatgaag catcatcaga    12000
aagtaggaag gcaacaacct gagcaacttc ttccggctgt cccaaacgac caatcggatg    12060
tagttttacc atttctgctt cttcaaattc tgcaatcaaa ggcgttttga tatagccagg    12120
atgtactgaa ttaatgcgaa tccctttatc tgcatattcc aatgccgccg ctttcgttag    12180
acccgttacg ccatgttttg cagcgacata gcctgaaata ttttgaatcc cgatcaagcc    12240
tgcaatagaa gcggtattga caatcgctcc gcccctgcg gccaagattg caggaacttc    12300
ataatgcatg ctgtagaaaa ccgcattcaa gttcacatca atcacacgac gccatccttc    12360
aatgctcaat tcttcggtgg agttaacttc acccagaatt cccgcattat tgaaggccaa    12420
```

```
atgcagtgca ccaaaagtgc tgaccgcaaa ctcgactgca gctttcatgt cttcaggctc   12480
agcagtattg gccttattcg cagccgcttt cccgcctaaa gcgacaattt cgtccacaac   12540
tttctgtgct gcttccaggt taatatctga accactaca cttacaccct gttgagccaa   12600
aagcagtgcg gtgcttttac caatacctga accagcgcca gtaattaaag cgactttatt   12660
gttgaattta tttgacataa ttttttccat ttcaaatttt aagcatcaaa gcttgtttca   12720
tattttaaga ttcaagaaac cagatccggt agatgactcg tctgccaagc gacaacccgt   12780
ctgatatcag gcttgcgatt caccctgtag acggttttca ttcctaaatt ctgtatttcc   12840
aagttatata aacaaaagtg ctaatctatg gggaattccc aggatccaaa caaatagaat   12900
gccatgaaag catcttttgc caagcgctgt gctgtatgtt tcctagacaa accaccaacg   12960
ataactgcaa cttttgaac tccttacaat ttccttattt tctttcccct tcatcgcata   13020
aaaatagttt ttgcattcac aacaaaatca gcatgaatag tttttaaact cactgtacat   13080
attttctata ttgatgacca agctggatat tgaattgcaa aattctatac agcctgttca   13140
acatgatcga tttagaaggc atacagtaaa cgtgactgaa gtccagaaat ttccaagcca   13200
ttttcaacat tcacatcttg tcgccattgt aataatagct gcagattcgg cttgatattg   13260
gtagaagcag aaacgacaaa ggtatctttt ctatcactgc cacgttcagt gacaccattc   13320
accttttctt taccgccatc ggtatgtctc caggtgacag ccaaattgga tttatcggtc   13380
actttataga gtgcggagaa atctgtctgg aaaaaaacct ctttctcaat gttggtatat   13440
ttttgctcgc tataaagttc aaactgcccc acccctcaa gcgcaaattt atcagttaaa   13500
gcatggtaat aaccggcctg aacattatat tgatagcgat cattactgat ggcaaaaccc   13560
ttcgtttcat tactgccggt aggtacggtc aaaaaccac cgaaaccaaa atagcgccct   13620
ttttcagcat catgcaatgg ccaggcgata ccacccacaa ttaaatcacc gacacccgag   13680
atatcatcag cgccattcat cttttgcttg gcaaaaggca agaggaattg aggatctaca   13740
atccaatccc ctacttcaat aaaacgaacg taacgcaata ttcccaaatc aatgcttaaa   13800
tcgagatcat cagcgacttt atcaccattt gcatacgcct tatccgcttc cgtatgctgg   13860
taataggcaa ccgctaagtt ggttcccct ggaagtgctt gataatcccc ggcatcagaa   13920 ctcaccctg cggcttgcag gtccaaagcg gcagttaaag caaagaccaa agcagctatt   13980
ttttgatttg aacgatgata gaaatagttt ttcatttgtt tcattttaa ctctccgttg   14040 ttttgactca tttttttaaa atgagtcttc ctagcacaaa gaccactcag gtctttgcgc   14100
aatttcttga ttttgatttg ggtattaaat atggaaaaac gttgggtgat cagttttcgt   14160
gcataagcac aatacgcccg atgacgttgc catctttcaa gtctccaaat gcggaattga   14220
tctgcgaaat tggcagtttt ttcacgggaa tggctgacat gtgggtttct ttcaccagct   14280
ccaccagctc tcttaattcc tctaccgtcc ctacataact gccctggatt gtgagtggtc   14340
tcattggaat caccggaatg gaaagcttaa tttctccccc catcaatccg cagatcacaa   14400
tatgcccacc acgtgcagca ctcgccaagg caaggctcaa tgttggatta ctgccaacca   14460
gatcaaggat cagacgtgca ccaccgtcag ttgcctgaat cagctgttga gcagcatcct   14520
cacttcggct attgatgacc gataatgcac cggcagcacg tgctgcttcc agtttgctgt   14580
catcaatatc aactacgatt gcgcctttgg cttgcatagc tttgagcaac tcgagtgcca   14640
tcagccctaa accaccggca ccaatgatca ccaccggctc gctttgaatc aaatcaccga   14700
attttttcag tgcactgtat gttgtcacgc ctgcacatgc caaaggtgca gcttcagcca   14760
```

```
gatccagacc tgcaatatcc accagatatc gtggatgcgg cacgatgata tattcggcaa   14820
aaccacccgg cttggcgatg cctaactgtt gcggtttggc acacaggttt tcttcgccac   14880
gtttacagta gttgcattca ccgcaaccaa tccatggatg aaccaagctg accatgccga   14940
ccttgactga ttccgcatct ggaccgacag caaccacctg acctgtaatt tcatgactta   15000
aggttaaggg tggcttcagc ccacgatctg caagggataa acgcttgccc ccacctagat   15060
cataataacc ttcccataag tgtaaatccg tatggcatag acctgcggct tttacatgga   15120
gtaaaacttc agtacctttc ggttgcggaa tttctttctc aacgtcttcg agtggttgtc   15180
catgatgcgt cacgcagtaa cagtgcatga atctctcctt tgaaacaata aaatagacgg   15240
ccttgtagtg aacaaagtct tttattcact aagttttata cgccgtgtgg gcactgattt   15300
atgctttaaa ccactgcgca attttcgcta attcttgatc agcttcactt gcacgcccag   15360
ctaggaaagg aaaaacgtgc tgcatgttgt ccaccacaga taaagtcaca tcaacaccct   15420 cttttttgc aatatcagca agacgtgttg cattgtctac aagtgattca actgatccgg   15480
cattgatata caaacgtggg aaaacctgat aattggcttt taacggattc gccaatggat   15540
ttgccggatc accatgttca cccaagaaca tttgtgacat gcctttaagc agatccactg   15600
taatcaaggc atcagtggca tcgttgctga tcagggtttc acctttgtgc tccatatcca   15660
gccaaggaga gaatgcaatc actgctcctg gcaactcaat cccttcattt cgtagattga   15720
gtacggttga tatcgccaga ttccccccg cagaatcccc tgcggtcagc atattttttg   15780
cagtaaagcc acgctggagt agttctttat atactgctgt cacgtcctga atttgtgccg   15840
ggaagacatg ttctggtgaa cgtcggtaat caaccacaaa tgcggatacc cctaaatact   15900
tggccaaatg ccccaccagc ttacggtgac tggccgaaga accgaccgca aatccaccgc   15960
catgggtata aatgatgact ttggataagt cagcatcttt cggataaatc caaagacctt   16020
ctacacctgc cacaacatcg aatttataag acacttcttc cggttccaat gtaggttgat   16080
gccattcatc aaacatactg cgaaagtctt caatggtcat attcggattt tcctgcatcc   16140
gtcttgacca gttcgcatat aaatcgaaaa gaaattgagt attgctttgt gtgctattca   16200
ttttaaaatc cttgatttga tatttaagga ataaatccta gttttattcc atgaagatat   16260
aaaaacttga gtgccatcac tcatggctag acactcagaa gatccaaatc taaagagtgg   16320
ctttgcatca ctggtttgat acaattttt gcatgactaa gtaatctacg gataatctaa   16380
ccgtttcaaa ttagtatttt aaaatgtaaa aaatacatac cagcgaatgt ttctgcaaa   16440 atcgcatcct gttcaatata gcttttgatc ctacttattc tcttttctat tccagtccgt   16500
tataaaaaag ctttcattca ttttcatgca atcatgagct atgaatgttc ttaaacatta   16560
aacgattgtg tgtatggctg acttgtacat tcttgtactt atttttgtat aaaatgatca   16620
ggctcatcaa tttatgggaa aaattacaat tcgggtacaa tatctttcct gtttcatgaa   16680
tctattcaac tcattaaact tacgaccctc aactgcccaa aatcatagga tctgccgatc   16740
cacttgcaga attagcaatg ctaaaacatg aactccaaag agttactaaa aaagagcat   16800 attaaaaaaa agccgtggca tattcgcaa gccagttcaa gtcaggtatg tctttattca   16860
gtacctcagt taaactttag atttcataa cgatggttat tctgcatggc taaatacgct   16920
aatcagcaaa aaactctcca aagatagc acagaaacac atatcaacca taaaaaccat   16980
ctcagacagt atatttacaa gcctctaatt caccgcactc acacttctct gcaagccttt   17040 ttaaatacc tgtacaaagt tctcagcctg atgaagcttc accttggact tagctttcag   17100
ttcagcctgt acttggtcag tttctgaatt ttcatttgca taaaactcct ccaccacatc   17160
```

```
catacoctcc tcaatgtcag tttcaaaatg tgcattgtca tagccttgcc gtgccatttg   17220
aatggcttat tgaagattaa tggcatcacg taaagttaaa tccacgtaat acacaggtgt   17280
tcgatagctt tgcgtcgtag actttctcga agagtcaatt gcagcggtag gcatgacagc   17340
aagccattca atgccgcatg gtaataactc agccgtgcgg ccaacgttcg tatgctgtta   17400
aaacccggtt attctaa                                                  17417
```

<210> SEQ ID NO 74
<211> LENGTH: 1164
<212> TYPE: DNA
<213> ORGANISM: Escherichia coli

<400> SEQUENCE: 74

```
atgaacaact ttaatctgca caccccaacc cgcattctgt ttggtaaagg cgcaatcgct     60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg gcacattctg    360
caaacgggcg gtaaagagat taaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacacccctg cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggcttttgct gaaaaaactg   1080 gaagagcacg gcatgaccca actgggcgaa atcatgaca ttacgttgga tgtcagccgc   1140
cgtatatacg aagccgcccg ctaa                                          1164
```

<210> SEQ ID NO 75
<211> LENGTH: 387
<212> TYPE: PRT
<213> ORGANISM: Escherichia coli

<400> SEQUENCE: 75

```
Met Asn Asn Phe Asn Leu His Thr Pro Thr Arg Ile Leu Phe Gly Lys
 1               5                  10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60
```

```
Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
             85                  90                  95

Val Leu Asp Gly Thr Lys Phe Ile Ala Ala Ala Asn Tyr Pro Glu
             100                 105                 110

Asn Ile Asp Pro Trp His Ile Leu Gln Thr Gly Gly Lys Glu Ile Lys
             115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
        290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 76
<211> LENGTH: 1623
<212> TYPE: DNA
<213> ORGANISM: Bacillus subtilis

<400> SEQUENCE: 76
atgtatttgg cattccaggt gcaaaaattg atgcggtatt tgacgcttta caagataaag      60
gacctgaaat tatcgttgcc cggcacgaac aaaacgcagc aattcatggc ccaagcagtc     120
ggccgtttaa ctgaaaaacc gggagtcgtg ttagtcacat caggaccggg tgcctctaac     180
ttggcaacag gcctgctgac agcgaacact gaaggagacc ctgtcgttgc gcttgctgga     240
```

```
aacgtgatcc gtgcatatcg tttaaaacgg acacatcaat ctttggataa tgcggcgcta    300
ttccagccga ttacaaaata cagtgtagaa gttcaagatg taaaaaatat accggaagct    360
gttacaaatg catttaggat agcgtcagca gggcaggctg gggccgcttt tgtgagcttt    420
ccgcaagatt ttgtgaatga agtcacaaat acgaaaaacg tgcgtgctgt tgcagcgcca    480
aaactcggtc ctgcagcaga tgatgcaatc agtgcggcca tagcaaaaat ccaaacagca    540
aaacttcctg tcgttttggt cggcatgaaa ggcggaagac cggaagcaat taaagcggtt    600
cgcaagcttt tgaaaaaggt tcagcttcca tttgttgaaa catatcaagc tgccggtacc    660
ctttctagag atttagagga tcaatatttt ggccgtatcg gtttgttccg caaccagcct    720
ggcgatttac tgctagagca ggcagatgtt gttctgacga tcggctatga cccgattgaa    780
tatgatccga attctggaa tatcaatgga accggacaa ttatccattt agacgagatt    840
atcgctgaca ttgatcatgc ttaccagcct gatcttgaat tgatcggtga cattccgtcc    900
acgatcaatc atatcgaaca cgatgctgtg aaagtggaat ttgcagagcg tgagcagaaa    960
atcctttctg atttaaaaca atatatgcat gaaggtgagc aggtgcctgc agattggaaa   1020
tcagacagag cgcaccctct tgaaatcgtt aaagagttgc gtaatgcagt cgatgatcat   1080
gttacagtaa cttgcgatat cggttcgcac tccatttgga tgtcacgtta tttccgcagc   1140
tacgagccgt taacattaat gatcagtaac ggtatgcaaa cactcggcgt tgcgcttcct   1200
tgggcaatcg cgcttcatt ggtgaaaccg ggagaaaaag tggtttctgt ctctggtgac   1260
ggcggtttct tattctcagc aatggaatta gagacagcag ttcgactaaa agcaccaatt   1320
gtacacattg tatggaacga cagcacatat gacatggtgc atttccagca attgaaaaaa   1380
tataaccgta catctgcggt cgatttcgga aatatcgata tcgtgaaata tgcggaaagc   1440
ttcggagcaa ctgcgttgcg cgtagaatca ccagaccagc tggcagatgt tctgcgtcaa   1500
ggcatgaacg ctgaaggtcc tgtcatcatc gatgtcccgg ttgactacag tgataacatt   1560
aatttagcaa gtgacaagct tccgaaagaa ttcggggaac tcatgaaaac gaaagctctc   1620
tag                                                                1623
```

<210> SEQ ID NO 77
<211> LENGTH: 540
<212> TYPE: PRT
<213> ORGANISM: Bacillus subtilis

<400> SEQUENCE: 77

```
Met Tyr Leu Ala Phe Gln Val Gln Lys Leu Met Arg Tyr Leu Thr Leu
1               5                   10                  15

Tyr Lys Ile Lys Asp Leu Lys Leu Ser Leu Pro Gly Thr Asn Lys Thr
            20                  25                  30

Gln Gln Phe Met Ala Gln Ala Val Gly Arg Leu Thr Gly Lys Pro Gly
        35                  40                  45

Val Val Leu Val Thr Ser Gly Pro Gly Ala Ser Asn Leu Ala Thr Gly
    50                  55                  60

Leu Leu Thr Ala Asn Thr Glu Gly Asp Pro Val Val Ala Leu Ala Gly
65                  70                  75                  80

Asn Val Ile Arg Ala Tyr Arg Leu Lys Arg Thr His Gln Ser Leu Asp
                85                  90                  95

Asn Ala Ala Leu Phe Gln Pro Ile Thr Lys Tyr Ser Val Glu Val Gln
            100                 105                 110

Asp Val Lys Asn Ile Pro Glu Ala Val Thr Asn Ala Phe Arg Ile Ala
        115                 120                 125
```

```
Ser Ala Gly Gln Ala Gly Ala Ala Phe Val Ser Phe Pro Gln Asp Val
        130                 135                 140

Val Asn Glu Val Thr Asn Thr Lys Asn Val Arg Ala Val Ala Ala Pro
145                 150                 155                 160

Lys Leu Gly Pro Ala Ala Asp Asp Ala Ile Ser Ala Ala Ile Ala Lys
                165                 170                 175

Ile Gln Thr Ala Lys Leu Pro Val Val Leu Val Gly Met Lys Gly Gly
                180                 185                 190

Arg Pro Glu Ala Ile Lys Ala Val Arg Lys Leu Leu Lys Lys Val Gln
            195                 200                 205

Leu Pro Phe Val Glu Thr Tyr Gln Ala Ala Gly Thr Leu Ser Arg Asp
210                 215                 220

Leu Glu Asp Gln Tyr Phe Gly Arg Ile Gly Leu Phe Arg Asn Gln Pro
225                 230                 235                 240

Gly Asp Leu Leu Leu Glu Gln Ala Asp Val Val Leu Thr Ile Gly Tyr
                245                 250                 255

Asp Pro Ile Glu Tyr Asp Pro Lys Phe Trp Asn Ile Asn Gly Asp Arg
                260                 265                 270

Thr Ile Ile His Leu Asp Glu Ile Ile Ala Asp Ile Asp His Ala Tyr
            275                 280                 285

Gln Pro Asp Leu Glu Leu Ile Gly Asp Ile Pro Ser Thr Ile Asn His
        290                 295                 300

Ile Glu His Asp Ala Val Lys Val Glu Phe Ala Glu Arg Glu Gln Lys
305                 310                 315                 320

Ile Leu Ser Asp Leu Lys Gln Tyr Met His Glu Gly Glu Gln Val Pro
                325                 330                 335

Ala Asp Trp Lys Ser Asp Arg Ala His Pro Leu Glu Ile Val Lys Glu
                340                 345                 350

Leu Arg Asn Ala Val Asp Asp His Val Thr Val Thr Cys Asp Ile Gly
            355                 360                 365

Ser His Ser Ile Trp Met Ser Arg Tyr Phe Arg Ser Tyr Glu Pro Leu
        370                 375                 380

Thr Leu Met Ile Ser Asn Gly Met Gln Thr Leu Gly Val Ala Leu Pro
385                 390                 395                 400

Trp Ala Ile Gly Ala Ser Leu Val Lys Pro Gly Glu Lys Val Val Ser
                405                 410                 415

Val Ser Gly Asp Gly Gly Phe Leu Phe Ser Ala Met Glu Leu Glu Thr
                420                 425                 430

Ala Val Arg Leu Lys Ala Pro Ile Val His Ile Val Trp Asn Asp Ser
            435                 440                 445

Thr Tyr Asp Met Val His Phe Gln Gln Leu Lys Lys Tyr Asn Arg Thr
450                 455                 460

Ser Ala Val Asp Phe Gly Asn Ile Asp Ile Val Lys Tyr Ala Glu Ser
465                 470                 475                 480

Phe Gly Ala Thr Ala Leu Arg Val Glu Ser Pro Asp Gln Leu Ala Asp
                485                 490                 495

Val Leu Arg Gln Gly Met Asn Ala Glu Gly Pro Val Ile Ile Asp Val
            500                 505                 510

Pro Val Asp Tyr Ser Asp Asn Ile Asn Leu Ala Ser Asp Lys Leu Pro
        515                 520                 525

Lys Glu Phe Gly Glu Leu Met Lys Thr Lys Ala Leu
530                 535                 540
```

<210> SEQ ID NO 78
<211> LENGTH: 1680
<212> TYPE: DNA
<213> ORGANISM: Klebsiella terrigena

<400> SEQUENCE: 78

```
atggacaaac cgcgtcacga acgtcaatgg gcccacggtg ccgacttaat cgtcagccag      60
cttgaggccc agggcgtacg ccaggtcttc ggcatcccg gtgccaaaat cgacaaggtg     120
tttgattccc tcctcgactc ctcaatccgc attattccgg tgcgccacga ggctaacgcc     180
gcctttatgg ccgcggcggt cgggcggatt accggtaaag cgggcgtcgc gctggtgacc     240
tccggtcccg gctgctcaaa cctgattacc ggcatggcca ccgccaatag cgaaggcgac     300
ccggtggtgg cgctgggcgg cgcggtgaag cgcgcggata aggccaagct ggttcaccaa     360
agcatggaca ccgtggcgat gttcagcccg gtcaccaaat acgccgtcga ggtgaccgcc     420
tccgacgcgc tggccgaggt ggtctccaac gcctttcgcg ccgccgaaca ggggcgtccg     480
gggagcgcgt ttgtcagcct gccgcaggat atcgttgacg cccccgccag cggcagcacg     540
ctgcccgcca gcagagcgcc gcagatgggc gccgcgccgg atggcgccgt tgacagcgtg     600
gcgcaggcga tcgccgcggc gaagaaccct atcttcctgc tcgggctgat ggccagccag     660
ccggaaaaca ccgcgcccct gcaccgccat gctggaaaaa agccatattc cggtcaccag     720
cacctatcag gcgccggggc ggtaaatcag gataacttcg cccgcttcgc cggccgggta     780
ggcctgttta ataaccaggc gggcgatcgc ctgctgcgtc aggcggacct gatcatctgc     840
atcggctata gccggttga gtacgaaccg gcgatgtgga acagcggcac ggcaaccctg     900
gtgcatatcg acgtgctgcc ggcctatgaa gagcggaact acgtcccgga tatcgagctg     960
gtgggcgaca tcgccgccac cctcgagaag ctggcccagc gcattgaaca tcggctggtg    1020
ttaactccgc aggcggcgga catcctcgcc gaccgccagc gccagcggga gctgcttgac    1080
cgccgcgggg cgcagctgaa tcagtttgcg ctccaccccg ctgcgcatcgt gcgggcgatg    1140
caggatatcg tcaatagcga cgtcaccttg accgtcgata tgggcagttt ccatatctgg    1200
attgcccgct acctctacag cttccgcgcc cgccaggtga tgatctccaa cggtcagcaa    1260
acgatgggcg tcgcgctgcc gtgggcaatc ggcgcgtggc tggtcaatcc gcagcgcaag    1320
gtggtctcgg tatccggcga tggcggcttc ctgcagtcga gcatggagct ggagaccgcc    1380
gtgcgcctgc acgccaatat tctgcacatc atctgggtcg ataacggcta caacatggtg    1440
gcgattcagg aacagaagaa atatcagcgc ctctccggcg tggagttcgg cccggtcgat    1500
ttcaaagtct acgccgaagc gttcggggcc tgcgggtttg cggtagagag cgccgaggcc    1560
ctggagccga ccctgcgcgc ggcgatggat gtcgacggcc cggcggtggt cgccattccg    1620
gtcgattacc gcgataaccc tctgctgatg ggccagctcc atctcagcca aatactgtga    1680
```

<210> SEQ ID NO 79
<211> LENGTH: 559
<212> TYPE: PRT
<213> ORGANISM: Klebsiella terrigena

<400> SEQUENCE: 79

Met Asp Lys Pro Arg His Glu Arg Gln Trp Ala His Gly Ala Asp Leu
1               5                   10                  15

Ile Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser

```
                35                  40                  45
Ile Arg Ile Ile Pro Val Arg His Glu Ala Asn Ala Ala Phe Met Ala
 50                  55                  60

Ala Ala Val Gly Arg Ile Thr Gly Lys Ala Gly Val Ala Leu Val Thr
 65                  70                  75                  80

Ser Gly Pro Gly Cys Ser Asn Leu Ile Thr Gly Met Ala Thr Ala Asn
                 85                  90                  95

Ser Glu Gly Asp Pro Val Val Ala Leu Gly Ala Val Lys Arg Ala
                100                 105                 110

Asp Lys Ala Lys Leu Val His Gln Ser Met Asp Thr Val Ala Met Phe
                115                 120                 125

Ser Pro Val Thr Lys Tyr Ala Val Glu Val Thr Ala Ser Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Ile Val Asp Gly Pro Ala
                165                 170                 175

Ser Gly Ser Thr Leu Pro Ala Ser Arg Ala Pro Gln Met Gly Ala Ala
                180                 185                 190

Pro Asp Gly Ala Val Asp Ser Val Ala Gln Ala Ile Ala Ala Ala Lys
    195                 200                 205

Asn Pro Ile Phe Leu Leu Gly Leu Met Ala Ser Gln Pro Glu Asn Ser
210                 215                 220

Arg Ala Leu His Arg His Ala Gly Lys Lys Pro Tyr Ser Gly His Gln
225                 230                 235                 240

His Leu Ser Gly Ala Gly Ala Val Asn Gln Asp Asn Phe Ala Arg Phe
                245                 250                 255

Ala Gly Arg Val Gly Leu Phe Asn Asn Gln Ala Gly Asp Arg Leu Leu
                260                 265                 270

Arg Gln Ala Asp Leu Ile Ile Cys Ile Gly Tyr Ser Pro Val Glu Tyr
    275                 280                 285

Glu Pro Ala Met Trp Asn Ser Gly Thr Ala Thr Leu Val His Ile Asp
290                 295                 300

Val Leu Pro Ala Tyr Glu Glu Arg Asn Tyr Val Pro Asp Ile Glu Leu
305                 310                 315                 320

Val Gly Asp Ile Ala Ala Thr Leu Glu Lys Leu Ala Gln Arg Ile Glu
                325                 330                 335

His Arg Leu Val Leu Thr Pro Gln Ala Ala Asp Ile Leu Ala Asp Arg
                340                 345                 350

Gln Arg Gln Arg Glu Leu Leu Asp Arg Arg Gly Ala Gln Leu Asn Gln
    355                 360                 365

Phe Ala Leu His Pro Leu Arg Ile Val Arg Ala Met Gln Asp Ile Val
370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
                420                 425                 430

Trp Leu Val Asn Pro Gln Arg Lys Val Val Ser Val Ser Gly Asp Gly
    435                 440                 445

Gly Phe Leu Gln Ser Ser Met Glu Leu Glu Thr Ala Val Arg Leu His
450                 455                 460
```

```
Ala Asn Ile Leu His Ile Ile Trp Val Asp Asn Gly Tyr Asn Met Val
465                 470                 475                 480

Ala Ile Gln Glu Gln Lys Lys Tyr Gln Arg Leu Ser Gly Val Glu Phe
            485                 490                 495

Gly Pro Val Asp Phe Lys Val Tyr Ala Glu Ala Phe Gly Ala Cys Gly
        500                 505                 510

Phe Ala Val Glu Ser Ala Glu Ala Leu Glu Pro Thr Leu Arg Ala Ala
        515                 520                 525

Met Asp Val Asp Gly Pro Ala Val Ala Ile Pro Val Asp Tyr Arg
    530                 535                 540

Asp Asn Pro Leu Leu Met Gly Gln Leu His Leu Ser Gln Ile Leu
545                 550                 555

<210> SEQ ID NO 80
<211> LENGTH: 768
<212> TYPE: DNA
<213> ORGANISM: Bacillus subtilis

<400> SEQUENCE: 80
atgaaacgag aaagcaacat tcaagtgctc agccgtggtc aaaaagatca gcctgtgagc        60
cagatttatc aagtatcaac aatgacttct ctattagacg gagtatatga cggagatttt       120
gaactgtcag agattccgaa atatggagac ttcggtatcg gaaccttaa caagcttgac       180 ggagagctga ttgggtttga cggcgaattt taccgtcttc gctcagacgg aaccgcgaca       240
ccggtccaaa atggagaccg ttcaccgttc tgttcattta cgttctttac accggacatg       300
acgcacaaaa ttgatgcgaa aatgcacgc gaagactttg aaaaagagat caacagcatg       360
ctgccaagca gaaacttatt ttatgcaatt cgcattgacg gattgtttaa aaaggtgcag       420
acaagaacag tagaacttca agaaaaacct tacgtgccaa tggttgaagc ggtcaaaaca       480
cagccgattt tcaacttcga caacgtgaga ggaacgattg taggtttctt gacaccagct       540
tatgcaaacg gaatcgccgt ttctggctat cacctgcact tcattgacga aggacgcaat       600
tcaggcggac acgtttttga ctatgtgctt gaggattgca cggttacgat ttctcaaaaa       660
atgaacatga atctcagact tccgaacaca gcggattttc ttaatgcgaa tctggataac       720
cctgattttg cgaaagatat cgaaacaact gaaggaagcc tgaataa                    768

<210> SEQ ID NO 81
<211> LENGTH: 255
<212> TYPE: PRT
<213> ORGANISM: Bacillus subtilis

<400> SEQUENCE: 81

Met Lys Arg Glu Ser Asn Ile Gln Val Leu Ser Arg Gly Gln Lys Asp
1               5                   10                  15

Gln Pro Val Ser Gln Ile Tyr Gln Val Ser Thr Met Thr Ser Leu Leu
            20                  25                  30

Asp Gly Val Tyr Asp Gly Asp Phe Glu Leu Ser Glu Ile Pro Lys Tyr
        35                  40                  45

Gly Asp Phe Gly Ile Gly Thr Phe Asn Lys Leu Asp Gly Glu Leu Ile
    50                  55                  60

Gly Phe Asp Gly Glu Phe Tyr Arg Leu Arg Ser Asp Gly Thr Ala Thr
65                  70                  75                  80

Pro Val Gln Asn Gly Asp Arg Ser Pro Phe Cys Ser Phe Thr Phe Phe
                85                  90                  95
```

Thr Pro Asp Met Thr His Lys Ile Asp Ala Lys Met Thr Arg Glu Asp
            100                 105                 110

Phe Glu Lys Glu Ile Asn Ser Met Leu Pro Ser Arg Asn Leu Phe Tyr
        115                 120                 125

Ala Ile Arg Ile Asp Gly Leu Phe Lys Lys Val Gln Thr Arg Thr Val
    130                 135                 140

Glu Leu Gln Glu Lys Pro Tyr Val Pro Met Val Glu Ala Val Lys Thr
145                 150                 155                 160

Gln Pro Ile Phe Asn Phe Asp Asn Val Arg Gly Thr Ile Val Gly Phe
                165                 170                 175

Leu Thr Pro Ala Tyr Ala Asn Gly Ile Ala Val Ser Gly Tyr His Leu
            180                 185                 190

His Phe Ile Asp Glu Gly Arg Asn Ser Gly Gly His Val Phe Asp Tyr
        195                 200                 205

Val Leu Glu Asp Cys Thr Val Thr Ile Ser Gln Lys Met Asn Met Asn
    210                 215                 220

Leu Arg Leu Pro Asn Thr Ala Asp Phe Phe Asn Ala Asn Leu Asp Asn
225                 230                 235                 240

Pro Asp Phe Ala Lys Asp Ile Glu Thr Thr Glu Gly Ser Pro Glu
                245                 250                 255

<210> SEQ ID NO 82
<211> LENGTH: 780
<212> TYPE: DNA
<213> ORGANISM: Klebsiella terrigena

<400> SEQUENCE: 82
gtgaatcatt atcctgaatg cacctgccag gagagcctgt gcgaaaccgt acgcggcttc      60
tccgcccacc accctgatag cgttatctat cagacctctc tgatgagcgc gctgctgagc     120
ggggtctatg agggtagcac caccatcgcc gacctgctga cccacggcga cttcggtctc     180
ggcacccttta cgaactcga tggcgaactg attgcctttta gcagcgaggt ctaccagctg     240
cgcgctgacg gcagcgcgcg taaagcccgg gcggatcaaa aaacgcccctt cgcggtgatg     300
acctggttca gaccgcagta ccgtaaaaacc tttgaccacc cggtcagccg ccagcagctg     360
cacgacgtta tcgaccagca aatcccctcc gataacctgt tctgcgccct gcatattgat     420
ggtcactttc gccacgccca cacccgcacc gtgccgcggc agacgccgcc ctatcgggcg     480
atgaccgacg tgctcgatga ccagccggtt ttccgcttca accagcgcaa ggggacgctg     540
gtcggctttc gcaccccgca gcatatgcag ggccttaacg ttgccggcta ccacgagcac     600
tttattaccg acgatcgcca gggcggcggc catctgctgg actaccagct cgatagcggc     660
gtgctgacct tcggcgagat ccacaagctg atgattgacc tcccggccga cagcgctttc     720
ctgcaggccg acctgcatcc tgacaatctc gatgccgcta ttcgtgcggt agaaaactaa     780

<210> SEQ ID NO 83
<211> LENGTH: 259
<212> TYPE: PRT
<213> ORGANISM: Klebsiella terrigena

<400> SEQUENCE: 83

Met Asn His Tyr Pro Glu Cys Thr Cys Gln Glu Ser Leu Cys Glu Thr
1               5                   10                  15

Val Arg Gly Phe Ser Ala His His Pro Asp Ser Val Ile Tyr Gln Thr
            20                  25                  30

Ser Leu Met Ser Ala Leu Leu Ser Gly Val Tyr Glu Gly Ser Thr Thr

-continued

```
        35                  40                  45

Ile Ala Asp Leu Leu Thr His Gly Asp Phe Gly Leu Gly Thr Phe Asn
    50                  55                  60

Glu Leu Asp Gly Glu Leu Ile Ala Phe Ser Ser Glu Val Tyr Gln Leu
65                  70                  75                  80

Arg Ala Asp Gly Ser Ala Arg Lys Ala Arg Ala Asp Gln Lys Thr Pro
                85                  90                  95

Phe Ala Val Met Thr Trp Phe Arg Pro Gln Tyr Arg Lys Thr Phe Asp
            100                 105                 110

His Pro Val Ser Arg Gln Gln Leu His Asp Val Ile Asp Gln Gln Ile
        115                 120                 125

Pro Ser Asp Asn Leu Phe Cys Ala Leu His Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Lys Gly Thr Leu Val Gly Phe Arg Thr Pro Gln His Met Gln Gly Leu
            180                 185                 190

Asn Val Ala Gly Tyr His Glu His Phe Ile Thr Asp Asp Arg Gln Gly
        195                 200                 205

Gly Gly His Leu Leu Asp Tyr Gln Leu Asp Ser Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asp Leu His Pro Asp Asn Leu Asp Ala Ala Ile Arg Ala
                245                 250                 255

Val Glu Asn
```

<210> SEQ ID NO 84
<211> LENGTH: 1053
<212> TYPE: DNA
<213> ORGANISM: Bacillus cereus

<400> SEQUENCE: 84

```
atgaaagcac tactttggca taatcaacgt gatgtacgag tagaagaagt accagaacca      60
acagtaaaac caggaacagt gaaaatcaaa gttaaatggt gtggtatttg tgggacagac     120
ttgcatgaat atttagcagg gcctattttt attccaacag aagaacatcc attaacacat     180
gtgaaagcac ctgttatttt aggtcatgag tttagtggtg aggtaataga gattggtgaa     240
ggagttacat ctcataaagt gggagaccgc gttgttgtag agccaattta ttcttgtggt     300
aaatgtgaag cttgtaaaca tggacattac aatgtttgtg aacaacttgt tttccacggt     360
cttggcggag aaggcggcgg tttctctgaa tatacagtag taccagaaga tatggttcat     420
cacattccag atgaaatgac gtatgaacaa ggtgcgcttg tagaaccagc agcagtagca     480
gttcatgcag tacgtcaaag taaattaaaa gaaggggaag ctgtagcggt atttggttgc     540
ggtccaattg gacttcttgt tatccaagca gctaaagcag caggagcaac tcctgttatt     600
gcagttgaac tttctaaaga acgtcaagag ttagcgaaat tagcaggtgc ggattatgta     660
ttaaatccag caactcaaga tgtgttagct gaaattcgta acttaacaaa tggtttaggt     720
gtaaatgtta gctttgaagt aacaggtgtt gaagttgtac tacgccaagc gattgaaagt     780
acaagcttcg aaggacaaac tgtaattgtt agtgtatggg aaaaagacgc aacaattact     840
```

```
ccaaataact tagtattaaa agaaaaagaa gttattggta ttttaggata ccgtcacatc    900
ttcccagctg ttattaaatt gattagctcc ggtcaaattc aagcagagaa attaattacg    960
aaaaaaatta cagtggatca agttgttgaa gaaggatttg aagcacttgt aaaagataaa   1020
acacaagtga aaattcttgt ttcacctaaa taa                                1053

<210> SEQ ID NO 85
<211> LENGTH: 350
<212> TYPE: PRT
<213> ORGANISM: Bacillus cereus

<400> SEQUENCE: 85

Met Lys Ala Leu Leu Trp His Asn Gln Arg Asp Val Arg Val Glu Glu
1               5                   10                  15

Val Pro Glu Pro Thr Val Lys Pro Gly Thr Val Lys Ile Lys Val Lys
            20                  25                  30

Trp Cys Gly Ile Cys Gly Thr Asp Leu His Glu Tyr Leu Ala Gly Pro
        35                  40                  45

Ile Phe Ile Pro Thr Glu Glu His Pro Leu Thr His

Val Lys Asp Lys Thr Gln Val Lys Ile Leu Val Ser Pro Lys
        340                 345                 350

<210> SEQ ID NO 86
<211> LENGTH: 1053
<212> TYPE: DNA
<213> ORGANISM: Bacillus cereus

<400> SEQUENCE: 86

| | | | | |
|---|---|---|---|---|
| atgaaagcac tactttggca taatcaacgt gatgtacgag tagaagaagt accagaacca | | | | 60 |
| acagtaaaac caggaacagt gaaaatcaaa gttaaatggt gtggtatttg tgggacagac | | | | 120 |
| ttgcatgaat atttagcag Ser Glu Tyr Thr Val Val Pro Glu Asp Met Val His His Ile Pro Asp
130                 135                 140

Glu Met Thr Tyr Glu Gln Gly Ala Leu Val Pro Ala Ala Val Ala
145                 150                 155                 160

Val His Ala Val Arg Gln Ser Lys Leu Lys Glu Gly Glu Ala Val Ala
                165                 170                 175

Val Phe Gly Cys Gly Pro Ile Gly Leu Leu Val Ile Gln Ala Ala Lys
            180                 185                 190

Ala Ala Gly Ala Thr Pro Val Ile Ala Val Glu Leu Ser Lys Glu Arg
        195                 200                 205

Gln Glu Leu Ala Lys Leu Ala Gly Ala Asp Tyr Val Leu Asn Pro Ala
210                 215                 220

Thr Gln Asp Val Leu Ala Glu Ile Arg Asn Leu Thr Asn Gly Leu Gly
225                 230                 235                 240

Val Asn Val Ser Phe Glu Val Thr Gly Val Glu Val Val Leu Arg Gln
                245                 250                 255

Ala Ile Glu Ser Thr Ser Phe Glu Gly Gln Thr Val Ile Val Ser Val
            260                 265                 270

Trp Glu Lys Asp Ala Thr Ile Thr Pro Asn Asn Leu Val Leu Lys Glu
        275                 280                 285

Lys Glu Val Ile Gly Ile Leu Gly Tyr Arg His Ile Phe Pro Ala Val
290                 295                 300

Ile Lys Leu Ile Ser Ser Gly Gln Ile Gln Ala Glu Lys Leu Ile Thr
305                 310                 315                 320

Lys Lys Ile Thr Val Asp Gln Val Val Glu Glu Gly Phe Glu Ala Leu
                325                 330                 335

Val Lys Asp Lys Thr Gln Val Lys Ile Leu Val Ser Pro Lys
            340                 345                 350

<210> SEQ ID NO 88
<211> LENGTH: 1113
<212> TYPE: DNA
<213> ORGANISM: Lactococcus lactis

<400> SEQUENCE: 88
ttgcctgaaa cgacaaccat cctatataga ggaggcgttt ttatgcgcgc agcacgtttt      60
tacgaccgcg gggatatccg cattgatgaa attaatgaac caatagtaaa agctggccaa     120
gttggcattg atgtggcttg tgtgtggaatt tgtggaacag atctccatga attttagat     180 ggcccaattt tttgtccgtc agcagaacat cctaatccaa ttactggaga agtaccacca     240
gtcactcttg gacatgaaat gtctggggtt gtaaattttta taggtgaagg agtaagcgga    300
cttaaagtag gtgaccatgt cgttgtcgaa ccttatatcg ttcccgaagg gactgataca     360
agtgaaactg gacattataa cctctcagaa ggctcaaact ttattggttt gggcggaaat    420
ggtggaggtt tggctgaaaa aatttctgtt gatgaacgtt gggttcacaa aattcctgat    480
aacttaccat tggatgaagc tgctctaatt gagccactat cagtcggcta tcacgctgtt    540
gaacgagcaa atttaagtga aaagagtacg gtattagttg ttggtgctgg accaattgga    600
ctattaactg ctgccgttgc aaaagcgcaa ggacatactg ttatcatcag tgaacctagt    660
ggacttcgtc gtaaaaaagc acaagaagca caagttgctg attatttctt caatccaatt    720
gaagatgaca ttcaagctaa agttcatgaa attaatgaaa aaggagtgga cgcagccttt    780
gaatgtacct ctgtccaacc gggatttgac gcttgtctag atgcgattcg tatgggtgga    840
acagttgtca ttgtcgcaat ttgggggcaag cctgctagtg ttgatatggc aaaattagta    900

```
atcaaagaag ctaaccttt aggaacgatt gcttataata acactcatcc aaaaacaatt      960
gatttagtat caacaggtaa aataaaattg gaccaattca tcacagctaa aatcggtttg     1020
gatgatttga ttgataaagg attcgatacg ctgattcatc ataatgaaac agctgttaaa    1080
attttagttt caccaactgg taaaggtcta taa                                 1113
```

<210> SEQ ID NO 89
<211> LENGTH: 370
<212> TYPE: PRT
<213> ORGANISM: Lactococcus lactis

<400> SEQUENCE: 89

```
Met Pro Glu Thr Thr Ile Leu Tyr Arg Gly Gly Val Phe Met Arg
1               5                   10                  15

Ala Ala Arg Phe Tyr Asp Arg Gly Asp Ile Arg Ile Asp Glu Ile Asn
            20                  25                  30

Glu Pro Ile Val Lys Ala Gly Gln Val Gly Ile Asp Val Ala Trp Cys
        35                  40                  45

Gly Ile Cys Gly Thr Asp Leu His Glu Phe Leu Asp Gly Pro Ile Phe
    50                  55                  60

Cys Pro Ser Ala Glu His Pro Asn Pro Ile Thr Gly Glu Val Pro Pro
65                  70                  75                  80

Val Thr Leu Gly His Glu Met Ser Gly Val Val Asn Phe Ile Gly Glu
                85                  90                  95

Gly Val Ser Gly Leu Lys Val Gly Asp His Val Val Glu Pro Tyr
            100                 105                 110

Ile Val Pro Glu Gly Thr Asp Thr Ser Glu Thr Gly His Tyr Asn Leu
        115                 120                 125

Ser Glu Gly Ser Asn Phe Ile Gly Leu Gly Gly Asn Gly Gly Gly Leu
    130                 135                 140

Ala Glu Lys Ile Ser Val Asp Glu Arg Trp Val His Lys Ile Pro Asp
145                 150                 155                 160

Asn Leu Pro Leu Asp Glu Ala Ala Leu Ile Glu Pro Leu Ser Val Gly
                165                 170                 175

Tyr His Ala Val Glu Arg Ala Asn Leu Ser Glu Lys Ser Thr Val Leu
            180                 185                 190

Val Val Gly Ala Gly Pro Ile Gly Leu Leu Thr Ala Ala Val Ala Lys
        195                 200                 205

Ala Gln Gly His Thr Val Ile Ile Ser Glu Pro Ser Gly Leu Arg Arg
    210                 215                 220

Lys Lys Ala Gln Glu Ala Gln Val Ala Asp Tyr Phe Phe Asn Pro Ile
225                 230                 235                 240

Glu Asp Asp Ile Gln Ala Lys Val His Glu Ile Asn Glu Lys Gly Val
                245                 250                 255

Asp Ala Ala Phe Glu Cys Thr Ser Val Gln Pro Gly Phe Asp Ala Cys
            260                 265                 270

Leu Asp Ala Ile Arg Met Gly Gly Thr Val Val Ile Val Ala Ile Trp
        275                 280                 285

Gly Lys Pro Ala Ser Val Asp Met Ala Lys Leu Val Ile Lys Glu Ala
    290                 295                 300

Asn Leu Leu Gly Thr Ile Ala Tyr Asn Asn Thr His Pro Lys Thr Ile
305                 310                 315                 320

Asp Leu Val Ser Thr Gly Lys Ile Lys Leu Asp Gln Phe Ile Thr Ala
                325                 330                 335
```

```
Lys Ile Gly Leu Asp Asp Leu Ile Asp Lys Gly Phe Asp Thr Leu Ile
            340                 345                 350

His His Asn Glu Thr Ala Val Lys Ile Leu Val Ser Pro Thr Gly Lys
        355                 360                 365

Gly Leu
    370

<210> SEQ ID NO 90
<211> LENGTH: 705
<212> TYPE: DNA
<213> ORGANISM: Pyrococcus furiosus

<400> SEQUENCE: 90
atgaaggttg ccgtaattac tggggcatcc cgtggaatcg gggaagctat agcaaaggcc      60
cttgctgaag atggatattc ccttgcctta ggggctagaa gtgttgatag gttagagaag     120
attgccaagg aactcagcga aaacatgggg tggaggtat tttacgacta cctcgatgta      180
tcaaaaccag aaagcgttga agagtttgca aggaaaacgc tagctcactt tggagatgtg     240
gacgttgttg tggccaatgc ggggcttggt tactttggta ggcttgaaga gcttacagaa     300
gagcagttcc acgaaatgat tgaagtaaac cttttgggag tttggagaac aataaaagct     360
ttcttaaact cctttaaagcg gactggagga gtggctattg ttgttacttc agatgtttct    420
gcaaggctac ttccatacgg tggaggttat gtggcaacta atgggctgc aagagcattg      480 gtaaggacct tccagattga gaatccagat gtgaggttct tcgagctaag acctggagca    540
gtagatacat attttggagg gagcaaagct gggaagccaa aggagcaagg gtatttaaaa     600
cctgaggaag ttgctgaggc agtaaaatac ctcctaagac ttccaaagga tgttagggtt    660
gaggaattaa tgttgcgctc aatttatcaa aaacctgagt attga                      705

<210> SEQ ID NO 91
<211> LENGTH: 234
<212> TYPE: PRT
<213> ORGANISM: Pyrococcus furiosus

<400> SEQUENCE: 91

Met Lys Val Ala Val Ile Thr Gly Ala Ser Arg Gly Ile Gly Glu Ala
1               5                   10                  15

Ile Ala Lys Ala Leu Ala Glu Asp Gly Tyr Ser Leu Ala Leu Gly Ala
            20                  25                  30

Arg Ser Val Asp Arg Leu Glu Lys Ile Ala Lys Glu Leu Ser Glu Lys
        35                  40                  45

His Gly Val Glu Val Phe Tyr Asp Tyr Leu Asp Val Ser Lys Pro Glu
    50                  55                  60

Ser Val Glu Glu Phe Ala Arg Lys Thr Leu Ala His Phe Gly Asp Val
65                  70                  75                  80

Asp Val Val Val Ala Asn Ala Gly Leu Gly Tyr Phe Gly Arg Leu Glu
                85                  90                  95

Glu Leu Thr Glu Glu Gln Phe His Glu Met Ile Glu Val Asn Leu Leu
            100                 105                 110

Gly Val Trp Arg Thr Ile Lys Ala Phe Leu Asn Ser Leu Lys Arg Thr
        115                 120                 125

Gly Gly Val Ala Ile Val Val Thr Ser Asp Val Ser Ala Arg Leu Leu
    130                 135                 140

Pro Tyr Gly Gly Gly Tyr Val Ala Thr Lys Trp Ala Ala Arg Ala Leu
145                 150                 155                 160
```

```
Val Arg Thr Phe Gln Ile Glu Asn Pro Asp Val Arg Phe Phe Glu Leu
            165                 170                 175

Arg Pro Gly Ala Val Asp Thr Tyr Phe Gly Gly Ser Lys Ala Gly Lys
        180                 185                 190

Pro Lys Glu Gln Gly Tyr Leu Lys Pro Glu Glu Val Ala Glu Ala Val
    195                 200                 205

Lys Tyr Leu Leu Arg Leu Pro Lys Asp Val Arg Val Glu Glu Leu Met
210                 215                 220

Leu Arg Ser Ile Tyr Gln Lys Pro Glu Tyr
225                 230

<210> SEQ ID NO 92
<211> LENGTH: 1665
<212> TYPE: DNA
<213> ORGANISM: Salmonella typhimurium

<400> SEQUENCE: 92
atgagatcga aagatttga agcactggcg aaacgccctg tgaatcagga cggctttgtt      60
aaggagtgga tcgaagaagg ctttatcgcg atggaaagcc cgaacgaccc aaaaccgtcg    120
ataaaaatcg ttaacggcgc ggtaaccgag ctggacggaa accggttag cgaattcgac     180 ctgatcgacc actttatcgc ccgctacggc atcaacctga accgcgccga agaagtgatg    240
gcgatggatt cggtcaagct ggctaacatg ctgtgcgatc gaacgtcaa gcgcagcgaa     300 atcgttccgc taaccaccgc gatgacccca gcgaaaattg tcgaagtggt ttcgcatatg    360
aacgtggttg agatgatgat ggcgatgcag aaaatgcgcg cccgccgtac tccatctcaa    420
caggcgcacg tcaccaacgt taaagacaac ccggtgcaaa ttgccgccga tgccgccgaa    480
ggcgcatggc gcgggtttga cgaacaagag acgacggttg cggtagcgcg ctatgcgccg    540
ttcaacgcca tcgcgctgct ggttggttct caggtaggtc gtccgggggt actgactcaa    600
tgctcgctgg aagaagccac cgagctgaag ctcggcatgc tgggccacac ctgctacgcc    660
gaaaccatct ccgtttacgg caccgagccg gtcttcaccg acggtgacga taccccatgg    720
tcgaagggct tcttagcctc ttcctacgcc tctcgcggcc tgaaaatgcg cttcacctcc    780
ggctccggct ccgaagtgca gatgggctac gccgaaggca atccatgct gtatctggaa    840 gcgcgctgca tctatatcac caaagccgcg ggcgttcagg ggctgcaaaa cggctccgta    900
agcagcatcg gcgtaccgtc tgccgtgccg tcaggcattc gtgccgtgct ggcggaaaac    960
ctgatctgct cttcgctgga tctggaatgc gcctccagta acgaccagac cttcacccac   1020
tccgatatgc gtcgtaccgc tcgcctgctg atgcagttcc tgccgggtac cgactttatc   1080
tcctccggtt attccgcggt gccgaactac gacaacatgt cgccggttc caacgaagat   1140 gcggaagact ttgacgacta caacgttatc cagcgtgacc tgaaagtgga cggcggtctg   1200
cgcccggttc gcgaagagga cgttatcgcc atccgtaaca agccgcccg cgcgctgcag   1260 gccgtgtttg ccgaatgggg actgccgccg attaccgatg aagaagttga agccgcgacc   1320
tatgcccacg gttcgaaaga tatgccggag cgcaacatcg tcgaagacat caagttcgcc   1380
caggaaatca tcaataaaaa ccgcaacggt ctggaagttg tgaaagcgct ggctcagggc   1440
gggtttaccg acgtggccca ggacatgctc aacatccaga aagccaagct aaccggcgac   1500
tatttgcaca cctccgccat tatcgtcggc gacggacaag tgctctctgc ggttaatgac   1560
gtcaatgact atgccggtcc ggcaacaggt tatcgcctgc aggagaacg ctgggaagag   1620 attaaaaaca tccctggcgc tcttgatccc aacgagattg attaa                   1665
```

<210> SEQ ID NO 93
<211> LENGTH: 554
<212> TYPE: PRT
<213> ORGANISM: Salmonella typhimurium

<400> SEQUENCE: 93

```
Met Arg Ser Lys Arg Phe Glu Ala Leu Ala Lys Arg Pro Val Asn Gln
1               5                   10                  15

Asp Gly Phe Val Lys Glu Trp Ile Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Glu Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Ser Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
```

```
           370                 375                 380
Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
            435                 440                 445

Pro Glu Arg Asn Ile Val Glu Asp Ile Lys Phe Ala Gln Glu Ile Ile
        450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
                500                 505                 510

Gln Val Leu Ser Ala Val Asn Asp Val Asn Asp Tyr Ala Gly Pro Ala
            515                 520                 525

Thr Gly Tyr Arg Leu Gln Gly Glu Arg Trp Glu Glu Ile Lys Asn Ile
        530                 535                 540

Pro Gly Ala Leu Asp Pro Asn Glu Ile Asp
545                 550
```

<210> SEQ ID NO 94
<211> LENGTH: 675
<212> TYPE: DNA
<213> ORGANISM: Salmonella typhimurium

<400> SEQUENCE: 94

```
atggaaatta atgaaaaatt gctgcgccag ataattgaag acgtactccg cgatatgaag      60
ggcagcgata aacccgtctc gtttaatgcg cctgcggcat ccacagcacc acagaccgct     120
gcgcctgcgg cgacggctt tctgaccgaa gtgggcgaag cgcgccaggg cactcagcag     180
gacgaagtca ttatcgccgt cggcccggca tttggcctgg cgcaaaccgt caatatcgtc     240
ggcttaccgc ataagagcat tctgcgcgaa gtcattgccg gtattgaaga agaaggcatc     300
aaggcgcgcg tgattcgctg ctttaaatct tccgacgtgg cgttcgtcgc cgttgaaggt     360
aaccgcctga gcggatccgg catctccatc ggcatccagt cgaaaggtac tacggttatc     420
caccagcagg ggctaccgcc gctctccaac ctggagctgt tcccgcaggc accgctgctg     480
acgctggaaa cctaccgtca gattggtaaa acgccgccc gctatgcgaa acgagaatca     540
ccgcagccgg tccctacgct caatgaccag atggcacgcc cgaagtacca ggcaaagtcg     600
gccattttgc atattaaaga gaccaagtac gtcgtgacgg gcaaaaaccc gcaggaactg     660
cgcgtggcgc tttga                                                      675
```

<210> SEQ ID NO 95
<211> LENGTH: 224
<212> TYPE: PRT
<213> ORGANISM: Salmonella typhimurium

<400> SEQUENCE: 95

```
Met Glu Ile Asn Glu Lys Leu Leu Arg Gln Ile Ile Glu Asp Val Leu
1               5                   10                  15

Arg Asp Met Lys Gly Ser Asp Lys Pro Val Ser Phe Asn Ala Pro Ala
```

```
            20                  25                  30
Ala Ser Thr Ala Pro Gln Thr Ala Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Leu Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 96
<211> LENGTH: 522
<212> TYPE: DNA
<213> ORGANISM: Salmonella typhimurium

<400> SEQUENCE: 96

```
atgaataccg acgcaattga atcgatggtc cgggacgtat tgagccgcat gaacagcctg      60
cagggcgatg cgccagcagc ggctcctgcg gcaggcggca cgtcccgcag cgcaaaggtc     120
agcgactacc cgctggcgaa caaacacccg gaatgggtga aaaccgccac caataaaacg     180
ctggacgact ttacgctgga aaacgtgctg agcaataaag tcaccgctca ggatatgcgt     240
attaccccgg aaaccctgcg cttacaggcc tctatcgcca agatgcgggt cgcgaccgg      300
ctggcgatga acttcgaacg cgccgccgaa ctgaccgcgg taccgacga tcgcattctt      360
gaaatctaca cgcccttcg tccgtatcgt tcaacgaaag aagagctgct cgctatcgcc      420
gacgatctcg aaaaccgtta tcaggcaaag atttgcgcag cttcgttcg tgaagcggca      480
gggctgtacg ttgagcgtaa aaaactcaaa ggcgacgatt aa                        522
```

<210> SEQ ID NO 97
<211> LENGTH: 173
<212> TYPE: PRT
<213> ORGANISM: Salmonella typhimurium

<400> SEQUENCE: 97

```
Met Asn Thr Asp Ala Ile Glu Ser Met Val Arg Asp Val Leu Ser Arg
1               5                   10                  15

Met Asn Ser Leu Gln Gly Asp Ala Pro Ala Ala Pro Ala Ala Gly
            20                  25                  30

Gly Thr Ser Arg Ser Ala Lys Val Ser Asp Tyr Pro Leu Ala Asn Lys
```

```
                35                  40                  45
His Pro Glu Trp Val Lys Thr Ala Thr Asn Lys Thr Leu Asp Asp Phe
 50                  55                  60

Thr Leu Glu Asn Val Leu Ser Asn Lys Val Thr Ala Gln Asp Met Arg
 65                  70                  75                  80

Ile Thr Pro Glu Thr Leu Arg Leu Gln Ala Ser Ile Ala Lys Asp Ala
                 85                  90                  95

Gly Arg Asp Arg Leu Ala Met Asn Phe Glu Arg Ala Ala Glu Leu Thr
                100                 105                 110

Ala Val Pro Asp Asp Arg Ile Leu Glu Ile Tyr Asn Ala Leu Arg Pro
                115                 120                 125

Tyr Arg Ser Thr Lys Glu Glu Leu Leu Ala Ile Ala Asp Asp Leu Glu
                130                 135                 140

Asn Arg Tyr Gln Ala Lys Ile Cys Ala Ala Phe Val Arg Glu Ala Ala
145                 150                 155                 160

Gly Leu Tyr Val Glu Arg Lys Lys Leu Lys Gly Asp Asp
                165                 170
```

<210> SEQ ID NO 98
<211> LENGTH: 1677
<212> TYPE: DNA
<213> ORGANISM: Lactobacillus collinoides

<400> SEQUENCE: 98

```
ttggaacgtc aaaaaagatt tgaaaaatta gagaaacgtc cagtgcattt agatgggttc      60
gttaagaact gggacgacga aggtttagtt gcccttaacg gtaagaacga tccaaagcca     120
agcattacga tcgaaaacgg tgttgttact gaaatggatg gtaagaagaa ggcagacttc     180
gaccttatcg acaagtacat cgctgaatac gggatcaact ggacaatgc tgaaaagact     240
ttaaacacag attcagttaa gatcgccaac atgatgtgtg atcctaacgt ctcccgtgct     300
gaaattattg aatatacaac tgctatgaca ccagccaagg ctgctgaagt tatcagccag     360
ttaaacttcg ctgaaatgat catggcaact caaaagatgc ggccacgtcg accccctatg     420
actcaagtcc acgctaccaa cactttggat aacccagttg aaatcgctgc tgatgctgcc     480
gaagctgcat acgtggggt tcctgaagaa gaaaccacca ctgccattgc tcggtatgcg     540
ccaatgaacg ctatttcaat catggttggg gcccaagcag gccgtcctgg tgttatcacc     600
caatgttcag ttgaagaagc tgacgaattg agtttgggga tgcgtgggtt tactgcctat     660
gctgaaacca tttcagtttta tgggactgac cgggtcttca ctgatggtga tgatacccct     720
tggtcaaaag gtttcttagc ttcttgctac gcttcacgtg gtttgaagat gcggtttact     780
tcaggtgccg gttcagaagc tatgatgggc tacactgaag gtaaatcaat gctttacctt     840
gaagctcgtt gtatctacat taccaaggcg tcaggtgttc aaggtctgca aaacggtggt     900
gttagttgta tcgggatgcc aggtgccgtc gttggtggta tccgtgaagt cttaggtgaa     960
aacttactat gtatgtcact tgatgttgaa atgtgcttctg gttgtgacca agccttctct    1020
cactctgaca ttcgtcggac tggccggatg attggccaat tcatcgctgg tactgattac    1080
ctgtcatcag gttacgctgc cgaagaaaac atggataaca ccttcgctgg ttcaaacatg    1140
gatgttctgg actacgatga ttacatcact ttggaacgtg atatggctat taacggtggt    1200
atcatgccaa ttaccgaaga ggaatctatt aagattcgtc acaaggctgc ggttgctatc    1260
caagctgtct tgatggctt aggcctacca cagatcactg atgaagaagt tgaagccgca    1320
acttatggca gcaattcaaa cgacatgcca aaacgtgaca tggttcaaga tatgaaagct    1380
```

```
gctcaaggtc tgatgactcg tggcattact gttgttgacg ttatcaaggc cttatatgac    1440
catgatatta aagacgtcgc tgaggctgtg cttaagttag cgcaacaaaa ggtttgtggt    1500
gattacctgc aaacatctgc tgtcttcttg gatggttgga agtgtacttc agctattaac    1560
aacgctaacg attacaaagg cccaggtact ggttaccgtc tatgggaaga caaagacaaa    1620
tgggatcgtc tagaaaacgt tccgtgggct ttggatcctc agaagttgga attctaa      1677

<210> SEQ ID NO 99
<211> LENGTH: 558
<212> TYPE: PRT
<213> ORGANISM: Lactobacillus collinoides

<400> SEQUENCE: 99

Met Glu Arg Gln Lys Arg Phe Glu Lys Leu Glu Lys Arg Pro Val His
1               5                   10                  15

Leu Asp Gly Phe Val Lys Asn Trp Asp Asp Glu Gly Leu Val Ala Leu
            20                  25                  30

Asn Gly Lys Asn Asp Pro Lys Pro Ser Ile Thr Ile Glu Asn Gly Val
        35                  40                  45

Val Thr Glu Met Asp Gly Lys Lys Ala Asp Phe Asp Leu Ile Asp
    50                  55                  60

Lys Tyr Ile Ala Glu Tyr Gly Ile Asn Leu Asp Asn Ala Glu Lys Thr
65                  70                  75                  80

Leu Asn Thr Asp Ser Val Lys Ile Ala Asn Met Met Cys Asp Pro Asn
                85                  90                  95

Val Ser Arg Ala Glu Ile Ile Glu Tyr Thr Thr Ala Met Thr Pro Ala
            100                 105                 110

Lys Ala Ala Glu Val Ile Ser Gln Leu Asn Phe Ala Glu Met Ile Met
        115                 120                 125

Ala Thr Gln Lys Met Arg Pro Arg Thr Pro Met Thr Gln Val His
    130                 135                 140

Ala Thr Asn Thr Leu Asp Asn Pro Val Glu Ile Ala Ala Asp Ala Ala
145                 150                 155                 160

Glu Ala Ala Leu Arg Gly Val Pro Glu Glu Thr Thr Thr Ala Ile
                165                 170                 175

Ala Arg Tyr Ala Pro Met Asn Ala Ile Ser Ile Met Val Gly Ala Gln
            180                 185                 190

Ala Gly Arg Pro Gly Val Ile Thr Gln Cys Ser Val Glu Glu Ala Asp
        195                 200                 205

Glu Leu Ser Leu Gly Met Arg Gly Phe Thr Ala Tyr Ala Glu Thr Ile
    210                 215                 220

Ser Val Tyr Gly Thr Asp Arg Val Phe Thr Asp Gly Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ala Gly Ser Glu Ala Met Met Gly Tyr Thr
            260                 265                 270

Glu Gly Lys Ser Met Leu Tyr Leu Glu Ala Arg Cys Ile Tyr Ile Thr
        275                 280                 285

Lys Ala Ser Gly Val Gln Gly Leu Gln Asn Gly Val Ser Cys Ile
    290                 295                 300

Gly Met Pro Gly Ala Val Val Gly Gly Ile Arg Glu Val Leu Gly Glu
305                 310                 315                 320
```

Asn Leu Leu Cys Met Ser Leu Asp Val Glu Cys Ala Ser Gly Cys Asp
                325                 330                 335

Gln Ala Phe Ser His Ser Asp Ile Arg Arg Thr Gly Arg Met Ile Gly
            340                 345                 350

Gln Phe Ile Ala Gly Thr Asp Tyr Leu Ser Ser Gly Tyr Ala Ala Glu
        355                 360                 365

Glu Asn Met Asp Asn Thr Phe Ala Gly Ser Asn Met Asp Val Leu Asp
    370                 375                 380

Tyr Asp Asp Tyr Ile Thr Leu Glu Arg Asp Met Ala Ile Asn Gly Gly
385                 390                 395                 400

Ile Met Pro Ile Thr Glu Glu Ser Ile Lys Ile Arg His Lys Ala
                405                 410                 415

Ala Val Ala Ile Gln Ala Val Phe Asp Gly Leu Gly Leu Pro Gln Ile
            420                 425                 430

Thr Asp Glu Glu Val Glu Ala Ala Thr Tyr Gly Ser Asn Ser Asn Asp
        435                 440                 445

Met Pro Lys Arg Asp Met Val Gln Asp Met Lys Ala Ala Gln Gly Leu
    450                 455                 460

Met Thr Arg Gly Ile Thr Val Val Asp Val Ile Lys Ala Leu Tyr Asp
465                 470                 475                 480

His Asp Ile Lys Asp Val Ala Glu Ala Val Leu Lys Leu Ala Gln Gln
                485                 490                 495

Lys Val Cys Gly Asp Tyr Leu Gln Thr Ser Ala Val Phe Leu Asp Gly
            500                 505                 510

Trp Lys Cys Thr Ser Ala Ile Asn Asn Ala Asn Asp Tyr Lys Gly Pro
        515                 520                 525

Gly Thr Gly Tyr Arg Leu Trp Glu Asp Lys Lys Trp Asp Arg Leu
    530                 535                 540

Glu Asn Val Pro Trp Ala Leu Asp Pro Gln Lys Leu Glu Phe
545                 550                 555

<210> SEQ ID NO 100
<211> LENGTH: 693
<212> TYPE: DNA
<213> ORGANISM: Lactobacillus collinoides

<400> SEQUENCE: 100
gtgagttcag aaatcgatga acattgctt agaaatatca ttaaaggcgt tttaaatgaa      60
gttcaaaact ctgatacgcc aatttccttt ggtggccaag atgcagcccc agttgccggt     120
gccaaggaag tgccgcacc agaaaagaag ttggattggt ccaacacgt tggaatcgcc      180 aaaccaggtt tgtcaaagga tgaagttgta attggtgttg ccccagcatt tgctgaagtg    240
ttgacgcaaa ctatgacgaa gatccaacac aaagacatcc tgcgtcaaat cattgccgga    300
gttgaagaag aaggtctcaa ggcccgtgtc gttaaggttt atcggacttc agacgttcc    360 ttcgtttccg ctgatgttga caagttgtca ggttcaggaa tttcagttgc cgttcaatca    420
aaggggacaa cgattattca ccaaaaggat caagcaccgt tgtcaaacct tgaattgttc    480
ccacaggctc cagttttgac attggacgct accgtcaaa tcggtaagaa cgctgcccag    540
tatgctaagg gtatgtcacc aaccccagtg ccaacaatta cgaccagat ggcacgtgtg    600 caatatcaag cactttctgc tttgatgcac atcaaggaaa caaaacaggt tgttgttggg    660
aagcctgctg aagaaattaa ggtaaccttt tag                                 693

<210> SEQ ID NO 101

<211> LENGTH: 230
<212> TYPE: PRT
<213> ORGANISM: Lactobacillus collinoides

<400> SEQUENCE: 101

```
Met Ser Ser Glu Ile Asp Glu Thr Leu Leu Arg Asn Ile Ile Lys Gly
1               5                   10                  15

Val Leu Asn Glu Val Gln Asn Ser Asp Thr Pro Ile Ser Phe Gly Gly
            20                  25                  30

Gln Asp Ala Ala Pro Val Ala Gly Ala Lys Gly Ala Ala Pro Glu
        35                  40                  45

Lys Lys Leu Asp Trp Phe Gln His Val Gly Ile Ala Lys Pro Gly Leu
    50                  55                  60

Ser Lys Asp Glu Val Val Ile Gly Val Ala Pro Ala Phe Ala Glu Val
65                  70                  75                  80

Leu Thr Gln Thr Met Thr Lys Ile Gln His Lys Asp Ile Leu Arg Gln
                85                  90                  95

Ile Ile Ala Gly Val Glu Glu Gly Leu Lys Ala Arg Val Val Lys
            100                 105                 110

Val Tyr Arg Thr Ser Asp Val Ser Phe Val Ser Ala Asp Val Asp Lys
        115                 120                 125

Leu Ser Gly Ser Gly Ile Ser Val Ala Val Gln Ser Lys Gly Thr Thr
    130                 135                 140

Ile Ile His Gln Lys Asp Gln Ala Pro Leu Ser Asn Leu Glu Leu Phe
145                 150                 155                 160

Pro Gln Ala Pro Val Leu Thr Leu Asp Ala Tyr Arg Gln Ile Gly Lys
                165                 170                 175

Asn Ala Ala Gln Tyr Ala Lys Gly Met Ser Pro Thr Pro Val Pro Thr
            180                 185                 190

Ile Asn Asp Gln Met Ala Arg Val Gln Tyr Gln Ala Leu Ser Ala Leu
        195                 200                 205

Met His Ile Lys Glu Thr Lys Gln Val Val Gly Lys Pro Ala Glu
    210                 215                 220

Glu Ile Lys Val Thr Phe
225                 230
```

<210> SEQ ID NO 102
<211> LENGTH: 522
<212> TYPE: DNA
<213> ORGANISM: Lactobacillus collinoides

<400> SEQUENCE: 102

```
atgagtgaag tagatgactt agtagctaga attgctgctc agctacaaca aagtggaaac      60
gcttctagtg cctcaactag tgccggtact tctgctggtt ccgagaaaga attaggcgca     120
gcagattacc cactatttga aaagcaccca gatcaaatca agacgccatc aggtaaaaat     180
gttgaagaaa tcaccttgga aaatgttatt aacggcaagg tagacgcaaa ggatatgcgg     240
attacgcccg caaccctgaa gttacaaggt gaaattgctg ccaacgcagg tcggccagca     300
atccaacgga acttccagcg ggcttctgaa ttaacttcag ttcccgatga tgttgttttg     360
gacttatata attcattacg gccattccgt tcaaccaagc aagaattatt ggataccgcc     420
aaggagcttc gtgacaagta tcacgcacct atctgtgccg gctggttcga agaagcagcc     480
gaaaactacg aagtcaacaa gaagttgaag ggcgataact ag                        522
```

<210> SEQ ID NO 103

<211> LENGTH: 173
<212> TYPE: PRT
<213> ORGANISM: Lactobacillus collinoides

<400> SEQUENCE: 103

Met Ser Glu Val Asp Asp Leu Val Ala Arg Ile Ala Ala Gln Leu Gln
1               5                   10                  15
Gln Ser Gly Asn Ala Ser Ser Ala Ser Thr Ser Ala Gly Thr Ser Ala
            20                  25                  30
Gly Ser Glu Lys Glu Leu Gly Ala Ala Asp Tyr Pro Leu Phe Glu Lys
        35                  40                  45
His Pro Asp Gln Ile Lys Thr Pro Ser Gly Lys Asn Val Glu Glu Ile
    50                  55                  60
Thr Leu Glu Asn Val Ile Asn Gly Lys Val Asp Ala Lys Asp Met Arg
65                  70                  75                  80
Ile Thr Pro Ala Thr Leu Lys Leu Gln Gly Glu Ile Ala Ala Asn Ala
                85                  90                  95
Gly Arg Pro Ala Ile Gln Arg Asn Phe Gln Arg Ala Ser Glu Leu Thr
            100                 105                 110
Ser Val Pro Asp Asp Val Val Leu Asp Leu Tyr Asn Ser Leu Arg Pro
        115                 120                 125
Phe Arg Ser Thr Lys Gln Glu Leu Leu Asp Thr Ala Lys Glu Leu Arg
    130                 135                 140
Asp Lys Tyr His Ala Pro Ile Cys Ala Gly Trp Phe Glu Glu Ala Ala
145                 150                 155                 160
Glu Asn Tyr Glu Val Asn Lys Lys Leu Lys Gly Asp Asn
                165                 170

<210> SEQ ID NO 104
<211> LENGTH: 1665
<212> TYPE: DNA
<213> ORGANISM: Klebsiella pneumoniae

<400> SEQUENCE: 104
atgagatcga aaagatttga agcactggcg aaacgccctg tgaatcagga tggtttcgtt      60
aaggagtgga ttgaagaggg ctttatcgcg atggaaagtc ctaacgatcc caaaccttct     120
atccgcatcg tcaacggcgc ggtgaccgaa ctcgacggta aaccggttga cgagttcgac     180
ctgattgacc actttatcgc gcgctacggc attaatctcg cccggggccga agaagtgatg     240
gccatggatt cggttaagct cgccaacatg ctctgcgacc cgaacgttaa acgcagcgac     300
atcgtgccgc tcactaccgc gatgaccccg gcgaaaatcg tggaagtggt gtcgcatatg     360
aacgtggtcg agatgatgat ggcgatgcaa aaaatgcgcg cccgccgcac gccgtcccag     420
caggcgcatg tcactaatat caaagataat ccggtacaga ttgccgccga cgccgctgaa     480
ggcgcatggc gcggctttga cgaacaggag accaccgtcg ccgtggcgcg ctacgcgcgg     540
ttcaacgcca tcgccctgct ggtgggttca caggttggcc gccccggcgt cctcacccag     600
tgttcgctgg aagaagccac cgagctgaaa ctgggcatgc tgggccacac ctgctatgcc     660
gaaaccattt cggtatacgg tacgaaccg gtgtttaccg atggcgatga cactccatgg     720
tcgaaaggct tcctcgcctc ctcctacgcc tcgcgcggcc tgaaaatgcg ctttacctcc     780
ggttccggtt ctgaagtaca gatgggctat gccgaaggca aatcgatgct ttatctcgaa     840
gcgcgctgca tctacatcac caaagccgcc ggggtgcaag gctgcagaa tggctccgtc     900
agctgtatcg gcgtaccgtc cgccgtgccg tcgggatcc gcgccgtact ggcggaaaac     960

```
ctgatctgct cagcgctgga tctggagtgc gcctccagca acgatcaaac ctttacccac   1020
tcggatatgc ggcgtaccgc gcgtctgctg atgcagttcc tgccaggcac cgacttcatc   1080
tcctccggtt actcggcggt gcccaactac gacaacatgt tcgccggttc caacgaagat   1140
gccgaagact tcgatgacta caacgtgatc cagcgcgacc tgaaggtcga tgggggtctg   1200
cggccggtgc gtgaagagga cgtgatcgcc attcgcaaca agccgcccg cgcgctgcag   1260 gcggtatttg ccggcatggg tttgccgcct attacggatg aagaggtaga agccgccacc   1320
tacgcccacg gttcaaaaga tatgcctgag cgcaatatcg tcgaggacat caagtttgct   1380
caggagatca tcaacaagaa ccgcaacggc ctggaggtgg tgaaagccct ggcgaaaggc   1440
ggcttccccg atgtcgccca ggacatgctc aatattcaga aagccaagct caccggcgac   1500
tacctgcata cctccgccat cattgttggc gagggccagg tgctctcggc cgtgaatgac   1560
gtgaacgatt atgccggtcc ggcaacaggc taccgcctgc aaggcgagcg ctgggaagag   1620
attaaaaata tcccgggcgc gctcgatccc aatgaacttg gctaa                  1665
```

<210> SEQ ID NO 105
<211> LENGTH: 554
<212> TYPE: PRT
<213> ORGANISM: Klebsiella pneumoniae

<400> SEQUENCE: 105

```
Met Arg Ser Lys Arg Phe Glu Ala Leu Ala Lys Arg Pro Val Asn Gln
1               5                  10                  15

Asp Gly Phe Val Lys Glu Trp Ile Glu Glu Gly Phe Ile Ala Met Glu
            20                  25                  30

Ser Pro Asn Asp Pro Lys Pro Ser Ile Arg Ile Val Asn Gly Ala Val
        35                  40                  45

Thr Glu Leu Asp Gly Lys Pro Val Asp Glu Phe Asp Leu Ile Asp His
    50                  55                  60

Phe Ile Ala Arg Tyr Gly Ile Asn Leu Ala Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Asp Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Ile Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Arg Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255
```

Arg Phe Thr Ser Gly Ser Gly Ser Glu Val Gln Met Gly Tyr Ala Glu
              260                 265                 270

Gly Lys Ser Met Leu Tyr Leu Glu Ala Arg Cys Ile Tyr Ile Thr Lys
         275                 280                 285

Ala Ala Gly Val Gln Gly Leu Gln Asn Gly Ser Val Ser Cys Ile Gly
 290                 295                 300

Val Pro Ser Ala Val Pro Ser Gly Ile Arg Ala Val Leu Ala Glu Asn
305                 310                 315                 320

Leu Ile Cys Ser Ala Leu Asp Leu Glu Cys Ala Ser Ser Asn Asp Gln
                 325                 330                 335

Thr Phe Thr His Ser Asp Met Arg Arg Thr Ala Arg Leu Leu Met Gln
             340                 345                 350

Phe Leu Pro Gly Thr Asp Phe Ile Ser Ser Gly Tyr Ser Ala Val Pro
         355                 360                 365

Asn Tyr Asp Asn Met Phe Ala Gly Ser Asn Glu Asp Ala Glu Asp Phe
370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                 405                 410                 415

Arg Ala Leu Gln Ala Val Phe Ala Gly Met Gly Leu Pro Pro Ile Thr
             420                 425                 430

Asp Glu Glu Val Glu Ala Ala Thr Tyr Ala His Gly Ser Lys Asp Met
         435                 440                 445

Pro Glu Arg Asn Ile Val Glu Asp Ile Lys Phe Ala Gln Glu Ile Ile
 450                 455                 460

Asn Lys Asn Arg Asn Gly Leu Glu Val Val Lys Ala Leu Ala Lys Gly
465                 470                 475                 480

Gly Phe Pro Asp Val Ala Gln Asp Met Leu Asn Ile Gln Lys Ala Lys
                 485                 490                 495

Leu Thr Gly Asp Tyr Leu His Thr Ser Ala Ile Ile Val Gly Glu Gly
             500                 505                 510

Gln Val Leu Ser Ala Val Asn Asp Val Asn Asp Tyr Ala Gly Pro Ala
         515                 520                 525

Thr Gly Tyr Arg Leu Gln Gly Glu Arg Trp Glu Glu Ile Lys Asn Ile
 530                 535                 540

Pro Gly Ala Leu Asp Pro Asn Glu Leu Gly
545                 550

<210> SEQ ID NO 106
<211> LENGTH: 687
<212> TYPE: DNA
<213> ORGANISM: Klebsiella pneumoniae

<400> SEQUENCE: 106
atggaaatta acgaaacgct gctgcgccag attatcgaag aggtgctgtc ggagatgaaa      60
tcaggcgcag ataagccggt ctcctttagc gcgccggcgt ctgtcgcctc tgccgcgccg     120
gtcgccgttg cgcctgtgtc cggcgacagc ttcctgacgg aaatcggcga agccaaaccc     180
ggcacgcagc aggatgaagt cattattgcc gtcgggccag cgtttggtct ggcgcaaacc     240
gccaatatcg tcggcattcc gcataaaaat attctgcgcg aagtgatcgc cggcattgag     300
gaagaaggca tcaaagcccg ggtgatccgc tgctttaagt catctgacgt cgccttcgtg     360
gcagtggaag caaccgcct gagcggctcc ggcatctcga tcggtattca gtcgaaaggc     420

```
accaccgtca tccaccagcg cggcctgccg ccgcttttcca atctggaact cttcccgcag    480
gcgccgctgt taacgctgga aacctaccgt cagattggca aaaacgccgc gcgctacgcc    540
aaacgcgagt cgccgcagcc ggtgccgacg cttaacgatc agatggctcg tcccaaatac    600
caggcgaagt cggccatttt gcacattaaa gagaccaaat acgtggtgac gggcaaaaac    660
ccgcaggaac tgcgcgtggc gcttttaa                                       687
```

<210> SEQ ID NO 107  
<211> LENGTH: 228  
<212> TYPE: PRT  
<213> ORGANISM: Klebsiella pneumoniae

<400> SEQUENCE: 107

```
Met Glu Ile Asn Glu Thr Leu Leu Arg Gln Ile Ile Glu Val Leu
1               5                   10                  15

Ser Glu Met Lys Ser Gly Ala Asp Lys Pro Val Ser Phe Ser Ala Pro
            20                  25                  30

Ala Ser Val Ala Ser Ala Ala Pro Val Ala Val Ala Pro Val Ser Gly
        35                  40                  45

Asp Ser Phe Leu Thr Glu Ile Gly Glu Ala Lys Pro Gly Thr Gln Gln
    50                  55                  60

Asp Glu Val Ile Ile Ala Val Gly Pro Ala Phe Gly Leu Ala Gln Thr
65                  70                  75                  80

Ala Asn Ile Val Gly Ile Pro His Lys Asn Ile Leu Arg Glu Val Ile
                85                  90                  95

Ala Gly Ile Glu Glu Gly Ile Lys Ala Arg Val Ile Arg Cys Phe
            100                 105                 110

Lys Ser Ser Asp Val Ala Phe Val Ala Val Glu Gly Asn Arg Leu Ser
        115                 120                 125

Gly Ser Gly Ile Ser Ile Gly Ile Gln Ser Lys Gly Thr Thr Val Ile
    130                 135                 140

His Gln Arg Gly Leu Pro Pro Leu Ser Asn Leu Glu Leu Phe Pro Gln
145                 150                 155                 160

Ala Pro Leu Leu Thr Leu Glu Thr Tyr Arg Gln Ile Gly Lys Asn Ala
                165                 170                 175

Ala Arg Tyr Ala Lys Arg Glu Ser Pro Gln Pro Val Pro Thr Leu Asn
            180                 185                 190

Asp Gln Met Ala Arg Pro Lys Tyr Gln Ala Lys Ser Ala Ile Leu His
        195                 200                 205

Ile Lys Glu Thr Lys Tyr Val Val Thr Gly Lys Asn Pro Gln Glu Leu
    210                 215                 220

Arg Val Ala Leu
225
```

<210> SEQ ID NO 108  
<211> LENGTH: 525  
<212> TYPE: DNA  
<213> ORGANISM: Klebsiella pneumoniae

<400> SEQUENCE: 108

```
atgaataccg acgcaattga atccatggta cgcgacgtgc tgagccggat gaacagccta    60
caggacgggg taacgcccgc gccagccgcg ccgacaaacg acaccgttcg ccagccaaaa    120
gttagcgact acccgttagc gacctgccat ccggagtggg tcaaaaccgc taccaataaa    180
acgctcgatg acctgacgct ggagaacgta ttaagcgatc gcgttacggc gcaggacatg    240
```

```
cgcatcactc cggaaacgct gcgtatgcag gcggcgatcg cccaggatgc cggacgcgat    300
cggctggcga tgaactttga gcgggccgca gagctcaccg cggttcccga cgaccgaatc    360
cttgagatct acaacgccct gcgcccatac cgttccaccc aggcggagct actggcgatc    420
gctgatgacc tcgagcatcg ctaccaggca cgactctgtg ccgcctttgt tcgggaagcg    480
gccgggctgt acatcgagcg taagaagctg aaaggcgacg attaa                    525
```

<210> SEQ ID NO 109
<211> LENGTH: 174
<212> TYPE: PRT
<213> ORGANISM: Klebsiella pneumoniae

<400> SEQUENCE: 109

```
Met Asn Thr Asp Ala Ile Glu Ser Met Val Arg Asp Val Leu Ser Arg
1               5                   10                  15

Met Asn Ser Leu Gln Asp Gly Val Thr Pro Ala Pro Ala Ala Pro Thr
            20                  25                  30

Asn Asp Thr Val Arg Gln Pro Lys Val Ser Asp Tyr Pro Leu Ala Thr
        35                  40                  45

Cys His Pro Glu Trp Val Lys Thr Ala Thr Asn Lys Thr Leu Asp Asp
    50                  55                  60

Leu Thr Leu Glu Asn Val Leu Ser Asp Arg Val Thr Ala Gln Asp Met
65                  70                  75                  80

Arg Ile Thr Pro Glu Thr Leu Arg Met Gln Ala Ala Ile Ala Gln Asp
                85                  90                  95

Ala Gly Arg Asp Arg Leu Ala Met Asn Phe Glu Arg Ala Ala Glu Leu
            100                 105                 110

Thr Ala Val Pro Asp Asp Arg Ile Leu Glu Ile Tyr Asn Ala Leu Arg
        115                 120                 125

Pro Tyr Arg Ser Thr Gln Ala Glu Leu Leu Ala Ile Ala Asp Asp Leu
    130                 135                 140

Glu His Arg Tyr Gln Ala Arg Leu Cys Ala Ala Phe Val Arg Glu Ala
145                 150                 155                 160

Ala Gly Leu Tyr Ile Glu Arg Lys Lys Leu Lys Gly Asp Asp
                165                 170
```

<210> SEQ ID NO 110
<211> LENGTH: 1833
<212> TYPE: DNA
<213> ORGANISM: Klebsiella oxytoca

<400> SEQUENCE: 110

```
atgcgatata tagctggcat tgatatcggc aactcatcga cggaagtcgc cctggcgacc    60
ctggatgagg ctggcgcgct gacgatcacc cacagcgcgc tggcggaaac caccggaatc    120
aaaggcacgt tgcgtaacgt gttcgggatt caggaggcgc tcgccctcgt cgccagaggc    180
gccgggatcg ccgtcagcga tatttcgctc atccgcatca acgaagcgac gccggtgatt    240
ggcgatgtgg cgatggaaac cattaccgaa accatcatca ccgaatcgac catgatcggc    300
cataacccga aaacgcccgg cggcgcgggg cttggcacag gcatcaccat tacgccgcag    360
gagctgctaa cccgcccggc ggacgcgccc tatatcctgg tggtgtcgtc ggcgttcgat    420
tttgccgata tcgccagcgt gattaacgct tccctgcgcg ccgggtatca gattaccggc    480
gtcattttac agcgcgacga tggcgtgctg gtcagcaacc ggctggaaaa accgctgccg    540
atcgttgacg aagtgctgta catcgaccgc attccgctgg ggatgctggc ggcgattgag    600
```

-continued

```
gtcgccgttc cggggaaggt catcgaaacc ctctctaacc cttacggcat cgccaccgtc    660
tttaacctca gccccgagga gacgaagaac atcgtcccga tggcccgggc gctgattggc    720
aaccgttccg ccgtggtggt caaaacgcca tccggcgacg tcaaagcgcg cgcgataccc    780
gccggtaatc ttgagctgct ggcccagggc cgtagcgtgc gcgtggatgt ggccgccggc    840
gccgaagcca tcatgaaagc ggtcgacggc tgcggcaggc tcgataacgt caccggcgaa    900
tccggcacca atatcggcgg catgctggaa cacgtgcgcc agaccatggc cgagctgacc    960
aacaagccga gcagcgaaat atttattcag gacctgctgg ccgttgatac ctcggtaccg   1020
gtgagcgtta ccgccggtct ggccggggag ttctcgctgg agcaggccgt gggcatcgcc   1080
tcgatggtga atcggatcg cctgcagatg gcaatgatcg cccgcgaaat cgagcagaag   1140
ctcaatatcg acgtgcagat cggcggcgca gaggccgaag ccgccatcct gggggcgctg   1200
accacgccgg gcaccacccg accgctggcg atcctcgacc tcggcgcggg ctccaccgat   1260
gcctccatca tcaaccccaa aggcgacatc atcgccaccc atctcgccgg cgcaggcgac   1320
atggtgacga tgattattgc ccgcgagctg gggctggaag accgctatct ggcggaagag   1380
atcaagaagt acccgctggc taaggtggaa agcctgttcc atttacgcca cgaggacggc   1440
agcgtgcagt tcttctccac gccgctgccg cccgccgtgt tcgcccgcgt ctgcgtggtg   1500
aaagcggacg aactggtgcc gctgcccggc gatttagcgc tggaaaaagt gcgcgccatt   1560
cgccgcagcg ccaaagagcg ggtctttgtc accaacgccc tgcgcgcgct cgtcaggtc    1620
agccccaccg gcaacattcg cgatattccg ttcgtggtgc tggtcggcgg ttcgtcgctg   1680
gatttcgaag tcccgcagct ggtcaccgat gcgctggcgc actaccgcct ggttgccgga   1740
cggggaaata ttcgcggcag cgagggcccc cgaaacgcgg tggccaccgg cctgattctc   1800
tcctggcata aggagtttgc gcatgaacgg taa                                1833
```

<210> SEQ ID NO 111
<211> LENGTH: 610
<212> TYPE: PRT
<213> ORGANISM: Klebsiella oxytoca

<400> SEQUENCE: 111

```
Met Arg Tyr Ile Ala Gly Ile Asp Ile Gly Asn Ser Ser Thr Glu Val
1               5                  10                  15

Ala Leu Ala Thr Leu Asp Glu Ala Gly Ala Leu Thr Ile Thr His Ser
            20                  25                  30

Ala Leu Ala Glu Thr Thr Gly Ile Lys Gly Thr Leu Arg Asn Val Phe
        35                  40                  45

Gly Ile Gln Glu Ala Leu Ala Leu Val Ala Arg Gly Ala Gly Ile Ala
    50                  55                  60

Val Ser Asp Ile Ser Leu Ile Arg Ile Asn Glu Ala Thr Pro Val Ile
65                  70                  75                  80

Gly Asp Val Ala Met Glu Thr Ile Thr Glu Thr Ile Ile Thr Glu Ser
                85                  90                  95

Thr Met Ile Gly His Asn Pro Lys Thr Pro Gly Gly Ala Gly Leu Gly
            100                 105                 110

Thr Gly Ile Thr Ile Thr Pro Gln Glu Leu Leu Thr Arg Pro Ala Asp
        115                 120                 125

Ala Pro Tyr Ile Leu Val Val Ser Ser Ala Phe Asp Phe Ala Asp Ile
    130                 135                 140

Ala Ser Val Ile Asn Ala Ser Leu Arg Ala Gly Tyr Gln Ile Thr Gly
```

-continued

```
            145                 150                 155                 160
        Val Ile Leu Gln Arg Asp Asp Gly Val Leu Val Ser Asn Arg Leu Glu
                        165                 170                 175
        Lys Pro Leu Pro Ile Val Asp Glu Val Leu Tyr Ile Asp Arg Ile Pro
                        180                 185                 190
        Leu Gly Met Leu Ala Ala Ile Glu Val Ala Val Pro Gly Lys Val Ile
                        195                 200                 205
        Glu Thr Leu Ser Asn Pro Tyr Gly Ile Ala Thr Val Phe Asn Leu Ser
                        210                 215                 220
        Pro Glu Glu Thr Lys Asn Ile Val Pro Met Ala Arg Ala Leu Ile Gly
        225                 230                 235                 240
        Asn Arg Ser Ala Val Val Lys Thr Pro Ser Gly Asp Val Lys Ala
                        245                 250                 255
        Arg Ala Ile Pro Ala Gly Asn Leu Glu Leu Leu Ala Gln Gly Arg Ser
                        260                 265                 270
        Val Arg Val Asp Val Ala Ala Gly Ala Glu Ala Ile Met Lys Ala Val
                        275                 280                 285
        Asp Gly Cys Gly Arg Leu Asp Asn Val Thr Gly Glu Ser Gly Thr Asn
        290                 295                 300
        Ile Gly Gly Met Leu Glu His Val Arg Gln Thr Met Ala Glu Leu Thr
        305                 310                 315                 320
        Asn Lys Pro Ser Ser Glu Ile Phe Ile Gln Asp Leu Leu Ala Val Asp
                        325                 330                 335
        Thr Ser Val Pro Val Ser Val Thr Gly Gly Leu Ala Gly Glu Phe Ser
                        340                 345                 350
        Leu Glu Gln Ala Val Gly Ile Ala Ser Met Val Lys Ser Asp Arg Leu
                        355                 360                 365
        Gln Met Ala Met Ile Ala Arg Glu Ile Glu Gln Lys Leu Asn Ile Asp
                        370                 375                 380
        Val Gln Ile Gly Gly Ala Glu Ala Glu Ala Ile Leu Gly Ala Leu
        385                 390                 395                 400
        Thr Thr Pro Gly Thr Thr Arg Pro Leu Ala Ile Leu Asp Leu Gly Ala
                        405                 410                 415
        Gly Ser Thr Asp Ala Ser Ile Ile Asn Pro Lys Gly Asp Ile Ile Ala
                        420                 425                 430
        Thr His Leu Ala Gly Ala Gly Asp Met Val Thr Met Ile Ile Ala Arg
                        435                 440                 445
        Glu Leu Gly Leu Glu Asp Arg Tyr Leu Ala Glu Glu Ile Lys Lys Tyr
                        450                 455                 460
        Pro Leu Ala Lys Val Glu Ser Leu Phe His Leu Arg His Glu Asp Gly
        465                 470                 475                 480
        Ser Val Gln Phe Phe Ser Thr Pro Leu Pro Pro Ala Val Phe Ala Arg
                        485                 490                 495
        Val Cys Val Val Lys Ala Asp Glu Leu Val Pro Leu Pro Gly Asp Leu
                        500                 505                 510
        Ala Leu Glu Lys Val Arg Ala Ile Arg Arg Ser Ala Lys Glu Arg Val
                        515                 520                 525
        Phe Val Thr Asn Ala Leu Arg Ala Leu Arg Gln Val Ser Pro Thr Gly
                        530                 535                 540
        Asn Ile Arg Asp Ile Pro Phe Val Val Leu Val Gly Gly Ser Ser Leu
        545                 550                 555                 560
        Asp Phe Glu Val Pro Gln Leu Val Thr Asp Ala Leu Ala His Tyr Arg
                        565                 570                 575
```

```
Leu Val Ala Gly Arg Gly Asn Ile Arg Gly Ser Glu Gly Pro Arg Asn
            580                 585                 590

Ala Val Ala Thr Gly Leu Ile Leu Ser Trp His Lys Glu Phe Ala His
        595                 600                 605

Glu Arg
    610

<210> SEQ ID NO 112
<211> LENGTH: 378
<212> TYPE: DNA
<213> ORGANISM: Klebsiella oxytoca

<400> SEQUENCE: 112
atgaacggta atcacagcgc cccggccatc gcgatcgccg tcatcgacgg ctgcgacggc    60
ctgtggcgcg aagtgctgct gggtatcgaa gaggaaggta tccctttccg gctccagcat   120 caccggccg agaggtcgt ggacagcgcc tggcaggcgg cgcgcagctc gccgctgctg     180
gtgggcatcg cctgcgaccg ccatatgctg gtcgtgcact acaagaattt acccgcatcg   240
gcgccgcttt ttacgctgat gcatcatcag acagtcagg cccatcgcaa caccggtaat    300
aacgcggcac ggctggtcaa ggggatccct tccgggatc tgaatagcga agcaacagga    360
gaacagcagg atgaataa                                                 378

<210> SEQ ID NO 113
<211> LENGTH: 125
<212> TYPE: PRT
<213> ORGANISM: Klebsiella oxytoca

<400> SEQUENCE: 113

Met Asn Gly Asn His Ser Ala Pro Ala Ile Ala Ile Ala Val Ile Asp
1               5                   10                  15

Gly Cys Asp Gly Leu Trp Arg Glu Val Leu Leu Gly Ile Glu Glu Glu
            20                  25                  30

Gly Ile Pro Phe Arg Leu Gln His His Pro Ala Gly Glu Val Val Asp
        35                  40                  45

Ser Ala Trp Gln Ala Ala Arg Ser Ser Pro Leu Leu Val Gly Ile Ala
    50                  55                  60

Cys Asp Arg His Met Leu Val Val His Tyr Lys Asn Leu Pro Ala Ser
65                  70                  75                  80

Ala Pro Leu Phe Thr Leu Met His His Gln Asp Ser Gln Ala His Arg
                85                  90                  95

Asn Thr Gly Asn Asn Ala Ala Arg Leu Val Lys Gly Ile Pro Phe Arg
            100                 105                 110

Asp Leu Asn Ser Glu Ala Thr Gly Glu Gln Gln Asp Glu
        115                 120                 125

<210> SEQ ID NO 114
<211> LENGTH: 1833
<212> TYPE: DNA
<213> ORGANISM: Salmonella typhimurium

<400> SEQUENCE: 114
atgcgatata tagctggcat tgacatcggt aactcatcaa cggaagtcgc actggcgcgg    60
caagatgaga ctggcgcact gacgattaca cacagcgcgc tggcggaaac caccgggatc   120
aaaggcacgt tgcgtaacgt gttcggcatt caggaagcgc tcgccctcgt cgcaaagcgc   180
gcggggatca atgtcagaga tatttcgctc atccgcatta acgaagccac gccggtgatt   240
```

-continued

```
ggcgatgtgg cgatggaaac cattaccgaa accatcatca ccgaatcgac aatgatcggc    300
cataacccaa aaacgccggg cggagcaggc cttggtgtgg gtatcacgat tacgccggag    360
gagctgttaa cccgcccggc ggactcgtcc tatattctgg tggtatcgtc agcctttgat    420
tttgctgata tcgccaatgt tatcaacgcc tcaatgcgcg ccggataccg gattaccggc    480
gtcattttgc agcgcgacga tggcgtactg gtcagcaacc ggctggaaaa atcgctaccg    540
attgtcgatg aagttctgta catcgaccgc attccgctgg ggatgctggc ggcgattgaa    600
gtcgccgtgc cgggaaaggt tatcgaaacc ctctctaacc cttacggcat cgccaccgta    660
tttaatctca acgccgatga acaaaaaaac atcgtcccga tggcgcgcgc gctgattggc    720
aaccgttccg ccgtggtggt aaaaacgcca tccggcgacg tcaaagcgcg cgcaataccc    780
gccggtaacc tggagctgca ggctcagggt cgtaccgtgc gcgtggatgt tgccgccggt    840
gccgaagcca tcatgaaagc ggtggacggt tgcggcaagc tcgacaacgt caccggcgag    900
gccgggacca atatcggcgg catgctggag cacgtgcgcc agaccatggc cgaactgacc    960
aacaagccga gcagtgagat tttcattcag gatctactgg ccgttgacac ctcggttccg   1020
gtgagcgtca ccggcggtct ggccggggag ttctcgctgg agcaggccgt cggcatcgcc   1080
tcgatggtga atcagaccg tctgcagatg gcgatgattg cccgtgaaat tgagcagaag   1140
cttaatatcg acgtgcagat cggcggcgct gaggctgaag ccgccattct gggcgcgctg   1200
accacgccgg gtaccacccg accgctggcg atcctcgacc tcggcgcggg ctccaccgat   1260
gcctccatca tcaaccctaa aggcgaaatc atcgccaccc atctcgccgg ggcaggcgac   1320
atggtcacga tgattattgc ccgcgaactg gggctggaag accgctatct ggcggaagag   1380
atcaaaaaat acccgctggc taaggtcgaa agcctgttcc acttacgcca cgaggacggc   1440
agcgtccagt tcttcccgac gccgctgcct cccgccgtgt tcgcccgcgt ctgcgtggtg   1500
aaaccggacg aactggtgcc gcttcccggc gacttagcgc tggaaaaagt gcgcgccatt   1560
cgccgcagcg ctaaagaacg cgtctttgtc accaacgccc tgcgcgcgct cgccaggtc   1620 agtccaaccg gcaacattcg cgatattccg ttcgtggtgc tggtcggcgg ctcgtcgctg   1680
gatttcgaag ttccgcagct ggtcaccgat gcgctggcgc actaccgcct ggtcgccggg   1740
cgaggaaata ttcgcggcag cgaaggccca agaaacgcgg tggccaccgg cctgattctc   1800
tcctggcata aggagtttgc gcatggacag taa                                1833
```

<210> SEQ ID NO 115
<211> LENGTH: 610
<212> TYPE: PRT
<213> ORGANISM: Salmonella typhimurium

<400> SEQUENCE: 115

Met Arg Tyr Ile Ala Gly Ile Asp Ile Gly Asn Ser Ser Thr Glu Val
1               5                   10                  15

Ala Leu Ala Arg Gln Asp Glu Thr Gly Ala Leu Thr Ile Thr His Ser
            20                  25                  30

Ala Leu Ala Glu Thr Thr Gly Ile Lys Gly Thr Leu Arg Asn Val Phe
        35                  40                  45

Gly Ile Gln Glu Ala Leu Ala Leu Val Ala Lys Arg Ala Gly Ile Asn
    50                  55                  60

Val Arg Asp Ile Ser Leu Ile Arg Ile Asn Glu Ala Thr Pro Val Ile
65                  70                  75                  80

Gly Asp Val Ala Met Glu Thr Ile Thr Glu Thr Ile Ile Thr Glu Ser

```
                85                  90                  95
Thr Met Ile Gly His Asn Pro Lys Thr Pro Gly Gly Ala Gly Leu Gly
            100                 105                 110

Val Gly Ile Thr Ile Thr Pro Glu Glu Leu Leu Thr Arg Pro Ala Asp
            115                 120                 125

Ser Ser Tyr Ile Leu Val Val Ser Ser Ala Phe Asp Phe Ala Asp Ile
            130                 135                 140

Ala Asn Val Ile Asn Ala Ser Met Arg Ala Gly Tyr Gln Ile Thr Gly
145                 150                 155                 160

Val Ile Leu Gln Arg Asp Asp Gly Val Leu Val Ser Asn Arg Leu Glu
                165                 170                 175

Lys Ser Leu Pro Ile Val Asp Glu Val Leu Tyr Ile Asp Arg Ile Pro
                180                 185                 190

Leu Gly Met Leu Ala Ala Ile Glu Val Ala Val Pro Gly Lys Val Ile
                195                 200                 205

Glu Thr Leu Ser Asn Pro Tyr Gly Ile Ala Thr Val Phe Asn Leu Asn
            210                 215                 220

Ala Asp Glu Thr Lys Asn Ile Val Pro Met Ala Arg Ala Leu Ile Gly
225                 230                 235                 240

Asn Arg Ser Ala Val Val Lys Thr Pro Ser Gly Asp Val Lys Ala
                245                 250                 255

Arg Ala Ile Pro Ala Gly Asn Leu Glu Leu Gln Ala Gln Gly Arg Thr
                260                 265                 270

Val Arg Val Asp Val Ala Ala Gly Ala Glu Ala Ile Met Lys Ala Val
                275                 280                 285

Asp Gly Cys Gly Lys Leu Asp Asn Val Thr Gly Glu Ala Gly Thr Asn
                290                 295                 300

Ile Gly Gly Met Leu Glu His Val Arg Gln Thr Met Ala Glu Leu Thr
305                 310                 315                 320

Asn Lys Pro Ser Ser Glu Ile Phe Ile Gln Asp Leu Leu Ala Val Asp
                325                 330                 335

Thr Ser Val Pro Val Ser Val Thr Gly Gly Leu Ala Gly Glu Phe Ser
                340                 345                 350

Leu Glu Gln Ala Val Gly Ile Ala Ser Met Val Lys Ser Asp Arg Leu
            355                 360                 365

Gln Met Ala Met Ile Ala Arg Glu Ile Glu Gln Lys Leu Asn Ile Asp
            370                 375                 380

Val Gln Ile Gly Gly Ala Glu Ala Glu Ala Ala Ile Leu Gly Ala Leu
385                 390                 395                 400

Thr Thr Pro Gly Thr Thr Arg Pro Leu Ala Ile Leu Asp Leu Gly Ala
                405                 410                 415

Gly Ser Thr Asp Ala Ser Ile Ile Asn Pro Lys Gly Glu Ile Ile Ala
                420                 425                 430

Thr His Leu Ala Gly Ala Gly Asp Met Val Thr Met Ile Ile Ala Arg
                435                 440                 445

Glu Leu Gly Leu Glu Asp Arg Tyr Leu Ala Glu Ile Lys Lys Tyr
                450                 455                 460

Pro Leu Ala Lys Val Glu Ser Leu Phe His Leu Arg His Glu Asp Gly
465                 470                 475                 480

Ser Val Gln Phe Phe Pro Thr Pro Leu Pro Pro Ala Val Phe Ala Arg
                485                 490                 495

Val Cys Val Val Lys Pro Asp Glu Leu Val Pro Leu Pro Gly Asp Leu
                500                 505                 510
```

```
Ala Leu Glu Lys Val Arg Ala Ile Arg Arg Ser Ala Lys Glu Arg Val
        515                 520                 525

Phe Val Thr Asn Ala Leu Arg Ala Leu Arg Gln Val Ser Pro Thr Gly
    530                 535                 540

Asn Ile Arg Asp Ile Pro Phe Val Val Leu Val Gly Gly Ser Ser Leu
545                 550                 555                 560

Asp Phe Glu Val Pro Gln Leu Val Thr Asp Ala Leu Ala His Tyr Arg
                565                 570                 575

Leu Val Ala Gly Arg Gly Asn Ile Arg Gly Ser Glu Gly Pro Arg Asn
            580                 585                 590

Ala Val Ala Thr Gly Leu Ile Leu Ser Trp His Lys Glu Phe Ala His
        595                 600                 605

Gly Gln
    610

<210> SEQ ID NO 116
<211> LENGTH: 372
<212> TYPE: DNA
<213> ORGANISM: Salmonella typhimurium

<400> SEQUENCE: 116
atggacagta atcacagcgc cccggctatc gtcattaccg ttatcaacga ctgcgccagc      60
ctctggcacg aagtgctgct gggcattgaa gaggaaggca tccctttcct gcttcagcat     120
cacccggctg agatatcgt tgacagcgcc tggcaggcgg cgcgcagctc gccgctgctg      180
gtcggcattg cctgcgatcg acactcgctg gtcgtgcatt acaagaattt acccgcatcg     240
gcgccgcttt ttacgctgat gcatcatcag gacagtcagg cccaacgcaa caccggtaat     300
aacgcggcac ggctggtcaa agggatccct ttcgggatct ccatgcttaa tcacaggaga     360
acggcagtat ga                                                         372

<210> SEQ ID NO 117
<211> LENGTH: 123
<212> TYPE: PRT
<213> ORGANISM: Salmonella typhimurium

<400> SEQUENCE: 117

Met Asp Ser Asn His Ser Ala Pro Ala Ile Val Ile Thr Val Ile Asn
1               5                   10                  15

Asp Cys Ala Ser Leu Trp His Glu Val Leu Leu Gly Ile Glu Glu Glu
            20                  25                  30

Gly Ile Pro Phe Leu Leu Gln His Pro Ala Gly Asp Ile Val Asp
        35                  40                  45

Ser Ala Trp Gln Ala Ala Arg Ser Ser Pro Leu Leu Val Gly Ile Ala
    50                  55                  60

Cys Asp Arg His Ser Leu Val Val His Tyr Lys Asn Leu Pro Ala Ser
65                  70                  75                  80

Ala Pro Leu Phe Thr Leu Met His His Gln Asp Ser Gln Ala Gln Arg
                85                  90                  95

Asn Thr Gly Asn Asn Ala Ala Arg Leu Val Lys Gly Ile Pro Phe Gly
            100                 105                 110

Ile Ser Met Leu Asn His Arg Arg Thr Ala Val
        115                 120

<210> SEQ ID NO 118
<211> LENGTH: 1833
```

<212> TYPE: DNA
<213> ORGANISM: Lactobacillus collinoides

<400> SEQUENCE: 118

```
atgacacgtg taattggtgt tgatatcggg aattcctcta cagaagttgc gcttgctgat      60
gtgtctgaca gtggtgaagt aaatttcatt aattctggaa tttccgatac aactggcatt     120
aaaggtacta acaaaattt gatcggggtg cgtaaatcca tccagatcgt tttgaaaaag     180
tcgaatatgc aaatttccga tgttgacctg attcggatca acgaagcaac gcccgttatc     240
ggtgatgttg ccatggagac catcaccgaa acggtgatta ctgaatcgac gatgatcggc     300
cacaacccag ggactcctgg gggtgtcggt actggttctg gttacacggt gaatttgctt     360
gatttgttga gccaaacgga taaggatcgt ccttatatcg ttatcatctc gaaagaaatc     420
gattttgctg acgcagctaa gctgatcaac gcttatgtgg cttctggtta taatattacc     480
gctgccattc tgcaaagtga tgatggggtg ctgatcaata atcggttgac ccataagatt     540
cccatcgtgg atgaagtctc acagatcgac aaggtaccgt tgaacatgct tgccgcagtg     600
gaagttgcac cgcctggcaa agtaattgct caactttcca acccgtatgg cattgccaca     660
ctgttcgaac tttcctctga agaaaccaag aacattgtgc cagttgcccg agccttaatc     720
ggaaaccggt cagcggttgt tattaaaacc cctgccggtg atgttaaagc tcgtgttatc     780
ccagccggga aaatcttgat caatggccaa ccgaatggtc atggtgaagt taacgttgcg     840
gctggtgccg atgccatcat gaaaaaggtg aacgagttcg atagtgtcga tgacattacc     900
ggtgaatcgg gcactaacgt tggtgggatg cttgaaaaag ttcgtcaaac aatggctgag     960
ttgaccgaca agcaaaatag cgacattgcc attcaagatt tattagctgt caatacgtcc    1020
gttccagtaa cggtgcgtgg tggtctggct ggtgaattct caatggaaca agccgttggg    1080
attgctgcta tggtcaaatc tgatcacttg caaatgcaag cgattgcaga cctgatgaaa    1140
gatgaatttc acgttcaagt cgaaatcggc ggtgctgaag ctgaatcagc catcctcggt    1200
gcgctaacaa cgccagggac gacaaaacca attgccatcc ttgatttggg ggctggttca    1260
acggatgcat caattatcaa ccaaaaggac gaaaaggtcg ctattcactt ggctggtgcc    1320
ggtgatatgg ttaccatgat catcaattct gaacttgggt tggaagaccc atatttagct    1380
gaggatatta agaaatatcc gctggctaaa gttgataatc tattccagct acggcatgaa    1440
gatggtgccg ttcaattctt tgaagatcca ttacctgctg atttatttgc cagagttgtg    1500
gctgttaaac cagatggtta cgaaccactt cctggtaatt tgagtatcga gaaagttaaa    1560
atcgtccgtc aaactgctaa gaagcgggtg ttcgtaacga acgcaattcg tgccttacac    1620
cacgttagcc caacaggtaa tatccgagat atcccatttg tggtcattgt cggcggctca    1680
gccctcgatt ttgaaattcc acaattggtc accgatgaat tatcacactt aacttagtt    1740
gcaggtcgtg gtaatattcg gggaattgaa ggtccacgga acgccgtggc aactggtttg    1800
attctttcat acgcgagtga aagaggggga tag                                  1833
```

<210> SEQ ID NO 119
<211> LENGTH: 610
<212> TYPE: PRT
<213> ORGANISM: Lactobacillus collinoides

<400> SEQUENCE: 119

```
Met Thr Arg Val Ile Gly Val Asp Ile Gly Asn Ser Ser Thr Glu Val
1               5                   10                  15

Ala Leu Ala Asp Val Ser Asp Ser Gly Glu Val Asn Phe Ile Asn Ser
```

```
                    20                  25                  30
Gly Ile Ser Asp Thr Thr Gly Ile Lys Gly Thr Lys Gln Asn Leu Ile
                35                  40                  45
Gly Val Arg Lys Ser Ile Gln Ile Val Leu Lys Lys Ser Asn Met Gln
            50                  55                  60
Ile Ser Asp Val Asp Leu Ile Arg Ile Asn Glu Ala Thr Pro Val Ile
65                  70                  75                  80
Gly Asp Val Ala Met Glu Thr Ile Thr Glu Thr Val Ile Thr Glu Ser
                85                  90                  95
Thr Met Ile Gly His Asn Pro Gly Thr Pro Gly Gly Val Gly Thr Gly
                100                 105                 110
Ser Gly Tyr Thr Val Asn Leu Leu Asp Leu Leu Ser Gln Thr Asp Lys
            115                 120                 125
Asp Arg Pro Tyr Ile Val Ile Ser Lys Glu Ile Asp Phe Ala Asp
            130                 135                 140
Ala Ala Lys Leu Ile Asn Ala Tyr Val Ala Ser Gly Tyr Asn Ile Thr
145                 150                 155                 160
Ala Ala Ile Leu Gln Ser Asp Asp Gly Val Leu Ile Asn Asn Arg Leu
                165                 170                 175
Thr His Lys Ile Pro Ile Val Asp Glu Val Ser Gln Ile Asp Lys Val
                180                 185                 190
Pro Leu Asn Met Leu Ala Ala Val Glu Val Ala Pro Pro Gly Lys Val
            195                 200                 205
Ile Ala Gln Leu Ser Asn Pro Tyr Gly Ile Ala Thr Leu Phe Glu Leu
            210                 215                 220
Ser Ser Glu Glu Thr Lys Asn Ile Val Pro Val Ala Arg Ala Leu Ile
225                 230                 235                 240
Gly Asn Arg Ser Ala Val Val Ile Lys Thr Pro Ala Gly Asp Val Lys
                245                 250                 255
Ala Arg Val Ile Pro Ala Gly Lys Ile Leu Ile Asn Gly Gln Pro Asn
                260                 265                 270
Gly His Gly Glu Val Asn Val Ala Ala Gly Ala Asp Ala Ile Met Lys
            275                 280                 285
Lys Val Asn Glu Phe Asp Ser Val Asp Ile Thr Gly Glu Ser Gly
            290                 295                 300
Thr Asn Val Gly Gly Met Leu Glu Lys Val Arg Gln Thr Met Ala Glu
305                 310                 315                 320
Leu Thr Asp Lys Gln Asn Ser Asp Ile Ala Ile Gln Asp Leu Leu Ala
                325                 330                 335
Val Asn Thr Ser Val Pro Val Thr Val Arg Gly Gly Leu Ala Gly Glu
                340                 345                 350
Phe Ser Met Glu Gln Ala Val Gly Ile Ala Ala Met Val Lys Ser Asp
            355                 360                 365
His Leu Gln Met Gln Ala Ile Ala Asp Leu Met Lys Asp Glu Phe His
            370                 375                 380
Val Gln Val Glu Ile Gly Gly Ala Glu Ala Glu Ser Ala Ile Leu Gly
385                 390                 395                 400
Ala Leu Thr Thr Pro Gly Thr Thr Lys Pro Ile Ala Ile Leu Asp Leu
                405                 410                 415
Gly Ala Gly Ser Thr Asp Ala Ser Ile Ile Asn Gln Lys Asp Glu Lys
                420                 425                 430
Val Ala Ile His Leu Ala Gly Ala Gly Asp Met Val Thr Met Ile Ile
            435                 440                 445
```

```
Asn Ser Glu Leu Gly Leu Glu Asp Pro Tyr Leu Ala Glu Asp Ile Lys
    450                 455                 460

Lys Tyr Pro Leu Ala Lys Val Asp Asn Leu Phe Gln Leu Arg His Glu
465                 470                 475                 480

Asp Gly Ala Val Gln Phe Phe Glu Asp Pro Leu Pro Ala Asp Leu Phe
                485                 490                 495

Ala Arg Val Val Ala Val Lys Pro Asp Gly Tyr Glu Pro Leu Pro Gly
                500                 505                 510

Asn Leu Ser Ile Glu Lys Val Lys Ile Val Arg Gln Thr Ala Lys Lys
            515                 520                 525

Arg Val Phe Val Thr Asn Ala Ile Arg Ala Leu His His Val Ser Pro
        530                 535                 540

Thr Gly Asn Ile Arg Asp Ile Pro Phe Val Val Ile Val Gly Gly Ser
545                 550                 555                 560

Ala Leu Asp Phe Glu Ile Pro Gln Leu Val Thr Asp Glu Leu Ser His
                565                 570                 575

Phe Asn Leu Val Ala Gly Arg Gly Asn Ile Arg Gly Ile Glu Gly Pro
                580                 585                 590

Arg Asn Ala Val Ala Thr Gly Leu Ile Leu Ser Tyr Ala Ser Glu Lys
            595                 600                 605

Arg Gly
    610

<210> SEQ ID NO 120
<211> LENGTH: 351
<212> TYPE: DNA
<213> ORGANISM: Lactobacillus collinoides

<400> SEQUENCE: 120
atggcatttg attctgaacg tccgtcaatt ctattggcga caccaacggg ttctaatggc      60
caacttccag aagttctaaa accaatgctc aatggtattg aagaagaaca gattcctttt     120
cagattctcg atatggaagg cggttcagca gttgagcggg cttataacgc gtcagttgct     180
tcacgattat cagtgggcgt tgggtttgat gatgcacata tcattgtgca ttataaaaac     240
ttgaaaccag aaaaaccgct gtttgatgtt gccatcactg atgcagcatc cattcgtaaa     300
gttggcgcaa acgccgctcg acttgtaaag ggagttccat tcaagaagta a              351

<210> SEQ ID NO 121
<211> LENGTH: 116
<212> TYPE: PRT
<213> ORGANISM: Lactobacillus collinoides

<400> SEQUENCE: 121

Met Ala Phe Asp Ser Glu Arg Pro Ser Ile Leu Leu Ala Thr Pro Thr
1               5                   10                  15

Gly Ser Asn Gly Gln Leu Pro Glu Val Leu Lys Pro Met Leu Asn Gly
            20                  25                  30

Ile Glu Glu Glu Gln Ile Pro Phe Gln Ile Leu Asp Met Glu Gly Gly
        35                  40                  45

Ser Ala Val Glu Arg Ala Tyr Asn Ala Ser Val Ala Ser Arg Leu Ser
    50                  55                  60

Val Gly Val Gly Phe Asp Asp Ala His Ile Ile Val His Tyr Lys Asn
65                  70                  75                  80

Leu Lys Pro Glu Lys Pro Leu Phe Asp Val Ala Ile Thr Asp Ala Ala
                85                  90                  95
```

Ser Ile Arg Lys Val Gly Ala Asn Ala Ala Arg Leu Val Lys Gly Val
            100                 105                 110

Pro Phe Lys Lys
        115

<210> SEQ ID NO 122
<211> LENGTH: 453
<212> TYPE: PRT
<213> ORGANISM: Vibrio fluvialis

<400> SEQUENCE: 122

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu

```
            340                 345                 350
Ala Pro Arg Phe Glu Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 123
<211> LENGTH: 1122
<212> TYPE: DNA
<213> ORGANISM: Erwinia caratovora subsp. atroseptica

<400> SEQUENCE: 123
atgtctgacg gacgactcac cgcactttt cctgcattcc cacacccggc gtccaatcag      60
cccgtatttg ccgaggcttc accgcacgac gacgagttaa tgacgcaggc cgtaccgcag     120
gtttcctgtc agcaggcgtt ggcgattgcg cagcaagaat atggcttgtc tgggcagatg     180
tcgctgcttc agggcgagcg tgatgtgaat ttctgtctga cggtgacgcc agatgaacgc     240
tacatgctga aagtcatcaa tgcggcagaa cctgccgacg tcagcaattt ccaaaccgcg     300
ctgctgctgc atcttgcccg tcaggcacct gaactgcccg taccgcgtat caggtcgaca     360
aaagcgggtc agtcggaaac aggcgttgag atcgatggtg tactgctgcg tgtgcggctt     420
gtgagctatc tggcaggaat gccgcagtat ctggcctcac cgtcaacggc gctgatgccg     480
cagtgggggg gaacgctggc gcagttggat aacgcgcttc acagctttac gcatccggcg     540
gcaaaccgtg cgctgctgtg ggatatcagc cgggcagagc aggtgcgtcc ttacctcgat     600
ttcgtttctg aaccgcagca gtatcagcat cttcagcgta ttttgaccg ttatgacagt      660 aacgttgctc ctctgttgac gacgctacgt cgtcaggtca ttcataacga tctgaatccg     720
cataacgtgc tggtggatgg atcgtcgccg acgcgggtta ctggcattat cgattttggc     780
gatgccgtat ttgccccgtt aatttgcgaa gtcgcgacgg cactggcgta tcagatcggc     840
gatggaaccg atttgttgga gcatgttgtg ccgtttgttg cggcctatca ccaacgcatt     900
ccgttagcac cggaggagat tgcgctgtta cccgatctga tagcgacccg tatggcgctg     960
accctgacca ttgcgcagtg gcgagcatcg cgttatcccg acaatcggga gtatctgctg    1020
cgtaacgtgc cgcgctgttg gcacagtttg cagcgcattg cgacctattc ccatgcgcaa    1080
tttttgactc gcctacagca ggtttgcccg gagaatgcgc ga                       1122

<210> SEQ ID NO 124
<211> LENGTH: 374
<212> TYPE: PRT
<213> ORGANISM: Erwinia caratovora subsp. atroseptica

<400> SEQUENCE: 124

Met Ser Asp Gly Arg Leu Thr Ala Leu Phe Pro Ala Phe Pro His Pro
1               5                   10                  15
```

Ala Ser Asn Gln Pro Val Phe Ala Glu Ala Ser Pro His Asp Asp Glu
            20                  25                  30

Leu Met Thr Gln Ala Val Pro Gln Val Ser Cys Gln Gln Ala Leu Ala
        35                  40                  45

Ile Ala Gln Gln Glu Tyr Gly Leu Ser Gly Met Ser Leu Leu Gln
 50                  55                  60

Gly Glu Arg Asp Val Asn Phe Cys Leu Thr Val Thr Pro Asp Glu Arg
 65                  70                  75                  80

Tyr Met Leu Lys Val Ile Asn Ala Ala Glu Pro Ala Asp Val Ser Asn
                85                  90                  95

Phe Gln Thr Ala Leu Leu Leu His Leu Ala Arg Gln Ala Pro Glu Leu
            100                 105                 110

Pro Val Pro Arg Ile Arg Ser Thr Lys Ala Gly Gln Ser Glu Thr Gly
        115                 120                 125

Val Glu Ile Asp Gly Val Leu Leu Arg Val Arg Leu Val Ser Tyr Leu
130                 135                 140

Ala Gly Met Pro Gln Tyr Leu Ala Ser Pro Ser Thr Ala Leu Met Pro
145                 150                 155                 160

Gln Leu Gly Gly Thr Leu Ala Gln Leu Asp Asn Ala Leu His Ser Phe
                165                 170                 175

Thr His Pro Ala Ala Asn Arg Ala Leu Leu Trp Asp Ile Ser Arg Ala
            180                 185                 190

Glu Gln Val Arg Pro Tyr Leu Asp Phe Val Ser Glu Pro Gln Gln Tyr
        195                 200                 205

Gln His Leu Gln Arg Ile Phe Asp Arg Tyr Asp Ser Asn Val Ala Pro
210                 215                 220

Leu Leu Thr Thr Leu Arg Arg Gln Val Ile His Asn Asp Leu Asn Pro
225                 230                 235                 240

His Asn Val Leu Val Asp Gly Ser Ser Pro Thr Arg Val Thr Gly Ile
                245                 250                 255

Ile Asp Phe Gly Asp Ala Val Phe Ala Pro Leu Ile Cys Glu Val Ala
            260                 265                 270

Thr Ala Leu Ala Tyr Gln Ile Gly Asp Gly Thr Asp Leu Leu Glu His
        275                 280                 285

Val Val Pro Phe Val Ala Ala Tyr His Gln Arg Ile Pro Leu Ala Pro
290                 295                 300

Glu Glu Ile Ala Leu Leu Pro Asp Leu Ile Ala Thr Arg Met Ala Leu
305                 310                 315                 320

Thr Leu Thr Ile Ala Gln Trp Arg Ala Ser Arg Tyr Pro Asp Asn Arg
                325                 330                 335

Glu Tyr Leu Leu Arg Asn Val Pro Arg Cys Trp His Ser Leu Gln Arg
            340                 345                 350

Ile Ala Thr Tyr Ser His Ala Gln Phe Leu Thr Arg Leu Gln Gln Val
        355                 360                 365

Cys Pro Glu Asn Ala Arg
    370

<210> SEQ ID NO 125
<211> LENGTH: 1272
<212> TYPE: DNA
<213> ORGANISM: Erwinia caratovora subsp. atroseptica

<400> SEQUENCE: 125
atgacagcga cagaagcttt gctggcgcgc cgtcagcgag tgttgggcgg cggttatcgc      60

```
ctgttttatg aagagccgct gcatgtcgcg cgcggcgagg gcgtgtggct gttcgatcac    120
caagggaaac gttatctgga tgtctacaat aatgtggctt cggtcggaca ttgccacccc    180
gcggtggttg aagccgtggc gcgacagagc gcacaactca atacccacac gcgctatttg    240
caccacgcga ttgtcgattt tgcggaagat ttgctgagcg aatttcccgc cgaattgaac    300
aatgtaatgc tgacctgtac cggcagtgag gctaacgatc tggcgctgcg tatcgcccga    360
catgtcacgg gcgggacggg gatgttggtg acgcgctggg cgtatcacgg cgtgaccagc    420
gcgctggcgg aactgtctcc gtcgctgggg gatggcgttg tgcgcggtag ccatgtgaag    480
ctgatcgacg cgccagacac ttatcgtcag cccggtgcat ttcttaccag cattcgtgaa    540
gcgctggcgc agatgcaacg ggaaggtatt cgtcctgcgg cgctgctggt agataccatt    600
ttttccagcg atggcgtgtt ctgtgcgccg gaaggcgaaa tggcacaggc ggcggcgttg    660
atccgtcagg cgggcgggct gtttattgcg gatgaagtgc agccgggctt cgggcgcacc    720
ggggaatcac tgtggggctt tgcgcgccac aatgtcgtcc ctgatttggt gagtctaggg    780
aaaccgatgg gcaacggaca tcccatcgct ggattggtgg ggcgttccgc tctgttcgac    840
gcatttgggc gcgatgtgcg ctatttcaat acctttggcg gcaatccggt ttcctgtcag    900
gcggcgcacg cggtgctgcg ggtgattcgg gaagagcagt tgcagcagaa tgcccagcgg    960
gtcggtgatt atctgcggca agggttgcag caactggcgc agcatttccc gctgattggt   1020
gatattcggg cttacggcct gtttattggt gcggagctgg tcagcgatcg cgaaagtaaa   1080
acgccggcaa gtgaatccgc gttgcaggtg gtgaatgcga tgcgccaacg tggtgtgctc   1140
atcagcgcga cggggccagc ggcgaacata ctgaaaattc gcccgccgct ggtgtttctg   1200
gaagaacacg ccgatgtgtt cttaaccacg ctgagtgacg ttttagcgct catcggcact   1260
cgtgcacaga ga                                                        1272
```

```

<210> SEQ ID NO 126
<211> LENGTH: 424
<212> TYPE: PRT
<213> ORGANISM: Erwinia caratovora subsp. atroseptica

<400> SEQUENCE: 126

Met Thr Ala Thr Glu Ala Leu Leu Ala Arg Arg Gln Arg Val Leu Gly
1               5                   10                  15

Gly Gly Tyr Arg Leu Phe Tyr Glu Glu Pro Leu His Val Ala Arg Gly
            20                  25                  30

Glu Gly Val Trp Leu Phe Asp His Gln Gly Lys Arg Tyr Leu Asp Val
        35                  40                  45

Tyr Asn Asn Val Ala Ser Val Gly His Cys His Pro Ala Val Val Glu
    50                  55                  60

Ala Val Ala Arg Gln Ser Ala Gln Leu Asn Thr His Thr Arg Tyr Leu
65                  70                  75                  80

His His Ala Ile Val Asp Phe Ala Glu Asp Leu Leu Ser Glu Phe Pro
                85                  90                  95

Ala Glu Leu Asn Asn Val Met Leu Thr Cys Thr Gly Ser Glu Ala Asn
            100                 105                 110

Asp Leu Ala Leu Arg Ile Ala Arg His Val Thr Gly Gly Thr Gly Met
        115                 120                 125

Leu Val Thr Arg Trp Ala Tyr His Gly Val Thr Ser Ala Leu Ala Glu
    130                 135                 140

Leu Ser Pro Ser Leu Gly Asp Gly Val Val Arg Gly Ser His Val Lys
```

```
            145                 150                 155                 160

Leu Ile Asp Ala Pro Asp Thr Tyr Arg Gln Pro Gly Ala Phe Leu Thr
                165                 170                 175

Ser Ile Arg Glu Ala Leu Ala Gln Met Gln Arg Glu Gly Ile Arg Pro
            180                 185                 190

Ala Ala Leu Leu Val Asp Thr Ile Phe Ser Ser Asp Gly Val Phe Cys
        195                 200                 205

Ala Pro Glu Gly Glu Met Ala Gln Ala Ala Leu Ile Arg Gln Ala
    210                 215                 220

Gly Gly Leu Phe Ile Ala Asp Glu Val Gln Pro Gly Phe Gly Arg Thr
225                 230                 235                 240

Gly Glu Ser Leu Trp Gly Phe Ala Arg His Asn Val Val Pro Asp Leu
                245                 250                 255

Val Ser Leu Gly Lys Pro Met Gly Asn Gly His Pro Ile Ala Gly Leu
                260                 265                 270

Val Gly Arg Ser Ala Leu Phe Asp Ala Phe Gly Arg Asp Val Arg Tyr
            275                 280                 285

Phe Asn Thr Phe Gly Gly Asn Pro Val Ser Cys Gln Ala Ala His Ala
        290                 295                 300

Val Leu Arg Val Ile Arg Glu Glu Gln Leu Gln Asn Ala Gln Arg
305                 310                 315                 320

Val Gly Asp Tyr Leu Arg Gln Gly Leu Gln Gln Leu Ala Gln His Phe
                325                 330                 335

Pro Leu Ile Gly Asp Ile Arg Ala Tyr Gly Leu Phe Ile Gly Ala Glu
            340                 345                 350

Leu Val Ser Asp Arg Glu Ser Lys Thr Pro Ala Ser Glu Ser Ala Leu
        355                 360                 365

Gln Val Val Asn Ala Met Arg Gln Arg Gly Val Leu Ile Ser Ala Thr
    370                 375                 380

Gly Pro Ala Ala Asn Ile Leu Lys Ile Arg Pro Pro Leu Val Phe Leu
385                 390                 395                 400

Glu Glu His Ala Asp Val Phe Leu Thr Thr Leu Ser Asp Val Leu Ala
                405                 410                 415

Leu Ile Gly Thr Arg Ala Gln Arg
            420

<210> SEQ ID NO 127
<211> LENGTH: 35
<212> TYPE: DNA
<213> ORGANISM: Artificial Seqquence
<220> FEATURE:
<223> OTHER INFORMATION: Primer

<400> SEQUENCE: 127
ctccggaatt catgtctgac ggacgactca ccgca                          35

<210> SEQ ID NO 128
<211> LENGTH: 46
<212> TYPE: DNA
<213> ORGANISM: Artificial Seqquence
<220> FEATURE:
<223> OTHER INFORMATION: Primer

<400> SEQUENCE: 128
ttccaatgca ttggctgcag ttatctctgt gcacgagtgc cgatga              46

<210> SEQ ID NO 129
```

```
<211> LENGTH: 40
<212> TYPE: DNA
<213> ORGANISM: Artificial Seqquence
<220> FEATURE:
<223> OTHER INFORMATION: Primer

<400> SEQUENCE: 129
aacagccaag cttggctgca gtcatcgcgc attctccggg              40

<210> SEQ ID NO 130
<211> LENGTH: 40
<212> TYPE: DNA
<213> ORGANISM: Artificial Seqquence
<220> FEATURE:
<223> OTHER INFORMATION: Primer

<400> SEQUENCE: 130
tctccggaat tcatgacgtc tgaaatgaca gcgacagaag              40

<210> SEQ ID NO 131
<211> LENGTH: 33
<212> TYPE: DNA
<213> ORGANISM: Artificial Sequence
<220> FEATURE:
<223> OTHER INFORMATION: Primer

<400> SEQUENCE: 131
gctaacagga ggaagaattc atgggggtt ctc                     33

<210> SEQ ID NO 132
<211> LENGTH: 33
<212> TYPE: DNA
<213> ORGANISM: Artificial Sequence
<220> FEATURE:
<223> OTHER INFORMATION: Primer

<400> SEQUENCE: 132
gagaaccccc catgaattct tcctcctgtt agc                    33

<210> SEQ ID NO 133
<211> LENGTH: 723
<212> TYPE: DNA
<213> ORGANISM: Klebsiella terrigena

<400> SEQUENCE: 133
atgcaaaaag tcgcacttgt caccggcgcc ggtcagggca tcggtaaagc tatcgccctg     60
cgtctggtga aggatggatt tgccgtggca atcgccgatt acaacgacgc tacgccaca     120
gcggtagccg ctgaaatcaa ccaggccggc ggccgcgcgg tggccattaa ggtcgacgtc    180
tcgcgccggg accaggtttt cgccgccgtt gagcaggcgc gtaaagccct gggcggattc    240
aacgttatcg tcaacaacgc cggcatcgcg ccgtcaacgc cgatcgagtc catcaccgag    300
gagatcgtcg accgggtcta taacatcaac gttaagggcg tcatctgggg gatgcaggcg    360
gcggtggagg ccttcaaaaa agaggggcac ggcgggaaga tcgtcaacgc ctgctcccag    420
gccggccacg tcggcaaccc ggagctggcg gtctacagtt cgagtaaatt cgccgtgcgc    480
ggcctgacgc aaaccgccgc ccgcgatctg gcgccgctgg gcatcaccgt taacggcttc    540
tgcccaggga tcgttaagac gccaatgtgg gcggagattg accgtcagtg tcggaagcgg    600
cgggcaaacc gctgggctac ggcacggctg aatttgccaa acgcatcacc cttggccgcc    660
tgtcggagcc tgaagacgtc gccgcctgcg tgtcgttcct cgccagcccg gattccgact    720
ata                                                                 723
```

<210> SEQ ID NO 134
<211> LENGTH: 241
<212> TYPE: PRT
<213> ORGANISM: Klebsiella terrigena

<400> SEQUENCE: 134

```
Met Gln Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Thr Ala Val Ala Ala Glu Ile Asn Gln
        35                  40                  45

Ala Gly Gly Arg Ala Val Ala Ile Lys Val Asp Val Ser Arg Arg Asp
    50                  55                  60

Gln Val Phe Ala Ala Val Glu Gln Ala Arg Lys Ala Leu Gly Gly Phe
65                  70                  75                  80

Asn Val Ile Val Asn Asn Ala Gly Ile Ala Pro Ser Thr Pro Ile Glu
                85                  90                  95

Ser Ile Thr Glu Glu Ile Val Asp Arg Val Tyr Asn Ile Asn Val Lys
            100                 105                 110

Gly Val Ile Trp Gly Met Gln Ala Ala Val Glu Ala Phe Lys Lys Glu
        115                 120                 125

Gly His Gly Gly Lys Ile Val Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Phe Cys Pro Gly Ile Val Lys Thr Pro Met Trp Ala Glu
            180                 185                 190

Ile Asp Arg Gln Cys Arg Lys Arg Ala Asn Arg Trp Ala Thr Ala
        195                 200                 205

Arg Leu Asn Leu Pro Asn Ala Ser Pro Leu Ala Ala Cys Arg Ser Leu
    210                 215                 220

Lys Thr Ser Pro Pro Ala Cys Arg Ser Ser Pro Ala Arg Ile Pro Thr
225                 230                 235                 240

Ile
```

<210> SEQ ID NO 135
<211> LENGTH: 554
<212> TYPE: PRT
<213> ORGANISM: Clostridium pasteurianum

<400> SEQUENCE: 135

```
Met Lys Ser Lys Arg Phe Gln Val Leu Ser Glu Arg Pro Val Asn Lys
1               5                   10                  15

Asp Gly Phe Ile Gly Glu Trp Pro Glu Gly Leu Ile Ala Met Ser
            20                  25                  30

Ser Pro Asn Asp Pro Lys Pro Ser Ile Lys Ile Lys Glu Gly Lys Val
        35                  40                  45

Ile Glu Leu Asp Gly Lys Asn Arg Glu Asp Phe Asp Met Ile Asp Arg
    50                  55                  60

Phe Ile Ala Asn Tyr Gly Ile Asn Leu Asn Arg Ala Glu Asp Val Ile
65                  70                  75                  80
```

```
Lys Met Asp Ser Val Lys Leu Ala Lys Met Leu Val Asp Ile Asn Val
                85                  90                  95

Asp Arg Lys Thr Ile Val Glu Leu Thr Thr Ala Met Thr Pro Ala Lys
            100                 105                 110

Ile Val Glu Val Val Gly Asn Met Asn Val Val Glu Met Met Met Ala
            115                 120                 125

Leu Gln Lys Met Arg Ala Arg Lys Thr Pro Ser Asn Gln Cys His Val
130                 135                 140

Thr Asn Leu Lys Asp Asn Pro Val Gln Ile Ala Ala Asp Ala Ala Glu
145                 150                 155                 160

Ala Ala Ile Arg Gly Phe Asp Glu Gln Glu Thr Thr Val Gly Ile Val
                165                 170                 175

Arg Tyr Ala Pro Phe Asn Ala Leu Ala Leu Leu Val Gly Ala Gln Val
            180                 185                 190

Gly Arg Gly Gly Val Leu Thr Gln Cys Ala Ile Glu Ala Thr Glu
            195                 200                 205

Leu Glu Leu Gly Met Arg Gly Leu Thr Ser Tyr Ala Glu Thr Val Ser
210                 215                 220

Val Tyr Gly Thr Glu Asn Val Phe Thr Asp Gly Asp Thr Pro Trp
225                 230                 235                 240

Ser Lys Ala Phe Leu Ala Ser Ala Tyr Ala Ser Arg Gly Leu Lys Met
                245                 250                 255

Arg Phe Thr Ser Gly Ser Gly Ser Glu Ala Leu Met Gly Tyr Ala Glu
            260                 265                 270

Gly Lys Ser Met Leu Tyr Leu Glu Ala Arg Cys Ile Tyr Ile Thr Lys
            275                 280                 285

Ala Ala Gly Val Gln Gly Leu Gln Asn Gly Ser Val Ser Cys Ile Gly
290                 295                 300

Met Thr Gly Ala Leu Pro Ser Gly Ile Arg Ala Val Leu Gly Glu Asn
305                 310                 315                 320

Leu Ile Thr Thr Met Leu Asp Ile Glu Val Ala Ser Ala Asn Asp Gln
                325                 330                 335

Thr Phe Ser His Ser Asp Ile Arg Arg Thr Ala Arg Met Leu Met Gln
            340                 345                 350

Met Leu Pro Gly Thr Asp Phe Ile Phe Ser Gly Tyr Ser Ser Val Pro
            355                 360                 365

Asn Tyr Asp Asn Met Phe Ala Gly Ser Asn Phe Asp Ala Glu Asp Phe
            370                 375                 380

Asp Asp Tyr Asn Val Ile Gln Arg Asp Leu Met Val Asp Gly Gly Leu
385                 390                 395                 400

Arg Pro Val Ser Glu Glu Val Ile Thr Ile Arg Asn Lys Ala Ala
                405                 410                 415

Arg Ala Ile Gln Ala Val Phe Glu Gly Leu Lys Leu Pro Ala Ile Thr
            420                 425                 430

Asp Glu Glu Val Glu Ala Val Thr Tyr Ser His Gly Ser Lys Asp Val
            435                 440                 445

Pro Glu Arg Asn Val Val Glu Asp Leu Lys Ala Ala Glu Glu Met Ile
450                 455                 460

Asn Arg Gly Ile Thr Gly Ile Asp Val Val Lys Ala Leu Ser Lys His
465                 470                 475                 480

Gly Phe Asp Asp Ile Ala Glu Asn Ile Leu Asn Met Leu Lys Gln Arg
                485                 490                 495

Ile Ser Gly Asp Tyr Leu Gln Thr Ser Ala Ile Ile Asp Lys Asn Phe
```

```
                500                 505                 510
Asn Val Val Ser Ala Val Asn Asp Cys Asn Asp Tyr Met Gly Pro Gly
            515                 520                 525

Thr Gly Tyr Arg Leu Ser Lys Glu Arg Trp Asp Glu Ile Lys Asn Ile
        530                 535                 540

Pro Asn Ala Met Lys Pro Glu Asp Ile Lys
545                 550

<210> SEQ ID NO 136
<211> LENGTH: 179
<212> TYPE: PRT
<213> ORGANISM: Clostridium pasteurianum

<400> SEQUENCE: 136

Met Glu Leu Lys Glu Lys Asp Ile Ala Leu Ser Gly Asn Gln Ser Asn
1               5                   10                  15

Glu Val Val Ile Gly Ile Ala Pro Ala Phe Gly Lys Tyr Gln His Gln
            20                  25                  30

Ser Ile Val Gly Val Pro His Asp Lys Ile Leu Arg Glu Leu Ile Ala
        35                  40                  45

Gly Ile Glu Glu Glu Gly Leu Lys Ser Arg Val Arg Ile Ile Arg
    50                  55                  60

Thr Ser Asp Val Ser Phe Ile Ala His Asp Ala Ala Val Leu Ser Gly
65                  70                  75                  80

Ser Gly Ile Gly Ile Gly Ile Gln Ser Lys Gly Thr Val Ile His
            85                  90                  95

Gln Lys Asp Leu Leu Pro Leu Asn Asn Leu Glu Leu Phe Pro Gln Ala
                100                 105                 110

Pro Leu Leu Asp Leu Asp Ile Phe Arg Leu Ile Gly Lys Asn Ala Ala
            115                 120                 125

Lys Tyr Ala Lys Gly Glu Ser Pro Asn Pro Val Pro Thr Arg Asn Asp
        130                 135                 140

Gln Met Val Arg Pro Lys Phe Gln Ala Lys Ala Ala Leu Leu His Ile
145                 150                 155                 160

Lys Glu Thr Lys His Val Val Gln Asn Ala Lys Pro Ile Glu Leu Glu
                165                 170                 175

Ile Ile Ser

<210> SEQ ID NO 137
<211> LENGTH: 146
<212> TYPE: PRT
<213> ORGANISM: Clostridium pasteurianum

<400> SEQUENCE: 137

Met Ser Asp Ile Thr Asn Asn Ile Lys Val Asp Tyr Glu Asn Asp Tyr
1               5                   10                  15

Pro Leu Ala Ala Lys Arg Ser Glu Trp Ile Lys Thr Pro Thr Gly Lys
            20                  25                  30

Asn Leu Lys Asp Ile Thr Leu Glu Ala Val Ile Asp Glu Asn Val Lys
        35                  40                  45

Ala Glu Asp Val Arg Ile Ser Arg Asp Thr Leu Glu Leu Gln Ala Gln
    50                  55                  60

Val Ala Glu Gly Ser Gly Arg Cys Ala Ile Ala Arg Asn Phe Arg Arg
65                  70                  75                  80

Ala Ala Glu Leu Ile Ser Ile Ser Asp Glu Arg Ile Leu Glu Ile Tyr
                85                  90                  95
```

```
Asn Ala Leu Arg Pro Tyr Arg Ser Thr Lys Asn Glu Leu Leu Ala Ile
            100                 105                 110

Ala Asp Glu Leu Glu Glu Lys Tyr Asp Ala Lys Val Asn Ala Asp Phe
        115                 120                 125

Ile Arg Glu Ala Ala Glu Val Tyr Ser Lys Arg Asn Lys Val Arg Ile
130                 135                 140

Glu Asp
145

<210> SEQ ID NO 138
<211> LENGTH: 555
<212> TYPE: PRT
<213> ORGANISM: Escherichia blattae

<400> SEQUENCE: 138

Met Arg Arg Ser Lys Arg Phe Glu Val Leu Glu Lys Arg Pro Val Asn
1               5                   10                  15

Gln Asp Gly Leu Ile Gly Glu Trp Pro Glu Gly Leu Ile Ala Met
            20                  25                  30

Gly Ser Pro Trp Asp Pro Pro Ser Ser Val Lys Val Glu Gln Gly Arg
        35                  40                  45

Ile Val Glu Leu Asp Gly Lys Ala Arg Ala Asp Phe Asp Met Ile Asp
    50                  55                  60

Arg Phe Ile Ala Asp Tyr Ala Ile Asn Ile Glu Thr Glu His Ala
65                  70                  75                  80

Met Gly Leu Asp Ala Leu Thr Ile Ala Arg Met Leu Val Asp Ile Asn
                85                  90                  95

Val Ser Arg Ala Glu Ile Ile Lys Val Thr Thr Ala Ile Thr Pro Ala
            100                 105                 110

Lys Ala Val Glu Val Met Ser His Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Gln Glu Thr Thr Val Gly Ile
                165                 170                 175

Ala Arg Tyr Ala Pro Phe Asn Ala Leu Ala Leu Ile Gly Ser Gln
            180                 185                 190

Ser Gly Arg Pro Gly Val Leu Thr Gln Cys Ser Val Gly Glu Ala Thr
        195                 200                 205

Glu Leu Glu Leu Gly Met Arg Gly Phe Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ala
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
```

```
305                 310                 315                 320
Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Ser Glu Glu Thr Ile Ala Ile Arg Asn Lys Ala
                405                 410                 415

Ala Arg Ala Val Gln Ala Val Phe Arg Glu Leu Gly Leu Pro Pro Val
            420                 425                 430

Thr Asp Glu Glu Val Thr Ala Ala Thr Tyr Ala His Gly Ser Lys Asp
        435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Arg Ala Leu Ser Val
465                 470                 475                 480

Asn Gly Phe Asp Asp Val Ala Asn Asn Ile Leu Asn Met Leu Arg Gln
                485                 490                 495

Arg Val Thr Gly Asp Tyr Leu Gln Thr Ser Ala Ile Leu Asp Arg Glu
            500                 505                 510

Phe Glu Val Val Ser Ala Val Asn Asp Ile Asn Asp Tyr Gln Gly Pro
        515                 520                 525

Gly Thr Gly Tyr Arg Ile Ser Pro Gln Arg Trp Glu Glu Ile Lys Asn
    530                 535                 540

Ile Ala Thr Val Ile Gln Pro Asp Ser Ile Glu
545                 550                 555

<210> SEQ ID NO 139
<211> LENGTH: 196
<212> TYPE: PRT
<213> ORGANISM: Escherichia blattae

<400> SEQUENCE: 139

Met Glu Thr Thr Gln Lys Lys Ala Pro Val Phe Thr Leu Asn Leu Val
1               5                   10                  15

Glu Ser Gly Val Ala Lys Pro Gly Glu Arg Ser Asp Glu Val Val Ile
                20                  25                  30

Gly Val Gly Pro Ala Phe Asp Lys Tyr Gln His Lys Thr Leu Ile Asp
        35                  40                  45

Met Pro His Lys Ala Ile Ile Lys Glu Leu Val Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125
```

```
Leu Glu Thr Tyr Arg Gln Ile Gly Lys Asn Ala Ala Arg Tyr Ala Arg
            130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Ala Asp Ala Lys Pro Val Thr Leu Asn Ile Glu Ile Thr
            180                 185                 190

Arg Glu Glu Ala
        195

<210> SEQ ID NO 140
<211> LENGTH: 141
<212> TYPE: PRT
<213> ORGANISM: Escherichia blattae

<400> SEQUENCE: 140

Met Thr Thr Thr Lys Met Ser Ala Ala Asp Tyr Pro Leu Ala Ser Arg
1               5                   10                  15

Cys Pro Glu Arg Ile Gln Thr Pro Thr Gly Lys Pro Leu Thr Asp Ile
            20                  25                  30

Thr Leu Glu Asn Val Leu Ala Gly Lys Val Gly Pro Gln Asp Val Arg
        35                  40                  45

Ile Ser Arg Glu Thr Leu Glu Tyr Gln Ala Gln Ile Ala Glu Gln Met
    50                  55                  60

His Arg His Ala Ile Ala Arg Asn Leu Arg Arg Ala Gly Glu Leu Ile
65                  70                  75                  80

Ala Ile Pro Asp Ala Arg Ile Leu Glu Ile Tyr Asn Ala Leu Arg Pro
                85                  90                  95

Tyr Arg Ser Ser Val Glu Glu Leu Leu Ala Ile Ala Asp Glu Leu Glu
            100                 105                 110

Thr Arg Tyr Gln Ala Thr Val Asn Ala Ala Phe Ile Arg Glu Ala Ala
        115                 120                 125

Glu Val Tyr Arg Gln Arg Asp Lys Leu Arg Lys Glu Ala
    130                 135                 140

<210> SEQ ID NO 141
<211> LENGTH: 555
<212> TYPE: PRT
<213> ORGANISM: Citrobacter freundii

<400> SEQUENCE: 141

Met Arg Arg Ser Lys Arg Phe Glu Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Glu Ser Pro Tyr Asp Pro Ala Ser Ser Val Lys Val Glu Asn Gly Arg
        35                  40                  45

Ile Val Glu Leu Asp Gly Lys Ser Arg Ala Glu Phe Asp Met Ile Asp
    50                  55                  60

Arg Phe Ile Ala Asp Tyr Ala Ile Asn Val Pro Glu Ala Glu Arg Ala
65                  70                  75                  80

Met Gln Leu Asp Ala Leu Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110
```

```
Lys Arg Leu Glu Val Met Ala Gln Met Asn Val Val Glu Met Met Met
        115                 120                 125
Ala Leu Gln Lys Met Arg Ala Arg Arg Thr Pro Ser Asn Gln Cys His
130                 135                 140
Val Thr Asn Leu Lys Asp Asn Pro Val Gln Ile Ala Ala Asp Ala Ala
145                 150                 155                 160
Glu Ala Gly Ile Arg Gly Phe Ser Glu Gln Glu Thr Thr Val Gly Ile
                165                 170                 175
Ala Arg Tyr Ala Pro Phe Asn Ala Leu Ala Leu Leu Val Gly Ser Gln
            180                 185                 190
Cys Gly Ala Pro Gly Val Leu Thr Gln Cys Ser Val Glu Glu Ala Thr
        195                 200                 205
Glu Leu Glu Leu Gly Met Arg Gly Leu Thr Ser Tyr Ala Glu Thr Val
210                 215                 220
Ser Val Tyr Gly Thr Glu Ser Val Phe Thr Asp Gly Asp Asp Thr Pro
225                 230                 235                 240
Trp Ser Lys Ala Phe Leu Ala Ser Ala Tyr Ala Ser Arg Gly Leu Lys
                245                 250                 255
Met Arg Tyr Thr Ser Gly Thr Gly Ser Glu Ala Leu Met Gly Tyr Ser
            260                 265                 270
Glu Ser Lys Ser Met Leu Tyr Leu Glu Ser Arg Cys Ile Phe Ile Thr
        275                 280                 285
Lys Gly Ala Gly Val Gln Gly Leu Gln Asn Gly Ala Val Ser Cys Ile
        290                 295                 300
Gly Met Thr Gly Ala Val Pro Ser Gly Ile Arg Ala Val Leu Ala Glu
305                 310                 315                 320
Asn Leu Ile Ala Ser Met Leu Asp Leu Glu Val Ala Ser Ala Asn Asp
                325                 330                 335
Gln Thr Phe Ser His Ser Asp Ile Arg Arg Thr Ala Arg Thr Leu Met
            340                 345                 350
Gln Met Leu Pro Gly Thr Asp Phe Ile Phe Ser Gly Tyr Ser Ala Val
        355                 360                 365
Pro Asn Tyr Asp Asn Met Phe Ala Gly Ser Asn Phe Asp Ala Glu Asp
370                 375                 380
Phe Asp Asp Tyr Asn Ile Leu Gln Arg Asp Leu Met Val Asp Gly Gly
385                 390                 395                 400
Leu Arg Pro Val Thr Glu Glu Thr Ile Ala Ile Arg Asn Lys Ala
                405                 410                 415
Ala Arg Ala Ile Gln Ala Val Phe Arg Glu Leu Gly Leu Pro Leu Ile
            420                 425                 430
Ser Asp Glu Glu Val Asp Ala Ala Thr Tyr Ala His Gly Ser Lys Asp
        435                 440                 445
Met Pro Ala Arg Asn Val Val Glu Asp Leu Ala Ala Val Glu Glu Met
450                 455                 460
Met Lys Arg Asn Ile Thr Gly Leu Asp Ile Val Gly Ala Leu Ser Ser
465                 470                 475                 480
Ser Gly Phe Glu Asp Ile Ala Ser Asn Ile Leu Asn Met Leu Arg Gln
                485                 490                 495
Arg Val Thr Gly Asp Tyr Leu Gln Thr Ser Ala Ile Leu Asp Arg Gln
            500                 505                 510
Phe Asp Val Val Ser Ala Val Asn Asp Ile Asn Asp Tyr Gln Gly Pro
        515                 520                 525
Gly Thr Gly Tyr Arg Ile Ser Ala Glu Arg Trp Ala Glu Ile Lys Asn
```

```
              530                 535                 540
Ile Ala Gly Val Val Gln Pro Gly Ser Ile Glu
545                 550                 555

<210> SEQ ID NO 142
<211> LENGTH: 194
<212> TYPE: PRT
<213> ORGANISM: Citrobacter freundii

<400> SEQUENCE: 142

Met Glu Cys Thr Thr Glu Arg Lys Pro Val Phe Thr Leu Gln Val Ser
1               5                   10                  15

Glu Gly Glu Ala Ala Lys Ala Asp Glu Arg Val Asp Glu Val Val Ile
                20                  25                  30

Gly Val Gly Pro Ala Phe Asp Lys Tyr Gln His Lys Thr Leu Ile Asp
            35                  40                  45

Met Pro His Lys Ala Ile Leu Lys Glu Leu Val Ala Gly Ile Glu Glu
        50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Arg Ala Pro Val Thr Leu His Ile Ala Leu Val
            180                 185                 190

Arg Glu

<210> SEQ ID NO 143
<211> LENGTH: 142
<212> TYPE: PRT
<213> ORGANISM: Citrobacter freundii

<400> SEQUENCE: 143

Met Asn Asp Asn Ile Met Thr Ala Gln Asp Tyr Pro Leu Ala Thr Arg
1               5                   10                  15

Cys Pro Glu Lys Ile Gln Thr Pro Thr Gly Lys Pro Leu Thr Glu Ile
                20                  25                  30

Thr Leu Glu Asn Val Leu Ala Gly Arg Val Gly Pro Gln Asp Val Arg
            35                  40                  45

Ile Ser Gln Gln Thr Leu Glu Tyr Gln Ala Gln Ile Ala Glu Gln Met
        50                  55                  60

Gln Arg His Ala Val Ala Arg Asn Phe Arg Arg Ala Ala Glu Leu Ile
65                  70                  75                  80

Ala Ile Pro Asp Ala Arg Ile Leu Glu Ile Tyr Asn Ala Leu Arg Pro
                85                  90                  95

Phe Arg Ser Ser Phe Ala Glu Leu Gln Ala Ile Ala Asp Glu Leu Glu
            100                 105                 110
```

His Thr Trp His Ala Thr Val Asn Ala Gly Phe Val Arg Glu Ser Ala
        115                 120                 125

Glu Val Tyr Leu Gln Arg Asn Lys Leu Arg Lys Gly Ser Gln
        130                 135                 140

<210> SEQ ID NO 144
<211> LENGTH: 1359
<212> TYPE: DNA
<213> ORGANISM: Artificial sequence
<220> FEATURE:
<223> OTHER INFORMATION: Codon optimized Vibrio fluvialis amine:pyruvate transaminase

<400> SEQUENCE: 144

```
atgaacaaac cacagtcttg ggaagctcgt gcagaaacct attctctgta cggcttcact      60
gacatgccgt ccctgcacca gcgtggtact gttgttgtca cgcacggcga aggtccgtac     120
attgttgacg tcaatggtcg ccgttatctg acgctaatt ctggcctgtg aatatggtt      180
gcaggttttg accataaggg tctgatcgac gcagctaagg ctcagtacga gcgttttccg     240
ggctaccatg cgttcttcgg tcgtatgagc gatcagacgg tgatgctgtc gaaaaactg     300
gtagaagtct ctccgttcga cagcggccgt gtgttctata cgaacagcgg tagcgaagca     360
aacgacacta tggttaagat gctgtggttc ctgcatgcgg cggaaggtaa gccacaaaag     420
cgcaaaattc tgacccgttg gaacgcgtat cacggcgtta ctgcagttag cgcctccatg     480
accggtaaac cgtacaacag cgttttcggt ctgccgctgc aggtttcgt tcacctgact     540
tgccctcact actggcgtta cggtgaagaa ggcgagacgg aagaacaatt cgttgcacgc     600
ctggcacgcg aactggaaga gactatccag cgtgagggtg ctgacactat cgctggcttc     660
tttgctgagc cggttatggg tgcaggtggt gttattccgc tgctaaagg ttatttcag      720
gctattctgc aatcctgcg taaatatgac atcccggtta tctctgacga gttatctgt      780
ggttttggtc gcactggcaa cacctggggt gcgtaactt atgatttac tccggatgct      840
atcatctcta gcaaaaacct gaccgccggt ttcttcccga tgggcgcagt gatcctgggt     900
ccagaactga gcagcgcct ggaaaccgca attgaagcaa tcgaggaatt ccgcacggc      960
tttaccgcgt ccggccatcc ggtaggctgt gcaatcgcgc tgaaagcgat cgatgttgtt    1020
atgaacgaag gcctggcgga aaacgttcgc gtctggcac cgcgcttcga agaacgtctg    1080
aaacatatcg cggaacgtcc gaacattggt gaatatcgtg gtatcggtttt tatgtgggct   1140
ctggaggcag tcaaagacaa agcgtctaaa actccgttcg atggcaatct gagcgtgagc    1200
gaacgtatcg ccaacacttg caccgacctg gtctgatct gccgtccact gggccaaagc    1260
gtagtgctgt gtccgccgtt tatcctgacc gaagcgcaaa tggacgaaat gttcgacaaa    1320
ctggagaaag cactggataa agtgttcgca gaggtggca                           1359
```

<210> SEQ ID NO 145
<211> LENGTH: 1668
<212> TYPE: DNA
<213> ORGANISM: Klebsiella pneumoniae

<400> SEQUENCE: 145

```
atgaaaagat caaaacgatt tgcagtactg gcccagcgcc ccgtcaatca ggacgggctg      60
attggcgagt ggcctgaaga ggggctgatc gccatggaca gcccctttga cccggtctct     120
tcagtaaaag tggacaacgg tctgatcgtc gaactggacg gcaaacgccg ggaccagttt     180
gacatgatcg accgatttat cgccgattac gcgatcaacg ttgagcgcac agagcaggca     240
```

```
atgcgcctgg aggcggtgga aatagcccgt atgctggtgg atattcacgt cagccgggag      300
gagatcattg ccatcactac cgccatcacg ccggccaaag cggtcgaggt gatggcgcag      360
atgaacgtgg tggagatgat gatggcgctg cagaagatgc gtgcccgccg gaccccctcc      420
aaccagtgcc acgtcaccaa tctcaaagat aatccggtgc agattgccgc tgacgccgcc      480
gaggccggga tccgcggctt ctcagaacag agaccacgg  tcggtatcgc gcgctacgcg      540
ccgtttaacg ccctggcgct gttggtcggt tcgcagtgcg gccgcccgg  cgtgttgacg      600
cagtgctcgg tggaagaggc caccgagctg agctgggca  tgcgtggctt aaccagctac      660
gccgagacgt gtcggtcta  cggcaccgaa gcggtattta ccgacggcga tgatacgccg      720
tggtcaaagg cgttcctcgc ctcggcctac gcctcccgcg ggttgaaaat cgctacacc       780
tccggcaccg atccgaagc  gctgatgggc tattcggaga gcaagtcgat gctctacctc      840
gaatcgcgct gcatcttcat tactaaaggc gccggggttc agggactgca aaacggcgcg      900
gtgagctgta tcggcatgac cggcgctgtg ccgtcgggca ttcgggcggt gctggcggaa      960
aacctgatcg cctctatgct cgacctcgaa gtggcgtccg ccaacgacca gactttctcc     1020
cactcggata ttcgccgcac cgcgcgcacc ctgatgcaga tgctgccggg caccgacttt     1080
attttctccg gctacagcgc ggtgccgaac tacgacaaca tgttcgccgg ctcgaacttc     1140
gatgcggaag attttgatga ttacaacatc ctgcagcgtg acctgatggt tgacggcggc     1200
ctgcgtccgg tgaccgaggc ggaaaccatt gccattcgcc agaaagcggc gcgggcgatc     1260
caggcggttt tccgcgagct ggggctgccg ccaatcgccg acgaggaggt ggaggccgcc     1320
acctacgcgc acggcagcaa cgagatgccg ccgcgtaacg tggtggagga tctgagtgcg     1380
gtggaagaga tgatgaagcg caacatcacc ggcctcgata ttgtcggcgc gctgagccgc     1440
agcggctttg aggatatcgc cagcaatatt ctcaatatgc tgcgccagcg ggtcaccggc     1500
gattacctgc agacctcggc cattctcgat cggcagttcg aggtggtgag tgcggtcaac     1560
gacatcaatg actatcaggg gccgggcacc ggctatcgca tctctgccga acgctgggcg     1620
gagatcaaaa atattccggg cgtggttcag cccgacacca ttgaataa                  1668
```

<210> SEQ ID NO 146  
<211> LENGTH: 555  
<212> TYPE: PRT  
<213> ORGANISM: Klebsiella pneumoniae

<400> SEQUENCE: 146

Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Val Glu Met Met Met

-continued

```
            115                 120                 125
Ala Leu Gln Lys Met Arg Ala Arg Arg Thr Pro Ser Asn Gln Cys His
130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Thr Thr Val Gly Ile
                    165                 170                 175

Ala Arg Tyr Ala Pro Phe Asn Ala Leu Ala Leu Val Gly Ser Gln
                180                 185                 190

Cys Gly Arg Pro Gly Val Leu Thr Gln Cys Ser Val Glu Glu Ala Thr
                195                 200                 205

Glu Leu Glu Leu Gly Met Arg Gly Leu Thr Ser Tyr Ala Glu Thr Val
210                 215                 220

Ser Val Tyr Gly Thr Glu Ala Val Phe Thr Asp Gly Asp Thr Pro
225                 230                 235                 240

Trp Ser Lys Ala Phe Leu Ala Ser Ala Tyr Ala Ser Arg Gly Leu Lys
                    245                 250                 255

Met Arg Tyr Thr Ser Gly Thr Gly Ser Glu Ala Leu Met Gly Tyr Ser
                260                 265                 270

Glu Ser Lys Ser Met Leu Tyr Leu Glu Ser Arg Cys Ile Phe Ile Thr
            275                 280                 285

Lys Gly Ala Gly Val Gln Gly Leu Gln Asn Gly Ala Val Ser Cys Ile
290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                    325                 330                 335

Gln Thr Phe Ser His Ser Asp Ile Arg Arg Thr Ala Arg Thr Leu Met
                340                 345                 350

Gln Met Leu Pro Gly Thr Asp Phe Ile Phe Ser Gly Tyr Ser Ala Val
            355                 360                 365

Pro Asn Tyr Asp Asn Met Phe Ala Gly Ser Asn Phe Asp Ala Glu Asp
370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                    405                 410                 415

Ala Arg Ala Ile Gln Ala Val Phe Arg Glu Leu Gly Leu Pro Pro Ile
                420                 425                 430

Ala Asp Glu Glu Val Glu Ala Ala Thr Tyr Ala His Gly Ser Asn Glu
            435                 440                 445

Met Pro Pro Arg Asn Val Val Glu Asp Leu Ser Ala Val Glu Glu Met
        450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                    485                 490                 495

Arg Val Thr Gly Asp Tyr Leu Gln Thr Ser Ala Ile Leu Asp Arg Gln
                500                 505                 510

Phe Glu Val Val Ser Ala Val Asn Asp Ile Asn Asp Tyr Gln Gly Pro
            515                 520                 525

Gly Thr Gly Tyr Arg Ile Ser Ala Glu Arg Trp Ala Glu Ile Lys Asn
        530                 535                 540
```

Ile Pro Gly Val Val Gln Pro Asp Thr Ile Glu
545                 550                 555

<210> SEQ ID NO 147
<211> LENGTH: 585
<212> TYPE: DNA
<213> ORGANISM: Klebsiella pneumoniae

<400> SEQUENCE: 147
gtgcaacaga caacccaaat tcagccctct tttaccctga aaacccgcga gggcggggta      60
gcttctgccg atgaacgcgc cgatgaagtg gtgatcggcg tcggccctgc cttcgataaa     120
caccagcatc acactctgat cgatatgccc catggcgcga tcctcaaaga gctgattgcc     180
ggggtggaag aagaggggct tcacgcccgg gtggtgcgca ttctgcgcac gtccgacgtc     240
tcctttatgg cctgggatgc ggccaacctg agcggctcgg ggatcggcat cggtatccag     300
tcgaagggga ccacggtcat ccatcagcgc gatctgctgc cgctcagcaa cctggagctg     360
ttctcccagg cgccgctgct gacgctggag acctaccggc agattggcaa aaacgctgcg     420
cgctatgcgc gcaaagagtc accttcgccg gtgccggtgg tgaacgatca gatggtgcgg     480
ccgaaattta tggccaaagc cgcgctattt catatcaaag agaccaaaca tgtggtgcag     540
gacgccgagc ccgtcaccct gcacatcgac ttagtaaggg agtga                    585

<210> SEQ ID NO 148
<211> LENGTH: 194
<212> TYPE: PRT
<213> ORGANISM: Klebsiella pneumoniae

<400> SEQUENCE: 148

Met Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
            180                 185                 190

Arg Glu

-continued

<210> SEQ ID NO 149
<211> LENGTH: 426
<212> TYPE: DNA
<213> ORGANISM: Klebsiella pneumoniae

<400> SEQUENCE: 149

| | |
|---|---|
| atgagcgaga aaaccatgcg cgtgcaggat tatccgttag ccacccgctg cccggagcat | 60 |
| atcctgacgc ctaccggcaa accattgacc gatattaccc tcgagaaggt gctctctggc | 120 |
| gaggtgggcc cgcaggatgt gcggatctcc cgccagaccc ttgagtacca ggcgcagatt | 180 |
| gccgagcaga tgcagcgcca tgcggtggcg cgcaatttcc gccgcgcggc ggagcttatc | 240 |
| gccattcctg acgagcgcat tctggctatc tataacgcgc tgcgcccgtt ccgctcctcg | 300 |
| caggcggagc tgctggcgat cgccgacgag ctggagcaca cctggcatgc gacagtgaat | 360 |
| gccgcctttg tccgggagtc ggcggaagtg tatcagcagc ggcataagct gcgtaaagga | 420 |
| agctaa | 426 |

<210> SEQ ID NO 150
<211> LENGTH: 141
<212> TYPE: PRT
<213> ORGANISM: Klebsiella pneumoniae

<400> SEQUENCE: 150

Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
                20                  25                  30

Thr Leu Glu Lys Val Leu Ser Gly Glu Val Gly Pro Gln Asp Val Arg
            35                  40                  45

Ile Ser Arg Gln Thr Leu Glu Tyr Gln Ala Gln Ile Ala Glu Gln Met
        50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
                100                 105                 110

His Thr Trp His Ala Thr Val Asn Ala Ala Phe Val Arg Glu Ser Ala
            115                 120                 125

Glu Val Tyr Gln Gln Arg His Lys Leu Arg Lys Gly Ser
        130                 135                 140

<210> SEQ ID NO 151
<211> LENGTH: 1824
<212> TYPE: DNA
<213> ORGANISM: Klebsiella pneumoniae

<400> SEQUENCE: 151

| | |
|---|---|
| atgccgttaa tagccgggat tgatatcggc aacgccacca ccgaggtggc gctggcgtcc | 60 |
| gactacccgc aggcgagggc gtttgttgcc agcgggatcg tcgcgacgac gggcatgaaa | 120 |
| gggacgcggg acaatatcgc cggaccctc gccgcgctgg agcaggccct ggcgaaaaca | 180 |
| ccgtggtcga tgagcgatgt ctctcgcatc tatcttaacg aagccgcgcc ggtgattggc | 240 |
| gatgtggcga tggagaccat caccgagacc attatcaccg aatcgaccat gatcggtcat | 300 |
| aacccgcaga cgccgggcgg ggtgggcgtt ggcgtgggga cgactatcgc cctcgggcgg | 360 |
| ctggcgacgc tgccggcggc gcagtatgcc gaggggtgga tcgtactgat tgacgacgcc | 420 |

```
gtcgatttcc ttgacgccgt gtggtggctc aatgaggcgc tcgaccgggg gatcaacgtg      480
gtggcggcga tcctcaaaaa ggacgacggc gtgctggtga caaccgcct gcgtaaaacc       540
ctgccggtgg tggatgaagt gacgctgctg gagcaggtcc ccgaggggt aatggcggcg       600
gtggaagtgg ccgcgccggg ccaggtggtg cggatcctgt cgaatcccta cgggatcgcc      660
accttcttcg ggctaagccc ggaagagacc caggccatcg tccccatcgc ccgcgccctg      720
attggcaacc gttccgcggt ggtgctcaag accccgcagg gggatgtgca gtcgcgggtg      780
atcccggcgg gcaacctcta cattagcggc gaaaagcgcc gcggagaggc cgatgtcgcc      840
gagggcgcgg aagccatcat gcaggcgatg agcgcctgcg ctccggtacg cgacatccgc      900
ggcgaaccgg gcacccacgc cggcggcatg cttgagcggg tgcgcaaggt aatggcgtcc      960
ctgaccggcc atgagatgag cgcgatatac atccaggatc tgctggcggt ggatacgttt     1020
attccgcgca aggtgcaggg cgggatggcc ggcgagtgcg ccatggagaa tgccgtcggg     1080
atggcggcga tggtgaaagc ggatcgtctg caaatgcagg ttatcgcccg cgaactgagc     1140
gcccgactgc agaccgaggt ggtggtgggc ggcgtggagg ccaacatggc catcgccggg     1200
gcgttaacca ctcccggctg tgcggcgccc ctggcgatcc tcgacctcgg cgccggctcg     1260
acggatgcgg cgatcgtcaa cgcggagggg cagataacgg cggtccatct cgccggggcg     1320
gggaatatgg tcagcctgtt gattaaaacc gagctgggcc tcgaggatct ttcgctggcg     1380
gaagcgataa aaaatacccc gctggccaaa gtggaaagcc tgttcagtat tcgtcacgag     1440
aatggcgcgg tggagttctt tcgggaagcc ctcagcccgg cggtgttcgc caaagtggtg     1500
tacatcaagg agggcgaact ggtgccgatc gataacgcca gcccgctgga aaaaattcgt     1560
ctcgtgcgcc ggcaggcgaa agagaaagtg tttgtcacca actgcctgcg cgcgctgcgc     1620
caggtctcac ccggcggttc cattcgcgat atcgccttg tggtgctggt gggcggctca     1680
tcgctggact ttgagatccc gcagcttatc acggaagcct tgtcgcacta tggcgtggtc     1740
gccgggcagg gcaatattcg gggaacagaa gggccgcgca atgcggtcgc caccgggctg     1800
ctactggccg gtcaggcgaa ttaa                                            1824
```

<210> SEQ ID NO 152
<211> LENGTH: 607
<212> TYPE: PRT
<213> ORGANISM: Klebsiella pneumoniae

<400> SEQUENCE: 152

Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
            20                  25                  30

Ile Val Ala Thr Thr Gly Met Lys Gly Thr Arg Asp Asn Ile Ala Gly
        35                  40                  45

Thr Leu Ala Ala Leu Glu Gln Ala Leu Ala Lys Thr Pro Trp Ser Met
    50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Thr Glu Ser Thr
                85                  90                  95

Met Ile Gly His Asn Pro Gln Thr Pro Gly Gly Val Gly Val Gly Val
            100                 105                 110

Gly Thr Thr Ile Ala Leu Gly Arg Leu Ala Thr Leu Pro Ala Ala Gln

-continued

```
            115                 120                 125
Tyr Ala Glu Gly Trp Ile Val Leu Ile Asp Ala Val Asp Phe Leu
130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                    165                 170                 175

Leu Arg Lys Thr Leu Pro Val Val Asp Glu Val Thr Leu Leu Glu Gln
                180                 185                 190

Val Pro Glu Gly Val Met Ala Ala Val Glu Val Ala Ala Pro Gly Gln
                195                 200                 205

Val Val Arg Ile Leu Ser Asn Pro Tyr Gly Ile Ala Thr Phe Phe Gly
210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                    245                 250                 255

Gln Ser Arg Val Ile Pro Ala Gly Asn Leu Tyr Ile Ser Gly Glu Lys
                260                 265                 270

Arg Arg Gly Glu Ala Asp Val Ala Glu Gly Ala Glu Ala Ile Met Gln
                275                 280                 285

Ala Met Ser Ala Cys Ala Pro Val Arg Asp Ile Arg Gly Glu Pro Gly
290                 295                 300

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
                    325                 330                 335

Val Asp Thr Phe Ile Pro Arg Lys Val Gln Gly Gly Met Ala Gly Glu
                340                 345                 350

Cys Ala Met Glu Asn Ala Val Gly Met Ala Ala Met Val Lys Ala Asp
                355                 360                 365

Arg Leu Gln Met Gln Val Ile Ala Arg Glu Leu Ser Ala Arg Leu Gln
370                 375                 380

Thr Glu Val Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
                    405                 410                 415

Gly Ala Gly Ser Thr Asp Ala Ala Ile Val Asn Ala Glu Gly Gln Ile
                420                 425                 430

Thr Ala Val His Leu Ala Gly Ala Gly Asn Met Val Ser Leu Leu Ile
                435                 440                 445

Lys Thr Glu Leu Gly Leu Glu Asp Leu Ser Leu Ala Glu Ala Ile Lys
                450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
                    485                 490                 495

Ala Lys Val Val Tyr Ile Lys Glu Gly Glu Leu Val Pro Ile Asp Asn
                500                 505                 510

Ala Ser Pro Leu Glu Lys Ile Arg Leu Val Arg Arg Gln Ala Lys Glu
                515                 520                 525

Lys Val Phe Val Thr Asn Cys Leu Arg Ala Leu Arg Gln Val Ser Pro
530                 535                 540
```

```
Gly Gly Ser Ile Arg Asp Ile Ala Phe Val Val Leu Val Gly Gly Ser
545                 550                 555                 560

Ser Leu Asp Phe Glu Ile Pro Gln Leu Ile Thr Glu Ala Leu Ser His
            565                 570                 575

Tyr Gly Val Val Ala Gly Gln Gly Asn Ile Arg Gly Thr Glu Gly Pro
        580                 585                 590

Arg Asn Ala Val Ala Thr Gly Leu Leu Leu Ala Gly Gln Ala Asn
    595                 600                 605

<210> SEQ ID NO 153
<211> LENGTH: 354
<212> TYPE: DNA
<213> ORGANISM: Klebsiella pneumoniae

<400> SEQUENCE: 153
atgtcgcttt caccgccagg cgtacgcctg ttttacgatc cgcgcgggca ccatgccggc    60
gccatcaatg agctgtgctg ggggctggag gagcaggggg tcccctgcca gaccataacc   120
tatgacggag gcggtgacgc cgctgcgctg gcgcccctgg cggccagaag ctcgcccctg   180
cgggtgggta tcgggctcag cgcgtccggc gagatagccc tcactcatgc ccagctgccg   240
gcggacgcgc cgctggctac cggacacgtc accgatagcg acgatcaact cgtacgctc    300 ggcgccaacg ccgggcagct ggttaaagtc ctgccgttaa gtgagagaaa ctga         354

<210> SEQ ID NO 154
<211> LENGTH: 117
<212> TYPE: PRT
<213> ORGANISM: Klebsiella pneumoniae

<400> SEQUENCE: 154

Met Ser Leu Ser Pro Pro Gly Val Arg Leu Phe Tyr Asp Pro Arg Gly
1               5                   10                  15

His His Ala Gly Ala Ile Asn Glu Leu Cys Trp Gly Leu Glu Glu Gln
            20                  25                  30

Gly Val Pro Cys Gln Thr Ile Thr Tyr Asp Gly Gly Gly Asp Ala Ala
        35                  40                  45

Ala Leu Gly Ala Leu Ala Ala Arg Ser Ser Pro Leu Arg Val Gly Ile
    50                  55                  60

Gly Leu Ser Ala Ser Gly Glu Ile Ala Leu Thr His Ala Gln Leu Pro
65                  70                  75                  80

Ala Asp Ala Pro Leu Ala Thr Gly His Val Thr Asp Ser Asp Asp Gln
                85                  90                  95

Leu Arg Thr Leu Gly Ala Asn Ala Gly Gln Leu Val Lys Val Leu Pro
            100                 105                 110

Leu Ser Glu Arg Asn
        115

<210> SEQ ID NO 155
<211> LENGTH: 1125
<212> TYPE: DNA
<213> ORGANISM: artificial sequence
<220> FEATURE:
<223> OTHER INFORMATION: Codon optimized amino alcohol kinase from
      Erwinia caratovora subsp. atroseptica

<400> SEQUENCE: 155
atgagcgatg gccgtctgac cgcactgttt cctgcatttc acatccggc atccaaccag    60 ccagtgtttg cggaggcttc cccgcacgac gatgaactga tgacgcaggc ggtgccgcag   120
```

-continued

```
gtttcctgcc agcaagccct ggcaattgcc cagcaggaat atggcctgag cggtcagatg    180
agcctgctgc agggcgaacg tgacgttaat ttctgtctga ccgtaacgcc agatgaacgc    240
tatatgctga aagtcatcaa cgctgctgaa ccggcagatg tgagcaactt tcagactgcg    300
ctgctgctgc acctggcacg tcaggcgcca gaactgccag tccctcgtat ccgctccacg    360
aaggctggtc agtctgaaac gggcgtcgaa attgatggtg ttctgctgcg tgtgcgtctg    420
gtttcctacc tggctggcat gccgcagtac ctggcgtctc cgagcacggc actgatgcca    480
cagctgggcg gtactctggc gcagctggac aacgctctgc actctttcac ccatccggcg    540
gctaaccgtg ctctgctgtg ggacatctcc cgcgcagagc aggtccgccc gtacctggac    600
ttcgttagcg agccgcagca gtatcagcac ctgcagcgca tctttgatcg ctatgactct    660
aacgtggcac gctgctgac gacgctgcgc gccaggtta tccacaacga cctgaacccg    720
cataacgtcc tggtcgatgg ttccagcccg acgcgcgtca cgggtatcat cgacttcggc    780
gatgcagtgt tcgcgccgct gatctgtgag gttgcgaccg ctctggcgta ccaaattggc    840
gacggcacgg atctgctgga acatgtggta ccgtttgtcg cagcgtatca ccagcgtatt    900
ccgctgcgcg cggaggaaat cgccctgctg ccagatctga tcgcgacccg catggcactg    960
actctgacca tcgctcagtg gcgtgcgtct cgctacccag ataaccgcga ataccctgctg   1020 cgcaacgtgc cgcgctgctg gcactccctg cagcgtatcg caacttacag ccacgcacaa   1080
tttctgacgc gcctgcagca ggtttgccca gaaaacgctc gttga                    1125
```

<210> SEQ ID NO 156
<211> LENGTH: 1275
<212> TYPE: DNA
<213> ORGANISM: artificial sequence
<220> FEATURE:
<223> OTHER INFORMATION: Codon optimized amino alcohol O-phosphate lyase
   from Erwinia caratovora subsp. atroseptica

<400> SEQUENCE: 156

```
atgactgcaa ctgaagctct gctggcacgt cgtcagcgcg ttctgggcgg tggctaccgt     60
ctgttctacg aagaaccgct gcatgttgca cgcggcgaag tgtatggcgt gttcgatcat    120
cagggtaaac gttacctgga cgtatataac aacgtagcta gcgtaggtca ctgtcacccg    180
gccgttgtag aagcggtcgc gcgtcaatct gcgcaactga acacccatac gcgctacctg    240
catcacgcga tcgtagattt tgctgaagat ctgctgtctg agttccccggc agaactgaac    300 aacgtcatgc tgacctgtac tggctccgaa gcgaacgacc tggccctgcg cattgcgcgt    360
cacgttacgg gtggtaccgg catgctggtg accccgttggg cctaccatgg tgttacgtcc    420
gctctggcgg agctgtcccc gtccctgggc gacgcgtag tacgcggttc ccacgtaaag    480
ctgatcgatg ctccggatac ctaccgtcag ccgggtgctt tcctgacctc tatccgcgaa    540
gcgctggcac agatgcagcg tgaaggtatt cgtccggcgg ctctgctggt tgatactatc    600
ttctcctccg acggtgtatt ctgtgcgccg gaaggtgaga tggcccaggc agccgcactg    660
atccgtcagg ccggtggcct gttcattgcg gacgaagtgc agccgggctt tggtcgtacc    720
ggtgaatccc tgtggggttt cgcacgtcat aacgtggttc cagatctggt ttctctgggc    780
aaaccgatgg gtaacggcca tccgattgct ggtctggtag tcgctccgc actgttcgac    840 gcttttggtc gtgatgttcg ctactttaat actttcggcg gtaacccagt atcctgccag    900
gcggcacatg ctgttctgcg cgttatccgt gaagaacagc tgcagcagaa cgcgcagcgt    960
gttggtgatt atctgcgcca aggtctgcag cagctggcac aacacttccc gctgatcggt   1020
```

| | |
|---|---|
| gacattcgtg catatggtct gtttatcggt gctgaactgg tttccgaccg tgaatccaaa | 1080 |
| accccagcga gcgagtctgc actgcaggtt gttaacgcga tgcgtcagcg tggtgtactg | 1140 |
| atctccgcaa ccggcccggc ggcgaacatt ctgaagatcc gtcctccgct ggtattcctg | 1200 |
| gaggaacacg cggacgtgtt cctgactacc ctgtccgacg tgctggcgct gatcggtact | 1260 |
| cgtgcacagc gttaa | 1275 |

<210> SEQ ID NO 157
<211> LENGTH: 77
<212> TYPE: DNA
<213> ORGANISM: artificial sequence
<220> FEATURE:
<223> OTHER INFORMATION: Primer

<400> SEQUENCE: 157

| | |
|---|---|
| caggaggaat taaccatggg gggttctcat catcatcatc atcatggtga cgatgacgat | 60 |
| aagatgagcg atggccg | 77 |

<210> SEQ ID NO 158
<211> LENGTH: 77
<212> TYPE: DNA
<213> ORGANISM: artificial sequence
<220> FEATURE:
<223> OTHER INFORMATION: Primer

<400> SEQUENCE: 158

| | |
|---|---|
| cggccatcgc tcatcttatc gtcatcgtca ccatgatgat gatgatgatg agaaccccc | 60 |
| atggttaatt cctcctg | 77 |

<210> SEQ ID NO 159
<211> LENGTH: 20
<212> TYPE: DNA
<213> ORGANISM: artificial sequence
<220> FEATURE:
<223> OTHER INFORMATION: Primer

<400> SEQUENCE: 159

| | |
|---|---|
| ggacctgctt cgctttatcg | 20 |

<210> SEQ ID NO 160
<211> LENGTH: 15
<212> TYPE: DNA
<213> ORGANISM: artificial sequence
<220> FEATURE:
<223> OTHER INFORMATION: Primer

<400> SEQUENCE: 160

| | |
|---|---|
| gctagagatg atagc | 15 |

<210> SEQ ID NO 161
<211> LENGTH: 18
<212> TYPE: DNA
<213> ORGANISM: artificial sequence
<220> FEATURE:
<223> OTHER INFORMATION: Primer

<400> SEQUENCE: 161

| | |
|---|---|
| ggaagagact atccagcg | 18 |

<210> SEQ ID NO 162
<211> LENGTH: 50
<212> TYPE: DNA

```
<213> ORGANISM: artificial sequence
<220> FEATURE:
<223> OTHER INFORMATION: Primer

<400> SEQUENCE: 162
gcgcgcccgg gaagaaggag ctcttcacca tgaacaaacc acagtcttgg          50

<210> SEQ ID NO 163
<211> LENGTH: 28
<212> TYPE: DNA
<213> ORGANISM: artificial sequence
<220> FEATURE:
<223> OTHER INFORMATION: Primer

<400> SEQUENCE: 163
gcgcgcccgg gttcatgcca cctctgcg                                  28

<210> SEQ ID NO 164
<211> LENGTH: 558
<212> TYPE: PRT
<213> ORGANISM: Lactobacillus brevis

<400> SEQUENCE: 164
```

Met Lys Arg Gln Lys Arg Phe Glu Glu Leu Glu Lys Arg Pro Ile His
1               5                   10                  15

Leu Asp Gly Phe Val Lys Glu Trp Pro Glu Gly Phe Val Ala Met
            20                  25                  30

Met Gly Pro Asn Asp Pro Lys Pro Ser Ile Lys Ile Glu Asn Gly Lys
        35                  40                  45

Val Thr Glu Met Asp Ser Lys Pro Ala Ala Asp Phe Asp Leu Ile Asp
    50                  55                  60

Leu Tyr Ile Ala Lys Tyr Gly Ile Lys Leu Glu Asn Ala Glu Lys Val
65                  70                  75                  80

Met Ala Met Asp Ser Thr Lys Ile Ala Asn Met Leu Cys Asp Pro Asn
                85                  90                  95

Val Pro Arg Lys Asp Ile Ile Glu Ile Thr Thr Ala Met Thr Pro Ala
            100                 105                 110

Lys Ala Glu Glu Val Ile Ser Lys Leu Asn Phe Ala Glu Met Ile Met
        115                 120                 125

Ala Thr Gln Lys Met Arg Pro Arg Arg Thr Pro Ala Thr Gln Cys His
    130                 135                 140

Val Thr Asn Ile Arg Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
                165                 170                 175

Ala Arg Tyr Ala Pro Leu Asn Ala Ile Ser Leu Met Val Gly Ala Gln
            180                 185                 190

Thr Gly Arg Pro Gly Val Ile Thr Gln Cys Ser Val Glu Glu Ala Glu
        195                 200                 205

Glu Leu Ser Leu Gly Met Arg Gly Phe Thr Gly Tyr Ala Glu Thr Ile
    210                 215                 220

Ser Val Tyr Gly Thr Asp Lys Val Phe Thr Asp Gly Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ser Gly Ser Glu Val Met Met Gly Tyr Thr
            260                 265                 270

```
Glu Gly Lys Ser Met Leu Tyr Leu Glu Ser Arg Cys Ile Phe Ile Thr
            275                 280                 285

Lys Ala Ser Gly Val Gln Gly Leu Gln Asn Gly Val Ser Cys Ile
    290                 295                 300

Gly Ile Pro Gly Ser Val Pro Ser Gly Ile Arg Ser Val Leu Gly Glu
305                 310                 315                 320

Asn Leu Leu Cys Met Met Leu Asp Leu Glu Cys Ala Ser Ala Asn Asp
                325                 330                 335

Gln Ala Phe Ser His Ser Asp Met Arg Arg Thr Glu Arg Leu Leu Gly
            340                 345                 350

Gln Phe Ile Ala Gly Thr Asp Tyr Ile Ser Ser Gly Tyr Ser Ser Thr
        355                 360                 365

Pro Asn Tyr Asp Asn Thr Phe Ala Gly Ser Asn Thr Asp Gly Leu Asp
    370                 375                 380

Tyr Asp Asp Tyr Tyr Val Met Glu Arg Asp Leu Ala Ile Asn Gly Gly
385                 390                 395                 400

Ile His Pro Val Asp Glu Gln Thr Ile Ile Lys Ala Arg Asn Lys Ala
                405                 410                 415

Ala Arg Ala Leu Gln Gly Val Phe Glu Asp Leu Gly Leu Pro Lys Ile
            420                 425                 430

Thr Asp Glu Glu Val Glu Ala Ala Thr Tyr Ala Asn Thr Ser Lys Asp
        435                 440                 445

Met Pro Glu Arg Asn Met Val Glu Asp Met Lys Ala Ala Gln Asp Leu
    450                 455                 460

Met Asp Arg Gly Ile Thr Gly Val Asp Ile Val Lys Ala Leu Phe Asn
465                 470                 475                 480

His Gly Phe Lys Asp Val Ala Gln Ala Val Leu Asp Leu Gln Lys Gln
                485                 490                 495

Lys Val Cys Gly Asp Phe Leu Gln Thr Ser Ala Ile Phe Asp Ser Lys
            500                 505                 510

Trp His Val Ile Ser Ala Val Asn Asp Ala Asn Asp Tyr Gln Gly Pro
        515                 520                 525

Gly Thr Gly Tyr Arg Leu Glu Glu Asp Thr Glu Glu Trp Glu Arg Ile
    530                 535                 540

Lys Asn Leu Pro Phe Ala Ile Asp Pro Gln Asn Met Gln Leu
545                 550                 555

<210> SEQ ID NO 165
<211> LENGTH: 239
<212> TYPE: PRT
<213> ORGANISM: Lactobacillus brevis

<400> SEQUENCE: 165

Met Ala Gln Glu Ile Asp Glu Asn Leu Leu Arg Asn Ile Ile Arg Asp
1               5                   10                  15

Val Ile Ala Glu Thr Gln Thr Gly Asp Thr Pro Ile Ser Phe Lys Ala
            20                  25                  30

Asp Ala Pro Ala Ala Ser Ser Ala Thr Thr Ala Thr Ala Ala Pro Val
        35                  40                  45

Asn Gly Asp Gly Pro Glu Pro Glu Lys Pro Val Asp Trp Phe Lys His
    50                  55                  60

Val Gly Val Ala Lys Pro Gly Tyr Ser Arg Asp Glu Val Val Ile Ala
65                  70                  75                  80

Val Ala Pro Ala Phe Ala Glu Val Met Asp His Asn Leu Thr Gly Ile
                85                  90                  95
```

```
Ser His Lys Glu Ile Leu Arg Gln Met Val Ala Gly Ile Glu Glu Glu
            100                 105                 110

Gly Leu Lys Ala Arg Ile Val Lys Val Tyr Arg Thr Ser Asp Val Ser
        115                 120                 125

Phe Cys Gly Ala Glu Gly Asp His Leu Ser Gly Ser Gly Ile Ala Ile
130                 135                 140

Ala Ile Gln Ser Lys Gly Thr Thr Ile Ile His Gln Lys Asp Gln Glu
145                 150                 155                 160

Pro Leu Ser Asn Leu Glu Leu Phe Pro Gln Ala Pro Val Leu Asp Gly
                165                 170                 175

Asp Thr Tyr Arg Ala Ile Gly Lys Asn Ala Ala Glu Tyr Ala Lys Gly
            180                 185                 190

Met Ser Pro Ser Pro Val Pro Thr Val Asn Asp Gln Met Ala Arg Val
        195                 200                 205

Gln Tyr Gln Ala Leu Ser Ala Leu Met His Ile Lys Glu Thr Lys Gln
    210                 215                 220

Val Val Met Gly Lys Pro Ala Glu Gln Ile Glu Val Asn Phe Asn
225                 230                 235

<210> SEQ ID NO 166
<211> LENGTH: 175
<212> TYPE: PRT
<213> ORGANISM: Lactobacillus brevis

<400> SEQUENCE: 166

Met Ser Glu Ile Asp Asp Leu Val Ala Lys Ile Val Gln Gln Ile Gly
1               5                   10                  15

Gly Thr Glu Ala Ala Asp Gln Thr Thr Ala Thr Pro Thr Ser Thr Ala
            20                  25                  30

Thr Gln Thr Gln His Ala Ala Leu Ser Lys Gln Asp Tyr Pro Leu Tyr
        35                  40                  45

Ser Lys His Pro Glu Leu Val His Ser Pro Ser Gly Lys Ala Leu Asn
    50                  55                  60

Asp Ile Thr Leu Asp Asn Val Leu Asn Asp Ile Lys Ala Asn Asp
65                  70                  75                  80

Leu Arg Ile Thr Pro Asp Thr Leu Arg Met Gln Gly Glu Val Ala Asn
                85                  90                  95

Asp Ala Gly Arg Asp Ala Val Gln Arg Asn Phe Gln Arg Ala Ser Glu
            100                 105                 110

Leu Thr Ser Ile Pro Asp Asp Arg Leu Leu Glu Met Tyr Asn Ala Leu
        115                 120                 125

Arg Pro Tyr Arg Ser Thr Lys Ala Glu Leu Leu Ala Ile Ser Ala Glu
130                 135                 140

Leu Lys Asp Lys Tyr His Ala Pro Val Asn Ala Gly Trp Phe Ala Glu
145                 150                 155                 160

Ala Ala Asp Tyr Tyr Glu Ser Arg Lys Lys Leu Lys Gly Asp Asn
                165                 170                 175

<210> SEQ ID NO 167
<211> LENGTH: 554
<212> TYPE: PRT
<213> ORGANISM: Salmonella enterica subsp. enterica serovar Choleraesuis

<400> SEQUENCE: 167

Met Arg Ser Lys Arg Phe Glu Ala Leu Ala Lys Arg Pro Val Asn Gln
1               5                   10                  15
```

```
Asp Gly Phe Val Lys Glu Trp Ile Glu Glu Gly Phe Ile Ala Met Glu
         20                  25                  30

Ser Pro Asn Asp Pro Lys Pro Ser Ile Lys Ile Val Asn Gly Ala Val
         35                  40                  45

Thr Glu Leu Asp Gly Lys Pro Val Ser Glu Phe Asp Leu Ile Asp His
 50                  55                  60

Phe Ile Ala Arg Tyr Gly Ile Asn Leu Asn Arg Ala Glu Glu Val Met
 65                  70                  75                  80

Ala Met Asp Ser Ile Lys Leu Ala Asn Met Leu Cys Asp Pro Asn Val
                 85                  90                  95

Lys Arg Ser Glu Ile Val Pro Leu Thr Thr Ala Met Thr Pro Ala Lys
                100                 105                 110

Ile Val Glu Val Val Ser His Met Asn Val Val Glu Met Met Met Ala
                115                 120                 125

Met Gln Lys Met Arg Ala Arg Arg Thr Pro Ser Gln Gln Ala His Val
130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
                180                 185                 190

Gly Arg Pro Gly Val Leu Thr Gln Cys Ser Leu Glu Glu Ala Thr Glu
                195                 200                 205

Leu Lys Leu Gly Met Leu Gly His Thr Cys Tyr Thr Glu Thr Ile Ser
210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
                260                 265                 270

Gly Lys Ser Met Leu Tyr Leu Glu Ala Arg Cys Ile Tyr Ile Thr Lys
                275                 280                 285

Ala Ala Gly Val Gln Gly Leu Gln Asn Gly Ser Val Ser Cys Ile Gly
                290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
                340                 345                 350

Phe Leu Pro Gly Thr Asp Phe Ile Ser Ser Gly Tyr Ser Ala Val Pro
                355                 360                 365

Asn Tyr Asp Asn Met Phe Ala Gly Ser Asn Glu Asp Ala Glu Asp Phe
                370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
                420                 425                 430
```

```
Asp Glu Glu Val Glu Ala Ala Thr Tyr Ala His Gly Ser Lys Asp Met
            435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
            515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550
```

<210> SEQ ID NO 168
<211> LENGTH: 224
<212> TYPE: PRT
<213> ORGANISM: Salmonella enterica subsp. enterica serovar Choleraesuis
      str. SC-B67

<400> SEQUENCE: 168

```
Met Glu Ile Asn Glu Lys Leu Leu Arg Gln Ile Ile Glu Asp Val Leu
1               5                   10                  15

Arg Asp Met Lys Gly Ser Asp Lys Pro Val Ser Phe Asn Ala Pro Ala
            20                  25                  30

Ala Ser Thr Ala Pro Gln Thr Ala Ala Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Leu Pro His Lys Ser Ile Leu Arg Glu Val Ile Ala Gly Ile Glu
                85                  90                  95

Glu Glu Gly Ile Arg Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 169
<211> LENGTH: 173
<212> TYPE: PRT

<213> ORGANISM: Salmonella enterica subsp. enterica serovar Choleraesuis str. SC-B67

<400> SEQUENCE: 169

| | | | | | | | | | | | | | | |
|---|---|---|---|---|---|---|---|---|---|---|---|---|---|---|
| Met | Asn | Thr | Asp | Ala | Ile | Glu | Ser | Met | Val | Arg | Asp | Val | Leu | Ser | Arg |
| 1 | | | | 5 | | | | | 10 | | | | | 15 | |
| Met | Asn | Ser | Leu | Gln | Gly | Asp | Ala | Pro | Ala | Ala | Ala | Ser | Ala | Ala | Gly |
| | | | 20 | | | | | 25 | | | | | 30 | | |
| Gly | Thr | Ser | Arg | Ser | Ala | Lys | Val | Ser | Asp | Tyr | Pro | Leu | Ala | Asn | Lys |
| | | 35 | | | | | 40 | | | | | 45 | | | |
| His | Pro | Glu | Trp | Val | Lys | Thr | Ala | Thr | Asn | Lys | Thr | Leu | Asp | Asp | Phe |
| | 50 | | | | | 55 | | | | | 60 | | | | |
| Thr | Leu | Glu | Asn | Val | Leu | Ser | Asn | Lys | Val | Thr | Ala | Gln | Asp | Met | Arg |
| 65 | | | | | 70 | | | | | 75 | | | | | 80 |
| Ile | Thr | Pro | Glu | Thr | Leu | Arg | Leu | Gln | Ala | Ser | Ile | Ala | Lys | Asp | Ala |
| | | | | 85 | | | | | 90 | | | | | 95 | |
| Gly | Arg | Asp | Arg | Leu | Ala | Met | Asn | Phe | Glu | Arg | Ala | Ala | Glu | Leu | Thr |
| | | | 100 | | | | | 105 | | | | | 110 | | |
| Ala | Val | Pro | Asp | Asp | Arg | Ile | Leu | Glu | Ile | Tyr | Asn | Ala | Leu | Arg | Pro |
| | | 115 | | | | | 120 | | | | | 125 | | | |
| Tyr | Arg | Ser | Thr | Lys | Glu | Glu | Leu | Met | Ala | Ile | Ala | Asp | Asp | Leu | Glu |
| | 130 | | | | | 135 | | | | | 140 | | | | |
| Asn | Arg | Tyr | Gln | Ala | Lys | Ile | Cys | Ala | Ala | Phe | Val | Arg | Glu | Ala | Ala |
| 145 | | | | | 150 | | | | | 155 | | | | | 160 |
| Thr | Leu | Tyr | Val | Glu | Arg | Lys | Lys | Leu | Lys | Gly | Asp | Asp | | | |
| | | | | 165 | | | | | 170 | | | | | | |

<210> SEQ ID NO 170
<211> LENGTH: 554
<212> TYPE: PRT
<213> ORGANISM: Escherichia coli

<400> SEQUENCE: 170

| | | | | | | | | | | | | | | |
|---|---|---|---|---|---|---|---|---|---|---|---|---|---|---|---|
| Met | Arg | Ser | Lys | Arg | Phe | Glu | Ala | Leu | Ala | Lys | Arg | Pro | Val | Asn | Gln |
| 1 | | | | 5 | | | | | 10 | | | | | 15 | |
| Asp | Gly | Phe | Val | Lys | Glu | Trp | Ile | Glu | Glu | Gly | Phe | Ile | Ala | Met | Glu |
| | | | 20 | | | | | 25 | | | | | 30 | | |
| Ser | Pro | Asn | Asp | Pro | Lys | Pro | Ser | Ile | Lys | Ile | Val | Asn | Gly | Val | Val |
| | | 35 | | | | | 40 | | | | | 45 | | | |
| Thr | Glu | Leu | Asp | Gly | Lys | Pro | Ala | Ser | Gln | Phe | Asp | Leu | Ile | Asp | His |
| | 50 | | | | | 55 | | | | | 60 | | | | |
| Phe | Ile | Ala | Arg | Tyr | Gly | Ile | Asn | Leu | Ala | Arg | Ala | Glu | Glu | Val | Ile |
| 65 | | | | | 70 | | | | | 75 | | | | | 80 |
| Ala | Met | Asp | Ser | Val | Lys | Leu | Ala | Asn | Met | Leu | Cys | Asp | Pro | Asn | Val |
| | | | | 85 | | | | | 90 | | | | | 95 | |
| Lys | Arg | Ser | Asp | Ile | Val | Pro | Leu | Thr | Thr | Ala | Met | Thr | Pro | Ala | Lys |
| | | | 100 | | | | | 105 | | | | | 110 | | |
| Ile | Val | Glu | Val | Val | Ser | Gln | Met | Asn | Val | Val | Glu | Met | Met | Met | Ala |
| | | 115 | | | | | 120 | | | | | 125 | | | |
| Met | Gln | Lys | Met | Arg | Ala | Arg | Arg | Thr | Pro | Ser | Gln | Gln | Ala | His | Val |
| | 130 | | | | | 135 | | | | | 140 | | | | |
| Thr | Asn | Val | Lys | Asp | Asn | Pro | Val | Gln | Ile | Ala | Ala | Asp | Ala | Ala | Glu |
| 145 | | | | | 150 | | | | | 155 | | | | | 160 |
| Gly | Ala | Trp | Arg | Gly | Phe | Asp | Glu | Gln | Glu | Thr | Thr | Val | Ala | Val | Ala |
| | | | | 165 | | | | | 170 | | | | | 175 | |

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Phe Leu Met Gln
            340                 345                 350

Phe Leu Pro Gly Thr Asp Phe Ile Ser Ser Gly Phe Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Ser Leu Glu Val Val Lys Ala Leu Ala Gln Gly
465                 470                 475                 480

Gly Phe Thr Asp Val Ala Gln Asp Met Leu Asn Met Gln Lys Ala Lys
                485                 490                 495

Leu Thr Gly Asp Tyr Leu His Thr Ser Ala Ile Ile Val Asp Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550

<210> SEQ ID NO 171
<211> LENGTH: 222
<212> TYPE: PRT
<213> ORGANISM: Escherichia coli

<400> SEQUENCE: 171

```
Met Glu Ile Asn Glu Lys Leu Leu Arg Gln Ile Ile Glu Asp Val Leu
1               5                   10                  15

Ala Glu Met Gln Pro Ser Asp Lys Ser Val Ser Phe Arg Ala Pro Val
            20                  25                  30

Ser Ala Thr Val Ser Ser Ala Pro Asp Thr Gly Asn Phe Leu Thr Glu
        35                  40                  45

Ile Gly Glu Ala Gln Gln Gly Thr Gln Gln Asp Glu Val Ile Ile Ala
    50                  55                  60

Val Gly Pro Ala Phe Gly Leu Ala Gln Thr Val Asn Ile Ile Gly Ile
65                  70                  75                  80

Pro His Lys Asn Ile Leu Arg Glu Val Ile Ala Gly Ile Glu Glu Glu
                85                  90                  95

Gly Ile Lys Ala Arg Val Ile Arg Cys Phe Lys Ser Ser Asp Val Ala
            100                 105                 110

Phe Val Ala Val Glu Gly Asp Arg Leu Ser Gly Ser Gly Ile Ala Ile
        115                 120                 125

Gly Ile Gln Ser Lys Gly Thr Thr Val Ile His Gln Gln Gly Leu Pro
    130                 135                 140

Pro Leu Ser Asn Leu Glu Leu Phe Pro Gln Ala Pro Leu Leu Thr Leu
145                 150                 155                 160

Asp Thr Tyr Arg Gln Ile Gly Lys Asn Ala Ala Arg Tyr Ala Lys Arg
                165                 170                 175

Glu Ser Pro Gln Pro Val Pro Thr Leu Asn Asp Gln Met Ala Arg Pro
            180                 185                 190

Lys Tyr Gln Ala Lys Ser Ala Ile Leu His Ile Lys Glu Thr Lys Tyr
        195                 200                 205

Val Val Thr Gly Lys Lys Pro Gln Glu Leu Arg Val Thr Phe
    210                 215                 220

<210> SEQ ID NO 172
<211> LENGTH: 172
<212> TYPE: PRT
<213> ORGANISM: Escherichia coli

<400> SEQUENCE: 172

Met Asn Thr Asp Ala Ile Glu Ser Met Val Arg Asp Val Leu Asn Arg
1               5                   10                  15

Met Asn Ser Leu Gln Asp Ala Ala Pro Val Ser Ala Val Pro Asn Ala
            20                  25                  30

Ser Ile Leu Ser Ala Lys Val Thr Asp Tyr Pro Leu Ala Asn Lys His
        35                  40                  45

Pro Glu Trp Val Lys Thr Ala Thr Asn Lys Thr Leu Asp Asp Phe Thr
    50                  55                  60

Leu Glu Asn Val Leu Ser Asp Asn Val Thr Ala Leu Asp Met Arg Ile
65                  70                  75                  80

Thr Pro Glu Thr Leu Arg Ile Gln Ala Ala Ile Ala Arg Asp Ala Gly
                85                  90                  95

Cys Asp Arg Leu Ala Met Asn Phe Glu Arg Ala Ala Glu Leu Thr Ser
            100                 105                 110

Val Pro Asp Asp Arg Ile Leu Glu Ile Tyr Asn Ala Leu Arg Pro Tyr
        115                 120                 125

Arg Ser Thr Lys Gln Glu Leu Ile Ala Ile Ala Asp Asp Leu Glu Gln
    130                 135                 140

Arg Tyr Gln Ala Lys Ile Cys Ala Ala Phe Val Arg Glu Ala Ala Glu
```

```
                145                 150                 155                 160
Leu Tyr Val Glu Arg Lys Lys Leu Lys Gly Asp Asp
                165                 170

<210> SEQ ID NO 173
<211> LENGTH: 554
<212> TYPE: PRT
<213> ORGANISM: Shigella sonnei

<400> SEQUENCE: 173

Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Val Val
        35                  40                  45

Thr Glu Leu Asp Gly Lys Pro Ala Ser Gln Phe Asp Leu Ile Asp His
    50                  55                  60

Phe Ile Ala Arg Tyr Gly Ile Asn Leu Ala Arg Ala Glu Glu Val Ile
65                  70                  75                  80

Ala Met Asp Ser Val Lys Leu Ala Asn Met Leu Cys Asp Pro Asn Val
                85                  90                  95

Lys Arg Ser Asp Ile Val Pro Leu Thr Thr Ala Met Thr Pro Ala Lys
            100                 105                 110

Ile Val Glu Val Val Ser Gln Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Phe Leu Met Gln
            340                 345                 350
```

```
Phe Leu Pro Gly Thr Asp Phe Ile Ser Ser Gly Phe Ser Ala Val Pro
            355                 360                 365

Asn Tyr Asp Asn Met Phe Ala Gly Ser Asn Glu Asp Ala Glu Asp Phe
        370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Ser Leu Glu Val Val Lys Ala Leu Ala Gln Gly
465                 470                 475                 480

Ser Phe Thr Asp Val Ala Gln Asp Met Leu Asn Met Gln Lys Ala Lys
                485                 490                 495

Leu Thr Gly Asp Tyr Leu His Thr Ser Ala Ile Ile Val Asp Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Ile Lys Asn Ile
    530                 535                 540

Pro Gly Ala Leu Asp Pro Asn Glu Ile Asp
545                 550

<210> SEQ ID NO 174
<211> LENGTH: 222
<212> TYPE: PRT
<213> ORGANISM: Shigella sonnei

<400> SEQUENCE: 174

Met Glu Ile Asn Glu Lys Leu Leu Arg Gln Ile Ile Glu Asp Val Leu
1               5                   10                  15

Ala Glu Met Gln Pro Ser Asp Lys Ser Val Ser Phe Arg Ala Pro Val
            20                  25                  30

Ser Ala Thr Val Pro Ser Ala Pro Asp Thr Gly Asn Phe Leu Thr Glu
        35                  40                  45

Ile Gly Glu Ala Gln Gln Gly Thr Gln Gln Asp Glu Val Ile Ile Ala
    50                  55                  60

Val Gly Pro Ala Phe Gly Leu Ala Gln Thr Val Asn Ile Ile Gly Ile
65                  70                  75                  80

Pro His Lys Asn Ile Leu Arg Glu Val Ile Ala Gly Ile Glu Glu Glu
                85                  90                  95

Gly Ile Lys Ala Arg Val Ile Arg Cys Phe Lys Ser Ser Asp Val Ala
            100                 105                 110

Phe Val Ala Val Glu Gly Asp Arg Leu Ser Gly Ser Gly Ile Ala Ile
        115                 120                 125

Gly Ile Gln Ser Lys Gly Thr Thr Val Ile His Gln Gln Gly Leu Pro
    130                 135                 140

Pro Leu Ser Asn Leu Glu Leu Phe Pro Gln Ala Pro Leu Leu Thr Leu
145                 150                 155                 160

Asp Thr Tyr Arg Gln Ile Gly Lys Asn Ala Ala Arg Tyr Ala Lys Arg
                165                 170                 175
```

```
Glu Ser Pro Gln Pro Val Pro Thr Leu Asn Asp Gln Met Ala Arg Pro
            180                 185                 190

Lys Tyr Gln Ala Lys Ser Ala Ile Leu His Ile Lys Glu Thr Lys Tyr
        195                 200                 205

Val Val Thr Gly Lys Lys Pro Gln Glu Leu Arg Val Thr Phe
    210                 215                 220

<210> SEQ ID NO 175
<211> LENGTH: 172
<212> TYPE: PRT
<213> ORGANISM: Shigella sonnei

<400> SEQUENCE: 175

Met Asn Thr Asp Ala Ile Glu Ser Met Val Arg Asp Val Leu Asn Arg
1               5                   10                  15

Met Asn Ser Leu Gln Asp Ala Ala Pro Val Ser Ala Val Pro Asn Ala
            20                  25                  30

Ser Ile Leu Ser Ala Lys Val Thr Asp Tyr Pro Leu Ala Asn Lys His
        35                  40                  45

Pro Glu Trp Val Lys Thr Ala Thr Asn Lys Thr Leu Asp Asp Phe Thr
    50                  55                  60

Leu Glu Asn Val Leu Ser Asp Asn Val Thr Ala Leu Asp Met Arg Ile
65                  70                  75                  80

Thr Pro Glu Thr Leu Arg Ile Gln Ala Ala Ile Ala Arg Asp Ala Gly
                85                  90                  95

Arg Asp Arg Leu Ala Met Asn Phe Glu Arg Ala Ala Glu Leu Thr Ser
            100                 105                 110

Val Pro Asp Asp Arg Ile Leu Glu Ile Tyr Asn Ala Leu Arg Pro Tyr
        115                 120                 125

Arg Ser Thr Lys Gln Glu Leu Ile Ala Ile Ala Asp Asp Leu Glu Gln
    130                 135                 140

Arg Tyr Gln Ala Lys Ile Cys Ala Ala Phe Val Arg Glu Ala Ala Glu
145                 150                 155                 160

Leu Tyr Val Glu Arg Lys Lys Leu Lys Gly Asp Asp
                165                 170

<210> SEQ ID NO 176
<211> LENGTH: 554
<212> TYPE: PRT
<213> ORGANISM: Yersinia bercovieri

<400> SEQUENCE: 176

Met Lys Ser Lys Arg Phe Glu Ala Leu Ala Lys Arg Pro Val Asn Gln
1               5                   10                  15

Asp Gly Phe Val Lys Glu Trp Ile Glu Gly Phe Ile Ala Met Glu
            20                  25                  30

Ser Pro Asn Asp Pro Lys Pro Ser Ile Lys Ile Val Asn Gly Val Val
        35                  40                  45

Thr Glu Leu Asp Gly Lys Pro Gln Ser Ser Phe Asp Leu Ile Asp His
    50                  55                  60

Phe Ile Ala Arg Tyr Gly Ile Asn Leu Asp His Ala Glu Glu Val Met
65                  70                  75                  80

Lys Met Asp Ser Ile Lys Leu Ala Asn Met Leu Cys Asp Pro Asn Val
                85                  90                  95

Ser Arg Arg Thr Ile Val Pro Leu Thr Thr Ala Met Thr Pro Ala Lys
            100                 105                 110
```

```
Ile Val Glu Val Val Ser His Met Asn Val Val Glu Met Met Met Ser
        115                 120                 125

Met Gln Lys Met Arg Ala Arg Arg Thr Pro Ser Gln Gln Ala His Val
130                 135                 140

Thr Asn Val Lys Asp Asn Pro Val Gln Ile Ala Ala Asp Ala Ala Glu
145                 150                 155                 160

Gly Ala Phe Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
                180                 185                 190

Gly Arg Pro Gly Val Leu Thr Gln Cys Ser Leu Glu Glu Ala Thr Glu
            195                 200                 205

Leu Lys Leu Gly Met Leu Gly His Thr Cys Tyr Ala Glu Thr Ile Ser
210                 215                 220

Val Tyr Gly Thr Glu Pro Val Phe Thr Asp Gly Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
                260                 265                 270

Gly Lys Ser Met Leu Tyr Leu Glu Ala Arg Cys Ile Tyr Ile Thr Lys
            275                 280                 285

Ala Ala Gly Val Gln Gly Leu Gln Asn Gly Ser Val Ser Cys Val Gly
290                 295                 300

Val Pro Ser Ala Val Pro Ser Gly Ile Arg Ala Ile Leu Ala Glu Asn
305                 310                 315                 320

Leu Ile Cys Ser Ala Leu Asp Leu Glu Cys Ala Ser Ser Asn Asp Gln
                325                 330                 335

Thr Phe Thr His Ser Asp Met Arg Arg Thr Ala Arg Leu Leu Met Gln
                340                 345                 350

Phe Leu Pro Gly Thr Asp Phe Ile Ser Ser Gly Tyr Ser Ala Val Pro
            355                 360                 365

Asn Tyr Asp Asn Met Phe Ala Gly Ser Asn Glu Asp Ala Glu Asp Phe
            370                 375                 380

Asp Asp Tyr Asn Val Leu Gln Arg Asp Leu Lys Val Asp Gly Gly Leu
385                 390                 395                 400

Arg Pro Val Leu Glu Ala Asp Val Val Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Ile Ala Ala Thr Tyr Ala His Gly Ser Lys Asp Met
            435                 440                 445

Pro Glu Arg Asn Ile Val Glu Asp Ile Lys Phe Ala Gln Glu Ile Ile
450                 455                 460

Ser Lys Asn Arg Thr Gly Leu Glu Val Val Lys Ala Leu Ala Gln Gly
465                 470                 475                 480

Gly Phe Glu Asp Val Ala Gln Asp Met Leu Asn Ile Gln Lys Ala Lys
                485                 490                 495

Ile Ala Gly Asp Tyr Leu His Thr Ser Ala Ile Ile Lys Gly Asp Asn
            500                 505                 510

Gln Val Leu Ser Ala Val Asn Asp Val Asn Asp Tyr Ala Gly Pro Ala
            515                 520                 525
```

```
Thr Gly Tyr Arg Leu Glu Gly Ala Arg Trp Glu Glu Ile Lys Asn Ile
            530                 535                 540

Pro Asn Ala Leu Asp Pro Asn Glu Leu Gly
545                 550

<210> SEQ ID NO 177
<211> LENGTH: 221
<212> TYPE: PRT
<213> ORGANISM: Yersinia bercovieri

<400> SEQUENCE: 177

Met Val Asp Ile Asn Glu Lys Leu Leu Arg Gln Ile Ile Glu Gly Val
1               5                   10                  15

Leu Gln Glu Met Gln Gly Glu Lys Asn Ser Val Ser Phe Lys Gln Glu
                20                  25                  30

Ser Gln Pro Ala Thr Ala Val Ala Ser Gly Asp Phe Leu Thr Glu Val
            35                  40                  45

Gly Glu Ala Arg Pro Gly Ser Asn Gln Asp Glu Val Ile Ile Ala Val
50                  55                  60

Gly Pro Ala Phe Gly Leu Ser Gln Thr Ala Asn Ile Val Gly Ile Pro
65                  70                  75                  80

His Lys Asn Ile Leu Arg Glu Leu Ile Ala Gly Ile Glu Glu Glu Gly
                85                  90                  95

Ile Lys Ala Arg Val Ile Arg Cys Phe Lys Ser Ser Asp Val Ala Phe
            100                 105                 110

Val Ala Val Glu Gly Asn Arg Leu Ser Gly Ser Gly Ile Ser Ile Gly
            115                 120                 125

Ile Gln Ser Lys Gly Thr Thr Val Ile His Gln Gln Gly Leu Pro Pro
130                 135                 140

Leu Ser Asn Leu Glu Leu Phe Pro Gln Ala Pro Leu Leu Thr Leu Glu
145                 150                 155                 160

Thr Tyr Arg Leu Ile Gly Lys Asn Ala Ala Arg Tyr Ala Lys Arg Glu
                165                 170                 175

Ser Pro Gln Pro Val Pro Thr Leu Asn Asp Gln Met Ala Arg Pro Lys
            180                 185                 190

Tyr Gln Ala Lys Ser Ala Ile Leu His Ile Lys Glu Thr Lys Tyr Val
            195                 200                 205

Val Thr Gly Lys Asn Pro Gln Glu Leu Arg Val Ala Leu
        210                 215                 220

<210> SEQ ID NO 178
<211> LENGTH: 174
<212> TYPE: PRT
<213> ORGANISM: Yersinia bercovieri

<400> SEQUENCE: 178

Met Asn Ser Glu

```
Arg Ile Thr Pro Glu Ile Leu Arg Ile Gln Ala Ser Ile Ala Lys Asp
                85                  90                  95

Ala Gly Arg Pro Leu Leu Ala Met Asn Phe Glu Arg Ala Ala Glu Leu
            100                 105                 110

Thr Ala Val Pro Asp Asp Lys Val Leu Asp Ile Tyr Asn Ala Leu Arg
            115                 120                 125

Pro Phe Arg Ser Ser Lys Glu Glu Leu Asn Ala Ile Ala Asp Asp Leu
130                 135                 140

Glu Lys Thr Tyr Gln Ala Thr Ile Cys Ala Ala Phe Val Arg Glu Ala
145                 150                 155                 160

Ala Val Leu Tyr Val Gln Arg Lys Lys Leu Lys Gly Asp Asp
                165                 170

<210> SEQ ID NO 179
<211> LENGTH: 551
<212> TYPE: PRT
<213> ORGANISM: Yersinia mollaretii

<400> SEQUENCE: 179

Met Lys Ser Lys Arg Phe Glu Ala Arg Pro Val Asn Gln Asp Gly Phe
1               5                   10                  15

Val Lys Glu Trp Ile Glu Gly Phe Ile Ala Met Glu Ser Pro Asn
                20                  25                  30

Asp Pro Lys Pro Ser Ile Lys Ile Val Asn Gly Val Val Thr Glu Leu
            35                  40                  45

Asp Gly Lys Pro Gln Ser Ser Phe Asp Leu Ile Asp His Phe Ile Ala
        50                  55                  60

Arg Tyr Gly Ile Asn Leu Asp His Ala Glu Glu Val Met Lys Met Asp
65                  70                  75                  80

Ser Ile Lys Leu Ala Asn Met Leu Cys Asp Pro Asn Val Ser Arg Arg
                85                  90                  95

Thr Ile Val Pro Leu Thr Thr Ala Met Thr Pro Ala Lys Ile Val Glu
            100                 105                 110

Val Val Ser His Met Asn Val Val Glu Met Met Met Ser Met Gln Lys
        115                 120                 125

Met Arg Ala Arg Thr Pro Ser Gln Gln Ala His Val Thr Asn Val
130                 135                 140

Lys Asp Asn Pro Val Gln Ile Ala Ala Asp Ala Ala Glu Gly Ala Phe
145                 150                 155                 160

Arg Gly Phe Asp Glu Gln Glu Thr Thr Val Ala Val Ala Arg Tyr Ala
                165                 170                 175

Pro Phe Asn Ala Ile Ala Leu Leu Val Gly Ser Gln Val Gly Arg Pro
            180                 185                 190

Gly Val Leu Thr Gln Cys Ser Leu Glu Glu Ala Thr Glu Leu Lys Leu
        195                 200                 205

Gly Met Leu Gly His Thr Cys Tyr Ala Glu Thr Ile Ser Val Tyr Gly
210                 215                 220

Thr Glu Pro Val Phe Thr Asp Gly Asp Asp Thr Pro Trp Ser Lys Gly
225                 230                 235                 240

Phe Leu Ala Ser Ser Tyr Ala Ser Arg Gly Leu Lys Met Arg Phe Thr
                245                 250                 255

Ser Gly Ser Gly Ser Glu Val Gln Met Gly Tyr Ala Glu Gly Lys Ser
            260                 265                 270

Met Leu Tyr Leu Glu Ala Arg Cys Ile Tyr Ile Thr Lys Ala Ala Gly
        275                 280                 285
```

```
Val Gln Gly Leu Gln Asn Gly Ser Val Ser Cys Val Gly Val Pro Ser
    290                 295                 300

Ala Val Pro Ser Gly Ile Arg Ala Ile Leu Ala Glu Asn Leu Ile Cys
305                 310                 315                 320

Ser Ala Leu Asp Leu Glu Cys Ala Ser Ser Asn Asp Gln Thr Phe Thr
                325                 330                 335

His Ser Asp Met Arg Arg Thr Ala Arg Leu Leu Met Gln Phe Leu Pro
            340                 345                 350

Gly Thr Asp Phe Ile Ser Ser Gly Tyr Ser Ala Val Pro Asn Tyr Asp
        355                 360                 365

Asn Met Phe Ala Gly Ser Asn Glu Asp Ala Glu Asp Phe Asp Asp Tyr
    370                 375                 380

Asn Val Leu Gln Arg Asp Leu Lys Val Asp Gly Gly Leu Arg Pro Val
385                 390                 395                 400

Leu Glu Ala Asp Val Val Ala Ile Arg Asn Lys Ala Ala Arg Ala Leu
                405                 410                 415

Gln Ala Val Phe Ala Gly Met Gly Leu Pro Pro Ile Thr Asp Glu Glu
            420                 425                 430

Val Ile Ala Ala Thr Tyr Ala His Gly Ser Lys Asp Met Pro Asp Arg
        435                 440                 445

Asn Ile Val Glu Asp Ile Lys Phe Ala Gln Glu Ile Ile Ser Lys Asn
    450                 455                 460

Arg Thr Gly Leu Glu Val Val Lys Ala Leu Ala Gln Gly Gly Phe Glu
465                 470                 475                 480

Asp Val Ala Gln Asp Met Leu Asn Ile Gln Lys Ala Lys Ile Ala Gly
                485                 490                 495

Asp Tyr Leu His Thr Ser Ala Ile Ile Lys Gly Asp Asn Gln Val Leu
            500                 505                 510

Ser Ala Val Asn Asp Val Asn Asp Tyr Ala Gly Pro Ala Thr Gly Tyr
        515                 520                 525

Arg Leu Glu Gly Ala Arg Trp Glu Glu Ile Lys Asn Ile Pro Asn Ala
    530                 535                 540

Leu Asp Pro Asn Glu Leu Gly
545                 550

<210> SEQ ID NO 180
<211> LENGTH: 224
<212> TYPE: PRT
<213> ORGANISM: Yersinia mollaretii

<400> SEQUENCE: 180

Met Val Asp Ile Asn Glu Lys Leu Leu Arg Gln Ile Ile Glu Gly Val
1               5                   10                  15

Leu Gln Glu Met Gln Gly Asp Asn Asn Thr Val Ser Phe Lys Pro Val
            20                  25                  30

Ser Gln Pro Ala Thr Ala Ala Thr Ala Val Ala Ala Gly Asp Phe Leu
        35                  40                  45

Thr Glu Val Gly Glu Ala Arg Pro Gly Ser Asn Gln Asp Glu Val Ile
    50                  55                  60

Ile Ala Val Gly Pro Ala Phe Gly Leu Ser Gln Thr Ala Asn Ile Val
65                  70                  75                  80

Gly Ile Pro His Lys Asn Ile Leu Arg Glu Leu Ile Ala Gly Ile Glu
                85                  90                  95

Glu Glu Gly Ile Lys Ala Arg Val Ile Arg Cys Phe Lys Ser Ser Asp
```

```
                100                 105                 110
Val Ala Phe Val Ala Val Glu Gly Asn Arg Leu Ser Gly Ser Gly Ile
            115                 120                 125

Ser Ile Gly Ile Gln Ser Lys Gly Thr Ile Val Ile His Gln Gln Gly
130                 135                 140

Leu Pro Pro Leu Ser Asn Leu Glu Leu Phe Pro Gln Ala Pro Leu Leu
145                 150                 155                 160

Thr Leu Asp Thr Tyr Arg Leu Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 181
<211> LENGTH: 175
<212> TYPE: PRT
<213> ORGANISM: Yersinia mollaretii

<400> SEQUENCE: 181

```
Met Asn Ser Glu Ala Ile Glu Ser Met Val Arg Asp Val Leu Asn Lys
1               5                   10                  15

Met Asn Ser Leu Gln Gly Gln Thr Pro Ala Ala Cys Ala Ala Pro
            20                  25                  30

Ala Ala Ser Ser Arg Ser Asn Ala Lys Val Ser Asp Tyr Pro Leu Ala
        35                  40                  45

Asn Lys His Pro Asp Trp Val Lys Thr Ala Thr Asn Lys Thr Leu Asp
    50                  55                  60

Asp Leu Thr Leu Ala Asn Val Leu Asn Gly Ser Val Thr Ser Gln Asp
65                  70                  75                  80

Leu Arg Ile Thr Pro Glu Ile Leu Arg Ile Gln Ala Ser Ile Ala Lys
                85                  90                  95

Asp Ala Gly Arg Pro Leu Leu Ala Met Asn Phe Glu Arg Ala Ala Glu
            100                 105                 110

Leu Thr Ala Val Pro Asp Asp Lys Val Leu Asp Ile Tyr Asn Ala Leu
        115                 120                 125

Arg Pro Phe Arg Ser Ser Lys Glu Glu Leu Asn Ala Ile Ala Asp Asp
    130                 135                 140

Leu Glu Lys Thr Tyr Lys Ala Thr Ile Cys Ala Ala Phe Val Arg Glu
145                 150                 155                 160

Ala Ala Val Leu Tyr Val Gln Arg Lys Lys Leu Lys Gly Asp Asp
                165                 170                 175
```

<210> SEQ ID NO 182
<211> LENGTH: 554
<212> TYPE: PRT
<213> ORGANISM: Yersinia enterocolitica subsp. enterocolitica

<400> SEQUENCE: 182

```
Met Lys Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Val Val
```

-continued

```
            35                  40                  45
Thr Glu Leu Asp Gly Lys Pro Gln Ser Ser Phe Asp Leu Ile Asp His
 50                  55                  60

Phe Ile Ala Arg Tyr Gly Ile Asn Leu Ala His Ala Glu Glu Val Met
 65                  70                  75                  80

Lys Met Asp Ser Ile Lys Leu Ala Asn Met Leu Cys Asp Pro Asn Val
                     85                  90                  95

Ser Arg Arg Thr Ile Val Pro Leu Thr Thr Ala Met Thr Pro Ala Lys
                    100                 105                 110

Ile Val Glu Val Val Ser His Met Asn Val Val Glu Met Met Met Ser
                115                 120                 125

Met Gln Lys Met Arg Ala Arg Arg Thr Pro Ser Gln Gln Ala His Val
                130                 135                 140

Thr Asn Val Lys Asp Asn Pro Val Gln Ile Ala Ala Asp Ala Ala Glu
145                 150                 155                 160

Gly Ala Phe Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
                180                 185                 190

Gly Arg Pro Gly Val Leu Thr Gln Cys Ser Leu Glu Glu Ala Thr Glu
                195                 200                 205

Leu Lys Leu Gly Met Leu Gly His Thr Cys Tyr Ala Glu Thr Ile Ser
210                 215                 220

Val Tyr Gly Thr Glu Pro Val Phe Thr Asp Gly Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
                260                 265                 270

Gly Lys Ser Met Leu Tyr Leu Glu Ala Arg Cys Ile Tyr Ile Thr Lys
                275                 280                 285

Ala Ala Gly Val Gln Gly Leu Gln Asn Gly Ser Val Ser Cys Val Gly
290                 295                 300

Val Pro Ser Ala Val Pro Ser Gly Ile Arg Ala Ile Leu Ala Glu Asn
305                 310                 315                 320

Leu Ile Cys Ser Ala Leu Asp Leu Glu Cys Ala Ser Ser Asn Asp Gln
                325                 330                 335

Thr Phe Thr His Ser Asp Met Arg Arg Thr Ala Arg Leu Leu Met Gln
                340                 345                 350

Phe Leu Pro Gly Thr Asp Phe Ile Ser Ser Gly Tyr Ser Ala Val Pro
                355                 360                 365

Asn Tyr Asp Asn Met Phe Ala Gly Ser Asn Glu Asp Ala Glu Asp Phe
                370                 375                 380

Asp Asp Tyr Asn Val Met Gln Arg Asp Leu Lys Val Asp Gly Gly Leu
385                 390                 395                 400

Arg Pro Val Leu Glu Ala Asp Val Val Ala Ile Arg Asn Lys Ala Ala
                    405                 410                 415

Arg Ala Leu Gln Ala Val Phe Ala Gly Met Gly Leu Pro Pro Ile Thr
                420                 425                 430

Asp Glu Glu Val Ile Ala Ala Thr Tyr Ala His Gly Ser Lys Asp Met
                435                 440                 445

Pro Glu Arg Asn Ile Val Glu Asp Ile Lys Phe Ala Gln Glu Ile Ile
                450                 455                 460
```

Ser Lys Asn Arg Thr Gly Leu Glu Val Val Lys Ala Leu Ala Gln Gly
465                 470                 475                 480

Gly Phe Glu Asp Val Ala Gln Asp Met Leu Asn Ile Gln Lys Ala Lys
            485                 490                 495

Ile Ala Gly Asp Tyr Leu His Thr Ser Ala Ile Ile Lys Gly Asp Asn
        500                 505                 510

Gln Val Leu Ser Ala Val Asn Asp Val Asn Asp Tyr Ala Gly Pro Ala
            515                 520                 525

Thr Gly Tyr Arg Leu Glu Gly Ala Arg Trp Glu Glu Ile Lys Asn Ile
    530                 535                 540

Pro Asn Ala Leu Asp Pro Asn Glu Leu Gly
545                 550

<210> SEQ ID NO 183
<211> LENGTH: 223
<212> TYPE: PRT
<213> ORGANISM: Yersinia enterocolitica subsp. enterocolitica

<400> SEQUENCE: 183

Met Val Asp Ile Asn Glu Lys Leu Leu Arg Gln Ile Ile Glu Gly Val
1               5                   10                  15

Leu Gln Glu Met Gln Gly Asp Ser Asn Thr Val Ser Phe Lys Gln Glu
            20                  25                  30

Thr Gln Pro Thr Ala Thr Ala Ala Val Ala Ser Gly Asp Phe Leu Thr
35 40 45

Glu Val Gly Glu Ala Arg Pro Gly Thr His Gln Asp Glu Val Ile Ile
50 55 60

Ala Val Gly Pro Ala Phe Gly Leu Ser Gln Thr Ala Asn Ile Val Gly
65 70 75 80

Ile Pro His Lys Asn Ile Leu Arg Glu Leu Ile Ala Gly Ile Glu Glu
85 90 95

Glu Gly Ile Lys Ala Arg Val Ile Arg Cys Phe Lys Ser Ser Asp Val
100 105 110

Ala Phe Val Ala Val Glu Gly Asn Arg Leu Ser Gly Ser Gly Ile Ser
115 120 125

Ile Gly Ile Gln Ser Lys Gly Thr Thr Val Ile His Gln Gln Gly Leu
130 135 140

Pro Pro Leu Ser Asn Leu Glu Leu Phe Pro Gln Ala Pro Leu Leu Thr
145 150 155 160

Leu Glu Thr Tyr Arg Leu Ile Gly Lys Asn Ala Ala Arg Tyr Ala Lys
165 170 175

Arg Glu Ser Pro Gln Pro Val Pro Thr Leu Asn Asp Gln Met Ala Arg
180 185 190

Pro Lys Tyr Gln Ala Lys Ser Ala Ile Leu His Ile Lys Glu Thr Lys
195 200 205

Tyr Val Val Thr Gly Lys Asn Pro Gln Glu Leu Arg Val Ala Leu
210 215 220

<210> SEQ ID NO 184
<211> LENGTH: 174
<212> TYPE: PRT
<213> ORGANISM: Yersinia enterocolitica subsp. enterocolitica

<400> SEQUENCE: 184

Met Asn Ser Glu Ala Ile Glu Ser Met Val Arg Asp Val Leu Ser Lys
1 5 10 15

```
Met Asn Ser Leu Gln Gly Gln Thr Pro Thr Thr Ala Cys Ala Pro Ala
             20                  25                  30

Ala Ser Ser Arg Ser Asp Ala Lys Val Ser Asp Tyr Pro Leu Ala Asn
         35                  40                  45

Lys His Pro Asp Trp Val Lys Thr Ala Thr Asn Lys Thr Leu Asp Asp
     50                  55                  60

Leu Thr Leu Ala Asn Val Leu Asn Gly Ser Val Thr Ser Gln Asp Leu
 65                  70                  75                  80

Arg Ile Thr Pro Glu Ile Leu Arg Ile Gln Ala Ser Ile Ala Lys Asp
                 85                  90                  95

Ala Gly Arg Pro Leu Leu Ala Met Asn Phe Glu Arg Ala Ala Glu Leu
            100                 105                 110

Thr Ala Val Pro Asp Asp Lys Val Leu Asp Ile Tyr Asn Ala Leu Arg
        115                 120                 125

Pro Phe Arg Ser Ser Lys Glu Glu Leu Asn Ala Ile Ala Asp Asp Leu
    130                 135                 140

Glu Gln Thr Tyr Lys Ala Thr Ile Cys Ala Ala Phe Val Arg Glu Ala
145                 150                 155                 160

Ala Val Leu Tyr Val Gln Arg Lys Lys Leu Lys Gly Asp Asp
                165                 170

<210> SEQ ID NO 185
<211> LENGTH: 554
<212> TYPE: PRT
<213> ORGANISM: Yersinia intermedia

<400> SEQUENCE: 185

Met Lys Ser Lys Arg Phe Glu Ala Leu Ala Lys Arg Pro Val Asn Gln
1               5                   10                  15

Asp Gly Phe Val Lys Glu Trp Ile Glu Gly Phe Ile Ala Met Glu
            20                  25                  30

Ser Pro Asn Asp Pro Lys Pro Ser Ile Lys Ile Val Asn Gly Val Val
        35                  40                  45

Thr Glu Leu Asp Gly Lys Pro Gln Ser Ser Phe Asp Leu Ile Asp His
    50                  55                  60

Phe Ile Ala Arg Tyr Gly Ile Asn Leu Ala His Ala Glu Glu Val Met
65                  70                  75                  80

Lys Met Asp Ser Ile Lys Leu Ala Asn Met Leu Cys Asp Pro Asn Val
                85                  90                  95

Ser Arg Arg Thr Ile Val Pro Leu Thr Thr Ala Met Thr Pro Ala Lys
            100                 105                 110

Ile Val Glu Val Val Ser His Met Asn Val Val Glu Met Met Met Ser
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Asp Ala Ala Glu
145                 150                 155                 160

Gly Ala Tyr Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
```

```
            210                 215                 220
Val Tyr Gly Thr Glu Pro Val Phe Thr Asp Gly Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
                260                 265                 270

Gly Lys Ser Met Leu Tyr Leu Glu Ala Arg Cys Ile Tyr Ile Thr Lys
                275                 280                 285

Ala Ala Gly Val Gln Gly Leu Gln Asn Gly Ser Val Ser Cys Val Gly
                290                 295                 300

Val Pro Ser Ala Val Pro Ser Gly Ile Arg Ala Ile Leu Ala Glu Asn
305                 310                 315                 320

Leu Ile Cys Ser Ala Leu Asp Leu Glu Cys Ala Ser Ser Asn Asp Gln
                325                 330                 335

Thr Phe Thr His Ser Asp Met Arg Arg Thr Ala Arg Leu Leu Met Gln
                340                 345                 350

Phe Leu Pro Gly Thr Asp Phe Ile Ser Ser Gly Phe Ser Ala Val Pro
                355                 360                 365

Asn Tyr Asp Asn Met Phe Ala Gly Ser Asn Glu Asp Ala Glu Asp Phe
                370                 375                 380

Asp Asp Tyr Asn Val Leu Gln Arg Asp Leu Lys Val Asp Gly Gly Leu
385                 390                 395                 400

Arg Pro Val Leu Glu Ala Asp Val Val Ala Ile Arg Asn Lys Ala Ala
                405                 410                 415

Arg Ala Leu Gln Ala Val Phe Ala Gly Met Gly Leu Pro Pro Ile Thr
                420                 425                 430

Asp Glu Glu Val Ile Ala Ala Thr Tyr Ala His Gly Ser Lys Asp Met
                435                 440                 445

Pro Glu Arg Asn Ile Val Glu Asp Ile Lys Phe Ala Gln Glu Ile Ile
                450                 455                 460

Ser Lys Asn Arg Thr Gly Leu Glu Val Val Lys Ala Leu Ala Gln Gly
465                 470                 475                 480

Gly Phe Glu Asp Val Ala Gln Asp Met Leu Asn Ile Gln Lys Ala Lys
                485                 490                 495

Ile Ala Gly Asp Tyr Leu His Thr Ser Ala Ile Ile Lys Gly Asp Asn
                500                 505                 510

Gln Val Leu Ser Ala Val Asn Asp Val Asn Asp Tyr Ala Gly Pro Ala
                515                 520                 525

Thr Gly Tyr Arg Leu Glu Gly Ala Arg Trp Glu Glu Ile Lys Asn Ile
                530                 535                 540

Pro Asn Ala Leu Asp Pro Asn Glu Leu Gly
545                 550

<210> SEQ ID NO 186
<211> LENGTH: 224
<212> TYPE: PRT
<213> ORGANISM: Yersinia intermedia

<400> SEQUENCE: 186

Met Val Asp Ile Asn Glu Lys Leu Leu Arg Gln Ile Ile Glu Gly Val
1               5                   10                  15

Leu Gln Glu Met Gln Gly Asp Lys Asn Thr Val Ser Phe Lys Gln Asp
                20                  25                  30
```

```
Thr Gln Pro Ala Ala Ala Ala Thr Val Ala Glu Gly Asn Phe Leu
         35                  40                  45

Thr Glu Val Gly Glu Ala Arg Pro Gly Ser Asn Gln Asp Glu Val Ile
 50                  55                  60

Ile Ala Val Gly Pro Ala Phe Gly Leu Ser Gln Thr Ala Asn Ile Val
 65                  70                  75                  80

Gly Ile Pro His Lys Asn Ile Leu Arg Glu Leu Ile Ala Gly Ile Glu
                 85                  90                  95

Glu Glu Gly Ile Lys Ala Arg Val Ile Arg Cys Phe Lys Ser Ser Asp
                100                 105                 110

Val Ala Phe Val Ala Val Glu Gly Asn Arg Leu Ser Gly Ser Gly Ile
            115                 120                 125

Ser Ile Gly Ile Gln Ser Lys Gly Thr Thr Val Ile His Gln Gln Gly
130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
210                 215                 220

<210> SEQ ID NO 187
<211> LENGTH: 175
<212> TYPE: PRT
<213> ORGANISM: Yersinia intermedia

<400> SEQUENCE: 187

Met Asn Ser Glu Ala Ile Glu Ser Met Val Arg Asp Val Leu Ser Lys
 1               5                  10                  15

Met Asn Ser Leu Gln Ser Gln Thr Pro Ala Ala Cys Ala Ala Pro
             20                  25                  30

Ala Thr Ser Ser Arg Asn Asp Ala Lys Val Ser Asp Tyr Pro Leu Ala
         35                  40                  45

Asn Lys His Pro Asp Trp Val Lys Thr Ala Thr Asn Lys Thr Leu Asp
 50                  55                  60

Asp Leu Thr Leu Ala Asn Val Leu Asn Gly Ser Val Thr Ser Gln Asp
 65                  70                  75                  80

Leu Arg Ile Thr Pro Glu Ile Leu Arg Ile Gln Ala Ser Ile Ala Arg
                 85                  90                  95

Asp Ala Gly Arg Pro Leu Leu Ala Ile Asn Phe Glu Arg Ala Ala Glu
                100                 105                 110

Leu Thr Ala Val Pro Asp Asp Lys Val Leu Asp Ile Tyr Asn Ala Leu
            115                 120                 125

Arg Pro Phe Arg Ser Ser Lys Glu Glu Leu Asn Ala Ile Ala Asp Asp
        130                 135                 140

Leu Glu Gln Thr Tyr Lys Ala Thr Ile Cys Ala Ala Phe Val Arg Glu
145                 150                 155                 160

Ala Ala Val Leu Tyr Val Gln Arg Lys Lys Leu Lys Gly Asp Asp
                165                 170                 175

<210> SEQ ID NO 188
```

-continued

<211> LENGTH: 554
<212> TYPE: PRT
<213> ORGANISM: Listeria welshimeri

<400> SEQUENCE: 188

```
Met Lys Ser Lys Arg Phe Glu Glu Leu Ala Lys Arg Pro Val Asn Gln
1               5                   10                  15

Asp Gly Phe Val Lys Glu Trp Ile Glu Gly Leu Ile Ala Met Glu
            20                  25                  30

Ser Pro Asn Asp Pro Lys Pro Ser Ile Lys Ile Glu Asn Gly Lys Val
        35                  40                  45

Val Glu Met Asp Ser Lys Lys Leu Ala Asp Phe Asp Leu Ile Asp His
50                  55                  60

Phe Ile Ala Lys Tyr Gly Val Asp Leu Ser Arg Ala Glu Glu Val Met
65                  70                  75                  80

Gln Met Asp Ser Val Lys Leu Ala Asn Met Leu Cys Asp Pro Asn Val
                85                  90                  95

Pro Arg Glu Lys Ile Val Leu Leu Thr Thr Ala Met Thr Pro Ala Lys
            100                 105                 110

Ile Val Glu Val Val Ser Gln Met Asn Val Val Glu Met Met Met Ser
        115                 120                 125

Met Gln Lys Met Arg Ser Arg Arg Thr Pro Thr Thr Gln Ala His Val
    130                 135                 140

Thr Asn Leu Arg Asp Asn Pro Val Gln Ile Ala Ala Asp Ala Ala Glu
145                 150                 155                 160

Ala Ala Ile Arg Gly Phe Asp Glu Gln Glu Thr Thr Val Ala Val Val
                165                 170                 175

Arg Tyr Ala Pro Phe Asn Ala Leu Ser Leu Leu Val Gly Ser Gln Thr
            180                 185                 190

Gly Arg Gly Gly Val Leu Thr Gln Cys Ser Leu Glu Glu Ala Thr Glu
        195                 200                 205

Leu Glu Leu Gly Met Arg Gly Leu Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Ile Leu Ala Ser Ala Tyr Ala Ser Arg Gly Leu Lys Met
                245                 250                 255

Arg Phe Thr Ser Gly Thr Gly Ser Glu Val Gln Met Gly Tyr Ala Glu
            260                 265                 270

Gly Lys Ser Met Leu Tyr Leu Glu Ser Arg Cys Ile Phe Ile Thr Lys
        275                 280                 285

Ala Ala Gly Val Gln Gly Leu Gln Asn Gly Ser Ile Ser Cys Ile Gly
    290                 295                 300

Ile Pro Gly Ala Val Pro Ser Gly Ile Arg Ala Val Leu Ala Glu Asn
305                 310                 315                 320

Leu Ile Ala Val Met Leu Asp Leu Glu Val Ala Ser Gly Asn Asp Gln
                325                 330                 335

Thr Phe Ser His Ser Asp Ile Arg Arg Thr Ala Arg Leu Leu Met Gln
            340                 345                 350

Phe Leu Pro Gly Thr Asp Tyr Ile Ser Ser Gly Tyr Ser Ala Thr Pro
        355                 360                 365

Asn Tyr Asp Asn Met Phe Ala Gly Ser Asn Phe Asp Ala Asp Asp Phe
    370                 375                 380

Asp Asp Tyr Asn Ile Leu Gln Arg Asp Leu Lys Val Asp Gly Gly Leu
```

```
           385                 390                 395                 400
Thr Pro Val Thr Glu Glu Val Val Ala Val Arg Asn Lys Ala Ala
                405                 410                 415

Arg Val Ile Gln Val Val Phe Glu Lys Leu Gly Leu Pro Thr Val Thr
            420                 425                 430

Asp Glu Glu Val Glu Ala Ala Thr Tyr Ala Arg Gly Ser Asn Asp Met
            435                 440                 445

Pro Glu Arg Asn Met Val Glu Asp Ile Lys Ala Ala Glu Met Met
450                 455                 460

Asp Arg Gly Val Thr Gly Leu Asp Val Lys Ala Leu Ser Ala Gly
465                 470                 475                 480

Gly Phe Asp Asp Val Ala Glu Ser Val Leu Asn Met Leu Lys Gln Arg
                485                 490                 495

Val Ser Gly Asp Phe Leu His Thr Ser Ala Ile Ile Asp Lys Asp Trp
            500                 505                 510

Asn Val Ile Ser Ser Val Asn Asp Leu Asn Asp Tyr Ala Gly Pro Gly
            515                 520                 525

Thr Gly Tyr Arg Leu Glu Gly Glu Arg Trp Glu Lys Leu Lys Asn Ile
            530                 535                 540

Ala Val Ala Val Asp Ala Asn Glu Leu Asp
545                 550

<210> SEQ ID NO 189
<211> LENGTH: 219
<212> TYPE: PRT
<213> ORGANISM: Listeria welshimeri

<400> SEQUENCE: 189

Met Val Glu Ile Asn Glu Lys Val Leu Arg Gly Ile Ile Ser Glu Val
1               5                   10                  15

Leu Asp Glu Leu Gln Leu Lys Glu Asp Lys Val Ser Phe Gln Lys Glu
            20                  25                  30

Pro Ser Asn Pro Val Val Ser Asp Glu Ser Phe Leu Thr Glu Val Gly
        35                  40                  45

Asp Ala Lys Pro Gly Arg Gln Lys Asp Glu Val Val Ile Ala Val Ala
    50                  55                  60

Pro Ala Phe Gly Lys Tyr Gln Thr Lys Asn Ile Val Gly Val Pro His
65                  70                  75                  80

Lys Gln Ile Leu Arg Glu Val Ile Ala Gly Ile Glu Glu Gly Leu
                85                  90                  95

Lys Ala Arg Val Val Arg Val Phe Arg Ser Ser Asp Val Ala Phe Val
            100                 105                 110

Ala Val Glu Gly Asp Arg Leu Ser Gly Ser Gly Ile Cys Ile Gly Ile
        115                 120                 125

Gln Ser Arg Gly Thr Ala Leu Ile His Gln Lys Asp Leu Gln Pro Leu
130                 135                 140

Ser Asn Leu Glu Leu Phe Pro Gln Ala Pro Leu Ile Thr Leu Glu Thr
145                 150                 155                 160

Tyr Arg Ala Ile Gly Lys Asn Ala Ala Lys Tyr Ala Lys Gly Glu Ser
                165                 170                 175

Pro Asn Pro Val Pro Met Val Asn Asp Gln Met Ala Arg Pro Lys Phe
            180                 185                 190

Gln Ala Lys Ala Ala Leu Leu His Ile Lys Glu Thr Lys His Val Val
        195                 200                 205
```

```
Gln Gly Lys Asn Ala Val Glu Leu Gln Val Asn
    210                 215
```

<210> SEQ ID NO 190
<211> LENGTH: 170
<212> TYPE: PRT
<213> ORGANISM: Listeria welshimeri

<400> SEQUENCE: 190

```
Met Asn Gln Glu Ala Leu Glu Asn Met Val Arg Asn Ile Leu Gln Glu
1               5                   10                  15

Val Asn Ser Gly Ala Val Ser Thr Thr Thr Ser Gln Lys Val Ser Gly
            20                  25                  30

Asp Thr Leu Thr Val Arg Asp Tyr Pro Leu Gly Lys Lys Arg Pro Glu
        35                  40                  45

Leu Val Lys Thr Ser Thr Ser Lys Ser Leu Asp Asp Ile Thr Leu Lys
    50                  55                  60

Ser Val Leu Asp Gly Thr Ile Lys Pro Glu Asp Val Arg Val Thr Ala
65                  70                  75                  80

Glu Thr Leu Lys Met Gln Ala Gln Val Ala Arg Asp Ala Gly Arg Ala
                85                  90                  95

Thr Leu Ala Asn Asn Phe Glu Arg Ala Ala Glu Leu Thr Ile Val Pro
            100                 105                 110

Asp Glu Arg Ile Leu Glu Ile Tyr Asn Ala Met Arg Pro Tyr Arg Ser
        115                 120                 125

Ser Lys Glu Glu Leu Leu Ala Ile Ala Asp Glu Leu Glu Ser Val Tyr
    130                 135                 140

His Ala Thr Ile Cys Ser Asn Tyr Val Arg Glu Ala Ala Gln Leu Tyr
145                 150                 155                 160

Gln Glu Arg Lys Lys Leu Lys Gly Asp Asn
                165                 170
```

<210> SEQ ID NO 191
<211> LENGTH: 554
<212> TYPE: PRT
<213> ORGANISM: Listeria innocua

<400> SEQUENCE: 191

```
Met Lys Ser Lys Arg Phe Glu Glu Leu Ala Lys Arg Pro Val Asn Gln
1               5                   10                  15

Asp Gly Phe Val Lys Glu Trp Ile Glu Gly Leu Ile Ala Met Glu
            20                  25                  30

Ser Pro Asn Asp Pro Lys Pro Ser Ile Lys Ile Glu Asn Gly Lys Val
        35                  40                  45

Val Glu Met Asp Ser Lys Lys Leu Ala Asp Phe Asp Leu Ile Asp His
    50                  55                  60

Phe Ile Ala Lys Tyr Gly Val Asp Leu Ser Arg Ala Glu Glu Val Met
65                  70                  75                  80

Lys Met Asp Ser Val Lys Leu Ala Asn Met Leu Cys Asp Pro Asn Val
                85                  90                  95

Pro Arg Glu Lys Ile Val Leu Leu Thr Thr Ala Met Thr Pro Ala Lys
            100                 105                 110

Ile Val Glu Val Val Ser Gln Met Asn Val Val Glu Met Met Met Ser
        115                 120                 125

Met Gln Lys Met Arg Ser Arg Thr Pro Thr Thr Gln Ala His Val
    130                 135                 140
```

```
Thr Asn Leu Arg Asp Asn Pro Val Gln Ile Ala Asp Ala Ala Glu
145                 150                 155                 160

Ala Ala Ile Arg Gly Phe Asp Glu Gln Glu Thr Thr Val Ala Val Val
            165                 170                 175

Arg Tyr Ala Pro Phe Asn Ala Leu Ser Leu Leu Val Gly Ser Gln Thr
                180                 185                 190

Gly Arg Gly Gly Val Leu Thr Gln Cys Ser Leu Glu Glu Ala Thr Glu
        195                 200                 205

Leu Glu Leu Gly Met Arg Gly Leu Thr Cys Tyr Ala Glu Thr Ile Ser
    210                 215                 220

Val Tyr Gly Thr Glu Pro Val Phe Thr Asp Gly Asp Thr Pro Trp
225                 230                 235                 240

Ser Lys Gly Ile Leu Ala Ser Ala Tyr Ala Ser Arg Gly Leu Lys Met
                245                 250                 255

Arg Phe Thr Ser Gly Thr Gly Ser Glu Val Gln Met Gly Tyr Ala Glu
                260                 265                 270

Gly Lys Ser Met Leu Tyr Leu Glu Ser Arg Cys Ile Phe Ile Thr Lys
        275                 280                 285

Ala Ala Gly Val Gln Gly Leu Gln Asn Gly Ser Ile Ser Cys Ile Gly
    290                 295                 300

Ile Pro Gly Ala Val Pro Ser Gly Ile Arg Ala Val Leu Ala Glu Asn
305                 310                 315                 320

Leu Ile Ala Val Met Leu Asp Leu Glu Val Ala Ser Gly Asn Asp Gln
                325                 330                 335

Thr Phe Ser His Ser Asp Ile Arg Arg Thr Ala Arg Leu Leu Met Gln
                340                 345                 350

Phe Leu Pro Gly Thr Asp Tyr Ile Ser Ser Gly Tyr Ser Ala Thr Pro
                355                 360                 365

Asn Tyr Asp Asn Met Phe Ala Gly Ser Asn Phe Asp Ala Asp Asp Phe
370                 375                 380

Asp Asp Tyr Asn Ile Leu Gln Arg Asp Leu Lys Val Asp Gly Gly Leu
385                 390                 395                 400

Thr Pro Val Thr Glu Glu Val Val Ala Val Arg Asn Lys Ala Ala
                405                 410                 415

Arg Val Ile Gln Val Val Phe Asp Lys Leu Gly Leu Pro Ala Val Thr
            420                 425                 430

Asp Glu Glu Val Glu Ala Ala Thr Tyr Ala Arg Gly Ser Asn Asp Met
        435                 440                 445

Pro Glu Arg Asn Met Val Glu Asp Ile Lys Ala Ala Glu Met Met
450                 455                 460

Asp Arg Gly Val Thr Gly Leu Asp Val Val Lys Ala Leu Ala Ala Gly
465                 470                 475                 480

Gly Phe Asp Asp Val Ala Glu Ser Val Leu Asn Met Leu Lys Gln Arg
                485                 490                 495

Val Ser Gly Asp Phe Leu His Thr Ser Ala Ile Ile Asp Lys Asp Trp
            500                 505                 510

Asn Val Ile Ser Ser Val Asn Asp Leu Asn Asp Tyr Ala Gly Pro Gly
                515                 520                 525

Thr Gly Tyr Arg Leu Glu Gly Glu Arg Trp Glu Lys Leu Lys Asp Ile
        530                 535                 540

Ala Val Ala Val Asp Ala Asn Glu Leu Asp
545                 550
```

```
<210> SEQ ID NO 192
<211> LENGTH: 219
<212> TYPE: PRT
<213> ORGANISM: Listeria innocua

<400> SEQUENCE: 192

Met Val Glu Ile Asn Glu Lys Val Leu Arg Gly Ile Ile Ser Glu Val
1               5                   10                  15

Leu Asp Glu Leu Gln Leu Lys Glu Asp Lys Val Ser Phe Gln Lys Glu
            20                  25                  30

Gln Pro Ser Val Ala Val Ser Asp Glu Ser Phe Leu Thr Glu Val Gly
        35                  40                  45

Asp Ala Lys Pro Gly Arg Gln Lys Asp Glu Val Val Ile Ala Val Ala
    50                  55                  60

Pro Ala Phe Gly Lys Tyr Gln Thr Lys Asn Ile Val Gly Val Pro His
65                  70                  75                  80

Lys Gln Ile Leu Arg Glu Val Ile Ala Gly Ile Glu Glu Gly Leu
                85                  90                  95

Lys Ala Arg Val Val Arg Val Phe Arg Ser Ser Asp Val Ala Phe Val
            100                 105                 110

Ala Val Glu Gly Asp Lys Leu Ser Gly Ser Gly Ile Cys Ile Gly Ile
        115                 120                 125

Gln Ser Arg Gly Thr Ala Leu Ile His Gln Lys Asp Leu Gln Pro Leu
    130                 135                 140

Ser Asn Leu Glu Leu Phe Pro Gln Ala Pro Leu Ile Thr Leu Glu Thr
145                 150                 155                 160

Tyr Arg Ala Ile Gly Lys Asn Ala Ala Lys Tyr Ala Lys Gly Glu Ser
                165                 170                 175

Pro Asn Pro Val Pro Met Val Asn Asp Gln Met Ala Arg Pro Lys Phe
            180                 185                 190

Gln Ala Lys Ala Ala Leu Leu His Ile Lys Glu Thr Lys His Val Val
        195                 200                 205

Gln Gly Lys Asn Ala Val Glu Leu Gln Val Asn
    210                 215

<210> SEQ ID NO 193
<211> LENGTH: 170
<212> TYPE: PRT
<213> ORGANISM: Listeria innocua

<400> SEQUENCE: 193

Met Asn Gln Glu Ala Leu Glu Asn Met Val Arg Asn Ile Leu Gln Glu
1               5                   10                  15

Val Asn Ser Gly Ala Val Thr Thr Thr Thr Ser Gln Lys Ala Ser Gly
            20                  25                  30

Asp Ser Leu Thr Val Arg Asp Tyr Pro Leu Gly Thr Lys Arg Pro Glu
        35                  40                  45

Leu Val Lys Thr Ala Ser Ser Lys Ser Leu Asp Asp Ile Thr Leu Lys
    50                  55                  60

Ser Val Leu Asp Gly Thr Ile Lys Pro Glu Asp Val Arg Val Thr Ala
65                  70                  75                  80

Glu Thr Leu Lys Met Gln Ala Gln Val Ala Arg Asp Ala Gly Arg Ala
                85                  90                  95

Thr Leu Ala Asn Asn Phe Glu Arg Ala Ala Glu Leu Thr Val Val Pro
            100                 105                 110

Asp Glu Arg Ile Leu Glu Ile Tyr Asn Ala Met Arg Pro Tyr Arg Ser
```

```
            115                 120                 125
Ser Arg Glu Leu Leu Ala Ile Ala Asp Glu Leu Glu Asn Val Tyr
    130                 135                 140

Gln Ala Thr Ile Cys Ser Asn Tyr Val Arg Glu Ala Ala Gln Leu Tyr
145                 150                 155                 160

Gln Glu Arg Lys Lys Leu Lys Gly Asp Asn
                165                 170

<210> SEQ ID NO 194
<211> LENGTH: 554
<212> TYPE: PRT
<213> ORGANISM: Listeria monocytogenes

<400> SEQUENCE: 194

Met Lys Ser Lys Arg Phe Glu Glu Leu Ala Lys Arg Pro Val Asn Gln
1               5                   10                  15

Asp Gly Phe Val Lys Glu Trp Ile Glu Glu Gly Leu Ile Ala Met Glu
                20                  25                  30

Ser Pro Asn Asp Pro Lys Pro Ser Ile Lys Ile Glu Asn Gly Lys Val
            35                  40                  45

Val Glu Met Asp Ser Lys Lys Leu Ala Asp Phe Asp Leu Ile Asp His
50                  55                  60

Phe Ile Ala Lys Tyr Gly Val Asp Leu Ser Arg Ala Glu Glu Val Met
65                  70                  75                  80

Gln Met Asp Ser Val Lys Leu Ala Asn Met Leu Cys Asp Pro Asn Val
                85                  90                  95

Pro Arg Glu Lys Ile Val Leu Leu Thr Thr Ala Met Thr Pro Ala Lys
            100                 105                 110

Ile Val Glu Val Ser Gln Met Asn Val Val Glu Met Met Met Ser
            115                 120                 125

Met Gln Lys Met Arg Ser Arg Arg Thr Pro Thr Thr Gln Ala His Val
    130                 135                 140

Thr Asn Leu Arg Asp Asn Pro Val Gln Ile Ala Ala Asp Ala Ala Glu
145                 150                 155                 160

Ala Ala Ile Arg Gly Phe Asp Glu Gln Glu Thr Thr Val Ala Val Val
                165                 170                 175

Arg Tyr Ala Pro Phe Asn Ala Leu Ser Leu Leu Val Gly Ser Gln Thr
            180                 185                 190

Gly Arg Gly Gly Val Leu Thr Gln Cys Ser Leu Glu Glu Ala Thr Glu
        195                 200                 205

Leu Glu Leu Gly Met Arg Gly Leu Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Ile Leu Ala Ser Ala Tyr Ala Ser Arg Gly Leu Lys Met
                245                 250                 255

Arg Phe Thr Ser Gly Thr Gly Ser Glu Val Gln Met Gly Tyr Ala Glu
            260                 265                 270

Gly Lys Ser Met Leu Tyr Leu Glu Ser Arg Cys Ile Phe Ile Thr Lys
        275                 280                 285

Ala Ala Gly Val Gln Gly Leu Gln Asn Gly Ser Ile Ser Cys Ile Gly
    290                 295                 300

Ile Pro Gly Ala Val Pro Ser Gly Ile Arg Ala Val Leu Ala Glu Asn
305                 310                 315                 320
```

```
Leu Ile Ala Val Met Leu Asp Leu Glu Val Ala Ser Gly Asn Asp Gln
            325                 330                 335

Thr Phe Ser His Ser Asp Ile Arg Arg Thr Ala Arg Leu Leu Met Gln
        340                 345                 350

Phe Leu Pro Gly Thr Asp Tyr Ile Ser Ser Gly Tyr Ser Ala Thr Pro
            355                 360                 365

Asn Tyr Asp Asn Met Phe Ala Gly Ser Asn Phe Asp Ala Asp Asp Phe
        370                 375                 380

Asp Asp Tyr Asn Ile Leu Gln Arg Asp Leu Lys Val Asp Gly Gly Leu
385                 390                 395                 400

Thr Pro Val Thr Glu Glu Val Val Ala Val Arg Asn Lys Ala Ala
            405                 410                 415

Arg Val Ile Gln Ala Val Phe Asp Lys Leu Gly Leu Pro Glu Val Thr
            420                 425                 430

Asp Ala Glu Val Glu Ala Ala Thr Tyr Ala Arg Gly Ser Lys Asp Met
        435                 440                 445

Pro Glu Arg Asn Met Val Glu Asp Ile Lys Ala Ala Glu Met Met
    450                 455                 460

Asp Arg Gly Val Thr Gly Leu Asp Val Val Lys Ala Leu Ser Ala Gly
465                 470                 475                 480

Gly Phe Asp Asp Val Ala Glu Ser Val Leu Asn Met Leu Lys Gln Arg
            485                 490                 495

Val Ser Gly Asp Phe Leu His Thr Ser Ala Ile Ile Asp Lys Asp Trp
        500                 505                 510

Asn Val Ile Ser Ser Val Asn Asp Leu Asn Asp Tyr Ala Gly Pro Gly
        515                 520                 525

Thr Gly Tyr Arg Leu Glu Gly Glu Arg Trp Glu Lys Leu Lys Asp Ile
    530                 535                 540

Ala Val Ala Val Asp Ala Asn Glu Leu Asp
545                 550

<210> SEQ ID NO 195
<211> LENGTH: 219
<212> TYPE: PRT
<213> ORGANISM: Listeria monocytogenes

<400> SEQUENCE: 195

Met Val Glu Ile Asn Glu Lys Val Leu Arg Gly Ile Ile Ser Glu Val
1               5                   10                  15

Leu Asp Glu Leu Gln Leu Lys Glu Asp Lys Val Ser Phe Gln Lys Glu
            20                  25                  30

Gln Pro Ser Val Ala Val Ser Asp Glu Ser Phe Leu Thr Glu Val Gly
        35                  40                  45

Asp Ala Glu Pro Gly Arg Gln Lys Asp Glu Val Val Ile Ala Val Ala
    50                  55                  60

Pro Ala Phe Gly Lys Tyr Gln Thr Lys Asn Ile Val Gly Val Pro His
65                  70                  75                  80

Lys Gln Ile Leu Arg Glu Leu Ile Ala Gly Ile Glu Glu Gly Leu
            85                  90                  95

Lys Ala Arg Val Val Arg Val Phe Arg Ser Ser Asp Val Ala Phe Val
            100                 105                 110

Ala Val Glu Gly Asp Lys Leu Ser Gly Ser Gly Ile Cys Ile Gly Ile
        115                 120                 125

Gln Ser Arg Gly Thr Ala Leu Ile His Gln Lys Asp Leu Gln Pro Leu
    130                 135                 140
```

```
Ser Asn Leu Glu Leu Phe Pro Gln Ala Pro Leu Ile Thr Leu Glu Thr
145                 150                 155                 160

Tyr Arg Ala Ile Gly Lys Asn Ala Ala Lys Tyr Ala Lys Gly Glu Ser
                165                 170                 175

Pro Asn Pro Val Pro Met Val Asn Asp Gln Met Ala Arg Pro Lys Phe
            180                 185                 190

Gln Ala Lys Ala Ala Leu Leu His Ile Lys Gly Thr Lys His Val Val
        195                 200                 205

Gln Gly Lys Asn Ala Val Glu Leu Gln Val Asn
    210                 215

<210> SEQ ID NO 196
<211> LENGTH: 170
<212> TYPE: PRT
<213> ORGANISM: Listeria monocytogenes

<400> SEQUENCE: 196

Met Asn Gln Glu Ala Leu Glu Asn Met Val Arg Asn Ile Leu Gln Glu
1               5                   10                  15

Val Asn Ser Gly Gly Val Ser Thr Thr Thr Ser Gln Lys Val Ser Gly
            20                  25                  30

Asp Thr Leu Thr Val Arg Asp Tyr Pro Leu Gly Thr Lys Arg Pro Glu
        35                  40                  45

Leu Val Lys Thr Ser Thr Ser Lys Ser Leu Asp Asp Ile Thr Leu Lys
    50                  55                  60

Ser Val Leu Asp Gly Thr Ile Lys Pro Glu Asp Val Arg Val Thr Ala
65                  70                  75                  80

Glu Thr Leu Lys Met Gln Ala Gln Val Ala Arg Asp Ala Gly Arg Ala
                85                  90                  95

Thr Leu Ala Asn Asn Phe Glu Arg Ala Ala Glu Leu Thr Ile Val Pro
            100                 105                 110

Asp Glu Arg Ile Leu Glu Ile Tyr Asn Ala Met Arg Pro Tyr Arg Ser
        115                 120                 125

Ser Arg Glu Glu Leu Leu Ala Ile Ala Asp Gly Leu Glu Ser Val Tyr
    130                 135                 140

His Ala Thr Ile Cys Ser Asn Tyr Val Arg Gly Ala Ala Gln Leu Tyr
145                 150                 155                 160

Gln Glu Arg Lys Lys Leu Lys Gly Asp Asn
                165                 170

<210> SEQ ID NO 197
<211> LENGTH: 554
<212> TYPE: PRT
<213> ORGANISM: Salmonella enterica subsp. enterica serovar Typhi

<400> SEQUENCE: 197

Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Glu Phe Asp Leu Ile Asp His
    50                  55                  60

Phe Ile Ala Arg Tyr Gly Ile Asn Leu Asn Arg Ala Glu Glu Val Met
65                  70                  75                  80
```

```
Ala Met Asp Ser Val Lys Leu Ala Asn Met Leu Cys Asp Pro Asn Val
            85                  90                  95
Lys Arg Ser Glu Ile Val Pro Leu Thr Thr Ala Met Thr Pro Ala Lys
            100                 105                 110
Ile Val Glu Val Val Ser His Met Asn Val Val Glu Met Met Met Ala
            115                 120                 125
Met Gln Lys Met Arg Ala Arg Arg Thr Pro Ser Gln Gln Ala His Val
    130                 135                 140
Thr Asn Val Lys Asp Asn Pro Val Gln Ile Ala Ala Asp Ala Ala Glu
145                 150                 155                 160
Gly Ala Trp Arg Gly Phe Asp Glu Gln Glu Thr Thr Val Ala Val Ala
                165                 170                 175
Arg Tyr Ala Pro Phe Asn Ala Ile Ala Leu Leu Val Gly Ser Gln Val
            180                 185                 190
Gly Arg Pro Gly Val Leu Thr Gln Cys Ser Leu Glu Glu Ala Thr Glu
            195                 200                 205
Leu Lys Leu Gly Met Leu Gly His Thr Cys Tyr Ala Glu Thr Ile Ser
    210                 215                 220
Val Tyr Gly Thr Glu Pro Val Phe Thr Asp Gly Asp Thr Pro Trp
225                 230                 235                 240
Ser Lys Gly Phe Leu Ala Ser Ser Tyr Ala Ser Arg Gly Leu Lys Met
            245                 250                 255
Arg Phe Thr Ser Gly Ser Gly Ser Glu Val Gln Met Gly Tyr Ala Glu
            260                 265                 270
Gly Lys Ser Met Leu Tyr Leu Glu Ala Arg Cys Ile Tyr Ile Thr Lys
            275                 280                 285
Ala Ala Gly Val Gln Gly Leu Gln Asn Gly Ser Val Ser Cys Ile Gly
    290                 295                 300
Val Pro Ser Ala Val Pro Ser Gly Ile Arg Ala Val Leu Ala Glu Asn
305                 310                 315                 320
Leu Ile Cys Ser Ser Leu Asp Leu Glu Cys Ser Ser Ser Asn Asp Gln
            325                 330                 335
Thr Phe Thr His Ser Asp Met Arg Arg Thr Ala Arg Leu Leu Met Gln
            340                 345                 350
Phe Leu Pro Gly Thr Asp Phe Ile Ser Ser Gly Tyr Ser Ala Val Pro
            355                 360                 365
Asn Tyr Asp Asn Met Phe Ala Gly Ser Asn Glu Asp Ala Glu Asp Phe
370                 375                 380
Asp Asp Tyr Asn Val Ile Gln Arg Asp Leu Lys Val Asp Gly Gly Leu
385                 390                 395                 400
Arg Pro Val Arg Glu Glu Asp Val Ile Ala Ile Arg Asn Lys Ala Ala
            405                 410                 415
Arg Ala Leu Gln Ala Val Phe Ala Gly Met Gly Leu Pro Pro Ile Thr
            420                 425                 430
Asp Glu Glu Val Glu Ala Ala Thr Tyr Ala His Gly Ser Lys Asp Met
            435                 440                 445
Pro Glu Arg Asn Ile Val Glu Asp Ile Lys Phe Ala Gln Glu Ile Ile
            450                 455                 460
Asn Lys Asn Arg Asn Gly Leu Glu Val Val Lys Ala Leu Ala Gln Gly
465                 470                 475                 480
Gly Phe Thr Asp Val Ala Gln Asp Met Leu Asn Ile Gln Lys Ala Lys
                485                 490                 495
```

```
Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550

<210> SEQ ID NO 198
<211> LENGTH: 224
<212> TYPE: PRT
<213> ORGANISM: Salmonella enterica subsp. enterica serovar Typhi

<400> SEQUENCE: 198

Met Glu Ile Asn Glu Lys Leu Leu Arg Gln Ile Ile Glu Asp Val Leu
1               5                   10                  15

Arg Asp Met Lys Gly Ser Asp Lys Pro Val Ser Phe Asn Thr Pro Ala
            20                  25                  30

Ala Ser Thr Ala Pro Gln Thr Ala Ala Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Leu Pro His Lys Ser Ile Leu Arg Glu Val Ile Ala Gly Ile Glu
                85                  90                  95

Glu Glu Gly Ile Arg Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Asp Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Thr Leu
    210                 215                 220

<210> SEQ ID NO 199
<211> LENGTH: 173
<212> TYPE: PRT
<213> ORGANISM: Salmonella enterica subsp. enterica serovar Typhi

<400> SEQUENCE: 199

Met Asn Thr Asp Ala Ile Glu Ser Met Val Arg Asp Val Leu Ser Arg
1               5                   10                  15

Met Asn Ser Leu Gln Gly Asp Ala Pro Ala Ala Pro Ala Ala Gly
            20                  25                  30

Gly Thr Ser Arg Ser Ala Lys Val Ser Asp Tyr Pro Leu Ala Asn Lys
        35                  40                  45
```

```
His Pro Glu Trp Val Lys Thr Ala Thr Asn Lys Thr Leu Asp Asp Phe
 50                  55                  60

Thr Leu Glu Asn Val Leu Ser Asn Lys Val Thr Ala Gln Asp Met Arg
 65                  70                  75                  80

Ile Thr Pro Lys Thr Leu Arg Leu Gln Ala Ser Ile Ala Lys Asp Ala
                 85                  90                  95

Gly Arg Asp Arg Leu Ala Met Asn Phe Glu Arg Ala Ala Glu Leu Thr
                100                 105                 110

Ala Val Pro Asp Asp Arg Ile Leu Glu Ile Tyr Asn Ala Leu Arg Pro
                115                 120                 125

Tyr Arg Ser Thr Lys Glu Glu Leu Leu Ala Ile Ala Asp Asp Leu Glu
            130                 135                 140

Asn Arg Tyr Gln Ala Lys Ile Cys Ala Ala Phe Val Arg Glu Ala Ala
145                 150                 155                 160

Gly Leu Tyr Val Glu Arg Lys Leu Lys Gly Asp Asp
                165                 170

<210> SEQ ID NO 200
<211> LENGTH: 554
<212> TYPE: PRT
<213> ORGANISM: Escherichia coli

<400> SEQUENCE: 200

Met Arg Ser Lys Arg Phe Glu Ala Leu Ala Lys Arg Pro Val Asn Gln
  1               5                  10                  15

Asp Gly Phe Val Lys Glu Trp Ile Glu Glu Gly Phe Ile Ala Met Glu
                 20                  25                  30

Ser Pro Asn Asp Pro Lys Pro Ser Ile Lys Ile Val Asn Gly Val Val
                 35                  40                  45

Thr Glu Leu Asp Gly Lys Pro Ala Ser Gln Phe Asp Leu Ile Asp His
 50                  55                  60

Phe Ile Ala Arg Tyr Gly Ile Asn Leu Ala Arg Ala Glu Glu Val Ile
 65                  70                  75                  80

Ala Met Asp Ser Val Lys Leu Ala Asn Met Leu Cys Asp Pro Asn Val
                 85                  90                  95

Lys Arg Ser Asp Ile Val Pro Leu Thr Thr Ala Met Thr Pro Ala Lys
                100                 105                 110

Ile Val Glu Val Val Ser Gln Met Asn Val Val Glu Met Met Met Ala
            115                 120                 125

Met Gln Lys Met Arg Ala Arg Arg Thr Pro Ser Gln Gln Ala His Val
            130                 135                 140

Thr Asn Ile Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
                180                 185                 190

Gly Arg Pro Gly Val Leu Thr Gln Cys Ser Leu Glu Glu Ala Thr Glu
            195                 200                 205

Leu Lys Leu Gly Met Leu Gly His Thr Cys Tyr Ala Glu Thr Ile Ser
            210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255
```

```
Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Phe Leu Met Gln
            340                 345                 350

Phe Leu Pro Gly Thr Asp Phe Ile Ser Ser Gly Phe Ser Ala Val Pro
        355                 360                 365

Asn Tyr Asp Asn Met Phe Ala Gly Ser Asn Glu Asp Ala Glu Asp Phe
370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
450                 455                 460

Asn Lys Asn Arg Asn Ser Leu Glu Val Val Lys Ala Leu Ala Gln Gly
465                 470                 475                 480

Gly Phe Thr Asp Val Ala Gln Asp Met Leu Asn Met Gln Lys Ala Lys
                485                 490                 495

Leu Thr Gly Asp Tyr Leu His Thr Ser Ala Ile Ile Val Asp Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
530                 535                 540

Pro Gly Ala Leu Asp Pro Asn Glu Ile Asp
545                 550

<210> SEQ ID NO 201
<211> LENGTH: 222
<212> TYPE: PRT
<213> ORGANISM: Escherichia coli

<400> SEQUENCE: 201

Met Glu Ile Asn Glu Lys Leu Leu Arg Gln Ile Ile Glu Asp Val Leu
1               5                   10                  15

Ala Glu Met Gln Thr Ser Asp Lys Ser Val Ser Phe Arg Ala Pro Val
            20                  25                  30

Ser Ala Thr Val Ser Ser Val Pro Asp Thr Glu Asn Phe Leu Thr Glu
        35                  40                  45

Ile Gly Glu Ala Gln Gln Gly Thr Gln Gln Asp Glu Val Ile Ile Ala
    50                  55                  60

Val Gly Pro Ala Phe Gly Leu Ala Gln Thr Val Asn Ile Ile Gly Ile
```

```
              65                  70                  75                  80
Pro His Lys Asn Ile Leu Arg Glu Val Ile Ala Gly Ile Glu Glu
                85                  90                  95

Gly Ile Lys Ala Arg Val Ile Arg Cys Phe Lys Ser Ser Asp Val Ala
                100                 105                 110

Phe Val Ala Val Glu Gly Asp Arg Leu Ser Gly Ser Gly Ile Ala Ile
                115                 120                 125

Gly Ile Gln Ser Lys Gly Thr Thr Val Ile His Gln Gln Gly Leu Pro
    130                 135                 140

Pro Leu Ser Asn Leu Glu Leu Phe Pro Gln Ala Pro Leu Leu Thr Leu
145                 150                 155                 160

Asp Thr Tyr Arg Gln Ile Gly Lys Asn Ala Ala Arg Tyr Ala Lys Arg
                165                 170                 175

Glu Ser Pro Gln Pro Val Pro Thr Leu Asn Asp Gln Met Ala Arg Pro
                180                 185                 190

Lys Tyr Gln Ala Lys Ser Ala Ile Leu His Ile Lys Glu Thr Lys Tyr
                195                 200                 205

Val Val Thr Gly Lys Lys Pro Gln Glu Leu Arg Val Thr Phe
    210                 215                 220

<210> SEQ ID NO 202
<211> LENGTH: 172
<212> TYPE: PRT
<213> ORGANISM: Escherichia coli

<400> SEQUENCE: 202

Met Asn Thr Asp Ala Ile Glu Ser Met Val Arg Asp Val Leu Asn Arg
1               5                   10                  15

Met Asn Ser Leu Gln Asp Ala Ala Pro Val Ser Ala Val Pro Ser Ala
                20                  25                  30

Ser Ile Gln Ser Ala Lys Val Thr Asp Tyr Pro Leu Ala Asn Lys His
                35                  40                  45

Pro Glu Trp Val Lys Thr Ala Thr Asn Lys Thr Leu Asp Asp Phe Thr
    50                  55                  60

Leu Glu Asn Val Leu Ser Asp Asn Val Thr Ala Gln Asp Met Arg Ile
65                  70                  75                  80

Thr Pro Glu Thr Leu Arg Ile Gln Ala Ala Ile Ala Arg Asp Ala Gly
                85                  90                  95

Arg Asp Arg Leu Ala Met Asn Phe Glu Arg Ala Ala Glu Leu Thr Ser
                100                 105                 110

Val Pro Asp Asp Arg Ile Leu Glu Ile Tyr Asn Ala Leu Arg Pro Tyr
                115                 120                 125

Arg Ser Thr Lys Gln Glu Leu Ile Ala Ile Ala Asp Asp Leu Glu Arg
    130                 135                 140

Arg Tyr Gln Ala Gln Ile Cys Ala Ala Phe Val Arg Glu Ala Ala Glu
145                 150                 155                 160

Leu Tyr Val Glu Arg Lys Lys Leu Lys Gly Asp Asp
                165                 170

<210> SEQ ID NO 203
<211> LENGTH: 554
<212> TYPE: PRT
<213> ORGANISM: Listeria monocytogenes

<400> SEQUENCE: 203

Met Lys Ser Lys Arg Phe Glu Glu Leu Ala Lys Arg Pro Val Asn Gln
```

-continued

```
1               5                   10                  15
Asp Gly Phe Val Lys Glu Trp Ile Glu Glu Gly Leu Ile Ala Met Glu
                20                  25                  30

Ser Pro Asn Asp Pro Lys Pro Ser Ile Lys Ile Glu Asn Gly Lys Val
                35                  40                  45

Val Glu Met Asp Ser Lys Lys Leu Ala Asp Phe Asp Leu Ile Asp His
50                  55                  60

Phe Ile Ala Lys Tyr Gly Val Asp Leu Ser Arg Ala Glu Glu Val Met
65                  70                  75                  80

Gln Met Asp Ser Val Lys Leu Ala Asn Met Leu Cys Asp Pro Asn Val
                85                  90                  95

Pro Arg Glu Lys Ile Val Leu Leu Thr Thr Ala Met Thr Pro Ala Lys
                100                 105                 110

Ile Val Glu Val Val Ser Gln Met Asn Val Val Glu Met Met Met Ser
                115                 120                 125

Met Gln Lys Met Arg Ser Arg Arg Thr Pro Thr Thr Gln Ala His Val
130                 135                 140

Thr Asn Leu Arg Asp Asn Pro Val Gln Ile Ala Ala Asp Ala Ala Glu
145                 150                 155                 160

Ala Ala Ile Arg Gly Phe Asp Glu Gln Glu Thr Thr Val Ala Val Val
                165                 170                 175

Arg Tyr Ala Pro Phe Asn Ala Leu Ser Leu Leu Val Gly Ser Gln Thr
                180                 185                 190

Gly Arg Gly Gly Val Leu Thr Gln Cys Ser Leu Glu Glu Ala Thr Glu
                195                 200                 205

Leu Glu Leu Gly Met Arg Gly Leu Thr Cys Tyr Ala Glu Thr Ile Ser
210                 215                 220

Val Tyr Gly Thr Glu Pro Val Phe Thr Asp Gly Asp Thr Pro Trp
225                 230                 235                 240

Ser Lys Gly Ile Leu Ala Ser Ala Tyr Ala Ser Arg Gly Leu Lys Met
                245                 250                 255

Arg Phe Thr Ser Gly Thr Gly Ser Glu Val Gln Met Gly Tyr Ala Glu
                260                 265                 270

Gly Lys Ser Met Leu Tyr Leu Glu Ser Arg Cys Ile Phe Ile Thr Lys
                275                 280                 285

Ala Ala Gly Val Gln Gly Leu Gln Asn Gly Ser Ile Ser Cys Ile Gly
                290                 295                 300

Ile Pro Gly Ala Val Pro Ser Gly Ile Arg Ala Val Leu Ala Glu Asn
305                 310                 315                 320

Leu Ile Ala Val Met Leu Asp Leu Glu Val Ala Ser Gly Asn Asp Gln
                325                 330                 335

Thr Phe Ser His Ser Asp Ile Arg Arg Thr Ala Arg Leu Leu Met Gln
                340                 345                 350

Phe Leu Pro Gly Thr Asp Tyr Ile Ser Ser Gly Tyr Ser Ala Thr Pro
                355                 360                 365

Asn Tyr Asp Asn Met Phe Ala Gly Ser Asn Phe Asp Ala Asp Asp Phe
                370                 375                 380

Asp Asp Tyr Asn Ile Leu Gln Arg Asp Leu Lys Val Asp Gly Gly Leu
385                 390                 395                 400

Thr Pro Val Thr Glu Glu Glu Val Val Ala Val Arg Asn Lys Ala Ala
                405                 410                 415

Arg Val Ile Gln Ala Val Phe Asp Lys Leu Gly Leu Pro Glu Val Thr
                420                 425                 430
```

```
Asp Ala Glu Val Glu Ala Ala Thr Tyr Ala Arg Gly Ser Lys Asp Met
            435                 440                 445

Pro Glu Arg Asn Met Val Glu Asp Ile Lys Ala Ala Ala Glu Met Met
450                 455                 460

Asp Arg Gly Val Thr Gly Leu Asp Val Val Lys Ala Leu Ser Ala Gly
465                 470                 475                 480

Gly Phe Asp Val Ala Glu Ser Val Leu Asn Met Leu Lys Gln Arg
                485                 490                 495

Val Ser Gly Asp Phe Leu His Thr Ser Ala Ile Ile Asp Lys Asp Trp
                500                 505                 510

Asn Val Ile Ser Ser Val Asn Asp Leu Asn Asp Tyr Ala Gly Pro Gly
                515                 520                 525

Thr Gly Tyr Arg Leu Glu Gly Glu Arg Trp Glu Lys Leu Lys Asp Ile
                530                 535                 540

Ala Val Ala Val Asp Ala Asn Glu Leu Glu
545                 550

<210> SEQ ID NO 204
<211> LENGTH: 219
<212> TYPE: PRT
<213> ORGANISM: Listeria monocytogenes

<400> SEQUENCE: 204

Met Val Glu Ile Asn Glu Lys Val Leu Arg Gly Ile Ile Ser Glu Val
1               5                   10                  15

Leu Asp Glu Leu Gln Leu Lys Glu Asp Lys Val Ser Phe Gln Lys Glu
            20                  25                  30

Gln Pro Ser Val Ala Val Ser Asp Glu Ser Phe Leu Thr Glu Val Gly
        35                  40                  45

Asp Ala Glu Pro Gly Arg Gln Lys Asp Glu Val Val Ile Ala Val Ala
    50                  55                  60

Pro Ala Phe Gly Lys Tyr Gln Thr Lys Asn Ile Val Gly Val Pro His
65                  70                  75                  80

Lys Gln Ile Leu Arg Glu Val Ile Ala Gly Ile Glu Glu Gly Leu
                85                  90                  95

Lys Ala Arg Val Val Arg Val Phe Arg Ser Ser Asp Val Ala Phe Val
            100                 105                 110

Ala Val Glu Gly Asp Lys Leu Ser Gly Ser Gly Ile Cys Ile Gly Ile
            115                 120                 125

Gln Ser Arg Gly Thr Ala Leu Ile His Gln Lys Asp Leu Gln Pro Leu
        130                 135                 140

Ser Asn Leu Glu Leu Phe Pro Gln Ala Pro Leu Ile Thr Leu Glu Thr
145                 150                 155                 160

Tyr Arg Ala Ile Gly Lys Asn Ala Ala Lys Tyr Ala Lys Gly Glu Ser
                165                 170                 175

Pro Asn Pro Val Pro Met Val Asn Asp Gln Met Ala Arg Pro Lys Phe
            180                 185                 190

Gln Ala Lys Ala Ala Leu Leu His Ile Lys Glu Thr Lys His Val Val
        195                 200                 205

Gln Gly Lys Asn Ala Val Glu Leu Gln Val Asn
    210                 215

<210> SEQ ID NO 205
<211> LENGTH: 170
<212> TYPE: PRT
```

<213> ORGANISM: Listeria monocytogenes

<400> SEQUENCE: 205

```
Met Asn Gln Glu Ala Leu Glu Asn Met Val Arg Asn Ile Leu Gln Glu
1               5                   10                  15

Val Asn Ser Gly Ala Val Ser Thr Thr Thr Ser Gln Lys Val Ser Gly
            20                  25                  30

Asp Thr Leu Thr Val Arg Asp Tyr Pro Leu Gly Thr Lys Arg Pro Glu
        35                  40                  45

Leu Val Lys Thr Ser Thr Ser Lys Ser Leu Asp Ile Thr Leu Lys
    50                  55                  60

Ser Val Leu Asp Gly Thr Ile Lys Pro Glu Asp Val Arg Val Thr Ala
65                  70                  75                  80

Glu Thr Leu Lys Met Gln Ala Gln Val Ala Arg Asp Ala Gly Arg Ala
                85                  90                  95

Thr Leu Ala Asn Asn Phe Glu Arg Ala Ala Glu Leu Thr Ile Val Pro
            100                 105                 110

Asp Glu Arg Ile Leu Glu Ile Tyr Asn Ala Met Arg Pro Tyr Arg Ser
        115                 120                 125

Ser Arg Glu Glu Leu Leu Ala Ile Ala Asp Glu Leu Glu Ser Val Tyr
    130                 135                 140

His Ala Thr Ile Cys Ser Asn Tyr Val Arg Glu Ala Ala Gln Leu Tyr
145                 150                 155                 160

Gln Glu Arg Lys Lys Leu Lys Gly Asp Asn
                165                 170
```

<210> SEQ ID NO 206
<211> LENGTH: 553
<212> TYPE: PRT
<213> ORGANISM: Streptococcus sanguinis

<400> SEQUENCE: 206

```
Met Arg Ser Lys Arg Phe Glu Val Leu Ser Glu Arg Pro Ile Asn Gln
1               5                   10                  15

Asp Gly Phe Val Lys Glu Trp Val Glu Glu Gly Leu Val Ala Met Glu
            20                  25                  30

Ser Pro Asn Asp Pro Lys Pro Ser Ile Lys Ile Gln Asn Gly Lys Val
        35                  40                  45

Val Glu Leu Asp Gly Lys Pro Lys Glu Glu Phe Asp Leu Ile Asp Gln
    50                  55                  60

Phe Ile Ala Asn Tyr Gly Ile Asp Leu Ser Leu Ala Glu Glu Val Ile
65                  70                  75                  80

Gln Met Asp Ser Arg Glu Ile Ala Asn Lys Ile Leu Thr Pro Ser Val
                85                  90                  95

Pro Arg Thr Glu Ile Ile Lys Leu Thr Lys Ala Met Thr Pro Ala Lys
            100                 105                 110

Ile Ile Glu Val Val Asn Gln Met Asn Val Val Glu Ile Met Met Cys
        115                 120                 125

Leu Gln Lys Met Arg Thr Arg Lys Gln Thr Ala Thr Gln Ala His Val
    130                 135                 140

Thr Asn Val Asn Asp Asn Pro Val Gln Ile Ala Asp Ala Ala Glu
145                 150                 155                 160

Gly Ala Leu Arg Gly Phe Ala Glu Gln Glu Thr Thr Val Ala Val Val
                165                 170                 175

Arg Tyr Ala Pro Phe Asn Ala Leu Ser Leu Met Ile Gly Ser Gln Val
```

```
            180                 185                 190
Gly Arg Pro Gly Val Leu Thr Gln Cys Ser Leu Glu Glu Ala Thr Glu
            195                 200                 205
Leu Glu Phe Gly Met Arg Gly Phe Thr Ala Tyr Ala Glu Thr Ile Ser
            210                 215                 220
Val Tyr Gly Thr Glu Asp Val Phe Thr Asp Gly Asp Asp Thr Pro Trp
225                 230                 235                 240
Ser Lys Ala Phe Leu Ala Ser Ala Tyr Ala Ser Arg Gly Leu Lys Met
                245                 250                 255
Arg Phe Thr Ser Gly Thr Gly Ser Glu Val Gln Met Gly Gln Ala Glu
            260                 265                 270
Gly Lys Ser Met Leu Tyr Leu Glu Ala Arg Cys Leu Tyr Val Thr Lys
            275                 280                 285
Ala Ala Gly Val Gln Gly Thr Gln Asn Gly Ser Val Ser Cys Ile Gly
            290                 295                 300
Ile Pro Ala Ala Val Pro Ser Gly Ile Arg Ala Val Ala Glu Asn
305                 310                 315                 320
Leu Ile Ala Ser Met Leu Asp Leu Glu Cys Ala Ser Ser Asn Asp Gln
                325                 330                 335
Thr Phe Thr His Ser Asp Leu Arg Arg Ser Val Arg Thr Leu Met Gln
                340                 345                 350
Phe Ala Pro Gly Thr Asp Phe Ile Asn Ser Gly Tyr Ser Ala Thr Pro
            355                 360                 365
Asn Tyr Asp Asn Met Phe Ala Gly Ser Asn Trp Asp Ala Glu Asp Phe
            370                 375                 380
Asp Asp Tyr Asn Val Leu Gln Arg Asp Leu Arg Val Asp Gly Gly Leu
385                 390                 395                 400
Arg Pro Val Arg Glu Glu Val Val Lys Val Arg Asn Lys Ala Ala
                405                 410                 415
Arg Val Met Gln Ala Leu Phe Lys Gly Leu Gly Leu Pro Gln Ile Thr
            420                 425                 430
Asp Glu Glu Val Glu Ala Ala Thr Tyr Ala His Gly Ser Lys Asp Met
            435                 440                 445
Pro Glu Arg Asp Lys Val Glu Asp Ile Lys Ala Ala Gln Gly Ile Leu
            450                 455                 460
Glu Arg Gly Val Gln Gly Ala Asp Leu Ile Lys Ala Leu Ala Asn Asn
465                 470                 475                 480
Gly Phe Pro Glu Val Ala Asn Glu Leu Leu Asn Leu Phe Lys Gln Arg
                485                 490                 495
Val Ala Gly Asp Phe Leu Gln Thr Ser Ala Ile Phe Asp Arg Asp Trp
            500                 505                 510
Asn Val Ile Ser Ala Val Asn Ser Pro Asn Asp Tyr Val Gly Val Gly
            515                 520                 525
Thr Gly His Arg Leu Val Gly Glu Glu Trp Glu Lys Val Lys Asp Ile
            530                 535                 540
Pro Lys Ala Ile Asp Pro Arg Asp Val
545                 550

<210> SEQ ID NO 207
<211> LENGTH: 222
<212> TYPE: PRT
<213> ORGANISM: Streptococcus sanguinis

<400> SEQUENCE: 207
```

```
Met Thr Glu Ile Asn Glu Thr Leu Leu Arg Ser Ile Ala Glu Val
1               5                   10                  15

Met Lys Glu Met Ser Ala Asn Thr Lys Glu Thr Ala Ala Glu Thr Ser
            20                  25                  30

Glu Lys Pro Val Thr Lys Pro Val Ser Asn Glu Lys Ala Val Ile Arg
            35                  40                  45

Thr Val Gly Val Ala Lys Pro Ser Gln Ser Thr Asp Glu Val Val Ile
 50                  55                  60

Ala Val Gly Pro Ala Phe Gly Glu Gln Gln Val Lys Thr Met Val Asp
 65                  70                  75                  80

Ile Pro His Thr Glu Val Leu Arg Gln Leu Val Ala Gly Ile Glu Glu
                85                  90                  95

Glu Gly Leu Lys Ala Arg Ile Val Lys Val Tyr Arg Ser Ser Asp Val
            100                 105                 110

Ala Phe Val Ala Val Glu Gly Asp His Leu Ser Gly Ser Gly Ile Ser
            115                 120                 125

Ile Gly Val Gln Ser Lys Gly Thr Thr Val Ile His Gln Arg Asp Leu
        130                 135                 140

Pro Pro Leu Ser Asn Leu Glu Leu Phe Pro Gln Ala Pro Leu Leu Thr
145                 150                 155                 160

Pro Glu Thr Tyr Arg Leu Ile Gly Lys Asn Ala Ala Lys Tyr Ala Lys
                165                 170                 175

Gly Glu Thr Pro Asn Pro Val Pro Thr Leu Asn Asp Gln Met Ala Arg
            180                 185                 190

Pro Lys Tyr Gln Ala Tyr Ser Ala Leu Leu His Ile Lys Glu Thr Lys
        195                 200                 205

Leu Val Lys Arg Gly Lys Pro Ala Asp Glu Cys Gln Val Ile
    210                 215                 220

<210> SEQ ID NO 208
<211> LENGTH: 171
<212> TYPE: PRT
<213> ORGANISM: Streptococcus sanguinis

<400> SEQUENCE: 208

Met Ser Glu Ser Val Glu Thr Leu Val Lys Gln Ile Leu Ala Glu Leu
1               5                   10                  15

Ser Asp Ser Gly Ser Ala Ser Gln Gly Ala Val Asn Arg Pro Val Ser
            20                  25                  30

Ser Asp Glu Ala Thr Ala Ala Asp Tyr Pro Ile Ser Lys Lys His Pro
        35                  40                  45

Asp Trp Ile Lys Val Gly Gln Asp Lys Lys Phe Glu Asp Ile Thr Leu
 50                  55                  60

Glu Asn Ile Leu Ser Gly Tyr Val Lys Ala Glu Asp Leu Arg Ile Lys
 65                  70                  75                  80

Pro Glu Ile Leu Ile Lys Gln Gly Glu Ile Ala Lys Asn Ala Gly Arg
                85                  90                  95

Glu Ala Ile Gln Tyr Asn Phe Ser Arg Ala Ala Glu Leu Thr Lys Val
            100                 105                 110

Pro Asp Ala Arg Val Leu Glu Ile Tyr Asn Ala Leu Arg Pro Tyr Arg
            115                 120                 125

Ser Ser Lys Gln Glu Leu Leu Asp Ile Ala Asn Glu Leu Glu Asn Gln
        130                 135                 140

Tyr Gly Ala Val Ile Cys Ala Gly Phe Val Arg Glu Ala Ala Glu Asn
145                 150                 155                 160
```

```
              Tyr Glu Arg Arg Lys Lys Leu Lys Gly Asp Asn
                              165                 170

<210> SEQ ID NO 209
<211> LENGTH: 555
<212> TYPE: PRT
<213> ORGANISM: Escherichia blattae

<400> SEQUENCE: 209

Met Arg Arg Ser Lys Arg Phe Glu Val Leu Glu Lys Arg Pro Val Asn
1               5                   10                  15

Gln Asp Gly Leu Ile Gly Glu Trp Pro Glu Glu Gly Leu Ile Ala Met
            20                  25                  30

Gly Ser Pro Trp Asp Pro Pro Ser Ser Val Lys Val Glu Gln Gly Arg
        35                  40                  45

Ile Val Glu Leu Asp Gly Lys Ala Arg Ala Asp Phe Asp Met Ile Asp
    50                  55                  60

Arg Phe Ile Ala Asp Tyr Ala Ile Asn Ile Asp Glu Thr Glu His Ala
65                  70                  75                  80

Met Gly Leu Asp Ala Leu Thr Ile Ala Arg Met Leu Val Asp Ile Asn
                85                  90                  95

Val Ser Arg Ala Glu Ile Ile Lys Val Thr Thr Ala Ile Thr Pro Ala
            100                 105                 110

Lys Ala Val Glu Val Met Ser His Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Ile Gly Ser Gln
            180                 185                 190

Ser Gly Arg Pro Gly Val Leu Thr Gln Cys Ser Val Glu Glu Ala Thr
        195                 200                 205

Glu Leu Glu Leu Gly Met Arg Gly Phe Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ala
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Gly Ser Cys Ile
    290                 295                 300

Gly Met Thr Gly Ala Val Pro Ser Gly Ile Arg Pro Gly Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
```

```
                        355                 360                 365
Pro Asn Tyr Asp Asn Met Phe Ala Gly Ser Asn Phe Asp Ala Glu Asp
    370                 375                 380

Phe Asp Gly Tyr Asn Ile Leu Gln Arg Asp Leu Met Val Asp Gly Gly
385                 390                 395                 400

Leu Arg Pro Val Ser Glu Glu Thr Ile Ala Ile Arg Asn Lys Ala
                    405                 410                 415

Ala Arg Ala Val Gln Ala Val Phe Arg Gly Leu Gly Leu Pro Pro Val
                420                 425                 430

Thr Asp Glu Glu Val Thr Ala Ala Thr Tyr Ala His Gly Ser Lys Asp
            435                 440                 445

Met Pro Pro Arg Asn Val Val Glu Asp Leu Ser Ala Val Glu Glu Met
        450                 455                 460

Met Lys Arg Asn Ile Thr Gly Leu Asp Ile Val Arg Ala Leu Ser Val
465                 470                 475                 480

Asn Gly Phe Asp Val Ala Asn Asn Ile Leu Asn Met Leu Arg Gln
                485                 490                 495

Arg Val Thr Gly Asp Tyr Leu Gln Thr Ser Ala Ile Leu Asp Arg Glu
                500                 505                 510

Phe Glu Val Val Ser Ala Val Asn Asp Ile Asn Asp Tyr Gln Gly Pro
            515                 520                 525

Gly Thr Gly Tyr Arg Ile Ser Pro Gln Arg Trp Glu Glu Ile Lys Asn
        530                 535                 540

Ile Ala Thr Val Ile Gln Pro Asp Ser Ile Glu
545                 550                 555

<210> SEQ ID NO 210
<211> LENGTH: 196
<212> TYPE: PRT
<213> ORGANISM: Escherichia blattae

<400> SEQUENCE: 210

Met Glu Thr Thr Gln Lys Lys Ala Pro Val Phe Thr Leu Asn Leu Val
1               5                   10                  15

Glu Ser Gly Val Ala Lys Pro Gly Glu Arg Ser Asp Glu Val Val Ile
                20                  25                  30

Gly Val Gly Pro Ala Phe Asp Lys Tyr Gln His Lys Thr Leu Ile Asp
            35                  40                  45

Met Pro His Lys Ala Ile Ile Lys Glu Met Val Ala Gly Val Glu Glu
        50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175
```

```
His Val Val Gly Asp Ala Lys Pro Val Thr Leu Asn Ile Glu Ile Thr
            180                 185                 190

Arg Glu Glu Ala
        195

<210> SEQ ID NO 211
<211> LENGTH: 140
<212> TYPE: PRT
<213> ORGANISM: Escherichia blattae

<400> SEQUENCE: 211

Met Thr Thr Thr Lys Met Ser Ala Ala Asp Tyr Pro Leu Ala Ser Arg
1               5                   10                  15

Cys Pro Glu Arg Ile Gln Thr Pro Thr Gly Lys Pro Leu Thr Asp Ile
            20                  25                  30

Thr Leu Glu Asn Val Leu Ala Gly Lys Val Gly Thr Gln Asp Glu Arg
        35                  40                  45

Ile Ser Arg Glu Thr Leu Glu Tyr Gln Ala Gln Ile Ala Glu Gln Met
    50                  55                  60

His Arg His Ala Ile Ala Arg Asn Leu Arg Arg Ala Gly Glu Leu Ile
65                  70                  75                  80

Ala Ile Pro Asp Ala Arg Ile Leu Glu Ile Tyr Asn Ala Leu Arg Pro
                85                  90                  95

Tyr Arg Ser Ser Val Glu Glu Leu Leu Ala Ile Ala Asp Glu Leu Glu
            100                 105                 110

Thr Arg Tyr Gln Ala Thr Val Asn Ala Ala Phe Ile Arg Glu Ala Ala
        115                 120                 125

Glu Val Tyr Arg Gln Arg Asp Lys Leu Arg Lys Glu
    130                 135                 140

<210> SEQ ID NO 212
<211> LENGTH: 554
<212> TYPE: PRT
<213> ORGANISM: Clostridium perfringens

<400> SEQUENCE: 212

Met Lys Ser Lys Arg Phe Gln Val Leu Ser Glu Arg Pro Val Asn Gln
1               5                   10                  15

Asp Gly Leu Ile Gly Glu Trp Ala Asp Glu Gly Leu Ile Ala Leu Asp
            20                  25                  30

Ser Pro Asn Asp Pro Lys Ser Ser Ile Lys Ile Glu Asn Gly Ile Ile
        35                  40                  45

Thr Glu Leu Asp Gly Arg Ser Arg Asp Glu Phe Asp Met Ile Asp Lys
    50                  55                  60

Phe Ile Ala Glu Tyr Ala Ile Asn Ile Glu Asp Ala Glu Ala Ser Met
65                  70                  75                  80

Lys Leu Ser Ser Lys Glu Ile Ala Arg Arg Leu Val Asp Ile Asn Val
                85                  90                  95

Ser Arg Asp Glu Ile Val Lys Ile Thr Thr Ser Ile Thr Pro Met Lys
            100                 105                 110

Ala Val Glu Val Ile Gln Glu Met Asn Val Val Glu Met Met Met Ala
        115                 120                 125

Leu Gln Lys Met Arg Ala Arg Arg Thr Pro Ala Asn Gln Cys His Val
    130                 135                 140

Thr Asn Val Lys Asp Asn Pro Val Gln Ile Ala Ala Asp Ala Ala Glu
145                 150                 155                 160
```

Ala Ala Leu Arg Gly Phe Ala Glu Gln Glu Thr Thr Val Gly Ile Val
            165                 170                 175

Arg Tyr Ala Pro Phe Asn Ala Leu Ala Ile Leu Val Gly Ser Gln Val
        180                 185                 190

Gly Arg Gly Gly Val Leu Thr Gln Cys Ala Val Glu Glu Ala Thr Glu
    195                 200                 205

Leu Asp Leu Gly Met Arg Gly Leu Thr Ser Tyr Ala Glu Thr Val Ser
210                 215                 220

Val Tyr Gly Thr Glu Ser Val Phe Thr Asp Gly Asp Thr Pro Trp
225                 230                 235                 240

Ser Lys Ala Phe Leu Ala Ser Ala Tyr Ala Ser Arg Gly Leu Lys Met
                245                 250                 255

Arg Phe Thr Ser Gly Ser Gly Ser Glu Ala Leu Met Gly Tyr Ser Glu
            260                 265                 270

Gly Arg Ser Met Leu Tyr Leu Glu Ser Arg Cys Ile Tyr Ile Thr Lys
        275                 280                 285

Gly Ala Gly Val Gln Gly Leu Gln Asn Gly Ala Val Ser Cys Ile Gly
    290                 295                 300

Met Thr Gly Ala Val Pro Ser Gly Ile Arg Ala Val Leu Gly Glu Asn
305                 310                 315                 320

Leu Ile Ala Ala Met Leu Asp Ile Glu Val Ala Ser Ala Asn Asp Gln
                325                 330                 335

Thr Phe Ser His Ser Asp Ile Arg Arg Thr Ala Arg Met Leu Met Gln
            340                 345                 350

Met Leu Pro Gly Thr Asp Phe Ile Phe Ser Gly Tyr Ser Ala Val Pro
        355                 360                 365

Asn Tyr Asp Asn Met Phe Ala Gly Ser Asn Phe Asp Ala Glu Asp Phe
    370                 375                 380

Asp Asp Tyr Asn Ile Leu Gln Arg Asp Leu Lys Val Asp Gly Gly Leu
385                 390                 395                 400

Arg Pro Val Thr Glu Glu Thr Ile Lys Val Arg Asn Lys Ala Ala
                405                 410                 415

Lys Cys Ile Gln Ile Ile Phe Arg Glu Leu Gly Phe Pro Glu Val Thr
            420                 425                 430

Asp Glu Glu Val Glu Ala Ala Thr Tyr Cys His Gly Ser Lys Glu Met
        435                 440                 445

Pro Asn Arg Asn Val Val Glu Asp Leu Lys Ala Ala Glu Glu Met Leu
    450                 455                 460

Glu Arg Arg Ile Thr Gly Leu Asp Ile Ile Lys Ala Leu Ser Lys Asn
465                 470                 475                 480

Gly Met Glu Asp Ile Ala Asn Asn Leu Leu Asn Met Leu Lys Gln Arg
                485                 490                 495

Val Thr Gly Asp Tyr Leu Gln Thr Ser Ala Ile Leu Asp Lys Asp Phe
            500                 505                 510

Asn Val Ile Ser Ala Val Asn Asp Val Asn Asp Tyr Met Gly Pro Gly
        515                 520                 525

Thr Gly Tyr Arg Leu Asp Gly Gln Arg Trp Glu Glu Ile Lys Lys Val
    530                 535                 540

Pro Thr Val Met Arg Pro Glu Asp Ile Glu
545                 550

<210> SEQ ID NO 213
<211> LENGTH: 190
<212> TYPE: PRT

<213> ORGANISM: Clostridium perfringens

<400> SEQUENCE: 213

```
Met Thr Met Glu Glu Arg Thr Phe Ile Pro Glu Ile Thr Val Glu
 1               5                  10                  15

Val Gly Glu Ala Lys Val Gly Leu Arg Ser Asp Glu Val Ile Gly
                20                  25                  30

Leu Ala Pro Ala Phe Leu Lys Tyr Gln Asn Lys Thr Ile Val Asp Val
                35                  40                  45

Pro His Thr Glu Thr Leu Leu Glu Ile Ile Ala Gly Ile Glu Glu Glu
            50                  55                  60

Gly Leu His Ala Arg Val Val Arg Ile Leu Arg Thr Ser Asp Val Ser
65                  70                  75                  80

Phe Ile Ala His Asp Ala Ala Cys Leu Ser Gly Ser Gly Ile Gly Ile
                85                  90                  95

Gly Ile Gln Ser Lys Gly Thr Thr Val Ile His Gln Lys Asp Leu Leu
                100                 105                 110

Pro Leu Asn Asn Leu Glu Leu Phe Ser Gln Ala Pro Leu Leu Thr Thr
                115                 120                 125

Glu Thr Tyr Arg Leu Ile Gly Lys Asn Ala Ala Lys Tyr Ala Lys Gly
            130                 135                 140

Glu Ser Pro Thr Pro Val Pro Val Lys Asn Asp Gln Met Val Arg Pro
145                 150                 155                 160

Lys Phe Met Ala Lys Ala Ala Leu Leu His Ile Lys Glu Thr Lys His
                165                 170                 175

Val Glu Pro Gly Lys Lys Pro Val Gln Leu Glu Val Lys Phe
                180                 185                 190
```

<210> SEQ ID NO 214
<211> LENGTH: 141
<212> TYPE: PRT
<213> ORGANISM: Clostridium perfringens

<400> SEQUENCE: 214

```
Met Glu Asn Lys Arg Met Thr Ala Ala Asp Tyr Pro Leu Thr Ser Lys
 1               5                  10                  15

Arg Lys Gly Asp Ile Lys Thr Pro Thr Gly Lys Ala Leu Glu Asp Ile
                20                  25                  30

Thr Leu Glu Lys Val Leu Ser Gly Glu Ile Asn Ala Asp Ile Arg
                35                  40                  45

Ile Ser Pro Glu Thr Leu Glu Met Gln Ala Gln Ile Ala Glu Ser Met
            50                  55                  60

Asn Arg Asp Ala Ile Ala Arg Asn Phe Arg Arg Ala Ala Glu Leu Ile
65                  70                  75                  80

Arg Val Pro Asp Asp Arg Ile Leu Glu Met Tyr Asn Ala Leu Arg Pro
                85                  90                  95

Tyr Arg Ser Thr Lys Glu Asp Leu Phe Lys Ile Ala Asp Glu Leu Glu
                100                 105                 110

Thr Lys Tyr Asp Ala Lys Val Asn Ala Asp Phe Val Arg Glu Ala Ala
                115                 120                 125

Glu Val Tyr Glu Thr Arg Asn Lys Leu Arg Ile Glu Glu
            130                 135                 140
```

<210> SEQ ID NO 215
<211> LENGTH: 408
<212> TYPE: PRT

<213> ORGANISM: Yersinia frederiksenii

<400> SEQUENCE: 215

```
Met Lys Asp Asn Pro Val Gln Ile Ala Ala Asp Ala Ala Glu Gly Ala
1               5                   10                  15

Phe Arg Gly Phe Asp Glu Gln Glu Thr Thr Val Ala Val Ala Arg Tyr
            20                  25                  30

Ala Pro Phe Asn Ala Ile Ala Leu Leu Val Gly Ser Gln Val Gly Arg
        35                  40                  45

Pro Gly Val Leu Thr Gln Cys Ser Leu Glu Glu Ala Thr Glu Leu Lys
    50                  55                  60

Leu Gly Met Leu Gly His Thr Cys Tyr Ala Glu Thr Ile Ser Val Tyr
65                  70                  75                  80

Gly Thr Glu Pro Val Phe Thr Asp Gly Asp Asp Thr Pro Trp Ser Lys
                85                  90                  95

Gly Phe Leu Ala Ser Ser Tyr Ala Ser Arg Gly Leu Lys Met Arg Phe
            100                 105                 110

Thr Ser Gly Ser Gly Ser Glu Val Gln Met Gly Tyr Ala Glu Gly Lys
        115                 120                 125

Ser Met Leu Tyr Leu Glu Ala Arg Cys Ile Tyr Ile Thr Lys Ala Ala
    130                 135                 140

Gly Val Gln Gly Leu Gln Asn Gly Ser Val Ser Cys Val Gly Val Pro
145                 150                 155                 160

Ser Ala Val Pro Ser Gly Ile Arg Ala Ile Leu Ala Glu Asn Leu Ile
                165                 170                 175

Cys Ser Ala Leu Asp Leu Glu Cys Ala Ser Ser Asn Asp Gln Thr Phe
            180                 185                 190

Thr His Ser Asp Met Arg Arg Thr Ala Arg Leu Leu Met Gln Phe Leu
        195                 200                 205

Pro Gly Thr Asp Phe Ile Ser Ser Gly Tyr Ser Ala Val Pro Asn Tyr
    210                 215                 220

Asp Asn Met Phe Ala Gly Ser Asn Glu Asp Ala Glu Asp Phe Asp Asp
225                 230                 235                 240

Tyr Asn Val Met Gln Arg Asp Leu Lys Val Asp Gly Gly Leu Arg Pro
                245                 250                 255

Val Leu Glu Ala Asp Val Val Ala Ile Arg Asn Lys Ala Ala Arg Ala
            260                 265                 270

Leu Gln Ala Val Phe Ala Gly Met Gly Leu Pro Pro Ile Thr Asp Glu
        275                 280                 285

Glu Val Ile Ala Ala Thr Tyr Ala His Gly Ser Lys Asp Met Pro Glu
    290                 295                 300

Arg Asn Ile Val Glu Asp Ile Lys Phe Ala Gln Glu Ile Ile Ser Lys
305                 310                 315                 320

Asn Arg Thr Gly Leu Glu Val Val Lys Ala Leu Ala Gln Gly Gly Phe
                325                 330                 335

Glu Asp Val Ala Gln Asp Met Leu Asn Ile Gln Lys Ala Lys Ile Ala
            340                 345                 350

Gly Asp Tyr Leu His Thr Ser Ala Ile Ile Lys Gly Asp Asn Gln Val
        355                 360                 365

Leu Ser Ala Val Asn Asp Val Asn Asp Tyr Ala Gly Pro Ala Thr Gly
    370                 375                 380

Tyr Arg Leu Glu Gly Ala Arg Trp Glu Glu Ile Lys Asn Ile Pro Asn
385                 390                 395                 400
```

```
Ala Leu Asp Pro Asn Glu Leu Gly
            405
```

```
<210> SEQ ID NO 216
<211> LENGTH: 224
<212> TYPE: PRT
<213> ORGANISM: Yersinia frederiksenii

<400> SEQUENCE: 216
```

```
Met Val Asp Ile Asn Glu Lys Leu Leu Arg Gln Ile Ile Glu Gly Val
1               5                   10                  15

Leu Gln Glu Met Gln Gly Asp Gln Asn Thr Val Ser Phe Lys Gln Glu
            20                  25                  30

Thr Gln Pro Ala Ala Ala Val Asn Thr Thr Ala Ser Gly Asp Phe Leu
        35                  40                  45

Thr Glu Val Gly Glu Ala Arg Pro Gly Thr His Gln Asp Glu Val Ile
    50                  55                  60

Ile Ala Val Gly Pro Ala Phe Gly Leu Ser Gln Thr Thr Asn Ile Val
65                  70                  75                  80

Gly Ile Pro His Lys Asn Ile Leu Arg Glu Leu Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Leu Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

```
<210> SEQ ID NO 217
<211> LENGTH: 175
<212> TYPE: PRT
<213> ORGANISM: Yersinia frederiksenii

<400> SEQUENCE: 217
```

```
Met Asn Ser Glu Ala Ile Glu Ser Met Val Arg Asp Val Leu Ser Lys
1               5                   10                  15

Met Asn Ser Leu Gln Gly Gln Ser Pro Ala Ala Ala Cys Pro Ala Pro
            20                  25                  30

Ala Ala Ser Ser Arg Ser Asp Ala Lys Val Ser Asp Tyr Pro Leu Ala
        35                  40                  45

Asn Lys His Pro Asp Trp Val Lys Thr Ala Thr Asn Lys Thr Leu Asp
    50                  55                  60

Asp Leu Thr Leu Ala Asn Val Leu Asn Gly Ser Val Thr Ser Gln Asp
65                  70                  75                  80

Leu Arg Ile Thr Pro Glu Ile Leu Arg Ile Gln Ala Ser Ile Ala Lys
                85                  90                  95
```

```
Asp Ala Gly Arg Pro Leu Leu Ala Met Asn Phe Glu Arg Ala Ala Glu
                100                 105                 110

Leu Thr Ala Val Pro Asp Asp Lys Val Leu Asp Ile Tyr Asn Ala Leu
            115                 120                 125

Arg Pro Phe Arg Ser Ser Lys Asp Glu Leu Asn Ala Ile Ala Asp Asp
        130                 135                 140

Leu Glu Lys Thr Tyr Lys Ala Thr Ile Cys Ala Ala Phe Val Arg Glu
145                 150                 155                 160

Ala Ala Val Leu Tyr Val Gln Arg Lys Lys Leu Lys Gly Asp Asp
                165                 170                 175

<210> SEQ ID NO 218
<211> LENGTH: 554
<212> TYPE: PRT
<213> ORGANISM: Thermoanaerobacter ethanolicus

<400> SEQUENCE: 218

Met Arg Ser Lys Arg Phe Glu Val Leu Ala Lys Arg Pro Val Asn Gln
1               5                   10                  15

Asp Gly Ile Ile Ala Glu Trp Pro Glu Val Gly Leu Ile Ala Val Asn
            20                  25                  30

Ser Pro Asn Asp Pro Lys Pro Ser Ile Lys Ile Glu Asn Gly Lys Ile
        35                  40                  45

Val Glu Met Asp Gly Lys Lys Arg Glu Glu Phe Asp Met Ile Glu Gln
50                  55                  60

Phe Ile Ala Asp Tyr Ala Ile Asn Ile Glu Met Ala Glu Lys Ala Met
65                  70                  75                  80

Gly Met Asp Ser Leu Glu Ile Ala Arg Met Leu Val Asp Ile Asn Val
                85                  90                  95

Pro Arg Glu Glu Ile Val Lys Ile Val Ser Gly Leu Thr Pro Ala Lys
                100                 105                 110

Val Val Glu Val Asn His Leu Asn Val Val Glu Ile Met Met Ala
            115                 120                 125

Ile Gln Lys Met Arg Ala Arg Lys Arg Pro Gly Asn Gln Ala His Val
130                 135                 140

Thr Asn Leu Arg Asp Asn Pro Val Leu Ile Ala Ala Asp Ala Ala Glu
145                 150                 155                 160

Ala Ala Leu Arg Gly Phe Asp Glu Leu Glu Thr Thr Val Gly Ile Thr
                165                 170                 175

Arg Tyr Ala Pro Phe Asn Ala Leu Ala Leu Leu Val Gly Ser Gln Thr
            180                 185                 190

Gly Arg Gly Gly Val Leu Thr Gln Asp Ala Leu Glu Glu Ser Phe Glu
        195                 200                 205

Leu Thr Ile Gly Met Arg Gly Phe Thr Ser Tyr Ala Glu Thr Ile Ser
210                 215                 220

Val Tyr Gly Thr Glu Gln Val Phe Val Asp Gly Asp Thr Pro Trp
225                 230                 235                 240

Ser Lys Ala Phe Leu Ala Ser Ala Tyr Ala Ser Arg Gly Leu Lys Met
                245                 250                 255

Arg Phe Thr Ser Gly Thr Gly Ser Glu Cys Gln Met Gly Phe Ala Glu
            260                 265                 270

Gly Lys Ser Met Leu Tyr Leu Glu Ala Arg Cys Val Met Ile Ala Lys
        275                 280                 285

Gly Ala Gly Val Gln Gly Leu Gln Asn Gly Ser Ile Ser Cys Ile Gly
        290                 295                 300
```

```
Val Pro Gly Ala Val Pro Gly Gly Ile Arg Ala Val Ala Ala Glu Asn
305                 310                 315                 320

Leu Ile Thr Met Met Glu Asp Leu Glu Val Ala Ser Gly Asn Asp Gln
            325                 330                 335

Thr Phe Ser His Ser Asp Ile Arg Arg Thr Ala Arg Thr Leu Leu Leu
            340                 345                 350

Met Leu Pro Gly Thr Asp Leu Ile Phe Ser Gly Tyr Ser Ala Val Pro
            355                 360                 365

Asn Tyr Asp Asn Met Phe Ala Gly Ser Asn Phe Asp Ala Glu Asp Phe
370                 375                 380

Asp Asp Tyr Leu Met Leu Gln Arg Asp Leu Met Val Glu Gly Gly Val
385                 390                 395                 400

Ser Pro Val Thr Glu Asp Glu Val Ile Ala Val Arg Asn Lys Ala Ala
                405                 410                 415

Arg Ala Leu Gln Ser Val Phe Lys Lys Leu Asn Leu Pro Pro Ile Thr
            420                 425                 430

Asp Glu Glu Val Glu Ala Ala Thr Tyr Ala His Gly Ser Lys Asp Met
            435                 440                 445

Pro Pro Arg Asp Val Asn Ala Asp Leu Lys Ala Ala Thr Glu Leu Met
            450                 455                 460

Glu Lys Gly Leu Thr Gly Leu Asp Val Val Lys Ala Leu Ala Glu Ser
465                 470                 475                 480

Gly Phe Thr Asp Val Ala Glu Asn Val Leu Asn Met Leu Lys Gln Arg
                485                 490                 495

Ile Ala Gly Asp Tyr Leu Gln Thr Ser Ala Val Leu Asp Lys Asp Phe
            500                 505                 510

Asn Ile Asp Ser Ala Val Asn Asn Ser Asn Asp Tyr Lys Gly Pro Gly
            515                 520                 525

Thr Gly Phe Arg Leu Ser Lys Glu Arg Trp Glu Arg Ile Lys Asn Val
            530                 535                 540

Pro Gln Ala Leu Lys Pro Glu Asp Leu Ala
545                 550

<210> SEQ ID NO 219
<211> LENGTH: 229
<212> TYPE: PRT
<213> ORGANISM: Thermoanaerobacter ethanolicus

<400> SEQUENCE: 219

Met Val Lys Thr Glu Ser Leu Val Glu Gln Ile Val Lys Glu Val Leu
1               5                   10                  15

Lys Lys Leu Glu Asn Val Glu Ile Ala Ala Pro Ala Thr Gln Ser Ser
            20                  25                  30

Asp Asp Ala Asn Gln Glu Trp Glu Met Ile Ile Glu Glu Ile Gly Glu
        35                  40                  45

Ala Lys Gln Gly Val Asn Val Asp Glu Val Val Ile Gly Val Ser Pro
    50                  55                  60

Gly Phe Tyr Ile Lys Phe Lys Lys Asn Ile Ile Gly Ile Pro Leu Gly
65                  70                  75                  80

Asn Ile Leu Arg Glu Ile Ile Ser Gly Ile Thr Glu Gln Gly Leu Lys
                85                  90                  95

Ala Arg Ile Val Arg Val Lys His Thr Ala Asp Val Gly Phe Ile Ala
            100                 105                 110

His Thr Ala Ala Lys Leu Ser Gly Ser Gly Ile Gly Ile Gly Ile Gln
```

```
            115                 120                 125
Ser Arg Gly Thr Val Val Ile His Gln Lys Asp Leu Gln Pro Leu Asn
    130                 135                 140

Asn Leu Glu Leu Phe Pro Gln Cys Pro Val Leu Thr Leu Glu Thr Tyr
145                 150                 155                 160

Arg Ala Ile Gly Arg Asn Ala Ala Leu Tyr Ala Lys Gly Glu Ser Pro
                165                 170                 175

Thr Pro Val Pro Val Gln Asn Asp Gln Met Ala Arg Pro Lys Tyr Gln
            180                 185                 190

Ala Ile Ala Ala Val Met His Asn Phe Glu Thr Lys Tyr Val Gln Thr
        195                 200                 205

Gly Ala Lys Pro Val Glu Leu Lys Val Ser Phe Ala Arg Lys Gly Gly
    210                 215                 220

Asn Lys Ser Asp Arg
225

<210> SEQ ID NO 220
<211> LENGTH: 182
<212> TYPE: PRT
<213> ORGANISM: Thermoanaerobacter ethanolicus

<400> SEQUENCE: 220

Met Leu Glu Lys Gly Gly Ile Arg Val Ile Asp Glu Lys Thr Leu Glu
1               5                   10                  15

Ile Ile Val Arg Glu Val Leu Thr Asn Leu Thr Ser Asp Lys Gly Thr
            20                  25                  30

Gln Asn Gln Gln Lys Thr Ala Ser Ser Ser Leu Pro Lys Leu Asp Pro
        35                  40                  45

Lys Arg Asp Tyr Pro Leu Ala Lys Asn Lys Pro Glu Leu Ala Lys Ser
    50                  55                  60

Ile Thr Gly Lys Thr Ile Asn Glu Ile Thr Leu Gln Ala Val Arg Glu
65                  70                  75                  80

Gly Lys Val Leu Pro Asp Asp Leu Lys Ile Ser Pro Glu Thr Leu Leu
                85                  90                  95

Ala Gln Ala Glu Ile Ala Glu Ala Ala Gly Arg Lys Gln Leu Ala Asn
            100                 105                 110

Asn Phe Arg Arg Ala Ala Glu Leu Thr Lys Val Pro Asp Lys Arg Ile
        115                 120                 125

Leu Glu Ile Tyr Asn Ala Leu Arg Pro Tyr Arg Ser Thr Lys Glu Glu
    130                 135                 140

Leu Leu Ala Ile Ala Asp Glu Leu Asp Asn Ala Tyr Gly Ala Lys Val
145                 150                 155                 160

Cys Ala Ala Phe Val Arg Glu Ala Ala Glu Val Tyr Glu Arg Arg Gly
                165                 170                 175

Arg Leu Lys Gly Met Glu
            180

<210> SEQ ID NO 221
<211> LENGTH: 558
<212> TYPE: PRT
<213> ORGANISM: Lactobacillus hilgardii

<400> SEQUENCE: 221

Met Lys Arg Gln Lys Arg Phe Glu Lys Leu Glu Lys Arg Pro Val His
1               5                   10                  15

Leu Asp Gly Phe Val Lys Glu Trp Asp Asp Glu Gly Leu Val Ala Met
```

```
                    20                  25                  30
Glu Gly Lys Asn Asp Pro Lys Pro Ser Ile Lys Ile Glu Asn Gly Val
             35                  40                  45

Val Thr Glu Leu Asp Gly Lys Lys Asp Asp Phe Asp Leu Ile Asp
 50                  55                  60

Gln Tyr Ile Ala Glu Tyr Gly Ile Asn Leu Asn Asn Ala Glu Lys Val
 65                  70                  75                  80

Met Lys Met Asp Ser Leu Lys Ile Ala Lys Met Leu Val Asp Pro Asn
                 85                  90                  95

Asp Ser Arg Ser Glu Ile Ile Gln Leu Thr Thr Ala Met Thr Pro Ala
             100                 105                 110

Lys Ala Glu Glu Val Ile Ser Lys Leu Asn Phe Ala Glu Met Ile Met
         115                 120                 125

Ala Ala Gln Lys Met Arg Pro Arg Thr Pro Ala Thr Gln Cys His
         130                 135                 140

Ile Thr Asn Thr Leu Asp Asn Pro Val Gln Ile Ala Ala Asp Ala Ala
145                 150                 155                 160

Glu Ala Ala Leu Arg Gly Phe Pro Glu Gln Glu Thr Thr Thr Ala Val
                 165                 170                 175

Ala Arg Tyr Ala Pro Met Asn Ala Ile Ser Ile Met Val Gly Ser Gln
             180                 185                 190

Thr Gly Arg Pro Gly Val Ile Thr Gln Cys Ser Val Glu Glu Ser Glu
         195                 200                 205

Glu Leu Ser Leu Gly Met Arg Gly Phe Thr Ala Tyr Ala Glu Thr Ile
     210                 215                 220

Ser Val Tyr Gly Thr Asp Arg Val Phe Thr Asp Gly Asp Asp Thr Pro
225                 230                 235                 240

Trp Ser Lys Gly Phe Leu Ala Ser Cys Tyr Ala Ser Arg Gly Leu Lys
                 245                 250                 255

Met Arg Phe Thr Ser Gly Ala Gly Ser Glu Ala Met Met Gly Tyr Thr
             260                 265                 270

Glu Gly Lys Ser Met Leu Tyr Leu Glu Ala Arg Cys Ile Phe Ile Thr
         275                 280                 285

Lys Ala Ser Gly Val Gln Gly Leu Gln Asn Gly Gly Val Ser Cys Ile
     290                 295                 300

Gly Ile Pro Gly Ala Val Pro Gly Gly Ile Arg Glu Val Leu Gly Glu
305                 310                 315                 320

Asn Leu Leu Cys Met Met Leu Asp Ile Glu Cys Ala Ser Gly Asn Asp
                 325                 330                 335

Gln Ala Phe Ser His Ser Asp Ile Arg Arg Thr Glu Arg Met Ile Gly
             340                 345                 350

Gln Phe Ile Ala Gly Thr Asp Tyr Ile Ser Ser Gly Tyr Ala Ala Glu
         355                 360                 365

Glu Asn Arg Asp Asn Thr Phe Ala Gly Ser Asn Met Asp Val Leu Asp
     370                 375                 380

Tyr Asp Asp Tyr Cys Ser Met Glu Arg Asp Leu Ala Val Asn Gly Ser
385                 390                 395                 400

Ile Leu Pro Ile His Glu Glu Asp Ala Ile Lys Ile Arg Asn Arg Ala
                 405                 410                 415

Ala Lys Ala Ile Gln Ala Val Phe Asp Gly Leu Gly Leu Pro Pro Ile
             420                 425                 430

Ser Asp Glu Glu Val Glu Ala Ala Thr Tyr Ala Ser Asn Ser Gly Asp
         435                 440                 445
```

```
Met Pro Lys Arg Asp Met Val Gln Asp Ile Lys Ala Ala Gln Asp Leu
    450                 455                 460

Met Asn Arg Asp Ile Thr Ile Ser Asp Ile Ile Lys Ala Leu Tyr Asn
465                 470                 475                 480

His Gly Phe Lys Asp Val Ala Gln Ala Val Leu Thr Leu Ala Gln Gln
                485                 490                 495

Lys Val Cys Gly Asp Tyr Leu Gln Thr Ser Ala Ile Phe Asn Gly Lys
            500                 505                 510

Trp His Cys Val Ser Ala Ile Asn Asp Ala Asn Asp Tyr Glu Gly Pro
        515                 520                 525

Gly Thr Gly Tyr Arg Val Trp Glu Asp Lys Glu Gln Trp Lys Lys Leu
    530                 535                 540

Lys Asp Ile Pro Trp Ala Val Asp Pro Gln His Met Asn Phe
545                 550                 555

<210> SEQ ID NO 222
<211> LENGTH: 217
<212> TYPE: PRT
<213> ORGANISM: Lactobacillus hilgardii

<400> SEQUENCE: 222

Met Asn Asp Thr Asp Gln Ala Ile Ser Phe Lys Ala Asp Ser Thr Thr
1               5                   10                  15

Ala Thr Asp Thr Ala Thr Ala Ala Lys Pro Ser Thr Ser Gln Glu Ser
                20                  25                  30

Asp Ile Lys Pro Val Asp Trp Phe Lys His Val Gly Val Ala Lys Pro
            35                  40                  45

Gly Phe Ser Lys Asp Glu Val Val Ile Ala Val Ala Pro Ala Phe Ala
        50                  55                  60

Glu Val Leu Thr Lys Thr Met Thr Lys Ile Ser His Arg Asp Val Leu
65                  70                  75                  80

Arg Gln Val Ile Ala Gly Ile Glu Glu Gly Ile Lys Ala Arg Val
                85                  90                  95

Ile Lys Val Tyr Arg Thr Ser Asp Val Ser Phe Cys Ser Val Glu Ala
                100                 105                 110

Asp Lys Leu Ser Gly Ser Gly Ile Ala Ile Ala Ile Gln Ser Lys Gly
            115                 120                 125

Thr Thr Ile Ile His Gln Arg Asp Gln Glu Pro Leu Asn Asn Leu Glu
130                 135                 140

Leu Phe Pro Gln Ala Pro Val Leu Thr Leu Asp Thr Tyr Arg Ala Ile
145                 150                 155                 160

Gly Lys Asn Ala Ala Gln Tyr Ala Arg Gly Met Ser Pro Asn Pro Val
                165                 170                 175

Pro Thr Val Asn Asp Gln Met Ala Arg Val Gln Tyr Gln Ala Leu Ser
                180                 185                 190

Thr Leu Met His Ile Gln Glu Thr Lys Gln Val Val Met Gly Lys Pro
            195                 200                 205

Ala Asp Glu Ile Gln Val Ser Val Glu
    210                 215

<210> SEQ ID NO 223
<211> LENGTH: 176
<212> TYPE: PRT
<213> ORGANISM: Lactobacillus hilgardii

<400> SEQUENCE: 223
```

```
Met Ser Glu Val Asp Glu Leu Val Ser Lys Ile Met Asn Glu Leu Lys
1               5                   10                  15

Asp Gly Gln Ser Ser Thr Pro Asn Ser Thr Pro Glu Ser Ala Pro
            20                  25                  30

Ser Gln Val Pro Thr Gly Lys Lys Leu Gly Lys Ser Asp Tyr Pro Leu
                35                  40                  45

Tyr Glu Lys His Pro Lys Asp Val Lys Ser Pro Thr Gly Lys Ser Leu
50                  55                  60

Asn Glu Ile Thr Leu Glu Asn Ile Ile Asn Gly Asn Val Thr Ser Lys
65                  70                  75                  80

Asp Leu Arg Ile Thr Pro Asp Thr Leu Arg Met Gln Gly Gln Ile Ala
                85                  90                  95

Ala Ser Ala Gly Arg Val Ala Ile Gln Arg Asn Phe Gln Arg Ala Ala
                100                 105                 110

Gly Leu Thr Ala Ile Pro Asp Asp Arg Val Leu Ala Leu Tyr Asn Ser
                115                 120                 125

Leu Arg Ala Tyr Arg Ser Phe Lys Gln Glu Leu Leu Asp Thr Ala Asn
130                 135                 140

Glu Leu Arg Thr Lys Tyr His Ala Pro Val Cys Ala Gly Trp Phe Glu
145                 150                 155                 160

Glu Ala Ala Glu Asn Tyr Glu Lys Asp Arg Lys Leu Lys Gly Asp Asn
                165                 170                 175

<210> SEQ ID NO 224
<211> LENGTH: 558
<212> TYPE: PRT
<213> ORGANISM: Lactobacillus reuteri

<400> SEQUENCE: 224

Met Lys Arg Gln Lys Arg Phe Glu Glu Leu Glu Lys Arg Pro Ile His
1               5                   10                  15

Gln Asp Thr Phe Val Lys Glu Trp Pro Glu Gly Phe Val Ala Met
            20                  25                  30

Met Gly Pro Asn Asp Pro Lys Pro Ser Val Lys Val Glu Asn Gly Lys
                35                  40                  45

Ile Val Glu Met Asp Gly Lys Lys Leu Glu Asp Phe Asp Leu Ile Asp
50                  55                  60

Leu Tyr Ile Ala Lys Tyr Gly Ile Asn Ile Asp Asn Val Glu Lys Val
65                  70                  75                  80

Met Asn Met Asp Ser Thr Lys Ile Ala Arg Met Leu Val Asp Pro Asn
                85                  90                  95

Val Ser Arg Asp Glu Ile Ile Glu Ile Thr Ser Ala Leu Thr Pro Ala
                100                 105                 110

Lys Ala Glu Glu Ile Ile Ser Lys Leu Asp Phe Gly Glu Met Ile Met
                115                 120                 125

Ala Val Lys Lys Met Arg Pro Arg Arg Lys Pro Asp Asn Gln Cys His
130                 135                 140

Val Thr Asn Thr Val Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
                165                 170                 175

Ala Arg Tyr Ala Pro Phe Asn Ala Ile Ser Ile Leu Ile Gly Ala Gln
                180                 185                 190

Thr Gly Arg Pro Gly Val Leu Thr Gln Cys Ser Val Glu Glu Ala Thr
```

```
                195                 200                 205
Glu Leu Gln Leu Gly Met Arg Gly Phe Thr Ala Tyr Ala Glu Thr Ile
210                 215                 220

Ser Val Tyr Gly Thr Asp Arg Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ala Gly Ser Glu Val Leu Met Gly Tyr Pro
                260                 265                 270

Glu Gly Lys Ser Met Leu Tyr Leu Glu Ala Arg Cys Ile Leu Leu Thr
                275                 280                 285

Lys Ala Ser Gly Val Gln Gly Leu Gln Asn Gly Ala Val Ser Cys Ile
290                 295                 300

Glu Ile Pro Gly Ala Val Pro Asn Gly Ile Arg Glu Val Leu Gly Glu
305                 310                 315                 320

Asn Leu Leu Cys Met Met Cys Asp Ile Glu Cys Ala Ser Gly Cys Asp
                325                 330                 335

Gln Ala Tyr Ser His Ser Asp Met Arg Arg Thr Glu Arg Phe Ile Gly
                340                 345                 350

Gln Phe Ile Ala Gly Thr Asp Tyr Ile Asn Ser Gly Tyr Ser Ser Thr
                355                 360                 365

Pro Asn Tyr Asp Asn Thr Phe Ala Gly Ser Asn Thr Asp Ala Met Asp
370                 375                 380

Tyr Asp Asp Met Tyr Val Met Glu Arg Asp Leu Gly Gln Tyr Tyr Gly
385                 390                 395                 400

Ile His Pro Val Lys Glu Thr Ile Ile Lys Ala Arg Asn Lys Ala
                405                 410                 415

Ala Lys Ala Leu Gln Ala Val Phe Glu Asp Leu Gly Leu Pro Lys Ile
                420                 425                 430

Thr Asp Glu Glu Val Glu Ala Ala Thr Tyr Ala Asn Thr His Asp Asp
                435                 440                 445

Met Pro Lys Arg Asp Met Val Ala Asp Met Lys Ala Ala Gln Asp Met
450                 455                 460

Met Asp Arg Gly Ile Thr Ala Ile Asp Ile Ile Lys Ala Leu Tyr Asn
465                 470                 475                 480

His Gly Phe Lys Asp Val Ala Glu Ala Ile Leu Asn Leu Gln Lys Gln
                485                 490                 495

Lys Val Val Gly Asp Tyr Leu Gln Thr Ser Ser Ile Phe Asp Lys Asp
                500                 505                 510

Trp Asn Val Thr Ser Ala Val Asn Asp Gly Asn Asp Tyr Gln Gly Pro
                515                 520                 525

Gly Thr Gly Tyr Arg Leu Tyr Glu Asp Lys Glu Glu Trp Asp Arg Ile
                530                 535                 540

Lys Asp Leu Pro Phe Ala Leu Asp Pro Glu His Leu Glu Leu
545                 550                 555

<210> SEQ ID NO 225
<211> LENGTH: 236
<212> TYPE: PRT
<213> ORGANISM: Lactobacillus reuteri

<400> SEQUENCE: 225

Met Ala Asp Ile Asp Glu Asn Leu Leu Arg Lys Ile Val Lys Glu Val
1               5                   10                  15
```

```
Leu Ser Glu Thr Asn Gln Ile Asp Thr Lys Ile Asp Phe Asp Lys Ser
             20                  25                  30

Asn Asp Ser Thr Ala Thr Ala Thr Gln Glu Val Gln Gln Pro Asn Ser
         35                  40                  45

Lys Ala Val Pro Glu Lys Lys Leu Asp Trp Phe Gln Pro Val Gly Glu
 50                  55                  60

Ala Lys Pro Gly Tyr Ser Lys Asp Glu Val Val Ile Ala Val Gly Pro
 65                  70                  75                  80

Ala Phe Ala Thr Val Leu Asp Lys Thr Glu Thr Gly Ile Pro His Lys
                 85                  90                  95

Glu Val Leu Arg Gln Val Ile Ala Gly Ile Glu Glu Gly Leu Lys
                100                 105                 110

Ala Arg Val Val Lys Val Tyr Arg Ser Ser Asp Val Ala Phe Cys Ala
            115                 120                 125

Val Gln Gly Asp His Leu Ser Gly Ser Gly Ile Ala Ile Gly Ile Gln
        130                 135                 140

Ser Lys Gly Thr Thr Val Ile His Gln Lys Asp Gln Asp Pro Leu Gly
145                 150                 155                 160

Asn Leu Glu Leu Phe Pro Gln Ala Pro Val Leu Thr Pro Glu Thr Tyr
                165                 170                 175

Arg Ala Ile Gly Lys Asn Ala Ala Met Tyr Ala Lys Gly Glu Ser Pro
            180                 185                 190

Glu Pro Val Pro Ala Lys Asn Asp Gln Leu Ala Arg Ile His Tyr Gln
        195                 200                 205

Ala Ile Ser Ala Ile Met His Ile Arg Glu Thr His Gln Val Val Val
210                 215                 220

Gly Lys Pro Glu Glu Glu Ile Lys Val Thr Phe Asp
225                 230                 235

<210> SEQ ID NO 226
<211> LENGTH: 172
<212> TYPE: PRT
<213> ORGANISM: Lactobacillus reuteri

<400> SEQUENCE: 226

Met Met Ser Glu Val Asp Asp Leu Val Ala Lys Ile Met Ala Gln Met
1               5                   10                  15

Gly Asn Ser Ser Ala Asn Ser Ser Thr Gly Thr Ser Thr Ala Ser
             20                  25                  30

Thr Ser Lys Glu Met Thr Ala Asp Asp Tyr Pro Leu Tyr Gln Lys His
         35                  40                  45

Arg Asp Leu Val Lys Thr Pro Lys Gly His Asn Leu Asp Asp Ile Asn
 50                  55                  60

Leu Gln Lys Val Val Asn Gln Val Asp Pro Lys Glu Leu Arg Ile
 65                  70                  75                  80

Thr Pro Glu Ala Leu Lys Leu Gln Gly Glu Ile Ala Ala Asn Ala Gly
                 85                  90                  95

Arg Pro Ala Ile Gln Lys Asn Leu Gln Arg Ala Ala Glu Leu Thr Arg
            100                 105                 110

Val Pro Asp Glu Arg Val Leu Glu Met Tyr Asp Ala Leu Arg Pro Phe
        115                 120                 125

Arg Ser Thr Lys Gln Glu Leu Leu Asn Ile Ala Lys Glu Leu Arg Asp
    130                 135                 140

Lys Tyr Asp Ala Asn Val Cys Ala Ala Trp Phe Glu Glu Ala Ala Asp
145                 150                 155                 160
```

```
Tyr Tyr Glu Ser Arg Lys Lys Leu Lys Gly Asp Asn
            165                 170
```

<210> SEQ ID NO 227
<211> LENGTH: 558
<212> TYPE: PRT
<213> ORGANISM: Lactobacillus diolivorans

<400> SEQUENCE: 227

```
Met Lys Arg Gln Lys Arg Phe Glu Lys Leu Glu Lys Arg Pro Val His
1               5                   10                  15

Leu Asp Gly Phe Val Lys Glu Trp Asp Asp Glu Gly Leu Val Ala Met
                20                  25                  30

Glu Gly Lys Asn Asp Pro Lys Pro Ser Val Lys Val Glu Asn Gly Val
            35                  40                  45

Val Thr Glu Leu Asp Gly Lys Lys Ala Asp Phe Asp Leu Ile Asp
        50                  55                  60

Lys Tyr Ile Ala Glu Tyr Gly Leu Asn Ile Asp Lys Ala Glu Val
65                  70                  75                  80

Met Ala Met Asp Ser Thr Lys Ile Ala Lys Met Leu Val Asp Pro Asn
                85                  90                  95

Val Pro Arg Ser Glu Ile Val Lys Leu Thr Thr Ala Met Thr Pro Ala
            100                 105                 110

Lys Ala Glu Glu Val Ile Ser Lys Leu Asn Phe Gly Glu Met Ile Met
        115                 120                 125

Ala Val Gln Lys Met Arg Pro Arg Arg Thr Pro Ala Thr Gln Cys His
130                 135                 140

Ile Thr Asn Thr Arg Asp Asn Pro Val Glu Ile Ala Ala Asp Ala Ala
145                 150                 155                 160

Glu Ala Ser Leu Arg Gly Phe Pro Glu Gln Glu Thr Thr Thr Ala Thr
                165                 170                 175

Ala Arg Tyr Ala Pro Leu Asn Ala Ile Ser Ile Met Val Gly Ser Gln
            180                 185                 190

Thr Gly Arg Pro Gly Val Ile Ser Gln Cys Ser Val Glu Gly Ser Glu
        195                 200                 205

Glu Leu Ser Leu Gly Met Arg Gly Phe Thr Ala Tyr Ala Glu Thr Ile
    210                 215                 220

Ser Val Tyr Gly Thr Asp Arg Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ala Gly Ser Glu Val Met Met Gly Tyr Thr
            260                 265                 270

Glu Gly Lys Ser Met Leu Tyr Leu Glu Ala Arg Cys Ile Phe Ile Thr
        275                 280                 285

Lys Gly Ser Gly Val Gln Gly Leu Gln Asn Gly Val Ser Cys Ile
    290                 295                 300

Gly Ile Pro Gly Ala Val Pro Ser Gly Leu Arg Gly Val Leu Gly Glu
305                 310                 315                 320

Asn Leu Leu Cys Met Met Ile Asp Val Glu Cys Ala Ser Gly Cys Asp
                325                 330                 335

Gln Ala Phe Ser His Ser Asp Ile Arg Arg Thr Glu Arg Met Ile Gly
            340                 345                 350

Gln Phe Ile Ala Gly Thr Asp Tyr Ile Ser Ser Gly Tyr Ala Ala Glu
```

```
                355                 360                 365
Glu Asn Arg Asp Asn Thr Phe Ala Gly Ser Asn Met Asp Val Leu Asp
    370                 375                 380

Tyr Asp Asp Tyr Cys Ser Met Glu Arg Asp Leu Ser Ile Asn Gly Gly
385                 390                 395                 400

Ile Val Pro Ile His Glu Asp Ala Ile Lys Ile Arg Asn Lys Gly
                405                 410                 415

Ala Lys Ala Ile Gln Ala Val Phe Asp Gly Leu Gly Leu Pro Lys Ile
            420                 425                 430

Thr Asp Glu Glu Val Glu Ala Ala Thr Tyr Gly Ser Asn Ser Asp Asp
        435                 440                 445

Met Pro Lys Arg Asp Met Val Gln Asp Met Lys Ala Ala Gln Asp Leu
    450                 455                 460

Met Asp Arg Gly Thr Thr Ile Ser Asp Val Ile Lys Ala Leu Tyr Asp
465                 470                 475                 480

His Asp Phe Lys Asp Val Ala Glu Ala Val Leu Lys Leu Ala Gln Gln
                485                 490                 495

Lys Val Cys Gly Asp Tyr Leu Gln Thr Ser Ala Ile Phe Asp Gly Asp
            500                 505                 510

Trp Asn Cys Ile Ser Ala Val Asn Asp Thr Asn Asp Tyr Met Gly Pro
        515                 520                 525

Gly Thr Gly Tyr Arg Leu Trp Glu Asp Lys Pro Gln Asp Gln Arg Tyr
    530                 535                 540

Ser Met Gly Asn Gly Ser Thr Thr Tyr Gly Leu Leu Ile Asp
545                 550                 555

<210> SEQ ID NO 228
<211> LENGTH: 245
<212> TYPE: PRT
<213> ORGANISM: Lactobacillus diolivorans

<400> SEQUENCE: 228

Met Lys Asp Thr Asp Thr Pro Ile Ser Phe Gly Lys Lys Asp Ser Ser
1               5                   10                  15

Ala Asn His Glu Ser Asn Gln Leu Ala Leu His Gly Asp Ser Trp Phe
            20                  25                  30

Lys Ser Gly Asp Asp Pro Val Ser Asn Ser Ser Ala Thr Ala Thr
        35                  40                  45

Ala Ser Ala Pro Ser Gln Ser Thr Ser Gly Asn Gly Asp Ile Lys Ser
    50                  55                  60

Leu Asp Trp Phe Lys His Val Gly Val Ala Lys Pro Gly Leu Ser Lys
65                  70                  75                  80

Asp Glu Val Val Ile Gly Val Ala Pro Ala Phe Ala Glu Val Leu Thr
                85                  90                  95

Lys Thr Met Thr Lys Ile Pro His Lys Asp Val Leu Arg Gln Ile Ile
            100                 105                 110

Ala Gly Ile Glu Glu Gly Leu Lys Ala Arg Val Lys Val Tyr
        115                 120                 125

Arg Thr Ser Asp Val Ser Phe Ile Ala Asp Glu Val Asp Lys Leu Ser
    130                 135                 140

Gly Ser Gly Ile Ala Val Ala Val Gln Ser Lys Gly Thr Ala Ile Ile
145                 150                 155                 160

His Gln Lys Asp Gln Glu Pro Leu Asn Asn Leu Glu Leu Phe Pro Gln
                165                 170                 175
```

```
Ala Pro Val Ile Asp Leu Pro Thr Tyr Arg Ala Ile Gly Lys Asn Ala
            180                 185                 190

Ala Gln Tyr Ala Lys Gly Leu Ser Pro Asp Pro Val Pro Thr Val Asn
        195                 200                 205

Asp Gln Met Ala Arg Val Gln Tyr Thr Ala Leu Ser Ser Leu Met His
    210                 215                 220

Ile Ala Glu Thr Lys Arg Val Val Gly Lys Pro Ala Glu Glu Ile
225                 230                 235                 240

Gln Val Thr Phe Asn
            245

<210> SEQ ID NO 229
<211> LENGTH: 180
<212> TYPE: PRT
<213> ORGANISM: Lactobacillus diolivorans

<400> SEQUENCE: 229

Met Ser Glu Val Asp Glu Leu Val Ser Lys Ile Leu Ser Gln Leu Asn
1               5                   10                  15

Asn Gly Asp Ser Ser Gln Ser Thr Gly Thr Thr Ala Ser Ser Val
            20                  25                  30

Thr Pro Thr Ser Ser Pro Ala Asn Ser Gly Lys Thr Phe Asp Lys Gly
        35                  40                  45

Asp Tyr Pro Leu Phe Arg Lys His Pro Asp Val Lys Thr Pro Thr
    50                  55                  60

Gly Lys Ala Val Ser Asp Ile Thr Leu Asp Asn Val Val Ser Gly Lys
65                  70                  75                  80

Val Asp Ser Lys Asp Leu Arg Ile Thr Ala Asn Thr Leu Arg Arg Gln
                85                  90                  95

Gly Glu Ile Ala Ala Ser Ala Gly Arg Pro Ala Ile Gln Arg Asn Phe
            100                 105                 110

Gln Arg Ala Ala Glu Leu Thr Lys Ile Pro Asp Asp Lys Val Leu Ser
        115                 120                 125

Phe Tyr His Ala Leu Arg Pro Phe Arg Ser Ser Lys Gln Asp Leu Leu
    130                 135                 140

Asp Ile Ala Lys Gln Leu Arg Asp Thr Tyr His Ala Pro Val Cys Ala
145                 150                 155                 160

Asn Trp Phe Glu Glu Ala Ala Gly Asn Tyr Glu Ile Ser Lys Lys Leu
                165                 170                 175

Lys Gly Asp Asn
            180

<210> SEQ ID NO 230
<211> LENGTH: 558
<212> TYPE: PRT
<213> ORGANISM: Lactobacillus reuteri

<400> SEQUENCE: 230

Met Lys Arg Gln Lys Arg Phe Glu Glu Leu Glu Lys Arg Pro Ile His
1               5                   10                  15

Gln Asp Thr Phe Val Lys Glu Trp Pro Glu Glu Gly Phe Val Ala Met
            20                  25                  30

Met Gly Pro Asn Asp Pro Lys Pro Ser Val Lys Val Glu Asn Gly Lys
        35                  40                  45

Ile Val Glu Met Asp Gly Lys Lys Leu Glu Asp Phe Asp Leu Ile Asp
    50                  55                  60
```

```
Leu Tyr Ile Ala Lys Tyr Gly Ile Asn Ile Asp Asn Val Glu Lys Val
 65                  70                  75                  80

Met Asn Met Asp Ser Thr Lys Ile Ala Arg Met Leu Val Asp Pro Asn
                 85                  90                  95

Val Ser Arg Glu Ser Ile Ile Glu Ile Thr Ser Ala Leu Thr Pro Ala
            100                 105                 110

Lys Ala Glu Glu Ile Ile Ser Lys Leu Asp Phe Gly Glu Met Ile Met
        115                 120                 125

Ala Ile Lys Lys Met Arg Pro Arg Lys Pro Asp Asn Gln Cys His
    130                 135                 140

Val Thr Asn Thr Val Asp Asn Pro Val Gln Ile Ala Ala Asp Ala Ala
145                 150                 155                 160

Asp Ala Ala Leu Arg Gly Phe Pro Gln Glu Thr Thr Thr Ala Val
                165                 170                 175

Ala Arg Tyr Ala Pro Phe Asn Ala Ile Ser Ile Leu Ile Gly Ala Gln
            180                 185                 190

Thr Gly Arg Pro Gly Val Leu Thr Gln Cys Ser Val Glu Glu Ala Thr
        195                 200                 205

Glu Leu Gln Leu Gly Met Arg Gly Phe Thr Ala Tyr Ala Glu Thr Ile
210                 215                 220

Ser Val Tyr Gly Thr Asp Arg Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ala Gly Ser Glu Val Leu Met Gly Tyr Pro
            260                 265                 270

Glu Gly Lys Ser Met Leu Tyr Leu Glu Ala Arg Cys Ile Leu Leu Thr
        275                 280                 285

Lys Ala Ser Gly Val Gln Gly Leu Gln Asn Gly Ala Val Ser Cys Ile
    290                 295                 300

Glu Ile Pro Gly Ala Val Pro Asn Gly Ile Arg Glu Val Leu Gly Glu
305                 310                 315                 320

Asn Leu Leu Cys Met Met Cys Asp Ile Glu Cys Ala Ser Gly Cys Asp
                325                 330                 335

Gln Ala Tyr Ser His Ser Asp Met Arg Arg Thr Glu Arg Phe Ile Gly
            340                 345                 350

Gln Phe Ile Ala Gly Thr Asp Tyr Ile Asn Ser Gly Tyr Ser Ser Thr
        355                 360                 365

Pro Asn Tyr Asp Asn Thr Phe Ala Gly Ser Asn Thr Asp Ala Met Asp
    370                 375                 380

Tyr Asp Asp Met Tyr Val Met Glu Arg Asp Leu Gly Gln Tyr Gly
385                 390                 395                 400

Ile His Pro Val Gln Glu Thr Ile Ile Lys Ala Arg Asn Lys Ala
                405                 410                 415

Ala Lys Ala Leu Gln Ala Val Phe Glu Asp Leu Gly Leu Pro Lys Ile
        420                 425                 430

Thr Asp Glu Glu Val Glu Ala Ala Thr Tyr Ala Asn Thr His Asp Asp
    435                 440                 445

Met Pro Lys Arg Asp Met Val Ala Asp Met Lys Ala Ala Gln Asp Met
    450                 455                 460

Met Asp Arg Gly Ile Thr Ala Val Asp Ile Ile Lys Ala Leu Tyr Asn
465                 470                 475                 480

His Gly Phe Lys Asp Val Ala Glu Ala Val Leu Asn Leu Gln Lys Gln
```

```
                    485                 490                 495
Lys Val Val Gly Asp Tyr Leu Gln Thr Ser Ser Ile Phe Asp Lys Asp
                500                 505                 510

Trp Asn Ile Thr Ser Ala Val Asn Asp Gly Asn Asp Tyr Gln Gly Pro
                515                 520                 525

Gly Thr Gly Tyr Arg Leu Tyr Glu Asp Lys Glu Glu Trp Asp Arg Ile
            530                 535                 540

Lys Asp Leu Pro Phe Ala Leu Asp Pro Glu His Leu Glu Leu
545                 550                 555
```

<210> SEQ ID NO 231
<211> LENGTH: 236
<212> TYPE: PRT
<213> ORGANISM: Lactobacillus reuteri

<400> SEQUENCE: 231

```
Met Ala Asp Ile Asp Glu Asn Leu Leu Arg Lys Ile Val Lys Glu Val
1               5                   10                  15

Leu Asn Glu Thr Asn Gln Ile Asp Thr Lys Ile Asn Phe Asp Lys Glu
                20                  25                  30

Asn Asn Ser Thr Ala Thr Ala Thr Glu Glu Val Gln Gln Pro Asn Ser
            35                  40                  45

Lys Ala Val Pro Glu Lys Lys Leu Asp Trp Phe Gln Pro Ile Gly Glu
50                  55                  60

Ala Lys Pro Gly Tyr Ser Lys Asp Glu Val Val Ile Ala Val Gly Pro
65                  70                  75                  80

Ala Phe Ala Thr Val Leu Asp Lys Thr Glu Thr Gly Ile Pro His Lys
                85                  90                  95

Glu Val Leu Arg Gln Val Ile Ala Gly Ile Glu Glu Gly Leu Lys
                100                 105                 110

Ala Arg Val Val Lys Val Tyr Arg Ser Ser Asp Val Ala Phe Cys Ala
            115                 120                 125

Val Gln Gly Asp His Leu Ser Gly Ser Gly Ile Ala Ile Gly Ile Gln
130                 135                 140

Ser Lys Gly Thr Thr Val Ile His Gln Lys Asp Gln Asp Pro Leu Gly
145                 150                 155                 160

Asn Leu Glu Leu Phe Pro Gln Ala Pro Val Leu Thr Pro Glu Thr Phe
                165                 170                 175

Arg Ala Ile Gly Lys Asn Ala Ala Met Tyr Ala Lys Gly Glu Ser Pro
                180                 185                 190

Glu Pro Val Pro Ala Lys Asn Asp Gln Leu Ala Arg Ile His Tyr Gln
            195                 200                 205

Ala Ile Ser Ala Ile Met His Ile Arg Glu Thr His Gln Val Val Val
210                 215                 220

Gly Lys Pro Glu Glu Glu Ile Lys Val Thr Phe Asp
225                 230                 235
```

<210> SEQ ID NO 232
<211> LENGTH: 171
<212> TYPE: PRT
<213> ORGANISM: Lactobacillus reuteri

<400> SEQUENCE: 232

```
Met Ser Glu Val Asp Asp Leu Val Ala Lys Ile Met Ala Gln Met Gly
1               5                   10                  15

Asn Ser Ser Ser Ser Asp Ser Ser Thr Ser Ala Thr Ser Thr Asn Asn
```

-continued

```
                 20                  25                  30
Gly Lys Glu Met Thr Ala Asp Asp Tyr Pro Leu Tyr Gln Lys His Arg
             35                  40                  45
Asp Leu Val Lys Thr Pro Ser Gly Lys Lys Leu Asp Asp Ile Thr Leu
         50                  55                  60
Gln Lys Val Val Asn Asp Gln Val Asn Pro Lys Glu Leu Arg Ile Thr
 65                  70                  75                  80
Pro Glu Ala Leu Lys Leu Gln Gly Glu Ile Ala Ala Asn Ala Gly Arg
                 85                  90                  95
Pro Ala Ile Gln Lys Asn Leu Gln Arg Ala Ala Glu Leu Thr Arg Val
            100                 105                 110
Pro Asp Glu Arg Val Leu Gln Met Tyr Asp Ala Leu Arg Pro Phe Arg
            115                 120                 125
Ser Thr Lys Gln Glu Leu Leu Asp Ile Ala Asn Glu Leu Arg Asp Lys
            130                 135                 140
Tyr His Ala Glu Val Cys Ala Ala Trp Phe Glu Ala Ala Asp Tyr
145                 150                 155                 160
Tyr Glu Ser Arg Lys Lys Leu Lys Gly Asp Asn
            165                 170

<210> SEQ ID NO 233
<211> LENGTH: 756
<212> TYPE: PRT
<213> ORGANISM: Mesorhizobium loti

<400> SEQUENCE: 233

Met Thr Pro Lys Leu Asn Arg Trp Lys Arg Phe Ala Asp Trp Asp Glu
  1               5                  10                  15
Arg Pro Leu Arg Leu Asp Lys Phe Ala Ala Glu Asp Pro Ala Asn Gly
             20                  25                  30
Phe Ser Ala Phe Ser Ser Pro Ala Asp Pro Lys Pro Gly Ile Gly Ile
             35                  40                  45
Lys Asp Gly Arg Val Ile Ser Leu Asp Gly Val Leu Glu His Asp Tyr
 50                  55                  60
Asp Met Ile Asp Arg Phe Ile Ala Arg His His Ile Asp Pro Glu Val
 65                  70                  75                  80
Ala Pro Glu Ala Met Ala Leu Asp Ser Ala Thr Val Ala Arg Trp Leu
                 85                  90                  95
Val Asp Met Asn Val Pro Arg Glu Thr Leu Val Arg Leu Ala His Gly
            100                 105                 110
Met Thr Pro Ala Lys Leu Ala Glu Val Val Ser Gln Leu Asn Ala Leu
            115                 120                 125
Glu Ile Ala Phe Ala Tyr Ser Lys Met Arg Ala Arg Lys Thr Pro Gly
            130                 135                 140
Asn Gln Ala His Val Thr Asn Ala Lys Asp Asp Pro Leu Gln Leu Ala
145                 150                 155                 160
Ala Asp Ala Ala Thr Ala Val Ala Phe Gly Phe Asp Glu Ile Glu Thr
                165                 170                 175
Thr Met Arg Val Ser Arg Asn Ala Trp Ser Asn Ala Val Ala Cys Ala
            180                 185                 190
Val Gly Gly Ala Val Gly Arg Trp Gly Thr Leu Phe Gln Cys Ser Ser
            195                 200                 205
Glu Glu Ala Glu Glu Leu Arg Ile Ala Met Ala Gly Phe Thr Ser Tyr
            210                 215                 220
```

```
Ala Glu Thr Val Ser Val Tyr Gly Thr Glu Lys Ser Phe Thr Asp Gly
225                 230                 235                 240

Asp Asp Thr Pro Trp Ser Lys Ala Phe Leu Ala Ala Tyr Ala Ser
            245                 250                 255

Arg Gly Val Lys Met Arg Cys Thr Ser Gly Ala Gly Ser Glu Leu Leu
            260                 265                 270

Met Gly Phe His Glu Ala Lys Ser Leu Leu Tyr Leu Glu Ala Arg Cys
            275                 280                 285

Leu Cys Leu Gln Arg Gly Met Gly Val Gln Gly Thr Gln Asn Gly Gly
        290                 295                 300

Ile Asp Gly Ala Pro Leu Thr Ala Thr Ile Pro Gly Val Arg Glu
305                 310                 315                 320

Leu Met Ala Glu Asn Leu Ile Ala Val Trp Leu Asp Leu Glu Cys Ala
                325                 330                 335

Ser Gly Asn Asp Ala Arg Ser Thr Glu Ser Glu Ile Arg Val Gly Ala
                340                 345                 350

Lys Ile Leu Pro Tyr Leu Ile Ala Gly Ser Asp Leu Ile Cys Ser Gly
            355                 360                 365

Met Gly Ser Ile Leu Lys Tyr Asp Asn Ser Phe Asn Pro Ser Leu Ile
370                 375                 380

Asn Gly Glu Glu Leu Glu Asp Tyr Leu Val Leu Gln Arg Asp Phe Glu
385                 390                 395                 400

Ala Asp Gly Gly Leu Thr Pro Leu Pro Glu Ser Arg Ala Ile Glu Leu
                405                 410                 415

Arg Glu Arg Ala Val Glu Ala Ile Ala Ala Val Phe Glu Glu Leu Gly
            420                 425                 430

Leu Ser Ser Pro Thr Glu Asp Met Lys Ser Ser Val Val Tyr Ala Ser
        435                 440                 445

Gly Ser Asp Asp Thr Arg Ser Leu Met Pro Arg Asp Val Ser Phe Ile
        450                 455                 460

Ser Glu Ala Ile Lys Glu Arg Gly Ile Thr Val Ile Asp Val Val Lys
465                 470                 475                 480

Ala Leu Ala Lys Arg Gly Phe Arg Glu Glu Ala Glu Asn Leu Leu Asp
                485                 490                 495

Val Val Lys Leu Arg Leu Ser Gly Asp Tyr Leu Gln Thr Ser Ala Met
            500                 505                 510

Ile Arg Asn Gly Arg Ile Val Ser Ala Val Asn Asp Pro Asn Asp Tyr
        515                 520                 525

Leu Gly Pro Gly Ser Gly Tyr Arg Val Ser Glu Glu Arg Arg Leu Gln
        530                 535                 540

Leu Asn Asp Ile Arg Asp Val Leu Asp Gln Lys Glu Val Leu Arg Ser
545                 550                 555                 560

Glu Ala Leu His Glu Lys Asp Glu Ala Arg His Ile Arg Tyr Arg Asn
                565                 570                 575

Leu Gly Pro Ala Ala Asn Gly Ser Ala Lys Asp Asp Val Ile Gly
            580                 585                 590

Ile Ser Pro Ala Phe Gly Leu Lys Leu Tyr Arg Thr Thr Ala Gly His
            595                 600                 605

Arg Leu Ser Glu Val Leu Gly Ala Met Leu Asp Ala Ile His Ala Arg
            610                 615                 620

Gly Leu Lys Ala Arg Val Val Arg Phe Arg His Thr Ala Asp Thr Ser
625                 630                 635                 640

Phe Leu Gly Leu Ser Ala Ala Arg Leu Ala Gly Ser Gly Ile Gly Ile
```

```
                  645                 650                 655
Gly Ile Gln Ala Lys Gly Thr Ala Val Ile His Gln Arg Asp Arg Gln
              660                 665                 670

Pro His Asn Asn Leu Glu Leu Phe Ser Asn Ala Pro Ile Thr Arg Leu
          675                 680                 685

Glu His Tyr Arg Ala Leu Gly Ala Asn Ala Ala Tyr Ala Leu Gly
      690                 695                 700

Glu Met Pro Glu Pro Val Val Pro Gln Arg Gly Glu Ala Met Gly
705                 710                 715                 720

Ser Arg Tyr His Ala Arg Val Ala Leu Ile Tyr Ala Ile Glu Thr Gly
              725                 730                 735

Leu Thr Glu Ala Gly Ala Ala Pro Glu Glu Val Asp Val Ile Leu Thr
          740                 745                 750

Gly Val Lys Ser
          755

<210> SEQ ID NO 234
<211> LENGTH: 139
<212> TYPE: PRT
<213> ORGANISM: Mesorhizobium loti

<400> SEQUENCE: 234

Met Thr His Thr Arg Ala Asp Tyr Pro Leu Ala Glu Thr Gln Pro Gly
1               5                   10                  15

Ala Val Lys Gly Lys Arg Gly Lys Ser Leu Ala Glu Ile Thr Leu Asp
            20                  25                  30

Ser Val Leu Ala Gly Asp Val Thr Met Glu Asp Leu Arg Ile Thr Pro
        35                  40                  45

Gln Ala Leu Gln Ala Gln Ala Asp Val Ala Arg Asp Val Gly Arg Pro
    50                  55                  60

Thr Leu Ala Leu Asn Phe Glu Arg Gly Ala Glu Leu Val Glu Val Pro
65                  70                  75                  80

Gln Asp Phe Ile Met Gln Val Tyr Glu Leu Leu Arg Pro Gly Arg Ala
                85                  90                  95

Lys Ser Lys Glu Glu Leu Leu Gln Ala Ala Thr Thr Met Arg Asp Thr
            100                 105                 110

Tyr Gln Ala Glu Arg Ile Ala Arg Phe Ile Glu Glu Ala Ala Glu Thr
        115                 120                 125

Tyr Ala Ala Arg Gly Leu Phe Thr Phe Arg Phe
    130                 135

<210> SEQ ID NO 235
<211> LENGTH: 746
<212> TYPE: PRT
<213> ORGANISM: Mycobacterium vanbaalenii

<400> SEQUENCE: 235

Met Ala Asp Glu Leu Gly Arg Phe Arg Val Leu Asn Ser Lys Pro Val
1               5                   10                  15

Asn Leu Asp Gly Phe Ser Val Pro Asp Ala Gly Leu Gly Leu Val Ala
            20                  25                  30

Met Ser Ser Pro His Asp Pro Ala Pro Ser Leu Lys Ile Arg Gly Gly
        35                  40                  45

Glu Val Val Glu Leu Asp Gly Lys Gly Ala Gly Glu Phe Asp Val Ile
    50                  55                  60

Asp Glu Phe Ile Ala Arg Tyr Gly Ile Asp Leu Thr Val Ala Glu Glu
```

-continued

```
            65                  70                  75                  80
Ala Met Ala Leu Gly Asp Glu Thr Leu Ala Arg Met Val Val Asp Ile
                    85                  90                  95
Asn Val Pro Arg Ala Glu Val Val Arg Leu Ile Gly Thr Thr Pro
            100                 105                 110
Ala Lys Leu Ala Arg Val Val Ala Leu Leu Ser Pro Val Glu Met Gln
                115                 120                 125
Met Ala Met Ala Lys Met Arg Ala Arg Thr Pro Ser Asn Gln Ala
130                 135                 140
His Val Thr Asn Gln Leu Asp Asp Pro Leu Leu Ile Ala Ala Asp Ala
145                 150                 155                 160
Ala Ser Ala Val Ala Tyr Gly Phe Arg Glu Val Glu Thr Thr Val Pro
                165                 170                 175
Val Leu Gly Asp Ala Pro Ser Asn Ala Val Ala Leu Leu Ile Gly Ser
                180                 185                 190
Gln Val Gly Ser Pro Gly Ala Met Ala Gln Cys Ser Ile Glu Glu Ala
                195                 200                 205
Leu Glu Leu Arg Leu Gly Leu Arg Gly Leu Thr Ser Tyr Ala Glu Thr
            210                 215                 220
Ile Ser Ile Tyr Gly Thr Glu Gln Val Phe Val Asp Gly Asp Asp Thr
225                 230                 235                 240
Pro Phe Ser Lys Ala Ile Leu Thr Ser Ala Tyr Ala Ser Arg Gly Leu
                245                 250                 255
Lys Met Arg Val Thr Ser Gly Gly Ala Glu Val Leu Met Gly Ala
                260                 265                 270
Ala Glu Lys Cys Ser Ile Leu Tyr Leu Glu Ser Arg Cys Val Ser Leu
            275                 280                 285
Ala Arg Ala Leu Gly Ser Gln Gly Val Gln Asn Gly Gly Ile Asp Gly
            290                 295                 300
Val Gly Val Val Ala Ser Val Pro Glu Gly Met Lys Glu Leu Leu Ala
305                 310                 315                 320
Glu Asn Leu Met Val Met Met Arg Asp Leu Glu Ser Cys Ala Gly Asn
                325                 330                 335
Asp Asn Leu Ile Ser Glu Ser Asp Ile Arg Arg Ser Ala His Thr Leu
            340                 345                 350
Pro Val Leu Leu Ala Gly Ala Asp Phe Val Phe Ser Gly Phe Gly Ser
            355                 360                 365
Ile Pro Arg Tyr Asp Asn Ala Phe Ala Leu Ser Asn Phe Asn Ser Asp
            370                 375                 380
Asp Met Asp Asp Phe Leu Val Leu Gln Arg Asp Trp Gly Ala Asp Gly
385                 390                 395                 400
Gly Leu Arg Thr Val Ser Pro Glu His Leu Glu Ala Val Arg Arg Arg
                405                 410                 415
Ala Ala Lys Ala Val Gln Ala Val Tyr Arg Asp Leu Gly Leu Ala Asp
                420                 425                 430
Tyr Glu Asp Ala Arg Val Glu Val Val Ala Ala Asn Gly Ser Arg
            435                 440                 445
Asp Leu Pro Ala Gly His Pro Lys Met Val Ala Glu Ala Ala Ser
            450                 455                 460
Ile Glu Ala Arg Gln Leu Thr Val Phe Asp Val Ile Ala Ser Leu His
465                 470                 475                 480
Arg Thr Gly Phe Thr Asp Glu Ala Glu Ala Ile Thr Thr Leu Thr Arg
                485                 490                 495
```

```
Glu Arg Leu Arg Gly Asp Gln Leu Gln Thr Ser Ala Ile Phe Asp Glu
                500                 505                 510

Lys Phe Arg Val Leu Ser Lys Leu Thr Asp Pro Asn Asp Tyr Thr Gly
            515                 520                 525

Pro Ala Thr Gly Tyr Ala Leu Thr Asp Arg Arg Ala Glu Ile Asp
        530                 535                 540

Ala Ile Arg Gln Ala Arg Ser Ser Ala Glu Leu Thr Ala Asp Gln Glu
545                 550                 555                 560

Ser Tyr Arg Gly His Val Leu Val Thr Asp Val Glu Pro Ala Gln Gln
                565                 570                 575

Gly Ser Asp Pro Arg Glu Val Cys Ile Gly Leu Ser Pro Ala Trp Gly
            580                 585                 590

Arg Ser Val Trp Leu Thr Leu Cys Gly Leu Thr Ile Gly Glu Val Leu
            595                 600                 605

Arg Gln Ile Ser Ala Gly Leu Glu Glu Gly Cys Ile Ala Arg Pro
        610                 615                 620

Val Arg Val Arg Ser Thr Ile Asp Val Gly Leu Ile Gly Leu Thr Ala
625                 630                 635                 640

Ala Arg Leu Ser Gly Ser Gly Ile Gly Ile Gly Leu Gln Gly Lys Gly
                645                 650                 655

Thr Ala Leu Ile His Arg Arg Asp Leu Ala Pro Leu Ala Asn Leu Glu
            660                 665                 670

Leu Phe Ser Val Ala Pro Leu Leu Thr Ala Lys Met Tyr Arg Glu Leu
            675                 680                 685

Gly Lys Asn Ala Ala Arg His Ala Lys Gly Met Ala Pro Val Pro Ile
        690                 695                 700

Phe Thr Gly Gly Thr Asp Glu Ser Ile Ser Ala Arg Tyr His Ala Arg
705                 710                 715                 720

Ala Val Ala Leu Val Ala Leu Glu Arg Glu Ser Cys Glu Pro Gly Gln
                725                 730                 735

Pro Pro Val Thr Val Lys Val Glu Trp Pro
            740                 745

<210> SEQ ID NO 236
<211> LENGTH: 119
<212> TYPE: PRT
<213> ORGANISM: Mycobacterium vanbaalenii

<400> SEQUENCE: 236

Met Ala Met Ser Glu Ile Ser Ala Ser Arg Glu Asn Ile Thr Val
1               5                   10                  15

Gly Asn Ala Val Asp Gly Lys Leu Gly Leu Gly Asp Leu Arg Met Asp
            20                  25                  30

Pro Ala Thr Leu Ala His Gln Ala Val Ala Glu Ala Gly Gly Asn
        35                  40                  45

Pro Gln Leu Ala Glu Asn Phe Arg Arg Ala Ala Glu Leu Ala Thr Ile
        50                  55                  60

Glu Asp Glu Gln Val Met Ala Leu Tyr Glu Ala Leu Arg Pro His Arg
65                  70                  75                  80

Ser Thr Ala Ala Glu Leu Glu Glu Leu Arg Ala Ser Leu Leu Ala Arg
                85                  90                  95

Gly Ala Pro Arg Cys Ala Ala Leu Val Glu Gln Ala Ala Ala Val Tyr
            100                 105                 110

Ala Arg Arg Gly Leu Leu Arg
```

-continued

```
        115

<210> SEQ ID NO 237
<211> LENGTH: 739
<212> TYPE: PRT
<213> ORGANISM: Mycobacterium sp.

<400> SEQUENCE: 237

Met Arg Ile Leu Asp Ala Lys Pro Val Asn Leu Asp Gly Phe Ser Val
1               5                   10                  15

Thr Asp Pro Ala Leu Gly Leu Val Ala Met His Ser Pro His Asp Pro
            20                  25                  30

Gln Pro Ser Leu Val Val Arg Asp Gly Arg Val Val Glu Leu Asp Gly
        35                  40                  45

Arg Pro Ala Ala Asp Phe Asp Val Ile Asp Glu Phe Ile Ala Arg Tyr
    50                  55                  60

Gly Ile Asp Leu Thr Val Ala Glu Glu Ala Met Ala Leu Asp Asp Ala
65                  70                  75                  80

Val Leu Ala Arg Met Ala Val Asp Val Asn Val Pro Arg Ala Glu Val
                85                  90                  95

Val Arg Leu Ile Gly Gly Thr Thr Pro Ala Lys Leu Ala Arg Val Met
            100                 105                 110

Ala Val Met Thr Pro Val Glu Met Gln Met Ala Met His Lys Met Arg
        115                 120                 125

Ala Arg Arg Thr Pro Ser Asn Gln Ala His Val Thr Asn Gln Leu Asp
    130                 135                 140

Asp Pro Leu Leu Ile Ala Ala Asp Ala Ala Ser Ala Val Ala Tyr Gly
145                 150                 155                 160

Phe Arg Glu Val Glu Thr Thr Val Pro Val Phe Gly Asp Ala Pro Ser
                165                 170                 175

Asn Ala Ile Ala Leu Leu Ile Gly Ser Gln Val Gly Val Pro Gly Ala
            180                 185                 190

Met Ala Gln Cys Ser Ile Glu Glu Ala Met Glu Leu Arg Leu Gly Leu
        195                 200                 205

Arg Gly Leu Thr Ser Tyr Ala Glu Thr Ile Ser Ile Tyr Gly Thr Glu
    210                 215                 220

Gln Val Phe Val Asp Gly Asp Asp Thr Pro Phe Ser Lys Ala Ile Leu
225                 230                 235                 240

Thr Ala Ala Tyr Ala Ser Arg Gly Leu Lys Met Arg Val Thr Ser Gly
                245                 250                 255

Gly Gly Ala Glu Val Leu Met Gly Ala Ala Glu Lys Cys Ser Ile Leu
            260                 265                 270

Tyr Leu Glu Ser Arg Cys Val Ser Leu Ala Arg Ala Leu Gly Ser Gln
        275                 280                 285

Gly Val Gln Asn Gly Gly Ile Asp Gly Val Gly Val Val Ala Ser Val
    290                 295                 300

Pro Glu Gly Met Lys Glu Leu Leu Ala Glu Asn Leu Met Val Met Met
305                 310                 315                 320

Arg Asp Leu Glu Ser Cys Ala Gly Asn Asp Asn Leu Ile Ser Glu Ser
                325                 330                 335

Asp Ile Arg Arg Ser Ala His Thr Leu Pro Val Leu Leu Ala Gly Ala
            340                 345                 350

Asp Phe Ile Phe Ser Gly Phe Gly Ser Ile Pro Arg Tyr Asp Asn Ala
        355                 360                 365
```

```
Phe Ala Leu Ser Asn Phe Asn Ala Asp Asp Met Asp Asp Phe Leu Val
        370                 375                 380

Leu Gln Arg Asp Trp Gly Ala Asp Gly Gly Leu Arg Thr Val Ser Arg
385                 390                 395                 400

Glu His Leu Ala Arg Val Arg Arg Ala Ala Thr Ala Val Gln Ala
                405                 410                 415

Val Tyr Arg Asp Leu Gly Leu Ala Asp Phe Asp Asp Thr Arg Ile Asp
                420                 425                 430

Ala Val Val Ala Asn Asp Ser Arg Asp Leu Pro Ala Gly Asp Pro
        435                 440                 445

Lys Ala Val Ala Glu Ala Ala Thr Ala Ile Glu Ala Arg Gln Leu Thr
450                 455                 460

Val Phe Asp Val Val Ala Ala Leu His Arg Thr Gly Tyr Ala Pro Glu
465                 470                 475                 480

Ala Glu Ala Ile Met Arg Leu Thr Arg Glu Arg Leu Arg Gly Asp Gln
                485                 490                 495

Leu Gln Thr Ser Ala Ile Phe Asp Gln Phe Gln Val Leu Ser Lys
                500                 505                 510

Ile Thr Asp Pro Asn Asp Tyr Ala Gly Pro Gly Ser Gly Tyr Thr Pro
        515                 520                 525

Thr Glu Lys Arg Arg Ala Glu Ile Asp Gly Ile Arg Gln Ala Arg Thr
530                 535                 540

Ser Ala Glu Leu Thr Ala Asp Gln Ala Glu His Arg Gly His Val Val
545                 550                 555                 560

Phe Ser Asp Val Glu Pro Ala His Gln Gly Ser Asp Pro Arg Glu Val
                565                 570                 575

Cys Ile Gly Leu Ser Pro Ala Leu Gly Arg Ser Val Trp Leu Thr Leu
                580                 585                 590

Cys Gly Leu Thr Val Gly Glu Val Leu Arg Gln Leu Ser Ala Gly Leu
        595                 600                 605

Glu Glu Glu Gly Cys Val Pro Arg Leu Val Arg Val Arg Ser Thr Ile
610                 615                 620

Asp Val Gly Leu Ile Gly Leu Thr Ala Ala Arg Leu Ser Gly Ser Gly
625                 630                 635                 640

Ile Gly Ile Gly Leu Gln Gly Lys Gly Thr Ala Leu Ile His Arg Arg
                645                 650                 655

Asp Leu Ala Pro Leu Ala Asn Leu Glu Leu Phe Ser Val Ala Pro Leu
                660                 665                 670

Leu Thr Ala Lys Met Tyr Arg Glu Leu Gly Arg Asn Ala Ala Arg His
        675                 680                 685

Ala Lys Gly Met Ala Pro Leu Pro Ile Leu Ala Gly Gly Thr Asp Glu
690                 695                 700

Ser Ile Ser Ala Arg Tyr His Ala Arg Ala Val Ala Leu Val Ala Leu
705                 710                 715                 720

Glu Arg Gln Ala Cys Glu Pro Gly Gln Ala Pro Ile Thr Val Glu Ala
                725                 730                 735

Lys Arg Val

<210> SEQ ID NO 238
<211> LENGTH: 110
<212> TYPE: PRT
<213> ORGANISM: Mycobacterium sp.

<400> SEQUENCE: 238
```

```
Met Thr Glu Lys Phe Thr Val Ala Ala Ala Val Asp Gly Lys Leu Thr
 1               5                  10                  15

Leu Ser Asp Leu Arg Met Asp Pro Ala Thr Leu Ala Tyr Gln Ala Val
                20                  25                  30

Val Ala Glu Gln Asp Gly Asn Pro Gln Leu Ala Glu Asn Phe Leu Arg
             35                  40                  45

Ala Ala Glu Leu Ala Val Ile Asp Asp Glu Ala Val Met Lys Phe Tyr
         50                  55                  60

Glu Ala Leu Arg Pro His Arg Ser Thr Ala Ala Glu Leu Glu Glu Leu
 65                  70                  75                  80

Arg Val Ser Leu Glu Thr Gly Gly Ala Ser Arg Cys Ala Glu Leu Val
                 85                  90                  95

Arg Gln Ala Ala Glu Val Tyr Ala Arg Arg Gly Leu Leu Arg
            100                 105                 110
```

<210> SEQ ID NO 239
<211> LENGTH: 746
<212> TYPE: PRT
<213> ORGANISM: Mycobacterium flavescens

<400> SEQUENCE: 239

```
Met Ala Asp Glu Leu Gly Arg Phe Arg Val Leu Asn Ser Lys Pro Val
 1               5                  10                  15

Asn Leu Asp Gly Phe Ser Val Pro Asp Ala Ala Leu Gly Leu Val Ala
                20                  25                  30

Met Ser Ser Pro His Asp Pro Ala Pro Ser Leu Val Ile Arg Asp Gly
             35                  40                  45

Ala Val Val Glu Leu Asp Ser Lys Asp Val Ala Glu Phe Asp Val Ile
         50                  55                  60

Asp Glu Phe Ile Ala Arg Tyr Gly Ile Asp Leu Ser Val Ala Glu Glu
 65                  70                  75                  80

Ala Met Ala Leu Asp Asp Glu Thr Leu Ala Arg Met Val Val Asp Ile
                 85                  90                  95

Asn Val Pro Arg Ala Gly Val Val Arg Leu Ile Gly Gly Thr Thr Pro
            100                 105                 110

Ala Lys Leu Ala Arg Val Val Ala Leu Leu Ser Pro Val Glu Met Gln
            115                 120                 125

Met Ala Met Val Lys Met Arg Ala Arg Arg Thr Pro Ser Asn Gln Ala
        130                 135                 140

His Val Thr Asn Gln Leu Asp Asp Pro Leu Leu Ile Ala Ala Asp Ala
145                 150                 155                 160

Ala Ser Ala Val Ala Tyr Gly Phe Arg Glu Val Glu Thr Thr Val Pro
                165                 170                 175

Val Leu Gly Asp Ala Pro Ser Asn Ala Val Ala Leu Leu Ile Gly Ser
            180                 185                 190

Gln Val Gly Thr Pro Gly Ala Met Ala Gln Cys Ser Ile Glu Glu Ala
            195                 200                 205

Leu Glu Leu Arg Leu Gly Leu Arg Gly Leu Thr Ser Tyr Ala Glu Thr
        210                 215                 220

Ile Ser Ile Tyr Gly Thr Glu Gln Val Phe Ile Asp Gly Asp Thr
225                 230                 235                 240

Pro Phe Ser Lys Ala Ile Leu Thr Ser Ala Tyr Ala Ser Arg Gly Leu
                245                 250                 255

Lys Met Arg Val Thr Ser Gly Gly Ala Glu Val Leu Met Gly Ala
            260                 265                 270
```

```
Ala Gln Lys Cys Ser Ile Leu Tyr Leu Glu Ser Arg Cys Val Ser Leu
            275                 280                 285

Ala Arg Ala Leu Gly Ser Gln Gly Val Gln Asn Gly Gly Ile Asp Gly
            290                 295                 300

Val Gly Val Val Ala Ser Val Pro Glu Gly Met Lys Glu Leu Leu Ala
305                 310                 315                 320

Glu Asn Leu Met Val Met Met Arg Asp Leu Glu Ser Cys Ala Gly Asn
                325                 330                 335

Asp Asn Leu Ile Ser Glu Ser Asp Ile Arg Arg Ser Ala His Thr Leu
            340                 345                 350

Pro Val Leu Leu Ala Gly Ala Asp Phe Ile Phe Ser Gly Phe Gly Ser
            355                 360                 365

Ile Pro Arg Tyr Asp Asn Ala Phe Ala Leu Ser Asn Phe Asn Ser Asp
            370                 375                 380

Asp Met Asp Asp Phe Leu Val Leu Gln Arg Asp Trp Gly Ala Asp Gly
385                 390                 395                 400

Gly Leu Arg Thr Val Ser Pro Glu His Leu Glu Ala Val Arg Arg Arg
                405                 410                 415

Ala Ala Gln Ala Val Gln Ala Val Tyr Arg Asp Leu Gly Leu Ala Asp
            420                 425                 430

Tyr Asp Asp Ala Arg Val Glu Asp Val Val Ala Ala Asn Gly Ser Arg
435                 440                 445

Asp Leu Pro Ala Gly His Pro Lys Met Val Ala Glu Ala Ala Ala Ser
            450                 455                 460

Ile Glu Ala Arg Gln Leu Thr Val Phe Asp Val Ile Ala Ala Leu His
465                 470                 475                 480

Arg Thr Gly Phe Thr Glu Glu Ala Glu Ala Ile Thr Thr Leu Thr Arg
                485                 490                 495

Glu Arg Leu Arg Gly Asp Gln Leu Gln Thr Ser Ala Ile Phe Asp Glu
            500                 505                 510

Gln Phe Arg Val Phe Ser Lys Leu Thr Asp Pro Asn Asp Tyr Arg Gly
            515                 520                 525

Pro Ala Thr Gly Tyr Ala Leu Thr Glu Gln Arg Arg Ala Glu Ile Asp
            530                 535                 540

Ala Ile Arg Gln Ala Arg Ser Gly Ala Glu Leu Thr Val Asp Gln Glu
545                 550                 555                 560

Glu His Arg Gly His Val Val Thr Asp Val Glu Pro Ala His Gln
                565                 570                 575

Gly Ser Asp Pro Arg Glu Val Cys Ile Gly Leu Ser Pro Ala Trp Gly
            580                 585                 590

Arg Ser Val Trp Leu Thr Leu Cys Gly Leu Thr Val Gly Glu Val Leu
            595                 600                 605

Arg Gln Ile Ala Ala Gly Leu Glu Glu Glu Gly Cys Ile Ala Arg Thr
610                 615                 620

Val Arg Val Cys Ser Thr Ile Asp Thr Gly Leu Ile Gly Leu Thr Ala
625                 630                 635                 640

Ala Arg Leu Ser Gly Ser Gly Ile Gly Ile Gly Leu Gln Gly Lys Gly
                645                 650                 655

Thr Ala Leu Ile His Arg Arg Asp Leu Ala Pro Leu Ala Asn Leu Glu
            660                 665                 670

Leu Phe Ser Val Ala Pro Leu Leu Thr Ala Lys Met Tyr Arg Glu Leu
            675                 680                 685
```

```
Gly Lys Asn Ala Ala Arg His Ala Lys Gly Met Ala Pro Val Pro Ile
    690                 695                 700

Phe Thr Gly Gly Thr Asp Glu Ser Ile Ser Ala Arg Tyr His Ala Arg
705                 710                 715                 720

Ala Val Ala Leu Val Ala Leu Glu Arg Asp Ala Cys Glu Pro Gly Arg
                725                 730                 735

Ala Pro Val Thr Val Lys Val Glu Ala Arg
                740                 745

<210> SEQ ID NO 240
<211> LENGTH: 109
<212> TYPE: PRT
<213> ORGANISM: Mycobacterium flavescens

<400> SEQUENCE: 240

Met Ser Glu Ile Thr Thr Gln Asn Ala Val Asp Gly Lys Leu Gly Leu
1               5                   10                  15

Gly Asp Leu Arg Met Asp Pro Ala Val Leu Glu His Gln Ala Ala Val
                20                  25                  30

Ala Glu Glu Gly Gly Asn Pro Gln Leu Ala Glu Asn Phe Arg Arg Ala
            35                  40                  45

Ala Glu Leu Ala Thr Ile Asp Asp Thr Val Met Ala Leu Tyr Glu
        50                  55                  60

Ala Leu Arg Pro His Arg Ser Thr Ala Ala Glu Leu Asp Glu Leu His
65                  70                  75                  80

Ser Ser Leu Ile Ala Arg Gly Ala Pro Arg Cys Ala Ala Leu Val Glu
                85                  90                  95

Gln Ala Ala Ala Val Tyr Ala Arg Arg Gly Leu Leu Arg
                100                 105

<210> SEQ ID NO 241
<211> LENGTH: 739
<212> TYPE: PRT
<213> ORGANISM: Mycobacterium sp.

<400> SEQUENCE: 241

Met Arg Ile Leu Asp Ala Lys Pro Val Asn Leu Asp Gly Phe Ser Val
1               5                   10                  15

Thr Asp Pro Ala Leu Gly Leu Val Ala Met His Ser Pro His Asp Pro
                20                  25                  30

Gln Pro Ser Leu Val Val Arg Asp Gly Arg Val Val Glu Leu Asp Gly
            35                  40                  45

Arg Pro Ala Ala Asp Phe Asp Val Ile Asp Glu Phe Ile Ala Arg Tyr
        50                  55                  60

Gly Ile Asp Leu Thr Val Ala Glu Glu Ala Met Ala Leu Asp Asp Ala
65                  70                  75                  80

Val Leu Ala Arg Met Ala Val Asp Val Asn Val Pro Arg Ala Glu Val
                85                  90                  95

Val Arg Leu Ile Gly Gly Thr Thr Pro Ala Lys Leu Ala Arg Val Met
                100                 105                 110

Ala Val Met Thr Pro Val Glu Met Gln Met Ala Met His Lys Met Arg
                115                 120                 125

Ala Arg Arg Thr Pro Ser Asn Gln Ala His Val Thr Asn Gln Leu Asp
            130                 135                 140

Asp Pro Leu Leu Ile Ala Ala Asp Ala Ala Ser Ala Val Ala Tyr Gly
145                 150                 155                 160
```

```
Phe Arg Glu Val Glu Thr Thr Val Pro Val Phe Gly Asp Ala Pro Ser
                165                 170                 175

Asn Ala Ile Ala Leu Leu Ile Gly Ser Gln Val Gly Val Pro Gly Ala
            180                 185                 190

Met Ala Gln Cys Ser Ile Glu Glu Ala Met Glu Leu Arg Leu Gly Leu
        195                 200                 205

Arg Gly Leu Thr Ser Tyr Ala Glu Thr Ile Ser Ile Tyr Gly Thr Glu
    210                 215                 220

Gln Val Phe Val Asp Gly Asp Asp Thr Pro Phe Ser Lys Ala Ile Leu
225                 230                 235                 240

Thr Ala Ala Tyr Ala Ser Arg Gly Leu Lys Met Arg Val Thr Ser Gly
                245                 250                 255

Gly Gly Ala Glu Val Leu Met Gly Ala Ala Glu Lys Cys Ser Ile Leu
            260                 265                 270

Tyr Leu Glu Ser Arg Cys Val Ser Leu Ala Arg Ala Leu Gly Ser Gln
        275                 280                 285

Gly Val Gln Asn Gly Gly Ile Asp Gly Val Gly Val Ala Ser Val
    290                 295                 300

Pro Glu Gly Met Lys Glu Leu Leu Ala Glu Asn Leu Met Val Met Met
305                 310                 315                 320

Arg Asp Leu Glu Ser Cys Ala Gly Asn Asp Asn Leu Ile Ser Glu Ser
                325                 330                 335

Asp Ile Arg Arg Ser Ala His Thr Leu Pro Val Leu Leu Ala Gly Ala
            340                 345                 350

Asp Phe Ile Phe Ser Gly Phe Gly Ser Ile Pro Arg Tyr Asp Asn Ala
        355                 360                 365

Phe Ala Leu Ser Asn Phe Asn Ala Asp Asp Met Asp Asp Phe Leu Val
    370                 375                 380

Leu Gln Arg Asp Trp Gly Ala Asp Gly Gly Leu Arg Thr Val Ser Arg
385                 390                 395                 400

Glu His Leu Ala Arg Val Arg Arg Ala Ala Thr Ala Val Gln Ala
                405                 410                 415

Val Tyr Arg Asp Leu Gly Leu Ala Asp Phe Asp Asp Thr Arg Ile Asp
            420                 425                 430

Ala Val Val Ala Asn Asp Ser Arg Asp Leu Pro Ala Gly Asp Pro
        435                 440                 445

Lys Ala Val Ala Glu Ala Ala Thr Ala Ile Glu Ala Arg Gln Leu Thr
    450                 455                 460

Val Phe Asp Val Val Ala Ala Leu His Arg Thr Gly Tyr Ala Pro Glu
465                 470                 475                 480

Ala Glu Ala Ile Met Arg Leu Thr Arg Glu Arg Leu Arg Gly Asp Gln
                485                 490                 495

Leu Gln Thr Ser Ala Ile Phe Asp Asp Gln Phe Gln Val Leu Ser Lys
            500                 505                 510

Ile Thr Asp Pro Asn Asp Tyr Ala Gly Pro Gly Ser Gly Tyr Thr Pro
        515                 520                 525

Thr Glu Lys Arg Arg Ala Glu Ile Asp Gly Ile Arg Gln Ala Arg Thr
    530                 535                 540

Ser Ala Glu Leu Thr Ala Asp Gln Ala Glu His Arg Gly His Val Val
545                 550                 555                 560

Phe Ser Asp Val Glu Pro Ala Arg Gln Gly Ser Asp Pro Arg Glu Val
                565                 570                 575

Cys Ile Gly Leu Ser Pro Ala Leu Gly Arg Ser Val Trp Leu Thr Leu
```

```
                580                 585                 590
Cys Gly Leu Thr Val Gly Glu Val Leu Arg Gln Leu Ser Ala Gly Leu
            595                 600                 605

Glu Glu Glu Gly Cys Val Pro Arg Leu Val Arg Val Arg Ser Thr Ile
610                 615                 620

Asp Val Gly Leu Ile Gly Leu Thr Ala Ala Arg Leu Ser Gly Ser Gly
625                 630                 635                 640

Ile Gly Ile Gly Leu Gln Gly Lys Gly Thr Ala Leu Ile His Arg Arg
                645                 650                 655

Asp Leu Ala Pro Leu Ala Asn Leu Glu Leu Phe Ser Val Ala Pro Leu
            660                 665                 670

Leu Thr Ala Lys Met Tyr Arg Glu Leu Gly Arg Asn Ala Ala Arg His
        675                 680                 685

Ala Lys Gly Met Ala Pro Leu Pro Ile Leu Ala Gly Gly Thr Asp Glu
    690                 695                 700

Ser Ile Ser Ala Arg Tyr His Ala Arg Ala Val Ala Leu Val Ala Leu
705                 710                 715                 720

Glu Arg Gln Ala Cys Glu Pro Gly Gln Ala Pro Ile Thr Val Glu Ala
                725                 730                 735

Lys Arg Val

<210> SEQ ID NO 242
<211> LENGTH: 110
<212> TYPE: PRT
<213> ORGANISM: Mycobacterium sp.

<400> SEQUENCE: 242

Met Thr Glu Lys Phe Thr Val Ala Ala Ala Val Asp Gly Lys Leu Thr
1               5                   10                  15

Leu Ser Asp Leu Arg Met Asp Pro Ala Thr Leu Ala Tyr Gln Ala Val
            20                  25                  30

Val Ala Glu Gln Asp Gly Asn Pro Gln Leu Ala Glu Asn Phe Leu Arg
        35                  40                  45

Ala Ala Glu Leu Ala Val Ile Asp Asp Glu Ala Val Met Lys Leu Tyr
    50                  55                  60

Glu Ala Leu Arg Pro His Arg Ser Thr Ala Ala Glu Leu Glu Glu Leu
65                  70                  75                  80

Arg Val Ser Leu Glu Thr Gly Gly Ala Ser Arg Cys Ala Glu Leu Val
                85                  90                  95

Arg Gln Ala Ala Glu Val Tyr Ala Arg Arg Gly Leu Leu Arg
            100                 105                 110

<210> SEQ ID NO 243
<211> LENGTH: 570
<212> TYPE: PRT
<213> ORGANISM: Mycobacterium smegmatis

<400> SEQUENCE: 243

Met Thr Thr Ala Arg Asn Leu Gly Thr Glu Ala Lys Arg Gln Ser Glu
1               5                   10                  15

Arg Thr Lys Leu Leu Glu Glu Arg Pro Val Asn Leu Asp Gly Phe Val
            20                  25                  30

Gln Glu Trp Pro Glu Val Gly Met Val Ala Met Asp Ser Ala Phe Asp
        35                  40                  45

Pro Glu Pro Ser Val Arg Val Glu Asn Gly Val Ile Val Glu Met Asp
    50                  55                  60
```

```
Gly Arg Ala Arg Ala Asp Phe Asp Phe Ile Asp Gln Phe Ile Ala Asp
 65                  70                  75                  80

His Ala Ile Asp Val Ala Thr Thr Glu Gln Ser Met Ala Leu Pro Ala
                 85                  90                  95

Val Glu Ile Ala Arg Met Leu Val Asp Pro Arg Val Thr Arg Asp Glu
            100                 105                 110

Val Ile Ala Val Thr Gly Gly Leu Thr Pro Ala Lys Leu Leu Glu Val
        115                 120                 125

Ala Lys Asn Leu Asn Ile Val Glu Ile Met Met Gly Ile Gln Lys Met
    130                 135                 140

Arg Ala Arg Arg Thr Pro Ala Asn Gln Ala His Cys Thr Ser Ala Arg
145                 150                 155                 160

Asp Asn Pro Leu Gln Val Ala Cys Glu Ala Ala Glu Ala Ser Leu Arg
                165                 170                 175

Gly Phe Ser Glu Val Glu Thr Thr Leu Gly Val Val Arg Tyr Ala Pro
            180                 185                 190

Leu Val Ala Met Ala Leu Gln Ile Gly Ser Gln Val Gly Ser Gly Gly
        195                 200                 205

Leu Leu Thr Gln Cys Ala Leu Glu Glu Ala Thr Glu Leu Glu Leu Gly
    210                 215                 220

Met Arg Gly Ile Thr Ala Tyr Ala Glu Thr Ile Ser Val Tyr Gly Thr
225                 230                 235                 240

Glu Ser Val Phe Val Asp Gly Asp Asp Thr Pro Trp Ser Lys Ala Phe
                245                 250                 255

Leu Ala Ala Ala Tyr Ala Ser Arg Gly Ile Lys Met Arg Phe Thr Ser
            260                 265                 270

Gly Thr Gly Ser Glu Val Gln Met Gly Asn Ala Glu Gly Arg Ser Met
        275                 280                 285

Leu Tyr Leu Glu Ile Arg Cys Ile Leu Val Ala Lys Gly Ala Gly Val
    290                 295                 300

Gln Gly Leu Gln Asn Gly Ser Ile Ser Cys Ile Gly Val Pro Gly Ala
305                 310                 315                 320

Val Pro Ala Gly Ile Arg Ala Val Ala Ala Glu Asn Leu Ile Ala Ser
                325                 330                 335

Ala Val Asp Leu Glu Cys Ala Ser Gly Asn Asp Gln Ser Phe Ser His
            340                 345                 350

Ser Pro Met Arg Arg Thr Ala Arg Leu Leu Pro Gln Met Leu Pro Gly
        355                 360                 365

Thr Asp Phe Val Cys Ser Gly Tyr Ser Ala Val Pro Asn Tyr Asp Asn
    370                 375                 380

Met Phe Ala Gly Ser Asn Leu Asp Ala Glu Asp Phe Asp Asp Phe Asn
385                 390                 395                 400

Thr Ile Gln Arg Asp Leu Gln Val Asp Gly Gly Leu Arg His Val Asn
                405                 410                 415

Glu Ala Glu Ile Val Ala Ala Arg Arg Ala Ala Gln Ala Leu Gln
            420                 425                 430

Ala Val Phe Arg Tyr Leu Asp Leu Pro Ala Ile Thr Asp Ala Glu Ile
        435                 440                 445

Glu Ala Ala Val Tyr Ala His Gly Ser Arg Glu Leu Ile Pro Arg Asp
    450                 455                 460

Val Leu Glu Asp Leu Lys Gly Ala Gln Gln Val Met Asp Arg Asn Val
465                 470                 475                 480
```

```
Thr Gly Leu Asp Leu Val Lys Ala Leu Glu Ser Thr Gly Phe Ala Asp
                485                 490                 495

Ile Ala Glu Asn Leu Leu Ala Val Leu Arg Gln Arg Val Ser Gly Asp
            500                 505                 510

Leu Leu Gln Thr Ser Ala Ile Met Thr Arg Asp Leu Lys Pro Leu Ser
        515                 520                 525

Ala Val Asn Asp Arg Asn Asp Tyr Ala Gly Pro Gly Thr Gly Tyr Arg
    530                 535                 540

Pro Ser Gly Ala Arg Trp Glu Glu Met Lys Arg Leu Arg His Val Thr
545                 550                 555                 560

Ser Ala Glu Asn Pro Glu Leu Glu Val Glu
                565                 570

<210> SEQ ID NO 244
<211> LENGTH: 200
<212> TYPE: PRT
<213> ORGANISM: Mycobacterium smegmatis

<400> SEQUENCE: 244

Met Ile Met Ser Ala Gln Ser Thr Gln Ala Gln Arg Thr Leu Glu Leu
1               5                   10                  15

Val Gly Asp Ser Pro Ala Glu Pro Gly Lys Arg Ser Asp Glu Val Val
            20                  25                  30

Leu Ala Val Ser Pro Ala Phe Ala Asp Phe Phe Ser Gln Thr Ile Ile
        35                  40                  45

Gly Leu Ser His Ala Asp Val Ile Arg Glu Ile Leu Ala Gly Ile Glu
    50                  55                  60

Glu Gln Glu Val His Ala Arg Cys Ile Arg Val Arg His Ser Ser Asp
65                  70                  75                  80

Leu Ala Val Leu Ala His Thr Ala Ala Lys Leu Ser Gly Ser Gly Ile
                85                  90                  95

Gly Ile Gly Ile Leu Ser Arg Gly Thr Ser Met Ile His Gln Arg Asp
            100                 105                 110

Leu Pro Arg Leu Ser Ser Leu Glu Leu Phe Pro Gln Ser Pro Leu Met
        115                 120                 125

Thr Leu Glu Thr Tyr Arg Ser Ile Gly Ser Asn Ala Ala Gln Tyr Ala
    130                 135                 140

Lys Gly Glu Ser Pro Glu Pro Val Pro Thr Leu Asn Asp Gln Met Ala
145                 150                 155                 160

Arg Pro Arg Trp Gln Ala Lys Ala Ala Leu Leu His Leu Lys Glu Thr
                165                 170                 175

Glu Gln Val Val Lys Gln Ala Lys Pro Val Glu Val Pro Gln Phe
            180                 185                 190

Gly Val Ala Glu Ala Leu Gly Thr
        195                 200

<210> SEQ ID NO 245
<211> LENGTH: 114
<212> TYPE: PRT
<213> ORGANISM: Mycobacterium smegmatis

<400> SEQUENCE: 245

Met Asn Asp Lys Phe Thr Asp Lys Tyr Thr Val Ala Ala Val Asp
1               5                   10                  15

Gly Lys Leu Asp Leu Ser Asp Leu Arg Met Asp Pro Ala Val Leu Ala
            20                  25                  30
```

His Gln Ala Val Ile Ala Glu Glu Asn Gly Asn Pro Gln Leu Ala Glu
            35                  40                  45

Asn Phe Leu Arg Ala Ala Glu Leu Ala Thr Ile Asp Asp Glu Asp Val
 50                  55                  60

Met Arg Leu Tyr Glu Ala Leu Arg Pro Tyr Arg Ser Ser Ala Glu Asp
 65                  70                  75                  80

Leu Asp Ala Leu Gln Ala Ser Leu Glu Ser Arg Gly Ala Ala Arg Cys
                    85                  90                  95

Ala Glu Leu Val Arg Gln Ala Ala Glu Ala Tyr Ala Arg Arg Gly Leu
                100                 105                 110

Leu Arg

<210> SEQ ID NO 246
<211> LENGTH: 754
<212> TYPE: PRT
<213> ORGANISM: Mycobacterium smegmatis

<400> SEQUENCE: 246

Met His Leu Asn Ser Thr Glu Val Asp Ser Arg Leu Gly Arg Ile Arg
 1               5                  10                  15

Leu Leu Asp Arg Gln Arg Val Asn Leu Asp Gly Phe Ala Asp Val Asp
                20                  25                  30

Ala Glu Leu Gly Met Ile Ser His Leu Ser Pro Asn Asp Pro Glu Pro
            35                  40                  45

Ser Trp Val Val Ala Asp Asp Gly Thr Val Leu Glu Met Asp Ser Lys
 50                  55                  60

Pro Ala Glu Asp Phe Asp Thr Ile Asp Glu Phe Ile Val Lys Tyr Ala
 65                  70                  75                  80

Ile Asp His Glu Gln Ala Pro Arg Ser Met Ala Met Thr Asp Leu Asp
                    85                  90                  95

Leu Ala Arg Met Ile Val Asp Pro Gly Arg Pro Arg Glu Glu Ile Leu
                100                 105                 110

Arg Val Cys Ser Gly Leu Thr Pro Ala Lys Met Ala Arg Val Val Ala
            115                 120                 125

Ser Leu Gln Pro Val Glu Ile Gln Met Ala Met Lys Met Arg Ala
 130                 135                 140

Arg Arg Thr Pro Ala Asn Gln Ala His Val Thr Asn Arg Leu Asp Asp
145                 150                 155                 160

Pro Leu Leu Ile Ala Ala Asp Ala Ala Thr Ala Val Val Tyr Gly Phe
                165                 170                 175

Arg Glu Leu Glu Ala Thr Val Pro Val Leu Asp Asp Ala Pro Ala Val
                180                 185                 190

Ala Val Gly Leu Leu Ile Gly Ser Gln Val Pro Ala Pro Gly Ala Leu
            195                 200                 205

Thr Gln Cys Ser Val Glu Glu Ala Arg Glu Leu Glu Leu Gly Val Arg
 210                 215                 220

Gly Leu Val Ser Tyr Ala Glu Thr Val Ser Val Tyr Gly Thr Glu Gln
225                 230                 235                 240

Val Phe Thr Asp Gly Asp Asp Thr Pro Trp Ser Lys Ala Phe Leu Thr
                245                 250                 255

Ser Cys Tyr Ala Ser Arg Gly Ile Lys Met Arg Leu Ser Ser Gly Ala
                260                 265                 270

Gly Ser Glu Val Leu Met Gly Gln Ala Glu Gly Lys Ser Met Asn Tyr
            275                 280                 285

-continued

```
Leu Glu Ala Arg Cys Val Ala Leu Ala Arg Gly Ile Gly Ala Gln Gly
290                 295                 300
Val Gln Asn Gly Gly Val Asp Gly Ala Ala Ile Thr Ala Ser Val Pro
305                 310                 315                 320
Gly Gly Val Lys Glu Leu His Ala Glu Asn Leu Met Val Met Leu Arg
            325                 330                 335
Gly Leu Glu Ser Cys Ser Gly Asn Asp Ser Leu Met Ser Glu Ser Thr
            340                 345                 350
Met Arg Arg Thr Ser Arg Thr Leu Pro Thr Leu Leu Ser Gly Ser Asp
        355                 360                 365
Phe Ile Phe Ser Gly Phe Gly Ser Val Ser Tyr Asp Asn Met Phe
370                 375                 380
Gly Pro Ser Asn Phe Asn Ala Ala Asp Leu Asp Asp Tyr Leu Val Leu
385                 390                 395                 400
Gln Arg Asp Trp Gly Val Asp Gly Gly Leu Arg Ser Val Asp Pro Thr
                405                 410                 415
Thr Leu Glu Ser Met Arg Arg Glu Ala Ala Glu Ala Thr Arg Ala Val
            420                 425                 430
Phe Glu Tyr Leu Gly Leu Ala Asp Phe Asp Asp Asp His Val Glu Ala
        435                 440                 445
Val Val Gly Ala Glu Gly Ser Lys Asp Leu Pro Gln Asp Asp Gly Val
450                 455                 460
Lys Val Leu Ser Ala Ala Arg Met Ile Asp Gln Ser Gly Leu Thr Val
465                 470                 475                 480
Leu Asp Ile Val Ser Ala Leu Ala Glu Thr Gly Phe Thr His Ile Ala
                485                 490                 495
Asp Arg Val Leu Gly Met Ala Arg Ala Arg Val Thr Gly Asp Tyr Leu
            500                 505                 510
Gln Thr Ala Ala Ile Phe Asp Glu Glu Met Asn Val Leu Ser Ala Leu
        515                 520                 525
His Asp Pro Asn Asp Tyr Arg Gly Pro Gly Thr Gly Tyr Arg Pro Thr
530                 535                 540
Pro Glu Arg Gln Ala Gln Ile Asp Ala Val Arg Gln Ala Arg Ser Val
545                 550                 555                 560
Ala Asp Leu Val Lys Glu Gln Ala Thr Ser Ala Gln Pro Asp Arg Leu
                565                 570                 575
Arg Val Leu Gly Ala Ala Thr Val Gly Glu Asp Pro Arg Glu Val Val
            580                 585                 590
Ile Gly Val Ser Pro Ala Phe Gly Thr Lys Leu Phe Arg Thr Leu Ser
        595                 600                 605
Gly Met Thr Ile Tyr Asp Val Leu Glu Gln Ile Leu Ala Gly Leu Glu
610                 615                 620
Glu Glu His Cys Val Pro Arg Leu Val Arg Ile Thr Asp Ser Ile Asp
625                 630                 635                 640
Leu Gly Ala Ile Gly Lys Ser Ala Ala Gln Leu Ser Gly Ser Gly Ile
                645                 650                 655
Gly Val Gly Leu Gln Ala Lys Gly Thr Thr Leu Ile His Arg Arg Asp
            660                 665                 670
Leu Pro Pro Leu Ala Asn Leu Glu Leu Ser Val Ala Pro Leu Ile
        675                 680                 685
Thr Pro Glu Met Tyr Arg Leu Ile Gly Ile Asn Ala Gly Arg His Ala
690                 695                 700
Lys Gly Ala Thr Pro Ser Pro Met Arg Asn Ala Tyr Thr Asp Glu Ala
```

```
                     705                 710                 715                 720

Ile Thr Ala Arg Tyr His Thr Lys Val Ser Met Val Ala Ile Glu
                725                 730                 735

Arg Glu Glu Ser Glu Arg Arg Glu Thr Gly Asn Val Glu Leu Glu Ile
            740                 745                 750

Thr Arg

<210> SEQ ID NO 247
<211> LENGTH: 757
<212> TYPE: PRT
<213> ORGANISM: Mycobacterium smegmatis

<400> SEQUENCE: 247

Met Val Ala Val Thr Glu Ser Gly Asp Pro Gly Gln Ser Pro Glu Leu
1               5                   10                  15

Gly Arg Met Arg Ile Leu Asp Ala Lys Pro Val Asn Leu Asp Gly Phe
            20                  25                  30

Ser Val Pro Asp Pro Asp Leu Gly Leu Ala Ala Met Ser Ser Pro His
        35                  40                  45

Asp Pro Gln Pro Ser Leu Val Ile Arg Asp Gly Arg Val Val Glu Met
    50                  55                  60

Asp Gly Lys Ala Ala Glu Asp Phe Asp Val Ile Asp Glu Phe Ile Ala
65                  70                  75                  80

Arg Tyr Gly Leu Asp Leu Asp Val Ala Pro Glu Ala Met Ala Met Ser
                85                  90                  95

Asp Ile Asp Leu Ala Arg Met Ala Val Asp Ile Asn Val Pro Arg Ala
            100                 105                 110

Glu Val Val Arg Leu Ile Ala Gly Thr Thr Pro Ala Lys Leu Ala Lys
        115                 120                 125

Val Ile Ala Val Leu Thr Pro Val Glu Met Gln Ala Ala Met Ala Lys
    130                 135                 140

Met Arg Ala Arg Arg Thr Pro Ser Asn Gln Ala His Val Thr Asn Gln
145                 150                 155                 160

Leu Asp Asp Pro Leu Leu Ile Ala Ala Asp Ala Ala Ser Ala Val Ala
                165                 170                 175

Tyr Gly Phe Arg Glu Val Glu Thr Thr Val Pro Val Leu Ala Asp Ala
            180                 185                 190

Pro Ser Asn Ala Val Ala Leu Leu Ile Gly Ser Gln Val Gly Val Pro
        195                 200                 205

Gly Ala Met Ala Gln Cys Ser Ile Glu Glu Ala Leu Glu Leu Arg Leu
    210                 215                 220

Gly Leu Arg Gly Leu Thr Ser Tyr Ala Glu Thr Ile Ser Ile Tyr Gly
225                 230                 235                 240

Thr Glu Gln Val Phe Val Asp Gly Asp Asp Thr Pro Phe Ser Lys Ala
                245                 250                 255

Ile Leu Thr Ser Ala Tyr Ala Ser Arg Gly Leu Lys Met Arg Val Thr
            260                 265                 270

Ser Gly Gly Gly Ala Glu Val Leu Met Gly Ala Ala Glu Lys Cys Ser
        275                 280                 285

Ile Leu Tyr Leu Glu Ser Arg Cys Val Ser Leu Ala Arg Ala Leu Gly
    290                 295                 300

Ser Gln Gly Val Gln Asn Gly Ile Asp Gly Val Gly Val Val Ala
305                 310                 315                 320

Ser Val Pro Asp Gly Met Lys Glu Leu Leu Ala Glu Asn Leu Met Val
```

```
                    325                 330                 335
Met Met Arg Asp Leu Glu Ser Cys Ala Gly Asn Asp Asn Leu Ile Ser
                340                 345                 350
Glu Ser Asp Ile Arg Arg Ser Ala His Thr Leu Pro Val Leu Leu Ala
                355                 360                 365
Gly Ala Asp Phe Ile Phe Ser Gly Phe Gly Ser Ile Pro Arg Tyr Asp
                370                 375                 380
Asn Ala Phe Ala Leu Ser Asn Phe Asn Ser Asp Asp Met Asp Asp Phe
385                 390                 395                 400
Leu Val Leu Gln Arg Asp Trp Gly Ala Asp Gly Gly Leu Arg Thr Val
                405                 410                 415
Pro Ala Asp Gln Leu Ala Ala Val Arg Arg Ala Ala Arg Ala Val
                420                 425                 430
Gln Ala Val Tyr Arg Asp Leu Gly Leu Ala Asp Phe Asp Asp Gln His
                435                 440                 445
Ile Glu Asn Val Val Ala Asn Gly Ser Arg Asp Leu Pro Pro Gly
                450                 455                 460
Asp Pro Lys Ala Val Leu Glu Ala Ala Asn Ala Ile Glu Ala Lys Gln
465                 470                 475                 480
Leu Thr Val Phe Asp Val Val Ala Ser Leu Lys Arg Thr Gly Phe Asp
                485                 490                 495
Pro Glu Ala Glu Ala Ile Met Arg Leu Thr Ala Glu Arg Met Arg Gly
                500                 505                 510
Asp Gln Leu Gln Thr Ser Ala Ile Phe Asp Glu Gln Phe Arg Val Leu
                515                 520                 525
Ser Lys Ile Thr Asp Pro Asn Asp Tyr Ala Gly Pro Gly Thr Gly Tyr
                530                 535                 540
Thr Leu Ser Glu Gln Arg Arg Ala Glu Ile Asp Asn Ile Arg Gln Gln
545                 550                 555                 560
Arg Ser Ala Ala Glu Leu Thr Ala Asp Gln Ala Glu His Ala Gly His
                565                 570                 575
Ile Thr Val Thr Glu Ile Glu Pro Ala Arg Gln Gly Ser Asp Pro Arg
                580                 585                 590
Glu Val Cys Ile Gly Leu Ser Pro Ala Leu Gly Arg Ser Val Trp Leu
                595                 600                 605
Ser Leu Cys Gly Leu Pro Ile Gly Glu Val Ile Arg Gln Ile Ser Ala
                610                 615                 620
Gly Leu Glu Glu Glu Gly Cys Val Pro Arg Phe Val Arg Val Arg Ser
625                 630                 635                 640
Thr Ile Asp Val Gly Leu Ile Gly Leu Thr Ala Ala Lys Leu Ala Gly
                645                 650                 655
Ser Gly Ile Gly Ile Gly Leu Gln Gly Lys Gly Thr Ala Leu Ile His
                660                 665                 670
Arg Arg Asp Leu Ala Pro Leu Ala Asn Leu Glu Leu Phe Ser Val Ala
                675                 680                 685
Pro Leu Leu Thr Ala Arg Asn Tyr Arg Glu Leu Gly Arg Asn Ala Ala
                690                 695                 700
Arg His Ala Lys Gly Met Ala Pro Val Pro Ile Leu Thr Gly Gly Thr
705                 710                 715                 720
Asp Glu Ser Ile Ser Ala Arg Tyr His Ala Arg Ala Val Ala Leu Val
                725                 730                 735
Ala Leu Glu Arg Gln Ala Ser Glu Pro Gly Glu Ala Pro Val Thr Val
                740                 745                 750
```

Glu Val Arg Arg Pro
         755

<210> SEQ ID NO 248
<211> LENGTH: 142
<212> TYPE: PRT
<213> ORGANISM: Mycobacterium smegmatis

<400> SEQUENCE: 248

Met Ser Glu Pro Val Leu Asp Pro Ala Val Asp Tyr Pro Leu Ser Leu
1               5                   10                  15

Asn Arg Lys Asp Leu Leu Thr Thr Pro Asn Gly Lys Pro Ile Asp Ala
            20                  25                  30

Ile Thr Met Asp Ala Val Met Ser Gly Glu Val Ser Ala Ser Asp Leu
        35                  40                  45

Arg Ile Thr Pro Glu Thr Leu Arg Leu Gln Ala Gln Ile Ala Glu Gly
    50                  55                  60

Val Gly Arg Lys Gln Leu Gly Ala Asn Leu Arg Arg Ala Ala Glu Met
65                  70                  75                  80

Thr Ala Ile Ser Asp Glu Arg Val Leu Gln Ile Tyr Asn Ala Leu Arg
                85                  90                  95

Pro Asn Ala Ser Thr Lys Ala Glu Leu Asp Ala Ile Ala Glu Glu Leu
            100                 105                 110

Glu Thr Gln Tyr Gly Ala Thr Met Leu Ala Gly Leu Val Arg Glu Ala
        115                 120                 125

Ala Asp Val Tyr Glu Arg Arg Asp Ile Leu Ala Thr Ser Glu
    130                 135                 140

<210> SEQ ID NO 249
<211> LENGTH: 119
<212> TYPE: PRT
<213> ORGANISM: Mycobacterium smegmatis

<400> SEQUENCE: 249

Met Thr Ile Thr Ser His Ser Gly Arg Ser Ile Asp Glu Val Thr Val
1               5                   10                  15

Glu Ala Ala Arg Gly Gly Asp Leu Thr Leu Asp Asp Ile Arg Ile Ser
            20                  25                  30

Arg Asp Thr Leu Ile Ser Gln Ala Glu Ala Ala Glu Arg Thr Gly Ser
        35                  40                  45

Glu Gln Leu Gly Leu Asn Leu Arg Arg Ala Ala Glu Leu Thr Ala Leu
    50                  55                  60

Ser Ser Asp Asp Met Leu Ala Ala Tyr Glu Ala Leu Arg Pro Gly Arg
65                  70                  75                  80

Ser Thr Phe Ser Glu Leu Glu Ala Leu Ala Gln Arg Leu Ala Ala Gln
                85                  90                  95

Glu Ala His Thr Cys Ala Gln Leu Val Arg Glu Ala Ala Ala Ala Tyr
            100                 105                 110

Arg Arg Arg Gly Leu Leu Arg
        115

<210> SEQ ID NO 250
<211> LENGTH: 224
<212> TYPE: PRT
<213> ORGANISM: Salmonella enterica subsp. enterica serovar Paratyphi

<400> SEQUENCE: 250

Met Glu Ile Asn Glu Lys Leu Leu Arg Gln Ile Ile Glu Asp Val Leu
1               5                   10                  15

Arg Asp Met Lys Gly Ser Asp Lys Pro Val Ser Phe Asn Thr Pro Ala
            20                  25                  30

Ala Ser Thr Ala Pro Gln Thr Ala Ala Pro Ala Gly Asp Gly Phe Leu
        35                  40                  45

Thr Glu Val Gly Glu Ala Arg Gln Gly Thr Gln Gln Asp Glu Val Ile
50                  55                  60

Ile Ala Val Gly Pro Ala Phe Gly Leu Ala Gln Thr Val Asn Ile Val
65                  70                  75                  80

Gly Leu Pro His Lys Ser Ile Leu Arg Glu Val Ile Ala Gly Ile Glu
                85                  90                  95

Glu Glu Gly Ile Arg Ala Arg Val Ile Arg Cys Phe Lys Ser Ser Asp
                100                 105                 110

Val Ala Phe Val Ala Val Glu Gly Asn Arg Leu Ser Gly Ser Gly Ile
            115                 120                 125

Ser Ile Gly Ile Gln Ser Lys Gly Thr Thr Val Ile His Gln Gln Gly
        130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Asp Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
210                 215                 220

<210> SEQ ID NO 251
<211> LENGTH: 173
<212> TYPE: PRT
<213> ORGANISM: Salmonella enterica subsp. enterica serovar Paratyphi

<400> SEQUENCE: 251

Met Asn Ile Asp Ala Ile Glu Ser Met Val Arg Asp Val Leu Ser Arg
1               5                   10                  15

Met Asn Ser Leu Gln Gly Asp Ala Pro Ala Ala Pro Ala Ala Gly
            20                  25                  30

Gly Thr Ser Arg Ser Ala Lys Val Ser Asp Tyr Pro Leu Ala Asn Lys
        35                  40                  45

His Pro Glu Trp Val Lys Thr Ala Thr Asn Lys Thr Leu Asp Asp Phe
50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Asn Arg Tyr Gln Ala Lys Ile Cys Ala Ala Phe Val Arg Glu Ala Ala
145                 150                 155                 160

```
Gly Leu Tyr Val Glu Arg Lys Lys Leu Lys Gly Asp Asp
                165                 170
```

<210> SEQ ID NO 252
<211> LENGTH: 188
<212> TYPE: PRT
<213> ORGANISM: Clostridium perfringens

<400> SEQUENCE: 252

```
Met Glu Glu Arg Thr Phe Ile Pro Glu Ile Thr Val Glu Val Gly
1               5                   10                  15

Glu Ala Lys Val Gly Leu Arg Ser Asp Glu Val Val Ile Gly Leu Ala
                20                  25                  30

Pro Ala Phe Leu Lys Tyr Gln Asn Lys Thr Ile Val Asp Val Pro His
                35                  40                  45

Thr Glu Thr Leu Leu Glu Ile Ile Ala Gly Ile Glu Glu Gly Leu
            50                  55                  60

His Ala Arg Val Val Arg Val Leu Arg Thr Ser Asp Val Ser Phe Ile
65                  70                  75                  80

Ala His Asp Ala Ala Cys Leu Ser Gly Ser Gly Ile Gly Ile Gly Ile
                85                  90                  95

Gln Ser Lys Gly Thr Thr Val Ile His Gln Lys Asp Leu Leu Pro Leu
                100                 105                 110

Asn Asn Leu Glu Leu Phe Ser Gln Ala Pro Leu Leu Thr Pro Glu Thr
                115                 120                 125

Tyr Arg Leu Ile Gly Lys Asn Ala Ala Lys Tyr Ala Lys Gly Glu Ser
                130                 135                 140

Pro Thr Pro Val Pro Val Lys Asn Asp Gln Met Val Arg Pro Lys Phe
145                 150                 155                 160

Met Ala Lys Ala Ala Leu Leu His Ile Lys Glu Thr Lys His Val Glu
                165                 170                 175

Pro Gly Lys Lys Pro Val Gln Leu Glu Val Lys Phe
                180                 185
```

<210> SEQ ID NO 253
<211> LENGTH: 141
<212> TYPE: PRT
<213> ORGANISM: Clostridium perfringens

<400> SEQUENCE: 253

```
Met Glu Asn Lys Arg Met Thr Ala Ala Asp Tyr Pro Leu Thr Ser Lys
1               5                   10                  15

Arg Lys Gly Asp Ile Lys Thr Pro Thr Gly Lys Ala Leu Glu Asp Ile
                20                  25                  30

Thr Leu Glu Lys Val Leu Ser Gly Glu Ile Asn Ala Asp Ile Arg
            35                  40                  45

Ile Ser Pro Glu Thr Leu Glu Met Gln Ala Gln Ile Ala Glu Ser Met
        50                  55                  60

Asn Arg Asp Ala Ile Ala Arg Asn Phe Arg Arg Ala Ala Glu Leu Ile
65                  70                  75                  80

Arg Val Pro Asp Asp Arg Ile Leu Glu Met Tyr Asn Ala Leu Arg Pro
                85                  90                  95

Tyr Arg Ser Thr Lys Glu Asp Leu Phe Lys Ile Ala Asp Glu Leu Glu
                100                 105                 110

Thr Lys Tyr Asp Ala Lys Val Asn Ala Asn Phe Val Arg Glu Ala Ala
                115                 120                 125
```

```
Glu Val Tyr Glu Thr Arg Asn Lys Leu Arg Ile Glu Glu
    130                 135                 140

<210> SEQ ID NO 254
<211> LENGTH: 554
<212> TYPE: PRT
<213> ORGANISM: Salmonella enterica subsp. enterica serovar Typhimurium

<400> SEQUENCE: 254

Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Glu Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Ser Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
```

```
                   355                 360                 365
Asn Tyr Asp Asn Met Phe Ala Gly Ser Asn Glu Asp Ala Glu Asp Phe
            370                 375                 380

Asp Asp Tyr Asn Val Ile Gln Arg Asp Leu Lys Val Asp Gly Gly Leu
385                 390                 395                 400

Arg Pro Val Arg Glu Asp Val Ile Ala Ile Arg Asn Lys Ala Ala
                    405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
            435                 440                 445

Pro Glu Arg Asn Ile Val Glu Asp Ile Lys Phe Ala Gln Glu Ile Ile
        450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
530                 535                 540

Pro Gly Ala Leu Asp Pro Asn Glu Ile Asp
545                 550

<210> SEQ ID NO 255
<211> LENGTH: 524
<212> TYPE: PRT
<213> ORGANISM: Listeria monocytogenes

<400> SEQUENCE: 255

Met Glu Ser Pro Asn Asp Pro Lys Pro Ser Ile Lys Ile Glu Asn Gly
1               5                   10                  15

Lys Val Glu Met Asp Ser Lys Lys Leu Ala Asp Phe Asp Leu Ile
            20                  25                  30

Asp His Phe Ile Ala Lys Tyr Gly Val Asp Leu Ser Arg Ala Glu Glu
        35                  40                  45

Val Met Gln Met Asp Ser Val Lys Leu Ala Asn Met Leu Cys Asp Pro
    50                  55                  60

Asn Val Pro Arg Glu Lys Ile Val Leu Leu Thr Thr Ala Met Thr Pro
65                  70                  75                  80

Ala Lys Ile Val Glu Val Ser Gln Met Asn Val Val Glu Met Met
                85                  90                  95

Met Ser Met Gln Lys Met Arg Ser Arg Arg Thr Pro Thr Thr Gln Ala
            100                 105                 110

His Val Thr Asn Leu Arg Asp Asn Pro Val Gln Ile Ala Ala Asp Ala
        115                 120                 125

Ala Glu Ala Ala Ile Arg Gly Phe Asp Glu Gln Glu Thr Thr Val Ala
    130                 135                 140

Val Val Arg Tyr Ala Pro Phe Asn Ala Leu Ser Leu Leu Val Gly Ser
145                 150                 155                 160

Gln Thr Gly Arg Gly Gly Val Leu Thr Gln Cys Ser Leu Glu Glu Ala
                165                 170                 175
```

Thr Glu Leu Glu Leu Gly Met Arg Gly Leu Thr Cys Tyr Ala Glu Thr
                180                 185                 190

Ile Ser Val Tyr Gly Thr Glu Pro Val Phe Thr Asp Gly Asp Asp Thr
            195                 200                 205

Pro Trp Ser Lys Gly Ile Leu Ala Ser Ala Tyr Ala Ser Arg Gly Leu
        210                 215                 220

Lys Met Arg Phe Thr Ser Gly Thr Ser Glu Val Gln Met Gly Tyr
225                 230                 235                 240

Ala Glu Gly Lys Ser Met Leu Tyr Leu Glu Ser Arg Cys Ile Phe Ile
                245                 250                 255

Thr Lys Ala Ala Gly Val Gln Gly Leu Gln Asn Gly Ser Ile Ser Cys
            260                 265                 270

Ile Gly Ile Pro Gly Ala Val Pro Ser Gly Ile Arg Ala Val Leu Ala
        275                 280                 285

Glu Asn Leu Ile Ala Val Met Leu Asp Leu Glu Val Ala Ser Gly Asn
290                 295                 300

Asp Gln Thr Phe Ser His Ser Asp Ile Arg Arg Thr Ala Arg Leu Leu
305                 310                 315                 320

Met Gln Phe Leu Pro Gly Thr Asp Tyr Ile Ser Ser Gly Tyr Ser Ala
                325                 330                 335

Thr Pro Asn Tyr Asp Asn Met Phe Ala Gly Ser Asn Phe Asp Ala Asp
            340                 345                 350

Asp Phe Asp Asp Tyr Asn Ile Leu Gln Arg Asp Leu Lys Val Asp Gly
        355                 360                 365

Gly Leu Thr Pro Val Thr Glu Glu Val Val Ala Val Arg Asn Lys
370                 375                 380

Ala Ala Arg Val Ile Gln Ala Val Phe Asp Lys Leu Gly Leu Pro Glu
385                 390                 395                 400

Val Thr Asp Ala Glu Val Ala Ala Thr Tyr Ala Arg Gly Ser Lys
                405                 410                 415

Asp Met Pro Glu Arg Asn Met Val Glu Asp Ile Lys Ala Ala Glu
            420                 425                 430

Met Met Asp Arg Gly Val Thr Gly Leu Asp Val Val Lys Ala Leu Ser
        435                 440                 445

Ala Gly Gly Phe Asp Asp Val Ala Glu Ser Val Leu Asn Met Leu Lys
450                 455                 460

Gln Arg Val Ser Gly Asp Phe Leu His Thr Ser Ala Ile Ile Asp Lys
465                 470                 475                 480

Asp Trp Asn Val Ile Ser Ser Val Asn Asp Leu Asn Asp Tyr Ala Gly
                485                 490                 495

Pro Gly Thr Gly Tyr Arg Leu Glu Gly Glu Arg Trp Glu Lys Leu Lys
            500                 505                 510

Asp Ile Ala Val Ala Val Asp Ala Asn Glu Leu Glu
        515                 520

<210> SEQ ID NO 256
<211> LENGTH: 555
<212> TYPE: PRT
<213> ORGANISM: Escherichia blattae

<400> SEQUENCE: 256

Met Arg Arg Ser Lys Arg Phe Glu Val Leu Glu Lys Arg Pro Val Asn
1               5                   10                  15

Gln Asp Gly Leu Ile Gly Glu Trp Pro Glu Glu Gly Leu Ile Ala Met
            20                  25                  30

-continued

Gly Ser Pro Trp Asp Pro Ser Val Lys Val Glu Gln Gly Arg
        35              40              45

Ile Val Glu Leu Asp Gly Lys Ala Arg Ala Asp Phe Asp Met Ile Asp
    50              55              60

Arg Phe Ile Ala Asp Tyr Ala Ile Asn Ile Glu Glu Thr Glu His Ala
65              70              75              80

Met Gly Leu Asp Ala Leu Thr Ile Ala Arg Met Leu Val Asp Ile Asn
                85              90              95

Val Ser Arg Ala Glu Ile Ile Lys Val Thr Thr Ala Ile Thr Pro Ala
            100             105             110

Lys Ala Glu Glu Val Met Ser His Met Asn Val Val Glu Met Met Val
            115             120             125

Ala Leu Gln Lys Met Arg Ala Arg Arg Thr Pro Ser Asn Gln Cys His
        130             135             140

Val Thr Asn Leu Lys Asp Asn Pro Val Gln Ile Ala Ala Asp Ala Ala
145             150             155             160

Glu Ala Gly Ile Arg Gly Phe Ser Glu Gln Glu Thr Thr Val Gly Ile
                165             170             175

Ala Arg Tyr Ala Pro Phe Asn Ala Leu Ala Leu Leu Ile Gly Ser Gln
            180             185             190

Ser Gly Arg Pro Gly Val Leu Thr Gln Cys Ser Val Glu Glu Ala Thr
        195             200             205

Glu Leu Glu Leu Gly Met Arg Gly Phe Thr Ser Tyr Ala Glu Thr Val
    210             215             220

Ser Val Tyr Gly Thr Glu Ala Val Phe Thr Asp Gly Asp Asp Thr Pro
225             230             235             240

Trp Ser Lys Ala Phe Leu Ala Ser Ala Tyr Ala Ser Arg Gly Leu Lys
                245             250             255

Met Arg Tyr Thr Ser Gly Thr Gly Ser Glu Ala Leu Met Gly Tyr Ala
            260             265             270

Glu Ser Lys Ser Met Leu Tyr Leu Glu Ser Arg Cys Ile Phe Ile Thr
        275             280             285

Lys Gly Ala Gly Val Gln Gly Leu Gln Asn Gly Ala Val Ser Cys Ile
    290             295             300

Gly Met Thr Gly Ala Val Pro Ser Gly Ile Arg Ala Val Leu Ala Glu
305             310             315             320

Asn Leu Ile Ala Ser Met Leu Asp Leu Glu Val Ala Ser Ala Asn Asp
                325             330             335

Gln Thr Phe Ser His Ser Asp Ile Arg Arg Thr Ala Arg Thr Leu Met
            340             345             350

Gln Met Leu Pro Gly Thr Asp Phe Ile Phe Ser Gly Tyr Ser Ala Val
        355             360             365

Pro Asn Tyr Asp Asn Met Phe Ala Gly Ser Asn Phe Asp Ala Glu Asp
    370             375             380

Phe Asp Asp Tyr Asn Ile Leu Gln Arg Asp Leu Met Val Asp Gly Gly
385             390             395             400

Leu Arg Pro Val Ser Glu Glu Thr Ile Ala Ile Arg Asn Lys Ala
                405             410             415

Ala Arg Ala Val Gln Ala Val Phe Arg Glu Leu Gly Leu Pro Pro Val
            420             425             430

Thr Asp Glu Glu Val Thr Ala Ala Thr Tyr Ala His Gly Ser Lys Asp
        435             440             445

```
Met Pro Pro Arg Asn Val Val Glu Asp Leu Ser Ala Val Glu Glu Met
    450                 455                 460

Met Lys Arg Asn Ile Thr Gly Leu Asp Ile Val Arg Ala Leu Ser Val
465                 470                 475                 480

Asn Gly Phe Asp Asp Val Ala Asn Asn Ile Leu Asn Met Leu Arg Gln
                485                 490                 495

Arg Val Thr Gly Asp Tyr Leu Gln Thr Ser Ala Ile Leu Asp Arg Glu
            500                 505                 510

Phe Glu Val Val Ser Ala Val Asn Asp Ile Asn Asp Tyr Gln Gly Pro
        515                 520                 525

Gly Thr Gly Tyr Arg Ile Ser Pro Gln Arg Trp Glu Glu Ile Lys Asn
    530                 535                 540

Ile Ala Thr Val Ile Gln Pro Asp Ser Ile Glu
545                 550                 555

<210> SEQ ID NO 257
<211> LENGTH: 555
<212> TYPE: PRT
<213> ORGANISM: unknown
<220> FEATURE:
<223> OTHER INFORMATION: reference listed organism as unidentified

<400> SEQUENCE: 257

Met Arg Arg Ser Lys Arg Phe Glu Val Leu Ala Gln Arg Pro Val Asn
1               5                   10                  15

Gln Asp Gly Leu Ile Gly Glu Trp Pro Glu Gly Leu Ile Ala Met
            20                  25                  30

Glu Ser Pro Tyr Asp Pro Ala Ser Ser Val Lys Val Glu Asn Gly Arg
        35                  40                  45

Ile Val Glu Leu Asp Gly Lys Ser Arg Ala Glu Phe Asp Met Ile Asp
    50                  55                  60

Arg Phe Ile Ala Asp Tyr Ala Ile Asn Val Pro Glu Ala Glu Arg Ala
65                  70                  75                  80

Met Gln Leu Asp Ala Leu Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Glu Met Met Met
        115                 120                 125

Ala Leu Gln Lys Met Arg Ala Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ser Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255
```

```
Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Glu Thr Ile Ala Ile Arg Asn Lys Ala
                405                 410                 415

Ala Arg Ala Ile Gln Ala Val Phe Arg Glu Leu Gly Leu Pro Leu Ile
            420                 425                 430

Ser Asp Glu Glu Val Glu Ala Ala Thr Tyr Ala His Gly Ser Lys Asp
        435                 440                 445

Met Pro Ala Arg Asn Val Val Glu Asp Leu Ala Ala Val Glu Glu Met
    450                 455                 460

Met Lys Arg Asn Ile Thr Gly Leu Asp Ile Val Gly Ala Leu Ser Ser
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Asp Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Ala Gly Val Val Gln Pro Gly Ser Ile Glu
545                 550                 555

<210> SEQ ID NO 258
<211> LENGTH: 555
<212> TYPE: PRT
<213> ORGANISM: unknown
<220> FEATURE:
<223> OTHER INFORMATION: reference listed organism as unidentified

<400> SEQUENCE: 258

Met Arg Arg Ser Lys Arg Phe Glu Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Glu Ser Pro Tyr Asp Pro Ala Ser Ser Val Lys Val Glu Asn Gly Arg
        35                  40                  45

Ile Val Glu Leu Asp Gly Lys Asp Arg Ala Gln Phe Asp Met Ile Asp
    50                  55                  60
```

```
Arg Phe Ile Ala Asp Tyr Ala Ile Asn Val Ala Glu Thr Glu Arg Ala
 65                  70                  75                  80

Met Gln Leu Asp Ala Leu Glu Ile Ala Arg Met Leu Val Asp Ile His
                 85                  90                  95

Val Ser Arg Glu Glu Ile Ile Ala Ile Thr Thr Ala Ile Thr Pro Ala
            100                 105                 110

Lys Ala Val Glu Val Met Ala Lys Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
210                 215                 220

Ser Val Tyr Gly Thr Glu Ser Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Glu Thr Ile Ala Ile Arg Asn Lys Ala
                405                 410                 415

Ala Arg Ala Ile Gln Ala Val Phe Arg Glu Leu Gly Leu Pro Leu Ile
            420                 425                 430

Ser Asp Glu Glu Val Asp Ala Ala Thr Tyr Ala His Gly Ser Lys Asp
        435                 440                 445

Met Pro Ala Arg Asn Val Val Glu Asp Leu Ala Glu Glu Glu Met
    450                 455                 460

Met Lys Arg Asn Ile Thr Gly Leu Asp Ile Val Gly Ala Leu Asn Ser
465                 470                 475                 480

Ser Gly Phe Glu Asp Ile Ala Ser Asn Ile Leu Asn Met Leu Lys Gln
```

```
                   485                 490                 495
Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
            515                 520                 525

Gly Thr Gly Tyr Arg Ile Ser Ala Glu Arg Trp Ala Glu Ile Lys Asn
            530                 535                 540

Ile Ala Gly Val Val Gln Pro Ser Ala Ile Glu
545                 550                 555

<210> SEQ ID NO 259
<211> LENGTH: 556
<212> TYPE: PRT
<213> ORGANISM: Lactobacillus collinoides

<400> SEQUENCE: 259

Met Glu Arg Gln Lys Arg Phe Glu Lys Leu Glu Glu Arg Pro Val His
1               5                   10                  15

Leu Asp Gly Phe Val Lys Asn Trp Asp Asp Glu Gly Leu Val Ala Leu
            20                  25                  30

Asn Gly Lys Asn Asp Pro Lys Pro Ser Ile Thr Ile Glu Asn Gly Val
        35                  40                  45

Val Thr Glu Met Asp Gly Lys Lys Ala Asp Phe Asp Leu Ile Asp
    50                  55                  60

Lys Tyr Ile Ala Glu Tyr Gly Ile Asn Leu Asp Asn Ala Glu Lys Thr
65                  70                  75                  80

Leu Asn Thr Asp Ser Val Lys Ile Ala Asn Met Met Cys Asp Pro Asn
                85                  90                  95

Val Ser Arg Ala Glu Ile Ile Glu Tyr Thr Thr Ala Met Thr Pro Ala
            100                 105                 110

Lys Ala Ala Glu Val Ile Ser Gln Leu Asn Phe Ala Glu Met Ile Met
        115                 120                 125

Ala Thr Gln Lys Met Arg Pro Arg Thr Pro Met Ala Gln Val His
130                 135                 140

Ala Thr Asn Thr Leu Asp Asn Pro Val Glu Ile Ala Ala Asp Ala Ala
145                 150                 155                 160

Glu Ala Ala Leu Arg Gly Val Pro Glu Glu Thr Thr Thr Ala Ile
            165                 170                 175

Ala Arg Tyr Ala Pro Met Asn Ala Ile Ser Ile Met Val Gly Ala Gln
        180                 185                 190

Ala Gly Arg Pro Gly Val Ile Thr Gln Cys Ser Val Glu Glu Ala Asp
    195                 200                 205

Glu Leu Ser Leu Gly Met Arg Gly Phe Thr Ala Tyr Ala Glu Thr Ile
210                 215                 220

Ser Val Tyr Gly Thr Asp Arg Val Phe Thr Asp Gly Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ala Gly Ser Glu Ala Met Met Gly Tyr Thr
            260                 265                 270

Glu Gly Lys Ser Met Leu Tyr Leu Glu Ala Arg Cys Ile Tyr Ile Thr
        275                 280                 285

Lys Ala Ser Gly Val Gln Gly Leu Gln Asn Gly Gly Val Ser Cys Ile
    290                 295                 300
```

Gly Met Pro Gly Ala Val Gly Gly Ile Arg Glu Val Leu Gly Glu
305                 310                 315                 320

Asn Leu Leu Cys Met Ser Leu Asp Val Glu Cys Ala Ser Gly Cys Asp
                325                 330                 335

Gln Ala Phe Ser His Ser Asp Ile Arg Arg Thr Gly Arg Met Ile Gly
            340                 345                 350

Gln Phe Ile Ala Gly Thr Asp Tyr Leu Ser Ser Tyr Ala Ala Glu
        355                 360                 365

Glu Asn Met Asp Asn Thr Phe Ala Gly Ser Asn Met Asp Val Leu Asp
370                 375                 380

Cys Asp Asp Tyr Ile Thr Leu Glu Arg Asp Met Ala Ile Asn Gly Gly
385                 390                 395                 400

Ile Met Pro Ile Thr Glu Glu Ser Ile Lys Ile Arg His Lys Ala
                405                 410                 415

Ala Val Ala Ile Gln Ala Val Phe Asp Gly Leu Gly Leu Pro Gln Ile
            420                 425                 430

Thr Asp Glu Glu Val Glu Ala Ala Thr Tyr Gly Ser Asn Ser Asn Asp
                435                 440                 445

Met Pro Lys Arg Asp Met Val Gln Asp Met Lys Ala Ala Gln Gly Leu
450                 455                 460

Met Thr Arg Gly Ile Thr Val Val Asp Val Ile Lys Ala Leu Tyr Asp
465                 470                 475                 480

His Asp Ile Lys Asp Val Ala Glu Ala Val Leu Lys Leu Ala Gln Gln
                485                 490                 495

Lys Val Cys Gly Asp Tyr Leu Gln Thr Ser Ala Val Phe Leu Asp Gly
            500                 505                 510

Trp Lys Cys Thr Ser Ala Ile Asn Asn Ala Asn Asp Tyr Lys Gly Pro
            515                 520                 525

Gly Thr Gly Tyr Arg Leu Trp Glu Asp Lys Asp Lys Trp Asp Arg Leu
            530                 535                 540

Glu Asn Val Pro Trp Ala Leu Asp Pro Gln Lys Leu
545                 550                 555

<210> SEQ ID NO 260
<211> LENGTH: 224
<212> TYPE: PRT
<213> ORGANISM: unknown
<220> FEATURE:
<223> OTHER INFORMATION: reference listed organism as unidentified

<400> SEQUENCE: 260

Met Glu Ile Asn Glu Lys Leu Leu Arg Gln Ile Ile Glu Asp Val Leu
1               5                   10                  15

Ser Glu Met Gln Thr Ser Asp Lys Pro Val Ser Phe Arg Ser Ser Ala
                20                  25                  30

Ala Ala Thr Ala Pro Gln Met Ala Thr Ala Pro Gly Asp Ser Phe Leu
            35                  40                  45

Thr Glu Ile Gly Glu Ala Lys Gln Gly Gln Gln Asp Glu Val Ile
        50                  55                  60

Ile Ala Val Gly Pro Ala Phe Gly Leu Ser Gln Thr Val Asn Ile Val
65                  70                  75                  80

Gly Ile Pro His Lys Asn Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
115                 120                 125

Ser Ile Gly Ile Gln Ser Lys Gly Thr Thr Val Ile His Gln Gln Gly
130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
210                 215                 220

<210> SEQ ID NO 261
<211> LENGTH: 224
<212> TYPE: PRT
<213> ORGANISM: unknown
<220> FEATURE:
<223> OTHER INFORMATION: reference listed organism as unidentified

<400> SEQUENCE: 261

Met Glu Ile Asn Glu Lys Leu Leu Arg Gln Ile Ile Glu Asp Val Leu
1               5                   10                  15

Ser Glu Met Gln Thr Ser Asp Lys Pro Val Ser Phe Arg Ser Ser Thr
            20                  25                  30

Ala Ala Ser Ala Pro Gln Ala Ala Ala Gln Gly Asp Ser Phe Leu
        35                  40                  45

Thr Glu Ile Gly Glu Ala Lys Gln Gly Gln Gln Asp Glu Val Ile
    50                  55                  60

Ile Ala Val Gly Pro Ala Phe Gly Leu Ser Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Val Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
210                 215                 220

<210> SEQ ID NO 262
<211> LENGTH: 194
<212> TYPE: PRT
<213> ORGANISM: unknown
<220> FEATURE:

<223> OTHER INFORMATION: reference listed organism as unidentified

<400> SEQUENCE: 262

```
Met Glu Cys Thr Ile Glu Arg Lys Pro Val Phe Ile Leu Gln Val Ser
1               5                   10                  15

Glu Gly Glu Ala Ala Lys Ala Gly Asp Arg Ala Asp Glu Val Val Ile
            20                  25                  30

Gly Val Gly Pro Ala Phe Asp Lys Tyr Gln His Lys Thr Leu Ile Asp
        35                  40                  45

Met Pro His Lys Ala Ile Leu Lys Glu Leu Val Ala Gly Ile Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Ala Pro Val Thr Leu His Ile Ala Leu Val
            180                 185                 190

Lys Glu
```

<210> SEQ ID NO 263
<211> LENGTH: 194
<212> TYPE: PRT
<213> ORGANISM: unknown
<220> FEATURE:
<223> OTHER INFORMATION: reference listed organism as unidentified

<400> SEQUENCE: 263

```
Met Glu Cys Thr Thr Glu Arg Lys Pro Val Phe Thr Leu Gln Val Ser
1               5                   10                  15

Glu Gly Glu Ala Ala Lys Ala Asp Asp Arg Ala Asp Glu Val Val Ile
            20                  25                  30

Gly Val Gly Pro Ala Phe Asp Lys Tyr Gln His Lys Thr Leu Ile Asp
        35                  40                  45

Met Pro His Lys Ala Ile Leu Lys Glu Leu Val Ala Gly Ile Glu Glu
    50                  55                  60

Glu Gly Leu His Ala Arg Val Val Arg Val Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140
```

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Ala Pro Val Thr Leu His Ile Ala Leu Val
            180                 185                 190

Arg Glu

<210> SEQ ID NO 264
<211> LENGTH: 194
<212> TYPE: PRT
<213> ORGANISM: unknown
<220> FEATURE:
<223> OTHER INFORMATION: reference listed organism as unidentified

<400> SEQUENCE: 264

Met Glu Cys Thr Thr Glu Arg Lys Pro Val Phe Thr Leu Gln Val Ser
1               5                   10                  15

Glu Gly Glu Ala Ala Lys Ala Asp Glu Arg Val Asp Glu Val Val Ile
            20                  25                  30

Gly Val Gly Pro Ala Phe Asp Lys Tyr Gln His Lys Thr Leu Ile Asp
        35                  40                  45

Met Pro His Asn Ala Ile Leu Lys Glu Leu Val Ala Gly Ile Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Ala Pro Val Thr Leu His Ile Ala Leu Val
            180                 185                 190

Arg Glu

<210> SEQ ID NO 265
<211> LENGTH: 188
<212> TYPE: PRT
<213> ORGANISM: Clostridium perfringens

<400> SEQUENCE: 265

Met Glu Glu Arg Thr Phe Ile Pro Glu Ile Thr Val Glu Glu Val Gly
1               5                   10                  15

Glu Ala Lys Val Gly Leu Arg Ser Asp Glu Val Val Ile Gly Leu Ala
            20                  25                  30

Pro Ala Phe Leu Lys Tyr Gln Asn Lys Thr Ile Val Asp Val Pro His
        35                  40                  45

Thr Glu Thr Leu Leu Glu Ile Ile Ala Gly Ile Glu Glu Glu Gly Leu
    50                  55                  60

```
His Ala Arg Val Val Arg Ile Leu Arg Thr Ser Asp Val Ser Phe Ile
 65                  70                  75                  80

Ala His Asp Ala Ala Cys Leu Ser Gly Ser Gly Ile Gly Ile Gly Ile
                 85                  90                  95

Gln Ser Lys Gly Thr Thr Val Ile His Gln Lys Asp Leu Leu Pro Leu
            100                 105                 110

Asn Asn Leu Glu Leu Phe Ser Gln Ala Pro Leu Leu Thr Pro Glu Thr
        115                 120                 125

Tyr Arg Leu Ile Gly Lys Asn Ala Ala Lys Tyr Ala Lys Gly Glu Ser
    130                 135                 140

Pro Thr Pro Val Pro Val Lys Asn Asp Gln Met Val Arg Pro Lys Phe
145                 150                 155                 160

Met Ala Lys Ala Ala Leu Leu His Ile Lys Glu Thr Lys His Val Glu
                165                 170                 175

Pro Gly Lys Lys Pro Val Gln Leu Glu Val Lys Phe
            180                 185

<210> SEQ ID NO 266
<211> LENGTH: 146
<212> TYPE: PRT
<213> ORGANISM: unknown
<220> FEATURE:
<223> OTHER INFORMATION: reference listed organism as unidentified

<400> SEQUENCE: 266

Met Pro His Gly Ala Ile Leu Lys Glu Leu Ile Ala Gly Val Glu Glu
1               5                   10                  15

Glu Gly Leu His Ala Arg Val Val Arg Ile Leu Arg Thr Ser Asp Val
            20                  25                  30

Ser Phe Met Ala Trp Asp Ala Ala Asn Leu Ser Gly Ser Gly Ile Gly
        35                  40                  45

Ile Gly Ile Gln Ser Lys Gly Thr Thr Val Ile His Gln Arg Asp Leu
    50                  55                  60

Leu Pro Leu Ser Asn Leu Glu Leu Phe Ser Gln Ala Pro Leu Leu Thr
65                  70                  75                  80

Leu Glu Thr Tyr Arg Gln Ile Gly Lys Asn Ala Ala Arg Tyr Ala Arg
                85                  90                  95

Lys Glu Ser Pro Ser Pro Val Pro Val Asn Asp Gln Met Val Arg
            100                 105                 110

Pro Lys Phe Met Ala Lys Ala Ala Leu Phe His Ile Lys Glu Thr Lys
        115                 120                 125

His Val Val Gln Asp Ala Glu Pro Val Thr Leu His Ile Asp Leu Val
    130                 135                 140

Arg Glu
145

<210> SEQ ID NO 267
<211> LENGTH: 148
<212> TYPE: PRT
<213> ORGANISM: Escherichia blattae

<400> SEQUENCE: 267

Met Pro His Lys Ala Ile Ile Lys Glu Leu Val Ala Gly Val Glu Glu
1               5                   10                  15

Glu Gly Leu His Ala Arg Val Val Arg Ile Leu Arg Thr Ser Asp Val
            20                  25                  30

Ser Phe Met Ala Trp Asp Ala Ala Asn Leu Ser Gly Ser Gly Ile Gly
```

```
                35                  40                  45
Ile Gly Ile Gln Ser Lys Gly Thr Thr Val Ile His Gln Arg Asp Leu
 50                  55                  60

Leu Pro Leu Ser Asn Leu Glu Leu Phe Ser Gln Ala Pro Leu Leu Thr
 65                  70                  75                  80

Leu Glu Thr Tyr Arg Gln Ile Gly Lys Asn Ala Ala Arg Tyr Ala Arg
                 85                  90                  95

Lys Glu Ser Pro Ser Pro Val Pro Val Val Asn Asp Gln Met Val Arg
                100                 105                 110

Pro Lys Phe Met Ala Lys Ala Ala Leu Phe His Ile Lys Glu Thr Lys
                115                 120                 125

His Val Val Ala Asp Ala Lys Pro Ala Thr Leu Asn Ile Glu Ile Thr
                130                 135                 140

Arg Glu Glu Ala
145

<210> SEQ ID NO 268
<211> LENGTH: 172
<212> TYPE: PRT
<213> ORGANISM: unknown
<220> FEATURE:
<223> OTHER INFORMATION: reference listed organism as unidentified

<400> SEQUENCE: 268

Met Asn Thr Asp Ala Ile Glu Ser Met Val Arg Asp Val Leu Ser Arg
 1               5                  10                  15

Met Asn Ser Leu Gln Gly Glu Thr Val Thr Pro Ser Ala Thr Val Ser
                20                  25                  30

Ser Thr His Thr Ala Lys Val Thr Asp Tyr Pro Leu Ala Asn Lys His
                35                  40                  45

Pro Glu Trp Val Lys Thr Ala Thr Asn Lys Thr Leu Asp Asp Phe Thr
 50                  55                  60

Leu Glu Asn Val Leu Ser Asn Lys Val Thr Ala Gln Asp Met Arg Ile
 65                  70                  75                  80

Thr Pro Glu Thr Leu Arg Leu Gln Ala Glu Ile Ala Lys Asp Ala Gly
                 85                  90                  95

Arg Asp Arg Leu Ala Met Asn Phe Glu Arg Ala Ala Glu Leu Thr Ala
                100                 105                 110

Val Pro Asp Asp Arg Ile Leu Glu Ile Tyr Asn Ala Leu Arg Pro Tyr
                115                 120                 125

Arg Ser Thr Lys Asp Glu Leu Met Ala Ile Ala Asp Asp Leu Glu Asn
                130                 135                 140

Arg Tyr Gln Ala Lys Ile Cys Ala Ala Phe Val Arg Glu Ala Ala Val
145                 150                 155                 160

Leu Tyr Val Glu Arg Lys Lys Leu Lys Gly Asp Asp
                165                 170

<210> SEQ ID NO 269
<211> LENGTH: 121
<212> TYPE: PRT
<213> ORGANISM: unknown
<220> FEATURE:
<223> OTHER INFORMATION: reference listed organism as unidentified

<400> SEQUENCE: 269

Met Asn Thr Asp Ala Ile Glu Ser Met Val Arg Asp Val Leu Ser Arg
 1               5                  10                  15
```

```
Met Asn Ser Leu Gln Gly Glu Thr Val Thr Pro Ala Ala Thr Gly Ser
                 20                  25                  30

Ser Ala His Thr Ala Lys Val Thr Asp Tyr Pro Leu Ala Asn Lys His
             35                  40                  45

Pro Glu Trp Val Lys Thr Ala Thr Asn Lys Thr Leu Asp Asp Phe Thr
 50                  55                  60

Leu Glu Asn Val Leu Ser Asn Lys Val Thr Ala Gln Asp Met Arg Ile
 65                  70                  75                  80

Thr Pro Glu Thr Leu Arg Ile Gln Ala Asp Ile Ala Lys Asp Ala Gly
                 85                  90                  95

Arg Asp Arg Leu Ala Met Asn Phe Glu Arg Ala Ala Glu Leu Thr Ala
            100                 105                 110

Val Pro Asp Asp Arg Ile Leu Glu Val
            115                 120

<210> SEQ ID NO 270
<211> LENGTH: 170
<212> TYPE: PRT
<213> ORGANISM: Listeria monocytogenes

<400> SEQUENCE: 270

Met Asn Gln Glu Ala Leu Glu Asn Met Val Arg Asn Ile Leu Gln Glu
  1               5                  10                  15

Val Asn Ser Gly Ala Val Ser Thr Thr Thr Ser Gln Lys Val Ser Gly
                 20                  25                  30

Asp Thr Leu Thr Val Arg Asp Tyr Pro Leu Gly Thr Lys Arg Pro Glu
             35                  40                  45

Leu Val Lys Thr Ser Thr Ser Lys Ser Leu Asp Ile Thr Leu Lys
 50                  55                  60

Ser Val Leu Asp Gly Thr Ile Lys Pro Glu Asp Val Arg Val Thr Ala
 65                  70                  75                  80

Glu Thr Leu Lys Met Gln Ala Gln Val Ala Arg Asp Ala Gly Arg Ala
                 85                  90                  95

Thr Leu Ala Asn Asn Phe Glu Arg Ala Ala Glu Leu Thr Ile Val Pro
            100                 105                 110

Asp Glu Arg Ile Leu Glu Ile Tyr Asn Ala Met Arg Pro Tyr Arg Ser
            115                 120                 125

Ser Arg Glu Glu Leu Leu Ala Ile Ala Asp Glu Leu Glu Ser Val Tyr
            130                 135                 140

His Ala Thr Ile Cys Ser Asn Tyr Val Arg Glu Ala Thr Gln Leu Tyr
145                 150                 155                 160

Gln Glu Arg Lys Lys Leu Lys Gly Asp Asn
                165                 170

<210> SEQ ID NO 271
<211> LENGTH: 142
<212> TYPE: PRT
<213> ORGANISM: unknown
<220> FEATURE:
<223> OTHER INFORMATION: reference listed organism as unidentified

<400> SEQUENCE: 271

Met Asn Asp Asn Ile Met Thr Ala Gln Asp Tyr Pro Leu Ala Thr Arg
  1               5                  10                  15

Cys Pro Glu Lys Ile Leu Thr Pro Thr Gly Lys Pro Leu Thr Asp Ile
                 20                  25                  30

Thr Leu Glu Asn Val Leu Ala Gly Arg Val Gly Pro Gln Asp Val Arg
```

```
                    35                  40                  45

Ile Ser Gln Gln Thr Leu Glu Tyr Gln Ala Gln Ile Ala Glu Gln Met
 50                  55                  60

Gln Arg His Ala Val Ala Arg Asn Phe Arg Arg Ala Ala Glu Leu Ile
 65                  70                  75                  80

Ala Ile Pro Asp Ala Arg Ile Leu Glu Ile Tyr Asn Ala Leu Arg Pro
                 85                  90                  95

Phe Arg Ser Ser Leu Ala Glu Leu Leu Ala Ile Ala Asp Glu Leu Glu
                100                 105                 110

His Thr Trp His Ala Thr Val Asn Ala Gly Phe Val Arg Glu Ser Ala
                115                 120                 125

Glu Val Tyr Gln Gln Arg Asn Lys Leu Arg Lys Gly Ser Gln
                130                 135                 140

<210> SEQ ID NO 272
<211> LENGTH: 142
<212> TYPE: PRT
<213> ORGANISM: unknown
<220> FEATURE:
<223> OTHER INFORMATION: reference listed organism as unidentified

<400> SEQUENCE: 272

Met Asn Glu Asn Ile Met Thr Ala Gln Asp Tyr Pro Leu Ala Thr Arg
 1               5                  10                  15

Cys Pro Glu Lys Ile Leu Thr Pro Thr Gly Lys Pro Leu Thr Asp Ile
                 20                  25                  30

Thr Leu Glu Asn Val Leu Ala Gly Arg Val Gly Pro Gln Asp Val Arg
                 35                  40                  45

Ile Ser Gln Gln Thr Leu Glu Tyr Gln Ala Gln Ile Ala Glu Gln Met
 50                  55                  60

Gln Arg His Ala Val Ala Arg Asn Phe Arg Arg Ala Ala Glu Leu Ile
 65                  70                  75                  80

Ala Ile Pro Asp Ala Arg Ile Leu Glu Ile Tyr Asn Ala Leu Arg Pro
                 85                  90                  95

Phe Arg Ser Ser Phe Thr Glu Leu Gln Ala Ile Ala Asp Glu Leu Glu
                100                 105                 110

His Thr Trp His Ala Thr Val Asn Ala Gly Phe Val Arg Glu Ser Ala
                115                 120                 125

Asp Val Tyr Gln Gln Arg Asn Lys Leu Arg Lys Gly Ser Gln
                130                 135                 140

<210> SEQ ID NO 273
<211> LENGTH: 142
<212> TYPE: PRT
<213> ORGANISM: unknown
<220> FEATURE:
<223> OTHER INFORMATION: reference listed organism as unidentified

<400> SEQUENCE: 273

Met Asn Asp Asn Ile Met Thr Ala Gln Asp Tyr Pro Leu Ala Thr Arg
 1               5                  10                  15

Cys Pro Glu Lys Ile Gln Thr Pro Thr Gly Lys Pro Leu Thr Glu Ile
                 20                  25                  30

Thr Leu Glu Asn Val Leu Ala Gly Arg Val Gly Pro Gln Asp Val Arg
                 35                  40                  45

Ile Ser Gln Gln Thr Leu Glu Tyr Gln Ala Gln Ile Ala Glu Gln Met
 50                  55                  60
```

```
Gln Arg His Ala Val Ala Arg Asn Phe Arg Arg Ala Ala Glu Leu Ile
 65                  70                  75                  80

Ala Ile Pro Asp Ala Arg Ile Leu Glu Ile Tyr Asn Ala Leu Arg Pro
                 85                  90                  95

Phe Arg Ser Ser Phe Ala Glu Leu Gln Ala Ile Ala Asp Glu Leu Glu
            100                 105                 110

His Thr Trp His Ala Thr Val Asn Ala Gly Phe Val Arg Glu Ser Ala
        115                 120                 125

Glu Val Tyr Gln Gln Arg Asn Lys Leu Arg Lys Gly Ser Gln
    130                 135                 140

<210> SEQ ID NO 274
<211> LENGTH: 170
<212> TYPE: PRT
<213> ORGANISM: Listeria monocytogenes

<400> SEQUENCE: 274

Met Asn Gln Glu Ala Leu Glu Asn Met Val Arg Asn Ile Leu Gln Glu
 1               5                  10                  15

Val Asn Ser Gly Ala Val Ser Thr Thr Thr Ser Gln Lys Val Ser Gly
             20                  25                  30

Asp Thr Leu Thr Val Arg Asp Tyr Pro Leu Gly Thr Lys Arg Pro Glu
         35                  40                  45

Leu Val Lys Thr Ser Thr Ser Lys Ser Leu Asp Asp Ile Thr Leu Lys
 50                  55                  60

Ser Val Leu Asp Gly Thr Ile Lys Pro Glu Asp Val Arg Val Thr Val
 65                  70                  75                  80

Glu Thr Leu Lys Met Gln Ala Gln Val Ala Arg Asp Ala Gly Arg Ala
                 85                  90                  95

Thr Leu Ala Asn Asn Phe Glu Arg Ala Ala Glu Leu Thr Ile Val Pro
            100                 105                 110

Asp Glu Arg Ile Leu Glu Ile Tyr Asn Ala Met Arg Pro Tyr Arg Ser
        115                 120                 125

Ser Arg Glu Glu Leu Leu Ala Ile Ala Asp Glu Leu Glu Ser Val Tyr
    130                 135                 140

His Ala Thr Ile Cys Ser Asn Tyr Val Arg Glu Ala Ala Gln Leu Tyr
145                 150                 155                 160

Gln Glu Arg Lys Lys Leu Lys Gly Asp Asn
                165                 170

<210> SEQ ID NO 275
<211> LENGTH: 2432
<212> TYPE: DNA
<213> ORGANISM: Erwinia caratovora subsp. atroseptica

<400> SEQUENCE: 275
atgtctgacg gacgactcac cgcactttt  cctgcattcc cacacccggc gtccaatcag      60
cccgtatttg ccgaggcttc accgcacgac gacgagttaa tgacgcaggc cgtaccgcag     120
gtttcctgtc agcaggcgtt ggcgattgcg cagcaagaat atggcttgtc tgggcagatg     180
tcgctgcttc agggcgagcg tgatgtgaat ttctgtctga cggtgacgcc agatgaacgc     240
tacatgctga aagtcatcaa tgcggcagaa cctgccgacg tcagcaattt ccaaaccgcg     300
ctgctgctgc atcttgcccg tcaggcacct gaactgcccg taccgcgtat caggtcgaca     360
aaagcgggtc agtcggaaac aggcgttgag atcgatggtg tactgctgcg tgtgcggctt     420
gtgagctatc tggcaggaat gccgcagtat ctggcctcac cgtcaacggc gctgatgccg     480
```

-continued

```
cagttggggg gaacgctggc gcagttggat aacgcgcttc acagctttac gcatccggcg      540
gcaaaccgtg cgctgctgtg ggatatcagc cgggcagagc aggtgcgtcc ttacctcgat      600
ttcgtttctg aaccgcagca gtatcagcat cttcagcgta tttttgaccg ttatgacagt      660
aacgttgctc ctctgttgac gacgctacgt cgtcaggtca ttcataacga tctgaatccg      720
cataacgtgc tggtggatgg atcgtcgccg acgcgggtta ctggcattat cgattttggc      780
gatgccgtat ttgccccgtt aatttgcgaa gtcgcgacgg cactggcgta tcagatcggc      840
gatggaaccg atttgttgga gcatgttgtg ccgtttgttg cggcctatca ccaacgcatt      900
ccgttagcac cggaggagat tgcgctgtta cccgatctga tagcgacccg tatggcgctg      960
accctgacca ttgcgcagtg gcgagcatcg cgttatcccg acaatcggga gtatctgctg     1020
cgtaacgtgc cgcgctgttg gcacagtttg cagcgcattg cgacctattc ccatgcgcaa     1080
tttttgactc gcctacagca ggtttgcccg gagaatgcgc gatgaaccag aaaggaatga     1140
cgtctatgac gtctgaaatg acagcgacag aagctttgct ggcgcgccgt cagcgagtgt     1200
tgggcggcgg ttatcgcctg ttttatgaag agccgctgca tgtcgcgcgc ggcgagggcg     1260
tgtggctgtt cgatcaccaa gggaaacgtt atctggatgt ctacaataat gtggcttcgg     1320
tcggacattg ccaccccgcg gtggttgaag ccgtggcgcg acagagcgca caactcaata     1380
cccacacgcg ctatttgcac cacgcgattg tcgattttgc ggaagatttg ctgagcgaat     1440
ttcccgccga attgaacaat gtaatgctga cctgtaccgg cagtgaggct aacgatctgg     1500
cgctgcgtat cgcccgacat gtcacgggcg ggacggggat gttggtgacg cgctgggcgt     1560
atcacggcgt gaccagcgcg ctggcggaac tgtctccgtc gctgggggat ggcgttgtgc     1620
gcggtagcca tgtgaagctg atcgacgcgc cagacactta tcgtcagccc ggtgcatttc     1680
ttaccagcat tcgtgaagcg ctggcgcaga tgcaacggga aggtattcgt cctgcggcgc     1740
tgctggtaga taccattttt tccagcgatg gcgtgttctg tgcgccggaa ggcgaaatgg     1800
cacaggcggc ggcgttgatc cgtcaggcgg gcgggctgtt tattgcggat gaagtgcagc     1860
cgggcttcgg gcgcaccggg gaatcactgt ggggctttgc gcgccacaat gtcgtccctg     1920
atttggtgag tctagggaaa ccgatgggca acggacatcc catcgctgga ttggtggggc     1980
gttccgctct gttcgacgca tttgggcgcg atgtgcgcta tttcaatacc tttggcggca     2040
atccggtttc ctgtcaggcg gcgcacgcgg tgctgcgggt gattcgggaa gagcagttgc     2100
agcagaatgc ccagcgggtc ggtgattatc tgcggcaagg gttgcagcaa ctggcgcagc     2160
atttcccgct gattggtgat attcgggctt acggcctgtt tattggtgcg gagctggtca     2220
gcgatcgcga aagtaaaacg ccggcaagtg aatccgcgtt gcaggtggtg aatgcgatgc     2280
gccaacgtgg tgtgctcatc agcgcgacgg ggccagcggc gaacatactg aaaattcgcc     2340
cgccgctggt gtttctggaa gaacacgccg atgtgttctt aaccacgctg agtgacgttt     2400
tagcgctcat cggcactcgt gcacagagat aa                                   2432
```